(12) United States Patent
Lee et al.

(10) Patent No.: US 11,897,968 B2
(45) Date of Patent: Feb. 13, 2024

(54) ANTI-MERTK ANTIBODIES AND METHODS OF USE THEREOF

(71) Applicant: Alector LLC, South San Francisco, CA (US)

(72) Inventors: Seung-Joo Lee, Benicia, CA (US); Spencer Liang, San Mateo, CA (US); Angie Yee, San Francisco, CA (US); Marina Roell, Concord, CA (US); Arnon Rosenthal, Woodside, CA (US)

(73) Assignee: ALECTOR LLC, South San Francisco, CA (US)

( * ) Notice: Subject to any disclaimer, the term of this patent is extended or adjusted under 35 U.S.C. 154(b) by 204 days.

(21) Appl. No.: 17/118,921

(22) Filed: Dec. 11, 2020

(65) Prior Publication Data

US 2021/0261685 A1     Aug. 26, 2021

Related U.S. Application Data

(60) Provisional application No. 63/121,773, filed on Dec. 4, 2020, provisional application No. 63/016,821, filed on Apr. 28, 2020, provisional application No. 62/947,855, filed on Dec. 13, 2019.

(51) Int. Cl.
| | |
|---|---|
| *C07K 16/40* | (2006.01) |
| *A61K 39/395* | (2006.01) |
| *A61P 35/00* | (2006.01) |
| *C07K 16/28* | (2006.01) |
| *A61K 39/00* | (2006.01) |

(52) U.S. Cl.
CPC .............. *C07K 16/40* (2013.01); *A61P 35/00* (2018.01); *C07K 16/2818* (2013.01); *C07K 16/2827* (2013.01); *A61K 2039/507* (2013.01); *C07K 2317/56* (2013.01); *C07K 2317/622* (2013.01); *C07K 2317/76* (2013.01)

(58) Field of Classification Search
None
See application file for complete search history.

(56) References Cited

U.S. PATENT DOCUMENTS

| | | | | |
|---|---|---|---|---|
| 10,017,564 | B2 * | 7/2018 | Sahin | A61P 35/04 |
| 10,221,248 | B2 * | 3/2019 | Tavazoie | C07K 16/40 |
| 2018/0002444 | A1 | 1/2018 | Tavazoie et al. | |
| 2020/0291135 | A1 | 9/2020 | Tavazoie et al. | |

FOREIGN PATENT DOCUMENTS

| | | | |
|---|---|---|---|
| WO | WO-2006058202 A2 | 6/2006 | |
| WO | WO-2009062112 A2 | 5/2009 | |
| WO | WO-2016001830 A1 | 1/2016 | |
| WO | WO-2016106221 A1 | 6/2016 | |
| WO | WO-2019005756 A1 | 1/2019 | |
| WO | WO-2019084307 A1 * | 5/2019 | |
| WO | WO-2020076799 A1 * | 4/2020 | ......... A61K 47/6803 |
| WO | WO-2020106461 A2 | 5/2020 | |
| WO | WO-2020176497 A1 | 9/2020 | |
| WO | WO-2020214995 A1 | 10/2020 | |
| WO | WO-2021119508 A1 | 6/2021 | |
| WO | WO-2021202590 A1 | 10/2021 | |
| WO | WO-2022266221 A1 | 12/2022 | |
| WO | WO-2022266223 A1 | 12/2022 | |

OTHER PUBLICATIONS

Grabiec et al (European J. Immunol., 2018, 48:855-860).*
R&D Systems product datasheet on antibody AF891 (Dec. 4, 2018).*
Eken et al (Journal of Biological Chemistry; 2010; 285:39914-39921).*
Alvarado, D., et al., "Monoclonal Antibodies Targeting the MerTK receptor de-repress the innate immune response," J. Immunother. Cancer 6(S1), 2 pages, BioMed Central Ltd., Netherlands (Nov. 2018).
Dondelinger, M., et al., "Understanding the Significance and Implications of Antibody Numbering and Antigen-Binding Surface/Residue Definition," Front. Immunol. 9:2278, 15 pages, Frontiers Media S.A., Switzerland (Oct. 2018).
Ginisty, A., et al., "Evidence for a subventricular zone neural stem cell phagocytic activity stimulated by the vitamin K-dependent factor protein S," Stem Cells 33(2):515-525, Wiley, United States (Oct. 2014).
Karl, M.O., et al., "Endogenous Gas6 and Ca2+—channel activation modulate phagocytosis by retinal pigment epithelium," Cellular Signaling 20(6): 1159-1168, Elsevier, Netherlands (Jun. 2008).
Santulli-Marotto, S., et al., "Discovering Molecules That Regulate Efferocytosis Using Primary Human Macrophages and High Content Imaging," PLOS One 10(12):e0145078, 21 pages, Public Library of Science, United States (Dec. 2015).
Stanford, J.C., et al., "Efferocytosis produces a prometastatic landscape during postpartum mammary gland involution," J. Clin. Invest. 124(11):4737-4752, American Society for Clinical Investigation, United States (Sep. 2014).
Qin, S., et al., "Roles of αvβ5, FAK and MerTK in oxidative stress inhibition of RPE cell phagocytosis," Experimental Eye Research 94(1):63-70, Academic Press Ltd., United Kingdom (Nov. 2011).
Takeda, S., et al., "Characterization of the anti-cancer and immunologic activity of RGX-019, a novel pre-clinical stage humanized monoclonal antibody targeting the MERTK receptor," Cancer Res. 79(S13): 1 page, American Association for Cancer Research, United States (Jul. 2019).

(Continued)

*Primary Examiner* — Laura B Goddard
(74) *Attorney, Agent, or Firm* — Sterne, Kessler, Goldstein & Fox P.L.L.C.

(57) ABSTRACT

The present disclosure is generally directed to compositions that include antibodies, e.g., monoclonal, antibodies, antibody fragments, etc., that specifically bind a MerTK polypeptide, e.g., a mammalian MerTK or human MerTK, and use of such compositions in treating an individual in need thereof.

23 Claims, 26 Drawing Sheets

Specification includes a Sequence Listing.

(56) References Cited

OTHER PUBLICATIONS

Todt, J.C., et al., "The receptor tyrosine kinase MerTK activates phospholipase C γ2 during recognition of apoptotic thymocytes by murine macrophages," J. Leukoc. Biol. 75(4):705-713, Wiley, United States (Apr. 2004).

Waterborg, C.E., et al., "Protective Role of the MER Tyrosine Kinase via Efferocytosis in Rheumatoid Arthritis Models," Front. Immunol. 9:742, 14 pages, Frontiers Media S.A., Switzerland (Apr. 2018).

White, K.F., et al., "MERTK-specific antibodies that have therapeutic antitumor activity in mice disrupt the integrity of the retinal pigmented epithelium in cynomolgus monkeys," Cancer Res. 79:S13, 2 pages, American Association for Cancer Research, United States (Jul. 2019).

Zhang, B., et al., "MerTK Downregulates Lipopolysaccharide-Induced Inflammation Through SOCS1 Protein but Does Not Affect Phagocytosis of *Escherichia coli* in Macrophages," Inflammation 42(1):113-123, SpringerLink, United States (Feb. 2019).

International Search Report and Written Opinion for International Application No. PCT/US2020/064640, dated May 11, 2021, European Patent Office, Netherlands, 27 pages.

Abcam.com, "Anti-MERTK (phospho Y749+Y753+Y754) antibody (ab14921)," Abcam.com, accessed at https://www.abcam.com/mertk-phospho-y749—y753—y754-antibody-ab14921.html, (Jun. 2021) accessed on Dec. 23, 2022, 3 pages.

Murase, H., et al., "TUDCA Promotes Phagocytosis by Retinal Pigment Epithelium via MerTK Activation," Invest. Ophthalmol. Vis. Sci. 56(4):2511-2518, Association for Research in Vision and Ophthalmology, United States (Apr. 2015).

R&D Systems, "Mouse Mer Antibody AF591: R&D Systems," Rndsystems.com, accessed at https://www.rndsystems.com/products/mouse-mer-antibody_af591, (Jun. 2021) accessed on Dec. 23, 2022, 7 pages.

International Search Report and Written Opinion for International Application No. PCT/US2021/024970, dated Aug. 27, 2021, European Patent Office, Netherlands, 28 pages.

Blander, J.M., et al., "MerTK Blockade Fuels Anti-tumor Immunity," Immunity 52(2):212-214, Cell Press, Netherlands (Feb. 2020).

International Search Report and Written Opinion for International Application No. PCT/US2022/033629, dated Sep. 16, 2022, European Patent Office, Netherlands, 18 pages.

Akalu, Y.T., et al., "TAM receptor tyrosine kinases as emerging targets of innate immune checkpoint blockade for cancer therapy," Immunological Reviews 276(1):165-177, Wiley, United States (2017).

Brinkmann, U., et al., "The making of bispecific antibodies," mAbs 9(2):182-212, Taylor & Francis, United Kingdom (2017).

Huelse, J.M., et al., "MERTK in cancer therapy: Targeting the receptor tyrosine kinase in tumor cells and the immune system," Pharmacology & Therapeutics 213:107577, 22 pages, Elsevier, United Kingdom (Sep. 2020).

International Search Report and Written Opinion for International Application No. PCT/US2022/033632, dated Oct. 28, 2022, European Patent Office, Netherlands, 28 pages.

Silva, J.S., et al., "The S228P mutation prevents in vivo and in vitro IgG4 Fab-arm exchange as demonstrated using a combination of novel quantitative immunoassays and physiological matrix preparation," J. Biol. Chem 290(9):5462-5469, American Society for Biochemistry and Molecular Biology, United States (Feb. 2015).

Co-pending U.S. Appl. No. 17/995,189, inventors Kurnellas, M., et al., international filing date: Mar. 30, 2021 (Not yet Published).

Al-Khersan, H., et al., "A novel MERTK mutation causing retinitis pigmentosa," *Graefe's Archive for Clinical and Experimental Ophthalmology* 255(8):1613-1619, Springer Verlag, Germany (May 2017).

Audo, I., et al., "MERTK mutation update in inherited retinal diseases," *Hum Mutat* 39(7):887-913, Wiley-Liss Inc., United States (May 2018).

Binder, M. D., et al., "Common and Low Frequency Variants in MERTK Are Independently Associated with Multiple Sclerosis Susceptibility with Discordant Association Dependent upon HLA-DRB1*15:01 Status," *PLoS Genetics* 12(3):e1005853, 25 pages, Public Library of Science, United States (Mar. 2016).

Cook, R. S., et al., "MerTK inhibition in tumor leukocytes decreases tumor growth and metastasis," *Journal of Clinical Investigation* 123(8):3231-3242, American Society for Clinical Investigation, United States (Jul. 2013).

Cummings, C. T., et al., "Molecular pathways: MERTK signaling in cancer," *Clinical Cancer Research* 19(19):5275-5280, American Association for Cancer Research Inc., United States (Jul. 2013).

Cummings, C. T., et al., "Mer590, a novel monoclonal antibody targeting MER receptor tyrosine kinase, decreases colony formation and increases chemosensitivity in non-small cell lung cancer," *Oncotarget* 5(21):10434-10445, Impact Journals LLC, United States (Jun. 2014).

Dayoub, A. S., and Brekken, R. A., "TIMs, TAMs, and PS-antibody targeting: implications for cancer immunotherapy," *Cell Communication and Signaling* 18:29, 11 pages, Signal Transduction Society, United Kingdom (Feb. 2020).

Graham, D. K., et al., "The TAM family: phosphatidylserine-sensing receptor tyrosine kinases gone awry in cancer," *Nat Rev Cancer* 14(12):769-785, Nature Publishing Group, United Kingdom (Dec. 2014).

Healy, L. M., et al., "MerTK Is a Functional Regulator of Myelin Phagocytosis by Human Myeloid Cells," *Journal of Immunology* 196(8):3375-3384, American Association of Immunologists, United States (Mar. 2016).

Healy, L. M., et al., "MerTK-mediated regulation of myelin phagocytosis by macrophages generated from patients with MS," *Neurology: Neuroimmunology & Neuroinflammation* 4(6):e402, 7 pages, Lippincott Williams and Wilkins Ltd., United States (Oct. 2017).

Huey, M. G., et al., "Targeting the TAM Receptors in Leukemia," *Cancers (Basel)* 8(11):101, 22 pages, MDPI Multidisciplinary Digital Publishing Institute, Switzerland (Nov. 2016).

Kedage, V., et al., "Harnessing MerTK agonism for targeted therapeutics," *MAbs* 12(1):e1685832, 8 pages, Landes Bioscience, United States (Dec. 2019).

Lavail, M. M., et al., "Gene Therapy for MERTK-Associated Retinal Degenerations," *Advances in Experimental Medicine and Biology* 854:487-493, Springer New York, United States (Oct. 2015).

Lorach, H., et al., "Long-term Rescue of Photoreceptors in a Rodent Model of Retinitis Pigmentosa Associated with MERTK Mutation," *Sci Rep* 8:11312, 10 pages, Nature Publishing Group, United Kingdom (Jul. 2018).

Ma, G. Z. M., et al., "Polymorphisms in the Receptor Tyrosine Kinase MERTK Gene Are Associated with Multiple Sclerosis Susceptibility," *PLoS One* 6(2):e16964, 6 pages, Public Library of Science, United States (Feb. 2011).

Rothlin, C. V., et al., "TAM receptor signaling in immune homeostasis," *Annual Review of Immunology* 33:355-391, Annual Reviews Inc., United States (Jan. 2015).

Shafit-Zagardo, B., et al., "The role of TAM family receptors and ligands in the nervous system: From development to pathobiology," *Pharmacol Ther* 188:97-117, Elsevier, Netherlands (Mar. 2018).

Shen, K., et al., "Multiple sclerosis risk gene Mertk is required for microglial activation and subsequent remyelination," *Cell Rep* 34(10): 108835, 20 pages, Cell Press, United States (Mar. 2021).

Tondo, G., et al., "TAM Receptor Pathways at the Crossroads of Neuroinflammation and Neurodegeneration," *Disease Markers* 2019(4):2387614, 14 pages, Hindawi Ltd., Egypt (Sep. 2019).

Ubil, E., et al., "Tumor-secreted Pros1 inhibits macrophage M1 polarization to reduce antitumor immune response," *Journal of Clinical Investigation* 128(6):2356-2369, American Society for Clinical Investigation, United States (Apr. 2018).

Verma, A., et al., "Targeting Axl and Mer kinases in cancer," *Mol Cancer Ther* 10(10):1763-1773, American Association for Cancer Research Inc., United States (Sep. 2011).

Weinger, J. G., et al., "Up-regulation of soluble Axl and Mer receptor tyrosine kinases negatively correlates with Gas6 in estab-

(56) References Cited

OTHER PUBLICATIONS lished multiple sclerosis lesions," *Am J Pathol* 175(1):283-293, Elsevier, Netherlands (Jun. 2009).
Zhou, Y., et al., "Blockade of the Phagocytic Receptor MerTK on Tumor-Associated Macrophages Enhances P2X7R-Dependent STING Activation by Tumor-Derived cGAMP," *Immunity* 52(2):357-373, Cell Press, United States (Feb. 2020).

* cited by examiner

ANTI-MERTK ANTIBODIES AND METHODS OF USE THEREOF

CROSS REFERENCE TO RELATED APPLICATIONS

This application claims the benefit of U.S. Provisional Application No. 62/947,855, filed Dec. 13, 2019, U.S. Provisional Application No. 63/016,821, filed Apr. 28, 2020, and U.S. Provisional Application No. 63/121,773, filed Dec. 4, 2020, each of which is herein incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 4503_0100003_SeqListing_ST25.TXT, date recorded: Dec. 11, 2020, size: 477,412 bytes).

FIELD OF THE PRESENT DISCLOSURE

The present disclosure relates to anti-MerTK antibodies and uses (e.g., therapeutic uses) of such antibodies.

BACKGROUND OF THE PRESENT DISCLOSURE

Mer Tyrosine Kinase (MerTK) belongs to the TAM (Tyro3, Axl, and MerTK) family of receptor tyrosine kinases. MerTK is a single-pass type 1 transmembrane protein with an extracellular domain having two immunoglobulin (Ig)-like and two fibronectin (FN) type III motifs (Graham et al, 2014, Nat Rev Cancer, 14:769-785; Rothlin et al, 2015, Annu Rev Immunol, 33:355-391).

Several ligands of MerTK have been identified, including Protein S (ProS or ProS1), Growth arrest specific gene 6 (Gas6), Tubby, Tubby-like protein 1 (TULP-1), and Galectin-3. MerTK transduces signals from the extracellular space via activation following ligand binding, leading to MerTK tyrosine auto-phosphorylation (Cummings et al, 2013, Clin Cancer Res, 19:5275-5280; Verma et al, 2011, Mol Cancer Ther, 10:1763-1773) and subsequent ERK and AKT-associated signal transduction.

MerTK regulates various physiological processes including cell survival, migration, and differentiation. MerTK ligands ProS and Gas6 contribute to several oncogenic processes, such as cell survival, invasion, migration, chemoresistance, and metastasis, in which their expression often correlates with poor clinical outcomes. Additionally, MerTK is implicated in numerous cancers, and MerTK or ProS deficiency is associated with anti-tumor effects (Cook et al, 2013, J Clin Invest, 123:3231-3242; Ubil et al, 2018, J Clin Invest, 128:2356-2369; Huey et al, 2016, Cancers, 8:101). However, MerTK is also expressed on retinal pigment epithelial cells and plays a critical role in clearing shed photoreceptor outer segment in the eye; loss of function mutations in MerTK result in retinitis pigmentosa and other retinal dystrophies (see, e.g. Al-khersan et al, Graefes Arch Clim Exp Ophthalmol, 2017, 255:1613-1619; Lorach et al, Nature Scientific Reports, 2018, 8:11312; Audo et al, Human Mutation, Wiley, 2018, 39:997-913; LaVail et al, Adv Exp Med Biol, 2016, 854:487-493).

MerTK plays an essential role in phagocytosis of apoptotic cells (efferocytosis) by phagocytic cells, leading to M2-like macrophage polarization, production of anti-inflammatory cytokines, and promoting an immunosuppressive tumor microenvironment. Reducing efferocytosis by phagocytic cells increases M1-like macrophage polarization, leading to the production of pro-inflammatory cytokines and an immune-active milieu. Modulating efferocytosis can provide an effective means for anti-tumor activity.

Anti-MerTK antibodies have been previously described in, e.g., International Patent Application Publication Nos: WO2020/214995, WO2020/076799, WO2020/106461, WO2020/176497, WO2019/084307, WO2019/005756, WO2016/106221, WO2016/001830, WO2009/062112, and WO2006/058202; and in, e.g., Dayoub and Brekken, 2020, Cell Communications and Signaling, 18:29; Zhou et al, 2020, Immunity, 52:1-17; Kedage et al, 2020, MABS, 12:e1685832; Cummings et al, 2014, Oncotarget, 5:10434-10445.

There is a need for novel therapeutic anti-MerTK antibodies that are effective at treating conditions such as cancer. The present disclosure meets this need by providing anti-MerTK antibodies effective at mediating anti-tumor immunity, reducing efferocytosis, and promoting M1-like macrophage polarization.

All references cited herein, including patent applications and publications, are hereby incorporated by reference in their entirety.

SUMMARY OF THE PRESENT DISCLOSURE

The present disclosure is generally directed to anti-Mer Tyrosine Kinase (MerTK) antibodies and methods of using such antibodies. The methods provided herein find use in treating an individual having cancer. In some embodiments, the present disclosure provides a method for treating an individual having cancer, the method including administering to the individual in need thereof a therapeutically effective amount of an anti-MerTK antibody.

In one aspect, the present disclosure relates to an isolated anti-MerTK antibody that binds to a MerTK protein, wherein the antibody comprises a heavy chain variable region and a light chain variable region, wherein the heavy chain variable region comprises: a) an HVR-H1 comprising the amino acid sequence of SEQ ID NO:83; b) an HVR-H2 comprising an amino acid sequence selected from the group consisting of SEQ ID NOs: 329, 330, 331, 332, and 333; and c) an HVR-H3 comprising an amino acid sequence selected from the group consisting of SEQ ID NOs: 138, 334, 335, 336, 337, 338, and 339; and wherein the light chain variable region comprises: d) an HVR-L1 comprising an amino acid sequence selected from the group consisting of SEQ ID NOs: 158, 340, 341, 342, 343, and 344; e) an HVR-L2 comprising the amino acid sequence of SEQ ID NO:187; and f) an HVR-L3 comprising the amino acid sequence of SEQ ID NO:210.

In one aspect, the present disclosure relates to an isolated anti-MerTK antibody that binds to a MerTK protein, wherein the antibody comprises: (a) HVR-H1 comprising the amino acid sequence of SEQ ID NO:83; (b) HVR-H2 comprising the amino acid sequence of SEQ ID NO:99; (c) HVR-H3 comprising the amino acid sequence of SEQ ID NO:138; (d) HVR-L1 comprising the amino acid sequence of SEQ ID NO:158; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO:334; (d) HVR-L1 comprising the amino acid sequence of SEQ ID NO:158; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:330; (c) HVR-H3 comprising the amino acid sequence of SEQ ID NO:138; (d) HVR-L1 comprising the amino acid sequence of SEQ ID NO:158; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO:138; (d) HVR-L1 comprising the amino acid sequence of SEQ ID NO:340; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO:138; (d) HVR-L1 comprising the amino acid sequence of SEQ ID NO:341; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO:335; (d) HVR-L1 comprising the amino acid sequence of SEQ ID NO:341; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:331; (c) HVR-H3 comprising the amino acid sequence of SEQ ID NO:138; (d) HVR-L1 comprising the amino acid sequence of SEQ ID NO:341; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO:138; (d) HVR-L1 comprising the amino acid sequence of SEQ ID NO:342; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO:336; (d) HVR-L1 comprising the amino acid sequence of SEQ ID NO:341; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO:337; (d) HVR-L1 comprising the amino acid sequence of SEQ ID NO:343; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:332; (c) HVR-H3 comprising the amino acid sequence of SEQ ID NO:338; (d) HVR-L1 comprising the amino acid sequence of SEQ ID NO:341; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:333; (c) HVR-H3 comprising the amino acid sequence of SEQ ID NO:334; (d) HVR-L1 comprising the amino acid sequence of SEQ ID NO:158; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:332; (c) HVR-H3 comprising the amino acid sequence of SEQ ID NO:336; (d) HVR-L1 comprising the amino acid sequence of SEQ ID NO:341; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO:339; (d) HVR-L1 comprising the amino acid sequence of SEQ ID NO:344; (e) HVR-L2 comprising the amino acid sequence of SEQ ID NO:187; and (f) HVR-L3 comprising the amino acid sequence of SEQ ID NO:210; or (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO:138; (d) HVR-L1 comprising the amino acid sequence of SEQ ID NO:158; (e) HVR-L2 comprising the amino acid sequence of SEQ ID NO:187; and (f) HVR-L3 comprising the amino acid sequence of SEQ ID NO:210.

In one aspect, the present disclosure relates to an isolated anti-MerTK antibody that binds to a MerTK protein, wherein the antibody comprises a heavy chain variable domain (VH) and a light chain variable domain (VL), wherein the VH and VL are selected from the group consisting of: VH comprising the amino acid sequence of SEQ ID NO:19 and VL comprising the amino acid sequence of SEQ ID NO:54; VH comprising the amino acid sequence of SEQ ID NO:234 and VL comprising the amino acid sequence of SEQ ID NO:247; VH comprising the amino acid sequence of SEQ ID NO:235 and VL comprising the amino acid sequence of SEQ ID NO:247; VH comprising the amino acid sequence of SEQ ID NO:236 and VL comprising the amino acid sequence of SEQ ID NO:248; VH comprising the amino acid sequence of SEQ ID NO:236 and VL comprising the amino acid sequence of SEQ ID NO:249; VH comprising the amino acid sequence of SEQ ID NO:237 and VL comprising the amino acid sequence of SEQ ID NO:249; VH comprising the amino acid sequence of SEQ ID NO:238 and VL comprising the amino acid sequence of SEQ ID NO:249; VH comprising the amino acid sequence of SEQ ID NO:239 and VL comprising the amino acid sequence of SEQ ID NO:250; VH comprising the amino acid sequence of SEQ ID NO:240 and VL comprising the amino acid sequence of SEQ ID NO:251; VH comprising the amino acid sequence of SEQ ID NO:241 and VL comprising the amino acid sequence of SEQ ID NO:252; VH comprising the amino acid sequence of SEQ ID NO:242 and VL comprising the amino acid sequence of SEQ ID NO:249; VH comprising the amino acid sequence of SEQ ID NO:243 and VL comprising the amino acid sequence of SEQ ID NO:247; VH comprising the amino acid sequence of SEQ ID NO:244 and VL comprising the amino acid sequence of SEQ ID NO:251; VH comprising the amino acid sequence of SEQ ID NO:245 and VL comprising the amino acid sequence of SEQ ID NO:253; VH comprising the amino acid sequence of SEQ ID NO:246 and VL comprising the amino acid sequence of SEQ ID NO:247; and VH comprising the amino acid sequence of SEQ ID NO:246 and VL comprising the amino acid sequence of SEQ ID NO:254.

In one aspect, the present disclosure relates to an isolated anti-MerTK antibody that binds to a MerTK protein, wherein the antibody comprises a heavy chain variable region and a light chain variable region, wherein the heavy chain variable region comprises: a) an HVR-H1 comprising the amino acid sequence of SEQ ID NO:84; b) an HVR-H2 comprising an amino acid sequence selected from the group consisting of SEQ ID NOs: 99 and 329; and c) an HVR-H3 comprising the amino acid sequence of SEQ ID NO: 139; and wherein the light chain variable region comprises: d) an HVR-L1 comprising an amino acid sequence selected from the group consisting of SEQ ID NOs: 169 and 345; e) an HVR-L2 comprising the amino acid sequence of SEQ ID NO:195; and f) an HVR-L3 comprising the amino acid sequence of SEQ ID NO:219.

In one aspect, the present disclosure relates to an isolated anti-MerTK antibody that binds to a MerTK protein, wherein the antibody comprises (a) HVR-H1 comprising the amino acid sequence of SEQ ID NO:84; (b) HVR-H2 comprising the amino acid sequence of SEQ ID NO:329; (c) HVR-H3 comprising the amino acid sequence of SEQ ID NO:139; (d) HVR-L1 comprising the amino acid sequence of SEQ ID NO:169; (e) HVR-L2 comprising the amino acid sequence of SEQ ID NO:195; and (f) HVR-L3 comprising the amino acid sequence of SEQ ID NO:219; or (a) HVR-H1 comprising the amino acid sequence of SEQ ID NO:84; (b) HVR-H2 comprising the amino acid sequence of SEQ ID NO:99; (c) HVR-H3 comprising the amino acid sequence of SEQ ID NO:139; (d) HVR-L1 comprising the amino acid sequence of SEQ ID NO:345; (e) HVR-L2 comprising the amino acid sequence of SEQ ID NO:195; and (f) HVR-L3 comprising the amino acid sequence of SEQ ID NO:219.

In one aspect, the present disclosure relates to an isolated anti-MerTK antibody that binds to a MerTK protein, wherein the antibody comprises a heavy chain variable domain (VH) and a light chain variable domain (VL), wherein the VH and VL are selected from the group consisting of: VH comprising the amino acid sequence of SEQ ID NO:255 and VL comprising the amino acid sequence of SEQ ID NO:257; and VH comprising the amino acid sequence of SEQ ID NO:256 and VL comprising the amino acid sequence of SEQ ID NO:258.

In one aspect, the present disclosure relates to an isolated anti-MerTK antibody that binds to a MerTK protein, wherein the antibody comprises a heavy chain variable region and a light chain variable region, wherein the heavy chain variable region comprises: a) an HVR-H1 comprising an amino acid sequence selected from the group consisting of SEQ ID NOs:95, 346, and 347; b) an HVR-H2 comprising an amino acid sequence selected from the group consisting of SEQ ID NOs: 119, 348, 349, 350, 351, 352, 353, and 354; and c) an HVR-H3 comprising an amino acid sequence selected from the group consisting of SEQ ID NOs: 151, 355, and 356; and wherein the light chain variable region comprises: d) an HVR-L1 comprising an amino acid sequence selected from the group consisting of SEQ ID NOs: 181, 341, 357, and 358; e) an HVR-L2 comprising an amino acid sequence selected from the group consisting of SEQ ID NOs:187 and 359; and 0 an HVR-L3 comprising an amino acid sequence selected from the group consisting of SEQ ID NOs:208, 360, 361, and 362.

In one aspect, the present disclosure relates to an isolated anti-MerTK antibody that binds to a MerTK protein, wherein the antibody comprises (a) HVR-H1 comprising the amino acid sequence of SEQ ID NO:95; (b) HVR-H2 comprising the amino acid sequence of SEQ ID NO:119; (c) HVR-H3 comprising the amino acid sequence of SEQ ID NO:151; (d) HVR-L1 comprising the amino acid sequence of SEQ ID NO:181; (e) HVR-L2 comprising the amino acid sequence of SEQ ID NO:187; and (f) HVR-L3 comprising the amino acid sequence of SEQ ID NO:208; (a) HVR-H1 comprising the amino acid sequence of SEQ ID NO:346; (b) HVR-H2 comprising the amino acid sequence of SEQ ID NO:348; (c) HVR-H3 comprising the amino acid sequence of SEQ ID NO:355; (d) HVR-L1 comprising the amino acid sequence of SEQ ID NO:341; (e) HVR-L2 comprising the amino acid sequence of SEQ ID NO:187; and (f) HVR-L3 comprising the amino acid sequence of SEQ ID NO:360; (a) HVR-H1 comprising the amino acid sequence of SEQ ID NO:95; (b) HVR-H2 comprising the amino acid sequence of SEQ ID NO:119; (c) HVR-H3 comprising the amino acid sequence of SEQ ID NO:355; (d) HVR-L1 comprising the amino acid sequence of SEQ ID NO:341; (e) HVR-L2 comprising the amino acid sequence of SEQ ID NO:187; and (f) HVR-L3 comprising the amino acid sequence of SEQ ID NO:361; (a) HVR-H1 comprising the amino acid sequence of SEQ ID NO:95; (b) HVR-H2 comprising the amino acid sequence of SEQ ID NO:349; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:187; and (0 HVR-L3 comprising the amino acid sequence of SEQ ID NO:362; (a) HVR-H1 comprising the amino acid sequence of SEQ ID NO:95; (b) HVR-H2 comprising the amino acid sequence of SEQ ID NO:119; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:359; and (f) HVR-L3 comprising the amino acid sequence of SEQ ID NO:362; (a) HVR-H1 comprising the amino acid sequence of SEQ ID NO:346; (b) HVR-H2 comprising the amino acid sequence of SEQ ID NO:119; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:359; and (f) HVR-L3 comprising the amino acid sequence of SEQ ID NO:362; (a) HVR-H1 comprising the amino acid sequence of SEQ ID NO:95; (b) HVR-H2 comprising the amino acid sequence of SEQ ID NO:350 (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:359; and (f) HVR-L3 comprising the amino acid sequence of SEQ ID NO:362; (a) HVR-H1 comprising the amino acid sequence of SEQ ID NO:347; (b) HVR-H2 comprising the amino acid sequence of SEQ ID NO:119; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:359; and (f) HVR-L3 comprising the amino acid sequence of SEQ ID NO:362; (a) HVR-H1 comprising the amino acid sequence of SEQ ID NO:95; (b) HVR-H2 comprising the amino acid sequence of SEQ ID NO:119; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:187; and (f) HVR-L3 comprising the amino acid sequence of SEQ ID NO:362; (a) HVR-H1 comprising the amino acid sequence of SEQ ID NO:95; (b) HVR-H2 comprising the amino acid sequence of SEQ ID NO:352; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:187; and (f) HVR-L3 comprising the amino acid sequence of SEQ ID NO:362; (a) HVR-H1 comprising the amino acid sequence of SEQ ID NO:95; (b) HVR-H2 comprising the amino acid sequence of SEQ ID NO:353; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:359; and (f) HVR-L3 comprising the amino acid sequence of SEQ ID NO:362; (a) HVR-H1 comprising the amino acid sequence of SEQ ID NO:346; (b) HVR-H2 comprising the amino acid sequence of SEQ ID NO:354; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:359; and (f) HVR-L3 comprising the amino acid sequence of SEQ ID NO:363; (a) HVR-H1 comprising the amino acid sequence of SEQ ID NO:346; (b) HVR-H2 comprising the amino acid sequence of SEQ ID NO:348; (c) HVR-H3 comprising the amino acid sequence of SEQ ID NO:356; (d) HVR-L1 comprising the amino acid sequence of SEQ ID NO:357; (e) HVR-L2 comprising the amino acid sequence of SEQ ID NO:359; and (f) HVR-L3 comprising the amino acid sequence of SEQ ID NO:362; (a) HVR-H1 comprising the amino acid sequence of SEQ ID NO:346; (b) HVR-H2 comprising the amino acid sequence of SEQ ID NO:354; (c) HVR-H3 comprising the amino acid sequence of SEQ ID NO:356; (d) HVR-L1 comprising the amino acid sequence of SEQ ID NO:358; (e) HVR-L2 comprising the amino acid sequence of SEQ ID NO:187; and (f) HVR-L3 comprising the amino acid sequence of SEQ ID NO:362; or (a) HVR-H1 comprising the amino acid sequence of SEQ ID NO:95; (b) HVR-H2 comprising the amino acid sequence of SEQ ID NO:348; (c) HVR-H3 comprising the amino acid sequence of SEQ ID NO:151; (d) HVR-L1 comprising the amino acid sequence of SEQ ID NO:181; (e) HVR-L2 comprising the amino acid sequence of SEQ ID NO:187; and (f) HVR-L3 comprising the amino acid sequence of SEQ ID NO:208.

In one aspect, the present disclosure relates to an isolated anti-MerTK antibody that binds to a MerTK protein, wherein the antibody comprises a heavy chain variable domain (VH) and a light chain variable domain (VL), wherein the VH and VL are selected from the group consisting of: VH comprising the amino acid sequence of SEQ ID NO:33 and VL comprising the amino acid sequence of SEQ ID NO:68; VH comprising the amino acid sequence of SEQ ID NO:259 and VL comprising the amino acid sequence of SEQ ID NO:274; VH comprising the amino acid sequence of SEQ ID NO:260 and VL comprising the amino acid sequence of SEQ ID NO:275; VH comprising the amino acid sequence of SEQ ID NO:261 and VL comprising the amino acid sequence of SEQ ID NO:276; VH comprising the amino acid sequence of SEQ ID NO:262 and VL comprising the amino acid sequence of SEQ ID NO:277; VH comprising the amino acid sequence of SEQ ID NO:263 and VL comprising the amino acid sequence of SEQ ID NO:277; VH comprising the amino acid sequence of SEQ ID NO:264 and VL comprising the amino acid sequence of SEQ ID NO:277; VH comprising the amino acid sequence of SEQ ID NO:265 and VL comprising the amino acid sequence of SEQ ID NO:277; VH comprising the amino acid sequence of SEQ ID NO:266 and VL comprising the amino acid sequence of SEQ ID NO:277; VH comprising the amino acid sequence of SEQ ID NO:267 and VL comprising the amino acid sequence of SEQ ID NO:278; VH comprising the amino acid sequence of SEQ ID NO:268 and VL comprising the amino acid sequence of SEQ ID NO:279; VH comprising the amino acid sequence of SEQ ID NO:269 and VL comprising the amino acid sequence of SEQ ID NO:279; VH comprising the amino acid sequence of SEQ ID NO:264 and VL comprising the amino acid sequence of SEQ ID NO:280; VH comprising the amino acid sequence of SEQ ID NO:270 and VL comprising the amino acid sequence of SEQ ID NO:281; VH comprising the amino acid sequence of SEQ ID NO:265 and VL comprising the amino acid sequence of SEQ ID NO:282; VH comprising the amino acid sequence of SEQ ID NO:264 and VL comprising the amino acid sequence of SEQ ID NO:283; VH comprising the amino acid sequence of SEQ ID NO:271 and VL comprising the amino acid sequence of SEQ ID NO:284; VH comprising the amino acid sequence of SEQ ID NO:272 and VL comprising the amino acid sequence of SEQ ID NO:285; VH comprising the amino acid sequence of SEQ ID NO:271 and VL comprising the amino acid sequence of SEQ ID NO:286; VH comprising the amino acid sequence of SEQ ID NO:273 and VL comprising the amino acid sequence of SEQ ID NO:287; VH comprising the amino acid sequence of SEQ ID NO:273 and VL comprising the amino acid sequence of SEQ ID NO:288; and VH comprising the amino acid sequence of SEQ ID NO:273 and VL comprising the amino acid sequence of SEQ ID NO:289.

In one aspect, the present disclosure relates to an isolated anti-MerTK antibody that binds to a MerTK protein, wherein the antibody comprises a heavy chain variable region and a light chain variable region, wherein the heavy chain variable region comprises: a) an HVR-H1 comprising the amino acid sequence of SEQ ID NO:90; b) an HVR-H2 comprising an amino acid sequence selected from the group consisting of SEQ ID NOs: 122, 364, 365, 366, 367, and 368; and c) an HVR-H3 comprising an amino acid sequence selected from the group consisting of SEQ ID NOs: 155, 373, 374, and 375; and wherein the light chain variable region comprises: d) an HVR-L1 comprising an amino acid sequence selected from the group consisting of SEQ ID NOs: 184, 376, 377, 378, 379, 380, 381, 382, 383, 384, 385, 386, and 387; e) an HVR-L2 comprising an amino acid sequence selected from the group consisting of SEQ ID NOs:203, 388, 389, 390, and 391; and f) an HVR-L3 comprising an amino acid sequence selected from the group consisting of SEQ ID NOs:231, 392, 393, and 394.

In one aspect, the present disclosure relates to an isolated anti-MerTK antibody that binds to a MerTK protein, wherein the antibody comprises (a) HVR-H1 comprising the amino acid sequence of SEQ ID NO:90; (b) HVR-H2 comprising the amino acid sequence of SEQ ID NO:122; (c) HVR-H3 comprising the amino acid sequence of SEQ ID NO:155; (d) HVR-L1 comprising the amino acid sequence of SEQ ID NO:184; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:364; (c) HVR-H3 comprising the amino acid sequence of SEQ ID NO:373; (d) HVR-L1 comprising the amino acid sequence of SEQ ID NO:376; (e) HVR-L2 comprising the amino acid sequence of SEQ ID NO:388; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:364; (c) HVR-H3 comprising the amino acid sequence of SEQ ID NO:155; (d) HVR-L1 comprising the amino acid sequence of SEQ ID NO:377; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:364; (c) HVR-H3 comprising the amino acid sequence of SEQ ID NO:374; (d) HVR-L1 comprising the amino acid sequence of SEQ ID NO:378; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:95; (b) HVR-H2 comprising the amino acid sequence of SEQ ID NO:119; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:359; and (f) HVR-L3 comprising the amino acid sequence of SEQ ID NO:362; (a) HVR-H1 comprising the amino acid sequence of SEQ ID NO:90; (b) HVR-H2 comprising the amino acid sequence of SEQ ID NO:365; (c) HVR-H3 comprising the amino acid sequence of SEQ ID NO:155; (d) HVR-L1 comprising the amino acid sequence of SEQ ID NO:276; (e) HVR-L2 comprising the amino acid sequence of SEQ ID NO:203; and (f) HVR-L3 comprising the amino acid sequence of SEQ ID NO:392; (a) HVR-H1 comprising the amino acid sequence of SEQ ID NO:90; (b) HVR-H2 comprising the amino acid sequence of SEQ ID NO:364; (c) HVR-H3 comprising the amino acid sequence of SEQ ID NO:155; (d) HVR-L1 comprising the amino acid sequence of SEQ ID NO:376; (e) HVR-L2 comprising the amino acid sequence of SEQ ID NO:389; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:364; (c) HVR-H3 comprising the amino acid sequence of SEQ ID NO:155; (d) HVR-L1 comprising the amino acid sequence of SEQ ID NO:379; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:366; (c) HVR-H3 comprising the amino acid sequence of SEQ ID NO:155; (d) HVR-L1 comprising the amino acid sequence of SEQ ID NO:380; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:364; (c) HVR-H3 comprising the amino acid sequence of SEQ ID NO:373; (d) HVR-L1 comprising the amino acid sequence of SEQ ID NO:381; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:367; (c) HVR-H3 comprising the amino acid sequence of SEQ ID NO:155; (d) HVR-L1 comprising the amino acid sequence of SEQ ID NO:382; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO:155; (d) HVR-L1 comprising the amino acid sequence of SEQ ID NO:383; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:364; (c) HVR-H3 comprising the amino acid sequence of SEQ ID NO:374; (d) HVR-L1 comprising the amino acid sequence of SEQ ID NO:384; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO:155; (d) HVR-L1 comprising the amino acid sequence of SEQ ID NO:376; (e) HVR-L2 comprising the amino acid sequence of SEQ ID NO:203; and (f) HVR-L3 comprising the amino acid sequence of SEQ ID NO:393; (a) HVR-H1 comprising the amino acid sequence of SEQ ID NO:90; (b) HVR-H2 comprising the amino acid sequence of SEQ ID NO:364; (c) HVR-H3 comprising the amino acid sequence of SEQ ID NO:155; (d) HVR-L1 comprising the amino acid sequence of SEQ ID NO:378; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO:155; (d) HVR-L1 comprising the amino acid sequence of SEQ ID NO:376; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:369; (c) HVR-H3 comprising the amino acid sequence of SEQ ID NO:155; (d) HVR-L1 comprising the amino acid sequence of SEQ ID NO:378; (e) HVR-L2 comprising the amino acid sequence of SEQ ID NO:203; and (f) HVR-L3 comprising the amino acid sequence of SEQ ID NO:394; (a) HVR-H1 comprising the amino acid sequence of SEQ ID NO:90; (b) HVR-H2 comprising the amino acid sequence of SEQ ID NO:370; (c) HVR-H3 comprising the amino acid sequence of SEQ ID NO:155; (d) HVR-L1 comprising the amino acid sequence of SEQ ID NO:378; (e) HVR-L2 comprising the amino acid sequence of SEQ ID NO:203; and (f) HVR-L3 comprising the amino acid sequence of SEQ ID NO:394; (a) HVR-H1 comprising the amino acid sequence of SEQ ID NO:90; (b) HVR-H2 comprising the amino acid sequence of SEQ ID NO:371; (c) HVR-H3 comprising the amino acid sequence of SEQ ID NO:155; (d) HVR-L1 comprising the amino acid sequence of SEQ ID NO:178; (e) HVR-L2 comprising the amino acid sequence of SEQ ID NO:203; and (f) HVR-L3 comprising the amino acid sequence of SEQ ID NO:394; (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO:155; (d) HVR-L1 comprising the amino acid sequence of SEQ ID NO:385; (e) HVR-L2 comprising the amino acid sequence of SEQ ID NO:203; and (f) HVR-L3 comprising the amino acid sequence of SEQ ID NO:394; (a) HVR-H1 comprising the amino acid sequence of SEQ ID NO:90; (b) HVR-H2 comprising the amino acid sequence of SEQ ID NO:368; (c)

HVR-H3 comprising the amino acid sequence of SEQ ID NO:155; (d) HVR-L1 comprising the amino acid sequence of SEQ ID NO:378; (e) HVR-L2 comprising the amino acid sequence of SEQ ID NO:203; and (f) HVR-L3 comprising the amino acid sequence of SEQ ID NO:395; (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO:155; (d) HVR-L1 comprising the amino acid sequence of SEQ ID NO:378; (e) HVR-L2 comprising the amino acid sequence of SEQ ID NO:390; and (f) HVR-L3 comprising the amino acid sequence of SEQ ID NO:394; (a) HVR-H1 comprising the amino acid sequence of SEQ ID NO:90; (b) HVR-H2 comprising the amino acid sequence of SEQ ID NO:372; (c) HVR-H3 comprising the amino acid sequence of SEQ ID NO:155; (d) HVR-L1 comprising the amino acid sequence of SEQ ID NO:378; (e) HVR-L2 comprising the amino acid sequence of SEQ ID NO:391; and (f) HVR-L3 comprising the amino acid sequence of SEQ ID NO:394; (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO:375; (d) HVR-L1 comprising the amino acid sequence of SEQ ID NO:386; (e) HVR-L2 comprising the amino acid sequence of SEQ ID NO:203; and (f) HVR-L3 comprising the amino acid sequence of SEQ ID NO:394; or (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO:155; (d) HVR-L1 comprising the amino acid sequence of SEQ ID NO:387; (e) HVR-L2 comprising the amino acid sequence of SEQ ID NO:203; and (f) HVR-L3 comprising the amino acid sequence of SEQ ID NO:394.

In one aspect, the present disclosure relates to an isolated anti-MerTK antibody that binds to a MerTK protein, wherein the antibody comprises a heavy chain variable domain (VH) and a light chain variable domain (VL), wherein the VH and VL are selected from the group consisting of: VH comprising the amino acid sequence of SEQ ID NO:37 and VL comprising the amino acid sequence of SEQ ID NO:72; VH comprising the amino acid sequence of SEQ ID NO:290 and VL comprising the amino acid sequence of SEQ ID NO:309; VH comprising the amino acid sequence of SEQ ID NO:291 and VL comprising the amino acid sequence of SEQ ID NO:310; VH comprising the amino acid sequence of SEQ ID NO:292 and VL comprising the amino acid sequence of SEQ ID NO:311; VH comprising the amino acid sequence of SEQ ID NO:293 and VL comprising the amino acid sequence of SEQ ID NO:312; VH comprising the amino acid sequence of SEQ ID NO:294 and VL comprising the amino acid sequence of SEQ ID NO:313; VH comprising the amino acid sequence of SEQ ID NO:295 and VL comprising the amino acid sequence of SEQ ID NO:314; VH comprising the amino acid sequence of SEQ ID NO:296 and VL comprising the amino acid sequence of SEQ ID NO:315; VH comprising the amino acid sequence of SEQ ID NO:290 and VL comprising the amino acid sequence of SEQ ID NO:316; VH comprising the amino acid sequence of SEQ ID NO:297 and VL comprising the amino acid sequence of SEQ ID NO:317; VH comprising the amino acid sequence of SEQ ID NO:298 and VL comprising the amino acid sequence of SEQ ID NO:318; VH comprising the amino acid sequence of SEQ ID NO:292 and VL comprising the amino acid sequence of SEQ ID NO:319; VH comprising the amino acid sequence of SEQ ID NO:299 and VL comprising the amino acid sequence of SEQ ID NO:320; VH comprising the amino acid sequence of SEQ ID NO:300 and VL comprising the amino acid sequence of SEQ ID NO:311; VH comprising the amino acid sequence of SEQ ID NO:301 and VL comprising the amino acid sequence of SEQ ID NO:321; VH comprising the amino acid sequence of SEQ ID NO:302 and VL comprising the amino acid sequence of SEQ ID NO:322; VH comprising the amino acid sequence of SEQ ID NO:303 and VL comprising the amino acid sequence of SEQ ID NO:311; VH comprising the amino acid sequence of SEQ ID NO:304 and VL comprising the amino acid sequence of SEQ ID NO:322; VH comprising the amino acid sequence of SEQ ID NO:305 and VL comprising the amino acid sequence of SEQ ID NO:322; VH comprising the amino acid sequence of SEQ ID NO:301 and VL comprising the amino acid sequence of SEQ ID NO:323; VH comprising the amino acid sequence of SEQ ID NO:301 and VL comprising the amino acid sequence of SEQ ID NO:324; VH comprising the amino acid sequence of SEQ ID NO:301 and VL comprising the amino acid sequence of SEQ ID NO:325; VH comprising the amino acid sequence of SEQ ID NO:306 and VL comprising the amino acid sequence of SEQ ID NO:326; VH comprising the amino acid sequence of SEQ ID NO:307 and VL comprising the amino acid sequence of SEQ ID NO:327; and VH comprising the amino acid sequence of SEQ ID NO:308 and VL comprising the amino acid sequence of SEQ ID NO:328.

In one aspect, the present disclosure relates to an isolated anti-MerTK antibody that binds to a MerTK protein, wherein the antibody includes a heavy chain variable region and a light chain variable region, wherein the heavy chain variable region includes: an HVR-H1 comprising an amino acid sequence selected from the group consisting of SEQ ID NOs:75, 76, 77, 78, 79, 80, 81, 82, 83, 84, 85, 86, 87, 88, 89, 90, 91, 92, 93, 94, 95, 96, 97, and 98; an HVR-H2 comprising an amino acid sequence selected from the group consisting of SEQ ID NOs:99, 100, 101, 102, 103, 104, 105, 106, 107, 108, 109, 110, 111, 112, 113, 114, 115, 116, 117, 118, 119, 120, 121, 122, 123, and 124; and an HVR-H3 comprising an amino acid sequence selected from the group consisting of SEQ ID NOs:125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, and 157; and the light chain variable region includes: an HVR-L1 comprising an amino acid sequence selected from the group consisting of SEQ ID NOs:158, 159, 160, 161, 162, 163, 164, 165, 166, 167, 168, 169, 170, 171, 172, 173, 174, 175, 176, 177, 178, 179, 180, 181, 182, 183, 184, 185, and 186; an HVR-L2 comprising an amino acid sequence selected from the group consisting of SEQ ID NOs:187, 188, 189, 190, 191, 192, 193, 194, 195, 196, 197, 198, 199, 200, 201, 202, 203, 204, and 205; and an HVR-L3 comprising an amino acid sequence selected from the group consisting of SEQ ID NOs:207, 208, 209, 210, 211, 212, 213, 214, 215, 216, 217, 218, 219, 220, 221, 222, 223, 224, 225, 226, 227, 228, 229, 230, 231, 232, and 233.

In one aspect, the present disclosure relates to an isolated anti-MerTK antibody that binds to a MerTK protein, wherein the antibody comprises an HVR-H1, HVR-H2, HVR-H3, HVR-L1, HVR-L2, and HVR-L3 comprising the amino acid sequences of (i) SEQ ID NOs: 75, 99, 125, 158, 187, and 207, respectively; (ii) SEQ ID NOs: 76, 100, 126, 159, 187, and 208, respectively; (iii) SEQ ID NOs: 77, 101, 127, 160, 188, and 209, respectively; (iv) SEQ ID NOs: 75, 99, 128, 158, 187, and 210, respectively; (v) SEQ ID NOs: 78, 102, 129, 161, 189, and 211, respectively; (vi) SEQ ID NOs: 75, 103, 130, 158, 187, and 212, respectively; (vii) SEQ ID NOs: 77, 101, 127, 162, 188, and 209, respectively; (viii) SEQ ID NOs: 75, 99, 131, 163, 187, and 213, respectively; (ix) SEQ ID NOs: 79, 104, 132, 164, 190, and 214, respectively; (x) SEQ ID NOs: 80, 105, 133, 165, 191, and 215, respectively; (xi) SEQ ID NOs: 81, 106, 134, 166, 192, and 216, respectively; (xii) SEQ ID NOs: 82, 107, 135, 167, 193, and 217, respectively; (xiii) SEQ ID NOs: 77, 108, 136, 167, 194, and 209, respectively; (xiv) SEQ ID NOs: 75, 109, 137, 168, 187, and 218, respectively; (xv) SEQ ID NOs: 83, 99, 138, 158, 187, and 210, respectively; (xvi) SEQ ID NOs: 84, 99, 139, 169, 195, and 219, respectively; (xvii) SEQ ID NOs: 85, 99, 140, 170, 196, and 220, respectively; (xviii) SEQ ID NOs: 86, 99, 141, 171, 191, and 221, respectively; (xix) SEQ ID NOs:87, 110, 142, 172, 197, and 222, respectively; (xx) SEQ ID NOs: 88, 99, 143, 173, 191, and 223, respectively; (xxi) SEQ ID NOs: 89, 111, 143, 173, 198, and 221, respectively; (xxii) SEQ ID NOs: 90, 112, 144, 174, 199, and 224, respectively; (xxiii) SEQ ID NOs: 91, 113, 145, 175, 200, and 225, respectively; (xxiv) SEQ ID NOs: 90, 114, 146, 176, 201, and 226, respectively; (xxv) SEQ ID NOs: 92, 115, 147, 177, 195, and 227, respectively; (xxvi) SEQ ID NOs: 93, 116, 148, 178, 188, and 209, respectively; (xxvii) SEQ ID NOs: 94, 117, 149, 179, 195, and 228, respectively; (xxviii) SEQ ID NOs: 95, 118, 150, 180, 187, and 229, respectively; (xxix) SEQ ID NOs: 95, 119, 151, 181, 187, and 208, respectively; (xxx) SEQ ID NOs: 90, 120, 152, 182, 202, and 230, respectively; (xxxi) SEQ ID NOs: 96, 118, 153, 183, 202, and 230, respectively; (xxxii) SEQ ID NOs: 96, 121, 154, 181, 187, and 210, respectively; (xxxiii) SEQ ID NOs: 90, 122, 155, 184, 203, and 231, respectively; (xxxiv) SEQ ID NOs: 90, 122, 155, 184, 203, and 231, respectively; (xxxv) SEQ ID NOs:97, 123, 156, 185, 204, and 232, respectively; or (xxxvi) SEQ ID NOs: 98, 124, 157, 186, 205, and 233, respectively.

In some embodiments that may be combined with any of the embodiments provided herein, an anti-MerTK antibody of the present disclosure is an isolated antibody that binds to a MerTK protein, wherein the antibody comprises the HVR-H1, HVR-H2, HVR-H3, HVR-L1, HVR-L2 and HVR-L3 sequences of MTK-01, MTK-02, MTK-03, MTK-04, MTK-05, MTK-06, MTK-07, MTK-08, MTK-09, MTK-10, MTK-11, MTK-12, MTK-13, MTK-14, MTK-15, MTK-16, MTK-17, MTK-18, MTK-19, MTK-20, MTK-21, MTK-22, MTK-23, MTK-24, MTK-25, MTK-26, MTK-27, MTK-28, MTK-29, MTK-30, MTK-31, MTK-32, MTK-33, MTK-34, MTK-35, or MTK-36 antibody. In some embodiments, the HVRs are the Kabat-defined HVRs, the Chothia-defined HVRs, or the AbM-defined HVRs.

In some embodiments that may be combined with any of the embodiments provided herein, an anti-MerTK antibody of the present disclosure is an isolated antibody that binds to a MerTK protein, wherein the antibody comprises the HVR-H1, HVR-H2, HVR-H3, HVR-L1, HVR-L2 and HVR-L3 sequences of MTK-15.1, MTK-15.2, MTK-15.3, MTK-15.4, MTK-15.5, MTK-15.6, MTK-15.7, MTK-15.8, MTK-15.9, MTK-15.10, MTK-15.11, MTK-15.12, MTK-15.13, MTK-15.14, and MTK-15.15, MTK-16.1 and MTK-16.2, MTK-29.1, MTK-29.2, MTK-29.3, MTK-29.4, MTK-29.5, MTK-29.6, MTK-29.7, MTK-29.8, MTK-29.9, MTK-29.10, MTK-29.11, MTK-29.12, MTK-29.13, MTK-29.14, MTK-29.15, MTK-29.16, MTK-29.17, MTK-29.18, MTK-29.19, MTK-29.20, and MTK-29.21, MTK-33.1, MTK-33.2, MTK-33.3, MTK-33.4, MTK-33.5, MTK-33.6, MTK-33.7, MTK-33.8, MTK-33.9, MTK-33.10, MTK-33.11, MTK-33.12, MTK-33.13, MTK-33.14, MTK-33.15, MTK-33.16, MTK-33.17, MTK-33.18, MTK-33.19, MTK-33.20, MTK-33.21, MTK-33.22, MTK-33.23, or MTK-33.24 antibody. In some embodiments, the HVRs are the Kabat-defined HVRs, the Chothia-defined HVRs, or the AbM-defined HVRs.

In some embodiments that may be combined with any of the embodiments provided herein, an anti-MerTK antibody of the present disclosure is an isolated antibody that binds to a MerTK protein, wherein the antibody includes a heavy chain variable region, wherein the heavy chain variable region includes an amino acid sequence selected from the group consisting of SEQ ID NOs:5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, and 39.

In some embodiments that may be combined with any of the embodiments provided herein, an anti-MerTK antibody of the present disclosure is an isolated antibody that binds to a MerTK protein, wherein the antibody includes a heavy chain variable region, wherein the heavy chain variable region includes an amino acid sequence selected from the group consisting of SEQ ID NOs:234-246, 255, 256, 259-379, and 290-308.

In some embodiments that may be combined with any of the embodiments provided herein, an anti-MerTK antibody of the present disclosure is an isolated antibody that binds to a MerTK protein, wherein the antibody includes a light chain variable region, wherein the light chain variable region includes an amino acid sequence selected from the group consisting of SEQ ID NOs:40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, and 74.

In some embodiments that may be combined with any of the embodiments provided herein, an anti-MerTK antibody of the present disclosure is an isolated antibody that binds to a MerTK protein, wherein the antibody includes a light chain variable region, wherein the light chain variable region includes an amino acid sequence selected from the group consisting of SEQ ID NOs:247-254, 257, 258, 274-289, and 309-328.

In some embodiments that may be combined with any of the embodiments provided herein, an anti-MerTK antibody of the present disclosure is an isolated antibody that binds to a MerTK protein, wherein the antibody includes a heavy chain variable region and a light chain variable region, wherein the heavy chain variable region includes an amino acid sequence selected from SEQ ID NOs:5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, and 39, and the light chain variable region includes an amino acid sequence selected from SEQ ID NOs: 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, and 74.

In some embodiments that may be combined with any of the embodiments provided herein, an anti-MerTK antibody of the present disclosure is an isolated antibody that binds to a MerTK protein, wherein the antibody includes a heavy chain variable region and a light chain variable region, wherein the heavy chain variable region includes an amino acid sequence selected from 234-246, 255, 256, 259-379, and 290-308, and the light chain variable region includes an amino acid sequence selected from SEQ ID NOs: 247-254, 257, 258, 274-289, and 309-328.

In some embodiments that may be combined with any of the embodiments provided herein, an anti-MerTK antibody of the present disclosure is an isolated antibody that binds to a MerTK protein, wherein the antibody a heavy chain variable region and a light chain variable region comprising the amino acid sequences of SEQ ID NOs:5 and 40, respectively; SEQ ID NOs:6 and 41, respectively; SEQ ID NOs:7 and 42, respectively; respectively; SEQ ID NOs:8 and 43, respectively; SEQ ID NOs:9 and 44, respectively; SEQ ID NOs:10 and 45, respectively; SEQ ID NOs:11 and 46, respectively; SEQ ID NOs:12 and 47, respectively; SEQ ID NOs:13 and 48, respectively; SEQ ID NOs:14 and 49, respectively; SEQ ID NOs:15 and 50, respectively; SEQ ID NOs:16 and 51, respectively; SEQ ID NOs:17 and 52, respectively; SEQ ID NOs:18 and 53, respectively; SEQ ID NOs:19 and 54, respectively; SEQ ID NOs:20 and 55, respectively; SEQ ID NOs:21 and 56, respectively; SEQ ID NOs:22 and 57, respectively; SEQ ID NOs:23 and 58, respectively; SEQ ID NOs:24 and 59, respectively; SEQ ID NOs:25 and 60, respectively; SEQ ID NOs:26 and 61, respectively; SEQ ID NOs:27 and 62, respectively; SEQ ID NOs:28 and 63, respectively; SEQ ID NOs:29 and 64, respectively; SEQ ID NOs:30 and 65, respectively; SEQ ID NOs:31 and 66, respectively; SEQ ID NOs:32 and 67, respectively; SEQ ID NOs:33 and 68, respectively; SEQ ID NOs:34 and 69, respectively; SEQ ID NOs:35 and 70, respectively; SEQ ID NOs:36 and 71, respectively; SEQ ID NOs:37 and 72, respectively; SEQ ID NOs:38 and 73, respectively; and SEQ ID NOs:39 and 74, respectively.

In one aspect, the present disclosure relates to an isolated antibody that binds to a MerTK protein, wherein the antibody competitively inhibits binding of one or more of the antibodies of any of the embodiments herein for binding to MerTK.

In another aspect, the present disclosure relates to an isolated antibody that binds to a MerTK protein, wherein the antibody binds essentially the same or an overlapping epitope on MerTK as an antibody of any of the embodiments herein.

In certain embodiments that may be combined with any of the embodiments herein, the MerTK protein is a mammalian protein or a human protein. In certain embodiments that may be combined with any of the embodiments herein, the MerTK protein is a wild-type protein. In certain embodiments that may be combined with any of the embodiments herein, the MerTK protein is a naturally occurring variant. In certain embodiments that may be combined with any of the embodiments herein, an anti-MerTK antibody binds to human MerTK and to cynomolgus monkey MerTK and/or murine MerTK. In certain embodiments that may be combined with any of the embodiments herein, an anti-MerTK antibody binds to human MerTK and murine MerTK, binds to human MerTK and cynomolgus MerTK, or binds to human MerTK, murine MerTK, and cynomolgus MerTK.

In some embodiments that may be combined with any of the embodiments herein, an anti-MerTK antibody of the present disclosure inhibits or reduces binding of one or more ligands to MerTK. In some embodiments that may be combined with any of the embodiments herein, an anti-MerTK antibody of the present disclosure inhibits or reduces binding of ProS to MerTK. In some embodiments that may be combined with any of the embodiments herein, an anti-MerTK antibody of the present disclosure inhibits or reduces binding of ProS to MerTK by at least 20%, by at least 25%, by at least 30%, by at least 40%, by at least 50%, by at least 60%, by at least 70%, by at least 80%, by at least 90%, or by at least 95%. In some embodiments that may be combined with any of the embodiments herein, an anti-MerTK antibody of the present disclosure inhibits or reduces binding of ProS to MerTK with an IC50 value of 0.58 nM to 25.9 nM. %. In some embodiments that may be combined with any of the embodiments herein, an anti-MerTK antibody of the present disclosure inhibits or reduces binding of ProS to MerTK with an IC50 value of 0.58 nM to 1 nM, 1 nM to 2.5 nM, 2.5 nM to 5 nM, 5 nM to 10 nM, or 10 nM to 25 nM.

In some embodiments that may be combined with any of the embodiments herein, an anti-MerTK antibody of the present disclosure inhibits or reduces binding of Gas6 to MerTK. In some embodiments that may be combined with any of the embodiments herein, an anti-MerTK antibody of the present disclosure inhibits or reduces binding of Gas6 to MerTK by at least 20%, by at least 25%, by at least 30%, by at least 40%, by at least 50%, by at least 60%, by at least 70%, by at least 80%, by at least 90%, or by at least 95%. In some embodiments that may be combined with any of the embodiments herein, an anti-MerTK antibody of the present disclosure inhibits or reduces binding of Gas6 to MerTK with an IC50 value of 0.29 nM to 32 nM. In some embodiments that may be combined with any of the embodiments herein, an anti-MerTK antibody of the present disclosure inhibits or reduces binding of Gas6 to MerTK with an IC50 value of 0.29 nM to 1 nM, 1 nM to 5 nM, 5 nM to 10 nM, 10 nM to 25 nM, or 25 nM to 32 nM.

In some embodiments that may be combined with any of the embodiments herein, an anti-MerTK antibody of the present disclosure inhibits or reduces binding of Gas6 to MerTK and inhibits or reduces binding of ProS to MerTK. In some embodiments that may be combined with any of the embodiments herein, an anti-MerTK antibody of the present disclosure inhibits or reduces binding of Gas6 to MerTK and inhibits or reduces binding of ProS to MerTK by at least 20%, by at least 25%, by at least 30%, by at least 40%, by at least 50%, by at least 60%, by at least 70%, by at least 80%, by at least 90%, or by at least 95% and wherein the antibody reduces or inhibits binding of Gas6 to MerTK by at least 20%, by at least 25%, by at least 30%, by at least 40%, by at least 50%, by at least 60%, by at least 70%, by at least 80%, by at least 90%, or by at least 95%. In some embodiments that may be combined with any of the embodiments herein, an anti-MerTK antibody of the present disclosure inhibits or reduces binding of Gas6 to MerTK and inhibits or reduces binding of ProS to MerTK with an IC50 value of 0.58 nM to 25.9 nM and wherein the antibody reduces or inhibits binding of Gas6 to MetTK with an IC50 value of 0.29 nM to 32 nM.

In some embodiments that may be combined with any of the embodiments herein, an anti-MerTK antibody of the present disclosure inhibits or reduces binding of ProS to MerTK and does not inhibit or reduce binding of Gas6 to MerTK.

In some embodiments that may be combined with any of the embodiments herein, an anti-MerTK antibody of the present disclosure does not inhibit or reduce binding of ProS to MerTK and does not inhibit binding of Gas6 to MerTK.

In some embodiments that may be combined with any of the embodiments herein, an anti-MerTK antibody of the present disclosure reduces Gas6-mediated phosphorylation of AKT. In some embodiments that may be combined with any of the embodiments herein, an anti-MerTK antibody of the present disclosure reduces Gas6-mediated phosphorylation of AKT with an IC50 value of 0.019 nM to 7.74 nM. In some embodiments that may be combined with any of the embodiments herein, an anti-MerTK antibody of the present disclosure reduces Gas6-mediated phosphorylation of AKT with an IC50 value of 0.019 nM to 0.25 nM, 0.25 nM to 0.5 nM, 0.5 nM to 1 nM, 1 nM to 2.5 nM, 2.5 nM to 5 nM, or 5 nM to 7.74 nM.

In some embodiments that may be combined with any of the embodiments herein, an anti-MerTK antibody of the present disclosure binds to human MerTK with a binding affinity of 1.4 nM to 81 nM. In some embodiments that may be combined with any of the embodiments herein, an anti-MerTK antibody of the present disclosure binds to human MerTK with a binding affinity of 1.6 nM to 107 nM. In some embodiments that may be combined with any of the embodiments herein, an anti-MerTK antibody of the present disclosure binds to human MerTK with a binding affinity of 30 nM to 186 nM.

In some embodiments that may be combined with any of the embodiments herein, an anti-MerTK antibody of the present disclosure is at least 1.7 times, at least 2.3 times, at least 2.4 times, at least 5 times, at least 7.7 times, or at least 8.5 times more effective at reducing or inhibiting the binding of ProS to MerTK than at reducing or inhibiting the binding of Gas6 to MerTK.

In some embodiments that may be combined with any of the embodiments provided here, an anti-MerTK antibody of the present disclosure decreases or reduces efferocytosis by phagocytic cells (e.g., by at least 50%). In some embodiments that may be combined with any of the embodiments provided here, an anti-MerTK antibody of the present disclosure decreases or reduces efferocytosis by phagocytic cells by at least 60%, by at least 70%, by at least 80%, by at least 90%, or by at least 95%.%). In some embodiments that may be combined with any of the embodiments provided here, an anti-MerTK antibody of the present disclosure decreases or reduces efferocytosis by phagocytic cells with an IC50 value of 0.13 nM to 30 nM. In some embodiments that may be combined with any of the embodiments provided here, an anti-MerTK antibody of the present disclosure decreases or reduces efferocytosis by phagocytic cells with an IC50 value of 0.13 nM to 1 nM, 1 nM to 5 nM, 5 nM to 10 nM, or 10 nM to 30 nM. In some embodiments, the phagocytic cells are macrophages. In some embodiments, the phagocytic cells are tumore-associated macrophages. In some embodiments, the phagocytic cells are dendritic cells.

In some embodiments that may be combined with any of the embodiments provided herein, an anti-MerTK antibody of the present disclosure increases or induces M1-like macrophage polarization. In some embodiments that may be combined with any of the embodiments provided herein, an anti-MerTK antibody of the present disclosure increases production, expression, and/or secretion of pro-inflammatory cytokines. In certain embodiments, the pro-inflammatory cytokines are tumor necrosis factor (TNF), interferon (IFN), or interleukin-12 (IL-12). In certain embodiments, the pro-inflammatory cytokines are chemokine (C-X-C motif) ligand 1 (CXCL-1, KC), monocyte chemoattractant protein-1 (MCP1, CCL2), macrophage inflammatory protein-1-alpha (MIP-1α, CCL3), macrophage inflammatory protein-1-beta (MIP-1β, CCL4), or interleukin-6 (IL-6). In some embodiments that may be combined with any of the embodiments provided herein, an anti-MerTK antibody of the present disclosure increases production, expression, and/or secretion of pro-inflammatory cytokines in vitro. In some embodiments that may be combined with any of the embodiments provided herein, an anti-MerTK antibody of the present disclosure increases production, expression, and/or secretion of pro-inflammatory cytokines in vivo.

In some embodiments that may be combined with any of the embodiments herein, the anti-MerTK antibody of the present disclosure is a monoclonal antibody. In some embodiments that may be combined with any of the embodiments herein, the antibody is a human antibody. In some embodiments that may be combined with any of the embodiments herein, the antibody is a humanized antibody. In some embodiments that may be combined with any of the embodiments herein, the antibody is a bispecific antibody. In some embodiments that may be combined with any of the embodiments herein, the antibody is a multivalent antibody. In some embodiments that may be combined with any of the embodiments herein, the antibody is a chimeric antibody.

In one aspect, the present disclosure relates to an isolated anti-MerTK antibody that binds to a MerTK protein, wherein the antibody is a humanized form of an anti-MerTK antibody provided herein.

In some embodiments that may be combined with any of the embodiments herein, the anti-MerTK antibody of the present disclosure is of the IgG class, the IgM class, or the IgA class. In some embodiments, the antibody is of the IgG class and has an IgG1, IgG2, or IgG4 isotype. In some embodiments, the antibody is of an IgG1 isotype with an Fc amino acid sequence selected from the group consisting of SEQ ID NOs: 396, 397, 398, 399, 400, and 401.

In certain embodiments that may be combined with any of the embodiments herein, the antibody is a full-length antibody. In certain embodiments that may be combined with any of the embodiments herein, the antibody is an antibody fragment. In certain embodiments that may be combined with any of the embodiments herein, the antibody is an antibody fragment that binds to an epitope on human MerTK or a mammalian MerTK protein. In certain embodiments that may be combined with any of the embodiments herein, the antibody fragment is a Fab, Fab', Fab'-SH, F(ab')2, Fv, or scFv fragment.

In another aspect, the present disclosure relates to an isolated nucleic acid including a nucleic acid sequence encoding an anti-MerTK antibody of any of the preceding embodiments. In some embodiments, the present disclosure relates to a vector including the nucleic acid of any of the preceding embodiments. In some embodiments, the present disclosure relates to an isolated host cell including the nucleic acid of any of the preceding embodiments or the vector of any of the preceding embodiments. In some embodiments, the present disclosure relates to an isolated host cell comprising (i) a nucleic acid comprising a nucleic acid sequence encoding the VH of an anti-MerTK antibody of any of the preceding embodiments and (ii) a nucleic acid comprising a nucleic acid sequence encoding the VL of the anti-MerTK antibody.

In another aspect, the present disclosure relates to a method of producing an antibody that binds to human MerTK antibody, including culturing the host cell of any of the preceding embodiments so that the anti-MerTK antibody is produced. In certain embodiments, the method further includes recovering the anti-MerTK antibody produced by the cell.

In another aspect, the present disclosure relates to a pharmaceutical composition including an anti-MerTK antibody of any one of the preceding embodiments and a pharmaceutically acceptable carrier.

In one aspect, the present disclosure relates to a method of treating an individual having cancer, the method comprising administering to an individual in need thereof a therapeutically effective amount of an anti-MerTK antibody of any of the preceding embodiments. In some embodiments, the cancer is colon cancer, ovarian cancer, liver cancer, or endometrial cancer. In some embodiments, the cancer is selected from sarcoma, bladder cancer, breast cancer, colon cancer, endometrial cancer, kidney cancer, renal cancer, leukemia, lung cancer, non-small cell lung cancer, melanoma, lymphoma, pancreatic cancer, prostate cancer, ovarian cancer, stomach cancer, thyroid cancer, cancer of the uterus, liver cancer, cervical cancer, testicular cancer, squamous cell carcinoma, glioma, glioblastoma, adenoma, and neuroblastoma. In some embodiments, the cancer is selected from glioblastoma multiforme, bladder carcinoma, and esophageal carcinoma. In some embodiments, the cancer is triple-negative breast carcinoma. In some embodiments, the cancer may be a primary tumor. In some embodiments, the cancer may be a metastatic tumor at a second site derived from any of the above types of cancer. In some embodiments, an anti-MerTK antibody of the present disclosure is useful for treating cancer in s subject in need thereof, wherein the cancer expresses MerTK. In some embodiments, the administration of an anti-MerTK antibody of the present disclosure which reduces efferocytosis does not lead to a retinal pathology in the individual. In some embodiments, the method further comprises administering an anti-PD-L1 antibody, an anti-PD-L2 antibody, or an anti-PD antibody (e.g., simultaneously or sequentially) to the individual.

In one aspect, the present disclosure relates to a method of detecting MerTK in a sample comprising contacting said sample with an anti-MerTK antibody of any of the preceding embodiments, optionally wherein the method further comprises detecting the binding of the antibody to MerTK in the sample.

It is to be understood that one, some, or all of the properties of the various embodiments described herein may be combined to form other embodiments of the present disclosure. These and other aspects of the disclosure will become apparent to one of skill in the art. These and other aspects of the disclosure are further described by the detailed description that follows.

DETAILED DESCRIPTION OF THE PRESENT DISCLOSURE

Figure 1:
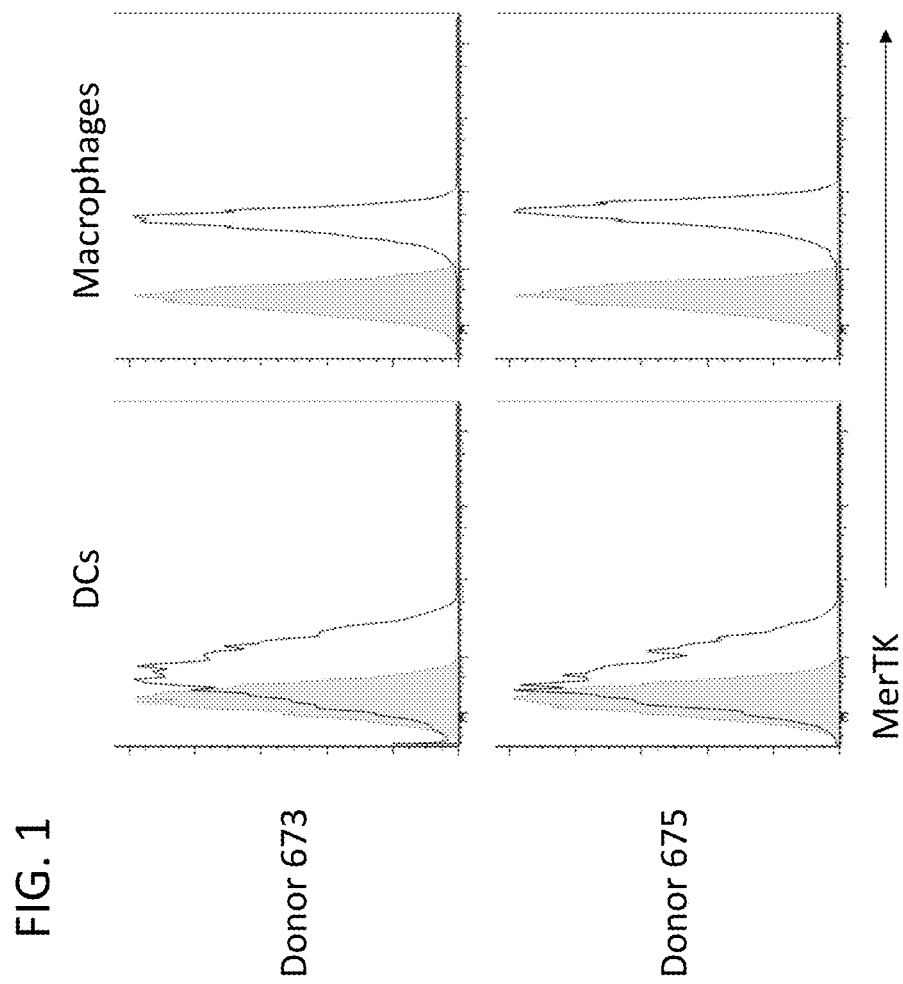
FIG. 1 sets forth data showing FACS analysis of human MerTK expression on dendritic cells (DCs) and macrophages from two human donors.

The present disclosure relates to anti-MerTK antibodies (e.g., monoclonal antibodies); methods of making and using such antibodies; pharmaceutical compositions comprising such antibodies; nucleic acids encoding such antibodies; and host cells comprising nucleic acids encoding such antibodies.

The techniques and procedures described or referenced herein are generally well understood and commonly employed using conventional methodology by those skilled in the art, such as, for example, the widely utilized methodologies such as those described in Sambrook et al. *Molecular Cloning: A Laboratory Manual* 3d edition (2001) Cold Spring Harbor Laboratory Press, Cold Spring Harbor, N.Y.; *Current Protocols in Molecular Biology* (F. M.

Ausubel, et al. eds., (2003); *Monoclonal Antibodies: A Practical Approach* (P. Shepherd and C. Dean, eds., Oxford University Press, 2000).

I. Definitions

The terms "MerTK" or "MerTK polypeptide" or "MerTK protein" are used interchangeably herein refer herein to any native MerTK from any vertebrate source, including mammals such as primates (e.g., humans and cynomolgus monkeys (cynos)) and rodents (e.g., mice and rats), unless otherwise indicated. MerTK is also referred to as c-mer, MER, Proto-oncogene c-Mer, Receptor Tyrosine Kinase MerTK, Tyrosine-protein Kinase Mer, STK Kinase, RP38, and MGC133349. In some embodiments, the term encompasses both wild-type sequences and naturally occurring variant sequences, e.g., splice variants or allelic variants. In some embodiments, the term encompasses "full-length," unprocessed MerTK as well as any form of MerTK that results from processing in the cell. In some embodiments, the MerTK is human MerTK. As used herein, the term "human MerTK" refers to a polypeptide with the amino acid sequence of SEQ ID NO: 1.

The terms "anti-MerTK antibody," an "antibody that binds to MerTK," and "antibody that specifically binds MerTK" refer to an antibody that is capable of binding MerTK with sufficient affinity such that the antibody is useful as a diagnostic and/or therapeutic agent in targeting MerTK. In one embodiment, the extent of binding of an anti-MerTK antibody to an unrelated, non-MerTK polypeptide is less than about 10% of the binding of the antibody to MerTK as measured, e.g., by a radioimmunoassay (RIA). In certain embodiments, an antibody that binds to MerTK has a dissociation constant (KD) of <1 μM, <100 nM, <10 nM, <1 nM, <0.1 nM, <0.01 nM, or <0.001 nM (e.g., $10^{-8}$ M or less, e.g. from $10^{-8}$ M to $10^{-13}$ M, e.g., from $10^{-9}$ M to $10^{-13}$ M). In certain embodiments, an anti-MerTK antibody binds to an epitope of MerTK that is conserved among MerTK from different species.

With regard to the binding of an antibody to a target molecule, the term "specific binding" or "specifically binds" or is "specific for" a particular polypeptide or an epitope on a particular polypeptide target means binding that is measurably different from a non-specific interaction. Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a KD for the target of about any of $10^{-4}$ M or lower, $10^{-5}$ M or lower, $10^{-6}$ M or lower, $10^{-7}$ M or lower, $10^{-8}$ M or lower, $10^{-9}$ M or lower, $10^{-10}$ M or lower, $10^{-11}$ M or lower, $10^{-12}$ M or lower or a KD in the range of $10^{-4}$ M to $10^{-6}$ M or $10^{-6}$ M to $10^{-10}$ M or $10^{-7}$ M to $10^{-9}$ M. As will be appreciated by the skilled artisan, affinity and KD values are inversely related. A high affinity for an antigen is measured by a low KD value. In one embodiment, the term "specific binding" refers to binding where a molecule binds to a particular polypeptide or epitope on a particular polypeptide without substantially binding to any other polypeptide or polypeptide epitope.

The term "immunoglobulin" (Ig) is used interchangeably with "antibody" herein. The term "antibody" herein is used in the broadest sense and specially covers monoclonal antibodies, polyclonal antibodies, multispecific antibodies (e.g., bispecific antibodies) including those formed from at least two intact antibodies, and antigen-binding antibody fragments so long as they exhibit the desired biological activity.

"Native antibodies" are usually heterotetrameric glycoproteins of about 150,000 Daltons, composed of two identical light ("L") chains and two identical heavy ("H") chains. Each light chain is linked to a heavy chain by one covalent disulfide bond, while the number of disulfide linkages varies among the heavy chains of different immunoglobulin isotypes. Each heavy and light chain also has regularly spaced intra-chain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

For the structure and properties of the different classes of antibodies, see, e.g., *Basic and Clinical Immunology*, 8th Ed., Daniel P. Stites, Abba I. Terr and Tristram G. Parslow (eds.), Appleton & Lange, Norwalk, CT, 1994, page 71 and Chapter 6.

The light chain from any vertebrate species can be assigned to one of two clearly distinct types, called kappa ("κ") and lambda ("λ"), based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated alpha ("α"), delta ("δ"), epsilon ("ε"), gamma ("γ"), and mu ("μ"), respectively. The γ and α classes are further divided into subclasses (isotypes) on the basis of relatively minor differences in the CH sequence and function, e.g., humans express the following subclasses: IgG1, IgG2, IgG3, IgG4, IgA1, and IgA2. The subunit structures and three-dimensional configurations of different classes of immunoglobulins are well known and described generally in, for example, Abbas et al., Cellular and Molecular Immunology, $4^{th}$ ed. (W.B. Saunders Co., 2000).

The "variable region" or "variable domain" of an antibody, such as an anti-MerTK antibody of the present disclosure, refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites.

The term "variable" refers to the fact that certain segments of the variable domains differ extensively in sequence among antibodies, such as anti-MerTK antibodies of the present disclosure. The variable domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Immunological Interest*, Fifth Edition, National Institute of Health, Bethesda, MD (1991)). The constant domains are not involved directly in the binding of antibody to an antigen, but exhibit various effector functions, such as participation of the antibody in antibody-dependent-cellular toxicity.

The term "monoclonal antibody" as used herein refers to an antibody, such as a monoclonal anti-MerTK antibody of the present disclosure, obtained from a population of substantially homogeneous antibodies, i.e., the individual antibodies comprising the population are identical except for possible naturally occurring mutations and/or post-translation modifications (e.g., isomerizations, amidations, etc.) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, but not limited to one or more of the following methods, immunization methods of animals including, but not limited to rats, mice, rabbits, guinea pigs, hamsters and/or chickens with one or more of DNA(s), virus-like particles, polypeptide(s), and/or cell(s), the hybridoma methods, B-cell cloning methods, recombinant DNA methods, and technologies for producing human or human-like antibodies in animals that have parts or all of the human immunoglobulin loci or genes encoding human immunoglobulin sequences.

The terms "full-length antibody," "intact antibody" or "whole antibody" are used interchangeably to refer to an antibody, such as an anti-MerTK antibody of the present disclosure, in its substantially intact form, as opposed to an antibody fragment. Specifically, whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" refers to a molecule other than an intact antibody that comprises a portion of an intact antibody that binds the antigen to which the intact antibody binds. Examples of antibody fragments include Fab, Fab', F(ab')$_2$ and Fv fragments; diabodies; linear antibodies (see U.S. Pat. No. 5,641,870, Example 2; Zapata et al., *Protein Eng.* 8(10):1057-1062 (1995)); single-chain antibody molecules and multispecific antibodies formed from antibody fragments.

Papain digestion of antibodies, such as anti-MerTK antibodies of the present disclosure, produces two identical antigen-binding fragments, called "Fab" fragments, and a residual "Fc" fragment, a designation reflecting the ability to crystallize readily. The Fab fragment consists of an entire light chain along with the variable region domain of the heavy chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both heavy chains held together by disulfides. The effector functions of antibodies are determined by sequences in the Fc region, the region which is also recognized by Fc receptors (FcR) found on certain types of cells.

"Functional fragments" of antibodies, such as anti-MerTK antibodies of the present disclosure, comprise a portion of an intact antibody, generally including the antigen binding or variable region of the intact antibody or the Fc region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the variable domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains.

As used herein, a "chimeric antibody" refers to an antibody (immunoglobulin), such as a chimeric anti-MerTK antibody of the present disclosure, in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity. Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies, such as humanized forms of anti-MerTK antibodies of the present disclosure, are chimeric antibodies comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

A "human antibody" is one that possesses an amino-acid sequence corresponding to that of an antibody, such as an anti-MerTK antibody of the present disclosure, produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries and yeast-display libraries. Human antibodies can be prepared by administering the antigen to a transgenic animal that has been modified to produce such antibodies in response to antigenic challenge, but whose endogenous loci have been disabled, e.g., immunized xenomice as well as generated via a human B-cell hybridoma technology.

The term "hypervariable region," "HVR," or "HV," when used herein refers to the regions of an antibody-variable domain, such as that of an anti-MerTK antibody of the present disclosure, that are hypervariable in sequence and/or form structurally defined loops. Generally, antibodies comprise six HVRs; three in the $V_H$ (H1, H2, H3), and three in the $V_L$ (L1, L2, L3). In native antibodies, H3 and L3 display the most diversity of the six HVRs, and H3 in particular is believed to play a unique role in conferring fine specificity to antibodies. Naturally occurring camelid antibodies consisting of a heavy chain only are functional and stable in the absence of light chain.

A number of HVR delineations are in use and are encompassed herein. In some embodiments, the HVRs may be Kabat complementarity-determining regions (CDRs) based on sequence variability and are the most commonly used (Kabat et al., supra). In some embodiments, the HVRs may be Chothia CDRs. Chothia refers instead to the location of the structural loops (Chothia and Lesk *J. Mol. Biol.* 196: 901-917 (1987)). In some embodiments, the HVRs may be AbM HVRs. The AbM HVRs represent a compromise between the Kabat CDRs and Chothia structural loops, and are used by Oxford Molecular's AbM antibody-modeling software. In some embodiments, the HVRs may be "contact" HVRs. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat numbering) |
| H1 | H31-H35 | H26-H35 | H26-H32 | H30-H35 (Chothia numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2), and 89-97 or 89-96 (L3) in the VL, and 26-35 (H1), 50-65 or 49-65 (a preferred embodiment) (H2), and 93-102, 94-102, or 95-102 (H3) in the VH. The variable-domain residues are numbered according to Kabat et al., supra, for each of these extended-HVR definitions.

"Framework" or "FR" residues are those variable-domain residues other than the HVR residues as herein defined.

An "acceptor human framework" as used herein is a framework comprising the amino acid sequence of a $V_L$ or $V_H$ framework derived from a human immunoglobulin framework or a human consensus framework. An acceptor human framework "derived from" a human immunoglobulin framework or a human consensus framework may comprise the same amino acid sequence thereof, or it may comprise pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less. Where pre-existing amino acid changes are present in a VH, preferable those changes occur at only three, two, or one of positions 71H, 73H and 78H; for instance, the amino acid residues at those positions may by 71A, 73T and/or 78A. In one embodiment, the VL acceptor human framework is identical in sequence to the $V_L$ human immunoglobulin framework sequence or human consensus framework sequence.

A "human consensus framework" is a framework that represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. Generally, the subgroup of sequences is a subgroup as in Kabat et al., *Sequences of Proteins of Immunological Interest,* 5th Ed. Public Health Service, National Institutes of Health, Bethesda, MD (1991). Examples include for the $V_L$, the subgroup may be subgroup kappa I, kappa II, kappa III or kappa IV as in Kabat et al., supra. Additionally, for the $V_H$, the subgroup may be subgroup I, subgroup II, or subgroup III as in Kabat et al., supra.

An "amino-acid modification" at a specified position, e.g., of an anti-MerTK antibody of the present disclosure, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

"Fv" is the minimum antibody fragment which comprises a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the $V_H$ and $V_L$ domains, which enables the sFv to form the desired structure for antigen binding.

Antibody "effector functions" refer to those biological activities attributable to the Fc region (a native sequence Fc region or amino acid sequence variant Fc region) of an antibody, and vary with the antibody isotype.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the present disclosure include human IgG1, IgG2, IgG3 and IgG4.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least 80% homology with a native sequence Fc region and/or with an Fc region of a parent polypeptide, and most preferably at least 90% homology therewith, more preferably at least 95% homology therewith.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif ("ITAM") in its cytoplasmic domain. Inhibiting receptor FcγRIIB contains an immunoreceptor tyrosine-based inhibition motif ("ITIM") in its cytoplasmic domain. Other FcRs, including those to be identified in the future, are encompassed by the term "FcR" herein. FcRs can also increase the serum half-life of antibodies.

As used herein, "percent (%) amino acid sequence identity" and "homology" with respect to a peptide, polypeptide or antibody sequence refers to the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms known in the art needed to achieve maximal alignment over the full-length of the sequences being compared.

The term "compete" when used in the context of antibodies that compete for the same epitope or overlapping epitopes means competition between antibody as determined by an assay in which the antibody being tested prevents or inhibits (e.g., reduces) specific binding of a reference molecule (e.g., a ligand, or a reference antibody) to a common antigen (e.g., MerTK or a fragment thereof). Numerous types of competitive binding assays can be used to determine if antibody competes with another, for example: solid phase direct or indirect radioimmunoassay (RIA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using 1-125 label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol. 32:77-82). Typically, such an assay involves the use of purified antigen bound to a solid surface or cells bearing either of these, an unlabeled test antibody and a labeled reference antibody. Competitive inhibition is measured by determining the amount of label bound to the solid surface or cells in the presence of the test antibody. Usually the test antibody is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit (e.g., reduce) specific binding of a reference antibody to a common antigen by at least 20%, 30%, 40%, 50%, 60%, 70%, 80%, 85%, 90%, 95%, 97.5%, and/or near 100%.

As used herein, an "interaction" between a MerTK polypeptide and a second polypeptide encompasses, without limitation, protein-protein interaction, a physical interaction, a chemical interaction, binding, covalent binding, and ionic binding. As used herein, an antibody "inhibits interaction" between two polypeptides when the antibody disrupts, reduces, or completely eliminates an interaction between the two polypeptides. An antibody of the present disclosure, thereof, "inhibits interaction" between two polypeptides when the antibody thereof binds to one of the two polypeptides. In some embodiments, the interaction can be inhibited by at least any of 20%, 30%, 40%, 50%, 60%, 70%, 80%, 85%, 90%, 95%, 97.5%, and/or near 100%.

The term "epitope" includes any determinant capable of being bound by an antibody. An epitope is a region of an antigen that is bound by an antibody that targets that antigen, and when the antigen is a polypeptide, includes specific amino acids that directly contact the antibody. Most often, epitopes reside on polypeptides, but in some instances, can reside on other kinds of molecules, such as nucleic acids. Epitope determinants can include chemically active surface groupings of molecules such as amino acids, sugar side chains, phosphoryl or sulfonyl groups, and can have specific three dimensional structural characteristics, and/or specific charge characteristics. Generally, antibodies specific for a particular target antigen will preferentially recognize an epitope on the target antigen in a complex mixture of polypeptides and/or macromolecules.

An "isolated" antibody, such as an isolated anti-MerTK antibody of the present disclosure, is one that has been identified, separated and/or recovered from a component of its production environment (e.g., naturally or recombinantly). Preferably, the isolated antibody is free of association with all other contaminant components from its production environment. Contaminant components from its production environment, such as those resulting from recombinant transfected cells, are materials that would typically interfere with research, diagnostic or therapeutic uses for the antibody, and may include enzymes, hormones, and other proteinaceous or non-proteinaceous solutes. In preferred embodiments, the antibody will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant T-cells since at least one component of the antibody's natural environment will not be present. Ordinarily, however, an isolated polypeptide or antibody will be prepared by at least one purification step.

An "isolated" nucleic acid molecule encoding an antibody, such as an anti-MerTK antibody of the present disclosure, is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors."

In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

"Carriers" as used herein include pharmaceutically acceptable carriers, excipients, or stabilizers that are non-toxic to the cell or mammal being exposed thereto at the dosages and concentrations employed.

As used herein, the term "treatment" refers to clinical intervention designed to alter the natural course of the individual being treated during the course of clinical pathology. Desirable effects of treatment include decreasing the rate of progression, ameliorating or palliating the pathological state, and remission or improved prognosis of a particular disease, disorder, or condition. An individual is successfully "treated", for example, if one or more symptoms associated with a particular disease, disorder, or condition are mitigated or eliminated.

An "effective amount" refers to at least an amount effective, at dosages and for periods of time necessary, to achieve the desired therapeutic result. An effective amount can be provided in one or more administrations. An effective amount is also one in which any toxic or detrimental effects of the treatment are outweighed by the therapeutically beneficial effects. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. An effective amount of drug, compound, or pharmaceutical composition is an amount sufficient to accomplish therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

An "individual" for purposes of treatment refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. In some embodiments, the individual is human.

As used herein, administration "in conjunction" with another compound or composition includes simultaneous administration and/or administration at different times. Administration in conjunction also encompasses administration as a co-formulation or administration as separate compositions, including at different dosing frequencies or intervals, and using the same route of administration or different routes of administration. In some embodiments, administration in conjunction is administration as a part of the same treatment regimen.

The term "about" as used herein refers to the usual error range for the respective value readily known to the skilled person in this technical field. Reference to "about" a value or parameter herein includes (and describes) embodiments that are directed to that value or parameter per se.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

It is understood that aspect and embodiments of the present disclosure described herein include "comprising," "consisting," and "consisting essentially of" aspects and embodiments.

I. Anti-MerTK Antibodies

Provided herein are anti-MerTK antibodies. Antibodies provided herein are useful, e.g., for the diagnosis or treatment of the MerTK associated disorders.

In one aspect, the present disclosure provides isolated (e.g., monoclonal) antibodies that bind to an epitope within a MerTK protein or polypeptide of the present disclosure. MerTK proteins or polypeptides of the present disclosure include, without limitation, a mammalian MerTK protein or polypeptide, human MerTK protein or polypeptide, mouse (murine) MerTK protein or polypeptide, and cynomogus MerTK protein or polypeptide. MerTK proteins and polypeptides of the present disclosure include naturally occurring variants of MerTK. In some embodiments, MerTK proteins and polypeptides of the present disclosure are membrane bound. In some embodiments, MerTK proteins and polypeptides of the present disclosure are a soluble extracellular domain of MerTK.

In some embodiments, MerTK is expressed in a cell. In some embodiments, MerTK is expressed in phagocytic cells, including without limitation, macrophages and dendritic cells. In some embodiments, MerTK is expressed in monocytes, natural killer cells, natural killer T cells, microglia, endothelial cells, megakaryocytes, and platelets. In some embodiments, high levels of MerTK expression are also found in ovary, prostate, testis, lung, retina, and kidney. Additionally, MerTK displays ectopic or overexpression in numerous cancers (Linger et al, 2008, Adv Cancer Res, 100:35-83).

Antibody Activities

In some embodiments, an anti-MerTK antibody is provided that binds to human MerTK but does not bind to cynomolgus MerTK. In some embodiments, an anti-MerTK antibody is provided that binds to human MerTK but does not bind to murine MerTK. In some embodiments, an anti-MerTK antibody is provided that binds to human MerTK but does not bind to cynomolgus MerTK and does not bind to murine MerTK. In some embodiments, an anti-MerTK antibody is provided that binds to human MerTK and binds to cynomolgus MerTK. In some embodiments, an anti-MerTK antibody is provided that binds to human MerTK and binds to cynomolgus MerTK but does not bind to murine MerTK. In some embodiments, an anti-MerTK antibody is provide that binds to human MerTK and binds to murine MerTK. In some embodiments, an anti-MerTK antibody is provide that binds to human MerTK and binds to murine MerTK but does not bind cynomolgus MerTK. In some embodiments, an anti-MerTK antibody is provide that binds to human MerTK, cynomolgus MerTK, and murine MerTK. An anti-MerTk antibody that binds to human, cynomolgus, and murine MerTK is advantageous for performing in vivo studies in mammalian animal models of disease (e.g., cancer) as well as studies in non-human primates.

MerTK Binding Partners

MerTK proteins of the present disclosure interact with (e.g., bind) one or more ligands or binding partners, including, without limitation, Protein S (ProS or ProS1), Growth arrest specific gene 6 (Gas6), Tubby, Tubby-like protein 1 (TULP-1), and Galectin-3. Anti-MerTK antibodies of the present disclosure can affect the interaction of MerTK with one or more of its various ligands and binding partners.

Anti-MerTK antibodies of the present disclosure that blocked both ProS binding and Gas6 binding to MerTK, that blocked only ProS binding to MerTK, or that did not block binding of either ProS or Gas6 binding to MerTK were identified. The ProS only blocking anti-MerTK antibodies did not bin with the ProS/Gas6 double blocking anti-MerTK antibodies (as shown in the Examples below), suggesting non-overlapping epitopes for these two classes of anti-MerTK antibodies identified herein. Accordingly, in some embodiments, an anti-MerTK antibody of the present disclosure inhibits (i.e., blocks) or reduces binding between MerTK and one or more MerTK ligands. In some embodiments, an anti-MerTK antibody of the present disclosure inhibits or reduces binding of ProS to MerTK. In some embodiments, an anti-MerTK antibody of the present disclosure inhibits or reduces binding of ProS to MerTK but does not inhibit or reduce binding of Gas6 to MerTK. In some embodiments, an anti-MerTK antibody of the present disclosure inhibits or reduces binding of Gas6 to MerTK. In some embodiments, an anti-MerTK antibody of the present disclosure inhibits or reduces binding to Gas6 to MerTK but does not inhibit or reduce binding of ProS to MerTK. In yet other embodiments, an anti-MerTK antibody of the present disclosure inhibits or reduces binding of ProS to MerTK and inhibits or reduces binding of Gas6 to MerTK. In other embodiments, an anti-MerTK antibody of the present disclosure does not inhibit or reduce binding of ProS to MerTK and does not inhibit or reduce binding of Gas6 to MerTK.

An IC50 value for inhibition or blocking of Gas6 ligand binding to MerTK or for inhibition or blocking of ProS ligand binding to MerTK can be determined using methods known by one of skill in the art, such as that described herein in the Example below (e.g., Example 13). In some embodiments, an anti-MerTK antibody of the present disclosure inhibits or reduces Gas6 ligand binding or inhibits or reduces ProS ligand binding to MerTK in vitro. In some embodiments, an anti-MerTK antibody of the the present disclosure inhibits or reduces Gas6 ligand binding to human MerTK with an IC50 value in the range of 0.29 nM to 32 nM. In some embodiments, an anti-MerTK antibody of the present disclosure inhibits or reduces Gas6 ligand binding to human MerTK with an IC50 value in the range of 0.29 nM to 1.0 nM, in the range of 1.0 nM to 5 nM, in the range of 5 nM to 10 nM, in the range of 10 nM to 25 nM, or in the range of 25 nM to 32 nM. In some embodiments, an anti-MerTK antibody of the present disclosure inhibits or reduces ProS ligand binding to human MerTK with an IC50 value in the range of 0.58 nM to 25.9 nM. In some embodiments, an anti-MerTK antibody of the present disclosure inhibits or reduces ProS ligand binding to human MerTK with an IC50 value in the range of 0.58 nM to 1 nM, in the range of 1 nM to 2.5 nM, in the range of 2.5 nM to 5 nM, in the range of 5 nM to 10 nM, in the range of 10 nM to 25 nM.

The relative effectiveness of an antibody at reducing or inhibiting the binding of ProS and Gas6 to MerTK can be determined using such IC50 values. For example, an antibody that inhibits binding of Gas6 to MerTK at an IC50 value that is 1.7 times greater than its IC50 value for inhibiting binding of ProS to MerTK is 1.7 times more effective at reducing or inhibiting the binding of ProS to MerTK than at reducing or inhibiting the binding of Gas6 to MerTK. In some embodiments, an anti-MerTK antibody is at least 1.7 times, at least 2.3 times, at least 2.4 times, at least 5 times, at least 7.7 times, or at least 8.5 times more effective at reducing or inhibiting the binding of ProS to MerTK than at reducing or inhibiting the binding of Gas6 to MerTK.

In some embodiments, an anti-MerTK antibody of the present disclosure inhibits or reduces Gas6 ligand binding to MerTK by at least 20%, by at least 25, by at least 30%, by at least 40%, by at least 50%, by at least 60%, by at least 70%, by at least 80%, by at least 90%, or by at least 95% compared to Gas6 ligand binding to MerTK in the absence of an anti-MerTK antibody of the present disclosure. In some embodiments, an anti-MerTK antibody of the present disclosure inhibits or reduces ProS ligand binding to MerTK by at least 20%, by at least 25%, by at least 30%, by at least 40%, by at least 50%, by at least 60%, by at least 70%, by at least 80%, by at least 90%, or by at least 95% compared to ProS ligand binding to MerTK in the absence of an anti-MerTK antibody of the present disclosure. Percent inhibition or reduction of Gas6 ligand binding to MerTK or of ProS ligand binding to MerTK can be determined by measuring IC50 values using standard methods known by one of skill in the art, such as described herein in Example 13.

Further provided herein are methods of screening for anti-MerTK antibodies that bind MerTK and that block or reduce the interactions between MerTK and one or more MerTK ligands or binding partners.

pAKT

AKT activity is a downstream target of Gas6 binding to MerTK, Axl, or Tyro-3 receptors. For example, the binding of MerTK ligand Gas6 to MerTK induces AKT phosphorylation (pAKT) (see, e.g., Angelillo-Scherrer et al, 2008, J Clin Invest, 118:583-596; Moody et al, 2016, Int J Cancer, 139:1340-1349). Anti-MerTK antibodies of the present disclosure were effective at inhibiting Gas6-mediated phospho-AKT (pAKT) activity in human macrophages (e.g., M2c macrophages) in a dose-dependent manner. Accordingly, anti-MerTK antibodies of the present disclosure were effective at inhibiting Gas6-mediated MerTK signaling as evidenced by inhibition of pAKT levels. In some embodiments, an anti-MerTK antibody of the present disclosure inhibits or reduces Gas6-mediated pAKT activity in vitro. The relative effectiveness of an anti-MerTK antibody at reducing or inhibiting pAKT activity in a cell can be determined by measuring the IC50 values. IC50 values for inhibition of Gas6-mediated pAKT activity can be determined using methods known by one of skill in the art, such as that described herein in Example 22 below. In some embodiments, an anti-MerTK antibody of the present disclosure inhibits Gas6-mediated pAKT activity in macrophages (e.g., M2c macrophages) with an IC50 value ranging from 0.019 nM to 7.74 nM. In some embodiments, an anti-MerTK antibody of the present disclosure inhibits Gas6-mediated pAKT activity in macrophages (e.g., M2c macrophages) with an IC50 value of 0.019 nM to 0.25 nM, 0.25 nM to 0.50 nM, 0.50 nM to 1.0 nM, 1.0 nM to 2.5 nM, 2.5 nM to 5.0 nM, or 5.0 nM to 10 nM.

Efferocytosis

Efferocytosis refers to phagocytic clearance of dying or apoptotic cells. Efferocytosis can be accomplished by professional phagocytes (e.g., macrophages, dendritic cells, microglia), non-professional phagocytes (e.g., epithelial cells, fibroblasts, retinal pigment epithelial cells), or specialized phagocytes. (Elliott et al, 2017, J Immunol, 198: 1387-1394). Efferocytosis leads to the removal of dead or dying cells before their membrane integrity is breached and their cellular contents leak into the surrounding tissue, thus preventing exposure of tissue to toxic enzymes, oxidants, and other intracellular components.

Apoptotic cells expose a variety of molecules on their cell surface ("eat-me" signals) that are recognized by receptors on phagocytic cells. One such "eat me" signaling molecules is phosphatidylserine (PtdSer), which is normally confined to the inner leaflet of the cell membrane. During apoptosis, PtdSer is exposed to the outer leaflet of the cell membrane. MerTK ligands ProS and Gas6 contain gamma-carboxylated glutamic acid residues near their N-terminal domains; gamma-carboxylation of the glutamic acid domain enables binding to phosphatidylserine. Gas6 or ProS bind to PtdSer on apoptotic cells and simultaneously bind MerTK on phagocytes. Such ligand engagement with MerTK activates efferocytosis.

As shown in the Examples below, anti-MerTK antibodies of the present disclosure were effective at reducing or decreasing efferocytosis in various phagocytic cells. Anti-MerTK antibodies that that block ProS only binding to MerTK showed robust inhibition of efferocytosis, having an IC50 comparable to anti-MerTK antibodies that block both ProS and Gas6 binding to MerTK. Considering that genetic deficiency of both ProS and Gas6 is required to develop vision loss by retinal degradation (ProS or Gas6 single genetic knockouts did not lead to retinal pathologies), anti-MerTK antibodies that are ProS-specific blockers may provide improved therapeutic index for use in anti-tumor responses without inducing eye toxicity issues.

Accordingly, in some embodiments, an anti-MerTK antibody of the present disclosure decreases or reduces efferocytosis by phagocytic cells. In some embodiments, an anti-MerTK antibody of the present disclosure decreases or reduces efferocytosis by macrophages. In some embodiments, an anti-MerTK antibody of the present disclosure decreases or reduces efferocytosis by dendritic cells. In some embodiments, an anti-MerTK antibody of the present disclosure decreases or reduces efferocytosis by bone marrow-derived macrophages. In some embodiments, an anti-MerTK antibody of the present disclosure decreases or reduces efferocytosis by phagocytic cells by at least 10%, by at least 20%, by at least 25%, by at least 30%, by at least 40%, by at least 50%, by at least 60%, by at least 70%, by at least 80%, by at least 90%, or by at least 95% compared to the level of efferocytosis in phagocytic cells in the absence of an anti-MerTK antibody. Percent reduction of efferocytosis can be determined using standard methods known to one of skill in the art, such as described herein in Example 11.

In some embodiments, an anti-MerTK antibody of the present disclosure decreases or reduces efferocytosis by a phagocytic cell (e.g., a human macrophage) with an IC50 in the range of about 0.13 nM to about 30 nM, as assessed by methods described herein in the Example below (e.g., Example 11). In some embodiments, an anti-MerTK antibody of the present disclosure decreases or reduces efferocytosis by a phagocytic cell with an IC50 value in the range of 0.13 nM to 1.0 nM, in the range of 1 nM to 5 nM, in the range of 5 nM to 10 nM, or in the range of 10 nM to 30 nM.

Blocking efferocytosis drives M1-like macrophage polarization, resulting in increased production of pro-inflammatory cytokines (e.g., TNF, IFN, IL-12) and recruitment of cytotoxic cells, such as CD8+ T cells and natural killer cells, that mediate anti-tumor immunity. By reducing efferocytosis by phagocytic cells, anti-MerTK antibodies of the present disclosure are effective at increasing M1-like macrophage polarization and at increasing production, expression, and/or secretion of pro-inflammatory cytokines/chemokines, including TNF, IFN, IL-6, IL-1, IL-12, chemokine (C-X-C motif) ligand 1 (CXCL-1, KC), monocyte chemoattractant protein-1 (MCP1, CCL2), macrophage inflammatory protein-1-alpha (MIP-1α, CCL3), and/or macrophage inflammatory protein-1-beta (MIP-1β, CCL4). Accordingly, in some embodiments, an anti-MerTK antibody of the present disclosure increases M1-like macrophage polarization. In some embodiments, an anti-MerTK antibody of the present disclosure increases macrophage production, expression, or secretion of one or more pro-inflammatory cytokines. In some embodiments, an anti-MerTK antibody of the present disclosure increases macrophage production, expression, or secretion of TNF, IFN, IL-6, IL-1, IL-12, CXCL-1, MCP1, MIP-1α, and/or MIP-1β.

Accordingly, in some embodiments, provided herein is a method for increasing pro-inflammatory cytokine production, expression, and/or secretion in a subject in need thereof, the method comprising administering to the subject an anti-MerTK antibody of the present disclosure such that the production, expression, and/or secretion of one or more pro-inflammatory cytokines in the subject is increased. In some embodiments, the production, expression, and/or secretion of TNF is increased. In some embodiments, the production, expression, and/or secretion of IFN is increased. In some embodiments, the production, expression, and/or secretion of IL-12 is increased. In some embodiments, the production, expression, and/or secretion of CXCL-1 is increased. In some embodiments, the production, expression, and/or secretion of MCP1 is increased. In some embodiments, the production, expression, and/or secretion of MIP-1α is increased. In some embodiments, the production, expression, and/or secretion of MIP-1β is increased.

In some embodiments, provided herein is a method for increasing M1-like macrophage polarization in a subject in need thereof, the method comprising administering to the subject an anti-MerTK antibody of the present disclosure such that M1-like macrophage polarization in the subject is increased. Increased M1-like macrophage polarization is measured by various methods known to one of skill in the art, such as increased production, expression, or secretion of one or more pro-inflammatory cytokines, including TNF, IFN, IL-12, CXCL1, MCP1, MIP-1α, and/or MIP-1β.

A link between efferocytosis and cancer progression has been described. For example, blockade of efferocytosis using Annexin V, which blocks PtdSer from interacting with the efferocytosis machinery of phagocytes, sufficiently reduces tumor progression and metastasis (Stach et al, 2000, Cell Death Diff, 7:911; Bondanza et al, 2004, J Exp Med, 200:1157; Werfel and Cook, 2018, Sem Immunopathology, 40:545-554). Further, MerTK correlates with poor prognosis and survival in numerous human cancers, as does its PtdSer bridging ligand Gas6 (Graham et al, 2014, Nat Rev Cancer, 14:769; Linger et al, 2010, Expert Opin Ther Targets, 14:1073-1090; Wang et al, 2013, Oncogene, 32:872; Jansen et al, 2011, J Proteome Res, 11:728-735; Tworkoski et al, 2011, Mol Cancer Res, p.molcanres-0512; Graham et al, 2006, Clin Cancer Res, 12:2662-2669; Keating et al, 2006, Oncogene, 25:6092). Accordingly, anti-MerTK antibodies of the present disclosure, which reduce efferocytosis by phagocytic cells, are thus effective at reducing tumor progression and metastasis.

Cynomolgus studies indicated that in some instances, anti-MerTK antibodies that block binding to both Gas6 and ProS (e.g., anti-MerTK antibody MTK-16) showed less in vivo toxicity (e.g., weight loss) compared to that observed in cynomolgus monkeys administered an anti-MerTK antibody that blocks ProS binding to MerTK but does not block binding of Gas6 to MerTK (e.g., anti-MerTK antibody MTK-15 or MTK-29). Accordingly, in some embodiments, an anti-MertK antibody of the present disclosure that blocks binding of both Gas6 and ProS to MerTK may display less systemic in vivo toxicity compared to an anti-MerTK antibody of the present disclosure that blocks binding of ProS to MerTK but does not block binding of Gas6 to MerTK. Anti-MerTk antibody MTK-16 (which blocks binding of both Gas6 and ProS to MerTK) binds to the Ig1 domain of MerTK protein, while anti-MerTK antibodies MTK-15 and MTK-29 (which block binding of ProS to MerTK but which do not block binding of Gas6 to MerTK) bind to both the Ig2 and the FN1 domain of MerTK protein. Accordingly, in some embodiments, an anti-MerTK antibody that binds to the Ig1 domain of MerTK may display less systemic in vivo toxicity than an anti-MerTK antibody that binds to both the Ig2 and FN1 domains of MerTK.

A. Exemplary Antibodies and Certain Other Antibody Embodiments

In some embodiments, provided herein are anti-MerTK antibodies comprising at least one, two, three, four, five, or six HVRs selected from: (a) HVR-H1 comprising an amino acid sequence selected from the group consisting of SEQ ID NOs:75, 76, 77, 78, 79, 80, 81, 82, 83, 84, 85, 86, 87, 88, 89, 90, 91, 92, 93, 94, 95, 96, 97, and 98; (b) HVR-H2 comprising an amino acid sequence selected from the group consisting of SEQ ID NOs:99, 100, 101, 102, 103, 104, 105, 106, 107, 108, 109, 110, 111, 112, 113, 114, 115, 116, 117, 118, 119, 120, 121, 122, 123, and 124; (c) HVR-H3 comprising an amino acid sequence selected from the group consisting of SEQ ID NOs:125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, and 157; (d) HVR-L1 comprising an amino acid sequence selected from the group consisting of SEQ ID NOs:158, 159, 160, 161, 162, 163, 164, 165, 166, 167, 168, 169, 170, 171, 172, 173, 174, 175, 176, 177, 178, 179, 180, 181, 182, 183, 184, 185, and 186; (e) HVR-L2 comprising an amino acid sequence selected from the group consisting of SEQ ID NOs:187, 188, 189, 190, 191, 192, 193, 194, 195, 196, 197, 198, 199, 200, 201, 202, 203, 204, and 205; and (f) HVR-L3 comprising an amino acid sequence selected from the group consisting of SEQ ID NOs:207, 208, 209, 210, 211, 212, 213, 214, 215, 216, 217, 218, 219, 220, 221, 222, 223, 224, 225, 226, 227, 228, 229, 230, 231, 232, and 233.

In some embodiments, provided herein are anti-MerTK antibodies comprising at least one, at least two, or all three $V_H$ HVR sequences selected from (a) HVR-H1 comprising an amino acid sequence selected from the group consisting of SEQ ID NOs: 75, 76, 77, 78, 79, 80, 81, 82, 83, 84, 85, 86, 87, 88, 89, 90, 91, 92, 93, 94, 95, 96, 97, and 98; (b) HVR-H2 comprising an amino acid sequence selected from the group consisting of SEQ ID NOs: 99, 100, 101, 102, 103, 104, 105, 106, 107, 108, 109, 110, 111, 112, 113, 114, 115, 116, 117, 118, 119, 120, 121, 122, 123, and 124; and (c) HVR-H3 comprising an amino acid sequence selected from the group consisting of SEQ ID NOs: 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, and 157.

In some embodiments, provided herein are anti-MerTK antibodies comprising at least one, at least two, or all three $V_L$ HVR sequences selected from (a) HVR-L1 comprising an amino acid sequence selected from the group consisting of SEQ ID NOs: 158, 159, 160, 161, 162, 163, 164, 165, 166, 167, 168, 169, 170, 171, 172, 173, 174, 175, 176, 177, 178, 179, 180, 181, 182, 183, 184, 185, and 186; (b) HVR-L2 comprising an amino acid sequence selected from the group consisting of SEQ ID NOs: 187, 188, 189, 190, 191, 192, 193, 194, 195, 196, 197, 198, 199, 200, 201, 202, 203, 204, and 205; and (c) HVR-L3 comprising an amino acid sequence selected from the group consisting of SEQ ID NOs: 207, 208, 209, 210, 211, 212, 213, 214, 215, 216, 217, 218, 219, 220, 221, 222, 223, 224, 225, 226, 227, 228, 229, 230, 231, 232, and 233.

In some embodiments, provided herein are anti-MerTK antibodies comprising (a) a $V_H$ domain comprising at least one, at least two, or all three $V_H$ HVR sequences selected from (i) HVR-H1 comprising an amino acid sequence selected from the group consisting of SEQ ID NOs: 75, 76, 77, 78, 79, 80, 81, 82, 83, 84, 85, 86, 87, 88, 89, 90, 91, 92, 93, 94, 95, 96, 97, and 98, (ii) HVR-H2 comprising an amino acid sequence selected from the group consisting of SEQ ID NOs: 99, 100, 101, 102, 103, 104, 105, 106, 107, 108, 109, 110, 111, 112, 113, 114, 115, 116, 117, 118, 119, 120, 121, 122, 123, and 124, and (iii) HVR-H3 comprising an amino acid sequence selected from the group consisting of SEQ ID NOs: 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, and 157, and (b) a $V_L$ domain comprising at least one, at least two, or all three $V_L$ HVR sequences selected from (i) HVR-L1 comprising an amino acid sequence selected from the group consisting of SEQ ID NOs: 158, 159, 160, 161, 162, 163, 164, 165, 166, 167, 168, 169, 170, 171, 172, 173, 174, 175, 176, 177, 178, 179, 180, 181, 182, 183, 184, 185, and 186, (ii) HVR-L2 comprising an amino acid sequence selected from the group consisting of SEQ ID NOs: 187, 188, 189, 190, 191, 192, 193, 194, 195, 196, 197, 198, 199, 200, 201, 202, 203, 204, and 205, and (iii) HVR-L3 comprising an amino acid sequence selected from the group consisting of SEQ ID NOs: 207, 208, 209, 210, 211, 212, 213, 214, 215, 216, 217, 218, 219, 220, 221, 222, 223, 224, 225, 226, 227, 228, 229, 230, 231, 232, and 233.

In some embodiments, provided herein are anti-MerTK antibodies comprising: (a) HVR-H1 comprising the amino acid sequence of SEQ ID NO:75; (b) HVR-H2 comprising the amino acid sequence of SEQ ID NO:99; (c) HVR-H3 comprising the amino acid sequence of SEQ ID NO:125; (d) HVR-L1 comprising the amino acid sequence of SEQ ID NO:158; (e) HVR-L2 comprising the amino acid sequence of SEQ ID NO:187; and (f) HVR-L3 comprising the amino acid sequence of SEQ ID NO:207; (a) HVR-H1 comprising the amino acid sequence of SEQ ID NO:76; (b) HVR-H2 comprising the amino acid sequence of SEQ ID NO:100; (c) HVR-H3 comprising the amino acid sequence of SEQ ID NO:126; (d) HVR-L1 comprising the amino acid sequence of SEQ ID NO:159; (e) HVR-L2 comprising the amino acid sequence of SEQ ID NO:187; and (f) HVR-L3 comprising the amino acid sequence of SEQ ID NO:208; (a) HVR-H1 comprising the amino acid sequence of SEQ ID NO:77; (b) HVR-H2 comprising the amino acid sequence of SEQ ID NO:101; (c) HVR-H3 comprising the amino acid sequence of SEQ ID NO:127; (d) HVR-L1 comprising the amino acid sequence of SEQ ID NO:160; (e) HVR-L2 comprising the amino acid sequence of SEQ ID NO:188; and (f) HVR-L3 comprising the amino acid sequence of SEQ ID NO:209; (a) HVR-H1 comprising the amino acid sequence of SEQ ID NO:75; (b) HVR-H2 comprising the amino acid sequence of SEQ ID NO:99; (c) HVR-H3 comprising the amino acid sequence of SEQ ID NO:128; (d) HVR-L1 comprising the amino acid sequence of SEQ ID NO:158; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:78; (b) HVR-H2 comprising the amino acid sequence of SEQ ID NO:102; (c) HVR-H3 comprising the amino acid sequence of SEQ ID NO:129; (d) HVR-L1 comprising the amino acid sequence of SEQ ID NO:161; (e) HVR-L2 comprising the amino acid sequence of SEQ ID NO:189; and (f) HVR-L3 comprising the amino acid sequence of SEQ ID NO:211; (a) HVR-H1 comprising the amino acid sequence of SEQ ID NO:75; (b) HVR-H2 comprising the amino acid sequence of SEQ ID NO:103; (c) HVR-H3 comprising the amino acid sequence of SEQ ID NO:130; (d) HVR-L1 comprising the amino acid sequence of SEQ ID NO:158; (e) HVR-L2 comprising the amino acid sequence of SEQ ID NO:187; and (f) HVR-L3 comprising the amino acid sequence of SEQ ID NO:212; (a) HVR-H1 comprising the amino acid sequence of SEQ ID NO:77; (b) HVR-H2 comprising the amino acid sequence of SEQ ID NO:101; (c) HVR-H3 comprising the amino acid sequence of SEQ ID NO:127; (d) HVR-L1 comprising the amino acid sequence of SEQ ID NO:162; (e) HVR-L2 comprising the amino acid sequence of SEQ ID NO:188; and (f) HVR-L3 comprising the amino acid sequence of SEQ ID NO:209; (a) HVR-H1 comprising the amino acid sequence of SEQ ID NO:75; (b) HVR-H2 comprising the amino acid sequence of SEQ ID NO:99; (c) HVR-H3 comprising the amino acid sequence of SEQ ID NO:131; (d) HVR-L1 comprising the amino acid sequence of SEQ ID NO:163; (e) HVR-L2 comprising the amino acid sequence of SEQ ID NO:187; and (f) HVR-L3 comprising the amino acid sequence of SEQ ID NO:213; (a) HVR-H1 comprising the amino acid sequence of SEQ ID NO:79; (b) HVR-H2 comprising the amino acid sequence of SEQ ID NO:104; (c) HVR-H3 comprising the amino acid sequence of SEQ ID NO:132; (d) HVR-L1 comprising the amino acid sequence of SEQ ID NO:164; (e) HVR-L2 comprising the amino acid sequence of SEQ ID NO:190; and (f) HVR-L3 comprising the amino acid sequence of SEQ ID NO:214; (a) HVR-H1 comprising the amino acid sequence of SEQ ID NO:80; (b) HVR-H2 comprising the amino acid sequence of SEQ ID NO:105; (c) HVR-H3 comprising the amino acid sequence of SEQ ID NO:133; (d) HVR-L1 comprising the amino acid sequence of SEQ ID NO:165; (e) HVR-L2 comprising the amino acid sequence of SEQ ID NO:191; and (f) HVR-L3 comprising the amino acid sequence of SEQ ID NO:215; (a) HVR-H1 comprising the amino acid sequence of SEQ ID NO:81; (b) HVR-H2 comprising the amino acid sequence of SEQ ID NO:106; (c) HVR-H3 comprising the amino acid sequence of SEQ ID NO:134; (d) HVR-L1 comprising the amino acid sequence of SEQ ID NO:166; (e) HVR-L2 comprising the amino acid sequence of SEQ ID NO:192; and (f) HVR-L3 comprising the amino acid sequence of SEQ ID NO:216; (a) HVR-H1 comprising the amino acid sequence of SEQ ID NO:82; (b) HVR-H2 comprising the amino acid sequence of SEQ ID NO:107; (c) HVR-H3 comprising the amino acid sequence of SEQ ID NO:135; (d) HVR-L1 comprising the amino acid sequence of SEQ ID NO:167; (e) HVR-L2 comprising the amino acid sequence of SEQ ID NO:193; and (f) HVR-L3 comprising the amino acid sequence of SEQ ID NO:217; (a) HVR-H1 comprising the amino acid sequence of SEQ ID NO:77; (b) HVR-H2 comprising the amino acid sequence of SEQ ID NO:108; (c) HVR-H3 comprising the amino acid sequence of SEQ ID NO:136; (d) HVR-L1 comprising the amino acid sequence of SEQ ID NO:167; (e) HVR-L2 comprising the amino acid sequence of SEQ ID NO:194; and (f) HVR-L3 comprising the amino acid sequence of SEQ ID NO:209; (a) HVR-H1 comprising the amino acid sequence of SEQ ID NO:75; (b) HVR-H2 comprising the amino acid sequence of SEQ ID NO:109; (c) HVR-H3 comprising the amino acid sequence of SEQ ID NO:137; (d) HVR-L1 comprising the amino acid sequence of SEQ ID NO:168; (e) HVR-L2 comprising the amino acid sequence of SEQ ID NO:187; and (f) HVR-L3 comprising the amino acid sequence of SEQ ID NO:218; (a) HVR-H1 comprising the amino acid sequence of SEQ ID NO:83; (b) HVR-H2 comprising the amino acid sequence of SEQ ID NO:999; (c) HVR-H3 comprising the amino acid sequence of SEQ ID NO:138; (d) HVR-L1 comprising the amino acid sequence of SEQ ID NO:158; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:84; (b) HVR-H2 comprising the amino acid sequence of SEQ ID NO:99; (c) HVR-H3 comprising the amino acid sequence of SEQ ID NO:139; (d) HVR-L1 comprising the amino acid sequence of SEQ ID NO:169; (e) HVR-L2 comprising the amino acid sequence of SEQ ID NO:195; and (f) HVR-L3 comprising the amino acid sequence of SEQ ID NO:219; (a) HVR-H1 comprising the amino acid sequence of SEQ ID NO:85; (b) HVR-H2 comprising the amino acid sequence of SEQ ID NO:99; (c) HVR-H3 comprising the amino acid sequence of SEQ ID NO:140; (d) HVR-L1 comprising the amino acid sequence of SEQ ID NO:170; (e) HVR-L2 comprising the amino acid sequence of SEQ ID NO:196; and (f) HVR-L3 comprising the amino acid sequence of SEQ ID NO:222; (a) HVR-H1 comprising the amino acid sequence of SEQ ID NO:86; (b) HVR-H2 comprising the amino acid sequence of SEQ ID NO:99; (c) HVR-H3 comprising the amino acid sequence of SEQ ID NO:141; (d) HVR-L1 comprising the amino acid sequence of SEQ ID NO:171; (e) HVR-L2 comprising the amino acid sequence of SEQ ID NO:191; and (f) HVR-L3 comprising the amino acid sequence of SEQ ID NO:221; (a) HVR-H1 comprising the amino acid sequence of SEQ ID NO:87; (b) HVR-H2 comprising the amino acid sequence of SEQ ID NO:110; (c) HVR-H3 comprising the amino acid sequence of SEQ ID NO:142; (d) HVR-L1 comprising the amino acid sequence of SEQ ID NO:172; (e) HVR-L2 comprising the amino acid sequence of SEQ ID NO:197; and (f) HVR-L3 comprising the amino acid sequence of SEQ ID NO:222; (a) HVR-H1 comprising the amino acid sequence of SEQ ID NO:88; (b) HVR-H2 comprising the amino acid sequence of SEQ ID NO:99; (c) HVR-H3 comprising the amino acid sequence of SEQ ID NO:143; (d) HVR-L1 comprising the amino acid sequence of SEQ ID NO:173; (e) HVR-L2 comprising the amino acid sequence of SEQ ID NO:191; and (f) HVR-L3 comprising the amino acid sequence of SEQ ID NO:223; (a) HVR-H1 comprising the amino acid sequence of SEQ ID NO:89; (b) HVR-H2 comprising the amino acid sequence of SEQ ID NO:111; (c) HVR-H3 comprising the amino acid sequence of SEQ ID NO:143; (d) HVR-L1 comprising the amino acid sequence of SEQ ID NO:173; (e) HVR-L2 comprising the amino acid sequence of SEQ ID NO:198; and (f) HVR-L3 comprising the amino acid sequence of SEQ ID NO:221; (a) HVR-H1 comprising the amino acid sequence of SEQ ID NO:90; (b) HVR-H2 comprising the amino acid sequence of SEQ ID NO:112; (c) HVR-H3 comprising the amino acid sequence of SEQ ID NO:144; (d) HVR-L1 comprising the amino acid sequence of SEQ ID NO:174; (e) HVR-L2 comprising the amino acid sequence of SEQ ID NO:199; and (f) HVR-L3 comprising the amino acid sequence of SEQ ID NO:224; (a) HVR-H1 comprising the amino acid sequence of SEQ ID NO:91; (b) HVR-H2 comprising the amino acid sequence of SEQ ID NO:113; (c) HVR-H3 comprising the amino acid sequence of SEQ ID NO:145; (d) HVR-L1 comprising the amino acid sequence of SEQ ID NO:175; (e) HVR-L2 comprising the amino acid sequence of SEQ ID NO:200; and (f) HVR-L3 comprising the amino acid sequence of SEQ ID NO:225; (a) HVR-H1 comprising the amino acid sequence of SEQ ID NO:90; (b) HVR-H2 comprising the amino acid sequence of SEQ ID NO:114; (c) HVR-H3 comprising the amino acid sequence of SEQ ID NO:146; (d) HVR-L1 comprising the amino acid sequence of SEQ ID NO:176; (e) HVR-L2 comprising the amino acid sequence of SEQ ID NO:201; and (f) HVR-L3 comprising the amino acid sequence of SEQ ID NO:226; (a) HVR-H1 comprising the amino acid sequence of SEQ ID NO:92; (b) HVR-H2 comprising the amino acid sequence of SEQ ID NO:115; (c) HVR-H3 comprising the amino acid sequence of SEQ ID NO:147; (d) HVR-L1 comprising the amino acid sequence of SEQ ID NO:177; (e) HVR-L2 comprising the amino acid sequence of SEQ ID NO:195; and (f) HVR-L3 comprising the amino acid sequence of SEQ ID NO:227; (a) HVR-H1 comprising the amino acid sequence of SEQ ID NO:93; (b) HVR-H2 comprising the amino acid sequence of SEQ ID NO:116; (c) HVR-H3 comprising the amino acid sequence of SEQ ID NO:148; (d) HVR-L1 comprising the amino acid sequence of SEQ ID NO:178; (e) HVR-L2 comprising the amino acid sequence of SEQ ID NO:188; and (f) HVR-L3 comprising the amino acid sequence of SEQ ID NO:209; (a) HVR-H1 comprising the amino acid sequence of SEQ ID NO:94; (b) HVR-H2 comprising the amino acid sequence of SEQ ID NO:117; (c) HVR-H3 comprising the amino acid sequence of SEQ ID NO:149; (d) HVR-L1 comprising the amino acid sequence of SEQ ID NO:179; (e) HVR-L2 comprising the amino acid sequence of SEQ ID NO:195; and (f) HVR-L3 comprising the amino acid sequence of SEQ ID NO:228; (a) HVR-H1 comprising the amino acid sequence of SEQ ID NO:95; (b) HVR-H2 comprising the amino acid sequence of SEQ ID NO:118; (c) HVR-H3 comprising the amino acid sequence of SEQ ID NO:150; (d) HVR-L1 comprising the amino acid sequence of SEQ ID NO:180; (e) HVR-L2 comprising the amino acid sequence of SEQ ID NO:187; and (f) HVR-L3 comprising the amino acid sequence of SEQ ID NO:229; (a) HVR-H1 comprising the amino acid sequence of SEQ ID NO:95; (b) HVR-H2 comprising the amino acid sequence of SEQ ID NO:119; (c) HVR-H3 comprising the amino acid sequence of SEQ ID NO:151; (d) HVR-L1 comprising the amino acid sequence of SEQ ID NO:181; (e) HVR-L2 comprising the amino acid sequence of SEQ ID NO:187; and (f) HVR-L3 comprising the amino acid sequence of SEQ ID NO:208; (a) HVR-H1 comprising the amino acid sequence of SEQ ID NO:90; (b) HVR-H2 comprising the amino acid sequence of SEQ ID NO:120; (c)

HVR-H3 comprising the amino acid sequence of SEQ ID NO:152; (d) HVR-L1 comprising the amino acid sequence of SEQ ID NO:182; (e) HVR-L2 comprising the amino acid sequence of SEQ ID NO:202; and (f) HVR-L3 comprising the amino acid sequence of SEQ ID NO:230; (a) HVR-H1 comprising the amino acid sequence of SEQ ID NO:96; (b) HVR-H2 comprising the amino acid sequence of SEQ ID NO:118; (c) HVR-H3 comprising the amino acid sequence of SEQ ID NO:153; (d) HVR-L1 comprising the amino acid sequence of SEQ ID NO:183; (e) HVR-L2 comprising the amino acid sequence of SEQ ID NO:202; and (f) HVR-L3 comprising the amino acid sequence of SEQ ID NO:230; (a) HVR-H1 comprising the amino acid sequence of SEQ ID NO:96; (b) HVR-H2 comprising the amino acid sequence of SEQ ID NO:121; (c) HVR-H3 comprising the amino acid sequence of SEQ ID NO:154; (d) HVR-L1 comprising the amino acid sequence of SEQ ID NO:181; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:90; (b) HVR-H2 comprising the amino acid sequence of SEQ ID NO:122; (c) HVR-H3 comprising the amino acid sequence of SEQ ID NO:155; (d) HVR-L1 comprising the amino acid sequence of SEQ ID NO:184; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:97; (b) HVR-H2 comprising the amino acid sequence of SEQ ID NO:123; (c) HVR-H3 comprising the amino acid sequence of SEQ ID NO:156; (d) HVR-L1 comprising the amino acid sequence of SEQ ID NO:185; (e) HVR-L2 comprising the amino acid sequence of SEQ ID NO:204; and (f) HVR-L3 comprising the amino acid sequence of SEQ ID NO:232; (a) HVR-H1 comprising the amino acid sequence of SEQ ID NO:98; (b) HVR-H2 comprising the amino acid sequence of SEQ ID NO:124; (c) HVR-H3 comprising the amino acid sequence of SEQ ID NO:157; (d) HVR-L1 comprising the amino acid sequence of SEQ ID NO:186; (e) HVR-L2 comprising the amino acid sequence of SEQ ID NO:205; and (f) HVR-L3 comprising the amino acid sequence of SEQ ID NO:233.

In another aspect, an anti-MerTK antibody comprises a heavy chain variable domain ($V_H$) sequence having at least 90%, 91%, 92%, 93%, 94%, 95%, 96%, 97%, 98%, 99%, or 100% sequence identity to an amino acid sequence selected from the group consisting of SEQ ID NOs:5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, and 39. In certain embodiments, a $V_H$ sequence having at least 90%, 91%, 92%, 93%, 94%, 95%, 96%, 97%, 98%, or 99% identity to an amino acid sequence selected from the group consisting of SEQ ID NOs: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, and 39 contains substitutions (e.g., conservative substitutions), insertions, or deletions relative to the reference sequence, but an anti-MerTK antibody comprising that sequence retains the ability to bind to MerTK. In certain embodiments, a total of 1 to 10 amino acids have been substituted, inserted, and/or deleted in SEQ ID NO: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39. In certain embodiments, a total of 1 to 5 amino acids have been substituted, inserted and/or deleted in SEQ ID NO: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39. In certain embodiments, substitutions, insertions, or deletions occur in regions outside the HVRs (i.e., in the FRs). Optionally, the anti-MerTK antibody comprises the $V_H$ sequence of SEQ ID NO: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39. including post-translational modifications of that sequence. In a particular embodiment, the $V_H$ comprises one, two or three HVRs selected from: (a) HVR-H1 comprising an amino acid sequence selected from the group consisting of SEQ ID NOs:75-98, (b) HVR-H2 comprising an amino acid sequence selected from the group consisting of SEQ ID NOs:99-124, and (c) HVR-H3 comprising an amino acid sequence selected from the group consisting of SEQ ID NOs:125-157.

In another aspect, an anti-MerTK antibody is provided, wherein the antibody comprises a light chain variable domain ($V_L$) having at least 90%, 91%, 92%, 93%, 94%, 95%, 96%, 97%, 98%, 99%, or 100% sequence identity to an amino acid sequence selected from the group consisting of SEQ ID NOs:40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, and 74. In certain embodiments, a $V_L$ sequence having at least 90%, 91%, 92%, 93%, 94%, 95%, 96%, 97%, 98%, or 99% identity to an amino acid sequence selected from the group consisting of SEQ ID NOs: 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, and 74, and contains substitutions (e.g., conservative substitutions), insertions, or deletions relative to the reference sequence, but an anti-MerTK antibody comprising that sequence retains the ability to bind to MerTK. In some embodiments, a total of 1 to 10 amino acids have been substituted, inserted and/or deleted in SEQ ID NO: 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, or 74. In certain embodiments, a total of 1 to 5 amino acids have been substituted, inserted and/or deleted in SEQ ID NO: 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, or 74. In certain embodiments, the substitutions, insertions, or deletions occur in regions outside the HVRs (i.e., in the FRs). Optionally, the anti-MerTK antibody comprises the $V_L$ sequence of SEQ ID NO: 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, or 74, including post-translational modifications of that sequence. In a particular embodiment, the $V_L$ comprises one, two or three HVRs selected from (a) HVR-L1 comprising an amino acid sequence selected from the group consisting of SEQ ID NOs:158-186, (b) HVR-L2 comprising an amino acid sequence selected from the group consisting of SEQ ID NOs: 187-205, and (c) HVR-L3 comprising an amino acid sequence selected from the group consisting of SEQ ID NOs: 207-233.

In some embodiments, an anti-MerTK antibody is provided, wherein the antibody comprises a $V_H$ as in any of the embodiments provided above, and a $V_L$ as in any of the embodiments provided above. In some embodiments, provided herein are anti-MerTK antibodies, wherein the antibody comprises a $V_H$ as in any of the embodiments provided above, and a $V_L$ as in any of the embodiments provided above. In one embodiment, the antibody comprises the $V_H$ and $V_L$ sequences in SEQ ID NOs:5-39 and SEQ ID NOs:40-74, respectively, including post-translational modifications of those sequences.

In some embodiments, provided herein are anti-MerTK antibodies comprising a heavy chain variable domain ($V_H$) and a light chain variable domain ($V_L$), wherein the $V_H$ and V_L are selected from the group consisting of: V_H comprising the amino acid sequence of SEQ ID NO:5 and V_L comprising the amino acid sequence of SEQ ID NO:40; V_H comprising the amino acid sequence of SEQ ID NO:6 and V_L comprising the amino acid sequence of SEQ ID NO:41; V_H comprising the amino acid sequence of SEQ ID NO:7 and V_L comprising the amino acid sequence of SEQ ID NO:42; V_H comprising the amino acid sequence of SEQ ID NO:8 and V_L comprising the amino acid sequence of SEQ ID NO:43; V_H comprising the amino acid sequence of SEQ ID NO:9 and V_L comprising the amino acid sequence of SEQ ID NO:44; V_H comprising the amino acid sequence of SEQ ID NO:10 and V_L comprising the amino acid sequence of SEQ ID NO:45; V_H comprising the amino acid sequence of SEQ ID NO:11 and V_L comprising the amino acid sequence of SEQ ID NO:46; V_H comprising the amino acid sequence of SEQ ID NO:12 and V_L comprising the amino acid sequence of SEQ ID NO:47; V_H comprising the amino acid sequence of SEQ ID NO:13 and V_L comprising the amino acid sequence of SEQ ID NO:48; V_H comprising the amino acid sequence of SEQ ID NO:14 and V_L comprising the amino acid sequence of SEQ ID NO:49; V_H comprising the amino acid sequence of SEQ ID NO:15 and V_L comprising the amino acid sequence of SEQ ID NO:50; V_H comprising the amino acid sequence of SEQ ID NO:16 and V_L comprising the amino acid sequence of SEQ ID NO:51; V_H comprising the amino acid sequence of SEQ ID NO:17 and V_L comprising the amino acid sequence of SEQ ID NO:52; V_H comprising the amino acid sequence of SEQ ID NO:18 and V_L comprising the amino acid sequence of SEQ ID NO:53; V_H comprising the amino acid sequence of SEQ ID NO:19 and V_L comprising the amino acid sequence of SEQ ID NO:54; V_H comprising the amino acid sequence of SEQ ID NO:20 and V_L comprising the amino acid sequence of SEQ ID NO:55; V_H comprising the amino acid sequence of SEQ ID NO:21 and V_L comprising the amino acid sequence of SEQ ID NO:56; V_H comprising the amino acid sequence of SEQ ID NO:22 and V_L comprising the amino acid sequence of SEQ ID NO:57; V_H comprising the amino acid sequence of SEQ ID NO:23 and V_L comprising the amino acid sequence of SEQ ID NO:58; V_H comprising the amino acid sequence of SEQ ID NO:24 and V_L comprising the amino acid sequence of SEQ ID NO:59; V_H comprising the amino acid sequence of SEQ ID NO:25 and V_L comprising the amino acid sequence of SEQ ID NO:60; V_H comprising the amino acid sequence of SEQ ID NO:26 and V_L comprising the amino acid sequence of SEQ ID NO:61; V_H comprising the amino acid sequence of SEQ ID NO:27 and V_L comprising the amino acid sequence of SEQ ID NO:62; V_H comprising the amino acid sequence of SEQ ID NO:28 and V_L comprising the amino acid sequence of SEQ ID NO:63; V_H comprising the amino acid sequence of SEQ ID NO:29 and V_L comprising the amino acid sequence of SEQ ID NO:64; V_H comprising the amino acid sequence of SEQ ID NO:30 and V_L comprising the amino acid sequence of SEQ ID NO:65; V_H comprising the amino acid sequence of SEQ ID NO:31 and V_L comprising the amino acid sequence of SEQ ID NO:66; V_H comprising the amino acid sequence of SEQ ID NO:32 and V_L comprising the amino acid sequence of SEQ ID NO:67; V_H comprising the amino acid sequence of SEQ ID NO:33 and V_L comprising the amino acid sequence of SEQ ID NO:68; V_H comprising the amino acid sequence of SEQ ID NO:34 and V_L comprising the amino acid sequence of SEQ ID NO:69; V_H comprising the amino acid sequence of SEQ ID NO:35 and V_L comprising the amino acid sequence of SEQ ID NO:70; V_H comprising the amino acid sequence of SEQ ID NO:36 and V_L comprising the amino acid sequence of SEQ ID NO:71; V_H comprising the amino acid sequence of SEQ ID NO:37 and V_L comprising the amino acid sequence of SEQ ID NO:72; V_H comprising the amino acid sequence of SEQ ID NO:38 and V_L comprising the amino acid sequence of SEQ ID NO:73; and V_H comprising the amino acid sequence of SEQ ID NO:39 and V_L comprising the amino acid sequence of SEQ ID NO:74.

In some embodiments, provided herein are anti-MerTK antibodies comprising at least one, two, three, four, five, or six HVRs selected from: (a) HVR-H1 comprising the amino acid sequence of SEQ ID NO:83; (b) HVR-H2 comprising an amino acid sequence selected from the group consisting of SEQ ID NOs:99, 329, 330, 331, 332, and 333; (c) HVR-H3 comprising an amino acid sequence selected from the group consisting of SEQ ID NOs:138, 334, 335, 336, 337, 338, and 339; (d) HVR-L1 comprising an amino acid sequence selected from the group consisting of SEQ ID NOs:158, 340, 341, 342, 343, and 344; (e) HVR-L2 comprising the amino acid sequence of SEQ ID NO:187; and (f) HVR-L3 comprising the amino acid sequence of SEQ ID NO:210.

In some embodiments, provided herein are anti-MerTK antibodies comprising at least one, at least two, or all three V_H HVR sequences selected from (a) HVR-H1 comprising the amino acid sequence of SEQ ID NO:83; (b) HVR-H2 comprising an amino acid sequence selected from the group consisting of SEQ ID NOs:99, 329, 330, 331, 332, and 333; and (c) HVR-H3 comprising an amino acid sequence selected from the group consisting of SEQ ID NOs:138, 334, 335, 336, 337, 338, and 339.

In some embodiments, provided herein are anti-MerTK antibodies comprising at least one, at least two, or all three V_L HVR sequences selected from (a) HVR-L1 comprising an amino acid sequence selected from the group consisting of SEQ ID NOs:158, 340, 341, 342, 343, and 344; (b) HVR-L2 comprising the amino acid sequence of SEQ ID NO:187; and (c) HVR-L3 comprising the amino acid sequence of SEQ ID NO:210.

In some embodiments, provided herein are anti-MerTK antibodies comprising (a) a V_H domain comprising at least one, at least two, or all three V_H HVR sequences selected from (i) HVR-H1 comprising the amino acid sequence of SEQ ID NO: 83, (ii) HVR-H2 comprising an amino acid sequence selected from the group consisting of SEQ ID NOs: 99, 329, 330, 331, 332, and 333, and (iii) HVR-H3 comprising an amino acid sequence selected from the group consisting of SEQ ID NOs: 138, 334, 335, 336, 337, 338, and 339, and (b) a V_L domain comprising at least one, at least two, or all three V_L HVR sequences selected from (i) HVR-L1 comprising an amino acid sequence selected from the group consisting of SEQ ID NOs: 158, 340, 341, 342, 343, and 344, (ii) HVR-L2 comprising the amino acid sequence of SEQ ID NO: 187, and (iii) HVR-L3 comprising the amino acid sequence of SEQ ID NO: 210.

In some embodiments, provided herein are anti-MerTK antibodies comprising: (a) HVR-H1 comprising the amino acid sequence of SEQ ID NO:83; (b) HVR-H2 comprising the amino acid sequence of SEQ ID NO:99; (c) HVR-H3 comprising the amino acid sequence of SEQ ID NO:138; (d) HVR-L1 comprising the amino acid sequence of SEQ ID NO:158; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO:334; (d) HVR-L1 comprising the amino acid sequence of SEQ ID NO:158; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:330; (c) HVR-H3 comprising the amino acid sequence of SEQ ID NO:138; (d) HVR-L1 comprising the amino acid sequence of SEQ ID NO:158; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO:138; (d) HVR-L1 comprising the amino acid sequence of SEQ ID NO:340; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO:138; (d) HVR-L1 comprising the amino acid sequence of SEQ ID NO:341; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO:335; (d) HVR-L1 comprising the amino acid sequence of SEQ ID NO:341; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:331; (c) HVR-H3 comprising the amino acid sequence of SEQ ID NO:138; (d) HVR-L1 comprising the amino acid sequence of SEQ ID NO:341; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO:138; (d) HVR-L1 comprising the amino acid sequence of SEQ ID NO:342; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO:336; (d) HVR-L1 comprising the amino acid sequence of SEQ ID NO:341; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO:337; (d) HVR-L1 comprising the amino acid sequence of SEQ ID NO:343; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:332; (c) HVR-H3 comprising the amino acid sequence of SEQ ID NO:338; (d) HVR-L1 comprising the amino acid sequence of SEQ ID NO:341; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:333; (c) HVR-H3 comprising the amino acid sequence of SEQ ID NO:334; (d) HVR-L1 comprising the amino acid sequence of SEQ ID NO:158; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:332; (c) HVR-H3 comprising the amino acid sequence of SEQ ID NO:336; (d) HVR-L1 comprising the amino acid sequence of SEQ ID NO:341; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO:339; (d) HVR-L1 comprising the amino acid sequence of SEQ ID NO:344; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO:138; (d) HVR-L1 comprising the amino acid sequence of SEQ ID NO:158; (e) HVR-L2 comprising the amino acid sequence of SEQ ID NO:187; and (f) HVR-L3 comprising the amino acid sequence of SEQ ID NO:210.

In another aspect, an anti-MerTK antibody comprises a heavy chain variable domain (V$_H$) sequence having at least 90%, 91%, 92%, 93%, 94%, 95%, 96%, 97%, 98%, 99%, or 100% sequence identity to an amino acid sequence selected from the group consisting of SEQ ID NOs:19, 234, 235, 236, 237, 238, 239, 240, 241, 242, 243, 244, 245, and 246. In certain embodiments, a V$_H$ sequence having at least 90%, 91%, 92%, 93%, 94%, 95%, 96%, 97%, 98%, or 99% identity to an amino acid sequence selected from the group consisting of SEQ ID NOs: 19, 234, 235, 236, 237, 238, 239, 240, 241, 242, 243, 244, 245, and 246 contains substitutions (e.g., conservative substitutions), insertions, or deletions relative to the reference sequence, but an anti-MerTK antibody comprising that sequence retains the ability to bind to MerTK. In certain embodiments, a total of 1 to 10 amino acids have been substituted, inserted, and/or deleted in SEQ ID NO: 19, 234, 235, 236, 237, 238, 239, 240, 241, 242, 243, 244, 245, or 246. In certain embodiments, a total of 1 to 5 amino acids have been substituted, inserted and/or deleted in SEQ ID NO: 19, 234, 235, 236, 237, 238, 239, 240, 241, 242, 243, 244, 245, or 246. In certain embodiments, substitutions, insertions, or deletions occur in regions outside the HVRs (i.e., in the FRs). Optionally, the anti-MerTK antibody comprises the V$_H$ sequence of SEQ ID NO: 19, 234, 235, 236, 237, 238, 239, 240, 241, 242, 243, 244, 245, or 246, including post-translational modifications of that sequence. In a particular embodiment, the V$_H$ comprises one, two or three HVRs selected from: (a) HVR-H1 comprising the amino acid sequence of SEQ ID NO:83, (b) HVR-H2 comprising an amino acid sequence selected from the group consisting of SEQ ID NOs:99, 329, 330, 331, 332, and 333, and (c) HVR-H3 comprising an amino acid sequence selected from the group consisting of SEQ ID NOs:138, 334, 335, 336, 337, 338, and 339.

In another aspect, an anti-MerTK antibody is provided, wherein the antibody comprises a light chain variable domain (V$_L$) having at least 90%, 91%, 92%, 93%, 94%, 95%, 96%, 97%, 98%, 99%, or 100% sequence identity to an amino acid sequence selected from the group consisting of SEQ ID NOs:54, 247, 248, 249, 250, 251, 252, 253, and 254. In certain embodiments, a V$_L$ sequence having at least 90%, 91%, 92%, 93%, 94%, 95%, 96%, 97%, 98%, or 99% identity to an amino acid sequence selected from the group consisting of SEQ ID NOs: 54, 247, 248, 249, 250, 251, 252, 253, and 254, and contains substitutions (e.g., conservative substitutions), insertions, or deletions relative to the reference sequence, but an anti-MerTK antibody comprising that sequence retains the ability to bind to MerTK. In some embodiments, a total of 1 to 10 amino acids have been substituted, inserted and/or deleted in SEQ ID NO: 54, 247, 248, 249, 250, 251, 252, 253, or 254. In certain embodiments, a total of 1 to 5 amino acids have been substituted, inserted and/or deleted in SEQ ID NO: 54, 247, 248, 249, 250, 251, 252, 253, or 254. In certain embodiments, the substitutions, insertions, or deletions occur in regions outside the HVRs (i.e., in the FRs). Optionally, the anti-MerTK antibody comprises the V$_L$ sequence of SEQ ID NO: 54, 247, 248, 249, 250, 251, 252, 253, or 254, including post-translational modifications of that sequence. In a particular embodiment, the V$_L$ comprises one, two or three HVRs selected from (a) HVR-L1 comprising an amino acid sequence selected from the group consisting of SEQ ID NOs:158, 340, 341, 342, 343, and 344, (b) HVR-L2 comprising the amino acid sequence of SEQ ID NO: 187, and (c) HVR-L3 comprising the amino acid sequence of SEQ ID NO: 210.

In some embodiments, an anti-MerTK antibody is provided, wherein the antibody comprises a V$_H$ as in any of the embodiments provided above, and a V$_L$ as in any of the embodiments provided above. In some embodiments, provided herein are anti-MerTK antibodies, wherein the antibody comprises a V$_H$ as in any of the embodiments provided above, and a V$_L$ as in any of the embodiments provided above. In one embodiment, the antibody comprises the V$_H$ and V$_L$ sequences in SEQ ID NOs:19, 234, 235, 236, 237, 238, 239, 240, 241, 242, 243, 244, 245, and 246 and SEQ ID NOs:54, 247, 248, 249, 250, 251, 252, 253, and 258, respectively, including post-translational modifications of those sequences.

In some embodiments, provided herein are anti-MerTK antibodies comprising a heavy chain variable domain (V$_H$) and a light chain variable domain (V$_L$), wherein the V$_H$ and V$_L$ are selected from the group consisting of: V$_H$ comprising the amino acid sequence of SEQ ID NO:19 and V$_L$ comprising the amino acid sequence of SEQ ID NO:54; V$_H$ comprising the amino acid sequence of SEQ ID NO:234 and V$_L$ comprising the amino acid sequence of SEQ ID NO:247; V$_H$ comprising the amino acid sequence of SEQ ID NO:235 and V$_L$ comprising the amino acid sequence of SEQ ID NO:247; V$_H$ comprising the amino acid sequence of SEQ ID NO:236 and V$_L$ comprising the amino acid sequence of SEQ ID NO:248; V$_H$ comprising the amino acid sequence of SEQ ID NO:236 and V$_L$ comprising the amino acid sequence of SEQ ID NO:249; V$_H$ comprising the amino acid sequence of SEQ ID NO:237 and V$_L$ comprising the amino acid sequence of SEQ ID NO:249; V$_H$ comprising the amino acid sequence of SEQ ID NO:238 and V$_L$ comprising the amino acid sequence of SEQ ID NO:249; V$_H$ comprising the amino acid sequence of SEQ ID NO:239 and V$_L$ comprising the amino acid sequence of SEQ ID NO:250; V$_H$ comprising the amino acid sequence of SEQ ID NO:240 and V$_L$ comprising the amino acid sequence of SEQ ID NO:251; V$_H$ comprising the amino acid sequence of SEQ ID NO:241 and V$_L$ comprising the amino acid sequence of SEQ ID NO:252; V$_H$ comprising the amino acid sequence of SEQ ID NO:242 and V$_L$ comprising the amino acid sequence of SEQ ID NO:249; V$_H$ comprising the amino acid sequence of SEQ ID NO:243 and V$_L$ comprising the amino acid sequence of SEQ ID NO:247; V$_H$ comprising the amino acid sequence of SEQ ID NO:244 and V$_L$ comprising the amino acid sequence of SEQ ID NO:251; V$_H$ comprising the amino acid sequence of SEQ ID NO:245 and V$_L$ comprising the amino acid sequence of SEQ ID NO:253; V$_H$ comprising the amino acid sequence of SEQ ID NO:246 and V$_L$ comprising the amino acid sequence of SEQ ID NO:247; and V$_H$ comprising the amino acid sequence of SEQ ID NO:246 and V$_L$ comprising the amino acid sequence of SEQ ID NO:254.

In some embodiments, provided herein are anti-MerTK antibodies comprising at least one, two, three, four, five, or six HVRs selected from: (a) HVR-H1 comprising the amino acid sequence of SEQ ID NO:84; (b) HVR-H2 comprising an amino acid sequence selected from the group consisting of SEQ ID NOs:99 and 329; (c) HVR-H3 comprising the amino acid sequence of SEQ ID NO:139; (d) HVR-L1 comprising an amino acid sequence selected from the group consisting of SEQ ID NOs:169 and 345; (e) HVR-L2 comprising the amino acid sequence of SEQ ID NO:195; and (f) HVR-L3 comprising the amino acid sequence of SEQ ID NO:219.

In some embodiments, provided herein are anti-MerTK antibodies comprising at least one, at least two, or all three V$_H$ HVR sequences selected from (a) HVR-H1 comprising the amino acid sequence of SEQ ID NO:84; (b) HVR-H2 comprising an amino acid sequence selected from the group consisting of SEQ ID NOs:99 and 329; and (c) HVR-H3 comprising the amino acid sequence of SEQ ID NO:139.

In some embodiments, provided herein are anti-MerTK antibodies comprising at least one, at least two, or all three V$_L$ HVR sequences selected from (a) HVR-L1 comprising an amino acid sequence selected from the group consisting of SEQ ID NOs:169 and 345; (b) HVR-L2 comprising the amino acid sequence of SEQ ID NO:195; and (c) HVR-L3 comprising the amino acid sequence of SEQ ID NO:219.

In some embodiments, provided herein are anti-MerTK antibodies comprising (a) a V$_H$ domain comprising at least one, at least two, or all three V$_H$ HVR sequences selected from (i) HVR-H1 comprising the amino acid sequence of SEQ ID NO: 84, (ii) HVR-H2 comprising an amino acid sequence selected from the group consisting of SEQ ID NOs: 99, 329, and (iii) HVR-H3 comprising the amino acid sequence of SEQ ID NO: 139, and (b) a V$_L$ domain comprising at least one, at least two, or all three V$_L$ HVR sequences selected from (i) HVR-L1 comprising an amino acid sequence selected from the group consisting of SEQ ID NOs: 169 and 345, (ii) HVR-L2 comprising the amino acid sequence of SEQ ID NO: 195, and (iii) HVR-L3 comprising the amino acid sequence of SEQ ID NO: 219.

In some embodiments, provided herein are anti-MerTK antibodies comprising: (a) HVR-H1 comprising the amino acid sequence of SEQ ID NO:84; (b) HVR-H2 comprising the amino acid sequence of SEQ ID NO:99; (c) HVR-H3 comprising the amino acid sequence of SEQ ID NO:139; (d) HVR-L1 comprising the amino acid sequence of SEQ ID NO:169; (e) HVR-L2 comprising the amino acid sequence of SEQ ID NO:195; and (f) HVR-L3 comprising the amino acid sequence of SEQ ID NO:219; (a) HVR-H1 comprising the amino acid sequence of SEQ ID NO:84; (b) HVR-H2 comprising the amino acid sequence of SEQ ID NO:329; (c) HVR-H3 comprising the amino acid sequence of SEQ ID NO:139; (d) HVR-L1 comprising the amino acid sequence of SEQ ID NO:169; (e) HVR-L2 comprising the amino acid sequence of SEQ ID NO:195; and (f) HVR-L3 comprising the amino acid sequence of SEQ ID NO:219; and (a) HVR-H1 comprising the amino acid sequence of SEQ ID NO:84; (b) HVR-H2 comprising the amino acid sequence of SEQ ID NO:99; (c) HVR-H3 comprising the amino acid sequence of SEQ ID NO:139; (d) HVR-L1 comprising the amino acid sequence of SEQ ID NO:345; (e) HVR-L2 comprising the amino acid sequence of SEQ ID NO:195; and (f) HVR-L3 comprising the amino acid sequence of SEQ ID NO:219.

In another aspect, an anti-MerTK antibody comprises a heavy chain variable domain ($V_H$) sequence having at least 90%, 91%, 92%, 93%, 94%, 95%, 96%, 97%, 98%, 99%, or 100% sequence identity to an amino acid sequence selected from the group consisting of SEQ ID NOs:20, 255, and 256. In certain embodiments, a $V_H$ sequence having at least 90%, 91%, 92%, 93%, 94%, 95%, 96%, 97%, 98%, or 99% identity to an amino acid sequence selected from the group consisting of SEQ ID NOs: 20, 255, and 256 contains substitutions (e.g., conservative substitutions), insertions, or deletions relative to the reference sequence, but an anti-MerTK antibody comprising that sequence retains the ability to bind to MerTK. In certain embodiments, a total of 1 to 10 amino acids have been substituted, inserted, and/or deleted in SEQ ID NO: 20, 255, or 256. In certain embodiments, a total of 1 to 5 amino acids have been substituted, inserted and/or deleted in SEQ ID NO: 20, 255, or 256. In certain embodiments, substitutions, insertions, or deletions occur in regions outside the HVRs (i.e., in the FRs). Optionally, the anti-MerTK antibody comprises the $V_H$ sequence of SEQ ID NO: 20, 255, or 256, including post-translational modifications of that sequence. In a particular embodiment, the $V_H$ comprises one, two or three HVRs selected from: (a) HVR-H1 comprising the amino acid sequence of SEQ ID NO:84, (b) HVR-H2 comprising an amino acid sequence selected from the group consisting of SEQ ID NOs:99 and 329, and (c) HVR-H3 comprising the amino acid sequence of SEQ ID NO:139.

In another aspect, an anti-MerTK antibody is provided, wherein the antibody comprises a light chain variable domain ($V_L$) having at least 90%, 91%, 92%, 93%, 94%, 95%, 96%, 97%, 98%, 99%, or 100% sequence identity to an amino acid sequence selected from the group consisting of SEQ ID NOs:55, 257, and 258. In certain embodiments, a $V_L$ sequence having at least 90%, 91%, 92%, 93%, 94%, 95%, 96%, 97%, 98%, or 99% identity to an amino acid sequence selected from the group consisting of SEQ ID NOs: 55, 257, and 258, and contains substitutions (e.g., conservative substitutions), insertions, or deletions relative to the reference sequence, but an anti-MerTK antibody comprising that sequence retains the ability to bind to MerTK. In some embodiments, a total of 1 to 10 amino acids have been substituted, inserted and/or deleted in SEQ ID NO: 55, 257, or 258. In certain embodiments, a total of 1 to 5 amino acids have been substituted, inserted and/or deleted in SEQ ID NO: 55, 257, or 258. In certain embodiments, the substitutions, insertions, or deletions occur in regions outside the HVRs (i.e., in the FRs). Optionally, the anti-MerTK antibody comprises the $V_L$ sequence of SEQ ID NO: 55, 257, or 258, including post-translational modifications of that sequence. In a particular embodiment, the $V_L$ comprises one, two or three HVRs selected from (a) HVR-L1 comprising an amino acid sequence selected from the group consisting of SEQ ID NOs:169 and 345, (b) HVR-L2 comprising the amino acid sequence of SEQ ID NO: 195, and (c) HVR-L3 comprising the amino acid sequence of SEQ ID NO: 219.

In some embodiments, an anti-MerTK antibody is provided, wherein the antibody comprises a $V_H$ as in any of the embodiments provided above, and a $V_L$ as in any of the embodiments provided above. In some embodiments, provided herein are anti-MerTK antibodies, wherein the antibody comprises a $V_H$ as in any of the embodiments provided above, and a $V_L$ as in any of the embodiments provided above. In one embodiment, the antibody comprises the $V_H$ and $V_L$ sequences in SEQ ID NOs:20, 255, and 256 and SEQ ID NOs:55, 257, and 258, respectively, including post-translational modifications of those sequences.

In some embodiments, provided herein are anti-MerTK antibodies comprising a heavy chain variable domain ($V_H$) and a light chain variable domain ($V_L$), wherein the $V_H$ and $V_L$ are selected from the group consisting of: $V_H$ comprising the amino acid sequence of SEQ ID NO:20 and $V_L$ comprising the amino acid sequence of SEQ ID NO:55; $V_H$ comprising the amino acid sequence of SEQ ID NO:255 and $V_L$ comprising the amino acid sequence of SEQ ID NO:257; and $V_H$ comprising the amino acid sequence of SEQ ID NO:256 and $V_L$ comprising the amino acid sequence of SEQ ID NO:258.

In some embodiments, provided herein are anti-MerTK antibodies comprising at least one, two, three, four, five, or six HVRs selected from: (a) HVR-H1 comprising an amino acid sequence selected from the group consisting of SEQ ID NOs:95, 346, and 347; (b) HVR-H2 comprising an amino acid sequence selected from the group consisting of SEQ ID NOs:119, 348, 349, 350, 351, 352, 353, and 354; (c) HVR-H3 comprising an amino acid sequence selected from the group consisting of SEQ ID NOs:151, 355, and 356; (d) HVR-L1 comprising an amino acid sequence selected from the group consisting of SEQ ID NOs:181, 341, 357, and 358; (e) HVR-L2 comprising an amino acid sequence selected from the group consisting of SEQ ID NOs:187 and 359; and (f) HVR-L3 comprising an amino acid sequence selected from the group consisting of SEQ ID NOs:208, 360, 361, and 362.

In some embodiments, provided herein are anti-MerTK antibodies comprising at least one, at least two, or all three $V_H$ HVR sequences selected from (a) HVR-H1 comprising an amino acid sequence selected from the group consisting of SEQ ID NOs:95, 346, and 347; (b) HVR-H2 comprising an amino acid sequence selected from the group consisting of SEQ ID NOs:119, 348, 349, 350, 351, 352, 353, and 354; and (c) HVR-H3 comprising an amino acid sequence selected from the group consisting of SEQ ID NOs:151, 355, and 356.

In some embodiments, provided herein are anti-MerTK antibodies comprising at least one, at least two, or all three $V_L$ HVR sequences selected from (a) HVR-L1 comprising an amino acid sequence selected from the group consisting of SEQ ID NOs:181, 341, 357, and 358; (b) HVR-L2 comprising an amino acid sequence selected from the group consisting of SEQ ID NOs:187 and 359; and (c) HVR-L3 comprising an amino acid sequence selected from the group consisting of SEQ ID NO:208. 360, 361, and 362.

In some embodiments, provided herein are anti-MerTK antibodies comprising (a) a $V_H$ domain comprising at least one, at least two, or all three $V_H$ HVR sequences selected from (i) HVR-H1 comprising an amino acid sequence selected from the group consisting of SEQ ID NOs: 95, 346, and 347, (ii) HVR-H2 comprising an amino acid sequence selected from the group consisting of SEQ ID NOs: 119, 348, 349, 350, 351, 352, 353, and 354, and (iii) HVR-H3 comprising an amino acid sequence selected from the group consisting of SEQ ID NOs: 151, 355, and 356, and (b) a $V_L$ domain comprising at least one, at least two, or all three $V_L$ HVR sequences selected from (i) HVR-L1 comprising an amino acid sequence selected from the group consisting of SEQ ID NOs: 181, 341, 357, and 358, (ii) HVR-L2 comprising an amino acid sequence selected from the group consisting of SEQ ID NOs: 187 and 359, and (iii) HVR-L3 comprising an amino acid sequence selected from the group consisting of SEQ ID NOs: 208, 360, 361, and 362.

In some embodiments, provided herein are anti-MerTK antibodies comprising: (a) HVR-H1 comprising the amino acid sequence of SEQ ID NO:95; (b) HVR-H2 comprising the amino acid sequence of SEQ ID NO:119; (c) HVR-H3 comprising the amino acid sequence of SEQ ID NO:151; (d) HVR-L1 comprising the amino acid sequence of SEQ ID NO:181; (e) HVR-L2 comprising the amino acid sequence of SEQ ID NO:187; and (f) HVR-L3 comprising the amino acid sequence of SEQ ID NO:208; (a) HVR-H1 comprising the amino acid sequence of SEQ ID NO:346; (b) HVR-H2 comprising the amino acid sequence of SEQ ID NO:348; (c) HVR-H3 comprising the amino acid sequence of SEQ ID NO:355; (d) HVR-L1 comprising the amino acid sequence of SEQ ID NO:341; (e) HVR-L2 comprising the amino acid sequence of SEQ ID NO:187; and (f) HVR-L3 comprising the amino acid sequence of SEQ ID NO:360; (a) HVR-H1 comprising the amino acid sequence of SEQ ID NO:95; (b) HVR-H2 comprising the amino acid sequence of SEQ ID NO:119; (c) HVR-H3 comprising the amino acid sequence of SEQ ID NO:355; (d) HVR-L1 comprising the amino acid sequence of SEQ ID NO:341; (e) HVR-L2 comprising the amino acid sequence of SEQ ID NO:187; and (f) HVR-L3 comprising the amino acid sequence of SEQ ID NO:361; (a) HVR-H1 comprising the amino acid sequence of SEQ ID NO:95; (b) HVR-H2 comprising the amino acid sequence of SEQ ID NO:349; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:187; and (f) HVR-L3 comprising the amino acid sequence of SEQ ID NO:362; (a) HVR-H1 comprising the amino acid sequence of SEQ ID NO:95; (b) HVR-H2 comprising the amino acid sequence of SEQ ID NO:119; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:359; and (f) HVR-L3 comprising the amino acid sequence of SEQ ID NO:362; (a) HVR-H1 comprising the amino acid sequence of SEQ ID NO:346; (b) HVR-H2 comprising the amino acid sequence of SEQ ID NO:119; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:359; and (f) HVR-L3 comprising the amino acid sequence of SEQ ID NO:362; (a) HVR-H1 comprising the amino acid sequence of SEQ ID NO:95; (b) HVR-H2 comprising the amino acid sequence of SEQ ID NO:350 (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:359; and (f) HVR-L3 comprising the amino acid sequence of SEQ ID NO:362; (a) HVR-H1 comprising the amino acid sequence of SEQ ID NO:347; (b) HVR-H2 comprising the amino acid sequence of SEQ ID NO:119; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:359; and (f) HVR-L3 comprising the amino acid sequence of SEQ ID NO:362; (a) HVR-H1 comprising the amino acid sequence of SEQ ID NO:95; (b) HVR-H2 comprising the amino acid sequence of SEQ ID NO:119; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:187; and (f) HVR-L3 comprising the amino acid sequence of SEQ ID NO:362; (a) HVR-H1 comprising the amino acid sequence of SEQ ID NO:95; (b) HVR-H2 comprising the amino acid sequence of SEQ ID NO:352; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:187; and (f) HVR-L3 comprising the amino acid sequence of SEQ ID NO:362; (a) HVR-H1 comprising the amino acid sequence of SEQ ID NO:95; (b) HVR-H2 comprising the amino acid sequence of SEQ ID NO:353; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:359; and (f) HVR-L3 comprising the amino acid sequence of SEQ ID NO:362; (a) HVR-H1 comprising the amino acid sequence of SEQ ID NO:346; (b) HVR-H2 comprising the amino acid sequence of SEQ ID NO:354; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:359; and (f) HVR-L3 comprising the amino acid sequence of SEQ ID NO:363; (a) HVR-H1 comprising the amino acid sequence of SEQ ID NO:346; (b) HVR-H2 comprising the amino acid sequence of SEQ ID NO:348; (c) HVR-H3 comprising the amino acid sequence of SEQ ID NO:356; (d) HVR-L1 comprising the amino acid sequence of SEQ ID NO:357; (e) HVR-L2 comprising the amino acid sequence of SEQ ID NO:359; and (f) HVR-L3 comprising the amino acid sequence of SEQ ID NO:362; (a) HVR-H1 comprising the amino acid sequence of SEQ ID NO:346; (b) HVR-H2 comprising the amino acid sequence of SEQ ID NO:354; (c) HVR-H3 comprising the amino acid sequence of SEQ ID NO:356; (d) HVR-L1 comprising the amino acid sequence of SEQ ID NO:358; (e) HVR-L2 comprising the amino acid sequence of SEQ ID NO:187; and (f) HVR-L3 comprising the amino acid sequence of SEQ ID NO:362; (a) HVR-H1 comprising the amino acid sequence of SEQ ID NO:95; (b) HVR-H2 comprising the amino acid sequence of SEQ ID NO:348; (c) HVR-H3 comprising the amino acid sequence of SEQ ID NO:151; (d) HVR-L1 comprising the amino acid sequence of SEQ ID NO:181; (e) HVR-L2 comprising the amino acid sequence of SEQ ID NO:187; and (f) HVR-L3 comprising the amino acid sequence of SEQ ID NO:208.

In another aspect, an anti-MerTK antibody comprises a heavy chain variable domain ($V_H$) sequence having at least 90%, 91%, 92%, 93%, 94%, 95%, 96%, 97%, 98%, 99%, or 100% sequence identity to an amino acid sequence selected from the group consisting of SEQ ID NOs:33, 259, 260, 261, 262, 263, 264, 265, 266, 267, 268, 269, 270, 271, 272, and 273. In certain embodiments, a $V_H$ sequence having at least 90%, 91%, 92%, 93%, 94%, 95%, 96%, 97%, 98%, or 99% identity to an amino acid sequence selected from the group consisting of SEQ ID NOs: 33, 259, 260, 261, 262, 263, 264, 265, 266, 267, 268, 269, 270, 271, 272, and 273 contains substitutions (e.g., conservative substitutions), insertions, or deletions relative to the reference sequence, but an anti- MerTK antibody comprising that sequence retains the ability to bind to MerTK. In certain embodiments, a total of 1 to 10 amino acids have been substituted, inserted, and/or deleted in SEQ ID NO: 33, 259, 260, 261, 262, 263, 264, 265, 266, 267, 268, 269, 270, 271, 272, or 273. In certain embodiments, a total of 1 to 5 amino acids have been substituted, inserted and/or deleted in SEQ ID NO: 33, 259, 260, 261, 262, 263, 264, 265, 266, 267, 268, 269, 270, 271, 272, or 273. In certain embodiments, substitutions, insertions, or deletions occur in regions outside the HVRs (i.e., in the FRs). Optionally, the anti-MerTK antibody comprises the $V_H$ sequence of SEQ ID NO: 33, 259, 260, 261, 262, 263, 264, 265, 266, 267, 268, 269, 270, 271, 272, or 273, including post-translational modifications of that sequence. In a particular embodiment, the $V_H$ comprises one, two or three HVRs selected from: (a) HVR-H1 comprising an amino acid sequence selected from the group consisting of SEQ ID NOs:95, 346, and 347, (b) HVR-H2 comprising an amino acid sequence selected from the group consisting of SEQ ID NOs:119, 348, 349, 350, 351, 352, 353, and 354, and (c) HVR-H3 comprising an amino acid sequence selected from the group consisting of SEQ ID NOs:151, 355, and 356.

In another aspect, an anti-MerTK antibody is provided, wherein the antibody comprises a light chain variable domain ($V_L$) having at least 90%, 91%, 92%, 93%, 94%, 95%, 96%, 97%, 98%, 99%, or 100% sequence identity to an amino acid sequence selected from the group consisting of SEQ ID NOs:68, 274, 275, 276, 277, 278, 279, 280, 281, 282, 283, 284, 285, 286, 287, 288, and 289. In certain embodiments, a $V_L$ sequence having at least 90%, 91%, 92%, 93%, 94%, 95%, 96%, 97%, 98%, or 99% identity to an amino acid sequence selected from the group consisting of SEQ ID NOs: 68, 274, 275, 276, 277, 278, 279, 280, 281, 282, 283, 284, 285, 286, 287, 288, and 289, and contains substitutions (e.g., conservative substitutions), insertions, or deletions relative to the reference sequence, but an anti-MerTK antibody comprising that sequence retains the ability to bind to MerTK. In some embodiments, a total of 1 to 10 amino acids have been substituted, inserted and/or deleted in SEQ ID NO: 68, 274, 275, 276, 277, 278, 279, 280, 281, 282, 283, 284, 285, 286, 287, 288, or 289. In certain embodiments, a total of 1 to 5 amino acids have been substituted, inserted and/or deleted in SEQ ID NO: 68, 274, 275, 276, 277, 278, 279, 280, 281, 282, 283, 284, 285, 286, 287, 288, or 289. In certain embodiments, the substitutions, insertions, or deletions occur in regions outside the HVRs (i.e., in the FRs). Optionally, the anti-MerTK antibody comprises the $V_L$ sequence of SEQ ID NO: 68, 274, 275, 276, 277, 278, 279, 280, 281, 282, 283, 284, 285, 286, 287, 288, or 289, including post-translational modifications of that sequence. In a particular embodiment, the $V_L$ comprises one, two or three HVRs selected from (a) HVR-L1 comprising an amino acid sequence selected from the group consisting of SEQ ID NOs:181, 341, 357, and 358, (b) HVR-L2 comprising an amino acid sequence selected from the group consisting of SEQ ID NOs: 187 and 359, and (c) HVR-L3 comprising an amino acid sequence selected from the group consisting of SEQ ID NOs: 208, 360, 361, and 362.

In some embodiments, an anti-MerTK antibody is provided, wherein the antibody comprises a $V_H$ as in any of the embodiments provided above, and a $V_L$ as in any of the embodiments provided above. In some embodiments, provided herein are anti-MerTK antibodies, wherein the antibody comprises a $V_H$ as in any of the embodiments provided above, and a $V_L$ as in any of the embodiments provided above. In one embodiment, the antibody comprises the $V_H$ and $V_L$ sequences in SEQ ID NOs: 33, 259, 260, 261, 262, 263, 264, 265, 266, 267, 268, 269, 270, 271, 272, and 273 and SEQ ID NOs: 68, 274, 275, 276, 277, 278, 279, 280, 281, 282, 283, 284, 285, 286, 287, 288, and 289, respectively, including post-translational modifications of those sequences.

In some embodiments, provided herein are anti-MerTK antibodies comprising a heavy chain variable domain ($V_H$) and a light chain variable domain ($V_L$), wherein the $V_H$ and $V_L$ are selected from the group consisting of: $V_H$ comprising the amino acid sequence of SEQ ID NO:33 and $V_L$ comprising the amino acid sequence of SEQ ID NO:68; $V_H$ comprising the amino acid sequence of SEQ ID NO:259 and $V_L$ comprising the amino acid sequence of SEQ ID NO:274; $V_H$ comprising the amino acid sequence of SEQ ID NO:260 and $V_L$ comprising the amino acid sequence of SEQ ID NO:275; $V_H$ comprising the amino acid sequence of SEQ ID NO:261 and $V_L$ comprising the amino acid sequence of SEQ ID NO:276; $V_H$ comprising the amino acid sequence of SEQ ID NO:262 and $V_L$ comprising the amino acid sequence of SEQ ID NO:277; $V_H$ comprising the amino acid sequence of SEQ ID NO:263 and $V_L$ comprising the amino acid sequence of SEQ ID NO:277; $V_H$ comprising the amino acid sequence of SEQ ID NO:264 and $V_L$ comprising the amino acid sequence of SEQ ID NO:277; $V_H$ comprising the amino acid sequence of SEQ ID NO:265 and $V_L$ comprising the amino acid sequence of SEQ ID NO:277; $V_H$ comprising the amino acid sequence of SEQ ID NO:266 and $V_L$ comprising the amino acid sequence of SEQ ID NO:277; $V_H$ comprising the amino acid sequence of SEQ ID NO:267 and $V_L$ comprising the amino acid sequence of SEQ ID NO:278; $V_H$ comprising the amino acid sequence of SEQ ID NO:268 and $V_L$ comprising the amino acid sequence of SEQ ID NO:279; $V_H$ comprising the amino acid sequence of SEQ ID NO:269 and $V_L$ comprising the amino acid sequence of SEQ ID NO:279; $V_H$ comprising the amino acid sequence of SEQ ID NO:264 and $V_L$ comprising the amino acid sequence of SEQ ID NO:280; $V_H$ comprising the amino acid sequence of SEQ ID NO:270 and $V_L$ comprising the amino acid sequence of SEQ ID NO:281; $V_H$ comprising the amino acid sequence of SEQ ID NO:265 and $V_L$ comprising the amino acid sequence of SEQ ID NO:282; $V_H$ comprising the amino acid sequence of SEQ ID NO:264 and $V_L$ comprising the amino acid sequence of SEQ ID NO:283; $V_H$ comprising the amino acid sequence of SEQ ID NO:271 and $V_L$ comprising the amino acid sequence of SEQ ID NO:284; $V_H$ comprising the amino acid sequence of SEQ ID NO:272 and $V_L$ comprising the amino acid sequence of SEQ ID NO:285; $V_H$ comprising the amino acid sequence of SEQ ID NO:271 and $V_L$ comprising the amino acid sequence of SEQ ID NO:286; $V_H$ comprising the amino acid sequence of SEQ ID NO:273 and $V_L$ comprising the amino acid sequence of SEQ ID NO:287; $V_H$ comprising the amino acid sequence of SEQ ID NO:273 and $V_L$ comprising the amino acid sequence of SEQ ID NO:288; and $V_H$ comprising the amino acid sequence of SEQ ID NO:273 and $V_L$ comprising the amino acid sequence of SEQ ID NO:289.

In some embodiments, provided herein are anti-MerTK antibodies comprising at least one, two, three, four, five, or six HVRs selected from: (a) HVR-H1 comprising the amino acid sequence of SEQ ID NO:90; (b) HVR-H2 comprising an amino acid sequence selected from the group consisting of SEQ ID NOs:122, 364, 365, 366, 367, and 368; (c) HVR-H3 comprising an amino acid sequence selected from the group consisting of SEQ ID NOs:155, 373, 374, and 375; (d) HVR-L1 comprising an amino acid sequence selected from the group consisting of SEQ ID NOs:184, 376, 377, 378, 379, 380, 381, 382, 383, 384, 385, 386, and 387; (e) HVR-L2 comprising an amino acid sequence selected from the group consisting of SEQ ID NOs:203, 388, 389, 390, and 391; and (f) HVR-L3 comprising an amino acid sequence selected from the group consisting of SEQ ID NOs:231, 392, 393, and 394.

In some embodiments, provided herein are anti-MerTK antibodies comprising at least one, at least two, or all three $V_H$ HVR sequences selected from (a) HVR-H1 comprising the amino acid sequence of SEQ ID NO:90; (b) HVR-H2 comprising an amino acid sequence selected from the group consisting of SEQ ID NOs: 122, 364, 365, 366, 367, and 368; and (c) HVR-H3 comprising an amino acid sequence selected from the group consisting of SEQ ID NOs: 155, 373, 374, and 375.

In some embodiments, provided herein are anti-MerTK antibodies comprising at least one, at least two, or all three $V_L$ HVR sequences selected from (a) HVR-L1 comprising an amino acid sequence selected from the group consisting of SEQ ID NOs: 184, 376, 377, 378, 379, 380, 381, 382, 383, 384, 385, 386, and 387; (b) HVR-L2 comprising an amino acid sequence selected from the group consisting of SEQ ID NOs: 203, 388, 389, 390, and 391 and (c) HVR-L3 comprising an amino acid sequence selected from the group consisting of SEQ ID NOs: 203, 388, 389, 390, and 391

In some embodiments, provided herein are anti-MerTK antibodies comprising (a) a $V_H$ domain comprising at least one, at least two, or all three $V_H$ HVR sequences selected from (i) HVR-H1 comprising the amino acid sequence of SEQ ID NO: 90, (ii) HVR-H2 comprising an amino acid sequence selected from the group consisting of SEQ ID NOs: 122, 364, 365, 366, 367, and 368, and (iii) HVR-H3 comprising an amino acid sequence selected from the group consisting of SEQ ID NOs: 155, 373, 374, and 375, and (b) a $V_L$ domain comprising at least one, at least two, or all three $V_L$ HVR sequences selected from (i) HVR-L1 comprising an amino acid sequence selected from the group consisting of SEQ ID NOs: 184, 376, 377, 378, 379, 380, 381, 382, 383, 384, 385, 386, and 387, (ii) HVR-L2 comprising an amino acid sequence selected from the group consisting of SEQ ID NOs: 203, 388, 389, 390, and 391, and (iii) HVR-L3 comprising an amino acid sequence selected from the group consisting of SEQ ID NOs: 231, 392, 393, and 394.

In some embodiments, provided herein are anti-MerTK antibodies comprising: (a) HVR-H1 comprising the amino acid sequence of SEQ ID NO:90; (b) HVR-H2 comprising the amino acid sequence of SEQ ID NO:122; (c) HVR-H3 comprising the amino acid sequence of SEQ ID NO:155; (d) HVR-L1 comprising the amino acid sequence of SEQ ID NO:184; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:364; (c) HVR-H3 comprising the amino acid sequence of SEQ ID NO:373; (d) HVR-L1 comprising the amino acid sequence of SEQ ID NO:376; (e) HVR-L2 comprising the amino acid sequence of SEQ ID NO:388; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:364; (c) HVR-H3 comprising the amino acid sequence of SEQ ID NO:155; (d) HVR-L1 comprising the amino acid sequence of SEQ ID NO:377; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:364; (c) HVR-H3 comprising the amino acid sequence of SEQ ID NO:374; (d) HVR-L1 comprising the amino acid sequence of SEQ ID NO:378; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:95; (b) HVR-H2 comprising the amino acid sequence of SEQ ID NO:119; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:359; and (f) HVR-L3 comprising the amino acid sequence of SEQ ID NO:362; (a) HVR-H1 comprising the amino acid sequence of SEQ ID NO:90; (b) HVR-H2 comprising the amino acid sequence of SEQ ID NO:365; (c) HVR-H3 comprising the amino acid sequence of SEQ ID NO:155; (d) HVR-L1 comprising the amino acid sequence of SEQ ID NO:276; (e) HVR-L2 comprising the amino acid sequence of SEQ ID NO:203; and (f) HVR-L3 comprising the amino acid sequence of SEQ ID NO:392; (a) HVR-H1 comprising the amino acid sequence of SEQ ID NO:90; (b) HVR-H2 comprising the amino acid sequence of SEQ ID NO:364; (c) HVR-H3 comprising the amino acid sequence of SEQ ID NO:155; (d) HVR-L1 comprising the amino acid sequence of SEQ ID NO:376; (e) HVR-L2 comprising the amino acid sequence of SEQ ID NO:389; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:364; (c) HVR-H3 comprising the amino acid sequence of SEQ ID NO:155; (d) HVR-L1 comprising the amino acid sequence of SEQ ID NO:379; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:366; (c) HVR-H3 comprising the amino acid sequence of SEQ ID NO:155; (d) HVR-L1 comprising the amino acid sequence of SEQ ID NO:380; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:364; (c) HVR-H3 comprising the amino acid sequence of SEQ ID NO:373; (d) HVR-L1 comprising the amino acid sequence of SEQ ID NO:381; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:367; (c) HVR-H3 comprising the amino acid sequence of SEQ ID NO:155; (d) HVR-L1 comprising the amino acid sequence of SEQ ID NO:382; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO:155; (d) HVR-L1 comprising the amino acid sequence of SEQ ID NO:383; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:364; (c) HVR-H3 comprising the amino acid sequence of SEQ ID NO:374; (d) HVR-L1 comprising the amino acid sequence of SEQ ID NO:384; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO:155; (d) HVR-L1 comprising the amino acid sequence of SEQ ID NO:376; (e) HVR-L2 comprising the amino acid sequence of SEQ ID NO:203; and (f) HVR-L3 comprising the amino acid sequence of SEQ ID NO:393; (a) HVR-H1 comprising the amino acid sequence of SEQ ID NO:90; (b) HVR-H2 comprising the amino acid sequence of SEQ ID NO:364; (c) HVR-H3 comprising the amino acid sequence of SEQ ID NO:155; (d) HVR-L1 comprising the amino acid sequence of SEQ ID NO:378; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO:155; (d) HVR-L1 comprising the amino acid sequence of SEQ ID NO:376; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:369; (c) HVR-H3 comprising the amino acid sequence of SEQ ID NO:155; (d) HVR-L1 comprising the amino acid sequence of SEQ ID NO:378; (e) HVR-L2 comprising the amino acid sequence of SEQ ID NO:203; and (f) HVR-L3 comprising the amino acid sequence of SEQ ID NO:394; (a) HVR-H1 comprising the amino acid sequence of SEQ ID NO:90; (b) HVR-H2 comprising the amino acid sequence of SEQ ID NO:370; (c) HVR-H3 comprising the amino acid sequence of SEQ ID NO:155; (d) HVR-L1 comprising the amino acid sequence of SEQ ID NO:378; (e) HVR-L2 comprising the amino acid sequence of SEQ ID NO:203; and (f) HVR-L3 comprising the amino acid sequence of SEQ ID NO:394; (a) HVR-H1 comprising the amino acid sequence of SEQ ID NO:90; (b) HVR-H2 comprising the amino acid sequence of SEQ ID NO:371; (c) HVR-H3 comprising the amino acid sequence of SEQ ID NO:155; (d) HVR-L1 comprising the amino acid sequence of SEQ ID NO:178; (e) HVR-L2 comprising the amino acid sequence of SEQ ID NO:203; and (f) HVR-L3 comprising the amino acid sequence of SEQ ID NO:394; (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO:155; (d) HVR-L1 comprising the amino acid sequence of SEQ ID NO:385; (e) HVR-L2 comprising the amino acid sequence of SEQ ID NO:203; and (f) HVR-L3 comprising the amino acid sequence of SEQ ID NO:394; (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO:155; (d) HVR-L1 comprising the amino acid sequence of SEQ ID NO:378; (e) HVR-L2 comprising the amino acid sequence of SEQ ID NO:203; and (f) HVR-L3 comprising the amino acid sequence of SEQ ID NO:395; (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO:155; (d) HVR-L1 comprising the amino acid sequence of SEQ ID NO:378; (e) HVR-L2 comprising the amino acid sequence of SEQ ID NO:390; and (f) HVR-L3 comprising the amino acid sequence of SEQ ID NO:394; (a) HVR-H1 comprising the amino acid sequence of SEQ ID NO:90; (b) HVR-H2 comprising the amino acid sequence of SEQ ID NO:372; (c) HVR-H3 comprising the amino acid sequence of SEQ ID NO:155; (d) HVR-L1 comprising the amino acid sequence of SEQ ID NO:378; (e) HVR-L2 comprising the amino acid sequence of SEQ ID NO:391; and (f) HVR-L3 comprising the amino acid sequence of SEQ ID NO:394; (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO:375; (d) HVR-L1 comprising the amino acid sequence of SEQ ID NO:386; (e) HVR-L2 comprising the amino acid sequence of SEQ ID NO:203; and (f) HVR-L3 comprising the amino acid sequence of SEQ ID NO:394; (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO:155; (d) HVR-L1 comprising the amino acid sequence of SEQ ID NO:387; (e) HVR-L2 comprising the amino acid sequence of SEQ ID NO:203; and (f) HVR-L3 comprising the amino acid sequence of SEQ ID NO:394.

In another aspect, an anti-MerTK antibody comprises a heavy chain variable domain ($V_H$) sequence having at least 90%, 91%, 92%, 93%, 94%, 95%, 96%, 97%, 98%, 99%, or 100% sequence identity to an amino acid sequence selected from the group consisting of SEQ ID NOs:37, 290, 291, 292, 293, 294, 295, 296, 297, 298, 299, 300, 301, 302, 303, 304, 305, 306, 307, and 308. In certain embodiments, a $V_H$ sequence having at least 90%, 91%, 92%, 93%, 94%, 95%, 96%, 97%, 98%, or 99% identity to an amino acid sequence selected from the group consisting of SEQ ID NOs: 37, 290, 291, 292, 293, 294, 295, 296, 297, 298, 299, 300, 301, 302, 303, 304, 305, 306, 307, and 308 contains substitutions (e.g., conservative substitutions), insertions, or deletions relative to the reference sequence, but an anti-MerTK antibody comprising that sequence retains the ability to bind to MerTK. In certain embodiments, a total of 1 to 10 amino acids have been substituted, inserted, and/or deleted in SEQ ID NO: 37, 290, 291, 292, 293, 294, 295, 296, 297, 298, 299, 300, 301, 302, 303, 304, 305, 306, 307, or 308. In certain embodiments, a total of 1 to 5 amino acids have been substituted, inserted and/or deleted in SEQ ID NO: 37, 290, 291, 292, 293, 294, 295, 296, 297, 298, 299, 300, 301, 302, 303, 304, 305, 306, 307, or 308. In certain embodiments, substitutions, insertions, or deletions occur in regions outside the HVRs (i.e., in the FRs). Optionally, the anti-MerTK antibody comprises the $V_H$ sequence of SEQ ID NO: 37, 290, 291, 292, 293, 294, 295, 296, 297, 298, 299, 300, 301, 302, 303, 304, 305, 306, 307, or 308, including post-translational modifications of that sequence. In a particular embodiment, the $V_H$ comprises one, two or three HVRs selected from: (a) HVR-H1 comprising the amino acid sequence of SEQ ID NO:90, (b) HVR-H2 comprising an amino acid sequence selected from the group consisting of SEQ ID NOs:122, 364, 365, 366, 367, and 368, and (c) HVR-H3 comprising an amino acid sequence selected from the group consisting of SEQ ID NOs:155, 373, 374, and 375.

In another aspect, an anti-MerTK antibody is provided, wherein the antibody comprises a light chain variable domain ($V_L$) having at least 90%, 91%, 92%, 93%, 94%, 95%, 96%, 97%, 98%, 99%, or 100% sequence identity to an amino acid sequence selected from the group consisting of SEQ ID NOs:72, 309, 310, 311, 312, 313, 314, 315, 316, 316, 318, 319, 320, 321, 322, 323, 324, 325, 326, 327, and 328. In certain embodiments, a $V_L$ sequence having at least 90%, 91%, 92%, 93%, 94%, 95%, 96%, 97%, 98%, or 99% identity to an amino acid sequence selected from the group consisting of SEQ ID NOs: 72, 309, 310, 311, 312, 313, 314, 315, 316, 316, 318, 319, 320, 321, 322, 323, 324, 325, 326, 327, and 328, and contains substitutions (e.g., conservative substitutions), insertions, or deletions relative to the reference sequence, but an anti-MerTK antibody comprising that sequence retains the ability to bind to MerTK. In some embodiments, a total of 1 to 10 amino acids have been substituted, inserted and/or deleted in SEQ ID NO: 72, 309, 310, 311, 312, 313, 314, 315, 316, 316, 318, 319, 320, 321, 322, 323, 324, 325, 326, 327, or 328. In certain embodiments, a total of 1 to 5 amino acids have been substituted, inserted and/or deleted in SEQ ID NO: 72, 309, 310, 311, 312, 313, 314, 315, 316, 316, 318, 319, 320, 321, 322, 323, 324, 325, 326, 327, or 328. In certain embodiments, the substitutions, insertions, or deletions occur in regions outside the HVRs (i.e., in the FRs). Optionally, the anti-MerTK antibody comprises the $V_L$ sequence of SEQ ID NO: 72, 309, 310, 311, 312, 313, 314, 315, 316, 316, 318, 319, 320, 321, 322, 323, 324, 325, 326, 327, or 328, including post-translational modifications of that sequence. In a particular embodiment, the $V_L$ comprises one, two or three HVRs selected from (a) HVR-L1 comprising an amino acid sequence selected from the group consisting of SEQ ID NOs:184, 376, 377, 378, 379, 380, 381, 382, 383, 384, 385, 386, and 387, (b) HVR-L2 comprising an amino acid sequence selected from the group consisting of SEQ ID NOs: 203, 388, 389, 390, and 391, and (c) HVR-L3 comprising an amino acid sequence selected from the group consisting of SEQ ID NOs: 231, 392, 393, and 394.

In some embodiments, an anti-MerTK antibody is provided, wherein the antibody comprises a $V_H$ as in any of the embodiments provided above, and a $V_L$ as in any of the embodiments provided above. In some embodiments, provided herein are anti-MerTK antibodies, wherein the antibody comprises a $V_H$ as in any of the embodiments provided above, and a $V_L$ as in any of the embodiments provided above. In one embodiment, the antibody comprises the $V_H$ and $V_L$ sequences in SEQ ID NOs: 37, 290, 291, 292, 293, 294, 295, 296, 297, 298, 299, 300, 301, 302, 303, 304, 305, 306, 307, and 308 and SEQ ID NOs: 72, 309, 310, 311, 312, 313, 314, 315, 316, 316, 318, 319, 320, 321, 322, 323, 324, 325, 326, 327, and 328, respectively, including post-translational modifications of those sequences.

In some embodiments, provided herein are anti-MerTK antibodies comprising a heavy chain variable domain ($V_H$) and a light chain variable domain ($V_L$), wherein the $V_H$ and $V_L$ are selected from the group consisting of: $V_H$ comprising the amino acid sequence of SEQ ID NO:37 and $V_L$ comprising the amino acid sequence of SEQ ID NO:72; $V_H$ comprising the amino acid sequence of SEQ ID NO:290 and $V_L$ comprising the amino acid sequence of SEQ ID NO:309; $V_H$ comprising the amino acid sequence of SEQ ID NO:291 and $V_L$ comprising the amino acid sequence of SEQ ID NO:310; $V_H$ comprising the amino acid sequence of SEQ ID NO:292 and $V_L$ comprising the amino acid sequence of SEQ ID NO:311; $V_H$ comprising the amino acid sequence of SEQ ID NO:293 and $V_L$ comprising the amino acid sequence of SEQ ID NO:312; $V_H$ comprising the amino acid sequence of SEQ ID NO:294 and $V_L$ comprising the amino acid sequence of SEQ ID NO:313; $V_H$ comprising the amino acid sequence of SEQ ID NO:295 and $V_L$ comprising the amino acid sequence of SEQ ID NO:314; $V_H$ comprising the amino acid sequence of SEQ ID NO:296 and $V_L$ comprising the amino acid sequence of SEQ ID NO:315; $V_H$ comprising the amino acid sequence of SEQ ID NO:290 and $V_L$ comprising the amino acid sequence of SEQ ID NO:316; $V_H$ comprising the amino acid sequence of SEQ ID NO:297 and $V_L$ comprising the amino acid sequence of SEQ ID NO:317; $V_H$ comprising the amino acid sequence of SEQ ID NO:298 and $V_L$ comprising the amino acid sequence of SEQ ID NO:318; $V_H$ comprising the amino acid sequence of SEQ ID NO:292 and $V_L$ comprising the amino acid sequence of SEQ ID NO:319; $V_H$ comprising the amino acid sequence of SEQ ID NO:299 and $V_L$ comprising the amino acid sequence of SEQ ID NO:320; $V_H$ comprising the amino acid sequence of SEQ ID NO:300 and $V_L$ comprising the amino acid sequence of SEQ ID NO:311; $V_H$ comprising the amino acid sequence of SEQ ID NO:301 and $V_L$ comprising the amino acid sequence of SEQ ID NO:321; $V_H$ comprising the amino acid sequence of SEQ ID NO:302 and $V_L$ comprising the amino acid sequence of SEQ ID NO:322; $V_H$ comprising the amino acid sequence of SEQ ID NO:303 and $V_L$ comprising the amino acid sequence of SEQ ID NO:311; $V_H$ comprising the amino acid sequence of SEQ ID NO:304 and $V_L$ comprising the amino acid sequence of SEQ ID NO:322; $V_H$ comprising the amino acid sequence of SEQ ID NO:305 and $V_L$ comprising the amino acid sequence of SEQ ID NO:322; $V_H$ comprising the amino acid sequence of SEQ ID NO:301 and $V_L$ comprising the amino acid sequence of SEQ ID NO:323; $V_H$ comprising the amino acid sequence of SEQ ID NO:301 and $V_L$ comprising the amino acid sequence of SEQ ID NO:324; $V_H$ comprising the amino acid sequence of SEQ ID NO:301 and $V_L$ comprising the amino acid sequence of SEQ ID NO:325; $V_H$ comprising the amino acid sequence of SEQ ID NO:306 and $V_L$ comprising the amino acid sequence of SEQ ID NO:326; $V_H$ comprising the amino acid sequence of SEQ ID NO:307 and $V_L$ comprising the amino acid sequence of SEQ ID NO:327; and $V_H$ comprising the amino acid sequence of SEQ ID NO:308 and $V_L$ comprising the amino acid sequence of SEQ ID NO:328.

In some embodiments, an anti-MerTK antibody of the present disclosure competitively inhibits binding of at least one reference antibody selected from MTK-01, MTK-02, MTK-03, MTK-04, MTK-05, MTK-06, MTK-07, MTK-08, MTK-09, MTK-10, MTK-11, MTK-12, MTK-13, MTK-14, MTK-15 (including MTK-15.1, MTK-15.2, MTK-15.3, MTK-15.4, MTK-15.5, MTK-15.6, MTK-15.7, MTK-15.8, MTK-15.9, MTK-15.10, MTK-15.11, MTK-15.12, MTK-15.13, MTK-15.14, and MTK-15.15), MTK-16 (including MTK-16.1 and MTK-16.2), MTK-17, MTK-18, MTK-19, MTK-20, MTK-21, MTK-22, MTK-23, MTK-24, MTK-25, MTK-26, MTK-27, MTK-28, MTK-29 (including MTK-29.1, MTK-29.2, MTK-29.3, MTK-29.4, MTK-29.5, MTK-29.6, MTK-29.7, MTK-29.8, MTK-29.9, MTK-29.10, MTK-29.11, MTK-29.12, MTK-29.13, MTK-29.14, MTK-29.15, MTK-29.16, MTK-29.17, MTK-29.18, MTK-29.19, MTK-29.20, and MTK-29.21), MTK-30, MTK-31, MTK-32, MTK-33 (including MTK-33.1, MTK-33.2, MTK-33.3, MTK-33.4, MTK-33.5, MTK-33.6, MTK-33.7, MTK-33.8, MTK-33.9, MTK-33.10, MTK-33.11, MTK-33.12, MTK-33.13, MTK-33.14, MTK-33.15, MTK-33.16, MTK-33.17, MTK-33.18, MTK-33.19, MTK-33.20, MTK-33.21, MTK-33.22, MTK-33.23, and MTK-33.24), MTK-34, MTK-35, and MTK-36, and any combination thereof, for binding to MerTK.

In some embodiments, an anti-MerTK antibody of the present disclosure binds to an epitope of human MerTK that is the same as or overlaps with the MerTK epitope bound by at least one reference antibody selected from MTK-01, MTK-02, MTK-03, MTK-04, MTK-05, MTK-06, MTK-07, MTK-08, MTK-09, MTK-10, MTK-11, MTK-12, MTK-13, MTK-14, MTK-15 (including MTK-15.1, MTK-15.2, MTK-15.3, MTK-15.4, MTK-15.5, MTK-15.6, MTK-15.7, MTK-15.8, MTK-15.9, MTK-15.10, MTK-15.11, MTK-15.12, MTK-15.13, MTK-15.14, and MTK-15.15), MTK-16 (including MTK-16.1 and MTK-16.2), MTK-17, MTK-18, MTK-19, MTK-20, MTK-21, MTK-22, MTK-23, MTK-24, MTK-25, MTK-26, MTK-27, MTK-28, MTK-29 (including MTK-29.1, MTK-29.2, MTK-29.3, MTK-29.4, MTK-29.5, MTK-29.6, MTK-29.7, MTK-29.8, MTK-29.9, MTK-29.10, MTK-29.11, MTK-29.12, MTK-29.13, MTK-29.14, MTK-29.15, MTK-29.16, MTK-29.17, MTK-29.18, MTK-29.19, MTK-29.20, and MTK-29.21), MTK-30, MTK-31, MTK-32, MTK-33 (including MTK-33.1, MTK-33.2, MTK-33.3, MTK-33.4, MTK-33.5, MTK-33.6, MTK-33.7, MTK-33.8, MTK-33.9, MTK-33.10, MTK-33.11, MTK-33.12, MTK-33.13, MTK-33.14, MTK-33.15, MTK-33.16, MTK-33.17, MTK-33.18, MTK-33.19, MTK-33.20, MTK-33.21, MTK-33.22, MTK-33.23, and MTK-33.24), MTK-34, MTK-35, and MTK-36. Detailed exemplary methods for mapping an epitope to which an antibody binds are provided in Morris (1996) "Epitope Mapping Protocols," in *Methods in Molecular Biology* vol. 66 (Humana Press, Totowa, NJ).

In some embodiments, an anti-MerTK antibody of the present disclosure competitively inhibits binding of at least one reference antibody, or binds to an epitope of human MerTK that is the same as or overlaps with the MerTK epitope bound by at least one reference antibody, wherein the reference antibody is an anti-MerTK antibody comprising a heavy chain variable domain ($V_H$) and a light chain variable domain ($V_L$), wherein the $V_H$ and $V_L$ are selected from the group consisting of: $V_H$ comprising the amino acid sequence of SEQ ID NO:5 and $V_L$ comprising the amino acid sequence of SEQ ID NO:40; $V_H$ comprising the amino acid sequence of SEQ ID NO:6 and $V_L$ comprising the amino acid sequence of SEQ ID NO:41; $V_H$ comprising the amino acid sequence of SEQ ID NO:7 and $V_L$ comprising the amino acid sequence of SEQ ID NO:42; $V_H$ comprising the amino acid sequence of SEQ ID NO:8 and $V_L$ comprising the amino acid sequence of SEQ ID NO:43; $V_H$ comprising the amino acid sequence of SEQ ID NO:9 and $V_L$ comprising the amino acid sequence of SEQ ID NO:44; $V_H$ comprising the amino acid sequence of SEQ ID NO:10 and $V_L$ comprising the amino acid sequence of SEQ ID NO:45; $V_H$ comprising the amino acid sequence of SEQ ID NO:11 and $V_L$ comprising the amino acid sequence of SEQ ID NO:46; $V_H$ comprising the amino acid sequence of SEQ ID NO:12 and $V_L$ comprising the amino acid sequence of SEQ ID NO:47; $V_H$ comprising the amino acid sequence of SEQ ID NO:13 and $V_L$ comprising the amino acid sequence of SEQ ID NO:48; $V_H$ comprising the amino acid sequence of SEQ ID NO:14 and $V_L$ comprising the amino acid sequence of SEQ ID NO:49; $V_H$ comprising the amino acid sequence of SEQ ID NO:15 and $V_L$ comprising the amino acid sequence of SEQ ID NO:50; $V_H$ comprising the amino acid sequence of SEQ ID NO:16 and $V_L$ comprising the amino acid sequence of SEQ ID NO:51; $V_H$ comprising the amino acid sequence of SEQ ID NO:17 and $V_L$ comprising the amino acid sequence of SEQ ID NO:52; $V_H$ comprising the amino acid sequence of SEQ ID NO:18 and $V_L$ comprising the amino acid sequence of SEQ ID NO:53; $V_H$ comprising the amino acid sequence of SEQ ID NO:19 and $V_L$ comprising the amino acid sequence of SEQ ID NO:54; $V_H$ comprising the amino acid sequence of SEQ ID NO:20 and $V_L$ comprising the amino acid sequence of SEQ ID NO:55; $V_H$ comprising the amino acid sequence of SEQ ID NO:21 and $V_L$ comprising the amino acid sequence of SEQ ID NO:56; $V_H$ comprising the amino acid sequence of SEQ ID NO:22 and $V_L$ comprising the amino acid sequence of SEQ ID NO:57; $V_H$ comprising the amino acid sequence of SEQ ID NO:23 and $V_L$ comprising the amino acid sequence of SEQ ID NO:58; $V_H$ comprising the amino acid sequence of SEQ ID NO:24 and $V_L$ comprising the amino acid sequence of SEQ ID NO:59; $V_H$ comprising the amino acid sequence of SEQ ID NO:25 and $V_L$ comprising the amino acid sequence of SEQ ID NO:60; $V_H$ comprising the amino acid sequence of SEQ ID NO:26 and $V_L$ comprising the amino acid sequence of SEQ ID NO:61; $V_H$ comprising the amino acid sequence of SEQ ID NO:27 and $V_L$ comprising the amino acid sequence of SEQ ID NO:62; $V_H$ comprising the amino acid sequence of SEQ ID NO:28 and $V_L$ comprising the amino acid sequence of SEQ ID NO:63; $V_H$ comprising the amino acid sequence of SEQ ID NO:29 and $V_L$ comprising the amino acid sequence of SEQ ID NO:64; $V_H$ comprising the amino acid sequence of SEQ ID NO:30 and $V_L$ comprising the amino acid sequence of SEQ ID NO:65; $V_H$ comprising the amino acid sequence of SEQ ID NO:31 and $V_L$ comprising the amino acid sequence of SEQ ID NO:66; $V_H$ comprising the amino acid sequence of SEQ ID NO:32 and $V_L$ comprising the amino acid sequence of SEQ ID NO:67; $V_H$ comprising the amino acid sequence of SEQ ID NO:33 and $V_L$ comprising the amino acid sequence of SEQ ID NO:68; $V_H$ comprising the amino acid sequence of SEQ ID NO:34 and $V_L$ comprising the amino acid sequence of SEQ ID NO:69; $V_H$ comprising the amino acid sequence of SEQ ID NO:35 and $V_L$ comprising the amino acid sequence of SEQ ID NO:70; $V_H$ comprising the amino acid sequence of SEQ ID NO:36 and $V_L$ comprising the amino acid sequence of SEQ ID NO:71; $V_H$ comprising the amino acid sequence of SEQ ID NO:37 and $V_L$ comprising the amino acid sequence of SEQ ID NO:72; $V_H$ comprising the amino acid sequence of SEQ ID NO:38 and $V_L$ comprising the amino acid sequence of SEQ ID NO:73; and $V_H$ comprising the amino acid sequence of SEQ ID NO:39 and $V_L$ comprising the amino acid sequence of SEQ ID NO:74.

In some embodiments, an anti-MerTK antibody of the present disclosure comprises a full-length heavy chain amino acid sequence comprising a variable heavy chain amino acid sequence of SEQ ID NO: 234, 235, 236, 237, 238, 239, 240, 241, 242, 243, 244, 245, or 246, and a heavy chain Fc selected from the group consisting of SEQ ID NOs: 396-411; and comprises a full-length light chain amino acid sequence comprising a variable light chain amino acid sequence of SEQ ID NO:247, 248, 249, 250, 251, 252, 253, or 254, and a light chain Fc comprising the amino acid sequence of SEQ ID NO:412.

In some embodiments, an anti-MerTK antibody of the present disclosure comprises a full-length heavy chain amino acid sequence comprising a variable heavy chain amino acid sequence of SEQ ID NO:255 or 256 and a heavy chain Fc selected from the group consisting of SEQ ID NOs: 396-411; and comprises a full-length light chain amino acid sequence comprising a variable light chain amino acid sequence of SEQ ID NO:257 or 258 and a light chain Fc comprising the amino acid sequence of SEQ ID NO:412.

In some embodiments, an anti-MerTK antibody of the present disclosure comprises a full-length heavy chain amino acid sequence of SEQ ID NO:413, 414, 415, 416, 417, 418, 419, or 420 and a full-length light chain amino acid sequence of SEQ ID NO: 421. Accordingly, in some embodiments, an anti-MerTK antibody comprises the heavy chain amino acid sequence of SEQ ID NO:413 and the light chain amino acid sequence of SEQ ID NO:421; the heavy chain amino acid sequence of SEQ ID NO:414 and the light chain amino acid sequence of SEQ ID NO:421; the heavy chain amino acid sequence of SEQ ID NO:415 and the light chain amino acid sequence of SEQ ID NO:421; the heavy chain amino acid sequence of SEQ ID NO:416 and the light chain amino acid sequence of SEQ ID NO:421; the heavy chain amino acid sequence of SEQ ID NO:417 and the light chain amino acid sequence of SEQ ID NO:421; the heavy chain amino acid sequence of SEQ ID NO:418 and the light chain amino acid sequence of SEQ ID NO:421; the heavy chain amino acid sequence of SEQ ID NO:419 and the light chain amino acid sequence of SEQ ID NO:421; or the heavy chain amino acid sequence of SEQ ID NO:420 and the light chain amino acid sequence of SEQ ID NO:421.

In some embodiments, an anti-MerTK antibody of the present disclosure comprises a full-length heavy chain amino acid sequence of SEQ ID NO:422, 423, 424, 425, 426, 427, 428, or 429 and a full-length light chain amino acid sequence of SEQ ID NO: 430. Accordingly, in some embodiments, an anti-MerTK antibody comprises the heavy chain amino acid sequence of SEQ ID NO:422 and the light chain amino acid sequence of SEQ ID NO:430; the heavy chain amino acid sequence of SEQ ID NO:423 and the light chain amino acid sequence of SEQ ID NO:430; the heavy chain amino acid sequence of SEQ ID NO:424 and the light chain amino acid sequence of SEQ ID NO:430; the heavy chain amino acid sequence of SEQ ID NO:425 and the light chain amino acid sequence of SEQ ID NO:430; the heavy chain amino acid sequence of SEQ ID NO:426 and the light chain amino acid sequence of SEQ ID NO:430; the heavy chain amino acid sequence of SEQ ID NO:427 and the light chain amino acid sequence of SEQ ID NO:430; the heavy chain amino acid sequence of SEQ ID NO:428 and the light chain amino acid sequence of SEQ ID NO:430; or the heavy chain amino acid sequence of SEQ ID NO:429 and the light chain amino acid sequence of SEQ ID NO:430.

In some embodiments, an anti-MerTK antibody of the present disclosure comprises a full-length heavy chain amino acid sequence comprising a variable heavy chain amino acid sequence of SEQ ID NO:259, 260, 261, 262, 263, 264, 265, 266, 267, 268, 269, 270, 271, 272, or 273, and a heavy chain Fc selected from the group consisting of SEQ ID NOs: 396-411; and comprises a full-length light chain amino acid sequence comprising a variable light chain amino acid sequence of SEQ ID NO:274, 275, 276, 277, 278, 279, 280, 281, 282, 283, 284, 285, 286, 287, 288, or 289, and a light chain Fc comprising the amino acid sequence of SEQ ID NO:412.

In some embodiments, an anti-MerTK antibody of the present disclosure comprises a full-length heavy chain amino acid sequence comprising a variable heavy chain amino acid sequence of SEQ ID NO: 290, 291, 292, 293, 294, 295, 296, 297, 298, 299, 300, 301, 302, 303, 304, 305, 306, 307, or 308, and a heavy chain Fc selected from the group consisting of SEQ ID NOs: 396-411; and comprises a full-length light chain amino acid sequence comprising a variable light chain amino acid sequence of SEQ ID NO:309, 310, 311, 312, 313, 314, 315, 316, 317, 318, 319, 320, 321, 322, 323, 324, 325, 326, 327, or 328, and a light chain Fc comprising the amino acid sequence of SEQ ID NO:412.

In some embodiments, an anti-MerTK antibody of the present disclosure comprises a full-length heavy chain amino acid sequence of SEQ ID NO: 431, 432, 433, 434, 435, 436, 437, or 438 and a full-length light chain amino acid sequence of SEQ ID NO:439. Accordingly, in some embodiments, an anti-MerTK antibody comprises the heavy chain amino acid sequence of SEQ ID NO:431 and the light chain amino acid sequence of SEQ ID NO:439; the heavy chain amino acid sequence of SEQ ID NO:432 and the light chain amino acid sequence of SEQ ID NO:439; the heavy chain amino acid sequence of SEQ ID NO:433 and the light chain amino acid sequence of SEQ ID NO:439; the heavy chain amino acid sequence of SEQ ID NO:434 and the light chain amino acid sequence of SEQ ID NO:439; the heavy chain amino acid sequence of SEQ ID NO:435 and the light chain amino acid sequence of SEQ ID NO:439; the heavy chain amino acid sequence of SEQ ID NO:436 and the light chain amino acid sequence of SEQ ID NO:439; the heavy chain amino acid sequence of SEQ ID NO:437 and the light chain amino acid sequence of SEQ ID NO:439; or the heavy chain amino acid sequence of SEQ ID NO:438 and the light chain amino acid sequence of SEQ ID NO:439.

In some embodiments, an anti-MerTK antibody of the present disclosure comprises a full-length heavy chain amino acid sequence of SEQ ID NO: 464, 465, 466, 467, 468, 469, 470, and 471 and a full-length light chain amino acid sequence of SEQ ID NO:472. Accordingly, in some embodiments, an anti-MerTK antibody comprises the heavy chain amino acid sequence of SEQ ID NO:464 and the light chain amino acid sequence of SEQ ID NO:472; the heavy chain amino acid sequence of SEQ ID NO:465 and the light chain amino acid sequence of SEQ ID NO:472; the heavy chain amino acid sequence of SEQ ID NO:466 and the light chain amino acid sequence of SEQ ID NO:472; the heavy chain amino acid sequence of SEQ ID NO:467 and the light chain amino acid sequence of SEQ ID NO:472; the heavy chain amino acid sequence of SEQ ID NO:468 and the light chain amino acid sequence of SEQ ID NO:472; the heavy chain amino acid sequence of SEQ ID NO:469 and the light chain amino acid sequence of SEQ ID NO:472; the heavy chain amino acid sequence of SEQ ID NO:470 and the light chain amino acid sequence of SEQ ID NO:472; or the heavy chain amino acid sequence of SEQ ID NO:471 and the light chain amino acid sequence of SEQ ID NO:472.

In some embodiments, an anti-MerTK antibody of the present disclosure comprises a full-length heavy chain amino acid sequence of SEQ D NO: 440, 441, 442, 443, 444, 445, 446, or 447 and a full-length light chain amino acid sequence of SEQ ID NO:448. Accordingly, in some embodiments, an anti-MerTK antibody comprises the heavy chain amino acid sequence of SEQ ID NO:440 and the light chain amino acid sequence of SEQ ID NO:448; the heavy chain amino acid sequence of SEQ ID NO:441 and the light chain amino acid sequence of SEQ ID NO:448; the heavy chain amino acid sequence of SEQ ID NO:442 and the light chain amino acid sequence of SEQ ID NO:448; the heavy chain amino acid sequence of SEQ ID NO:443 and the light chain amino acid sequence of SEQ ID NO:448; the heavy chain amino acid sequence of SEQ ID NO:444 and the light chain amino acid sequence of SEQ ID NO:448; the heavy chain amino acid sequence of SEQ ID NO:445 and the light chain amino acid sequence of SEQ ID NO:448; the heavy chain amino acid sequence of SEQ ID NO:446 and the light chain amino acid sequence of SEQ ID NO:448; or the heavy chain amino acid sequence of SEQ ID NO:447 and the light chain amino acid sequence of SEQ ID NO:448.

In some embodiments, an anti-MerTK antibody of the present disclosure competitively inhibits binding of at least one reference antibody, or binds to an epitope of human MerTK that is the same as or overlaps with the MerTK epitope bound by at least one reference antibody, wherein the reference antibody is an anti-MerTK antibody comprising a heavy chain variable domain ($V_H$) and a light chain variable domain (V$_L$), wherein the V$_H$ and V$_L$ are selected from the group consisting of: V$_H$ comprising the amino acid sequence of SEQ ID NO:19 and V$_L$ comprising the amino acid sequence of SEQ ID NO:54; V$_H$ comprising the amino acid sequence of SEQ ID NO:234 and V$_L$ comprising the amino acid sequence of SEQ ID NO:247; V$_H$ comprising the amino acid sequence of SEQ ID NO:235 and V$_L$ comprising the amino acid sequence of SEQ ID NO:247; V$_H$ comprising the amino acid sequence of SEQ ID NO:236 and V$_L$ comprising the amino acid sequence of SEQ ID NO:248; V$_H$ comprising the amino acid sequence of SEQ ID NO:236 and V$_L$ comprising the amino acid sequence of SEQ ID NO:249; V$_H$ comprising the amino acid sequence of SEQ ID NO:237 and V$_L$ comprising the amino acid sequence of SEQ ID NO:249; V$_H$ comprising the amino acid sequence of SEQ ID NO:238 and V$_L$ comprising the amino acid sequence of SEQ ID NO:249; V$_H$ comprising the amino acid sequence of SEQ ID NO:239 and V$_L$ comprising the amino acid sequence of SEQ ID NO:250; V$_H$ comprising the amino acid sequence of SEQ ID NO:240 and V$_L$ comprising the amino acid sequence of SEQ ID NO:251; V$_H$ comprising the amino acid sequence of SEQ ID NO:241 and V$_L$ comprising the amino acid sequence of SEQ ID NO:252; V$_H$ comprising the amino acid sequence of SEQ ID NO:242 and V$_L$ comprising the amino acid sequence of SEQ ID NO:249; V$_H$ comprising the amino acid sequence of SEQ ID NO:243 and V$_L$ comprising the amino acid sequence of SEQ ID NO:247; V$_H$ comprising the amino acid sequence of SEQ ID NO:244 and V$_L$ comprising the amino acid sequence of SEQ ID NO:251; V$_H$ comprising the amino acid sequence of SEQ ID NO:245 and V$_L$ comprising the amino acid sequence of SEQ ID NO:253; V$_H$ comprising the amino acid sequence of SEQ ID NO:246 and V$_L$ comprising the amino acid sequence of SEQ ID NO:247; and V$_H$ comprising the amino acid sequence of SEQ ID NO:246 and V$_L$ comprising the amino acid sequence of SEQ ID NO:254.

In some embodiments, an anti-MerTK antibody of the present disclosure competitively inhibits binding of at least one reference antibody, or binds to an epitope of human MerTK that is the same as or overlaps with the MerTK epitope bound by at least one reference antibody, wherein the reference antibody is an anti-MerTK antibody comprising a heavy chain variable domain (V$_H$) and a light chain variable domain (V$_L$), wherein the V$_H$ and V$_L$ are selected from the group consisting of: V$_H$ comprising the amino acid sequence of SEQ ID NO:20 and V$_L$ comprising the amino acid sequence of SEQ ID NO:55; V$_H$ comprising the amino acid sequence of SEQ ID NO:255 and V$_L$ comprising the amino acid sequence of SEQ ID NO:257; and V$_H$ comprising the amino acid sequence of SEQ ID NO:256 and V$_L$ comprising the amino acid sequence of SEQ ID NO:258.

In some embodiments, an anti-MerTK antibody of the present disclosure competitively inhibits binding of at least one reference antibody, or binds to an epitope of human MerTK that is the same as or overlaps with the MerTK epitope bound by at least one reference antibody, wherein the reference antibody is an anti-MerTK antibody comprising a heavy chain variable domain (V$_H$) and a light chain variable domain (V$_L$), wherein the V$_H$ and V$_L$ are selected from the group consisting of: V$_H$ comprising the amino acid sequence of SEQ ID NO:33 and V$_L$ comprising the amino acid sequence of SEQ ID NO:68; V$_H$ comprising the amino acid sequence of SEQ ID NO:259 and V$_L$ comprising the amino acid sequence of SEQ ID NO:274; V$_H$ comprising the amino acid sequence of SEQ ID NO:260 and V$_L$ comprising the amino acid sequence of SEQ ID NO:275; V$_H$ comprising the amino acid sequence of SEQ ID NO:261 and V$_L$ comprising the amino acid sequence of SEQ ID NO:276; V$_H$ comprising the amino acid sequence of SEQ ID NO:262 and V$_L$ comprising the amino acid sequence of SEQ ID NO:277; V$_H$ comprising the amino acid sequence of SEQ ID NO:263 and V$_L$ comprising the amino acid sequence of SEQ ID NO:277; V$_H$ comprising the amino acid sequence of SEQ ID NO:264 and V$_L$ comprising the amino acid sequence of SEQ ID NO:277; V$_H$ comprising the amino acid sequence of SEQ ID NO:265 and V$_L$ comprising the amino acid sequence of SEQ ID NO:277; V$_H$ comprising the amino acid sequence of SEQ ID NO:266 and V$_L$ comprising the amino acid sequence of SEQ ID NO:277; V$_H$ comprising the amino acid sequence of SEQ ID NO:267 and V$_L$ comprising the amino acid sequence of SEQ ID NO:278; V$_H$ comprising the amino acid sequence of SEQ ID NO:268 and V$_L$ comprising the amino acid sequence of SEQ ID NO:279; V$_H$ comprising the amino acid sequence of SEQ ID NO:269 and V$_L$ comprising the amino acid sequence of SEQ ID NO:279; V$_H$ comprising the amino acid sequence of SEQ ID NO:264 and V$_L$ comprising the amino acid sequence of SEQ ID NO:280; V$_H$ comprising the amino acid sequence of SEQ ID NO:270 and V$_L$ comprising the amino acid sequence of SEQ ID NO:281; V$_H$ comprising the amino acid sequence of SEQ ID NO:265 and V$_L$ comprising the amino acid sequence of SEQ ID NO:282; V$_H$ comprising the amino acid sequence of SEQ ID NO:264 and V$_L$ comprising the amino acid sequence of SEQ ID NO:283; V$_H$ comprising the amino acid sequence of SEQ ID NO:271 and V$_L$ comprising the amino acid sequence of SEQ ID NO:284; V$_H$ comprising the amino acid sequence of SEQ ID NO:272 and V$_L$ comprising the amino acid sequence of SEQ ID NO:285; V$_H$ comprising the amino acid sequence of SEQ ID NO:271 and V$_L$ comprising the amino acid sequence of SEQ ID NO:286; V$_H$ comprising the amino acid sequence of SEQ ID NO:273 and V$_L$ comprising the amino acid sequence of SEQ ID NO:287; V$_H$ comprising the amino acid sequence of SEQ ID NO:273 and V$_L$ comprising the amino acid sequence of SEQ ID NO:288; and V$_H$ comprising the amino acid sequence of SEQ ID NO:273 and V$_L$ comprising the amino acid sequence of SEQ ID NO:289.

In some embodiments, an anti-MerTK antibody of the present disclosure competitively inhibits binding of at least one reference antibody, or binds to an epitope of human MerTK that is the same as or overlaps with the MerTK epitope bound by at least one reference antibody, wherein the reference antibody is an anti-MerTK antibody comprising a heavy chain variable domain (V$_H$) and a light chain variable domain (V$_L$), wherein the V$_H$ and V$_L$ are selected from the group consisting of: V$_H$ comprising the amino acid sequence of SEQ ID NO:37 and V$_L$ comprising the amino acid sequence of SEQ ID NO:72; V$_H$ comprising the amino acid sequence of SEQ ID NO:290 and V$_L$ comprising the amino acid sequence of SEQ ID NO:309; V$_H$ comprising the amino acid sequence of SEQ ID NO:291 and V$_L$ comprising the amino acid sequence of SEQ ID NO:310; V$_H$ comprising the amino acid sequence of SEQ ID NO:292 and V$_L$ comprising the amino acid sequence of SEQ ID NO:311; V$_H$ comprising the amino acid sequence of SEQ ID NO:293 and V$_L$ comprising the amino acid sequence of SEQ ID NO:312; V$_H$ comprising the amino acid sequence of SEQ ID NO:294 and V$_L$ comprising the amino acid sequence of SEQ ID NO:313; V$_H$ comprising the amino acid sequence of SEQ ID NO:295 and V$_L$ comprising the amino acid sequence of SEQ ID NO:314; V$_H$ comprising the amino acid sequence of SEQ ID NO:296 and V$_L$ comprising the amino acid sequence of SEQ ID NO:315; V$_H$ comprising the amino acid sequence of SEQ ID NO:290 and V$_L$ comprising the amino acid sequence of SEQ ID NO:316; V$_H$ comprising the amino acid sequence of SEQ ID NO:297 and $V_L$ comprising the amino acid sequence of SEQ ID NO:317; $V_H$ comprising the amino acid sequence of SEQ ID NO:298 and $V_L$ comprising the amino acid sequence of SEQ ID NO:318; $V_H$ comprising the amino acid sequence of SEQ ID NO:292 and $V_L$ comprising the amino acid sequence of SEQ ID NO:319; $V_H$ comprising the amino acid sequence of SEQ ID NO:299 and $V_L$ comprising the amino acid sequence of SEQ ID NO:320; $V_H$ comprising the amino acid sequence of SEQ ID NO:300 and $V_L$ comprising the amino acid sequence of SEQ ID NO:311; $V_H$ comprising the amino acid sequence of SEQ ID NO:301 and $V_L$ comprising the amino acid sequence of SEQ ID NO:321; $V_H$ comprising the amino acid sequence of SEQ ID NO:302 and $V_L$ comprising the amino acid sequence of SEQ ID NO:322; $V_H$ comprising the amino acid sequence of SEQ ID NO:303 and $V_L$ comprising the amino acid sequence of SEQ ID NO:311; $V_H$ comprising the amino acid sequence of SEQ ID NO:304 and $V_L$ comprising the amino acid sequence of SEQ ID NO:322; $V_H$ comprising the amino acid sequence of SEQ ID NO:305 and $V_L$ comprising the amino acid sequence of SEQ ID NO:322; $V_H$ comprising the amino acid sequence of SEQ ID NO:301 and $V_L$ comprising the amino acid sequence of SEQ ID NO:323; $V_H$ comprising the amino acid sequence of SEQ ID NO:301 and $V_L$ comprising the amino acid sequence of SEQ ID NO:324; $V_H$ comprising the amino acid sequence of SEQ ID NO:301 and $V_L$ comprising the amino acid sequence of SEQ ID NO:325; $V_H$ comprising the amino acid sequence of SEQ ID NO:306 and $V_L$ comprising the amino acid sequence of SEQ ID NO:326; $V_H$ comprising the amino acid sequence of SEQ ID NO:307 and $V_L$ comprising the amino acid sequence of SEQ ID NO:327; and $V_H$ comprising the amino acid sequence of SEQ ID NO:308 and $V_L$ comprising the amino acid sequence of SEQ ID NO:328.

In some embodiments, an anti-MerTK antibody of the present disclosure comprises: (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO:155; (d) HVR-L1 comprising the amino acid sequence of SEQ ID NO:383; (e) HVR-L2 comprising the amino acid sequence of SEQ ID NO:203; and (f) HVR-L3 comprising the amino acid sequence of SEQ ID NO:232. In some embodiments, an anti-MerTK antibody of the present disclosure comprises a heavy chain variable domain ($V_H$) and a light chain variable domain ($V_L$), wherein the $V_H$ comprises the amino acid sequence of SED ID NO: 298 and the $V_L$ comprises the amino acid sequence of SEQ ID NO:318. In some embodiments, an anti-MerTK antibody of the present disclosure comprises a heavy chain and a light chain, wherein the heavy chain comprises the amino acid sequence of SEQ ID NO: 464 and the light chain comprises the amino acid sequence of SEQ ID NO:472. In some embodiments, an anti-MerTK antibody of the present disclosure comprises a heavy chain and a light chain, wherein the heavy chain comprises the amino acid sequence of SEQ ID NO: 465 and the light chain comprises the amino acid sequence of SEQ ID NO:472. In some embodiments, an anti-MerTK antibody of the present disclosure comprises a heavy chain and a light chain, wherein the heavy chain comprises the amino acid sequence of SEQ ID NO: 466 and the light chain comprises the amino acid sequence of SEQ ID NO:472. In some embodiments, an anti-MerTK antibody of the present disclosure comprises a heavy chain and a light chain, wherein the heavy chain comprises the amino acid sequence of SEQ ID NO: 467 and the light chain comprises the amino acid sequence of SEQ ID NO:472. In some embodiments, an anti-MerTK antibody of the present disclosure comprises a heavy chain and a light chain, wherein the heavy chain comprises the amino acid sequence of SEQ ID NO: 468 and the light chain comprises the amino acid sequence of SEQ ID NO:472. In some embodiments, an anti-MerTK antibody of the present disclosure comprises a heavy chain and a light chain, wherein the heavy chain comprises the amino acid sequence of SEQ ID NO: 469 and the light chain comprises the amino acid sequence of SEQ ID NO:472.

In some embodiments, an anti-MerTK antibody of the present disclosure comprises: (a) HVR-H1 comprising the amino acid sequence of SEQ ID NO:84; (b) HVR-H2 comprising the amino acid sequence of SEQ ID NO:99; (c) HVR-H3 comprising the amino acid sequence of SEQ ID NO:139; (d) HVR-L1 comprising the amino acid sequence of SEQ ID NO:345; (e) HVR-L2 comprising the amino acid sequence of SEQ ID NO:195; and (f) HVR-L3 comprising the amino acid sequence of SEQ ID NO:219. In some embodiments, an anti-MerTK antibody of the present disclosure comprises a heavy chain variable domain ($V_H$) and a light chain variable domain ($V_L$), wherein the $V_H$ comprises the amino acid sequence of SED ID NO: 256 and the $V_L$ comprises the amino acid sequence of SEQ ID NO:258. In some embodiments, an anti-MerTK antibody of the present disclosure comprises a heavy chain and a light chain, wherein the heavy chain comprises the amino acid sequence of SEQ ID NO: 422 and the light chain comprises the amino acid sequence of SEQ ID NO:430. In some embodiments, an anti-MerTK antibody of the present disclosure comprises a heavy chain and a light chain, wherein the heavy chain comprises the amino acid sequence of SEQ ID NO: 423 and the light chain comprises the amino acid sequence of SEQ ID NO:430. In some embodiments, an anti-MerTK antibody of the present disclosure comprises a heavy chain and a light chain, wherein the heavy chain comprises the amino acid sequence of SEQ ID NO: 424 and the light chain comprises the amino acid sequence of SEQ ID NO:430. In some embodiments, an anti-MerTK antibody of the present disclosure comprises a heavy chain and a light chain, wherein the heavy chain comprises the amino acid sequence of SEQ ID NO: 425 and the light chain comprises the amino acid sequence of SEQ ID NO:430. In some embodiments, an anti-MerTK antibody of the present disclosure comprises a heavy chain and a light chain, wherein the heavy chain comprises the amino acid sequence of SEQ ID NO: 426 and the light chain comprises the amino acid sequence of SEQ ID NO:430. In some embodiments, an anti-MerTK antibody of the present disclosure comprises a heavy chain and a light chain, wherein the heavy chain comprises the amino acid sequence of SEQ ID NO: 427 and the light chain comprises the amino acid sequence of SEQ ID NO:430.

In some embodiments, an anti-MerTK antibody of the present disclosure comprises: (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO:155; (d) HVR-L1 comprising the amino acid sequence of SEQ ID NO:376; (e) HVR-L2 comprising the amino acid sequence of SEQ ID NO:203; and (f) HVR-L3 comprising the amino acid sequence of SEQ ID NO:393. In some embodiments, an anti-MerTK antibody of the present disclosure comprises a heavy chain variable domain ($V_H$) and a light chain variable domain ($V_L$), wherein the $V_H$ comprises the amino acid sequence of SED ID NO: 299 and the $V_L$ comprises the amino acid sequence of SEQ ID NO:320. In some embodiments, an anti-MerTK antibody of the present disclosure comprises a heavy chain and a light chain, wherein the heavy chain comprises the amino acid sequence of SEQ ID NO: 440 and the light chain comprises the amino acid sequence of SEQ ID NO:448. In some embodiments, an anti-MerTK antibody of the present disclosure comprises a heavy chain and a light chain, wherein the heavy chain comprises the amino acid sequence of SEQ ID NO: 441 and the light chain comprises the amino acid sequence of SEQ ID NO:448. In some embodiments, an anti-MerTK antibody of the present disclosure comprises a heavy chain and a light chain, wherein the heavy chain comprises the amino acid sequence of SEQ ID NO: 442 and the light chain comprises the amino acid sequence of SEQ ID NO:448. In some embodiments, an anti-MerTK antibody of the present disclosure comprises a heavy chain and a light chain, wherein the heavy chain comprises the amino acid sequence of SEQ ID NO: 443 and the light chain comprises the amino acid sequence of SEQ ID NO:448. In some embodiments, an anti-MerTK antibody of the present disclosure comprises a heavy chain and a light chain, wherein the heavy chain comprises the amino acid sequence of SEQ ID NO: 444 and the light chain comprises the amino acid sequence of SEQ ID NO:448. In some embodiments, an anti-MerTK antibody of the present disclosure comprises a heavy chain and a light chain, wherein the heavy chain comprises the amino acid sequence of SEQ ID NO: 445 and the light chain comprises the amino acid sequence of SEQ ID NO:448.

In some embodiments, an anti-MerTK antibody of the present disclosure comprises: (a) HVR-H1 comprising the amino acid sequence of SEQ ID NO:84; (b) HVR-H2 comprising the amino acid sequence of SEQ ID NO:329; (c) HVR-H3 comprising the amino acid sequence of SEQ ID NO:139; (d) HVR-L1 comprising the amino acid sequence of SEQ ID NO:169; (e) HVR-L2 comprising the amino acid sequence of SEQ ID NO:195; and (f) HVR-L3 comprising the amino acid sequence of SEQ ID NO:219. In some embodiments, an anti-MerTK antibody of the present disclosure comprises a heavy chain variable domain ($V_H$) and a light chain variable domain ($V_L$), wherein the $V_H$ comprises the amino acid sequence of SED ID NO: 225 and the $V_L$ comprises the amino acid sequence of SEQ ID NO:257. In some embodiments, an anti-MerTK antibody of the present disclosure comprises a heavy chain and a light chain, wherein the heavy chain comprises the amino acid sequence of SEQ ID NO: 413 and the light chain comprises the amino acid sequence of SEQ ID NO:421. In some embodiments, an anti-MerTK antibody of the present disclosure comprises a heavy chain and a light chain, wherein the heavy chain comprises the amino acid sequence of SEQ ID NO: 414 and the light chain comprises the amino acid sequence of SEQ ID NO:421. In some embodiments, an anti-MerTK antibody of the present disclosure comprises a heavy chain and a light chain, wherein the heavy chain comprises the amino acid sequence of SEQ ID NO: 415 and the light chain comprises the amino acid sequence of SEQ ID NO:421. In some embodiments, an anti-MerTK antibody of the present disclosure comprises a heavy chain and a light chain, wherein the heavy chain comprises the amino acid sequence of SEQ ID NO: 416 and the light chain comprises the amino acid sequence of SEQ ID NO:421. In some embodiments, an anti-MerTK antibody of the present disclosure comprises a heavy chain and a light chain, wherein the heavy chain comprises the amino acid sequence of SEQ ID NO: 417 and the light chain comprises the amino acid sequence of SEQ ID NO:421. In some embodiments, an anti-MerTK antibody of the present disclosure comprises a heavy chain and a light chain, wherein the heavy chain comprises the amino acid sequence of SEQ ID NO: 418 and the light chain comprises the amino acid sequence of SEQ ID NO:421.

In some embodiments, an anti-MerTK antibody of the present disclosure binds to the extracellular domain (ECD) of human MerTK. In some embodiments, an anti-MerTK antibody of the present disclosure binds to the N-terminal domain of human MerTK. In some embodiments, an anti-MerTK antibody of the present disclosure binds to one or more amino acids within the amino acid sequence of SEQ ID NO:449. In some embodiments, an anti-MerTK antibody of the present disclosure binds to the immunoglobulin-like domain 1 (Ig1) of human MerTK. In some embodiments, an anti-MerTK antibody of the present disclosure binds to one or more amino acid residues within the amino acid sequence of SED ID NO:450. In some embodiments, an anti-MerTK antibody of the present disclosure binds to the immunoglobulin-like domain 2 (Ig2) of human MerTK. In some embodiments, an anti-MerTK antibody of the present disclosure binds to one or more amino acid residues within the amino acid sequence of SEQ ID NO:451. In some embodiments, an anti-MerTK antibody of the present disclosure binds to the fibronectin type III domain 1 (FN1) of human MerTK. In some embodiments, an anti-MerTK antibody of the present disclosure binds to one or more amino acid residues within the amino acid sequence of SEQ ID NO: 452. In some embodiments, an anti-MerTK antibody of the present disclosure binds to the juxta membrane domain (JM) of human MerTK. In some embodiments, an anti-MerTK antibody of the present disclosure binds to one or more amino acid residues within the amino acid sequence of SEQ ID NO:454. In some embodiments, an anti-MerTK antibody of the present disclosure binds to the extracellular domain of human MerTK protein but does not bind to the extracellular domain of human Axl protein.

In some embodiments, an anti-MerTK antibody of the present disclosure binds to one or more domains within the extracellular domain of human MerTK. In some embodiments, an anti-MerTK antibody of the present disclosure binds to the immunoglobulin-like 1 domain 1 (Ig1) and the fibronectin type III domain 1 (FN1) of human MerTK. In some embodiments, an anti-MerTK antibody of the present disclosure binds to the immunoglobulin-like domain 2 (Ig2) and the fibronectin type III domain 1 (FN1) of human MerTK.

In some embodiments, the anti-MerTK antibody according to any of the above embodiments is a monoclonal antibody, including a humanized and/or human antibody. In some embodiments, the anti-MerTK antibody is an antibody fragment, e.g., a Fv, Fab, Fab', scFv, diabody, or F(ab')2 fragment. In some embodiments, the anti-MerTK antibody is a substantially full-length antibody, e.g., an IgG1 antibody, IgG2a antibody or other antibody class or isotype as defined herein.

In some embodiments, an anti-MerTK antibody according to any of the above embodiments may incorporate any of the features, singly or in combination, as described in Sections 1-7 below:

(1) Anti MerTK Antibody Binding Affinity

In some embodiments of any of the antibodies provided herein, the antibody has a dissociation constant ($K_D$) of <1 µM, <100 nM, <10 nM, <1 nM, <0.1 nM, <0.01 nM, or <0.001 nM (e.g., $10^{-8}$ M or less, e.g., from $10^{-8}$ M to $10^{-13}$ M, e.g., from $10^{-9}$ M to $10^{-13}$ M). Dissociation constants may be determined through any analytical technique, including any biochemical or biophysical technique such as ELISA, surface plasmon resonance (SPR), bio-layer interferometry (see, e.g., Octet System by ForteBio), isothermal titration calorimetry (ITC), differential scanning calorimetry (DSC), circular dichroism (CD), stopped-flow analysis, and colorimetric or fluorescent protein melting analyses. In one embodiment, Kd is measured by a radiolabeled antigen binding assay (RIA). In some embodiment, an RIA is performed with the Fab version of an antibody of interest and its antigen, for example as described in Chen et al. *J. Mol. Biol.* 293:865-881(1999)). In some embodiments, $K_D$ is measured using a BIACORE surface plasmon resonance assay, for example, an assay using a BIACORE-2000 or a BIACORE-3000 (BIAcore, Inc., Piscataway, NJ) is performed at 25° C. with immobilized antigen CM5 chips at ~10 response units (RU). In some embodiments, the $K_D$ is determined using a monovalent antibody (e.g., a Fab) or a full-length antibody. In some embodiments, the $K_D$ is determined using a full-length antibody in a monovalent form.

In some embodiments, an anti-MerTK antibody of the present disclosure binds to human MerTK, wherein the $K_D$ of binding to human MerTK is from about 1.4 nM to about 81 nM. In some embodiments, an anti-MerTK antibody binds to cyno MerTK, wherein the $K_D$ of binding to cyno MerTK is from about 1.6 nM to about 107 nM. In some embodiments, an anti-MerTK antibody of the present disclosure binds to murine MerTK, wherein the $K_D$ of binding to murine MerTK is from about 30 nM to about 186 nM.

(2) Antibody Fragments

In some embodiments of any of the antibodies provided herein, the antibody is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP404097; WO 1993/01161; Hudson et al. *Nat. Med.* 9:129-134 (2003). Triabodies and tetrabodies are also described in Hudson et al. *Nat. Med.* 9:129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (see, e.g., U.S. Pat. No. 6,248,516).

Antibody fragments can be made by various techniques, including but not limited to proteolytic digestion of an intact antibody as well as production by recombinant host cells (e.g., *E. coli* or phage), as described herein.

(3) Chimeric and Humanized Antibodies

In some embodiments of any of the antibodies provided herein, the antibody is a chimeric antibody. Certain chimeric antibodies are described, e.g., in U.S. Pat. No. 4,816,567. In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In some embodiments of any of the antibodies provided herein, the antibody is a humanized antibody. Typically, a non-human antibody is humanized to reduce immunogenicity to humans, while retaining the specificity and affinity of the parental non-human antibody. In certain embodiments, a humanized antibody is substantially non-immunogenic in humans. In certain embodiments, a humanized antibody has substantially the same affinity for a target as an antibody from another species from which the humanized antibody is derived. See, e.g., U.S. Pat. Nos. 5,530,101, 5,693,761; 5,693,762; and 5,585,089. In certain embodiments, amino acids of an antibody variable domain that can be modified without diminishing the native affinity of the antigen binding domain while reducing its immunogenicity are identified. See, e.g., U.S. Pat. Nos. 5,766,886 and 5,869,619. Generally, a humanized antibody comprises one or more variable domains in which HVRs (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), for example, to restore or improve antibody specificity or affinity.

Humanized antibodies and methods of making them are reviewed, for example, in Almagro et al. *Front. Biosci.* 13:161 9-1633 (2008), and are further described, e.g., in U.S. Pat. Nos. 5,821,337, 7,527,791, 6,982,321, and 7,087, 409. Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA* 89:4285 (1992); and Presta et al., *J. Immunol.* 151:2623 (1993)); human mature (somatically mutated) framework regions or human germline framework regions (see, e.g., Almagro and Fransson *Front. Biosci.* 13:1619-1633 (2008)); and framework regions derived from screening FR libraries (see, e.g., Baca et al. *J. Biol. Chem.* 272:10678-10684 (1997) and Rosok et al. *J. Biol. Chem.* 271:22611-22618 (1996)).

(4) Human Antibodies

In some embodiments of any of the antibodies provided herein, the antibody is a human antibody. Human antibodies can be produced using various techniques known in the art. Human antibodies are described generally in van Dijk et al. *Curr. Opin. Pharmacol.* 5:368-74 (2001) and Lonberg *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. One can engineer mouse strains deficient in mouse antibody production with large fragments of the human Ig loci in anticipation that such mice would produce human antibodies in the absence of mouse antibodies. Large human Ig fragments can preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains can yield high affinity fully human antibodies against any antigen of interest, including human antigens. Using the hybridoma technology, antigen-specific human MAbs with the desired specificity can be produced and selected. Certain exemplary methods are described in U.S. Pat. No. 5,545,807, EP 546073, and EP 546073. See also, for example, U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology. Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.* 133:3001 (1984) and Boerner et al. *J. Immunol.* 147:86 (1991)). Human antibodies generated via human B-cell hybridoma technology are also described in Li et al. *Proc. Natl. Acad. Sci. USA,* 1 03:3557-3562 (2006). Additional methods include those described, for example, in U.S. Pat. No. 7,189,826 (describing production of monoclonal human IgM antibodies from hybridoma cell lines). Human hybridoma technology (Trioma technology) is also described in Vollmers et al. *Histology and Histopathology* 20(3):927-937 (2005) and Vollmers et al. *Methods and Findings in Experimental and Clinical Pharmacology* 27(3): 185-91 (2005). Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

In some embodiments of any of the antibodies provided herein, the antibody is a human antibody isolated by in vitro methods and/or screening combinatorial libraries for antibodies with the desired activity or activities. Suitable examples include but are not limited to phage display (CAT, Morphosys, Dyax, Biosite/Medarex, Xoma, Symphogen, Alexion (formerly Proliferon), Affimed) ribosome display (CAT), yeast display (Adimab), and the like. In certain phage display methods, repertoires of VH and VL genes are separately cloned by polymerase chain reaction (PCR) and recombined randomly in phage libraries, which can then be screened for antigen-binding phage as described in Winter et al. *Ann. Rev. Immunol.* 12: 433-455 (1994). For example, a variety of methods are known in the art for generating phage display libraries and screening such libraries for antibodies possessing the desired binding characteristics. See also Sidhu et al. *J. Mol. Biol.* 338(2): 299-310, 2004; Lee et al. *J. Mol. Biol.* 340(5): 1073-1093, 2004; Fellouse *Proc. Natl. Acad. Sci. USA* 101(34):12467-12472 (2004); and Lee et al. *J. Immunol. Methods* 284(-2):1 19-132 (2004). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al. *EMBO J.* 12: 725-734 (1993). Finally, naive libraries can also be made synthetically by cloning unrearranged V-gene segments from stem cells, and using PCR primers comprising random sequence to encode the highly variable HVR3 regions and to accomplish rearrangement in vitro, as described by Hoogenboom et al. *J. Mol. Biol.,* 227: 381-388, 1992. Patent publications describing human antibody phage libraries include, for example: U.S. Pat. No. 5,750,373, and US Patent Publication Nos. 2007/0292936 and 2009/0002360. Antibodies isolated from human antibody libraries are considered human antibodies or human antibody fragments herein.

(5) Constant Regions Including Fc Regions

In some embodiments of any of the antibodies provided herein, the antibody comprises an Fc. In some embodiments, the Fc is a human IgG1, IgG2, IgG3, and/or IgG4 isotype. In some embodiments, the antibody is of the IgG class, the IgM class, or the IgA class.

In certain embodiments of any of the antibodies provided herein, the antibody has an IgG2 isotype. In some embodiments, the antibody contains a human IgG2 constant region. In some embodiments, the human IgG2 constant region includes an Fc region. In some embodiments, the antibody induces the one or more MerTK activities or independently of binding to an Fc receptor. In some embodiments, the antibody binds an inhibitory Fc receptor. In certain embodiments, the inhibitory Fc receptor is inhibitory Fc-gamma receptor IIB (FcγIIB).

In certain embodiments of any of the antibodies provided herein, the antibody has an IgG1 isotype. In some embodiments, the antibody contains a mouse IgG1 constant region. In some embodiments, the antibody contains a human IgG1 constant region. In some embodiments, the human IgG1 constant region includes an Fc region. In some embodiments, the antibody binds an inhibitory Fc receptor. In certain embodiments, the inhibitory Fc receptor is inhibitory Fc-gamma receptor IIB (FcγIIB).

In certain embodiments of any of the antibodies provided herein, the antibody has an IgG4 isotype. In some embodiments, the antibody contains a human IgG4 constant region. In some embodiments, the human IgG4 constant region includes an Fc region. In some embodiments, the antibody binds an inhibitory Fc receptor. In certain embodiments, the inhibitory Fc receptor is inhibitory Fc-gamma receptor IIB (FcγIIB).

In certain embodiments of any of the antibodies provided herein, the antibody has a hybrid IgG2/4 isotype. In some embodiments, the antibody includes an amino acid sequence comprising amino acids 118 to 260 according to EU numbering of human IgG2 and amino acids 261-447 according to EU numbering of human IgG4 (WO 1997/11971; WO 2007/106585).

In some embodiments, the Fc region increases clustering without activating complement as compared to a corresponding antibody comprising an Fc region that does not comprise the amino acid substitutions. In some embodiments, the antibody induces one or more activities of a target specifically bound by the antibody. In some embodiments, the antibody binds to MerTK.

It may also be desirable to modify an anti-MerTK antibody of the present disclosure to modify effector function and/or to increase serum half-life of the antibody. For example, the Fc receptor binding site on the constant region may be modified or mutated to remove or reduce binding affinity to certain Fc receptors, such as FcγRI, FcγRII, and/or FcγRIII to reduce Antibody-dependent cell-mediated cytotoxicity. In some embodiments, the effector function is impaired by removing N-glycosylation of the Fc region (e.g., in the CH2 domain of IgG) of the antibody. In some embodiments, the effector function is impaired by modifying regions such as 233-236, 297, and/or 327-331 of human IgG as described in WO 99/58572 and Armour et al. *Molecular Immunology* 40: 585-593 (2003); Reddy et al. *J. Immunology* 164:1925-1933 (2000). In other embodiments, it may also be desirable to modify an anti-MerTK antibody of the present disclosure to modify effector function to increase finding selectivity toward the ITIM-containing FcgRIIb (CD32b) to increase clustering of MerTK antibodies on adjacent cells without activating humoral responses including Antibody-dependent cell-mediated cytotoxicity and antibody-dependent cellular phagocytosis.

To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule. Other amino acid sequence modifications.

(6) Antibody Variants

In some embodiments of any of the antibodies provided herein, amino acid sequence variants of the antibodies are contemplated. For example, it may be desirable to improve the binding affinity and/or other biological properties of the antibody.

(i) Substitution, Insertion, and Deletion Variants

In some embodiments of any of the antibodies provided herein, antibody variants having one or more amino acid substitutions are provided. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody.

TABLE A

| Amino Acid Substitutions | | |
|---|---|---|
| Original Residue | Exemplary Substitutions | Preferred Substitutions |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Tyr |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro; and
(6) aromatic: Trp, Tyr, Phe.

For example, non-conservative substitutions can involve the exchange of a member of one of these classes for a member from another class. Such substituted residues can be introduced, for example, into regions of a human antibody that are homologous with non-human antibodies, or into the non-homologous regions of the molecule.

In making changes to the polypeptide or antibody described herein, according to certain embodiments, the hydropathic index of amino acids can be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al. *J. Mol. Biol.,* 157:105-131 (1982). It is known that certain amino acids can be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0±1); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included. One can also identify epitopes from primary amino acid sequences on the basis of hydrophilicity. These regions are also referred to as "epitopic core regions".

In certain embodiments of the variant VH and VL sequences provided above, each HVR is unaltered.

Amino acid sequence insertions include amino- and/or carboxyl-terminal fusions ranging in length from one residue to polypeptides comprising a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

Any cysteine residue outside the HVRs and not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment, such as an Fv fragment).

(ii) Glycosylation Variants

In some embodiments of any of the antibodies provided herein, the antibody is altered to increase or decrease the extent to which the antibody is glycosylated. Addition or deletion of glycosylation sites to an antibody may be conveniently accomplished by altering the amino acid sequence such that one or more glycosylation sites is created or removed.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. Native antibodies produced by mammalian cells typically comprise a branched, biantennary oligosaccharide that is generally attached by an N-linkage to Asn297 according to Kabat numbering of the CH2 domain of the Fc region. The oligosaccharide may include various carbohydrates, for example, mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the disclosure may be made in order to create antibody variants with certain improved properties.

In one embodiment, antibody variants are provided having a carbohydrate structure that lacks fucose attached (directly or indirectly) to an Fc region. See, e.g., US Patent Publication Nos. 2003/0157108 and 2004/0093621. Examples of publications related to "defucosylated" or "fucose-deficient" antibody variants include: US 2003/0157108; US 2003/0115614; US 2002/0164328; US 2004/0093621; US 2004/0132140; US 2004/0110704; US 2004/0110282; US 2004/0109865; Okazaki et al. *J Mol. Biol.* 336:1239-1249 (2004); Yamane-Ohnuki et al. *Biotech. Bioeng.* 87:614 (2004). Examples of cell lines capable of producing defucosylated antibodies include Led 3 CHO cells deficient in protein fucosylation (Ripka et al. *Arch. Biochem. Biophys.* 249:533-545 (1986); US 2003/0157108), and knockout cell lines, such as alpha-1,6-fucosyltransferase gene, FUT8, knockout CHO cells (see, e.g., Yamane-Ohnuki et al. *Biotech. Bioeng.* 87: 614 (2004) and Kanda et al. *Biotechnot Bioeng.* 94(4):680-688 (2006)).

(iii) Modified Constant Regions

In some embodiments of any of the antibodies provided herein, the antibody Fc is an antibody Fc isotypes and/or modifications. In some embodiments, the antibody Fc isotype and/or modification is capable of binding to Fc gamma receptor.

In some embodiments of any of the antibodies provided herein, the modified antibody Fc is an IgG1 modified Fc. In some embodiments, the IgG1 modified Fc comprises one or more modifications. For example, in some embodiments, the IgG1 modified Fc comprises one or more amino acid substitutions (e.g., relative to a wild-type Fc region of the same isotype). In some embodiments, the one or more amino acid substitutions are selected from N297A (Bolt S et al. (1993) *Eur J Immunol* 23:403-411), D265A (Shields et al. (2001) *R. J Biol. Chem.* 276, 6591-6604), L234A, L235A (Hutchins et al. (1995) *Proc Natl Acad Sci USA,* 92:11980-11984; Alegre et al., (1994) *Transplantation* 57:1537-1543. 31; Xu et al., (2000) *Cell Immunol,* 200:16-26), G237A (Alegre et al. (1994) *Transplantation* 57:1537-1543. 31; Xu et al. (2000) *Cell Immunol,* 200:16-26), C226S, C229S, E233P, L234V, L234F, L235E (McEarchern et al., (2007) *Blood,* 109:1185-1192), P331S (Sazinsky et al., (2008) *Proc Natl Acad Sci USA* 2008, 105:20167-20172), S267E, L328F, A330L, M252Y, S254T, and/or T256E, where the amino acid position is according to the EU numbering convention.

In some embodiments of any of the IgG1 modified Fc, the Fc comprises N297A mutation according to EU numbering. In some embodiments of any of the IgG1 modified Fc, the Fc comprises D265A and N297A mutations according to EU numbering. In some embodiments of any of the IgG1 modified Fc, the Fc comprises D270A mutations according to EU numbering. In some embodiments, the IgG1 modified Fc comprises L234A and L235A mutations according to EU numbering. In some embodiments of any of the IgG1 modified Fc, the Fc comprises L234A and G237A mutations according to EU numbering. In some embodiments of any of the IgG1 modified Fc, the Fc comprises L234A, L235A and G237A mutations according to EU numbering. In some embodiments of any of the IgG1 modified Fc, the Fc comprises one or more (including all) of P238D, L328E, E233, G237D, H268D, P271G and A330R mutations according to EU numbering. In some embodiments of any of the IgG1 modified Fc, the Fc comprises one or more of S267E/L328F mutations according to EU numbering. In some embodiments of any of the IgG1 modified Fc, the Fc comprises P238D, L328E, E233D, G237D, H268D, P271G and A330R mutations according to EU numbering. In some embodiments of any of the IgG1 modified Fc, the Fc comprises P238D, L328E, G237D, H268D, P271G and A330R mutations according to EU numbering. In some embodiments of any of the IgG1 modified Fc, the Fc comprises P238D, S267E, L328E, E233D, G237D, H268D, P271G and A330R mutations according to EU numbering. In some embodiments of any of the IgG1 modified Fc, the Fc comprises P238D, S267E, L328E, G237D, H268D, P271G and A330R mutations according to EU numbering. In some embodiments of any of the IgG1 modified Fc, the Fc comprises C226S, C229S, E233P, L234V, and L235A mutations according to EU numbering. In some embodiments of any of the IgG1 modified Fc, the Fc comprises L234F, L235E, and P331S mutations according to EU numbering. In some embodiments of any of the IgG1 modified Fc, the Fc comprises S267E and L328F mutations according to EU numbering. In some embodiments of any of the IgG1 modified Fc, the Fc comprises N325S and L328F mutations according to EU numbering. In some embodiments of any of the IgG1 modified Fc, the Fc comprises S267E mutations according to EU numbering. In some embodiments of any of the IgG1 modified Fc, the Fc comprises a substitute of the constant heavy 1 (CH1) and hinge region of IgG1 with CH1 and hinge region of IgG2 (amino acids 118-230 of IgG2 according to EU numbering) with a Kappa light chain.

In some embodiments of any of the IgG1 modified Fc, the Fc includes two or more amino acid substitutions that increase antibody clustering without activating complement as compared to a corresponding antibody having an Fc region that does not include the two or more amino acid substitutions. Accordingly, in some embodiments of any of the IgG1 modified Fc, the IgG1 modified Fc is an antibody comprising an Fc region, where the antibody comprises an amino acid substitution at position E430G and one or more amino acid substitutions in the Fc region at a residue position selected from: L234F, L235A, L235E, S267E, K322A, L328F, A330S, P331S, and any combination thereof according to EU numbering. In some embodiments, the IgG1 modified Fc comprises an amino acid substitution at positions E430G, L243A, L235A, and P331S according to EU numbering. In some embodiments, the IgG1 modified Fc comprises an amino acid substitution at positions E430G and P331S according to EU numbering. In some embodiments, the IgG1 modified Fc comprises an amino acid substitution at positions E430G and K322A according to EU numbering. In some embodiments, the IgG1 modified Fc comprises an amino acid substitution at positions E430G, A330S, and P331S according to EU numbering. In some embodiments, the IgG1 modified Fc comprises an amino acid substitution at positions E430G, K322A, A330S, and P331S according to EU numbering. In some embodiments, the IgG1 modified Fc comprises an amino acid substitution at positions E430G, K322A, and A330S according to EU numbering. In some embodiments, the IgG1 modified Fc comprises an amino acid substitution at positions E430G, K322A, and P331S according to EU numbering.

In some embodiments of any of the IgG1 modified Fc, the IgG1 modified Fc may further comprise herein may be combined with an A330L mutation (Lazar et al. Proc Natl Acad Sci USA, 103:4005-4010 (2006)), or one or more of L234F, L235E, and/or P331S mutations (Sazinsky et al. Proc Natl Acad Sci USA, 105:20167-20172 (2008)), according to the EU numbering convention, to eliminate complement activation. In some embodiments of any of the IgG1 modified Fc, the IgG1 modified Fc may further comprise one or more of A330L, A330S, L234F, L235E, and/or P331S according to EU numbering. In some embodiments of any of the IgG1 modified Fc, the IgG1 modified Fc may further comprise one or more mutations to enhance the antibody half-life in human serum (e.g., one or more (including all) of M252Y, S254T, and T256E mutations according to the EU numbering convention). In some embodiments of any of the IgG1 modified Fc, the IgG1 modified Fc may further comprise one or more of E430G, E430S, E430F, E430T, E345K, E345Q, E345R, E345Y, S440Y, and/or S440W according to EU numbering.

Other aspects of the present disclosure relate to antibodies having modified constant regions (i.e., Fc regions). An antibody dependent on binding to FcgR receptor to activate targeted receptors may lose its agonist activity if engineered to eliminate FcgR binding (see, e.g., Wilson et al. *Cancer Cell* 19:101-113 (2011); Armour at al. *Immunology* 40:585-593 (2003); and White et al. *Cancer Cell* 27:138-148 (2015)). As such, it is thought that an anti-MerTK antibody of the present disclosure with the correct epitope specificity can activate the target antigen, with minimal adverse effects, when the antibody has an Fc domain from a human IgG2 isotype (CHI and hinge region) or another type of Fc domain that is capable of preferentially binding the inhibitory FcgRIIB r receptors, or a variation thereof.

In some embodiments of any of the antibodies provided herein, the modified antibody Fc is an IgG2 modified Fc. In some embodiments, the IgG2 modified Fc comprises one or more modifications. For example, in some embodiments, the IgG2 modified Fc comprises one or more amino acid substitutions (e.g., relative to a wild-type Fc region of the same isotype). In some embodiments of any of the IgG2 modified Fc, the one or more amino acid substitutions are selected from V234A (Alegre et al. *Transplantation* 57:1537-1543 (1994); Xu et al. *Cell Immunol,* 200:16-26 (2000)); G237A (Cole et al. *Transplantation,* 68:563-571 (1999)); H268Q, V309L, A330S, P331S (US 2007/0148167; Armour et al. *Eur J Immunol* 29: 2613-2624 (1999); Armour et al. *The Haematology Journal* 1(Suppl. 1):27 (2000); Armour et al. *The Haematology Journal* 1(Suppl. 1):27 (2000)), C219S, and/or C220S (White et al. *Cancer Cell* 27, 138-148 (2015)); S267E, L328F (Chu et al. *Mol Immunol,* 45:3926-3933 (2008)); and M252Y, S254T, and/or T256E according to the EU numbering convention. In some embodiments of any of the IgG2 modified Fc, the Fc comprises an amino acid substitution at positions V234A and G237A according to EU numbering. In some embodiments of any of the IgG2 modified Fc, the Fc comprises an amino acid substitution at positions C219S or C220S according to EU numbering. In some embodiments of any of the IgG2 modified Fc, the Fc comprises an amino acid substitution at positions A330S and P331S according to EU numbering. In some embodiments of any of the IgG2 modified Fc, the Fc comprises an amino acid substitution at positions S267E and L328F according to EU numbering.

In some embodiments of any of the IgG2 modified Fc, the Fc comprises a C127S amino acid substitution according to the EU numbering convention (White et al., (2015) *Cancer Cell* 27, 138-148; Lightle et al. *Protein Sci.* 19:753-762 (2010); and WO 2008/079246). In some embodiments of any of the IgG2 modified Fc, the antibody has an IgG2 isotype with a Kappa light chain constant domain that comprises a C214S amino acid substitution according to the EU numbering convention (White et al. *Cancer Cell* 27:138-148 (2015); Lightle et al. *Protein Sci.* 19:753-762 (2010); and WO 2008/079246).

In some embodiments of any of the IgG2 modified Fc, the Fc comprises a C220S amino acid substitution according to the EU numbering convention. In some embodiments of any of the IgG2 modified Fc, the antibody has an IgG2 isotype with a Kappa light chain constant domain that comprises a C214S amino acid substitution according to the EU numbering convention.

In some embodiments of any of the IgG2 modified Fc, the Fc comprises a C219S amino acid substitution according to the EU numbering convention. In some embodiments of any of the IgG2 modified Fc, the antibody has an IgG2 isotype with a Kappa light chain constant domain that comprises a C214S amino acid substitution according to the EU numbering convention.

In some embodiments of any of the IgG2 modified Fc, the Fc includes an IgG2 isotype heavy chain constant domain 1(CH1) and hinge region (White et al. *Cancer Cell* 27:138-

148 (2015)). In certain embodiments of any of the IgG2 modified Fc, the IgG2 isotype CH1 and hinge region comprise the amino acid sequence of 118-230 according to EU numbering. In some embodiments of any of the IgG2 modified Fc, the antibody Fc region comprises a S267E amino acid substitution, a L328F amino acid substitution, or both, and/or a N297A or N297Q amino acid substitution according to the EU numbering convention.

In some embodiments of any of the IgG2 modified Fc, the Fc further comprises one or more amino acid substitution at positions E430G, E430S, E430F, E430T, E345K, E345Q, E345R, E345Y, S440Y, and S440W according to EU numbering. In some embodiments of any of the IgG2 modified Fc, the Fc may further comprise one or more mutations to enhance the antibody half-life in human serum (e.g., one or more (including all) of M252Y, S254T, and T256E mutations according to the EU numbering convention). In some embodiments of any of the IgG2 modified Fc, the Fc may further comprise A330S and P331S.

In some embodiments of any of the IgG2 modified Fc, the Fc is an IgG2/4 hybrid Fc. In some embodiments, the IgG2/4 hybrid Fc comprises IgG2 aa 118 to 260 and IgG4 aa 261 to 447. In some embodiments of any IgG2 modified Fc, the Fc comprises one or more amino acid substitutions at positions H268Q, V309L, A330S, and P331S according to EU numbering.

In some embodiments of any of the IgG1 and/or IgG2 modified Fc, the Fc comprises one or more additional amino acid substitutions selected from A330L, L234F; L235E, or P331S according to EU numbering; and any combination thereof.

In certain embodiments of any of the IgG1 and/or IgG2 modified Fc, the Fc comprises one or more amino acid substitutions at a residue position selected from C127S, L234A, L234F, L235A, L235E, S267E, K322A, L328F, A330S, P331S, E345R, E430G, S440Y, and any combination thereof according to EU numbering. In some embodiments of any of the IgG1 and/or IgG2 modified Fc, the Fc comprises an amino acid substitution at positions E430G, L243A, L235A, and P331S according to EU numbering. In some embodiments of any of the IgG1 and/or IgG2 modified Fc, the Fc comprises an amino acid substitution at positions E430G and P331S according to EU numbering. In some embodiments of any of the IgG1 and/or IgG2 modified Fc, the Fc comprises an amino acid substitution at positions E430G and K322A according to EU numbering. In some embodiments of any of the IgG1 and/or IgG2 modified Fc, the Fc comprises an amino acid substitution at positions E430G, A330S, and P331S according to EU numbering. In some embodiments of any of the IgG1 and/or IgG2 modified Fc, the Fc comprises an amino acid substitution at positions E430G, K322A, A330S, and P331S according to EU numbering. In some embodiments of any of the IgG1 and/or IgG2 modified Fc, the Fc comprises an amino acid substitution at positions E430G, K322A, and A330S according to EU numbering. In some embodiments of any of the IgG1 and/or IgG2 modified Fc, the Fc comprises an amino acid substitution at positions E430G, K322A, and P331S according to EU numbering. In some embodiments of any of the IgG1 and/or IgG2 modified Fc, the Fc comprises an amino acid substitution at positions S267E and L328F according to EU numbering. In some embodiments of any of the IgG1 and/or IgG2 modified Fc, the Fc comprises an amino acid substitution at position C127S according to EU numbering. In some embodiments of any of the IgG1 and/or IgG2 modified Fc, the Fc comprises an amino acid substitution at positions E345R, E430G and S440Y according to EU numbering.

In some embodiments of any of the antibodies provided herein, the modified antibody Fc is an IgG4 modified Fc. In some embodiments, the IgG4 modified Fc comprises one or more modifications. For example, in some embodiments, the IgG4 modified Fc comprises one or more amino acid substitutions (e.g., relative to a wild-type Fc region of the same isotype). In some embodiments of any of the IgG4 modified Fc, the one or more amino acid substitutions are selected from L235A, G237A, S229P, L236E (Reddy et al. *J Immunol* 164:1925-1933(2000)), S267E, E318A, L328F, M252Y, S254T, and/or T256E according to the EU numbering convention. In some embodiments of any of the IgG4 modified Fc, the Fc may further comprise L235A, G237A, and E318A according to the EU numbering convention. In some embodiments of any of the IgG4 modified Fc, the Fc may further comprise S228P and L235E according to the EU numbering convention. In some embodiments of any of the IgG4 modified Fc, the IgG4 modified Fc may further comprise S267E and L328F according to the EU numbering convention.

In some embodiments of any of the IgG4 modified Fc, the IgG4 modified Fc comprises may be combined with an S228P mutation according to the EU numbering convention (Angal et al. *Mol Immunol.* 30:105-108 (1993)) and/or with one or more mutations described in (Peters et al. *J Biol Chem.* 287(29):24525-33 (2012)) to enhance antibody stabilization.

In some embodiments of any of the IgG4 modified Fc, the IgG4 modified Fc may further comprise one or more mutations to enhance the antibody half-life in human serum (e.g., one or more (including all) of M252Y, S254T, and T256E mutations according to the EU numbering convention).

In some embodiments of any of the IgG4 modified Fc, the Fc comprises L235E according to EU numbering. In certain embodiments of any of the IgG4 modified Fc, the Fc comprises one or more amino acid substitutions at a residue position selected from C127S, F234A, L235A, L235E, S267E, K322A, L328F, E345R, E430G, S440Y, and any combination thereof, according to EU numbering. In some embodiments of any of the IgG4 modified Fc, the Fc comprises an amino acid substitution at positions E430G, L243A, L235A, and P331S according to EU numbering. In some embodiments of any of the IgG4 modified Fc, the Fc comprises an amino acid substitution at positions E430G and P331S according to EU numbering. In some embodiments of any of the IgG4 modified Fc, the Fc comprises an amino acid substitution at positions E430G and K322A according to EU numbering. In some embodiments of any of the IgG4 modified Fc, the Fc comprises an amino acid substitution at position E430 according to EU numbering. In some embodiments of any of the IgG4 modified Fc, the Fc region comprises an amino acid substitution at positions E430G and K322A according to EU numbering. In some embodiments of any of the IgG4 modified Fc, the Fc comprises an amino acid substitution at positions S267E and L328F according to EU numbering. In some embodiments of any of the IgG4 modified Fc, the Fc comprises an amino acid substitution at position C127S according to EU numbering. In some embodiments of any of the IgG4 modified Fc, the Fc comprises an amino acid substitution at positions E345R, E430G and S440Y according to EU numbering.

(7) Other Antibody Modifications

In some embodiments of any of the antibodies, the antibody is a derivative. The term "derivative" refers to a molecule that includes a chemical modification other than an insertion, deletion, or substitution of amino acids (or nucleic acids). In certain embodiments, derivatives comprise covalent modifications, including, but not limited to, chemical bonding with polymers, lipids, or other organic or inorganic moieties. In certain embodiments, a chemically modified antigen binding protein can have a greater circulating half-life than an antigen binding protein that is not chemically modified. In certain embodiments, a chemically modified antigen binding protein can have improved targeting capacity for desired cells, tissues, and/or organs. In some embodiments, a derivative antigen binding protein is covalently modified to include one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative antigen binding protein comprises one or more polymer, including, but not limited to, monomethoxy-polyethylene glycol, dextran, cellulose, copolymers of ethylene glycol/propylene glycol, carboxymethylcellulose, polyvinyl pyrrolidone, poly-1, 3-dioxolane, poly-1,3,6-trioxane, ethylene/maleic anhydride copolymer, polyaminoacids (either homopolymers or random copolymers), poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers.

In certain embodiments, a derivative is covalently modified with polyethylene glycol (PEG) subunits. In certain embodiments, one or more water-soluble polymer is bonded at one or more specific position, for example at the amino terminus, of a derivative. In certain embodiments, one or more water-soluble polymer is randomly attached to one or more side chains of a derivative. In certain embodiments, PEG is used to improve the therapeutic capacity for an antigen binding protein. In certain embodiments, PEG is used to improve the therapeutic capacity for a humanized antibody. Certain such methods are discussed, for example, in U.S. Pat. No. 6,133,426, which is hereby incorporated by reference for any purpose.

Peptide analogs are commonly used in the pharmaceutical industry as non-peptide drugs with properties analogous to those of the template peptide. These types of non-peptide compound are termed "peptide mimetics" or "peptidomimetics." Fauchere, *J. Adv. Drug Res.*, 15:29 (1986); and Evans et al. *J. Med. Chem.*, 30:1229 (1987), which are incorporated herein by reference for any purpose. Such compounds are often developed with the aid of computerized molecular modeling. Peptide mimetics that are structurally similar to therapeutically useful peptides can be used to produce a similar therapeutic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from: —CH$_2$NH—, —CH$_2$S—, —CH$_2$—CH$_2$—, —CH=CH-(cis and trans), —COCH$_2$—, —CH(OH)CH$_2$—, and —CH$_2$SO—, by methods well known in the art. Systematic substitution of one or more amino acids of a consensus sequence with a D-amino acid of the same type (e.g., D-lysine in place of L-lysine) can be used in certain embodiments to generate more stable peptides. In addition, constrained peptides comprising a consensus sequence or a substantially identical consensus sequence variation can be generated by methods known in the art (Rizo and Gierasch *Ann. Rev. Biochem.*, 61:387 (1992), incorporated herein by reference for any purpose); for example, by adding internal cysteine residues capable of forming intramolecular disulfide bridges which cyclize the peptide.

Drug conjugation involves coupling of a biological active cytotoxic (anticancer) payload or drug to an antibody that specifically targets a certain tumor marker (e.g. a polypeptide that, ideally, is only to be found in or on tumor cells). Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is internalized, the cytotoxic drug is released and kills the cancer. Due to this targeting, ideally the drug has lower side effects and gives a wider therapeutic window than other chemotherapeutic agents. Technics to conjugate antibodies are disclosed are known in the art (see, e.g., Jane de Lartigue OncLive Jul. 5, 2012; ADC Review on antibody-drug conjugates; and Ducry et al. *Bioconjugate Chemistry* 21 (1):5-13 (2010).

II. Nucleic Acids, Vectors, and Host Cells

Anti-MerTK antibodies of the present disclosure may be produced using recombinant methods and compositions, e.g., as described in U.S. Pat. No. 4,816,567. In some embodiments, isolated nucleic acids having a nucleotide sequence encoding any of the anti-MerTK antibodies of the present disclosure are provided. Such nucleic acids may encode an amino acid sequence comprising the $V_L$ and/or an amino acid sequence comprising the $V_H$ of the anti-MerTK antibody (e.g., the light and/or heavy chains of the antibody). In some embodiments, one or more vectors (e.g., expression vectors) comprising such nucleic acids are provided. In some embodiments, a host cell comprising such nucleic acid is also provided. In some embodiments, the host cell comprises (e.g., has been transduced with): (1) a vector comprising a nucleic acid that encodes an amino acid sequence comprising the $V_L$ of the antibody and an amino acid sequence comprising the $V_H$ of the antibody, or (2) a first vector comprising a nucleic acid that encodes an amino acid sequence comprising the $V_L$ of the antibody and a second vector comprising a nucleic acid that encodes an amino acid sequence comprising the $V_H$ of the antibody. In some embodiments, the host cell is eukaryotic, e.g., a Chinese Hamster Ovary (CHO) cell or lymphoid cell (e.g., Y0, NS0, Sp20 cell). Host cells of the present disclosure also include, without limitation, isolated cells, in vitro cultured cells, and ex vivo cultured cells.

Methods of making an anti-MerTK antibody of the present disclosure are provided. In some embodiments, the method includes culturing a host cell of the present disclosure comprising a nucleic acid encoding the anti-MerTK antibody, under conditions suitable for expression of the antibody. In some embodiments, the antibody is subsequently recovered from the host cell (or host cell culture medium).

For recombinant production of an anti-MerTK antibody of the present disclosure, a nucleic acid encoding the anti-MerTK antibody is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable vectors comprising a nucleic acid sequence encoding any of the anti-MerTK antibodies of the present disclosure, or cell-surface expressed fragments or polypeptides thereof polypeptides (including antibodies) described herein include, without limitation, cloning vectors and expression vectors. Suitable cloning vectors can be constructed according to standard techniques, or may be selected from a large number of cloning vectors available in the art. While the cloning vector selected may vary according to the host cell intended to be used, useful cloning vectors generally have the ability to self-replicate, may possess a single target for a particular restriction endonuclease, and/or may carry genes for a marker that can be used in selecting clones comprising the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Suitable host cells for cloning or expression of antibody-encoding vectors include prokaryotic or eukaryotic cells. For example, anti-MerTK antibodies of the present disclosure may be produced in bacteria, in particular when glycosylation and Fc effector function are not needed. For expression of antibody fragments and polypeptides in bacteria (e.g., U.S. Pat. Nos. 5,648,237, 5,789,199, and 5,840,523. After expression, the antibody may be isolated from the bacterial cell paste in a soluble fraction and can be further purified.

In addition to prokaryotes, eukaryotic microorganisms, such as filamentous fungi or yeast, are also suitable cloning or expression hosts for antibody-encoding vectors, including fungi and yeast strains whose glycosylation pathways have been "humanized," resulting in the production of an antibody with a partially or fully human glycosylation pattern (e.g., Gerngross *Nat. Biotech.* 22:1409-1414 (2004); and Li et al. *Nat. Biotech.* 24:210-215 (2006)).

Suitable host cells for the expression of glycosylated antibody can also be derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts (e.g., U.S. Pat. Nos. 5,959,177, 6,040,498, 6,420,548, 7,125,978, and 6,417,429, describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al. *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al. *Annals N.Y. Acad. Sci.* 383:44-68 (1982); MRC 5 cells; and FS4 cells. Other useful mammalian host cell lines include Chinese hamster ovary (CHO) cells, including DHFR-CHO cells (Urlaub et al. *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, NJ), pp. 255-268 (2003).

III. Pharmaceutical Compositions/Formulations

Provided herein are pharmaceutical compositions and/or pharmaceutical formulations comprising the anti-MerTK antibodies of the present disclosure and a pharmaceutically acceptable carrier.

In some embodiments, pharmaceutically acceptable carrier preferably are nontoxic to recipients at the dosages and concentrations employed. The pharmaceutical compositions and/or pharmaceutical formulations to be used for in vivo administration can be sterile. This is readily accomplished by filtration through, e.g., sterile filtration membranes Pharmaceutical compositions and/or pharmaceutical formulations provided herein are useful as a medicament, e.g., for treating cancer.

IV. Therapeutic Uses

As disclosed herein, anti-MerTK antibodies of the present disclosure may be used for treating diseases and disorders. In some embodiments, the present disclosure provides methods for treating an individual having cancer comprising administering to the individual a therapeutically effective amount of an anti-MerTK antibody of the present disclosure.

Ectopic or expression of MerTK has been observed in various tumors; overexpression and activation of MerTK has been implicated in lymphoid leukemia, lymphoma, adenoma, melanoma, gastric, prostate, and breast cancers; and MerTK overexpression has been associated with metastasis. (Schlegel et al, 2013, J Clin Invest, 123:2257-2267; Tworkoski et al, 2013, Pigment Cell Melanoma, 26:527-541; Yi et al, 2017, Oncotarget, 8:96656-96667; Linger et al, 2013, Blood, 122:1599-1609; Lee-Sherick et al, 2013, Oncogene, 32:5359-5368; Brandao et al, 2013, Blood Cancer, 3:e101; Xie et al, 2015, Oncotarget, 6:9206-9219; Shi et al, 2018, J Hematology & Oncology, 11:43). Accordingly, modulating the activity of MerTK with an anti-MerTK antibody of the present disclosure is an effective means of treating cancer.

In certain aspects, provided herein are methods for treating cancer in a subject in need thereof, the method comprising administering to the subject an anti-MerTK antibody of the present disclosure, or a pharmaceutical composition comprising an anti-MerTK antibody of the present disclosure. In some embodiments, a method is provided for treating cancer in a subject in need thereof, the method comprising administering to the subject an anti-MerTK antibody of the present disclosure, wherein the anti-MerTK antibody reduces efferocytosis by phagocytic cells. In some embodiments, a method is provided for treating cancer in a subject in need thereof, the method comprising administering to the subject an anti-MerTK antibody of the present disclosure, wherein the anti-MerTK antibody induces M1-like macrophage polarization.

In some embodiments, the cancer is selected from sarcoma, bladder cancer, breast cancer, colon cancer, endometrial cancer, kidney cancer, renal cancer, leukemia, lung cancer, non-small cell lung cancer, melanoma, lymphoma, pancreatic cancer, prostate cancer, ovarian cancer, stomach cancer, thyroid cancer, cancer of the uterus, liver cancer, cervical cancer, testicular cancer, squamous cell carcinoma, glioma, glioblastoma, adenoma, and neuroblastoma. In some embodiments, the cancer is selected from glioblastoma multiforme, bladder carcinoma, and esophageal carcinoma. In some embodiments, the cancer is triple-negative breast carcinoma. In some embodiments, the cancer may be a primary tumor. In some embodiments, the cancer may be a metastatic tumor at a second site derived from any of the above types of cancer. In some embodiments, an anti-MerTK antibody of the present disclosure is useful for treating cancer in s subject in need thereof, wherein the cancer expresses MerTK.

In some embodiments, an anti-MerTK antibody of the present disclosure may be administered in conjunction with one or more therapeutic agents that act as a checkpoint inhibitor. In some embodiments, the method further includes administering to the individual at least one antibody that specifically binds to an inhibitory immune checkpoint molecule, and/or another standard or investigational anti-cancer therapy. In some embodiments, the inhibitory checkpoint molecule is selected from PD1, PD-L1, and PD-L2, In some embodiments, the at least one antibody that specifically binds to an inhibitory checkpoint molecule is administered in combination with the anti-MerTK antibody of the present disclosure In some embodiments, the at least one antibody that specifically binds to an inhibitory checkpoint molecule is selected from an anti-PD-L1 antibody, an anti-PD-L2 antibody, and an anti-PD-1 antibody In some embodiments, a subject or individual is a mammal. Mammals include, without limitation, domesticated animals (e.g., cows, sheep, cats, dogs, and horses), primates (e.g., humans and non-human primates such as monkeys), rabbits, and rodents (e.g., mice and rats). In some embodiments, the subject or individual is a human.

V. Diagnostic Uses

In some embodiments of any of the antibodies, any of the anti-MerTK antibodies provided herein is useful for detecting the presence of MerTK in a sample or an individual. The term "detecting" as used herein encompasses quantitative or qualitative detection. Provided herein are methods of using the antibodies of this disclosure for diagnostic purposes, such as the detection of MerTK in an individual or in tissue samples derived from an individual. In some embodiments, the individual is a human. In some embodiments, the tissue sample is phagocytic cells (e.g., macrophages, dendritic cells), tumor tissue, cancer cells, etc.

The detection method may involve quantification of the antigen-bound antibody. Antibody detection in biological samples may occur with any method known in the art, including immunofluorescence microscopy, immunocytochemistry, immunohistochemistry, ELISA, FACS analysis, immunoprecipitation, or micro-positron emission tomography. In certain embodiments, the antibody is radiolabeled, for example with $^{18}$F and subsequently detected utilizing micro-positron emission tomography analysis. Antibody-binding may also be quantified in a patient by non-invasive techniques such as positron emission tomography (PET), X-ray computed tomography, single-photon emission computed tomography (SPECT), computed tomography (CT), and computed axial tomography (CAT).

VI. Articles of Manufacture

Provided herein are articles of manufacture (e.g., kit) comprising an anti-MerTK antibody described herein. Article of manufacture may include one or more containers comprising an antibody described herein. Containers may be any suitable packaging including, but is not limited to, vials, bottles, jars, flexible packaging (e.g., sealed Mylar or plastic bags), and the like. The containers may be unit doses, bulk packages (e.g., multi-dose packages) or sub-unit doses.

In some embodiments, the kits may further include a second agent. In some embodiments, the second agent is a pharmaceutically-acceptable buffer or diluting agent including. In some embodiments, the second agent is a pharmaceutically active agent.

In some embodiments of any of the articles of manufacture, the article of manufactures further include instructions for use in accordance with the methods of this disclosure. The instructions generally include information as to dosage, dosing schedule, and route of administration for the intended treatment. In some embodiments, these instructions comprise a description of administration of the isolated antibody of the present disclosure (e.g., an anti-MerTK antibody described herein) to treat an individual having a disease, disorder, or injury, such as for example cancer, according to any methods of this disclosure. In some embodiments, the instructions include instructions for use of the anti-MerTK antibody and the second agent (e.g., second pharmaceutically active agent).

The present disclosure will be more fully understood by reference to the following Examples. They should not, however, be construed as limiting the scope of the present disclosure. All citations throughout the disclosure are hereby expressly incorporated by reference.

EXAMPLES

Example 1: Production of his-Conjugated and Murine Fc-Conjugated MerTK Polypeptides Human, cyno, and murine MerTK polypeptides containing polyHis or TEVS/Thrombin/murine IgG2a-Fc tagged fusion proteins for use in the generation and characterization of anti-MerTK antibodies of the present disclosure were generated as follows. Nucleic acid encoding the extracellular domain (ECD) of human MerTK (SEQ ID NO: 2), cyno MerTK (SEQ ID NO: 3), and murine MerTK (SEQ ID NO: 4) were each cloned into a mammalian expression vector containing nucleic acid encoding a heterologous signal peptide as well as containing either a PolyHis Fc tag or TEVS/Thrombin/murine IgG2a Fc tag.

The amino acid sequences of human MerTK, human MerTK extracellular domain, cyno MerTK extracellular domain, and murine MerTK extracellular domain are set forth below.

```
Human MerTK amino acid sequence (SEQ ID NO: 1):

MGPAPLPLLLGLFLPALWRRAITEAREEAKPYPLFPGPFPGSLQTDHTP

LLSLPHASGYQPALMFSPTQPGRPHTGNVAIPQVTSVESKPLPPLAFKH

TVGHIILSEHKGVKFNCSISVPNIYQDTTISWWKDGKELLGAHHAITQF

YPDDEVTAIIASFSITSVQRSDNGSYICKMKINNEEIVSDPIYIEVQGL

PHFTKQPESMNVTRNTAFNLTCQAVGPPEPVNIFWVQNSSRVNEQPEKS

PSVLTVPGLTEMAVFSCEAHNDKGLTVSKGVQINIKAIPSPPTEVSIRN

STAHSILISWVPGFDGYSPFRNCSIQVKEADPLSNGSVMIFNTSALPHL
```

```
YQIKQLQALANYSIGVSCMNEIGWSAVSPWILASTTEGAPSVAPLNVTV

FLNESSDNVDIRWMKPPTKQQDGELVGYRISHVWQSAGISKELLEEVGQ

NGSRARISVQVHNATCTVRIAAVTRGGVGPFSDPVKIFIPAHGWVDYAP

SSTPAPGNADPVLIIFGCFCGFILIGLILYISLAIRKRVQETKFGNAFT

EEDSELVVNYIAKKSFCRRAIELTLHSLGVSEELQNKLEDVVIDRNLLI

LGKILGEGEFGSVMEGNLKQEDGTSLKVAVKTMKLDNSSQREIEEFLSE

AACMKDFSHPNVIRLLGVCIEMSSQGIPKPMVILPFMKYGDLHTYLLYS

RLETGPKHIPLQTLLKFMVDIALGMEYLSNRNFLHRDLAARNCMLRDDM

TVCVADFGLSKKIYSGDYYRQGRIAKMPVKWIAIESLADRVYTSKSDVW

AFGVTMWELATRGMTPYPGVQNHEMYDYLLHGHRLKQPEDCLDELYEIM

YSCWRTDPLDRPTFSVLRLQLEKLLESLPDVRNQADVIYVNTQLLESSE

GLAQGSTLAPLDLNIDPDSIIASCTPRAAISVVTAEVHDSKPHEGRYIL

NGGSEEWEDLTSAPSAAVTAEKNSVLPGERLVRNGVSWSHSSMLPLGSS

LPDELLFADDSSEGSEVLM

Human MerTK ECD amino acid sequence
(SEQ ID NO: 2):
MGPAPLPLLLGLFLPALWRRAITEAREEAKPYPLFPGPFPGSLQTDHTP

LLSLPHASGYQPALMFSPTQPGRPHTGNVAIPQVTSVESKPLPPLAFKH

TVGHIILSEHKGVKFNCSISVPNIYQDTTISWWKDGKELLGAHHAITQF

YPDDEVTAIIASFSITSVQRSDNGSYICKMKINNEEIVSDPIYIEVQGL

PHFTKQPESMNVTRNTAFNLTCQAVGPPEPVNIFWVQNSSRVNEQPEKS

PSVLTVPGLTEMAVFSCEAHNDKGLTVSKGVQINIKAIPSPPTEVSIRN

STAHSILISWVPGFDGYSPFRNCSIQVKEADPLSNGSVMIFNTSALPHL

YQIKQLQALANYSIGVSCMNEIGWSAVSPWILASTTEGAPSVAPLNVTV

FLNESSDNVDIRWMKPPTKQQDGELVGYRISHVWQSAGISKELLEEVGQ

NGSRARISVQVHNATCTVRIAAVTRGGVGPFSDPVKIFIPAHGWVDYAP

SSTPAPGNADPVLII

Cyno MerTK ECD amino acid sequence
(SEQ ID NO: 3):
MGLAPLPLPLLLGLFLPALWSRAITEAREEAKPYPLFPGPLPGSLQTDH

TSLLSLPHTSGYQPALMFSPTQPGRPYTGNVAIPRVTSAGSKLLPPLAF

KHTVGHIILSEHKDVKFNCSISVPNIYQDTTISWWKDGKELLGAHHAIT

QFYPDDEVTAIIASFSITSVQRSDNGSYICKMKINNEEIVSDPIYIEVQ

GLPHFTKQPESMNVTRNTAFNLTCQAVGPPEPVNIFWVQNSSRVNEQPE

KSPSVLTVPGLTEMAVFSCEAHNDKGLTVSKGVQINIKAIPSPPTEVSI

HNSTAHSILISWVPGFDGYSPFRNCSVQVKEVDPLSNGSVMIFNTSASP

HMYQIKQLQALANYSIGVSCMNEIGWSAVSPWILASTTEGAPSVAPLNV

TVFLNESRDNVDIRWMKPLTKRQAGELVGYRISHVWQSAGISKELLEEV

GQNNSRAQISVQVHNATCTVRIAAVTKGGVGPFSDPVKIFIPAHGWVDH

APSSTPAPGNADPVLII

Murine MerTK ECD amino acid sequence
(SEQ ID NO: 4):
MVLAPLLLGLLLLPALWSGGTAEKWEETELDQLFSGPLPGRLPVNHRPF

SAPHSSRDQLPPPQTGRSHPAHTAAPQVTSTASKLLPPVAFNHTIGHIV

LSEHKNVKFNCSINIPNTYQETAGISWWKDGKELLGAHHSITQFYPDEE

GVSIIALFSIASVQRSDNGSYFCKMKVNNREIVSDPIYVEVQGLPYFIK

QPESVNVTRNTAFNLTCQAVGPPEPVNIFWVQNSSRVNEKPERSPSVLT

VPGLTETAVFSCEAHNDKGLTVSKGVHINIKVIPSPPTEVHILNSTAHS

ILVSWVPGFDGYSPLQNCSIQVKEADRLSNGSVMVFNTSASPHLYEIQQ

LQALANYSIAVSCRNEIGWSAVSPWILASTTEGAPSVAPLNITVFLNES

NNILDIRWTKPPIKRQDGELVGYRISHVWESAGTYKELSEEVSQNGSWA

QIPVQIHNATCTVRIAAITKGGIGPFSEPVNIIIPEHSKVDYAPSSTPA

PGNTDSM
```

The human, cyno, and murine MerTK nucleic acid fusion constructs were transiently transfected into HEK293 cells. The recombinant fusion polypeptides were purified from the supernatants of the cells using Mabselect resin (GE Healthcare, Cat #17519902) following the manufacturer's instructions. Additionally, commercially available DDDDK-tagged human MerTK fusion polypeptide (Sino Biological, Wayne, PA, Cat #10298-HCCH) or human IgG1 Fc-tagged murine MerTK fusion proteins (R&D systems, Minneapolis, MA, Cat #591-MR-100) were also used for anti-MerTK antibody characterization as described below.

Example 2: Generation of Human and Murine MerTK Overexpressing CHO Cell Lines Human MerTK and murine MerTK overexpressing CHO cell lines were prepared as follows. Human MerTK open reading frame (ORF) clone Lentivirus particle (Cat #RC215289L4V) and mouse MerTK ORF clone Lentivirus particle (Cat #MR225392L4V) (Origene, Rockville, MD) (both mGFP-tagged) were used for preparing human MerTK overexpressing CHO-K1 and murine MerTK overexpressing CHO-K1 stable cell line generation, respectively.

CHO cells were cultured in F12-K media (ATCC, Cat #ATCC 30-2004) containing 10% FBS (Gibco) until >80% confluent. The cells were then dissociated with Trypsin buffer (0.25% EDTA/Trypsin, Gibco, Cat #25200056) and plated at 70-80% confluency in 6-well plates 24 hours prior to transduction with either the human or murine MerTK lentivirus construct. The following day, cells were incubated with the lentiviral particle at 4° C. for 2 hours and then the plates were incubated at 37° C. in 5% $CO_2$. Two days later, puromycin (Invivogen, San Diego, CA, Cat #ant-pr-1) was added for selection; selected puromycin-resistant cells were frozen in Cell Recovery Freezing Medium (Gibco, Cat #12648010) for subsequent use.

For FACS analysis of these cell lines, human MerTK overexpressing CHO cells (CHO-huMerTK OE cells) and mouse MerTK overexpressing CHO cells (CHO-muMerTK OE cells) generated as described above were plated at $1-2\times10^5$ cells per well in 96-well U-bottom plates and incubated with a commercially available mouse anti-human MerTK monoclonal antibody (BioLegend, Clone: 590H11G1E3, Cat #367608, San Diego, CA) or a commercially available rat anti-mouse MerTK monoclonal antibody (ThermoFisher, Clone: DS5MMER, Cat #12-5751-82) for 30 minutes on ice. Cells were rinsed twice with ice-cold FACS buffer (2% FBS+PBS) and then incubated with APC-conjugated goat anti-mouse antibody (Jackson ImmunoResearch, West Grove, PA, Cat #115-606-071) or goat-anti-rat antibody (Jackson ImmunoResearch, Cat #112-606-071) for 30 min on ice. Following the secondary antibody incubation, the cells were washed with ice-cold FACS buffer and then resuspended in a final volume of 50-200 µl of FACS buffer containing 0.25 µl/well propidium iodide (BD, Cat #556463). Analysis was performed using a FACS CantoII system (BD Biosciences).

The resulting human MerTK and murine MerTK overexpressing CHO cell lines were used for subsequent studies to characterize anti-MerTK antibodies as described below.

Example 3: MerTK Expression Profile

MerTK expression was examined on various human cell types and tissues, including U937 cells (ATCC CRL-1593.2; human macrophage cell line), SK-MEL-5 cells (ATCC HTB-70; human melanoma cell line), A375 cells (ATCC CRL-1619; human melanoma cell line), THP-1 cells (ATCC TIB-202; human monocyte-like cell line), CHO-huMerTK OE cells, human monocytes, human monocyte-derived macrophages, and human monocyte-derived dendritic cells. Additionally, MerTK expression was examined on human monocytes, macrophages, and dendritic cells obtained from human tumor samples as outlined below.

Monocytes were isolated from peripheral blood mononuclear cells (PBMCs) from healthy human donors using RosetteSep monocyte isolation antibody cocktail (StemCell Technologies). The isolated human monocytes were either differentiated into human macrophages with 50 ng/mL M-CSF (Peprotech) or were differentiated into human dendritic cells (DCs) with 100 ng/mL GM-CSF and 100 ng/mL IL-4 (Peprotech). The human macrophages or human dendritic cells were incubated with a commercially available fluorochrome-conjugated anti-human MerTK antibody (BioLegend, clone 590H11G1E3) for 30 minutes on ice in the dark. Cells were washed twice in FACS buffer (PBS+2% FBS, 2 mM EDTA), and analysis of MerTK expression on the surface of the cells was performed using a BD FACS CantoII system.

Figure 2:
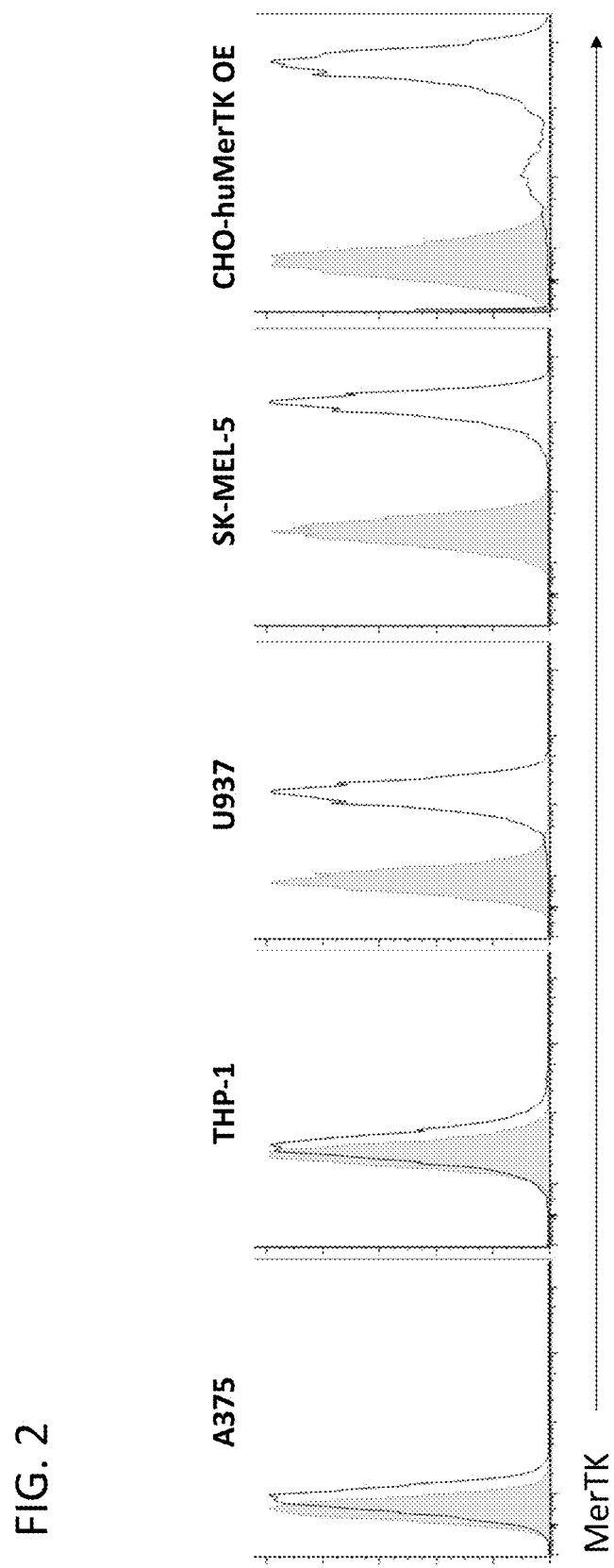
FIG. 2 sets forth data showing FACS analysis of human MerTK expression on various cell lines, including A375, THP-1, U937, SK-MEL-5, and CHO-huMerTK OE cells.

FIG. 1 shows results of FACS analysis of human MerTK expression on human myeloid cells (i.e., dendritic cells, macrophages). As shown in FIG. 1, dendritic cells (DCs) and macrophages from two different human donors displayed anti-MerTK antibody reactivity, indicating these cells express MerTK on their cell surface. FIG. 2 shows results of FACS analysis of human MerTK expression on various cell lines, including A375 cells, THP-1 cells, U937 cells, SK-MEL-5 cells, and CHO-huMerTK OE cells. As shown in FIG. 2, U937 cells, SK-MEL-5 cells, and CHO-huMerTK OE cells displayed anti-MerTK antibody reactivity, indicating that these cell lines express MerTK on their cell surface.

For analysis of MerTK expression on various myeloid cell types (e.g., monocytes, macrophages, dendritic cells) obtained from tumor samples, the following experiments were performed. Various tumor samples (from ovary, liver, and endometrial cancer) obtained from human subjects were cut into small pieces with a scalpel and transferred to GentleMACS C tubes (Miltenyi Biotec, Sunnyvale, CA) containing an enzyme mix. Samples were dissociated on GentleMACS (Miltenyi Biotec) as per the manufacturer's protocol. After dissociation, cells were filtered through a 100 µm filter prior to FACS staining. Samples were then stained with Aqua Live Dead (Thermo Scientific, Cat #L34957) and a mixture of anti-human CD16 (Clone 3G8, BioLegend, Cat #302002), anti-human CD32 (Clone AT10, Thermo Scientific, Cat #MA1-81191), and anti-human CD64 (Clone 10.1, BioLegend, Cat #305002) antibodies at 4° C. for 30 min.

After washing with FACS buffer, the cells were then stained with the following antibodies for FACS sorting and analysis: anti-human CD45-Alexa Fluor 700 (Clone HI30, BioLegend, Cat #304024), anti-human CD3-APCCy7 (clone OKT3, BioLegend, Cat #317342), anti-human HLA-DR-BV711 (Clone L243, BioLegend, Cat #307644), anti-human CD15-BV605 (Clone W6D3, BioLegend, Cat #323032), anti-human CD14-BUV395 (Clone MoP9, BD bioscience, Cat #563561), anti-human CD19-BV650 (Clone HIB19, BioLegend, Cat #302238), anti-human CD56-PE Dazzle 594 (Clone HCD56, BioLegend, Cat #318348), anti-human CD1c-PerCPCy5.5 (Clone L161, BioLegend, Cat #331514), anti-human CD206-PECy5 (Clone 15-2, BioLegend, Cat #321108), and anti-human MerTK-BV421 (Clone 590H11G1E3, BioLegend, Cat #367604) at 4° C. for 30 min. Cells were washed with FACS buffer and acquired on a BD FACS Fortessa X20. All FACS data were analyzed using FlowJo software. Monocytes (defined and gated as CD45+CD3−CD14+), macrophages (defined and gated as CD45+CD3−CD14+CD206+), and dendritic cells (defined and gated as CD45+CD3−CD14−CD56−HLA-DR+CD1c+) were identified.

Figure 3:
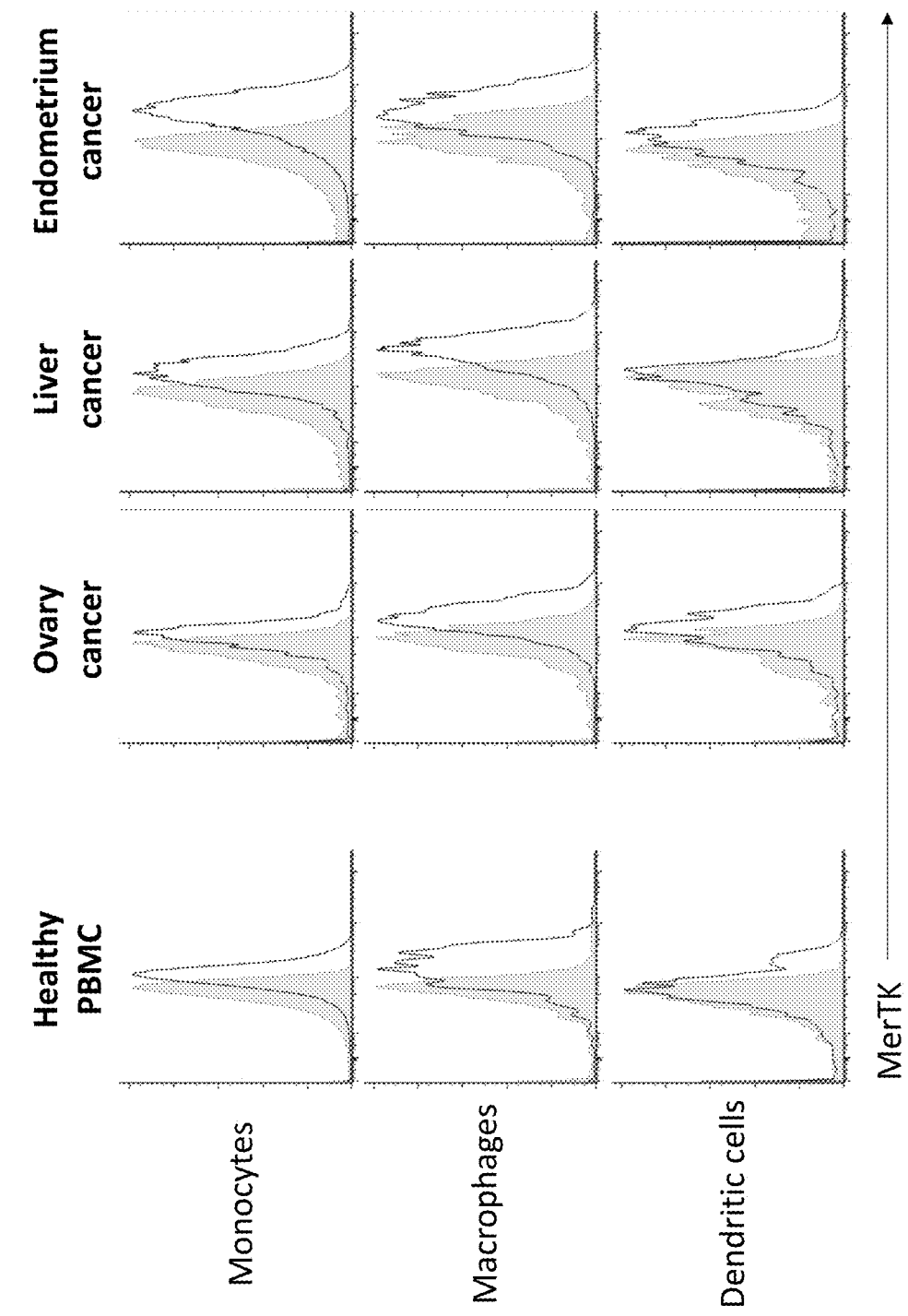
FIG. 3 sets forth data showing FACS analysis of human MerTK expression in monocytes, macrophages, and dendritic cells obtained from healthy human subjects or obtained from ovary, liver, or endometrial tumors obtained from human subjects.

As shown in FIG. 3, MerTK expression was observed by FACS analysis in monocytes, macrophages, and dendritic cells obtained from peripheral blood mononuclear cells (PBMCs) from healthy human subjects. MerTK expression was also observed in tumor-derived monocytes, macrophages, and dendritic cells obtained from ovary, liver, and endometrial cancers obtained from human subjects.

Taken together, this data showed that MerTK expression was detected on various human cells and human cell lines, on monocytes, macrophages, and dendritic cells isolated from health human subjects, and on monocytes, macrophages, and dendritic cells obtained from human ovary, liver, and endometrial cancer tumor tissue.

Example 4: Generation of Anti-MerTK Hybridoma Antibodies

In order to obtain antibodies against MerTK, the following experiments were performed in order to generate anti-MerTK hybridomas. BALB/c mice (Charles River Laboratories, Wilmington, MA) or MerTK knock-out (KO) mice (Jackson Laboratories, Bar Harbor, ME) were immunized twice a week by subcutaneous or intraperitoneal injections of purified extracellular domain polypeptides of human, cyno, and mouse MerTK (obtained as described above in Example 1) with or without adjuvant. A total of 8 injections were performed over 4 weeks. Three days following the final injection, spleens and lymph nodes were harvested from the mice for hybridoma cell line generation.

Lymphocytes from the spleens and lymph nodes of the immunized mice were isolated and then fused with P3×63Ag8.653 (CRL-1580, American Type Culture Collection, Rockville, MD) or SP2/mIL-6 (CRL-2016, American Type Culture Collection, Rockville, MD) mouse myeloma cells via electrofusion (Hybrimmune, BTX, Holliston, MA) and incubated at 37° C., 5% $CO_2$, overnight in Clonacell-HY Medium C (STEMCELL Technologies, Vancouver, BC, Canada, Cat #03803). The following day, the fused cells were centrifuged and resuspended in 10 ml of ClonaCell-HY Medium C with anti-mouse IgG Fc-FITC (Jackson ImmunoResearch, West Grove, PA) and then gently mixed with 90 ml of methylcellulose-based ClonaCell-HY Medium D (STEMCELL Technologies, Cat #03804) containing HAT components. The cells were plated into Nunc OmniTrays (Thermo Fisher Scientific, Rochester, N.Y.) and allowed to grow at 37° C., 5% $CO_2$ for seven days. Fluorescent colonies were then selected and transferred into 96-well plates containing Clonacell-HY Medium E (STEMCELL Technologies, Cat #03805) using a Clonepix 2 (Molecular Devices, Sunnyvale, CA). In total, 1,728 IgG-secreting hybridoma clones were selected. After six days of culture, tissue culture supernatants from the hybridomas were screened by FACS analysis for specificity to bind human or mouse MerTK as described below.

Example 5: Screening of Anti-MerTK Antibody Hybridoma Supernatants by FACS

Hybridoma culture supernatants from 1,728 hybridomas obtained as described above were screened for their ability to bind MerTK on various cell types, including CHO cells stably overexpressing human MerTK (CHO-huMerTK OE cells) or stably overexpressing mouse MerTK (CHO-muMerTK OE cells) (generated as described above), and CHO parental cells; U937 cells (ATCC CRL-1593.2), SK-MEL-5 cells (ATCC HTB-70) (which endogenously express human MerTK), J774A.1 cells (ATCC TIB-67) (which endogenously express mouse MerTK), and A375 cells (ATCC CRL-1619). THP-1 cells (ATCC TIB-202), which have no or minimal expression of MerTK, served as non-MerTK expressing negative control cells in these experiments.

For screening of the hybridoma cell culture supernatants, a multiplexed FACS experimental design was utilized to determine binding of anti-MerTK antibodies to these multiple cell lines. Briefly, cells were stained with various concentrations and combinations of CellTrace cell proliferation dyes CFSE and Violet (ThermoFisher, Cat #C34554 and Cat #34557, respectively) to create uniquely barcoded cell populations. 70,000 cells of each barcoded cell type were aliquoted into 96-well U-bottom plates and incubated with 50 µl of hybridoma cell culture supernatant or 5 µg/ml of commercially available purified mouse anti-human MerTK monoclonal antibody (BioLegend, Cat #367602; serving as a positive anti-MerTK antibody) on ice for 30 minutes. After this primary anti-MerTK hybridoma supernatant incubation with the various MerTK expressing cell types, the supernatants were removed via centrifugation, the cells were washed twice with 175 µl of ice-cold FACS buffer (PBS+1% FBS+2 mM EDTA), and the cells were then further incubated on ice for 20 minutes with anti-mouse IgG Fc-allophycocyanin (APC) (Jackson Labs, Cat #115-136-071) (diluted 1:1000). Following this secondary antibody incubation, the cells were again washed twice with ice-cold FACS buffer and resuspended in a final volume of 30 µl of FACS buffer containing 0.25 µl/well propidium iodide (BD Biosciences, Cat #556463). Binding intensity on cells was analyzed using the FACS Canto system (BD Biosciences), with sorting gates drawn to exclude dead (i.e., propidium iodide-positive) cells. The ratio of APC Mean Fluorescence Intensity (MFI) on each barcoded cell population was determined for each anti-MerTK hybridoma supernatant tested.

From this specific hybridoma supernatant screen, a total of 308 anti-MerTK hybridoma clones were identified that displayed greater than 2-fold difference in binding (as determined by MFI) to cells stably overexpressing or endogenously expressing human or mouse MerTK compared to the binding observed on parental or negative control cell types. Anti-MerTK antibodies identified using this screen were further characterized as described below.

Example 6: Screening of Anti-MerTK Antibody Hybridoma Supernatants by Recombinant MerTK Protein Binding Assay Hybridoma culture supernatants from 1,728 hybridomas obtained as described above were screened for their ability to bind polyHis-tagged human, cyno, and mouse MerTK (prepared as described above in Example 1) as compared to binding to an irrelevant His-tagged control protein. Briefly, 96-well polystyrene plates were coated with 1 µg/ml of human, cyno, or mouse poly-His-tagged MerTK polypeptide in coating buffer (0.05M carbonate buffer, pH 9.6, Sigma, Cat #C3041) overnight at 4° C. Coated plates were then blocked with ELISA diluent (PBS+0.5% BSA+0.05% Tween20) for one hour and washed three times with 300 µl of PBST (PBS+0.05% Tween20, Thermo 28352). The hybridoma cell culture supernatants or two commercially available purified mouse anti-human MerTK monoclonal antibodies (BioLegend Cat #367602; R&D Cat #MAB8912) were added (50 µl/well) to each well. After 30 mins incubation (room temperature, with shaking), the plates were washed three times with 300 µl of PBST. Anti-mouse IgG Fc-HRP (Jackson Immunoresearch, Cat #115-035-071) secondary antibody was diluted 1:5000 in ELISA diluent, added to each well at 50 µl/well, and incubated for 30 minutes at room temperature with shaking. After a final set of washes (3×300 µl in PBST), 50 µl/well of TMB substrate (BioFx, Cat #TMBW-1000-01) was added to the wells. The reaction was then quenched after 5-10 mins with 50 µl/well of stop solution (BioFx, Cat #BSTP-1000-01). The quenched reaction wells were detected for absorbance at 650 nm with a BioTek Synergy Microplate Reader using GENS 2.04 software. From this hybridoma supernatant screen, a total of 326 anti-MerTK hybridoma clones were identified that displayed greater than 10-fold difference in binding to recombinant MerTK over background. Anti-MerTK antibodies identified using this screen were further characterized as described below.

Example 7: MerTK Ligand Gas6 and Ligand ProS Blocking Assay Using Anti-MerTK Hybridoma Supernatants Anti-MerTK antibody hybridoma supernatants identified as described above were evaluated for their ability to block binding of human Gas6 ligand and/or block binding of human ProS ligand to human MerTK by ELISA. Briefly, rabbit anti-human IgG antibody (Jackson ImmunoResearch, Cat #309-005-008) was coated at 2 µg/ml onto high-protein binding plates at 4° C. overnight. After washing with 0.05% Tween20 in PBS three times, 5% BSA in PBS was added for 1 hour. Recombinant human MerTK-human Fc Chimera protein (R&D systems, Cat #391-MR-100) was added at 2 µg/ml for 1 hour and plates were washed before the addition of 40 µl of anti-MerTK hybridoma supernatants and 40 µl of His tag-conjugated recombinant Gas6 (R&D systems, Cat #885-GSB-050) at 3 µg/ml or His tag-conjugated recombinant ProS (R&D systems, Cat #9489-PS-100) at 20 µg/ml. After a further incubation for 1 hour, plates were washed and incubated for 1 hour with HRP-conjugated anti-6×His tagged antibody (Abcam, Cambridge, MA, Cat #ab1187). Plates were then washed and an HRP substrate, TMB, was added to develop the plates. The reaction was stopped by adding 50 µl 2N $H_2SO_4$ and the OD was measured using a spectrophotometer (BioTek).

A total of 308 anti-MerTK hybridoma supernatant clones were screened for their ability to block Gas6 and/or block ProS ligand binding to MerTK. Twenty-nine (29) anti-MerTK hybridoma clones blocked the binding of both ProS ligand and Gas6 ligand to recombinant human MerTK protein. One hundred forty-five (145) anti-MerTK hybridoma clones blocked binding of ProS ligand to human MerTK protein only and did not block the binding of Gas6 ligand to recombinant human MerTK protein. The remainder of the 308 anti-MerTK hybridoma clones screened by this assay did not block either ProS ligand or Gas6 ligand binding to recombinant human MerTK protein in this assay. The hybridoma supernatants were characterized further regarding their ability to block efferocytosis by phagocytic cells as described below.

Example 8: Efferocytosis Blocking Assay Using Anti-MerTK Hybridoma Supernatants Anti-MerTK antibody hybridoma supernatants identified above as positive for MerTK binding reactivity were evaluated for their ability to block efferocytosis by human macrophages as follows. Human macrophages were differentiated from human monocytes for 7 days in the presence of human M-CSF. Macrophages were harvested (by scraping), resuspended in PBS, and plated on 96-well plates at $5 \times 10^4$ cells/well. Cells were starved for 1 hour followed by the addition of anti-MerTK hybridoma supernatants to each well for 30 min at 37° C. Jurkat cells were treated with 1 µM staurosporin (SigmaAldrich) for 3 hours at 37° C. (to induce apoptosis) and labeled with pHrodo (ThermoFisher) for 30 min at room temperature. After washing with PBS, pHrodo labeled Jurkat cells were added into each well at 1:4 ratio (1 macrophage cell to 4 Jurkat cells) for 1 hour. The plates were washed with PBS and then cells were stained with APC-conjugated anti-human CD14 for 30 minutes on ice in the dark. Cells were then washed twice in FACS buffer (PBS+ 2% FBS), and flow cytometry was performed on a BD FACS CantoII. Data were analyzed using FlowJo software. Macrophages that are capable of efferocytosis engulf the labeled apoptotic Jurkat cells, which are then be detected, whereas macrophages that are blocked from carrying out efferocytosis show decreased engulfment of the labeled apoptotic Jurkat cells.

In these experiments, efferocytosis-positive macrophages were identified by setting pHrodo CD14 double positive cells as an analysis gate and then applying this exact gate to all the samples. Baseline efferocytosis levels were established using macrophages cultured with media alone and this was set to 100% efferocytosis activity. Relative efferocytosis levels were calculated as a percent of efferocytosis observed in cells treated with media alone compared to that observed in cells treated with anti-MerTK hybridoma supernatants. In these experiments, the following additional anti-MerTK antibodies were used: mouse anti-human MerTK antibody H1 (BioLegend, Clone ID: 590H11G1E3, mouse IgG1) and human anti-human MerTK antibody M6 (disclosed in WO2016/106221).

Table 1 and Table 2 below show results from these efferocytosis experiments, as % efferocytosis (media alone was set to 100% efferocytosis). In Table 1 below, exemplary hybridoma supernatants tested are indicated on the left and labeled as hybridoma supernatant ID number; these supernatants were from hybridoma clones identified from immunization of wildtype BALB/c mice. In Table 2 below, exemplary hybridoma supernatants tested are indicated on the left and labeled as hybridoma supernatant ID number; these supernatants were from hybridoma clones identified from immunization of MerTK KO mice. In both Table 1 and Table 2, antibody ID refers to anti-MerTK antibodies of the present disclosure that were selected for additional characterization and thus given a specific anti-MerTK antibody name, as indicated. The third, fourth and fifth columns ("Donor" identification numbers) indicate the percent efferocytosis relative to media treatment alone. Note that in comparison to efferocytosis in macrophages in the absence of antibody (media treatment alone), no significant change in efferocytosis was observed in cells treated with isotype control mouse IgG1 antibody.

TABLE 1

| Hybridoma supernatant ID | Antibody ID | Donor 689 | Donor 692 | Donor 806 |
|---|---|---|---|---|
| 1 |  | 89.4 | 80.8 | 94.4 |
| 2 |  | 126.0 | 105.3 | 109.0 |
| 3 | MTK-01 | 34.1 | 34.2 | 70.1 |
| 4 | MTK-02 | 20.8 | 32.2 | 62.9 |
| 5 |  | 68.9 | 101.6 | 73.1 |
| 6 | MTK-03 | 25.2 | 16.9 | 53.6 |
| 7 | MTK-04 | 23.8 | 25.6 | 58.3 |
| 8 |  | 107.7 | 109.0 | 112.6 |
| 9 |  | 86.3 | 109.0 | 88.3 |
| 10 | MTK-05 | 36.1 | 18.2 | 43.0 |
| 11 | MTK-06 | 16.1 | 16.0 | 67.5 |
| 12 | MTK-07 | 18.8 | 17.4 | 56.8 |
| 13 |  | 68.9 | 101.6 | 73.1 |
| 14 | MTK-08 | 30.9 | 19.0 | 35.7 |
| 15 |  | 65.4 | n.a. | 88.8 |
| 16 | MTK-09 | 19.9 | 17.6 | 50.5 |
| 17 |  | 68.5 | 72.2 | 71.8 |
| 18 | MTK-10 | 18.8 | 12.6 | 50.0 |
| 19 | MTK-11 | 14.3 | 11.9 | 30.8 |
| 20 | MTK-12 | 14.6 | 12.4 | 38.6 |
| 21 |  | 67.6 | 74.6 | 83.0 |
| 22 | MTK-13 | 21.8 | 12.2 | 45.6 |
| 23 |  | 88.1 | 92.9 | 82.5 |
| 24 | MTK-14 | 25.2 | 17.5 | 55.3 |
| 25 |  | 82.4 | n.a. | n.a. |
| 26 | MTK-15 | 27.2 | 23.7 | n.a. |
| 27 |  | 86.8 | 61.8 | 78.9 |
| 28 |  | 65.8 | 79.9 | n.a. |
| 29 | MTK-16 | 25.6 | n.a. | n.a. |
| 30 | MTK-17 | 22.7 | n.a. | n.a. |
| 31 |  | 75.9 | 74.7 | 89.3 |
| 32 | MTK-18 | 24.2 | n.a. | n.a. |
| 33 |  | 106.0 | 76.1 | 116.5 |
| 34 | MTK-19 | 48.0 | n.a. | n.a. |
| 35 | MTK-20 | 21.4 | n.a. | n.a. |
| 36 |  | 98.1 | 86.1 | 85.7 |
| 37 |  | 106.0 | 87.1 | 93.7 |
| 38 |  | 74.1 | 62.8 | 90.5 |
| 39 |  | 115.1 | 106.8 | 80.6 |
| 40 |  | 108.1 | 62.0 | 100.2 |
| 41 | MTK-21 | 22.2 | n.a. | n.a. |
| 42 | MTK-22 | 25.7 | n.a. | n.a. |
| 43 |  | 76.7 | 61.1 | 87.4 |
| 44 |  | 97.2 | 71.8 | 69.4 |
| 45 |  | 75.4 | 73.0 | 73.3 |
| 46 | MTK-23 | 17.0 | n.a. | n.a. |
| 47 |  | 100.3 | n.a. | 95.9 |
| 48 |  | 65.4 | n.a. | 71.6 |
| 49 |  | 56.7 | 66.9 | 69.9 |
| 50 |  | 63.7 | n.a. | 74.0 |
|  | Media | 100.0 | 100.0 | 100.0 |
|  | mIgG1 | 104.5 | 95.6 | 96.0 |
|  | H1 | 31.2 | 16.5 | 57.9 |
|  | M6 | 14.9 | n.a. | 35.1 | n.a. means data not available

TABLE 2

| Hybridoma supernatant ID | Antibody ID | Donor 914 | Donor 915 | Donor 916 | Donor 783 |
|---|---|---|---|---|---|
| 1 | MTK-24 | 25.42 | 40.49 | 43.39 | 70.57 |
| 2 |  | 86.61 | 66.80 | 72.73 | 106.69 |
| 3 |  | 80.65 | 56.68 | 55.79 | 109.36 |
| 4 | MTK-25 | 44.05 | 31.01 | 25.50 | 21.37 |
| 5 | MTK-26 | 24.67 | 24.25 | 37.73 | 30.80 |
| 6 |  | 83.04 | 73.28 | 68.18 | 103.01 |
| 7 |  | 77.98 | 92.31 | 114.05 | 142.47 |
| 8 |  | 100.30 | 92.71 | 102.07 | 123.08 |
| 9 | MTK-27 | 33.63 | 27.49 | 34.59 | 19.26 |
| 10 |  | 78.87 | 63.56 | 73.14 | 92.31 |
| 11 | MTK-28 | 38.10 | 42.91 | 51.65 | 69.23 |
| 12 |  | 96.73 | 87.85 | 102.48 | 123.08 |
| 13 | MTK-29 | 32.14 | 36.40 | 28.26 | 49.83 |
| 14 |  | 97.92 | 73.68 | 80.99 | 122.07 |
| 15 |  | 94.64 | 73.28 | 88.84 | 126.76 |
| 16 |  | 106.55 | 86.23 | 97.93 | 130.43 |
| 17 |  | 98.81 | 66.80 | 87.19 | 128.76 |
| 18 |  | 101.79 | 95.55 | 100.00 | 115.72 |
| 19 | MTK-30 | 30.65 | 29.27 | 34.71 | 33.78 |
| 20 | MTK-31 | 41.37 | 37.85 | 32.60 | 32.78 |
| 31 |  | 89.58 | 65.59 | 72.31 | 79.60 |
| 21 |  | 79.17 | 47.37 | 68.60 | 93.98 |
| 22 | MTK-32 | 63.10 | 54.25 | 57.44 | 73.24 |
| 23 | MTK-33 | 25.54 | 22.35 | 36.61 | 13.55 |
| 24 |  | 80.06 | 67.61 | 66.94 | 100.00 |
| 25 |  | 68.15 | 51.42 | 55.37 | 62.21 |
| 26 | MTK-35 | 40.48 | 24.21 | 39.34 | 30.37 |
| 27 |  | 86.61 | 64.37 | 88.02 | 119.40 |
| 28 |  | 84.82 | 83.40 | 88.84 | 112.37 |
| 29 |  | 78.57 | 61.94 | 73.97 | 122.41 |
| 30 |  | 75.60 | 76.92 | 71.90 | 111.04 |
| 31 |  | 75.30 | 78.95 | 76.86 | 117.39 |
| 32 |  | 79.76 | 89.88 | 83.06 | 118.73 |
| 33 |  | 72.02 | 75.30 | 68.60 | 98.33 |
| 34 | MTK-36 | 73.51 | 93.52 | 82.23 | 120.74 |
| 35 |  | 71.73 | 82.59 | 74.79 | 128.76 |
|  | Media alone | 100.00 | 100.00 | 100.00 | 100.00 |
|  | M6 | 17.47 | 20.40 | 28.31 | 14.82 |
|  | Isotype control | 88.99 | 104.05 | 104.55 | 93.65 |
|  | H1 | 24.76 | 34.33 | 40.79 | 34.78 |

In Table 1 and Table 2, percent of efferocytosis by human macrophages from different donors is shown, with media alone (no antibody addition) set to 100% efferocytosis in both Tables. Although the degree of efferocytosis blocking activity by various anti-MerTK antibody hybridoma supernatants was different in macrophages obtained from each donor, the efferocytosis blocking trend for anti-MerTK antibodies was consistent among macrophages from different donors. As shown in Tables 1 and 2 above, anti-MerTK hybridoma supernatants of the present disclosure reduced efferocytosis by human macrophages to varying extents (e.g., reduced efferocytosis by about 50%-85%). These results indicated that anti-MerTK antibodies obtained as described herein were effective at reducing or blocking efferocytosis by phagocytic cells.

Example 9: Molecular Cloning of Anti-MerTK Antibodies

Anti-MerTK antibodies from the hybridomas described above were subcloned as follows. $5 \times 10^5$ hybridoma cells were harvested and washed with PBS and then the cell pellets were flash frozen in dry ice and stored at −20° C. Total RNA was extracted by using RNeasy Mini Kit (QIAGEN, Cat #74104) following the manufacturer's protocol. cDNA was generated using Clontech's SMARTer RACE 5'/3' Kit (Takara Bio USA, Cat #634859) following the manufacturer's protocol. Variable heavy and light immunoglobulin regions were cloned separately by touchdown PCR using the 5' UPM primer provided in the RACE kit and reverse primers recognizing the heavy chain and light chain constant regions. The resulting PCR products were purified and ligated into a pCR2.1-TOPO cloning vector (TOPO TA cloning Kit, Invitrogen Cat #450641) and transformed into *Escherichia coli* (*E. coli*) cells. Transformed colonies were isolated and the variable heavy chain (VH) and variable light chain (VL) nucleic acids were sequenced for each corresponding hybridoma cell line. Following the sequence determinations, variable heavy chain regions and variable light chain regions were amplified by PCR using primers containing endonuclease restriction sites and then subcloned into pLEV-123 (LakePharma, San Carlos, CA) mammalian expression vector encoding human IgG1-Fc-LALAPS (human IgG1 Fc comprising amino acid substitutions L234A, L235A, and P331S by EU numbering) and IgG Kappa.

Amino acid sequences of the variable heavy chains and variable light chains of anti-MerTK antibodies of the present disclosure are provided below in Table 3. In Table 3, the CDR/HVR sequences (according to Kabat) are underlined.

TABLE 3

| Antibody | Heavy Chain Variable | SEQ ID NO: | Light Chain Variable | SEQ ID NO: |
|---|---|---|---|---|
| MTK-01 | QIQLVQSGPELKKPGETVKISC KASGYTFTNYGMNWVKQAPGKG LKCMGWINTYTGEPTYADDFKG RFAFSLETSATTAYLQINNLKN EDTATYFCARRDRYTWFAYWGQ GTLVTVSA | 5 | QIVLSQSPAILSASPGEKVTMTC RASSSVSYMHWYQQKPGSSPKPW IYATSNLASGVPARFSGSGSGTS YSLTISRVEAEDAATYYCQQWSS NPPTFGGGTKLEIK | 40 |
| MTK-02 | QIQLVQSGPELKQPGETVKISC KASGYTFTDYGVNWVKQAPGKG LKWMGWINTYSGEPTYAGDFKG RFAFSLESSASTAFLQINNLKN EDMATYFCARRVRYWYFDVWGA GTSVTVSS | 6 | QIVLSQSPAILSASPGERVTMTC RANSSVSYMHWYQQKPGSSPKPW IYATSNLASGVPARFSASGSGTS YSLTVSRVEAEDAATYYCQQWGS NPFTFGSGTKLEIK | 41 |
| MTK-03 | DVQLQESGPGLVKPSQSLSLTC SVTGYSITSGYYWNWIRQFPGN TLEWMGYMSFDGDNKFNPSLKN RISITRDTSKNQFFLRLNSVTT EDTATYYCARGGYNYGSTEANW GQGTLVTVSA | 7 | QIVLTQSPAIMSAFPGEKVTITC SASSSVNYMHWFQQKPGTSPKLW IYSTSNLASGVPARFSGSGSGTS YSLTISRMEAEDAATYYCQQRSS YPFTFGSGTKLEIK | 42 |

TABLE 3-continued

| Antibody | Heavy Chain Variable | SEQ ID NO: | Light Chain Variable | SEQ ID NO: |
|---|---|---|---|---|
| MTK-04 | QIQLVQSGPELKKPGETVKISCKASGYTFTNYGMNWVKQAPGKGLKCMGWINTYTGEPTYADDFKGRFAFSLETSASTAYLQINNLKNEDMATYFCAKYDNYAWFAYWGQGTLVTVSA | 8 | QIVLSQSPAFLSASPGEKVTMTCRASSSVSYMHWYLQKPGSSPKPWIYATSNLASGVPVRFSGSGSGTSYSLTISRVEAEDAATYYCQQWSSNPRTFGGGTKLEIR | 43 |
| MTK-05 | QVQLQQSGAELVQPGTSVRLSCKTSGYTFTSYWIQWVKQRPGQGLGWIGEIFPGTGTTYYNEKFKGKATLTIDTSSSTAYMQLSSLTSEDSAVYFCARDGAYFDVWGAGTTVTVSS | 9 | DIQMTQSPASLSASVGETVTFTCRASENIFSYLAWYQQKQGKSPQLLVYNAKTLAEGVPSRFSGSGSGTHFSLKINSLQPEDFGSYYCLHHYGTPLTFGAGTKLELK | 44 |
| MTK-06 | QIQLVQSGPELKKPGETVKISCKASGYTFTNYGMNWVKQAPGKGLKWMGWINTNTGEPTYAEEFKGRFAFSLETSASTAYLQINNLKNEDTATYFCARYYNYWYFDVWGAGTTVTVSS | 10 | QIVLSQSPAILSASPGEKVTMTCRASSSVSYMHWYQQKPGSSPKPWIYATSNLASGVPARFSGSGSGTSYSLTISRVEAEDAATYYCQQWSSKPPTFGGGTKLEIK | 45 |
| MTK-07 | DVQLQESGPGLVKPSQSLSLTCSVTGYSITSGYYWNWIRQFPGNTLEWMGYMSFDGDNKFNPSLKNRISITRDTSKNQFFLRLNSVTTEDTATYYCARGGYNYGSTEANWGQGTLVTVST | 11 | QIVLTQSPAIMSAFPGEKVTITCSASSSVTYMHWFQQKPGTSPKLWIFSTSNLASGVPARFSGSGSGTSYSLTISRMEAEDAATYYCQQRSSYPFTFGSGTKLEIK | 46 |
| MTK-08 | QIQLVQSGPELKKPGETVKISCKASGYTFTNYGMNWVKQAPGKGLKWMGWINTYTGEPTYADDFKGRFAFSLETSASTAYLQINNLKNEDTATYFCAREVRYWYFDVWGAGTTVTVSS | 12 | QIVLSQSPAILSASPGEKVTMTCRATSSVSYMHWFQQKPGSSPKPWIYATSNLASGVPARFSGSGSGTSYSLTISRVEAEDAAYYCQHWSGNPRTFGGGTKLEIK | 47 |
| MTK-09 | QVQLQQSGAELVRPGASVKISCKAFGYTFTNHHIKWVKQRPGQGLDWIGYIDPYNDYTTYNQNFKGKATLTVDKSSSTAYMELSSLTSEDSAVYYCARRAYDGYYVDWYFDVWGAGTTVTVSS | 13 | DIVMTQSHKFMSTSVGDRVSITCKASQDVTTSVAWYHQKPGQSPELLIYSASYRYTGVPDRFTGSGSGTDFTFTISSVQAEDLAIYYCQQHYSTPLTFGSGTKLQLK | 48 |
| MTK-10 | QVTLKESGPGILQPSQTLSLTCSFSGFSLTTSGMGVGWIRQPSGKGLEWLAHIWSDDDKRSNPALKSRLTISQDSSTNQVFLKIASVDTADSATYYCSHLTPVREFAYWGPGTLVTVSE | 14 | DIQMTQTTSSLSASLGDRVTISCSASQGISNYLNWFQQKPDGTVKLLIYYTSRLHSGVPSRFSGSGSGTDFSLTISNLEPEDIATYYCQQYTKLPYTFGGGTKLEIK | 49 |
| MTK-11 | QVQLKQSGPGLVQPSQSLSITCTVSGFSLTDYGVHWVRQSPGKGLEWLGVIWSSGTTDYNEAFISRLSISKDNSKSHVFFKMNSLQAIDTAIYYCARKGHDPYAMDYWGQGTSVTVSS | 15 | QIVLTQSPAIMSASLGERVTMTCTASSSISSSYFHWYQQKPGSSPKLWIYSTSNLPSGVPARFSGSGSGTSYSLTISSMEAEDAATYYCHQYYRSPLTFGAGTKLELK | 50 |
| MTK-12 | QVQLQQSGPQLVRPGASVKISCKASGYSFTSHWMHWVKQRPGQGLEWIGMIDPSDGESRLNQKFKDKATLTVDKSSSTAYMQLSSPTFEDSAVYYCARGIYYYGITYAMDYWGQGTSVTVSS | 16 | QIVLTQSPAIMSASPGEKVTMTCSASSSVSYMYWYQQKPRSSPRLLIYDTSNLASGVPVRFSGSGSGTSYSLTISRMEAEDAATYYCQQWSSYPLTFGAGTKLELK | 51 |
| MTK-13 | DVQLQESGPGLVKPSQSLSLTCSVTGYSITSGYYWNWIRQFPGNKLEWMGNIDYDGSNKYNPSLKNRISITRDTSKNHFFLKLNSVTPEDTATYFCARDGGNYRSFAYWGQGTLVTVSA | 17 | QIVLTQSPPIMSASPGEKVTITCSASSSVSYMYWFQQKPGTSPKLWIYSTFNLASGVPARFSGSGSGTSYSLTISRMEAEDVATYYCQQRSSYPFTFGSGTKLEIK | 52 |

TABLE 3-continued

| Antibody | Heavy Chain Variable | SEQ ID NO: | Light Chain Variable | SEQ ID NO: |
|---|---|---|---|---|
| MTK-14 | QIQLVQSGPELKKPGETVKISCKASGYTFTNYGMNWVKQAPGKDLQWMGWINTYTGEPTYADDFTGRFAFSLETSASTAYLQINNLKNEDTATYFCAKGGHYAWFAYWGQGTLVTSA | 18 | QIVLSQSPAILSASPGEKVTMTCRSSSSVSYMHWYQQKPGSSPKPWIYATSNLASGVPGRFSGSGSTSYSLTISRVEAEDAATYYCQQWGSNPRTFGGGTKLEIK | 53 |
| MTK-15 | QIQLVQSGPELKKPGETVKISCKASGYTFTNYGVHWVKQAPGKGLKWMGWINTYTGEPTYADDFKGRFAFSLETSASTAYLQINNLKNEDMATYFCARGNRYAYMDYWGQGTSVTVSS | 19 | QIVLSQSPAILSASPGEKVTMTCRASSSVSYMHWYQQKSGSSPKPWIYATSNLASGVPARFSGSGSTSYSLTISRVEAEDAATYYCQQWSSNPRTFGGGTKLEIK | 54 |
| MTK-16 | LIQLVQSGPELKKPGETVKISCKASGYTFTNHGMNWVKQDPGKGLKWMGWINTYTGEPTYADDFKGRFVFSMETSASAAFLQINNLKNEDTATYFCARKGVTAARYFDYWGQGTTLTVSS | 20 | DIVMTQSPKFMSTSVGDRVSITCKASQNVRTAVAWYKKKPGQSPKALINLASNRHTGVPDRFTGSGSGTDFTLTISNVQSEDLADYFCLQHWNYPLTFGGGTKLEIK | 55 |
| MTK-17 | QIQLVQSGPELKKPGETVKISCKASGYTFTNFGMNWVKQAPGKGLKWMGWINTYTGEPTYADDFKGRFAFSLETSASTAYLQINNLKNEDTATYFCSRGAVLRAGAMDCWGQGTSVTVSS | 21 | DIQMTQSSSYLSVSLGGRVTITCKASDHINNWLAWYQQKPGNAPRLLISGATSLETGVPSRFSGSGSGKDYTLSITSLQTEDVATYYCQQYWSTPRTFGGGTKLEIK | 56 |
| MTK-18 | QIQLVQSGPELKKPGETVKISCKASGYTFTHYGMTWVKQAPGKGLKWMGWINTYTGEPTYADDFKGRFAFSLETSASTAYLQINNLKNEDTATYFCARGGGQLGLRPLDYWGQGTTLTVSS | 22 | DIQMTQTTSSLSASLGDRVTFSCRASQAISNYLNWYQQKPDGTVKLLIYYTSRLHSGVPSRFSGSGSGTDYSLTISNLEQEDIATYFCQQGNTLPWTFGGGTKLEIK | 57 |
| MTK-19 | EVQLQQSGPELVKPGASVKISCKTSGYTFTEYTMHWVKQSHGKSLEWLGGFNPNNVITSYNQRFQGRATLTVDKSSSTAYMELRSLTSDDSAVYYCTRGDLLWSLLLPGNYFDYWGQGTTLTVSS | 23 | DVVMTQSSLTLSVTIGQPASISCKSSQSLLDSDGKTYLNWLLQRPGQSPKRLIYLVSKLDSGVPDRFTGSGSGTDFTLKISRVEAEDLGVYYCWQGTHFPWTFGGGTKLEIK | 58 |
| MTK-20 | QIQLVQSGPELKKPGETVKISCKASGYTFTNYGMTWVKQAPGKGLKWMGWINTYTGEPTYADDFKGRFALSLETSASTAYLQINNLKNEDTATYFCARGGGRLGLRPLDYWGQGTTLTVSS | 24 | DIQMTQTTSSLSASLGDRVTISCRASQDINNYLNWYQQKPDGTVKLLIYYTSRLHSGVPSRFSGSGSGTDYSLTISNLEQEDIATYFCQQGNTLPWTFGGGTKLEIK | 59 |
| MTK-21 | QIQLVQSGPELKKPGETVKISCKASGYTFTNFGMTWVRQAPGMDLKWMGWINTYTGEPKYADDFKGRFALSLETSASTAYLQITNFKNEDTATYFCARGGGRLGLRPLDYWGQGTTLTVSS | 25 | DIQMTQTTSSLSASLGDRVTISCRASQDINNYLNWYQQKPDGTVKLLIYYTSSLHSGVPSRFSGSGSGTDYSLTITNLEQEDIATYFCQQGNTLPWTFGGGTRLEIK | 60 |
| MTK-22 | QVQLQQPGADLVEPGASVKLSCKASGYTFTSYWMHWVKQRPGQGLEWIGEIDPSDSSSNYNQKFKGKATLTVDKSSSTAYMHLNSLTSEDSAVYYCARRYYYGSLYFDNWGQGTTLTVSS | 26 | DVVMTQSHKFMSTSVGDRVSITCKASQDVGTAIAWYQQKPGQSPKLLIYWASTRHTGVPDRFTGSRSGTVFTLTISNVQSEDLADYFCQQYTSYPLTFGSGTKLEIK | 61 |
| MTK-23 | QVQLQQSGADLVRPGASVKISCKAFGYTFTNHHINWVKQRPGQGLDWIGNVDPYNDYSTYNQKFKGKATLTVDKSSSTAYMELSSLTSEDSAVYYCARRVYDGFYVDWYFDVWGAGTTVTVSS | 27 | DIVMTQSHKFMSTPVGDRVSITCKASRDVSTAVAWFHQKPGQSPKLLIYSASYRSTGVPDRFTGSGSGTDFTFTISSVQAEDLAVYYCQQHYSAPLTFGAGTKLELK | 62 |
| MTK-24 | QVQLQQPGAELVKPGASVKLSCKASGYTFTSYWMHWVKQRPGQGLEWIGMIHPNINTNYNEKFKSKATLTVDISSSTAYMQLSSLTSEDSAVYYCAKRSPYSNYDWYFDVWGTGTTVTVSS | 28 | DIQMTQSPASLSVSVGETVTITCRASENIYSNLAWYQQKQGKSPQLLVYAATNLADGVPSRFSGSGSGTQYSLKINSLQSEDFGSYYCQHFWGTPLTFGAGTKLELK | 63 |

TABLE 3-continued

| Antibody | Heavy Chain Variable | SEQ ID NO: | Light Chain Variable | SEQ ID NO: |
|---|---|---|---|---|
| MTK-25 | EVKLVESEGGLVQPGSSMKLSCTASGFTFSDYYMAWVRQVPEKGLEWVANINYEGSSTYYLGSLKSRFIISRDNAENILYLQMSSLKSEDTATYYCARYYYGSVDYWGQGTTLTVSS | 29 | DIVMTQSQKFMSTSVGDRVSITCKASQNVRTTVAWYQQKPGQSPKTLIYLASNRHTGVPDRFTGSGSGTDFTLTISNVQSEDLADYFCLQLWNYPWTFGGGTKLEIK | 64 |
| MTK-26 | AVQFQESGPGLVKLSQSLSLTCSVTGYSITSGYYWDWIRQFPGNKLEWMGYISYDGSNNYNPSLKNRISITRDTSKNQFFLKLNSVTTEDTATYYCAREGGYYRSMDYWGQGTSVTVSS | 30 | QIVLTQSPAIMSASPGEKVTIACSASSSVSFMHWFQQKPGTSPRLWIYSTSNLASGVPARFSGSGSGTSYSLTISRMEAEDAATYYCQQRSSYPFTFGSGTKLEIK | 65 |
| MTK-27 | EVQLQQSGTELVRPGASVKLSCTASGFNIKDDYMHWVQQRPEQGLEWIGWIDPENGNTEYASKFQGKATITADASSNTAYLQLSSLTSEDTAVYYCSTLFSNYFDYWGQGTTLTVSS | 31 | DIVMTQSQKFMSTSVGDRVSITCKASQNVRTSVAWYQQKPGQSPKALIYLASNRHTGVPDRFTGSGSGTDFTLTISNVRSEDLADYFCLQHWNYPYTFGGGTKLEIK | 66 |
| MTK-28 | QIQLVQSGPELKKPGETVKISCKASGYTFTTYGMSWVKQAPGKGLKWMGWINTYSGVPTYADDFKGRFAFSLETSASTAYLQINTLKNEDTTTYFCARFLRYYYFDYWGQGTTLTVSS | 32 | QIVLSQSPVILSASPGEKVTMTCRASSSVTYMHWYQQPGSSPKPWIYATSNLASGVPARFSGSGSGTSYSLTISRVETEDAATYYCHQWSGNPTFGGGTKLEIN | 67 |
| MTK-29 | QIQLVQSGPELKKPGETVKISCKSSGFTFTTYGMSWVKQAPGKGLKWMGWINTYSGVPTYTDDFKGRFAFSLETSASTASLQINNLKNEDTATYFCARYTNYGYFDYWGQGTTLTVSS | 33 | QIVLSQSPAILSASPGEKVTMTCRATSSVGYMHWYQQKPGSSPKPWIYATSNLASGVPARFSGSGSGTSYSLTISRVEAEHAATYYCQQWGSNPFTFGSGTKLEIK | 68 |
| MTK-30 | QVQLQQPGTELVRPGASVKLSCKASGYTFTSYWMHWVKQRPGQGLEWIGNLNPNNGGTYYNEKFKSKATLTVDKSSSTAYMQLSSLTSEDSAVYYCARQILLYFDYWGQGTTLTVSS | 34 | DVLMTQTPLSLPVSLGDQASISCRSSQSIVHSNGDTYLEWYLQKPGQSPKLLIYKVSNRFSGVPDRFSGSGSGTDFTLKISRVEAEDLGVYYCFQGSHVPWTFGGGTKLEIK | 69 |
| MTK-31 | QIQLVQSGPELKKSGETVKISCKASGYTFTSYGMSWVKQAPGKGLKWMGWINTYSGVPTYADDFKGRFAFSLETSASTAYLQINNLKNEDTATYFCASLSYDGSLYHAMDYWGQGTSVTVSS | 35 | DVSMTQTPLSLPVSLGDQASISSRSSQTIVHSNGNTYLEWYLQKPGQSPKLLIYKVSNRFSGVPDRFSGSGSGTDFTLKISRVEAEDLGVYYCFQGSHVPWTFGGGTKLEIK | 70 |
| MTK-32 | QIQLVQSGPELKKPGETVKISCKASGYTFTSYGMSWVHQAPGKGLKWLGWINTYSGVPTYADDFRGRFAFSLDTSVSTASLEINNLQNEDTATYFCAREDNWAWFAYWGQGTLVTVST | 36 | QIVLSQSPAILSASPGEKVTMTCRATSSVGYMHWYQRKPGSSPKPWIYATSNLASGVPARFSGSGSGTSYSLTISRVEAEDAATYYCQQWSSNPRTFGGGTKLEIK | 71 |
| MTK-33 | QVQLQQPGPELVRPGTSVKLSCKASGYTFTSYWMHWIKQRPGQGLEWIGVIDPSDNYINYNQKFKGKATLTVDTSSSTAYLQLSSLTSEDSAVYYCAREAGTRGYFDYWGQGTTLTVSS | 37 | SIVMTQTPKFLLVSAGDRVIITCKASQSVSNTVAWYQQKPGQSPKLLIYYASNRYTGVPDRFTGSGYGTDFTFTISTVQAEDLAVYFCQQDYRSPFTFGSGTQLEMK | 72 |
| MTK-34 | QVQLQQPGPELVRPGTSVKLSCKASGYTFTSYWMHWIKQRPGQGLEWIGVIDPSDNYINYNQKFKGKATLTVDTSSSTAYLQLSSLTSEDSAVYYCAREAGTRGYFDYWGQGTTLTVSS | 37 | SIVMTQTPKFLLVSAGDRVIITCKASQSVSNTVAWYQQKPGQSPKLLIYYASNRYTGVPDRFTGSGYGTDFTFTISTVQAEDLAVYFCQQDYRSPFTFGSGTQLEMK | 72 |

TABLE 3-continued

| Antibody | Heavy Chain Variable | SEQ ID NO: | Light Chain Variable | SEQ ID NO: |
|---|---|---|---|---|
| MTK-35 | QVLLQQSGPELVKPGASVQLSC KASDYTFTSYDIHWVKQRPGQG LEWIGWIYPRDGYTKYNEIFKG KATLTVDTSSTTAYMELHSLTS EDSAVYFCARAYYTNWYYFDYW GQGTTLTVSS | 38 | EIVLTQSPTTMAASPGEKITITC RASSSISSHYLHWYQQKPGFSPK LLIYRTSNLASGVPARFSGSGSG TSYSLTIGTMEAEDVATYYCQQG STIPLTFGAGTKLVLK | 73 |
| MTK-36 | QVTLKESGPGILQPSQTLSLTC SFSGFSLSTFGMGVGWIRQPSG KGLEWLAHIWWYDDKYYEPALK SRLTISKDSSKNQVFLKIANVD TADTATYYCARIYYGTSYRYFD VWGTGTTVTVSS | 39 | QIVLSQSPAILSAFPGEKVTMTC RATSSVRYMHWYQQKPGSSPKPW IYATYNLTSGVPARFSGSGSTS YSLTISRVEAEDAATYYCHQWSS NPYTFGGGTKLEIK | 74 |

The CDR sequences according to Kabat for the anti-MerTK antibodies of the present disclosure are provided below in Table 4 (heavy chain) and Table 5 (light chain).

TABLE 4

| Antibody | HVR-H1 | SEQ ID NO: | HVR-H2 | SEQ ID NO: | HVR-H3 | SEQ ID NO: |
|---|---|---|---|---|---|---|
| MTK-01 | NYGMN | 75 | WINTYTGEPTYADDFKG | 99 | RDRYTWFAY | 125 |
| MTK-02 | DYGVN | 76 | WINTYSGEPTYAGDFKG | 100 | RVRYWYFDV | 126 |
| MTK-03 | SGYYWN | 77 | YMSFDGDNKFNPSLKN | 101 | GGYNYGSTEAN | 127 |
| MTK-04 | NYGMN | 75 | WINTYTGEPTYADDFKG | 99 | YDNYAWFAY | 128 |
| MTK-05 | SYWIQ | 78 | EIFPGTGTTYYNEKFKG | 102 | DGAYFDV | 129 |
| MTK-06 | NYGMN | 75 | WINTNTGEPTYAEEFKG | 103 | YYNYWYFDV | 130 |
| MTK-07 | SGYYWN | 77 | YMSFDGDNKFNPSLKN | 101 | GGYNYGSTEAN | 127 |
| MTK-08 | NYGMN | 75 | WINTYTGEPTYADDFKG | 99 | EVRYWYFDV | 131 |
| MTK-09 | NHHIK | 79 | YIDPYNDYTTYNQNFKG | 104 | RAYDGYYVDWYFDV | 132 |
| MTK-10 | TSGMGVG | 80 | HIWSDDDKRSNPALKS | 105 | LTPVREFAY | 133 |
| MTK-11 | DYGVH | 81 | VIWSSGTTDYNEAFIS | 106 | KGHDPYAMDY | 134 |
| MTK-12 | SHWMH | 82 | MIDPSDGESRLNQKFKD | 107 | GIYYYGITYAMDY | 135 |
| MTK-13 | SGYYWN | 77 | NIDYDGSNKYNPSLKN | 108 | DGGNYRSFAY | 136 |
| MTK-14 | NYGMN | 75 | WINTYTGEPTYADDFTG | 109 | GGHYAWFAY | 137 |
| MTK-15 | NYGVH | 83 | WINTYTGEPTYADDFKG | 99 | GNRYAYMDY | 138 |
| MTK-16 | NHGMN | 84 | WINTYTGEPTYADDFKG | 99 | KGVTAARYFDY | 139 |
| MTK-17 | NFGMN | 85 | WINTYTGEPTYADDFKG | 99 | GAVLRAGAMDC | 140 |

TABLE 4-continued

| Antibody | HVR-H1 | SEQ ID NO: | HVR-H2 | SEQ ID NO: | HVR-H3 | SEQ ID NO: |
|---|---|---|---|---|---|---|
| MTK-18 | HYGMT | 86 | WINTYTGEPTYADDFKG | 99 | GGGQLGLRPLDY | 141 |
| MTK-19 | EYTMH | 87 | GFNPNNVITSYNQRFQG | 110 | GDLLWSLLLPGNYFDY | 142 |
| MTK-20 | NYGMT | 88 | WINTYTGEPTYADDFKG | 99 | GGGRLGLRPLDY | 143 |
| MTK-21 | NFGMT | 89 | WINTYTGEPKYADDFKG | 111 | GGGRLGLRPLDY | 143 |
| MTK-22 | SYWMH | 90 | EIDPSDSSSNYNQKFKG | 112 | RYYYGSLYFDN | 144 |
| MTK-23 | NHHIN | 91 | NVDPYNDYSTYNQKFKG | 113 | RVYDGFYVDWYFDV | 145 |
| MTK-24 | SYWMH | 90 | MIHPNINTNYNEKFKS | 114 | RSPYSNYDWYFDV | 146 |
| MTK-25 | DYYMA | 92 | NINYEGSSTYYLGSLKS | 115 | YYYGSVDY | 147 |
| MTK-26 | SGYYWD | 93 | YISYDGSNNYNPSLKN | 116 | EGGYYRSMDY | 148 |
| MTK-27 | DDYMH | 94 | WIDPENGNTEYASKFQG | 117 | LFSNYFDY | 149 |
| MTK-28 | TYGMS | 95 | WINTYSGVPTYADDFKG | 118 | FLRYYYFDY | 150 |
| MTK-29 | TYGMS | 95 | WINTYSGVPTYTDDFKG | 119 | YTNYGYFDY | 151 |
| MTK-30 | SYWMH | 90 | NLNPNNGGTYYNEKFKS | 120 | QILLYFDY | 152 |
| MTK-31 | SYGMS | 96 | WINTYSGVPTYADDFKG | 118 | LSYDGSLYHAMDY | 153 |
| MTK-32 | SYGMS | 96 | WINTYSGVPTYADDFRG | 121 | EDNWAWFAY | 154 |
| MTK-33 | SYWMH | 90 | VIDPSDNYINYNQKFKG | 122 | EAGTRGYFDY | 155 |
| MTK-34 | SYWMH | 90 | VIDPSDNYINYNQKFKG | 122 | EAGTRGYFDY | 155 |
| MTK-35 | SYDIH | 97 | WIYPRDGYTKYNEIFKG | 123 | AYYTNWYYFDY | 156 |
| MTK-36 | TFGMGVG | 98 | HIWWYDDKYYEPALKS | 124 | IYYGTSYRYFDV | 157 |

TABLE 5

| Antibody | HVR-L1 | SEQ ID NO: | HVR-L2 | SEQ ID NO: | HVR-L3 | SEQ ID NO: |
|---|---|---|---|---|---|---|
| MTK-01 | RASSSVSYMH | 158 | ATSNLAS | 187 | QQWSSNPPT | 207 |
| MTK-02 | RANSSVSYMH | 159 | ATSNLAS | 187 | QQWGSNPFT | 208 |
| MTK-03 | SASSSVNYMH | 160 | STSNLAS | 188 | QQRSSYPFT | 209 |
| MTK-04 | RASSSVSYMH | 158 | ATSNLAS | 187 | QQWSSNPRT | 210 |

TABLE 5-continued

| Antibody | HVR-L1 | SEQ ID NO: | HVR-L2 | SEQ ID NO: | HVR-L3 | SEQ ID NO: |
|---|---|---|---|---|---|---|
| MTK-05 | RASENIFSYLA | 161 | NAKTLAE | 189 | LHHYGTPLT | 211 |
| MTK-06 | RASSSVSYMH | 158 | ATSNLAS | 187 | QQWSSKPPT | 212 |
| MTK-07 | SASSSVTYMH | 162 | STSNLAS | 188 | QQRSSYPFT | 209 |
| MTK-08 | RATSSVSYMH | 163 | ATSNLAS | 187 | QHWSGNPRT | 213 |
| MTK-09 | KASQDVTTSVA | 164 | SASYRYT | 190 | QQHYSTPLT | 214 |
| MTK-10 | SASQGISNYLN | 165 | YTSRLHS | 191 | QQYTKLPYT | 215 |
| MTK-11 | TASSSISSSYFH | 166 | STSNLPS | 192 | HQYYRSPLT | 216 |
| MTK-12 | SASSSVSYMY | 167 | DTSNLAS | 193 | QQWSSYPLT | 217 |
| MTK-13 | SASSSVSYMY | 167 | STFNLAS | 194 | QQRSSYPFT | 209 |
| MTK-14 | RSSSVSYMH | 168 | ATSNLAS | 187 | QQWGSNPRT | 218 |
| MTK-15 | RASSSVSYMH | 158 | ATSNLAS | 187 | QQWSSNPRT | 210 |
| MTK-16 | KASQNVRTAVA | 169 | LASNRHT | 195 | LQHWNYPLT | 219 |
| MTK-17 | KASDHINNWLA | 170 | GATSLET | 196 | QQYWSTPRT | 220 |
| MTK-18 | RASQAISNYLN | 171 | YTSRLHS | 191 | QQGNTLPWT | 221 |
| MTK-19 | KSSQSLLDSDGKTYLN | 172 | LVSKLDS | 197 | WQGTHFPWT | 222 |
| MTK-20 | RASQDINNYLN | 173 | YTSRLHS | 191 | QQGNTLPW | 223 |
| MTK-21 | RASQDINNYLN | 173 | YTSSLHS | 198 | QQGNTLPWT | 221 |
| MTK-22 | KASQDVGTAIA | 174 | WASTRHT | 199 | QQYTSYPLT | 224 |
| MTK-23 | KASRDVSTAVA | 175 | SASYRST | 200 | QQHYSAPLT | 225 |
| MTK-24 | RASENIYSNLA | 176 | AATNLAD | 201 | QHFWGTPLT | 226 |
| MTK-25 | KASQNVRTTVA | 177 | LASNRHT | 195 | LQLWNYPWT | 227 |
| MTK-26 | SASSSVSFMH | 178 | STSNLAS | 188 | QQRSSYPFT | 209 |
| MTK-27 | KASQNVRTSVA | 179 | LASNRHT | 195 | LQHWNYPYT | 228 |
| MTK-28 | RASSSVTYMH | 180 | ATSNLAS | 187 | HQWSGNPT | 229 |
| MTK-29 | RATSSVGYMH | 181 | ATSNLAS | 187 | QQWGSNPFT | 208 |

TABLE 5-continued

| Antibody | HVR-L1 | SEQ ID NO: | HVR-L2 | SEQ ID NO: | HVR-L3 | SEQ ID NO: |
|---|---|---|---|---|---|---|
| MTK-30 | RSSQSIVHSNGDTYLE | 182 | KVSNRFS | 202 | FQGSHVPWT | 230 |
| MTK-31 | RSSQTIVHSNGNTYLE | 183 | KVSNRFS | 202 | FQGSHVPWT | 230 |
| MTK-32 | RATSSVGYMH | 181 | ATSNLAS | 187 | QQWSSNPRT | 210 |
| MTK-33 | KASQSVSNTVA | 184 | YASNRYT | 203 | QQDYRSPFT | 231 |
| MTK-34 | KASQSVSNTVA | 184 | YASNRYT | 203 | QQDYRSPFT | 231 |
| MTK-35 | RASSSISSHYLH | 185 | RTSNLAS | 204 | QQGSTIPLT | 232 |
| MTK-36 | RATSSVRYMH | 186 | ATYNLTS | 205 | HQWSSNPYT | 233 |

Example 10: Production of Anti-MerTK Antibodies

Anti-MerTK hybridoma clones were cultured in serum free hybridoma media and the anti-MerTK antibodies in the supernatants purified on Hamilton STAR platform (Hamilton Company, Reno, NV) using Protein A tips (Phynexus Inc, San Jose, CA). Anti-MerTK antibodies were also produced via direct cloning of the variable gene regions obtained from the hybridomas into a recombinant expression plasmid for production of chimeric antibodies containing a human Fc domain (human IgG1 containing LALAPS amino acid substitutions described above). Using the Tuna293™ Process (LakePharma, San Carlos, CA), HEK293 cell were seeded into shake flasks and expanded using serum-free chemically defined media. The expression plasmids were transiently transfected into the cells and the culture supernatants were harvested 7 days later. After clarification by centrifugation and filtration, the anti-MerTK antibodies in the supernatants were purified via Protein A chromatography.

Example 11: Blocking Efferocytosis with Recombinant Anti-MerTK Antibodies

The ability of anti-MerTK antibodies of the present disclosure to block efferocytosis by phagocytic cells (e.g., human macrophages or mouse bone-marrow derived macrophages) was evaluated as follows. Human macrophages were differentiated from human monocytes for 7 days in the presence of human M-CSF. Mouse bone marrow derived macrophages were differentiated from mouse bone marrow cells for 7 days in the presence of mouse M-CSF (Peprotech, Cat #315-02). After 7 days, human macrophages and mouse macrophages were harvested (by scraping), resuspended in PBS, and plated on 96-well plates at $5\times10^4$ cells/well. For efferocytosis IC50 determinations, cells were starved for 1 hour followed by the addition of 10 μl of recombinant anti-MerTK antibody to each well for 30 min at 37° C. For other studies described herein, recombinant anti-MerTK antibodies were titrated to a final concentration range of between 66.6 nM to 4 pM and then each serially diluted antibody was added to each well for 30 min at 37° C.

Jurkat cells were treated with 1 μM staurosporin (SigmaAldrich) for 3 hours at 37° C. (to induce apoptosis) and labeled with pHrodo (ThermoFisher) for 30 min at room temperature. After washing with PBS, pHrodo labeled Jurkat cells were added into each well at 1:4 ratio (1 macrophage:4 Jurkat cells) for 1 hour. The plates were washed with PBS and then the cells were stained with APC-conjugated anti-human CD14 or anti-mouse CD11b for 30 minutes on ice in the dark. Cells were then washed twice in FACS buffer (PBS+2% FBS), and flow cytometry was performed on a BD FACS Canto II. Data were analyzed using FlowJo software.

In addition to anti-MerTK antibodies of the present disclosure, the following anti-MerTK antibodies were also used in these efferocytosis studies: rat anti-mouse MerTK antibody DS5MMER (eBioscience, Clone ID DS5MMER, rat IgG2a), mouse anti-human MerTK antibody H1 (BioLegend, Clone ID: 590H11G1E3, mouse IgG1), mouse anti-human MerTK antibody H2 (R&D systems, Clone ID: 125518, mouse IgG2b), mouse anti-human MerTK antibody H3 (R&D systems, Clone ID 125508, mouse IgG2b), mouse anti-human MerTK antibody H6 (eBioscience, Clone ID: A3KCAT, mouse IgG1), mouse anti-human MerTK antibody H7 (Sino Biological, Clone ID: 09, Mouse IgG2b), human anti-human MerTK antibody M6 (disclosed in WO2016/106221, huIgG1 LALAPS), and human anti-human MerTK antibody CDX AB2000-A7 (disclosed in WO2019/084307, huIgG1).

In these experiments, efferocytosis-positive macrophages were identified by setting pHrodo CD14 double positive cells as an analysis gate and then applying this exact gate to all the samples. Baseline efferocytosis levels were established using macrophages cultured with media alone and this was set to 100% efferocytosis activity. Relative efferocytosis levels were calculated as a percent of efferocytosis observed in cells treated with media alone compared to that observed in cells treated with anti-MerTK antibodies.

In comparison to macrophages in the absence of antibody (media alone treatment), no significant change in efferocytosis with isotype control human IgG1 LALAPS, mouse IgG1, or mouse IgG2b was observed.

Efferocytosis blocking studies were performed by addition of 10 μg/ml of recombinant anti-MerTK antibody of the present disclosure to the macrophages. Table 6 and Table 7 show % efferocytosis of anti-MerTK antibodies of the present disclosure on efferocytosis activity by macrophages obtained from various human donors.

TABLE 6

| | % Efferocytosis at 10 μg/mL | | |
|---|---|---|---|
| Antibody | donor 922 | donor 923 | donor 924 |
| MTK-01 | 14.45 | 12.45 | 18.20 |
| MTK-02 | 4.27 | 8.11 | 6.59 |
| MTK-03 | 11.64 | 14.51 | 14.55 |
| MTK-04 | 21.24 | 15.71 | 20.20 |
| MTK-05 | 34.72 | 27.78 | 47.61 |
| MTK-06 | 14.41 | 10.71 | 13.79 |
| MTK-07 | 11.98 | 14.35 | 15.75 |
| MTK-08 | 9.51 | 11.25 | 10.86 |
| MTK-09 | 9.42 | 17.54 | 16.06 |
| MTK-10 | 2.55 | 5.00 | 3.84 |
| MTK-11 | 5.99 | 6.56 | 6.10 |
| MTK-12 | 5.78 | 0.57 | 3.85 |
| MTK-13 | 4.04 | 8.03 | 5.43 |
| MTK-14 | 8.67 | 12.53 | 11.03 |
| MTK-15 | 5.57 | 8.30 | 8.50 |
| MTK-16 | 1.79 | 2.68 | 1.40 |
| MTK-17 | 3.43 | 4.35 | 3.98 |
| MTK-18 | 3.33 | 2.91 | 2.92 |
| MTK-19 | 4.31 | 4.15 | 3.41 |
| MTK-20 | 4.08 | 4.42 | 4.13 |
| MTK-21 | 4.08 | 3.13 | 3.28 |
| MTK-22 | 4.94 | 1.65 | 4.29 |
| MTK-23 | 3.12 | 3.83 | 3.98 |
| huIgG1 LALAPS | 114.35 | 96.22 | 131.70 |
| muIgG1 | 119.37 | 101.26 | 97.44 |
| muIgG2b | 121.88 | 111.35 | 112.12 |
| M6 | 4.52 | 1.04 | 1.22 |
| H1 | 7.87 | 21.38 | 23.36 |
| H2 | 8.96 | 13.50 | 16.60 |
| H3 | 88.8 | 111.35 | 104.56 |
| H6 | 103.04 | 119.11 | 124.14 |
| H7 | 108.9 | 100.1 | 99.22 |

TABLE 7

| | % Efferocytosis at 10 μg/mL | |
|---|---|---|
| Antibody | donor 930 | donor 929 |
| MTK-24 | 26.16 | 11.29 |
| MTK-25 | 30.93 | 41.66 |
| MTK-26 | 23.85 | 13.07 |
| MTK-27 | 35.26 | 17.57 |
| MTK-28 | 33.40 | 19.38 |
| MTK-29 | 41.75 | 20.49 |
| MTK-30 | 38.66 | 20.36 |
| MTK-31 | 22.59 | 18.02 |
| MTK-32 | 48.56 | 28.05 |
| MTK-33 | 24.90 | 21.63 |
| MTK-35 | 30.03 | 19.52 |
| MTK-36 | 21.68 | 21.43 |
| Media | 96.49 | 93.73 |
| M6 | 21.49 | 13.17 |
| H1 | 24.09 | 14.31 |

As shown in Table 6 and Table 7 above, anti-MerTK antibodies of the present disclosure reduced or decreased efferocytosis by human macrophages (e.g., reduced efferocytosis by about 50% to about 98%). Although the efferocytosis blocking activity by anti-MerTK antibodies was different depending on donors, there was a general trend of each antibody.

Figure 4:
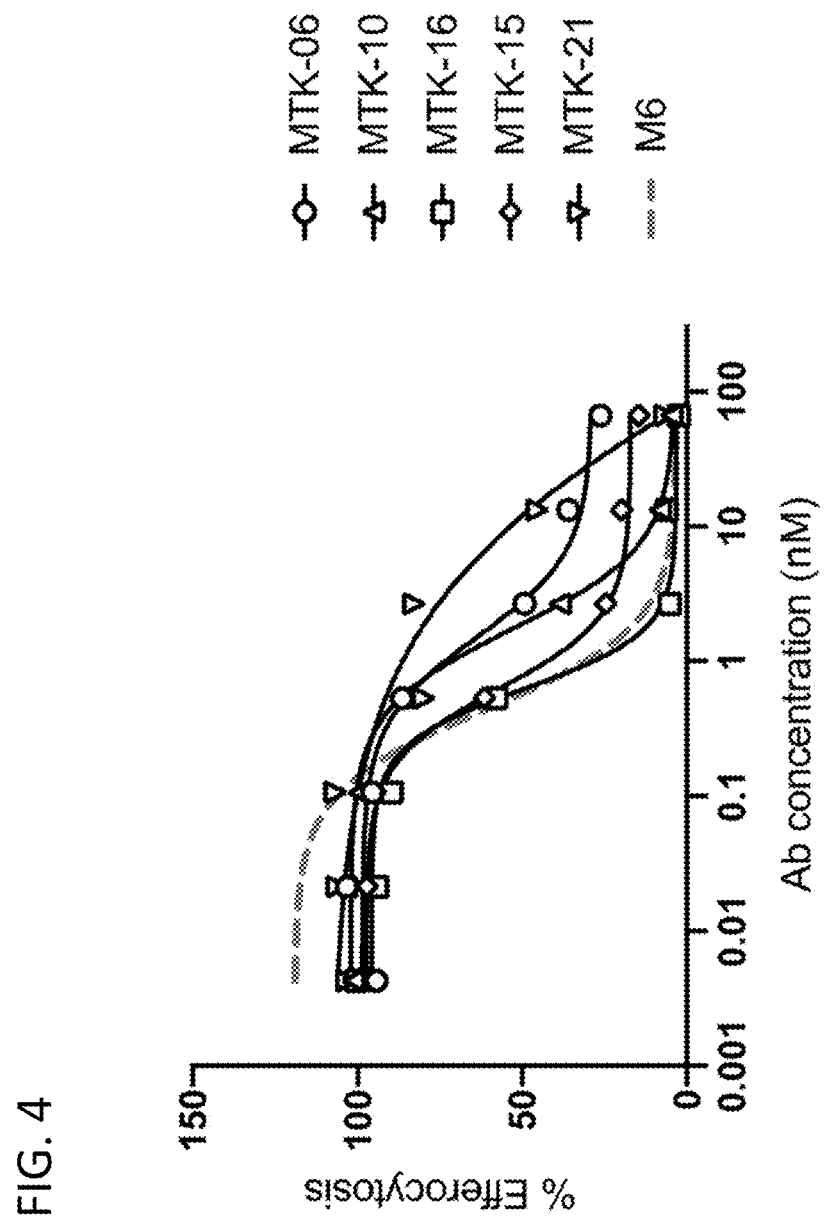
FIG. 4 sets forth data showing the effect of anti-MerTK antibodies of the present disclosure on reducing efferocytosis in human macrophages.
Figure 5:
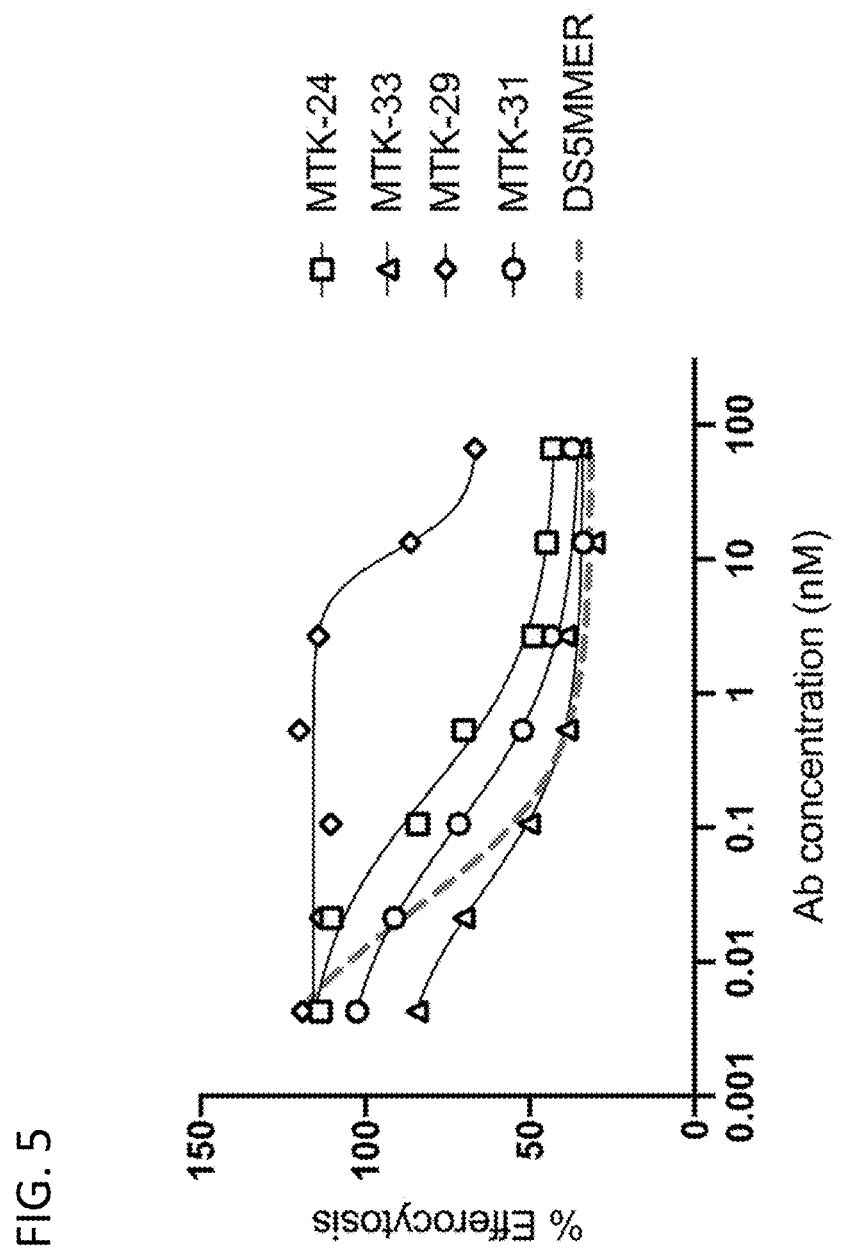
FIG. 5 sets forth data showing the effect of anti-MerTK antibodies of the present disclosure on reducing efferocytosis in mouse bone marrow-derived macrophages.

FIG. 4 and FIG. 5 shows efferocytosis blocking results of exemplary anti-MerTK antibodies of the present disclosure. As shown in FIG. 4, anti-MerTK antibodies MTK-06, MTK-10, MTK-15, MTK-16, and MTK-21 of the present disclosure inhibited efferocytosis of apoptotic cells by human macrophages in a dose dependent manner. These results indicated that anti-MerTK antibodies of the present disclosure are effective at reducing or decreasing efferocytosis activity by human macrophages.

As shown in FIG. 5, anti-MerTK antibodies MTK-24, MTK-29, MTK-31, and MTK-33 of the present disclosure inhibited efferocytosis of apoptotic cells by mouse bone marrow derived macrophages in a dose dependent manner. These results indicated that anti-MerTK antibodies of the present disclosure are effective at reducing or decreasing efferocytosis activity by mouse bone marrow derived macrophages.

Table 8 below shows IC50 values of anti-MerTK antibodies of the present disclosure for reducing or decreasing efferocytosis by human macrophages with a range of IC50 values. As shown in Table 8, anti-MerTK antibodies of the present disclosure reduced or decreased efferocytosis by human macrophages with an IC50 range of about 1.2 nM to about 28 nM.

TABLE 8

| | Efferocytosis IC50 (nM) |
|---|---|
| Antibody | donor 940 |
| MTK-01 | 6.91 |
| MTK-02 | 1.20 |
| MTK-03 | 14.16 |
| MTK-05 | 28.12 |
| MTK-06 | 0.77 |
| MTK-08 | 1.31 |
| MTK-10 | 1.45 |
| MTK-11 | 1.36 |
| MTK-13 | 4.90 |
| MTK-14 | 1.79 |
| MTK-15 | 0.86 |
| MTK-16 | 0.80 |
| MTK-17 | 7.76 |
| MTK-18 | 1.53 |
| MTK-19 | 10.50 |
| MTK-20 | 1.42 |
| MTK-21 | 14.11 |
| MTK-22 | 16.62 |
| M6 | 0.56 |

Table 9 and Table 10 show IC50 values of anti-MerTK antibodies of the present disclosure on efferocytosis activity by mouse macrophages and macrophages obtained from various human donors.

TABLE 9

| | Efferocytosis IC50 (nM) | | |
|---|---|---|---|
| Antibody | donor 673 | donor 960 | Mouse Mac |
| MTK-24 | 3.89 | 1.09 | 0.18 |
| MTK-26 | 0.54 | 0.43 | — |
| MTK-27 | 0.71 | 0.21 | — |
| MTK-28 | 0.15 | 0.08 | — |
| MTK-29 | 0.33 | 0.23 | 11.5 |
| MTK-30 | 0.45 | 0.13 | 0.10 |
| MTK-31 | 8.447 | 1.42E+24* | — |
| MTK-32 | 29.95 | 7.04 | — |
| MTK-33 | 0.25 | 0.33 | 0.03607 |
| MTK-35 | 19856 | 3.70 | — |

TABLE 9-continued

| | Efferocytosis IC50 (nM) | | |
|---|---|---|---|
| Antibody | donor 673 | donor 960 | Mouse Mac |
| MTK-36 | 0.41 | 0.44 | — |
| M6 | 0.11 | 0.12 | |
| CDX AB2000-A7 | n.a | 0.09402 | |
| DS5MMER | n.a | — | 0.02361 | n.a. means data not available
*indicates aberrant value

TABLE 10

| | [nM] | | | |
|---|---|---|---|---|
| Antibody | donor 993 | donor 996 | donor 896 | donor 897 |
| MTK-09 | 0.3418 | 0.7776 | 0.712 | 0.603 |
| MTK-23 | 0.1518 | 0.365 | 0.600 | 0.488 |
| MTK-25 | 0.1125 | 0.1584 | n.a | n.a |
| MTK-27 | 0.3386 | 0.5349 | n.a | n.a |
| MTK-31 | 0.9309 | 5.551 | n.a | n.a |
| MTK-36 | 0.128 | 0.2313 | n.a | n.a |
| CDX AB2000-A7 | 0.1099 | 0.2517 | n.a | n.a |
| H1 | 0.4212 | 1.905 | 1.631 | 0.847 |
| H2 | 0.6921 | 1.474 | n.a | n.a |
| M6 | 0.04335 | 0.1086 | 0.222 | 0.213 | n.a. means data not available

As shown in Table 8, Table 9, and Table 10 above, anti-MerTK antibodies of the present disclosure were effective at reducing efferocytosis by human macrophages and mouse macrophages. Additionally, these results showed that anti-MerTK antibodies of the present disclosure reduced efferocytosis by human macrophages at an IC50 of about 0.13 nM to about 30 nM.

Example 12: Anti-MerTK Antibodies Bind to SK-MEL-5 Cells and CHO-muMerTK OE Cells To determine whether recombinant anti-human MerTK antibodies of the present disclosure bind to human MerTK endogenously expressed on SK-MEL-5 cells and to CHO cells overexpressing mouse MerTK (CHO-muMerTK OE cells), the following experiments were performed. SK-MEL-5 cells and CHO-muMerTK OE cells were plated at 40,000 cells/well. Anti-MerTK antibodies were titrated to a final concentration range of between 66.6 nM to 4 pM and then added to the cells. After 30 min on ice, cells were washed and then stained with APC-conjugated mouse anti-human Kappa antibody (Southern Biotech Cat #9230-11, Birmingham, Ala.) and a viability die (Life Technologies) in the presence of Fc block solution on ice for 30 minutes, and then washed twice with cold FACS buffer (2% FBS in PBS). Cells were fixed with 4% paraformaldehyde in PBS. Stained cells were acquired on a BD FACS Canto II cytometer and the mean fluorescence intensity (MFI) was calculated with FlowJo software and K value was calculated with Prism software. Kd values in these results are similar to EC50 values but are calculated by Prism software from data generated by FACS analysis. A lower Kd value reflects higher binding of antibody to cells.

Figure 6:
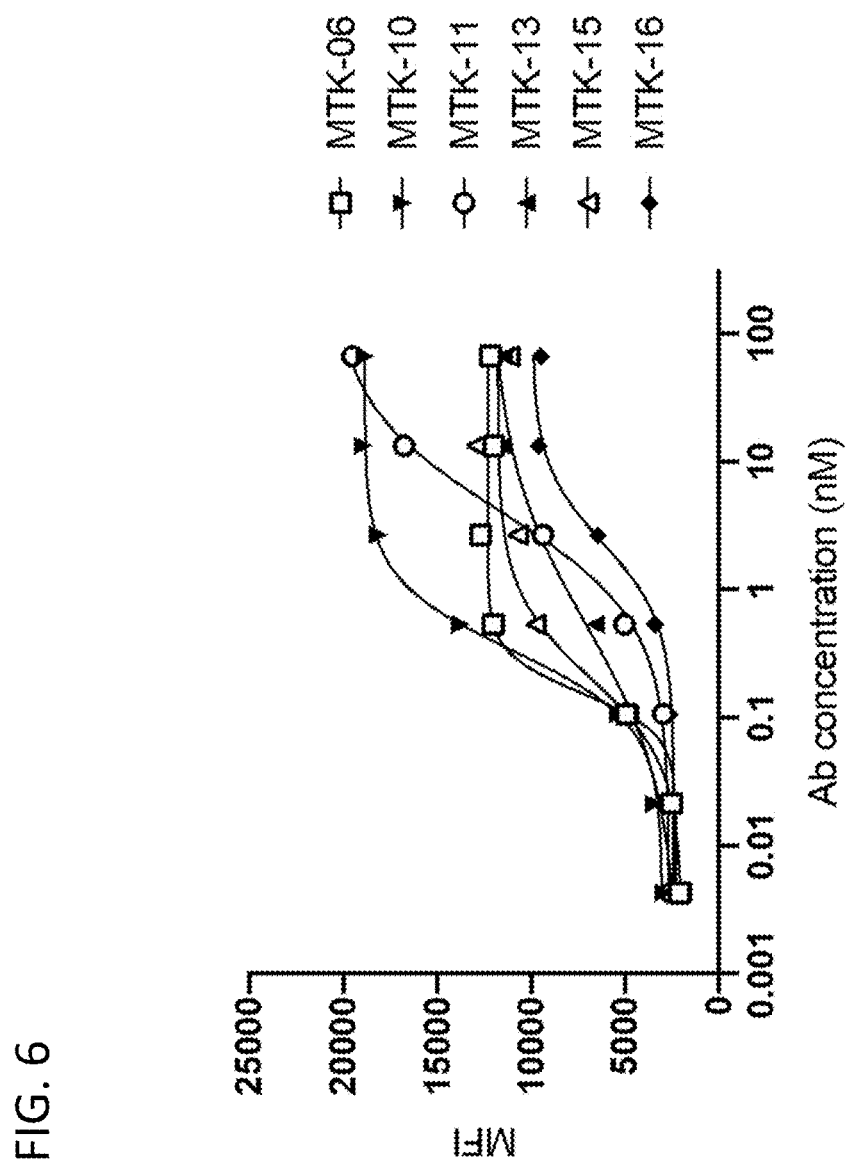
FIG. 6 sets forth data showing anti-MerTK antibodies of the present disclosure bind SK-MEL-5 cells.

FIG. 6 shows anti-human MerTK antibodies MTK-06, MTK-10, MTK-11, MTK-13, MTK-15, and MTK-16 bind to MerTK endogenously expressed on SK-MEL-5 in a dose dependent manner.

Table 11, Table 12, and Table 13 below show Kd values from FACS analysis of anti-MerTK antibodies binding to SK-MEL-5 cells (Table 11 and Table 12) and to CHO-muMerTK-OE cells (Table 13).

TABLE 11

| Antibody | FACS Kd value (nM) |
|---|---|
| MTK-01 | 0.049 |
| MTK-02 | 0.024 |
| MTK-03 | 2.64 |
| MTK-04 | 0.037 |
| MTK-06 | 0.005 |
| MTK-07 | 3.21 |
| MTK-08 | 0.079 |
| MTK-10 | 0.076 |
| MTK-11 | 3.54 |
| MTK-12 | 0.009 |
| MTK-13 | 0.68 |
| MTK-14 | 0.021 |
| MTK-15 | 0.19 |
| MTK-16 | 1.66 |
| MTK-17 | 12.68 |
| MTK-18 | 0.38 |
| MTK-19 | 3.07 |
| MTK-20 | 0.11 |
| MTK-21 | 23.36 |
| MTK-22 | 2.78E−06* |
| M6 | 0.27 |
| H1 | 0.22 |
| H2 | 0.03 |

*indicates aberrant value

TABLE 12

| Antibody | FACS Kd value (nM) |
|---|---|
| MTK-24 | 0.59 |
| MTK-26 | 1.38 |
| MTK-27 | 2.55 |
| MTK-28 | 0.52 |
| MTK-29 | 0.14 |
| MTK-30 | 0.47 |
| MTK-31 | 2.311E−11* |
| MTK-32 | 0.40 |
| MTK-33 | 0.93 |
| MTK-35 | 1.29 |
| MTK-36 | 1.42 |
| M6 | 5.302E−13* |
| CDX AB2000-A7 | 0.19 |
| H1 | 0.06436 |
| H2 | 2.455E−08* |

*indicates aberrant value

TABLE 13

| Antibody | FACS Kd value (nM) |
|---|---|
| MTK-24 | 0.22 |
| MTK-29 | 5.22 |
| MTK-30 | 0.24 |
| MTK-31 | 2.913 |
| MTK-32 | 2.455E−08* |
| MTK-33 | 0.53 |

*indicates aberrant value

Anti-MerTK antibodies binds to SK-MEL-5 or CHO-muMerTK overexpressing cells in a dose dependent manner with Kd value in the picomolar to nanomolar range. Anti-MerTK antibody such as MTK-06 or MTK-12 showed better binding to SK-MEL-5 compared to M6 antibody. Data in Tables 11, 12, and 13 above also show that anti-MerTK antibodies MTK-24, MTK-29, MTK-30, MTK-31, and MTK-33 bind to human MerTK endogenously expressed on human SK-MEL-5 cells and to murine MerTK recombinantly expressed in CHO cells.

Example 13: Anti-MerTK Antibody Blocking of Ligand Gas6 and Ligand ProS Binding to MerTK To determine the ligand blocking activity of anti-MerTK antibodies of the present disclosure, ligand blocking assays was performed to test whether a given anti-MerTK antibody blocks binding of ligand Gas6 or ligand ProS to human MerTK.

Rabbit anti-human IgG polyclonal antibody (Jackson ImmunoResearch, Cat #309-005-008) was captured to a high-protein binding plate at 2 µg/ml 4° C. overnight. After washing with 0.05% Tween20 in PBS three times, 5% BSA in PBS was added for 1 hour. Recombinant human MerTK human Fc Chimera protein (R&D systems, Cat #391-MR-100) was added at 2 µg/ml for 1 hour and the plates were then washed. Anti-MerTK antibodies were titrated to final concentration range of between 66.6 nM to 4 pM and then 40 µl of serially diluted antibody and 40 µl of His tag-conjugated recombinant Gas6 protein (R&D systems, Cat #885-GSB-050) at 3 µg/ml or His tag-conjugated recombinant ProS protein (R&D systems, Cat #9489-PS-100) at 20 µg/ml. After a further incubation for 1 hour, plates were washed and incubated for 1 hour with HRP-conjugated anti-6xHis tag antibody (Abcam, Cat #ab1187). Plates were then washed and an HRP substrate (TMB) was used to develop the plates. After sufficient color change was observed, the reaction was stopped by adding 50 µl 2N $H_2SO_4$ and the OD was measured using a spectrophotometer (BioTek).

Figure 7:
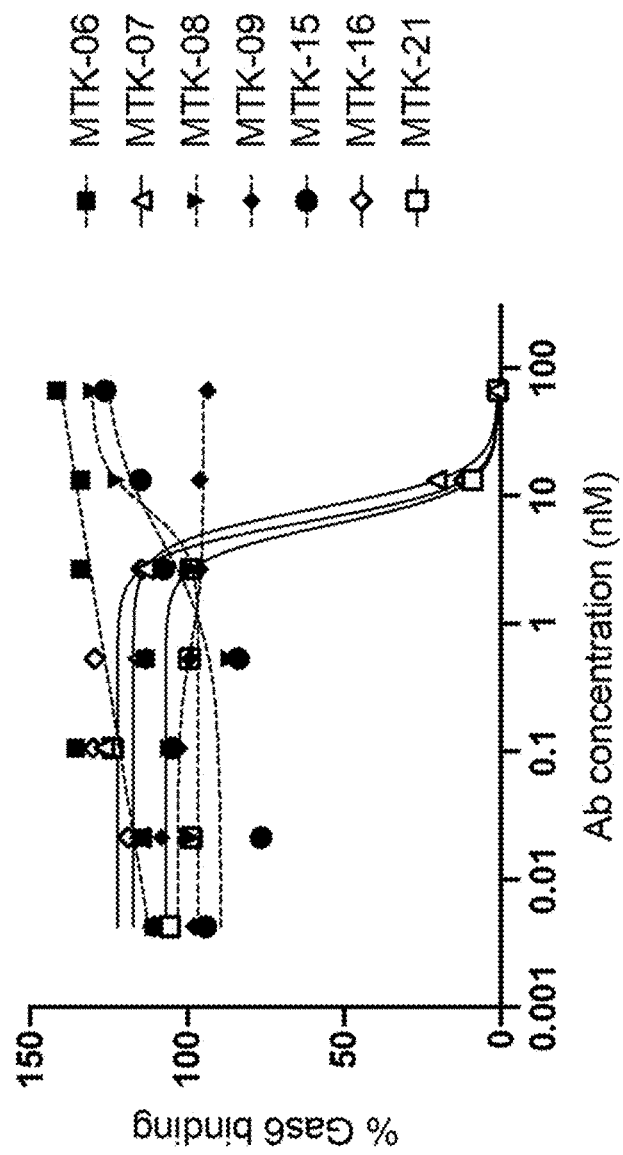
FIG. 7 sets forth data showing anti-MerTK antibodies of the present disclosure blocked Gas6 ligand binding to human MerTK in a dose-dependent manner.

FIG. 7 shows that exemplary anti-MerTK antibodies of the present disclosure (MTK-07, MTK-16, and MTK-21) inhibited (e.g., blocked) Gas6 ligand binding to human MerTK in a dose dependent manner. As shown in FIG. 7, anti-MerTK antibodies MTK-06, MTK-08, MTK-09, and MTK-15 did not block Gas6 ligand binding to human MerTK.

Figure 8:
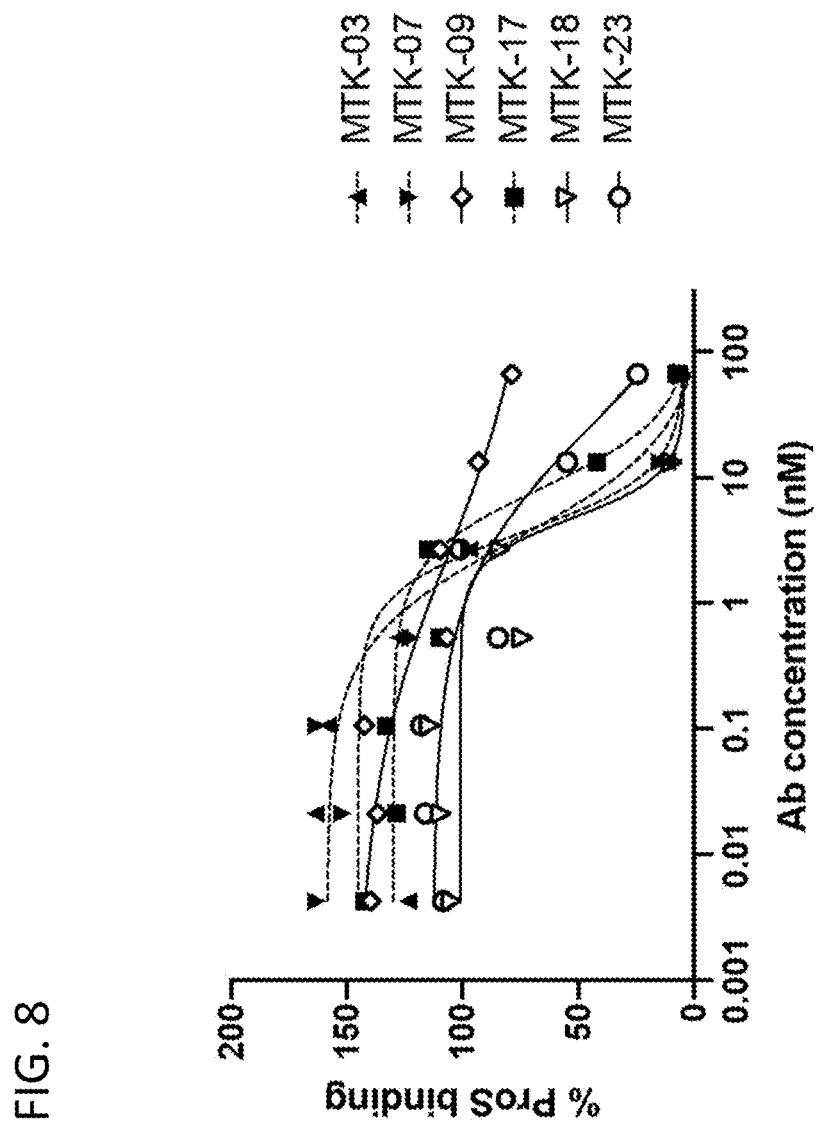
FIG. 8 sets forth data showing anti-MerTK antibodies of the present disclosure blocked ProS ligand binding to human MerTK in a dose-dependent manner.

FIG. 8 shows that exemplary anti-MerTK antibodies of the present disclosure (MTK-03, MTK-07, MTK-09, MTK-17, MTK-18, and MTK-23) inhibited (e.g., blocked) ProS ligand binding to human MerTK in a dose dependent manner.

From these experiments, IC50 values [nM] were determined using OD450 values obtained from the dose-response curves analyzed with Prism software. Table 14 and Table 15 show IC50 values determined for anti-MerTK antibody blocking of Gas6 ligand binding and ProS ligand binding to MerTK. Anti-MerTK antibody MTK-22 did not block Gas6 ligand binding or ProS ligand biding to MerTK; however, anti-MerTK antibody MTK-22 was effective at reducing efferocytosis as shown in Examples above. Dashes indicate lack of significant blocking; "n.a." indicates data not available.

TABLE 14

| Antibody | Gas6 ligand blocking IC50 | ProS ligand blocking IC50 |
|---|---|---|
| MTK-01 | — | 2.85 |
| MTK-02 | — | 3.94 |
| MTK-03 | 8.53 | 3.65 |
| MTK-04 | — | 12.81 |
| MTK-05 | — | 6.51 |
| MTK-06 | — | 2.17 |
| MTK-07 | 7.97 | 3.27 |
| MTK-08 | — | 3.80 |
| MTK-09 | — | 7.84 |
| MTK-10 | 32.38 | 3.80 |
| MTK-11 | — | 24.24 |
| MTK-12 | 25.97 | 3.36 |
| MTK-13 | 18.93 | 3.76 |
| MTK-14 | n.a. | 7.61 |
| MTK-15 | — | 4.20 |
| MTK-16 | 6.32 | 8.59 |
| MTK-17 | 14.47 | 8.35 |
| MTK-18 | 4.22 | 4.76 |
| MTK-19 | n.a. | 11.27 |
| MTK-20 | 4.96 | 5.16 |
| MTK-21 | 5.98 | 13.50 |
| MTK-23 | — | 25.92 |

TABLE 15

| Antibody | Gas6 blocking IC50 | ProS blocking IC50 |
|---|---|---|
| MTK-24 | 0.74 | 0.5792 |
| MTK-26 | 2.93 | 1.203 |
| MTK-27 | 1.42 | 2.543 |
| MTK-28 | — | 2.781 |
| MTK-29 | — | 2.664 |
| MTK-30 | 1.26 | 1.572 |
| MTK-31 | 1.29 | 1.51E+15* |
| MTK-32 | — | 2.781 |
| MTK-33 | n.a. | 0.6005 |
| MTK-35 | 0.31 | 0.924 |
| MTK-36 | 0.29 | 1.402 |
| M6 | 0.28 | 1.339 |
| CDX AB2000-A7 | 0.49 | 2.514 |
| H1 | — | 2.513 |

*indicates aberrant value

In these studies, thirty-five (35) anti-MerTK antibodies of the present disclosure were tested for their ability to block Gas6 ligand binding and/or ProS ligand binding to human MerTK. Nineteen (19) anti-MerTK antibodies of the present disclosure (MTK-03, MTK-07, MTK-10, MTK-12, MTK-13, MTK-16, MTK-17, MTK-18, MTK-20, MTK-21, MTK-24, MTK-25, MTK-26, MTK-27, MTK-30, MTK-31, MTK-33, MTK-35, and MTK-36) blocked the binding of both ProS ligand and Gas6 ligand to recombinant human MerTK protein (herein referred to as ProS/Gas6 double blockers); fifteen (15) anti-MerTK antibodies of the present disclosure (MTK-01, MTK-02, MTK-04, MTK-05, MTK-06, MTK-08, MTK-09, MTK-11, MTK-14, MTK-15, MTK-19, MTK-23, MTK-28, MTK-29, MTK-32) blocked ProS ligand binding (but did not block Gas6 ligand binding) to recombinant human MerTK (herein referred to as ProS specific blockers). Anti-MerTK antibody MTK-22 did not block either ProS ligand or Gas6 ligand binding to recombinant human MerTK protein as measured in this assay; however, anti-MerTK antibody MTK-22 was effective at reducing efferocytosis as shown in Examples above. Anti-MerTK antibody M6 and anti-MerTK antibody CDX AB2000-A7 displayed ProS ligand and Gas6 ligand blocking. Anti-MerTK antibody H1 and anti-MerTK antibody H2 displayed ProS ligand blocking only; neither of these antibodies displayed Gas6 ligand blocking.

These results suggested that anti-MerTK antibodies of the present disclosure can selectively modulate Gas6 and ProS binding to MerTK and can selectively modulate Gas6 and ProS activity.

Example 14: Binding Kinetics of Anti-MerTK Antibodies

Binding kinetics of human anti-MerTK IgG1 LALAPS antibodies of the present disclosure to human, cyno, and murine MerTK were evaluated using a Carterra LSA instrument (Carterra, Salt Lake City, UT). Briefly, anti-MerTK antibodies were prepared by diluting to 10 μg/ml in 10 mM Acetate, pH 4.25 (Carterra), at 300 μl/well. A HC200M sensor chip (Carterra) was activated using the single channel flow cell with a 7-minute injection of a 1:1:1 mixture of 100 mM MES pH 5.5, 100 mM sulfo-NHS, 400 mM EDC (all reconstituted in MES pH 5.5; 100 μl of each mixed in vial immediately before running assay). After switching to the multi-channel array flow cell, the antibodies were injected over the activated chip in a 96-spot array for 15 minutes. The remaining unconjugated active groups on the chip were then blocked by injecting 1M Ethanolamine pH 8.5 (Carterra) for 7 minutes using the single channel flow cell.

After priming with running buffer (HBS-TE, Carterra) with 0.5 mg/ml BSA (Sigma), the immobilized anti-MerTK antibodies were tested for their ability to bind to several forms of recombinant MerTK extracellular domain, including human, cynomolgus, and mouse orthologs as described above. Estimates of affinity were generated by injecting each analyte over the entire antibody array using the single channel flow cell. MerTK analytes were diluted to 33.3, 100, and 300 nM in running buffer, and injected in serial from lowest to highest concentration without regeneration. Two buffer blanks were run between each series (one species per series). Data were processed and analyzed using NextGen-KIT high-throughput kinetics analysis software (Carterra).

The equilibrium dissociation constants ($K_D$) were then calculated from the fitted association and dissociation rate constants (k-on and k-off) for anti-MerTK antibodies of the present disclosure. Binding kinetic analysis was also performed on anti-MerTK antibodies H1 (BioLegend, Clone ID: 590H11G1E3), H2 (R&D systems, Clone ID: 125518), M6 (WO2016/106221), and CDX AB2000-A7 hIgG1 (WO2019/084307). The $K_D$ values are summarized in Table 16 below.

TABLE 16

| Antibody | $K_D$ (nM) human | $K_D$ (nM) cyno | $K_D$ (nM) mouse |
| --- | --- | --- | --- |
| MTK-01 | NF | 99 | NB |
| MTK-02 | 22 | 24 | NB |
| MTK-03 | 54 | 55 | NB |
| MTK-04 | 33 | 44 | NB |
| MTK-05 | 6.7 | NB | NB |
| MTK-06 | 18 | 17 | NB |
| MTK-07 | 43 | 53 | NB |
| MTK-08 | 37 | 42 | NB |
| MTK-10 | 2.0 | 1.9 | NB |
| MTK-11 | 3.0 | 2.9 | NB |
| MTK-12 | 5.3 | NB | NB |
| MTK-13 | 37 | 39 | NB |
| MTK-14 | 45 | 53 | NB |
| MTK-15 | 2.7 | 3.0 | NB |
| MTK-16 | 1.4 | 1.6 | NB |
| MTK-17 | 25 | 24 | NB |
| MTK-18 | 18 | 18 | NB |
| MTK-19 | 2.4 | 12 | 130 |

TABLE 16-continued

| Antibody | $K_D$ (nM) human | $K_D$ (nM) cyno | $K_D$ (nM) mouse |
| --- | --- | --- | --- |
| MTK-20 | 9.3 | 9.2 | NB |
| MTK-21 | 40 | 43 | NB |
| MTK-22 | 54 | LB | NB |
| MTK-24 | 41 | 44 | 55 |
| MTK-26 | 30 | 30 | NB |
| MTK-27 | 71 | 71 | NB |
| MTK-28 | 4.1 | 4.5 | NB |
| MTK-30 | 23 | 24 | 30 |
| MTK-31 | 81 | 91 | 165 |
| MTK-32 | 59 | 107 | 186 |
| MTK-33 | 6.5 | 6.6 | 75 |
| MTK-35 | 14 | 13 | NB |
| MTK-36 | 6.4 | 5.9 | NB |
| CDX AB2000-A7 | 38 | 52 | NB |
| H1 | 7.2 | 6.8 | NB |
| H2 | 18 | 18 | NB |
| H3 | 151 | LB | NB |
| H6 | 26 | 116 | NB |
| H7 | 6.1 | 10 1 | NB |
| M6 | 5.6 | 5.4 | NB |

NB = No binding; LB = Low binding; NF = No fit, meaning the data obtained did not fit a 1:1 binding equilibrium model.

These results showed that anti-MerTK antibodies of the present disclosure showed a range of affinities to MerTK and species binding specificity. In particular, affinity of anti-MerTK antibodies of the present disclosure for binding to human MerTK ranged from 1.4 nm to 81 nM; affinity of anti-MerTK antibodies of the present disclosure for binding to cyno MerTK ranged from 1.6 nm to 107 nM; and affinity of anti-MerTK antibodies of the present disclosure for binding to murine MerTK ranged from 30 nM to 186 nM.

Example 15: Cross-Reactivity of Anti-MerTK Antibodies to Human, Cyno, and Mouse MerTK Species cross-reactivity of anti-MerTK antibodies of the present disclosure was determined from the binding kinetic analysis data described above. The results of species binding cross-reactivity analysis are shown below in Table 17.

TABLE 17

| Human MerTK Reactive | Human-Cyno MerTK Cross Reactive | Human-Mouse MerTK Cross Reactive |
| --- | --- | --- |
| MTK-05 MTK-12 | MTK-01, MTK-02, MTK-03, MTK-04, MTK-06, MTK-07, MTK-08, MTK-09, MTK-10, MTK-11, MTK-13, MTK-14, MTK-15, MTK-16, MTK-17, MTK-18, MTK-19, MTK-20, MTK-21, MTK-22, MTK-24, MTK-26, MTK-27, MTK-28, MTK-30, MTK-31, MTK-32, MTK-33, MTK-34, MTK-35, MTK-36 CDX AB2000-A7, H1, H2, H7, M6 Weak cross reactivity: H3, H6 | MTK-19, MTK-24, MTK-30, MTK-31, MTK-32, MTK-33 |

These binding experiments showed that the majority of the anti-MerTK antibodies of the present disclosure tested showed binding cross-reactivity to both human and cyno MerTK (MTK-01, MTK-02, MTK-03, MTK-04, MTK-06, MTK-07, MTK-08, MTK-09, MTK-10, MTK-11, MTK-13, MTK-14, MTK-15, MTK-16, MTK-17, MTK-18, MTK-19, MTK-20, MTK-21, MTK-22, MTK-24, MTK-26, MTK-27, MTK-28, MTK-30, MTK-31, MTK-32, MTK-33, MTK-34, MTK-35, and MTK-36). Two anti-MerTK antibodies of the present disclosure showed specific binding only to human MerTK and did not show binding to cyno or mouse MerTK (antibody MTK-05 and antibody MTK-12). Six anti-MerTK antibodies of the present disclosure tested displayed cross-reactivity to both human and mouse MerTK (MTK-19, MTK-24, MTK-30, MTK-31, MTK-32, and MTK-33). Six anti-MerTK antibodies of the present disclosure tested displayed cross-reactivity to human, cyno, and mouse MerTK (MTK-19, MTK-24, MTK-30, MTK-31, MTK-32, and MTK-33). Additionally, Example 12 above showed that anti-MerTK antibodies MTK-24 and MTK-29 also bind to human and murine MerTK.

Example 16: Epitope Binning Analysis of Anti-MerTK Antibodies

Epitope binning analysis was performed on the anti-MerTK antibodies of the present disclosure by performing a tandem injection approach using a Carterra LSA instrument (Carterra, Salt Lake City, UT). Briefly, hybridoma purified mouse anti-MerTK antibodies of the present disclosure, anti-MerTK antibodies H1, H2, H3, H6, and M6, and anti-his IgG were diluted to 15 µg/ml in 10 mM Acetate, pH 4.75 (Carterra), at 300 µl/well. A second set of samples was prepared by 5-fold dilution of the antibodies to 3 µg/ml in the same buffer. A HC200M sensor chip (Carterra) was activated using the single channel flow cell with a 7-minute injection of a 1:1:1 mixture of 100 mM MES pH 5.5, 100 mM sulfo-NHS, 400 mM EDC (as described above). After switching to the multi-channel array flow cell, the 15 µg/ml dilutions of antibodies were injected over the activated chip in a 96-spot array for 15 minutes. A second array was printed by injection of the 3 µg/ml dilutions of the antibodies in a second 96-spot array. The remaining unconjugated active groups on the chip were then blocked by injecting 1M Ethanolamine pH 8.5 (Carterra) over the entire chip surface for 7 minutes using the single channel flow cell.

After priming with running buffer (HBS-TE, Carterra) containing 0.5 mg/ml BSA (Sigma), the immobilized antibodies were tested for their ability to bind to recombinant human MerTK extracellular domain. Bound MerTK was removed by two 30-second injections of 0.425% phosphoric acid (Carterra). For each cycle, MerTK was injected over the chip, followed by a test antibody diluted to 30 µg/ml in running buffer. Data were processed and analyzed using Epitope high-throughput binning analysis software (Carterra). Antibodies which were able to bind antigen captured by an immobilized antibody were designated as "sandwich" or "pairing" antibodies, and these antibodies were assigned into a different epitope bin from that of the immobilized antibody. A matrix of pairing and non-pairing antibodies was constructed from the binding results of these experiments, which allowed for an epitope bin landscape of the anti-MerTK antibodies to be generated.

Figure 9:
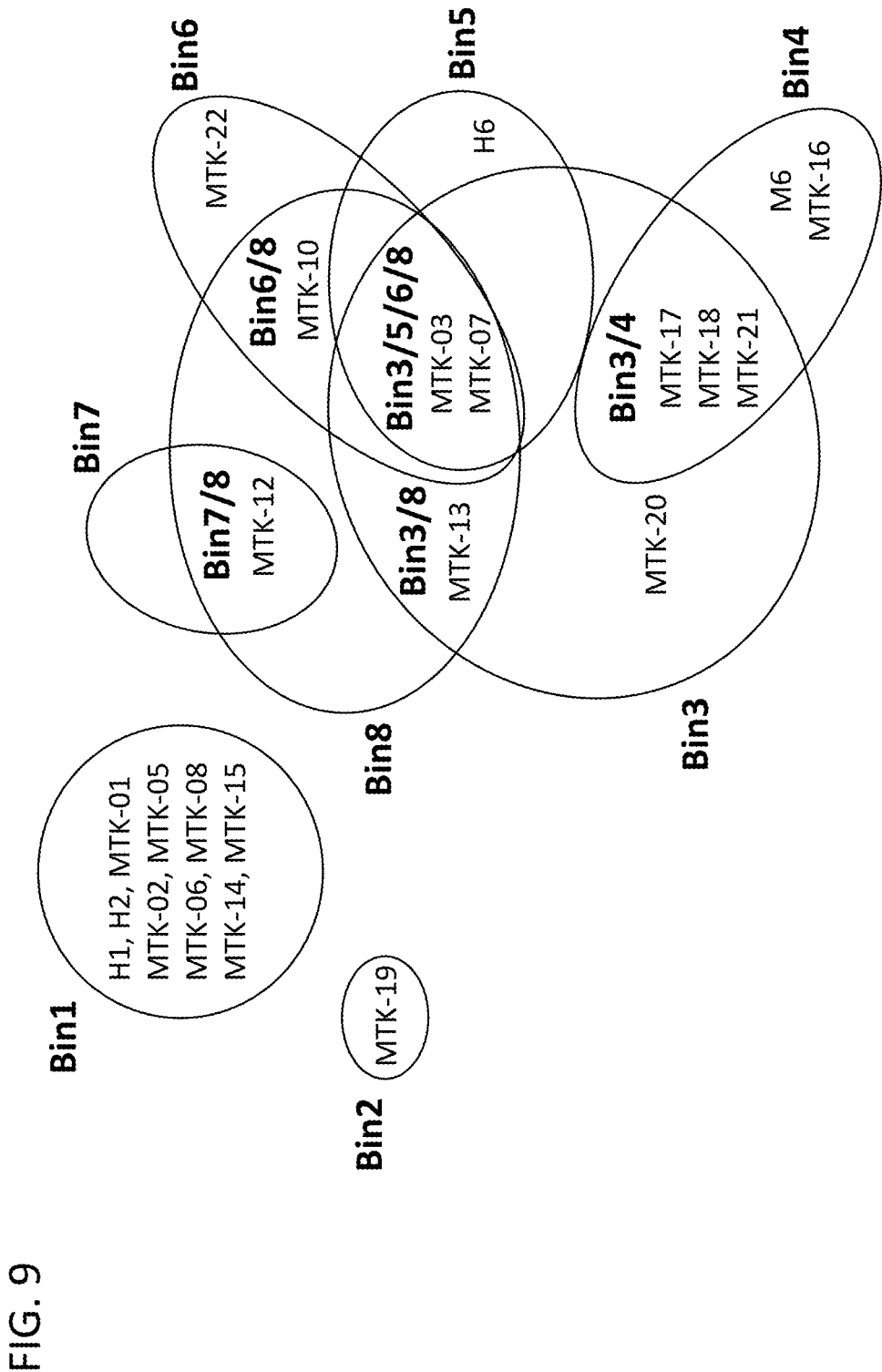
FIG. 9 sets forth data showing epitope binning results of anti-MerTK antibodies of the present disclosure.

The epitope bins identified from these studies for the anti-MerTK antibodies are summarized in FIG. 9. The results showed that most of the ProS ligand-specific blockers belong to Bin 1 group except MTK-19, which is included in Bin 2. Anti-MerTK control antibody H1, a ProS-specific blocker belongs to Bin 1 group. All the ProS/Gas6 double blockers belong to Bin 3 through Bin 8 groups. Some of antibodies recognize partially adjacent epitopes, so have overlapping binning. For example, MTK-03 and MTK-07 have most broad overlapping epitopes of Bin 3, Bin 5, Bin 6, and Bin 8. Anti-MerTK control antibody M6, a ProS/Gas6 double blocker belongs to Bin 4 and H6 belongs to Bin 5 group. These results suggested that ProS and Gas6 may bind to different epitopes or regions on MerTK.

Example 17: Anti-MerTK Antibody Inhibition of Tumor Growth In Vivo

An in vivo efficacy study was performed using MC38 mouse syngeneic colon cancer model to determine the effect of anti-MerTK antibodies on tumor growth. MC38 cells were resuspended at $5\times10^6$ cells/ml in PBS. 100 µl of cells was injected subcutaneously on the shaved right flank of C57BL/6 mice. When tumor size reached approximately 60-100 mm³ in volume, mice were randomized based on tumor volumes into treatment (N=10) or control groups. Treatment groups received 10 mg/kg of control antibodies, 3 mg/kg of anti-PDL1 (clone: BM1) alone, 10 mg/kg of anti-MerTK antibody DS5MMER alone, or 3 mg/kg of anti-PDL1 plus anti-MerTK antibody DS5MMER together. Following the initiation of antibody dosing, mice were weighed, and tumor volume was measured using a caliber twice per week. The study was terminated when tumors in the control group reached approximately 2000 mm³.

Figure 10B:
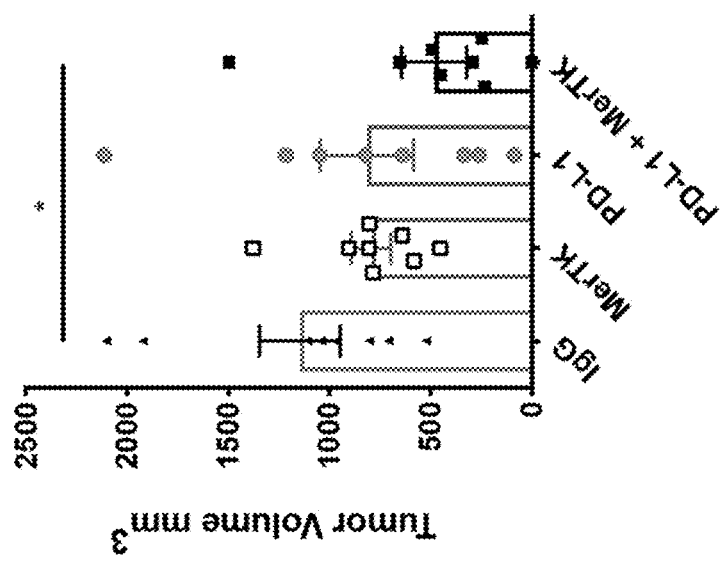
FIGS. 10A and 10B set forth data showing anti-MerTK antibody treatment alone or in combination with anti-PD-L1 antibody treatment reduced tumor growth in vivo.
Figure 10A:
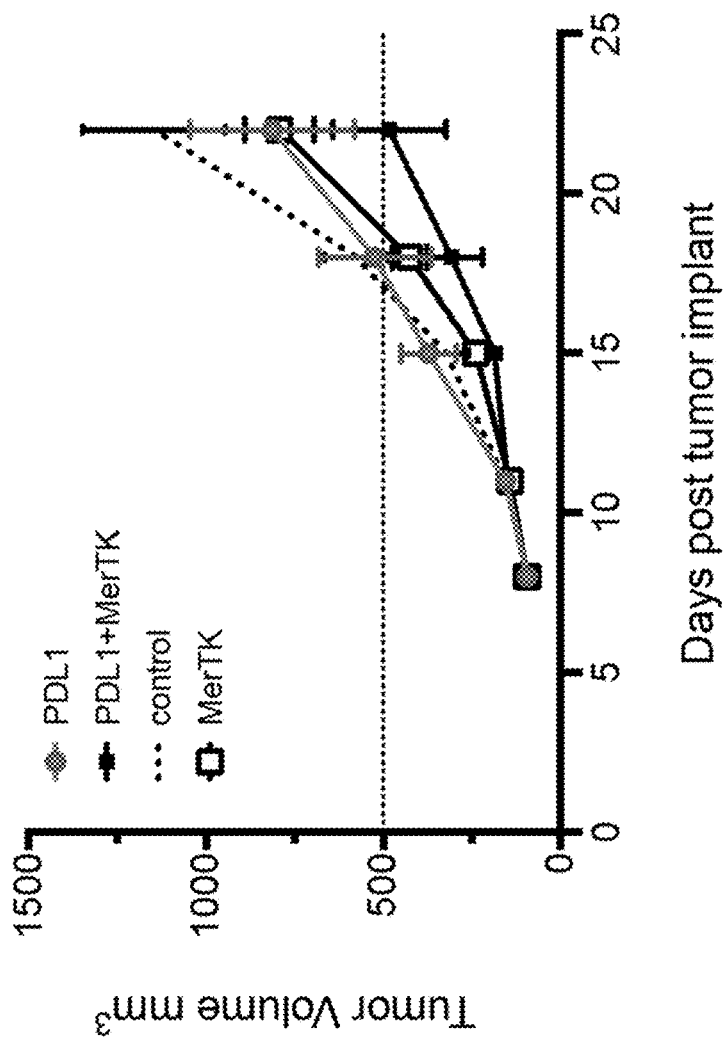
Figure 11B:
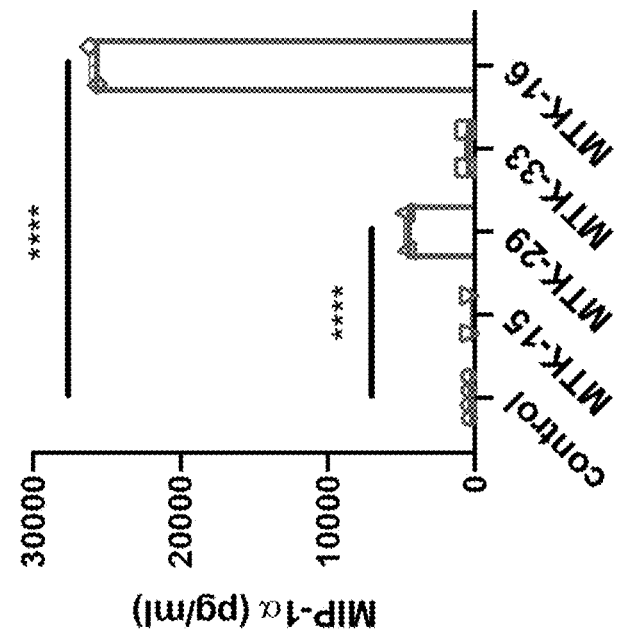
FIGS. 11A, 11B, 11C, and 11D set forth data showing changes in the level of MCP1, MIP-1α, MIP-1β, and TNF in human macrophages following overnight treatment with anti-MerTK antibodies of the present disclosure.
Figure 11A:
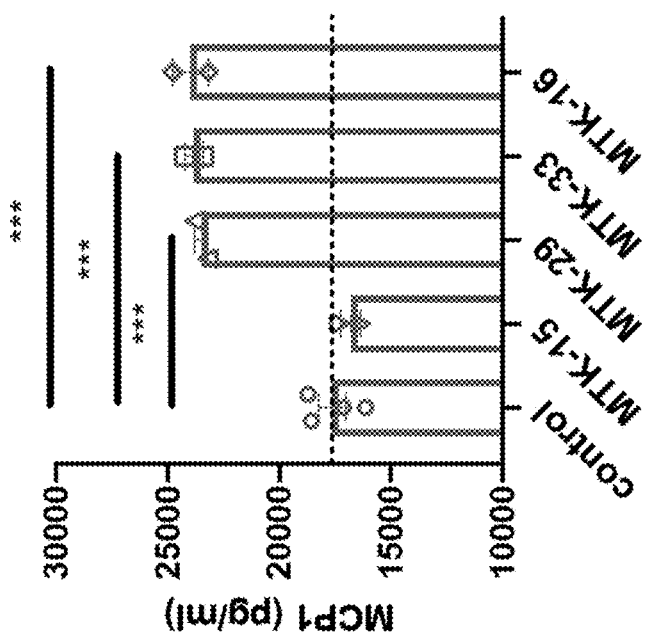
Figure 11D:
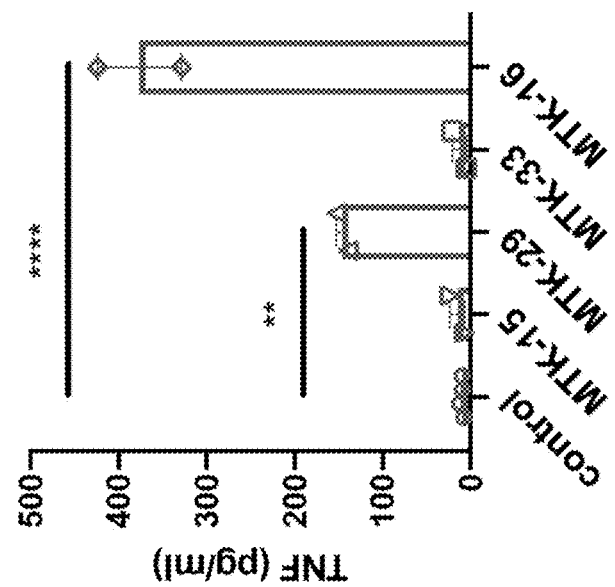
Figure 11C:
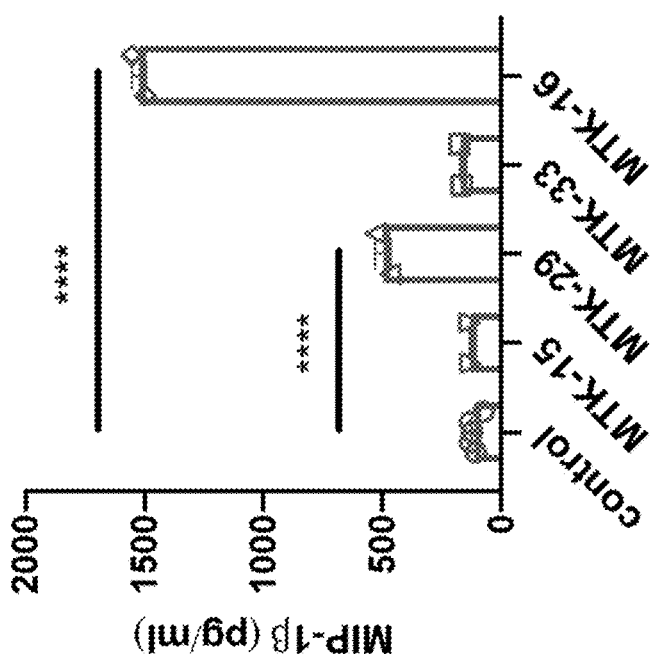

FIGS. 10A and 10B show that either anti-MerTK antibody DS5MMER treatment alone or combination treatment with anti-PDL1 antibody reduced tumor growth in vivo. These results indicated that anti-MerTK antibodies are effective at reducing tumor volume and delaying tumor growth in vivo. These results further showed that anti-MerTK antibodies, when used in combination with an anti-PD-L1 antibody, displayed greater reduction of tumor volume and growth compared to either antibody alone.

Example 18: Modulating Pro-Inflammatory Cytokine Production

The effect of anti-MerTK antibodies on pro-inflammatory cytokine production in myeloid cells was examined as follows. To generate monocyte-derived macrophages and dendritic cells, human primary monocytes were isolated from heparinized human blood (Blood Centers of the Pacific) using RosetteSep Human Monocyte Enrichment Cocktail (STEMCELL Technologies), according to the manufacturer's protocol. Monocytes were seeded in RPMI (Invitrogen) containing 10% Fetal Bovine Serum (Hyclone) and 50 ng/mL IL-4 and GM-CSF (Peprotech) to induce differentiation of dendritic cells or 50 ng/mL M-CSF (Biolegend) to induce differentiation of macrophages. After 6-7 days, dendritic cells or macrophages were harvested by scraping cells. Macrophages or dendritic cells were plated on 96-well plates at $5\times10^4$ cells/well and cultured with 10 µg/mL of antibody at 37° C. for overnight. The following day, supernatants were collected and a 13-plex human proinflammatory chemokine and human macrophages/microglia LEGENDplex bead array (BioLegend) was used according to the manufacturer's protocol. All samples were run on BD FACS Canto II and analysis was performed using LEGENDplex analysis software (BioLegend).

FIGS. 11A, 11B, 11C, and 11D show changes in the level of MCP1 (CCL2), MIP-1α(CCL3), MIP-1β (CCL4), and TNF, respectively, from human macrophages following overnight treatment with anti-MerTK antibody MTK-15, MTK-16, MTK-29, or MTK-33. Anti-MerTK antibodies MTK-16 and MTK-29 markedly increased the level of MCP1, MIP-1α, MIP-1β, and TNF in human macrophages. The level of MCP1 significantly increased in response to anti-MerTK antibody MTK-33 compared to that observed upon treatment with control antibody. These results demonstrated that anti-MerTK antibodies MTK-15, MTK-16, MTK-29, and MTK-33 induce pro-inflammatory chemokine or cytokine production in human macrophages in a MerTK-dependent way. These results further showed that anti-MerTK antibodies of the present disclosure are effective at increasing pro-inflammatory cytokines and chemokines in myeloid cells, indicative that anti-MerTK antibodies of the present disclosure are effective at activating myeloid cells (e.g., macrophages). These results also showed that anti-MerTK antibodies of the present disclosure are effective at increasing M1-like macrophage polarization and thus mediating anti-tumor immunity.

Example 19: Effect of Anti-MerTK Antibody Treatment in Colon Cancer In Vivo

The following studies were performed to test the ability of anti-MerTK antibodies of the present disclosure to reduce tumor burden in vivo. In these experiments, 400,000 MC38 mouse colon cancer cells were implanted subcutaneously on the shaved right flank of C57BL/6 mice. When tumor size reached approximately 80-120 mm$^3$ in volume, mice were grouped based on tumor volume to ensure the distribution of starting tumor volume was similar for analyses purposes. Anti-MerTK antibody MTK-29 and MTK33, or control antibody, were administered via intraperitoneal injection at a dose of 10 mg/kg, twice a week (N=9 per group). At the same time, anti-PDL1 antibody (clone BM1) was administered intraperitoneally at 3 mg/kg to all the treatment groups twice a week. Tumor volume was measured three times per week using a caliber. Mice were humanely euthanized when either tumor volume reached approximately 2000 mm$^3$ or ulceration occurred. Two independent in vivo experiments were performed in these studies.

Figure 12B:
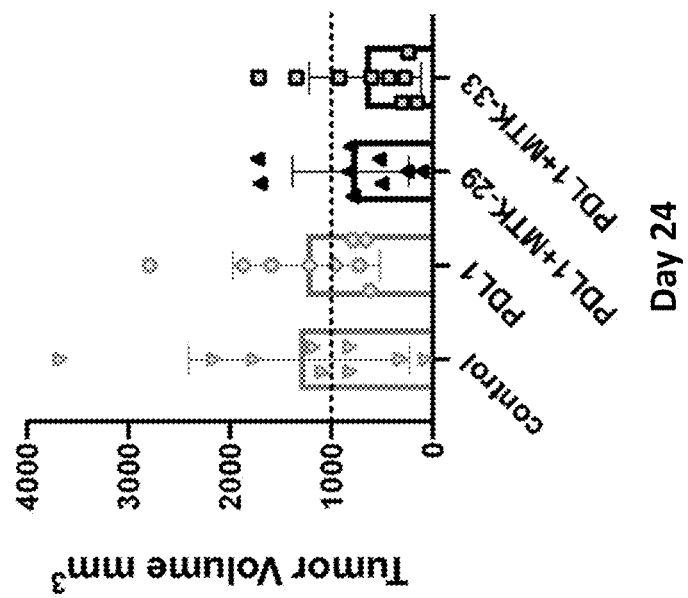
FIGS. 12A and 12B set forth data showing reduced tumor growth in mice administered anti-PDL1 antibody in combination with anti-MerTK antibodies of the present disclosure.
Figure 12A:
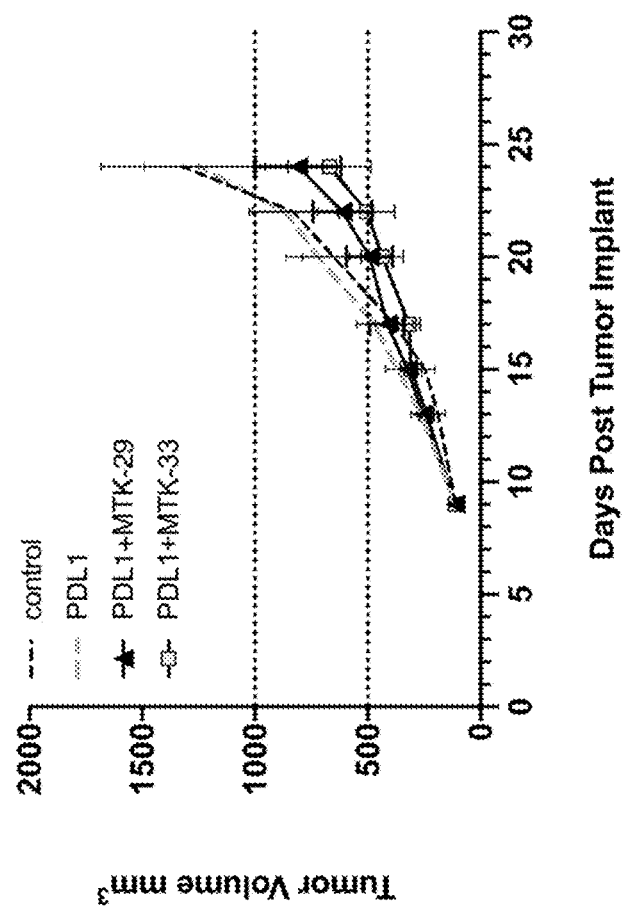

FIG. 12A and FIG. 12B show that treatment of mice with anti-PDL1 antibody and either anti-MerTK antibody MTK-29 or MTK-33 reduced tumor growth rate (shown as tumor volume over time) compared to that observed in mice treated with either anti-PDL1 antibody alone or with control antibody. These results showed that anti-MerTK antibody MTK-29 and MTK-33 are synergistic at reducing tumor volume (reduced tumor growth rate) when administered in combination with anti-PDL1 antibody compared to that observed upon treatment with anti-PDL1 antibody alone.

Figure 13:
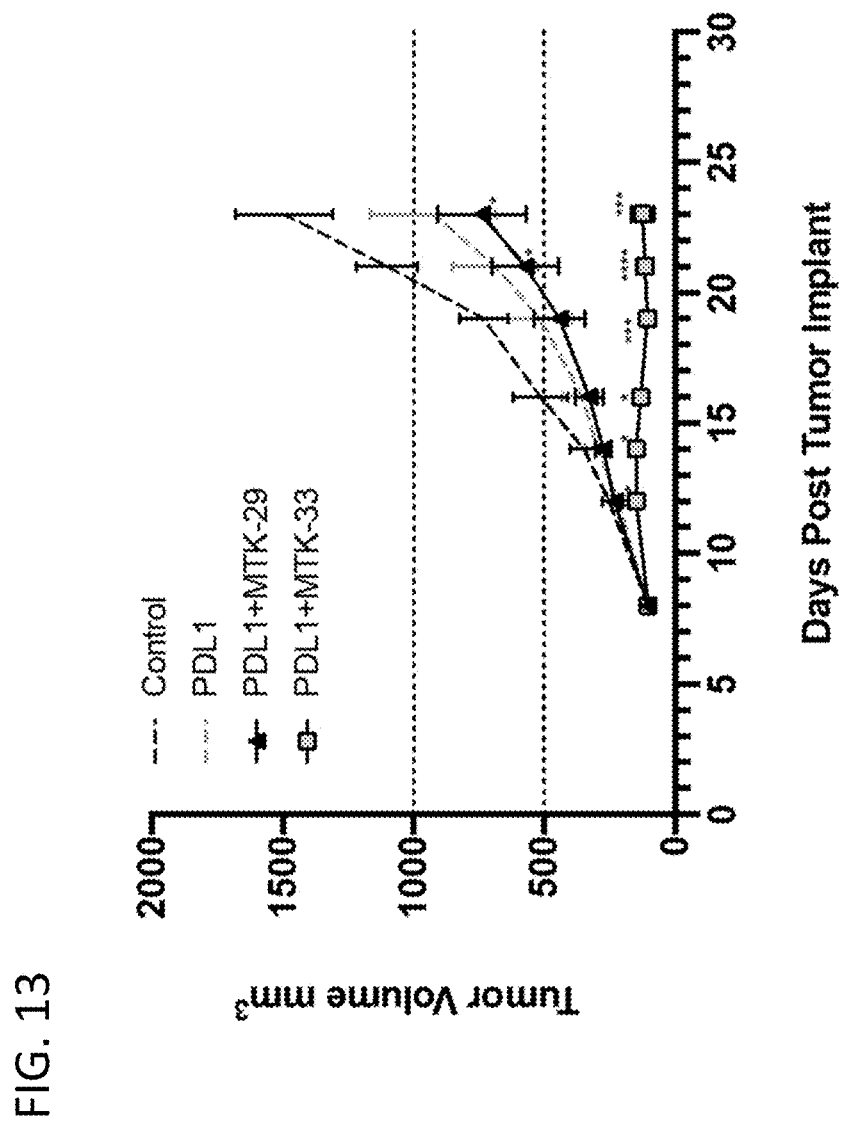
FIG. 13 sets forth data showing reduced tumor growth in mice administered anti-PDL1 antibody in combination with anti-MerTK antibodies of the present disclosure.
Figure 14A:
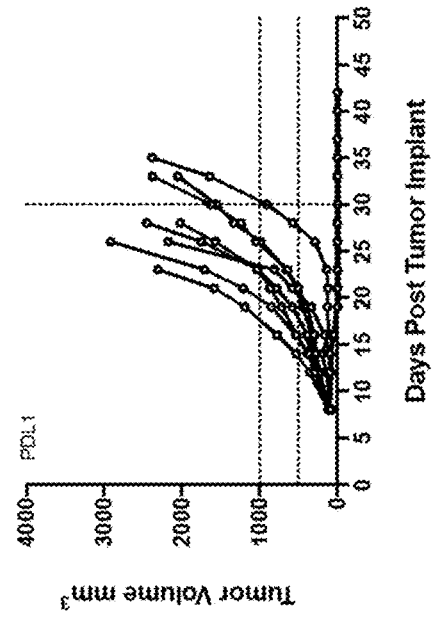
FIGS. 14A, 14B, 14C, and 14D set forth data showing differences in tumor growth rate in mice administered anti-PDL1 antibody in combination with anti-MerTK antibodies of the present disclosure, plotted using a linear scale y-axis.
Figure 14B:
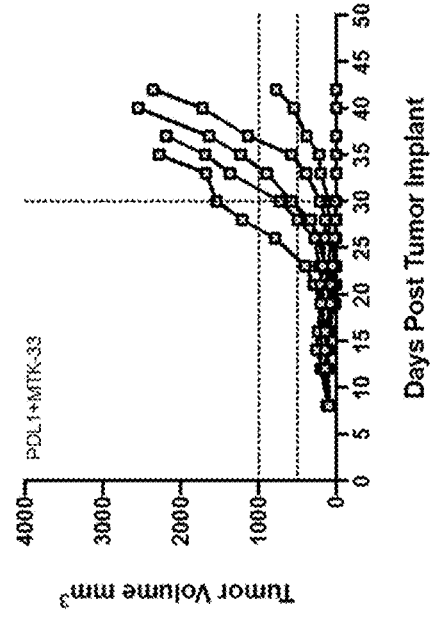
Figure 14C:
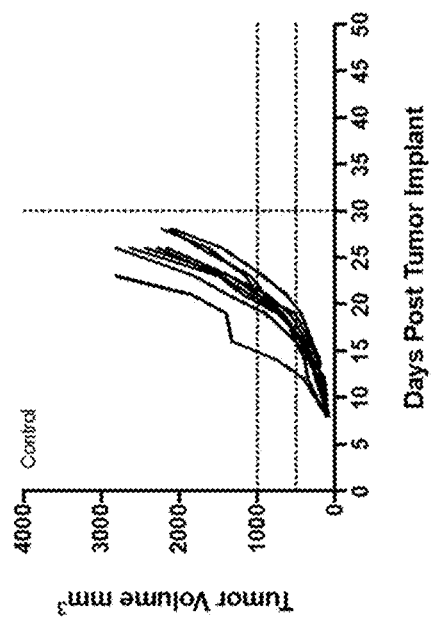
Figure 14D:
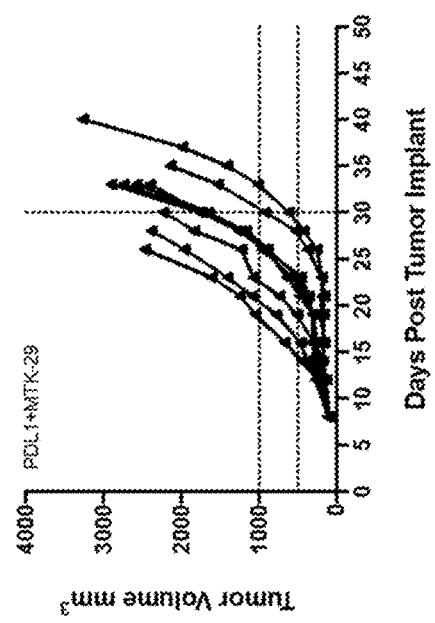
Figure 15B:
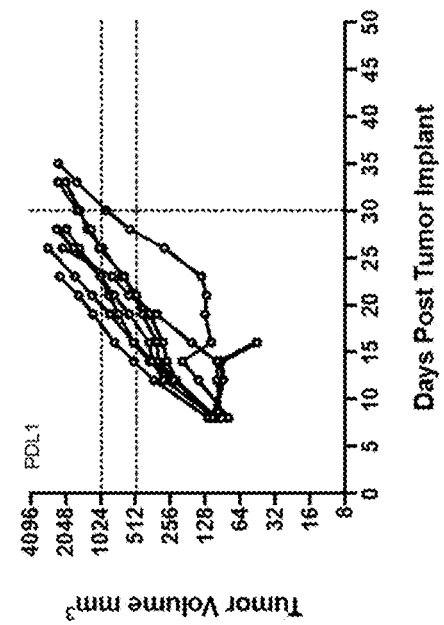
FIGS. 15A, 15B, 15C, and 15D set forth data showing differences in tumor growth rate in mice administered anti-PDL1 antibody in combination with anti-MerTK antibodies of the present disclosure, plotted using a log 2 scale y-axis.
Figure 15D:
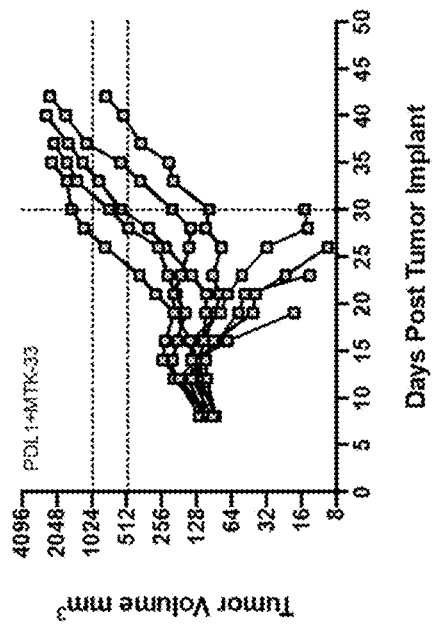
Figure 15A:
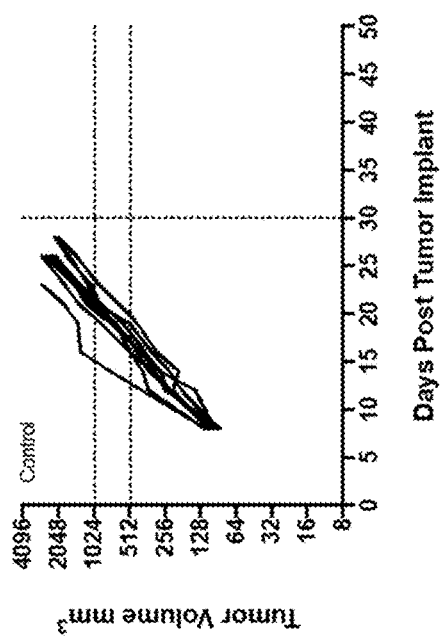
Figure 15C:
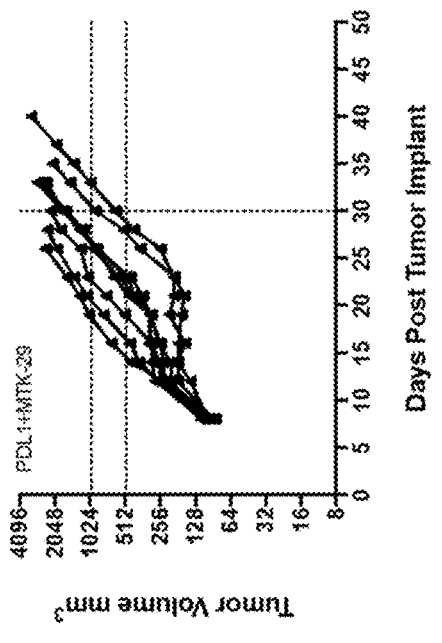

A separate set of in vivo experiments was also performed, using a combination of anti-PDL1 antibody and anti-MerTK antibody MTK-29 or anti-MerTK antibody MTK-33. As shown in FIG. 13, administration of anti-PDL1 antibody lead to reduced tumor volume compared to that observed with control antibody treatment. Administration of a combination of anti-PDL1 antibody and either anti-MerTK antibody MTK-29 or MTK-33 resulted in a greater reduction in tumor volume compared to mice administered anti-PDL1 antibody alone. Specifically, anti-MerTK antibody MTK-29 administered in combination with anti-PDL1 antibody resulted in a significantly greater ($p \leq 0.05$) reduction in tumor growth rate compared to that observed in mice treated with anti-PDL1 antibody alone. Treatment with anti-PDL1 antibody in combination with anti-MerTK antibody MTK-33, in particular, significantly reduced the growth rate of MC38 colon cancer cells in these studies compared to that observed in mice treated with anti-PDL1 antibody alone. Animals treated with 20 mg/kg of anti-MerTK antibody MTK-33 as mono-therapy also showed a reduction in tumor volume compared to that observed in animals treated with control antibody (data not shown).

FIGS. 14A, 14B, 14C, and 14D (as well as FIGS. 15A, 15B, 15C, and 15D) show the differences in tumor growth rate (tumor volume over time) of individual mice in control, anti-PDL1 antibody alone, anti-PDL1 antibody in combination with anti-MerTK antibody MTK-29, and anti-PDL1 antibody in combination with anti-MerTK antibody MTK-33, respectively. FIGS. 14A, 14B, 14C, and 14D are plotted using a linear scale on the y-axis. FIGS. 15A, 15B, 15C, and 15D are these same results plotted using a Log 2 scale on the y-axis. As shown in these Figures, combination treatment with anti-PDL1 antibody and either anti-MerTK antibody MTK-29 or MTK-33 resulted in near complete regression of tumors in 4 out of 9 mice examined in these studies.

Figure 16:
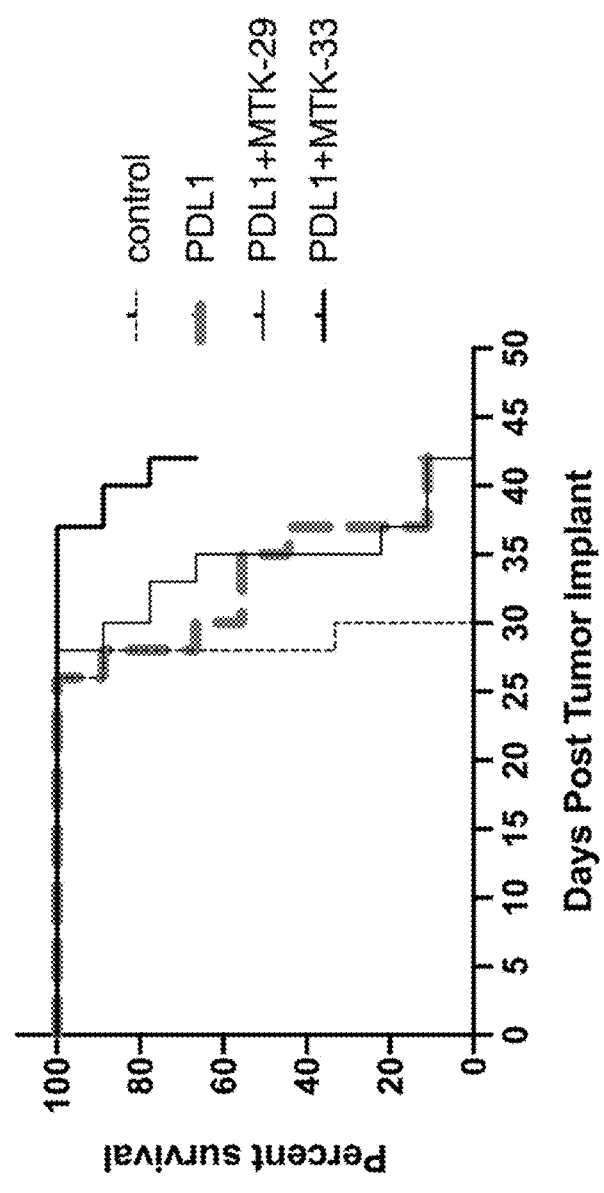
FIG. 16 sets forth data showing survival curves of tumor-bearing mice administered anti-PDL1 antibody in combination with anti-MerTK antibodies of the present disclosure.
Figure 17A:
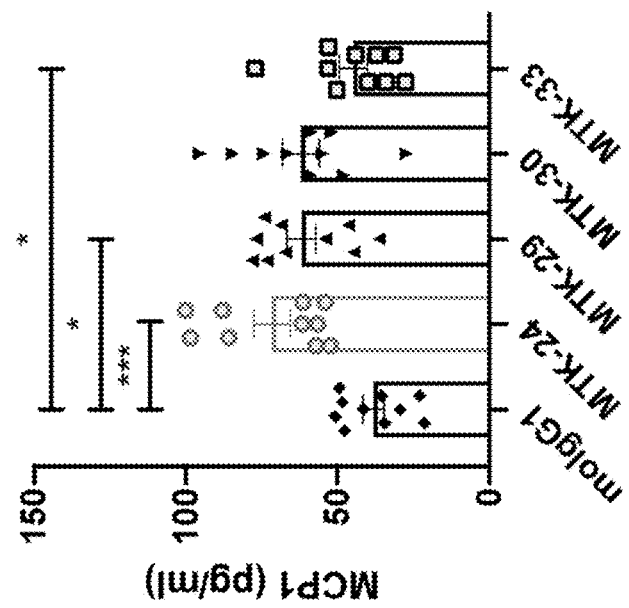
FIGS. 17A, 17B, 17C, 17D, and 17E set forth data showing changes in levels of chemokine (C-X-C motif) ligand 1 (CXCL-1, KC), monocyte chemoattractant protein-1 (MCP1, CCL2), macrophage inflammatory protein-1-alpha (MIP-1α, CCL3), macrophage inflammatory protein-1-beta (MIP-1β, CCL4), and interleukin-6 (IL-6) in plasma from mice following administration of anti-MerTK antibodies of the present disclosure.
Figure 17B:
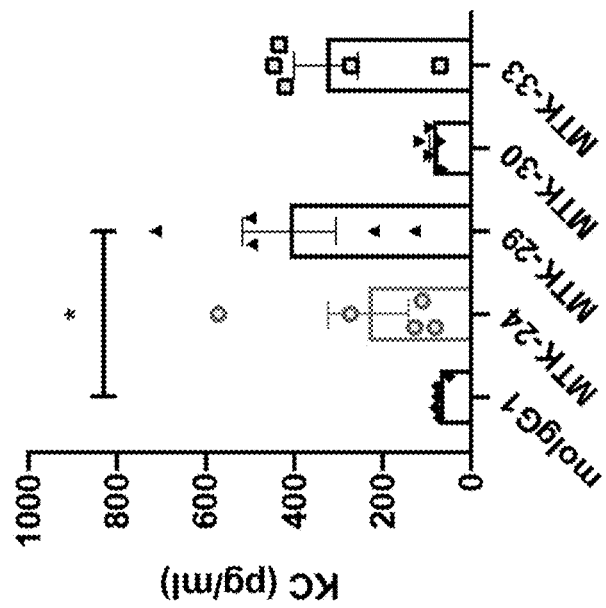
Figure 17D:
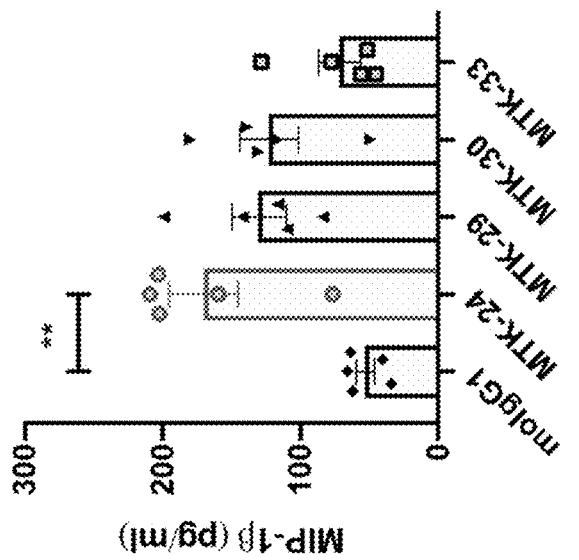
Figure 17C:
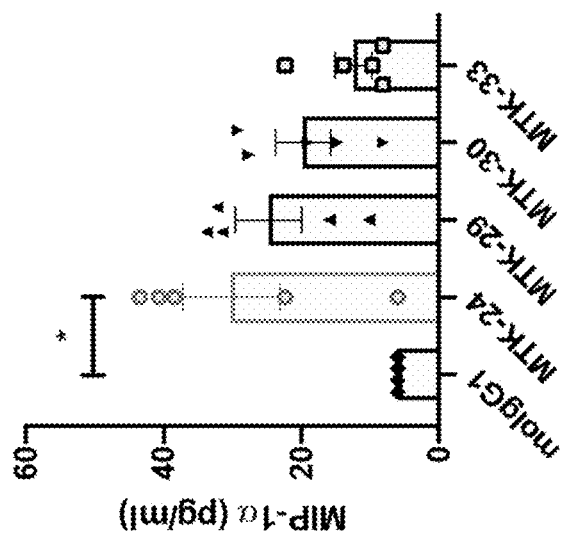
Figure 17E:
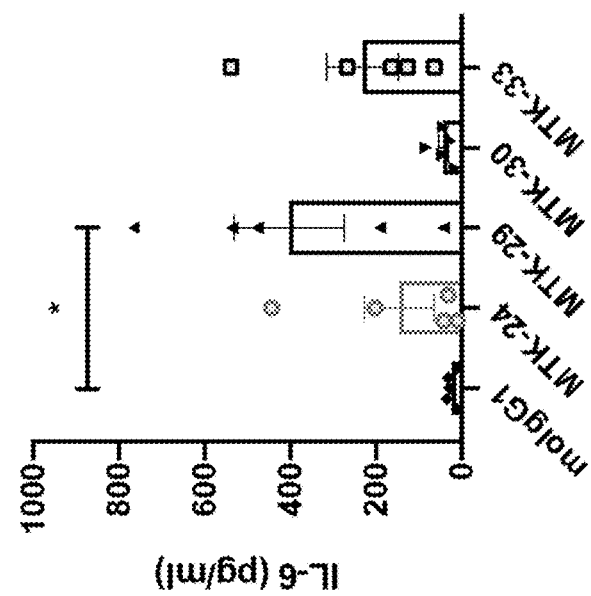
Figure 18B:
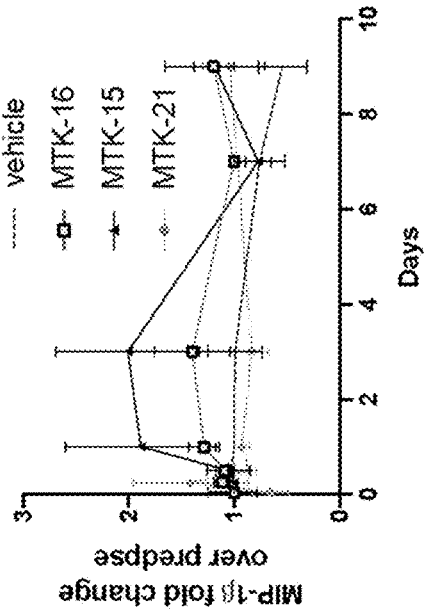
FIGS. 18A, 18B, 18C, and 18D set forth data showing changes in levels of MCP1, MIP-1β, tumor necrosis factor (TNF), and interferon (IFN) in plasma from cynomolgus monkeys administered anti-MerTK antibodies of the present disclosure.
Figure 18D:
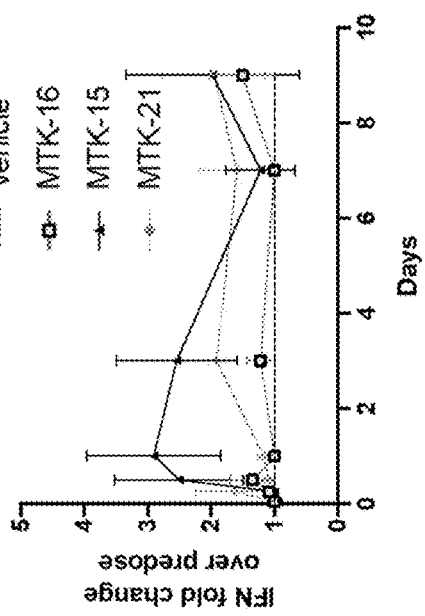
Figure 18A:
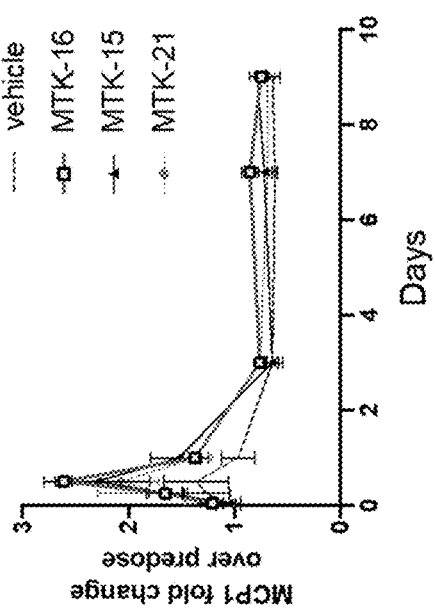
Figure 18C:
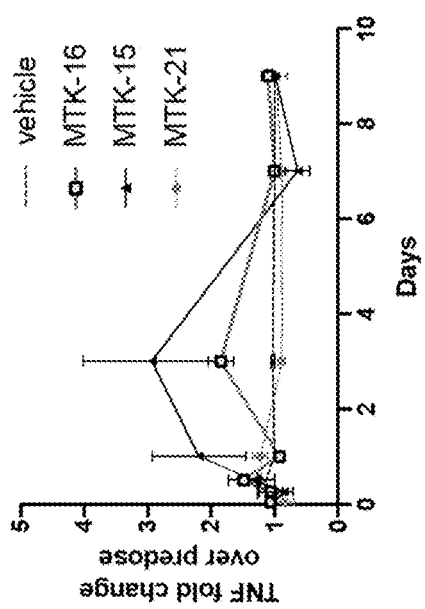

FIG. 16 shows a survival curve of the tumor-bearing mice from these studies. Median survival time of mice administered control antibody was 28 days; median survival time of mice administered anti-PDL1 antibody alone was 35 days; median survival time of mice administered anti-PDL1 antibody in combination with anti-MerTK antibody MTK-29 was 35 days; and median survival time of mice administered anti-PDL1 antibody in combination with anti-MerTK antibody MTK-33 extends beyond the final 42-day post tumor implant time-point: 6 out of 9 mice were still alive on day 42 following this combination treatment. Taken together, the results presented in FIGS. 12A, 12B, 13, 14A, 14B, 14C, 14D, 15A, 15B, 15C, 15D, and 16 demonstrated that anti-MerTK antibodies MTK-29 and MTK-33 in combination with anti-PDL1 antibody have enhanced efficacy in inhibiting tumor growth and improving cancer immunotherapy compared to treatment with anti-PDL1 antibody alone.

Example 20: Modulation of Pro-Inflammatory Cytokine or Chemokine Production in Mice The effect of anti-MerTK antibodies of the present disclosure on pro-inflammatory cytokine or chemokine production in mice was examined as follows. Control antibody or anti-MerTK antibody MTK-24, MTK-29, MTK-30, or MTK-33 was administered to C57BL/6 mice via intraperitoneal injection at a dose of 20 mg/kg (N=5 per group). One hour later, blood was withdrawn from each animal for use in measuring changes in pro-inflammatory cytokine or chemokine levels. LEGENDplex mouse proinflammatory chemokine panel (Biolegend, Catalog #740451) and LEGENDplex mouse macrophage/microglia panel (Biolegend, Catalog #740846) were used according to the manufacturer's instructions as follows. Briefly, serum samples from the mice were diluted 4-fold with Assay Buffer. Standard Cocktail was serially diluted with Assay Buffer. For setting up the standard, 25 μl of Matrix B, 25 μl of standard solution, and 25 μl of Mixed Beads were added. For setting up sample wells, 25 μl of Assay Buffer, 25 μl of diluted serum samples, and 25 μl of Mixed Beads were added. Each plate was placed on a plate shaker at 500 rpm for 2 hours. After washing the plates, 25 μl of Detection Antibodies was added to each well, and then plate was placed on a plate shaker for 1 hour. 25 μl of SA-PE was added, and then plate was shaken for 30 minutes. After washing, samples were resuspended with 1× Wash Buffer and acquired on a BD FACS CantoII (Becton Dickinson, San Jose, CA) and data were analyzed with LEGENDplex software (Biolegend).

FIGS. 17A, 17B, 17C, 17D, and 17E show the levels of KC (CXCL1), MCP1 (CCL2), MIP-1α(CCL3), MIP-1β (CCL4), and IL-6, respectively, in mice following administration of anti-MerTK antibodies of the present disclosure. As shown in these Figures, the level of each of these chemokines or cytokines increased in response to anti- MerTK antibody MTK-24, MTK-29, MTK-30, and MTK-33 administration in mice compared to that observed in mice administered control antibody. These results showed that anti-MerTK antibody MTK-24, MTK-29, MTK-30, or MTK-33 induced pro-inflammatory chemokine or cytokine production in mouse peripheral cells in a MerTK-dependent way. These results also demonstrated that anti-MerTK antibodies of the present disclosure are effective at increasing pro-inflammatory chemokine/cytokine levels in vivo, thus providing further evidence that anti-MerTK antibodies of the present disclosure are effective at activating an anti-tumor immune response.

Example 21: Modulation of Pro-Inflammatory Cytokine or Chemokine Production in Non-Human Primates The effect of anti-MerTK antibodies of the present disclosure on pro-inflammatory cytokine or chemokine production in vivo was tested in cynomolgus monkeys as follows. Anti-MerTK antibody MTK-15, MTK-16, or MTK-21 was given to cynomolgus monkeys via intravenous injection at a dose of 10 mg/kg (N=3 per group). Blood was withdrawn before dosing (pre-dose) and at 1 hour, 6 hours, 12 hours, 24 hours, 72 hours, 168 hours, and 216 hours post-dose. Levels of pro-inflammatory cytokines and chemokines were determined using LEGENDplex NHP Inflammation panel (Biolegend, Catalog #740389) and LEGENDplex NHP Chemokine/cytokine panel (Biolegend, Catalog #740317) according to the manufacturer's instructions. Briefly, plasma samples were diluted 4-fold with Assay Buffer. The Standard Cocktail was serially diluted with Assay Buffer. For setting up standard wells, 25 µl of Matrix B, 25 µl of standard solution, and 25 µl of Mixed Beads was added. For setting up sample wells, 25 µl of Assay Buffer, 25 µl of diluted plasma samples, and 25 µl of Mixed Beads was added. Plates were placed on a plate shaker at 500 rpm for 2 hours. After washing, 25 µl of Detection Antibodies was added, and then plate was shaken for 1 hour. 25 µl of SA-PE was added and then plate was shaken for 30 minutes. After washing, samples were resuspended with 1× Wash Buffer and acquired on a BD FACS CantoII (Becton Dickinson, San Jose, CA) and data were analyzed with LEGENDplex software (Biolegend). Graphs were plotted as fold increase in cytokine/chemokine levels at each specific time point over cytokine/chemokine levels at pre-dose.

FIGS. 18A, 18B, 18C, and 18D show the time course of changes in levels of MCP1 (CCL2), MIP-1β (CCL4), TNF, and IFN, respectively, in plasma obtained from cynomolgus monkeys administered anti-MerTK antibody MTK-15, MTK-16, or MTK-21, or vehicle control. The peak levels of MCP1 occurred around 12 hours post-dose. Administration of anti-MerTK antibody MTK-15 resulted in an increase in the levels of MIP-1β, TNF, and IFN up to 72 hours post-dose. Taken together, these results demonstrated that anti-MerTK antibody MTK15, MTK-16, or MTK-21 increased pro-inflammatory chemokine or cytokine production in cynomolgus monkey peripheral cells in a MerTK-dependent way. These results further indicated that anti-MerTK antibodies of the present disclosure are effective at increasing MCP1, MIP-1b, TNF, and IFN (which are pro-inflammatory cytokines/chemokines) in vivo in non-human primates.

Two additional studies were performed in cynomolgus monkeys administered anti-MerTK antibody MTK-15 or anti-MerTK antibody MTK-29 (both of which block binding of ProS to MerTK but do not block binding of Gas6 to MerTK, and both of which bind to the Ig2 and FN1 domains of MerTK) or administered anti-MerTK antibody MTK-16 (which blocks binding of both ProS and Gas6 to MerTK and which binds to the Ig1 domain of MerTK). In these preliminary studies, animals administered anti-MerTK antibody MTK-16 displayed decreased systemic toxicity compared to animals administered anti-MerTK antibody MTK-15 or anti-MerTK antibody MTK-29. These preliminary results suggested that anti-MerTK antibodies that block binding of both ProS and Gas6 to MerTK may provide a better in vivo safety profile than anti-MerTK antibodies that block binding of ProS to MerTK but that do not block binding of Gas6 to MerTK. These preliminary results also suggested that anti-MerTK antibodies that bind to the Ig1 domain of MerTK may provide a better in vivo safety profile than anti-MerTK antibodies that bind to both the Ig2 and FN1 domains of MerTK.

Example 22: Phospho-AKT Assay in Human Macrophages

The ability of anti-MerTK antibodies of the present disclosure to block phospho-AKT signaling in the presence of human Gas6 (huGas6) protein was evaluated as follows. Differentiated human macrophages were treated with 100 nM Dexamethasone (Sigma-Aldrich, Cat #D4902) and 10 ng/ml huM-CSF (R&D systems, Cat #216MC25CF) for 2 days to polarize into M2c macrophages. 100,000 cells were seeded in 96-well plate. Next day, cells were serum starved for 4 hours. Cells were treated with anti-MerTK antibodies for 30 min at 37° C. and then 200 nM of huGas6 (R&D systems, Cat #885-GSB-050) was added to the cells. After 30 min incubation, cells were lysed to determine phospho-AKT (pAKT) (CisBio, Cat #63ADK082PEG) or total AKT (CisBio, Cat #64NKTPEG) Homogeneous Time Resolved Fluorescence (HTRF) assays following the manufacturer's instructions. The pAKT signal was normalized to total AKT signal to quantitiate the final pAKT activity.

TABLE 18

| Antibody | Average IC50 (nM) From two different donors |
|---|---|
| MTK-01 | 1.28 |
| MTK-03 | 0.019 |
| MTK-05 | 0.2464 |
| MTK-07 | 0.371 |
| MTK-09 | 1.665 |
| MTK-11 | 2.627 |
| MTK-12 | 1.283 |
| MTK-15 | 2.8 |
| MTK-16 | 7.74 |
| MTK-17 | 3.422 |
| MTK-18 | 1.30 |
| MTK-19 | 0.902 |
| MTK-20 | 1.483 |
| MTK-22 | 0.531 |
| MTK-29 | 5.37 |
| MTK-33 | 4.28 |

Figure 19B:
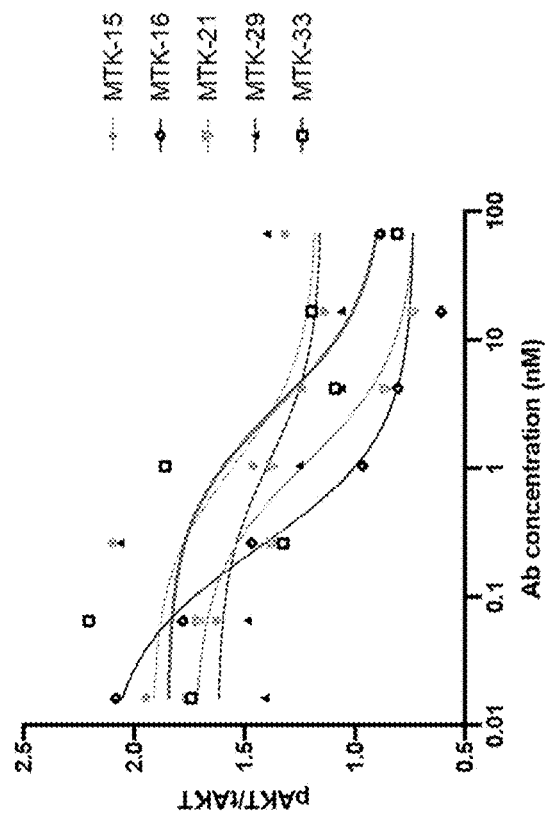
FIGS. 19A and 19B set forth data showing changes in the ratio of phosphor-AKT (pAKT) to total AKT (tAKT) in cells treated with various anti-MerTK antibodies of the present disclosure.
Figure 19A:
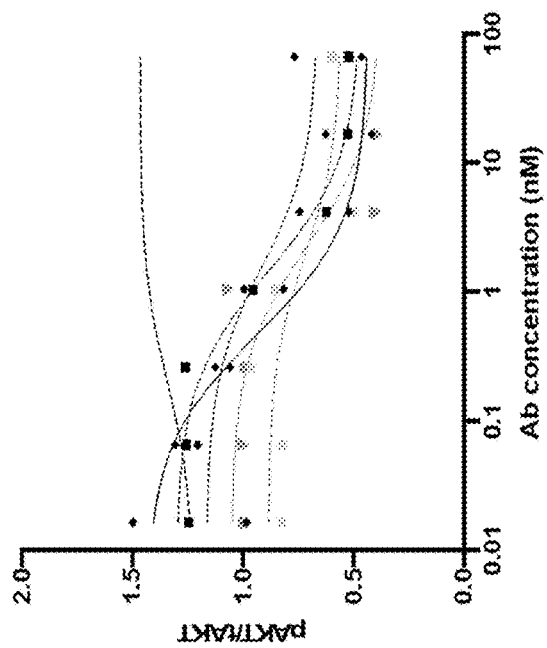

FIGS. 19A and 19B show exemplary anti-MerTK antibodies of the present disclosure (MTK-9, MTK-12, MTK-15, MTK-16, MTK-18, MTK-20, MTK-21, MTK-22, MTK-29, and MTK-33) inhibited Gas6-mediated pAKT activity in a dose-dependent manner. Table 18 above shows IC50 values determined for anti-MerTK antibody blocking of Gas6-mediated pAKT activity. As shown in Table 18, anti-MerTK antibodies of the present disclosure inhibited ligand (e.g., Gas6) mediated MerTK signaling. These results further showed that anti-MerTK antibodies of the present disclosure inhibited Gas6-mediated MerTK signaling, as measured by pAKT levels, with IC50 values ranging from 0.019 nM to 7.74 nM.

Example 23: Domain Binding Analysis of Anti-MerTK Antibodies

The following studies were performed to analyze the binding sites of various anti-MerTK antibodies of the present disclosure on human MerTK.

MerTK is a member of the TAM family, whose members share a unique domain structure containing an N-terminal region (N), two Immunoglobulin-like domains (Ig1 and Ig2), two Fibronectin type III domains (FN1 and FN2), a juxta-membrane region (JM), and an intracellular tyrosine kinase domain. MerTK also contains less-structured regions both at the N-terminus of the protein and in the juxta-membrane (JM) region of the MerTK protein; cleavage at the juxta-membrane region leads to release of soluble MerTK extracellular domain (ECD). Human MerTK ECD can be divided into the following domains, the amino acid sequences of which are shown below in Table 19:

TABLE 19

| Human MerTK domain | Sequence | SEQ ID NO: |
|---|---|---|
| N-terminal domain (N) of human MerTK ECD | AITEAREEAKPYPLFPGPFPGSLQTDHTPLLSLPHASGY QPALMFSPTQPGRPHTGNVAIPQVTSVE | 449 |
| Immunoglobulin-like domain (Ig1) of human MerTK ECD | SKPLPPLAFKHTVGHIILSEHKGVKFNCSISVPNIYQDT TISWWKDGKELLGAHHAITQFYPDDEVTAIIASFSITSV QRSDNGSYICKMKINNEEIVSDPIYIEVQ | 450 |
| Immunoglobulin-like domain (Ig2) of human MerTK ECD | GLPHFTKQPESMNVTRNTAFNLTCQAVGPPEPVNIFWVQ NSSRVNEQPEKSPSVLTVPGLTEMAVFSCEAHNDKGLTV SKGVQIN | 451 |
| Fibronectin type III domain (FN1) of human MerTK ECD | IKAIPSPPTEVSIRNSTAHSILISWVPGFDGYSPFRNCS IQVKEADPLSNGSVMIFNTSALPHLYQIKQLQALANYSI GVSCMNEIGWSAVSPWILAST | 452 |
| Fibronectin type III domain (FN2) of human MerTK ECD | TEGAPSVAPLNVTVFLNESSDNVDIRWMKPPTKQQDGEL VGYRISHVWQSAGISKELLEEVGQNGSRARISVQVHNAT CTVRIAAVTRGGVGPFSDPV | 453 |
| Juxta membrane domain region (JM) of human MerTK ECD | KIFIPAHGWVDYAPSSTPAPGNADPVLII | 454 |

Axl protein, another member of the TAM family, shares a common domain structure to that of MerTK, having the following domains and associated amino acid sequences in its ECD:

TABLE 20

| Human Axl domain | Sequence | SEQ ID NO: |
|---|---|---|
| N-terminal domain (N) of human Axl ECD | APRGTQAEESPFVGNPGNITGARGLTG | 455 |
| Immunoglobulin-like domain (Ig1) of human Axl ECD | TLRCQLQVQGEPPEVHWLRDGQILELADSTQTQVPLGED EQDDWIVVSQLRITSLQLSDTGQYQCLVFLGHQTFVSQP GYVGLE | 456 |
| Immunoglobulin-like domain (Ig2) of human Axl ECD | GLPYFLEEPEDRTVAANTPFNLSCQAQGPPEPVDLLWLQ DAVPLATAPGHGPQRSLHVPGLNKTSSFSCEAHNAKGVT TSRTATITVLP | 457 |
| Fibronectin type III domain (FN1) of human Axl ECD | QQPRNLHLVSRQPTELEVAWTPGLSGIYPLTHCTLQAVL SDDGMGIQAGEPDPPEEPLTSQASVPPHQLRLGSLHPHT PYHIRVACTSSQGPSSWTHWLPVETPEG | 458 |
| Fibronectin type III domain (FN2) of human Axl ECD | VPLGPPENISATRNGSQAFVHWQEPRAPLQGTLLGYRLA YQGQDTPEVLMDIGLRQEVTLELQGDGSVSNLTVCVAAY TAAGDGPWS | 459 |
| Juxta membrane domain (JM) of human Axl ECD | LPVPLEAWRPGQAQPVHQLVKEPSTPAFSWPWW | 460 |

In these experiments, a series of chimeric proteins were recombinantly expressed in which various domains of human MerTK were swapped with corresponding human Axl domains. The resulting chimeic proteins were recombinantly expressed in Expi293 cells and binding of various anti-MerTK antibodies of the present disclosure were then analyzed for their ability to bind the Axl/MerTK domain-swapped chimeras. DNA encoding the domain-swapped chimeras and deletion mutants, with a signal sequence (MGWSCIILFLVATATGVHS (SEQ ID NO:461) in MerTK constructs, and MGWSCIILFLVATATG (SEQ ID NO:462) in Axl constructs) and a linker+His+Avi tag (GGSGHHHHHHGGGLNDIFEAQKIEWHE; SEQ ID NO:463) were prepared by gene synthesis and cloned into the expression vector pcDNAtopo3.4 (GeneArt, ThermoFisher). Expi293 cells were transfected with 20 µg of plasmids and ExpiFectamine following recommended procedures (ThermoFisher). Transfected cells were grown in 20 mL cultures with shaking at 37° C. and 5% $CO_2$ for four days. Cells were pelleted by centrifugation and the supernatants were filtered through 0.2 µM filters by vacuum.

Table 21 shows the configurations of the various Axl/MerTK domain-swapped chimeras that were generated for use in these studies. In Table 21, an M (MerTK) or an A (Axl) indicates from which protein that particular domain was included (i.e., swapped) in the corresponding chimeric protein construct; N (N-terminal domain), Ig1 (immunoglobulin-like domain 1), Ig2 (immunoglobulin-like domain 2), FN1 (fibronectin type III domain 1), FN2 (fibronectin type III domain 2), and JM (juxta-membrane domain).

TABLE 21

| Axl/MerTK Chimeric | N | Ig1 | Ig2 | FN1 | FN2 | JM |
|---|---|---|---|---|---|---|
| Full MerTK | M | M | M | M | M | M |
| MerTK with swapped N | A | M | M | M | M | M |
| MerTK with swapped Ig1 | M | A | M | M | M | M |
| MerTK with swapped Ig2 | M | M | A | M | M | M |
| MerTK with swapped FN1 | M | M | M | A | M | M |
| MerTK with swapped FN2 | M | M | M | M | A | M |
| MerTK with swapped JM | M | M | M | M | M | A |
| Full Axl | A | A | A | A | A | A |
| Axl with swapped N | M | A | A | A | A | A |
| Axl with swapped Ig1 | A | M | A | A | A | A |
| Axl with swapped Ig2 | A | A | M | A | A | A |
| Axl with swapped FN1 | A | A | A | M | A | A |
| Axl with swapped FN2 | A | A | A | A | M | A |
| Axl with swapped JM | A | A | A | A | A | M |
| MerTK with deleted N |   | M | M | M | M | M |
| MerTK with deleted N/Ig1 |   |   | M | M | M | M |
| MerTK with deleted N/Ig1/Ig2 |   |   |   | M | M | M |
| MerTK with deleted N/Ig1/Ig2/FN1 |   |   |   |   | M | M |
| MerTK with deleted N/Ig1/Ig2/FN1/FN2 |   |   |   |   |   | M |

Binding of anti-MerTK antibodies of the present disclosure to these domain-swapped chimera or deletion mutants (prepared as described above) was tested by Surface Plasmon Resonance (SPR) using Carterra LSA. Purified anti-MerTK antibodies were immobilized in duplicate on a HC30M chip (Carterra) by amine coupling, following the manufacturer's instructions (described previously). Supernatants containing the constructs were diluted 1:1 with running buffer containing 0.5 mg/mL BSA (HBS-TE, Carterra) and injected over the immobilized antibodies. The surface was regenerated with 10 mM Glycine pH2.0 after each construct injection. Sensorgrams were analyzed using Carterra Epitope software to identify patterns of construct binding. Loss of binding to MerTK constructs with domains deleted or swapped in from Axl and/or gain of binding to Axl constructs with MerTK domains swapped in were evaluated. Data from these studies was used to construct a domain binding map for anti-MerTK antibodies and their binding to various domains of human MerTK.

In addition to anti-MerTK antibodies of the present disclosure, the following anti-MerTK antibodies were also used in these studies: rat anti-mouse MerTK antibody DS5MMER (eBioscience, Clone ID DS5MMER, rat IgG2a), mouse anti-human MerTK antibody H1 (BioLegend, Clone ID: 590H11G1E3, mouse IgG1), mouse anti-human MerTK antibody H2 (R&D systems, Clone ID: 125518, mouse IgG2b), mouse anti-human MerTK antibody H3 (R&D systems, Clone ID 125508, mouse IgG2b), mouse anti-human MerTK antibody H6 (eBioscience, Clone ID: A3KCAT, mouse IgG1), mouse anti-human MerTK antibody H7 (Sino Biological, Clone ID: 09, Mouse IgG2b), human anti-human MerTK antibody M6 (disclosed in WO2016/106221, huIgG1 LALAPS), and human anti-human MerTK antibody CDX AB3000 (disclosed in WO2020/106461).

TABLE 22

| Antibody | Binding domain |
|---|---|
| H6 | N-terminal |
| MTK-10 | Ig1 |
| MTK-16 |   |
| MTK-21 |   |
| MTK-25 |   |
| MTK-33 |   |
| M6 |   |
| MTK-22 |   |
| MTK-06 | Ig2/FN1 |
| MTK-15 |   |
| MTK-29 |   |
| MTK-30 |   |
| CDX AB3000 |   |
| H1 |   |
| H2 |   |
| H3 | Juxta membrane domain |
| H7 |   |

The results of these binding studies are shown above in Table 22. As shown in Table 22, anti-MerTK antibody H6 bound to chimeric protein constructs containing the N-terminal region of human MerTK. Anti-MerTK antibodies MTK-10, MTK-16, MTK-21, MTK-25, MTK-33, and M6 bound to constructs that contained the MerTK Ig1 domain. Anti-MerTK antibody MTK-22 bound to chimeric protein constructs that contained the MerTK Ig1; however, anti-MerTK antibody MTK-22 binding was affected by the presence of the MerTK FN1 domain. Anti-MerTK antibodies MTK-06, MTK-15, MTK-29, MTK-30, CDX AB3000, H1, and H2 bound only to chimeric protein constructs that contained both the MerTK Ig2 and FN1 domains. Anti-MerTK antibodies H3 and H7 bound to chimeric protein constructs containing the MerTK juxta membrane region. None of the anti-MerTK antibodies tested above bound to the ECD domain of human Axl (data not shown).

These results showed that anti-MetTK antibodies of the present disclosure that blocked binding of both Gas6 and ProS to MerTK generally bound to the Ig1 domain of human MerTK. These results also showed that anti-MerTK antibodies of the present disclosure that blocked binding of only ProS to MerTK generally bound to a combination of both Ig2/FN1 domains.

Example 24: Effect of Anti-MerTK Antibody Treatment in Transgenic Mouse Colon Cancer Model The effect of anti-MerTK antibodies on tumor growth in vivo was performed as follows using an in vivo mouse colon cancer model in which the mice were transgenic to include human MerTK. MC38 mouse cancer cells were implanted subcutaneously on the shaved right flank of huMerTK Knock-In (KI) mice (Ozgene, Perth, Australia), where human MerTK was introduced into the mouse genome. When tumor size reached approximately 80-130 mm³ in volume, mice were treated with 10 mg/kg of MTK-33 plus 3 mg/kg of anti-PDL1 (clone BM1), 10 mg/kg of MTK-16 plus 3 mg/kg of anti-PDL1, 3 mg/kg of anti-PDL1 alone, or 10 mg/kg of control antibody twice a week. Tumor volume was measured three times a week.

Figure 20A:
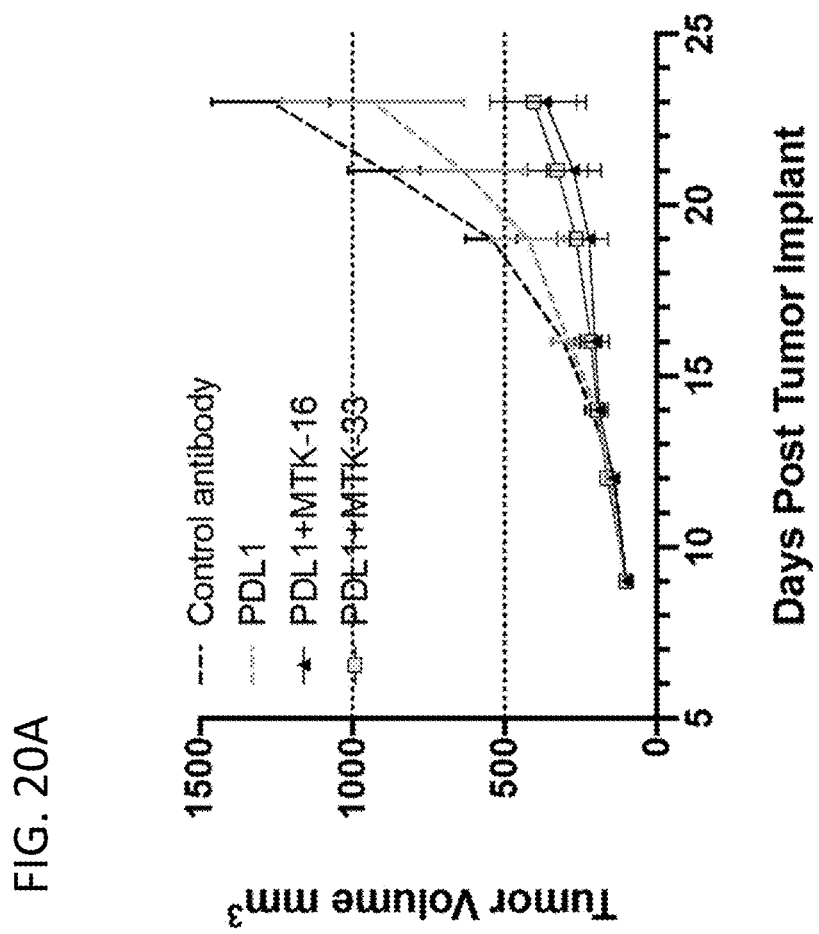
FIGS. 20A, 20B, 20C, 20D, and 20E set forth data showing changes in tumor volume in a MC38 tumor mouse model in vivo in animals administered anti-PDL-1 antibody in combination with various anti-MerTK antibodies of the present disclosure.
Figure 20C:
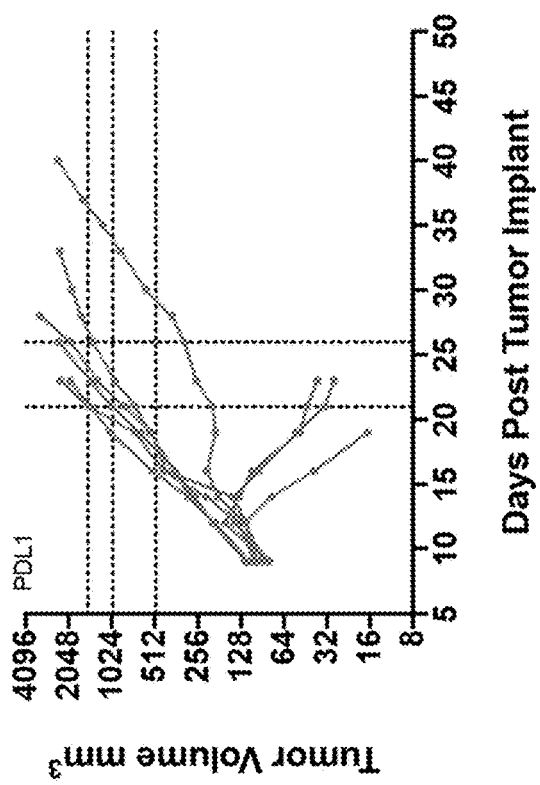
Figure 20B:
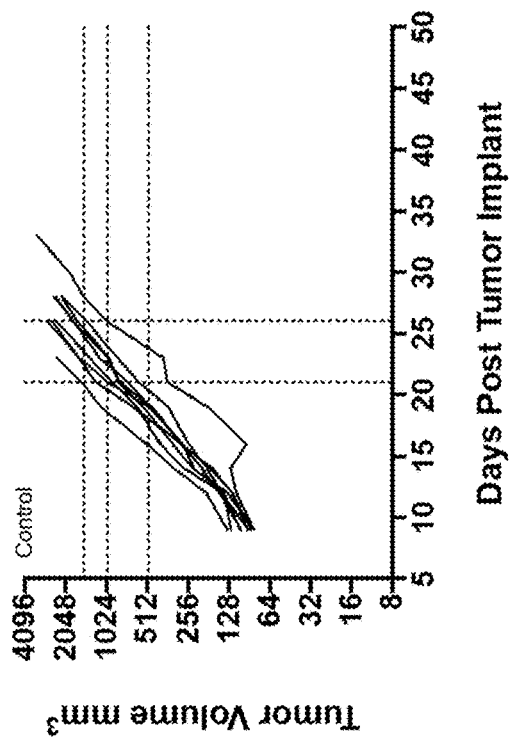
Figure 20E:
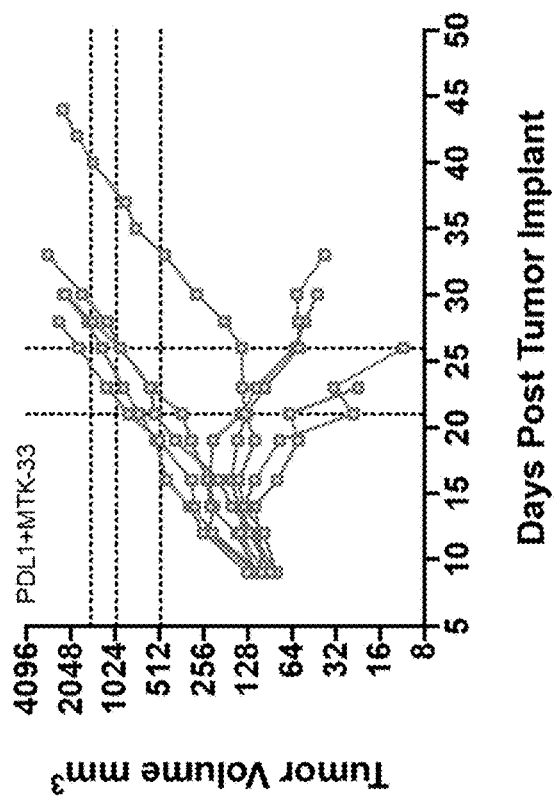
Figure 20D:
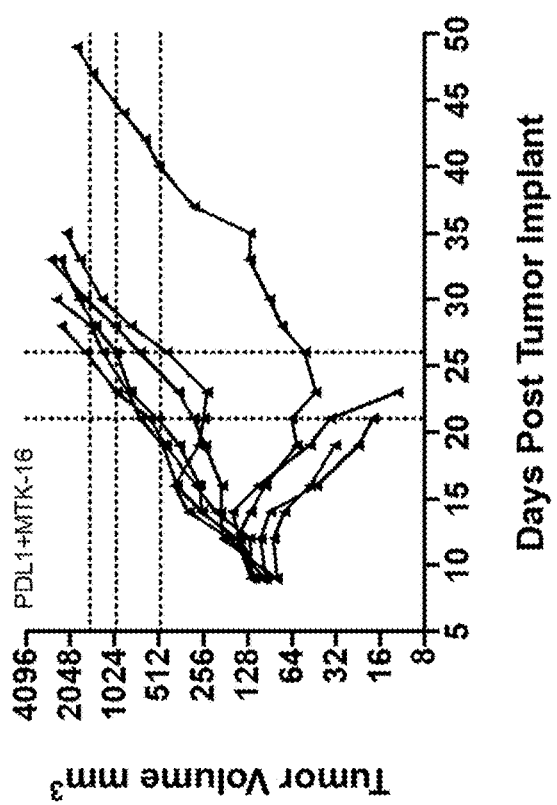
Figure 21:
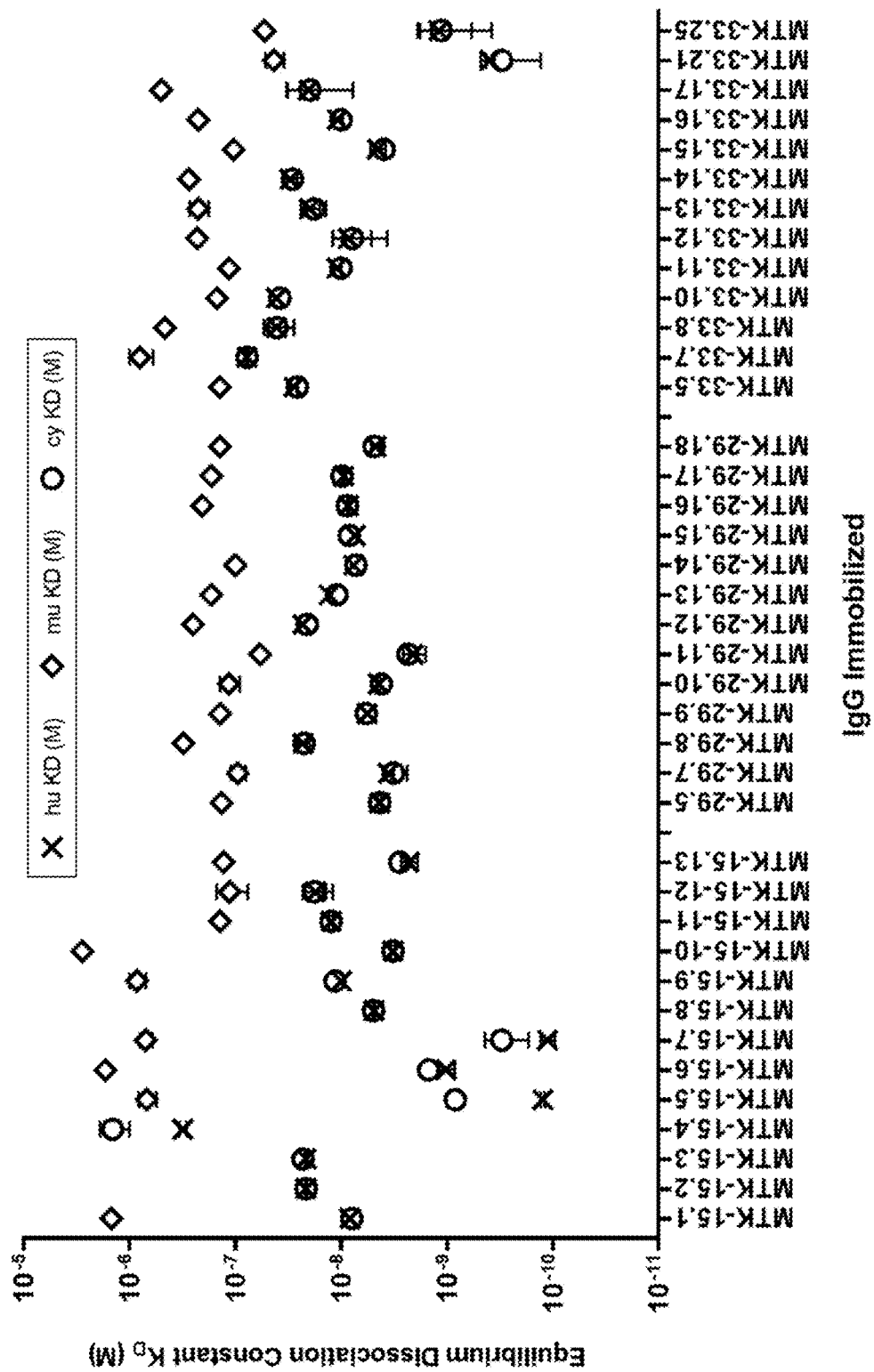
FIG. 21 sets forth data showing binding equilibrium dissociation constants ($K_D$) of anti-MerTK antibodies of the present disclosure to human (hu), murine (mu), and cynomolgus (cy) MerTK protein.

FIG. 20A shows that a combination of anti-PDL1 antibody with either anti-MerTK antibody MTK-16 or anti-MerTK antibody MTK-33 moderately reduced the tumor growth rate compared to that observed in mice treated with either anti-PDL1 antibody alone or with control antibody. FIG. 20B shows the tumor growth of individual mouse in each group and the combination treatment of anti-PDL1 with either MTK-16 or MTK-33 led to the complete regression of tumors from 3 or 4 out of 9 mice. Thus, this data show that human MerTK binding anti-MerTK antibody MTK-16 or MTK-33 in combination with anti-PDL1 antibody improved efficacy in inhibiting tumor growth

Example 25: Humanization of Murine Anti-MERTK Mouse Antibodies

Humanized variants of certain parental mouse anti-MerTK antibodies of the present disclosure were generated as follows.

The parental mouse anti-MerTK antibody MTK-16 contains a heavy chain variable region comprising the amino acid sequence of:

```
                                         (SEQ ID NO: 20)
LIQLVQSGPELKKPGETVKISCKASGYTFTNHGMNWVKQDPGKGLKWMGW

INTYTGEPTYADDFKGRFVFSMETSASAAFLQINNLKNEDTATYFCARKG

VTAARYFDYWGQGTTLTVSS,
``` and a light chain variable region comprising the amino acid sequence of:

```
                                         (SEQ ID NO: 55)
DIVMTQSPKFMSTSVGDRVSITCKASQNVRTAVAWYKKKPGQSPKALINL

ASNRHTGVPDRFTGSGSGTDFTLTISNVQSEDLADYFCLQHWNYPLTFGG

GTKLEIK.
```

The parental mouse anti-MerTK antibody MTK-33 contains a heavy chain variable region comprising the amino acid sequence of:

```
                                         (SEQ ID NO: 37)
QVQLQQPGPELVRPGTSVKLSCKASGYTFTSYWMHWIKQRPGQGLEWIGV

IDPSDNYINYNQKFKGKATLTVDTSSSTAYLQLSSLTSEDSAVYYCAREA

GTRGYFDYWGQGTTLTVSS,
``` and a light chain variable region comprising the amino acid sequence of:

```
                                         (SEQ ID NO: 72)
SIVMTQTPKFLLVSAGDRVIITCKASQSVSNTVAWYQQKPGQSPKLLIYY

ASNRYTGVPDRFTGSGYGTDFTFTISTVQAEDLAVYFCQQDYRSPFTFGS

GTQLEMK.
```

The parental mouse anti-MerTK antibody MTK-15 contains a heavy chain variable region comprising the amino acid sequence of:

```
                                         (SEQ ID NO: 19)
QIQLVQSGPELKKPGETVKISCKASGYTFTNYGVHWVKQAPGKGLKWMGW

INTYTGEPTYADDFKGRFAFSLETSASTAYLQINNLKNEDMATYFCARGN

RYAYMDYWGQGTSVTVSS,
``` and a light chain variable region comprising the amino acid sequence of:

```
                                         (SEQ ID NO: 54)
QIVLSQSPAILSASPGEKVTMTCRASSSVSYMHWYQQKSGSSPKPWIYAT

SNLASGVPARFSGSGSGTSYSLTISRVEAEDAATYYCQQWSSNPRTFGGG

TKLEIK.
```

The parent mouse anti-MerTK antibody MTK-29 contains a heavy chain variable region comprising the amino acid sequence of:

```
                                         (SEQ ID NO: 33)
QIQLVQSGPELKKPGETVKISCKSSGFTFTTYGMSWVKQAPGKGLKWMGW

INTYSGVPTYTDDFKGRFAFSLETSASTASLQINNLKNEDTATYFCARYT

NYGYFDYWGQGTTLTVSS,
``` and a light chain variable region comprising the amino acid sequence of:

```
                                         (SEQ ID NO: 68)
QIVLSQSPAILSASPGEKVTMTCRATSSVGYMHWYQQKPGSSPKPWIYAT

SNLASGVPARFSGSGSGTSYSLTISRVEAEHAATYYCQQWGSNPFTFGSG

TKLEIK.
```

One method of humanizing non-human antibodies is to transplant the CDRs from a non-human (e.g., murine) antibody onto a human antibody acceptor framework. Such CDR transplantation may result in attenuation or complete loss of affinity of the humanized antibody to its target due to perturbation in its framework. As a result, certain amino acid residues in the human framework may need to be replaced by amino acid residues from the corresponding positions of the murine antibody framework (referred to as back mutations) in order to restore attenuated or lost affinity as a result of humanization. Therefore, the amino acid residues to be replaced in the context of the selected human antibody germline acceptor framework must be determined so that the humanized antibody substantially retains functions and paratopes. In addition, retained or improved thermal stability and solubility are desired for good manufacturability and downstream development.

Briefly, VH and VL amino acid sequences of the mouse anti-MerTK monoclonal antibodies to be humanized were compared to human VL, VH, U, and HJ functional germline amino acid sequences taken from IMGT (http://www.imgt.org/). Pseudo-genes and open reading frames were excluded from these analyses. Per one mouse monoclonal antibody (query), one or two of the most similar VH and one of the most similar VL germline amino acid sequences were selected and combined with the most similar VJ and HJ genes, producing one or two humanized amino acid sequences. The CDRs to be transplanted onto the human framework were defined according to the AbM definition.

Structure-based antibody modeling was applied in the process of humanizing mouse anti-MerTK monoclonal antibodies MTK-15 and MTK-29 utilizing the BioMOE module of MOE (Molecular Operating Environment, Chemical Computing Group, Montreal, Canada). Briefly, VH and VL amino acid sequences of the mouse monoclonal antibodies MTK-15 and MTK-29 were compared to human VL, VH, U, HJ functional germline amino acid sequences taken from IMGT (http://www.imgt.org/) as mentioned above. Three of the most similar VH and three of the most similar VL germline amino acid sequences were selected and combined with the most similar VJ and HJ genes, producing five to eight humanized amino acid sequences.

The query and the humanized amino acid sequences were used to create Fv homology models using BioMOE module or the Antibody Modeler module of MOE (Molecular Operating Environment, Chemical Computing Group, Montreal, Canada). AMBER10:EHT force field analysis was used for energy minimization through the entire antibody homology modeling process. Based on the Fv homology models obtained, molecular descriptors such as interaction energy between VL and VH, coordinate-based isoelctric point (3D pI), hydrophobic patch, and charged surface area were calculated, analyzed, and sorted by scoring metrics provided by MOE. These molecular descriptors were utilized to prioritize the humanized monoclonal antibodies for downstream experimental procedures, including protein expression, purification, binding affinity studies, and functional assays.

The BioMOE module of MOE provides a tool, Mutation Site Properties, to visualize and classify potential residues for back-mutation. In this context, back-mutation is defined as amino acid substitution which is reverted to the original query amino acid sequence replacing the humanized amino acid sequence. Using this tool, the original query (reference) was compared individually to the selected humanized variants for both the primary amino acid sequence and the 3D structure of the 3D Fv homology model.

Changes between the reference (i.e., parental) antibody and the humanized variant were classified based on amino acid type difference, interaction potential with CDR residues, impact potential for VL/VH pairing, and potential change in hydrophobic and charged surface area in and near the CDRs.

Mutations near the CDRs or the VL/VH interface having a significant charge difference or containing strong H-bond interactions were individually evaluated and the significantly disrupting mutations were reverted to the original query residues.

Affinity maturation of humanized anti-MerTK antibodies MTK-33, MTK-29, and MTK-16 were also performed. Briefly, certain amino acid residues in the heavy chain or light chain were selectively mutagenized and mutants that improved binding were selected through additional rounds of screening. This process simultaneously improved specificity, species cross-reactivity, and developability profiles. Characterization of the affinity-matured anti-MerTK antibodies described herein included SPR affinity measurements on Carterra LSA and efferocytosis blocking assays on human macrophage. After multiple rounds of affinity maturation, anti-MerTK antibodies with desired affinity were obtained. Amino acid sequences of the variable heavy chains (VH) and variable light (VL) chains are provided below in Table 23 (MTK-15 variants), Table 24 (MTK-16 variants), Table 25 (MTK-29 variants), and Table 26 (MTK-33 variants). In Tables 23, 24, 25, and 26, the hypervariable regions (HVR) in each of the chains are underlined.

Table 27 and Table 28 provide amino acid sequences for the heavy chain HVRs and the light chain HVRs, respectively, for anti-MerTK antibody MTK-15 variants. Table 29 and Table 30 provide amino acid sequences for the heavy chain HVRs and the light chain HVRs, respectively, for anti-MerTK antibody MTK-16 variants. Table 31 and Table 32 provide amino acid sequences for the heavy chain HVRs and the light chain HVRs, respectively, for anti-MerTK antibody MTK-29 variants. Table 33 and Table 34 provide amino acid sequences for the heavy chain HVRs and the light chain HVRs, respectively, for anti-MerTK antibody MTK-33 variants.

TABLE 23

| Antibody | Heavy Chain Variable | SEQ ID NO: | Light Chain Variable | SEQ ID NO: |
| --- | --- | --- | --- | --- |
| MTK-15.1 | QVQLVQSGSELKKPGASVKVSC KASGYTFTNYGVHWVRQAPGQG LEWMGWINTYTGEPTYAQGFTG RFVFSLDTSVSTAYLQISSLKA EDTAVYYCARGNRYAYQDYWGQ GTLVTVSS | 234 | EIVLTQSPATLSLSPGERATLSC RASSSVSYMHWYQQKPGQAPRPL IYATSNLASGIPARFSGSGSGTS YTLTISSLEPEDFAVYYCQQWSS NPRTFGGGTKVEIK | 247 |
| MTK-15.2 | QVQLVQSGSELKKPGASVKVSC KASGYTFTNYGVHWVRQAPGQG LEWMGWGNTYTGEPTYAQGFTG RFVFSLDTSVSTAYLQISSLKA EDTAVYYCARGNRYAYMDYWGQ GTLVTVSS | 235 | EIVLTQSPATLSLSPGERATLSC RASSSVSYMHWYQQKPGQAPRPL IYATSNLASGIPARFSGSGSGTS YTLTISSLEPEDFAVYYCQQWSS NPRTFGGGTKVEIK | 247 |

TABLE 23-continued

| Antibody | Heavy Chain Variable | SEQ ID NO: | Light Chain Variable | SEQ ID NO: |
|---|---|---|---|---|
| MTK-15.3 | QVQLVQSGSELKKPGASVKVSC KASGYTFTNYGVHWVRQAPGQG LEWMGWINTYTGEPTYAQGFTG RFVFSLDTSVSTAYLQISSLKA EDTAVYYCARGNRYAYMDYWGQ GTLVTVSS | 236 | EIVLTQSPATLSLSPGERATLSC RASSHVSYMHWYQQKPGQAPRPL IYATSNLASGIPARFSGSGSGTS YTLTISSLEPEDFAVYYCQQWSS NPRTFGGGTKVEIK | 248 |
| MTK-15.4 | QVQLVQSGSELKKPGASVKVSC KASGYTFTNYGVHWVRQAPGQG LEWMGWINTYTGEPTYAQGFTG RFVFSLDTSVSTAYLQISSLKA EDTAVYYCARGNRYAYMDYWGQ GTLVTVSS | 236 | EIVLTQSPATLSLSPGERATLSC RASSSVGYMHWYQQKPGQAPRPL IYATSNLASGIPARFSGSGSGTS YTLTISSLEPEDFAVYYCQQWSS NPRTFGGGTKVEIK | 249 |
| MTK-15.5 | QVQLVQSGSELKKPGASVKVSC KASGYTFTNYGVHWVRQAPGQG LEWMGWINTYTGEPTYAQGFTG RFVFSLDTSVSTAYLQISSLKA EDTAVYYCTRGTRYAYMDYWGQ GTLVTVSS | 237 | EIVLTQSPATLSLSPGERATLSC RASSSVGYMHWYQQKPGQAPRPL IYATSNLASGIPARFSGSGSGTS YTLTISSLEPEDFAVYYCQQWSS NPRTFGGGTKVEIK | 249 |
| MTK-15.6 | QVQLVQSGSELKKPGASVKVSC KASGYTFTNYGVHWVRQAPGQG LEWMGWINTYTGEPYYAQGFTG RFVFSLDTSVSTAYLQISSLKA EDTAVYYCARGNRYAYMDYWGQ GTLVTVSS | 238 | EIVLTQSPATLSLSPGERATLSC RASSSVGYMHWYQQKPGQAPRPL IYATSNLASGIPARFSGSGSGTS YTLTISSLEPEDFAVYYCQQWSS NPRTFGGGTKVEIK | 249 |
| MTK-15.7 | QVQLVQSGSELKKPGASVKVSC KASGYTFTNYGVHWVRQAPGQG LEWMGWINTYTGEPTYAQGFTG RFVFSLDTSVSTAYLQISSLKA EDTAVYYCVRGNRYAYMDYWGQ GTLVTVSS | 239 | EIVLTQSPATLSLSPGERATLSC RASSGVSYMHWYQQKPGQAPRPL IYATSNLASGIPARFSGSGSGTS YTLTISSLEPEDFAVYYCQQWSS NPRTFGGGTKVEIK | 250 |
| MTK-15.8 | QVQLVQSGSELKKPGASVKVSC KASGYTFTNYGVHWVRQAPGQG LEWMGWINTYTGEPTYAQGFTG RFVFSLDTSVSTAYLQISSLKA EDTAVYYCARGVRYAYMDYWGQ GTLVTVSS | 240 | EIVLTQSPATLSLSPGERATLSC RASSSVGYMHWYQQKPGQAPRPL IYATSNLASGIPARFSGSGSGTS YTLTISSPEPEDFAVYYCQQWSS NPRTFGGGTKVEIK | 251 |
| MTK-15.9 | QVQLVQSGSELKKPGASVKVSC KASGYTFTNYGVHWVRQAPGQG LEWMGWINTYTGEPTYAQGFTG RFVFSLDTSVSTAYLQISSLKA EDTAVYYCARGYRYAYMDYWGQ GTLVTVSS | 241 | EIVLTQSPATLSLSPGERATLSC RASSSTSYMHWYQQKPGQAPRPL IYATSNLASGIPARFSGSGSGTS YTLTISSLEPEDFAVYYCQQWSS NPRTFGGGTKVEIK | 252 |
| MTK-15.10 | QVQLVQSGSELKKPGASVKVSC KASGYTFANYGVHWVRQAPGQG LEWMGWINTYQGEPTYAQGFTG RFVFSLDTSVSTAYLQISSLKA EDTAVYYCTRGARYAYMDYWGQ GTLVTVSS | 242 | EIVLTQSPATLSLSPGERATLSC RASSSVGYMHWYQQKPGQAPRPL IYATSNLASGIPARFSGSGSGTS YTLTISSLEPEDFAVYYCQQWSS NPRTFGGGTKVEIK | 249 |
| MTK-15.11 | QVQLVQSGSELKKPGASVKVSC KASGYTFANYGVHWVRQAPGQG LEWMGWINTYEGEPTYAQGFTG RFVFSLDTSVSTAYLQISSLKA EDTAVYYCARGNRYAYQDYWGQ GTLVTVSS | 243 | EIVLTQSPATLSLSPGERATLSC RASSSVSYMHWYQQKPGQAPRPL IYATSNLASGIPARFSGSGSGTS YTLTISSLEPEDFAVYYCQQWSS NPRTFGGGTKVEIK | 247 |
| MTK-15.12 | QVQLVQSGSELKKPGASVKVSC KASGYTFANYGVHWVRQAPGQG LEWMGWINTYQGEPTYAQGFTG RFVFSLDTSVSTAYLQISSLKA EDTAVYYCARGVRYAYMDYWGQ GTLVTVSS | 244 | EIVLTQSPATLSLSPGERATLSC RASSSVGYMHWYQQKPGQAPRPL IYATSNLASGIPARFSGSGSGTS YTLTISSPEPEDFAVYYCQQWSS NPRTFGGGTKVEIK | 251 |
| MTK-15.13 | QVQLVQSGSELKKPGASVKVSC KASGYTFTNYGVHWVRQAPGQG LEWMGWINTYTGEPTYAQGFTG RFVFSLDTSVSTAYLQISSLKA EDTAVYYCARGNRYAYEDYWGQ GTLVTVSS | 245 | EIVLTQSPATLSLSPGERATLSC RASSSVQYMHWYQQKPGQAPRPL IYATSNLASGIPARFSGSGSGTS YTLTISSLEPEDFAVYYCQQWSS NPRTFGGGTKVEIK | 253 |

TABLE 23-continued

| Antibody | Heavy Chain Variable | SEQ ID NO: | Light Chain Variable | SEQ ID NO: |
|---|---|---|---|---|
| MTK-15.14 | QVQLVQSGSELKKPGASVKVSC KASGYTFTNYGVHWVRQAPGQG LEWMGWINTYTGEPTYAQGFTG RFVFSLDTSVSTAYLQICSLKA EDTAVYYCARGNRYAYMDYWGQ GTLVTVSS | 246 | EIVLTQSPATLSLSPGERATLSC RASSSVSYMHWYQQKPGQAPRPL IYATSNLASGIPARFSGSGSGTS YTLTISSLEPEDFAVYYCQQWSS NPRTFGGGTKVEIK | 247 |
| MTK-15.15 | QVQLVQSGSELKKPGASVKVSC KASGYTFTNYGVHWVRQAPGQG LEWMGWINTYTGEPTYAQGFTG RFVFSLDTSVSTAYLQICSLKA EDTAVYYCARGNRYAYMDYWGQ GTLVTVSS | 246 | QIVLTQSPGTLSLSPGERATLSC RASSSVSYMHWYQQKPGQAPRPL IYATSNLASGIPDRFSGSGSGTS YTLTISRLEPEDFAVYYCQQWSS NPRTFGGGTKVEIK | 254 |

TABLE 24

| Antibody | Heavy Chain Variable | SEQ ID NO: | Light Chain Variable | SEQ ID NO: |
|---|---|---|---|---|
| MTK-16.1 | QVQLVQSGSELKKPGASVKVSC KASGYTFTNHGMNWVRQAPGQG LEWMGWINTYTGEPTYAQGFTG RFVFSLDTSVSTAYLQISSLKA EDTAVYYCARKGVTAARYFDYW GQGTLVTVSS | 255 | DIQMTQSPSSLSASVGDRVTITC KASQNVRTAVAWYQQKPGKAPKR LIYLASNRHTGVPSRFSGSGSGT EFTLTISNLQPEDFATYYCLQHW NYPLTFGGGTKVEIK | 257 |
| MTK-16.2 | QVQLVQSGSELKKPGASVKVSC KASGYTFTNHGMNWVRQAPGQG LEWMGWINTYTGEPTYADDFKG RFVFSLDTSVSTAYLQISSLKA EDTAVYYCARKGVTAARYFDYW GQGTLVTVSS | 256 | DIQMTQSPSSLSASVGDRVTITC RASQNVRTAVAWYQQKPGKAPKR LIYLASNRHTGVPSRFSGSGSGT EFTLTISNLQPEDFATYYCLQHW NYPLTFGGGTKLEIK | 258 |

TABLE 25

| Antibody | Heavy Chain Variable | SEQ ID NO: | Light Chain Variable | SEQ ID NO: |
|---|---|---|---|---|
| MTK-29.1 | QVQLVQSGSELKKPGASVKVSC KASGYIFTSYGLSWVRQAPGQG LEWMGWINTYSGVPTYAQGFTG RFVFSLDTSVSTAYLQISSLKA EDTAVYYCARYTNYGIFDYWGQ GTLVTVSS | 259 | EIVLTQSPATLSLSPGERATLSC RASSSVGYMHWYQQKPGQAPRPL IYATSNLASGIPARFSGSGSGTD FTLTISRLEPEDFAVYYCQQWGS WPFTFGQGTKLEIK | 274 |
| MTK-29.2 | QVQLVQSGSELKKPGASVKVSC KASGFTFTTYGMSWVRQAPGQG LEWMGWINTYSGVPTYTDDFKG RFVFSLDTSVSTAYLQISSLKA EDTAVYYCARYTNYGIFDYWGQ GTLVTVSS | 260 | DIQLTQSPSFLSASVGDRVTITC RASSSVGYMHWYQQKPGKAPKPL IYATSNLASGVPSRFSGSGSGTE FTLTISSLQPEDFATYYCQQWGS IPFTFGGGTKVEIK | 275 |
| MTK-29.3 | QVQLVQSGSELKKPGASVKVSC KASGFTFTTYGMSWVRQAPGQG LEWMGWINTYSGVPAYTDDFKG RFVFSLDTSVSTAYLQISSLKA EDTAVYYCARYTNYGVFDYWGQ GTLVTVSS | 261 | DIQLTQSPSFLSASVGDRVTITC RASSSVGYMHWYQQKPGKAPKLL IYATSNLASGVPSRFSGSGSGTE FTLTISSLQPEDFATYYCQQWGS LPFTFGQGTKLEIK | 276 |
| MTK-29.4 | QVQLVQSGSELKKPGASVKVSC KASSYTFTTYGMSWVRQAPGQG LEWMGWINTYSGVPTYTDDFKG RFVFSLDTSVSTAYLQISSLKA EDTAVYYCARYTNYGVFDYWGQ GTLVTVSS | 262 | DIQLTQSPSFLSASVGDRVTITC RASSSVGYMHWYQQKPGKAPKLL IYATSNLAQGVPSRFSGSGSGTE FTLTISSLQPEDFATYYCQQWGS LPFTFGQGTKLEIK | 277 |

TABLE 25-continued

| Antibody | Heavy Chain Variable | SEQ ID NO: | Light Chain Variable | SEQ ID NO: |
|---|---|---|---|---|
| MTK-29.5 | QVQLVQSGSELKKPGASVKVSCKASGYIFTSYGLSWVRQAPGQGLEWMGWINTYSGVPTYTDDFKGRFVFSLDTSVSTAYLQISPLKAEDTAVYYCARYTNYGVFDYWGQGTLVTVSS | 263 | DIQLTQSPSFLSASVGDRVTITCRASSSVGYMHWYQQKPGKAPKLLIYATSNLAQGVPSRFSGSGSGTEFTLTISSLQPEDFATYYCQQWGSLPFTFGQGTKLEIK | 277 |
| MTK-29.6 | QVQLVQSGSELKKPGASVKVSCKASSYTFTTYGMSWVRQAPGQGLEWMGWINTMSGVPTYTDDFKGRFVFSLDTSVSTAYLQISSLKAEDTAVYYCARYTNYGVFDYWGQGTLVTVSS | 264 | DIQLTQSPSFLSASVGDRVTITCRASSSVGYMHWYQQKPGKAPKLLIYATSNLAQGVPSRFSGSGSGTEFTLTISSLQPEDFATYYCQQWGSLPFTFGQGTKLEIK | 277 |
| MTK-29.7 | QVQLVQSGSELKKPGASVKVSCKASSYTFTTYGMSWVRQAPGQGLEWMGWINTYSGVPTYTDDFKARFVFSLDTSVSTAYLQISSLKAEDTAVYYCARYTNYGVFDYWGQGTLVTVSS | 265 | DIQLTQSPSFLSASVGDRVTITCRASSSVGYMHWYQQKPGKAPKLLIYATSNLAQGVPSRFSGSGSGTEFTLTISSLQPEDFATYYCQQWGSLPFTFGQGTKLEIK | 277 |
| MTK-29.8 | QVQLVQSGSELKKPGASVKVSCKASGYIFTTYGLSWVRQAPGQGLEWMGWINTYSGVPTYTDDFKGRFVFSLDTNVSTAYLQISSLKAEDTAVYYCARYTNYGVFDYWGQGTLVTVSS | 266 | DIQLTQSPSFLSASVGDRVTITCRASSSVGYMHWYQQKPGKAPKLLIYATSNLAQGVPSRFSGSGSGTEFTLTISSLQPEDFATYYCQQWGSLPFTFGQGTKLEIK | 277 |
| MTK-29.9 | QVQLVQSGSELKKPGASVKVSCKASGYIFTSYGLSWVRQAPGQGLEWMGWINTYSGVPTYTDDFKGRFVFSLDTSVSTAYLQISSLKAEDTAVYYCARYTNYGVFDYWGQGTLVTVSS | 267 | DIQLTQSPSFLSASVGDRVTITCRASSSVGYMHWYQQKPGKAPKLLIYATSNLAQGVPSRFSGSGSGTGFTLTISSLQPEDFATYYCQQWGSLPFTFGQGTKLEIK | 278 |
| MTK-29.10 | QVQLVQSGSELKKPGASVKVSCKTSSYTFTTYGMSWVRQAPGQGLEWMGWINTYSGVPTYTDDFKGRFVFSLDTSVSTAYLQISSLKAEDTAVYYCARYTNYGVFDYWGQGTLVTVSS | 268 | EIVLTQSPATLSLSPGERATLSCRASSSVGYMHWYQQKPGQAPRLLIYATSNLASGIPARFSGSGSGTDFTLTISRLEPEDFAVYYCQQWGSLPFTFGGGTKLEIK | 279 |
| MTK-29.11 | QVQLVQSGSELKKPGASVKVSCKASSYTFTTYGMSWVRQAPGQGLEWMGWINTDSGVPTYTDDFKGRFVFSLDTSVSTAYLQISSLKAEDTAVYYCARYTNYGVFDYWGQGTLVTVSS | 269 | EIVLTQSPATLSLSPGERATLSCRASSSVGYMHWYQQKPGQAPRLLIYATSNLASGIPARFSGSGSGTDFTLTISRLEPEDFAVYYCQQWGSLPFTFGGGTKLEIK | 279 |
| MTK-29.12 | QVQLVQSGSELKKPGASVKVSCKASSYTFTTYGMSWVRQAPGQGLEWMGWINTMSGVPTYTDDFKGRFVFSLDTSVSTAYLQISSLKAEDTAVYYCARYTNYGVFDYWGQGTLVTVSS | 264 | DIQLTQSPGFLSASVGDRVTITCRASSSVGYMHWYQQKPGKAPKLLIYATSNLAQGVPSRFSGSGSGTEFTLTISSLQPEDFATYYCQQWGSLPFTFGQGTKLEIK | 280 |
| MTK-29.13 | QVQLVQSGSELKKPGASVKVSCKASSYTFTTYGMSWVRQAPGQGLEWMGWINTASGVPTYTDDFKGRFVFSLDTSVSTAYLQISSLKAEDTAVYYCARYTNYGVFDYWGQGTLVTVSS | 270 | DIQLTQSPSFLSASVGDRVTITCRASSSVGYMHWYQQEPGKAPKLLIYATSNLAQGVPSRFSGSGSGTEFTLTISSLQPEDFATYYCQQWGSLPFTFGQGTKLEIK | 281 |
| MTK-29.14 | QVQLVQSGSELKKPGASVKVSCKASSYTFTTYGMSWVRQAPGQGLEWMGWINTYSGVPSYTDDFKARFVFSLDTSVSTAYLQISSLKAEDTAVYYCARYTNYGVFDYWGQGTLVTVSS | 265 | DIQLTQSPSFLSASVGDRVTITCRASSSVGYMHWYQQKPGKAPKLLIYATSNLAQGVPSRFSGSGSGTEFTLTIFSLQPEDFATYYCQQWGSLPFTFGQGTKLEIK | 282 |
| MTK-29.15 | QVQLVQSGSELKKPGASVKVSCKASSYTFTTYGMSWVRQAPGQGLEWMGWINTMSGVPTYTDDFKGRFVFSLDTSVSTAYLQISSLKAEDTAVYYCARYTNYGVFDYWGQGTLVTVSS | 264 | DIQLTQSPSFPSASVGDRVTITCRASSSVGYMHWYQQKPGKAPKLLIYATSNLAQGVPSRFSGSGSGTEFTLTISSLQPEDFATYYCQQWGSLPFTFGQGTKLEIK | 283 |

TABLE 25-continued

| Antibody | Heavy Chain Variable | SEQ ID NO: | Light Chain Variable | SEQ ID NO: |
|---|---|---|---|---|
| MTK-29.16 | QVQLVQSGSELKKPGASVKVSC KASGYIFTSYGLSWVRQAPGQG LEWMGWVNTYSGVPTYTDDFKG RFVFSLDTSVSTAYLQISSLKA EDTAVYYCARYTNYGVFDYWGQ GTLVTVSS | 271 | DIQLTQSPSFLSASVGDRVTITC RASSSVGYMHWYQQKPGKAPKLL IYATSNLAQGVPSRFSGSGSGTE FTLTISSLQPEDFATYYCQQWGR LPFTFGQGTKLEIK | 284 |
| MTK-29.17 | QVQLVQSGSELKKPGASVKVSC KASGYIFTSYGLSWVRQAPGQG LEWMGWINTYSGVPTYAQGFTG RFVFSLDTSVSTAYLQISSLKA EDTAVYYCARYTNYGVFDYWGQ GTLVTVSS | 272 | DIQLTQSPSFLSASVGDRVTITC RSSSSVGYMHWYQQKPGKAPKLL IYATSNLAQGVPSRFSGSGSGTE FTLTISSLQPEDFATYYCQQWGS LPFTFGQGTKLEIK | 285 |
| MTK-29.18 | QVQLVQSGSELKKPGASVKVSC KASGYIFTSYGLSWVRQAPGQG LEWMGWVNTYSGVPTYTDDFKG RFVFSLDTSVSTAYLQISSLKA EDTAVYYCARYTNYGVFDYWGQ GTLVTVSS | 271 | EIVLTQSPATLSLSPGERATLSC RASSTVGYMHWYQQKPGQAPRLL IYATSNLASGIPARFSGSGSGTD FTLTISRLEPEDFAVYYCQQWGS LPFTFGGGTKLEIK | 286 |
| MTK-29.19 | QVQLVQSGSELKKPGASVKVSC KASGFTFTTYGMSWVRQAPGQG LEWMGWINTYSGVPTYAQGFTG RFVFSLDTSVSTAYLQICSLKA EDTAVYYCARYTNYGYFDYWGQ GTLVTVSS | 273 | QIVLTQSPGTLSLSPGERATLSC RATSSVGYMHWYQQKPGQAPRPL IYATSNLASGIPDRFSGSGSGTS YTLTISRLEPEDFAVYYCQQWGS NPFTFGQGTKLEIK | 287 |
| MTK-29.20 | QVQLVQSGSELKKPGASVKVSC KASGFTFTTYGMSWVRQAPGQG LEWMGWINTYSGVPTYAQGFTG RFVFSLDTSVSTAYLQICSLKA EDTAVYYCARYTNYGYFDYWGQ GTLVTVSS | 273 | QIVLTQSPATLSLSPGERATLSC RATSSVGYMHWYQQKPGLAPRPL IYATSNLASGIPDRFSGSGSGTS YTLTISRLEPEDFAVYYCQQWGS NPFTFGQGTKLEIK | 288 |
| MTK-29.21 | QVQLVQSGSELKKPGASVKVSC KASGFTFTTYGMSWVRQAPGQG LEWMGWINTYSGVPTYAQGFTG RFVFSLDTSVSTAYLQICSLKA EDTAVYYCARYTNYGYFDYWGQ GTLVTVSS | 273 | QIVLTQSPATLSLSPGERATLSC RATSSVGYMHWYQQKPGQAPRPL IYATSNLASGIPARFSGSGSGTS YTLTISSLEPEDFAVYYCQQWGS NPFTFGQGTKLEIK | 289 |

TABLE 26

| Antibody | Heavy Chain Variable | SEQ ID NO: | Light Chain Variable | SEQ ID NO: |
|---|---|---|---|---|
| MTK-33.1 | QVQLVQSGAEVKKPGASVKVSC KASGYTFTSYWMHWVRQAPGQG LEWIGVIDPSDNYINYNQKFQG RVTMTRDTSTSTVYMELSSLRS EDTAVYYCAREAWTRGYFNYWG QGTLVTVSS | 290 | DIQMTQSPSSLSASVGDRVTITC QASQSVSNTVAWYQQKPGKAPKL LIYYASLRYTGVPSRFSGSGSGT DFTFTISSLQPEDIATYYCQQDY RSPFTFGQGTKLEIK | 309 |
| MTK-33.2 | QVQLVQSGAEVKKPGASVKVSC KASGYTSTSYWMHWVRQAPGQG LEWIGVIDPSDNYINYNQKFQG RVTMTRDTSTSTVYMELSSLRS EDTAVYYCAREAGTRGYFDYWG QGTLVTVSS | 291 | DIQMTQSPSSLSASVGDRVTITC QASGSVSNTVAWYQQKPGKAPKL LIYYASNRYTGVPSRFSGSGSGT DFTFTISSLQPEDIATYYCQQDY RSPFTFGQGTKLEIK | 310 |
| MTK-33.3 | QVQLVQSGAEVKKPGASVKVSC KASGYTFTSYWMHWVRQAPGQG LEWIGVIDPSDNYINYNQKFQG RVTMTRDTSTSTVYMELSSLRS EDTAVYYCAREAWTRGYFDYWG QGTLVTVSS | 292 | DIQMTQSPSSLSASVGDRVTITC QASRSVSNTVAWYQQKPGKAPKL LIYYASNRYTGVPSRFSGSGSGT DFTFTISSLQPEDIATYYCQQDY RSPFTFGQGTKLEIK | 311 |
| MTK-33.4 | QVQLVQSGAEVKKPGASVKVSC KASGYTFTSYWMHWVRQAPGQG LEWIGVIDPSDNYINMNQKFQG | 293 | DIQMTQSPSSLSASVGDRVTITC QASQSVSNTVAWYQQKPGKAPKL LIYYASNRYTGVPSRFSGSGSGT | 312 |

TABLE 26-continued

| Antibody | Heavy Chain Variable | SEQ ID NO: | Light Chain Variable | SEQ ID NO: |
|---|---|---|---|---|
| | RVTMTRDTSTSTVYMELSSLRS EDTAVYYCAREAGTRGYFDYWG QGTLVTVSS | | DFTFTISSLQPEDIATYYCQQDR RSPFTFGQGTKLEIK | |
| MTK-33.5 | QVQLVQSGAEVKKPGASVKVSC MASGYTFGSYWMHWVRQAPGQG LEWIGVIDPSDNYINYNQKFQG RVTMTRDTSTSTVYMELSSLRS EDTAVYYCAREAGTRGYFDYWG QGTLVTVSS | 294 | DIQMTQSPSSLSASVGDRVTITC QASQSVSNTVAWYQQKPGKAPKL LIYYASNRETGVPSRFSGSGSGT DFTFTISSLQPEDIGTYYCQQDY RSPFTFGQGTKLEIK | 313 |
| MTK-33.6 | QVQLVQSGAEVKKPGASVKVSC MASGYTFRSYWMHWVRQAPGQG LEWIGVIDPSDNYINYNQKFQG RVTMTRDTSTSTVYMELSSLRS EDTAVYYCAREAGTRGYFDYWG QGTLVTVSS | 295 | DIQMTQSPSSLSASVGDRVTITC QASRSVSNTVAWYQQKPGKAPKL LIYYASNRYTGVPSRFSGSGSGT DFTFTISSLQPEDIATYYCQQDY RSPFTFGQGTKLEIK | 314 |
| MTK-33.7 | QVQLVQSGAEVKKPGASVKVSC KASGYTFTSYWMHWVRQAPGQG LEWIGVIDPSDNYINYNAKFQG RVTMTRDTSTSTVYMELSSLRS EDTAVYYCAREAGTRGYFDYWG QGTLVTVSS | 296 | DIQMTQSPSSLSASVGDRVTITC GASQSVSNTVAWYQQKPGKAPKL LIYYASNRYTGVPSRFSGSGSGT DFTFTISSLQPEDIATYYCQQDY RSPFTFGQGTKLEIK | 315 |
| MTK-33.8 | QVQLVQSGAEVKKPGASVKVSC KASGYTFTSYWMHWVRQAPGQG LEWIGVIDPSDNYINYNQKFQG RVTMTRDTSTSTVYMELSSLRS EDTAVYYCAREAWTRGYFNYWG QGTLVTVSS | 290 | DIQMTQSPSSLSASVGDRVTITC QASQSVSRTVAWYQQKPGKAPKL LIYYASNRYTGVPSRFSGSGSGT DFTFTISSLQPEDIATYYCQQDY RSPFTFGQGTKLEIK | 316 |
| MTK-33.9 | QVQLVQSGAEVKKPGASVKVSC KASGYTFTSYWMHWVRQAPGQG LEWIGVIDPSDRYINYNQKFQG RVTMTRDTSTSTVYMELSSLRS EDTAVYYCAREAGTRGYFDYWG QGTLVTVSS | 297 | DIQMTQSPSSLSASVGDRVTITC QASASVSNTVAWYQQKPGKAPKL LIYYASNRYTGVPSRFSGSGSGT DFTFTISSLQPEDIATYYCQQDY RSPFTFGQGTKLEIK | 317 |
| MTK-33.10 | QVQLVQSGAEVKKPGASVKVSC KASSYSFTSYWMHWVRQAPGQG LEWIGVIDPSDNYINYNQKFRG RVTMTRDTSTSTVYMELSSLRS EDTAVYYCAREAGTRGYFDYWG QGTLVTVSS | 298 | DIQMTQSPSSLSASVGDRVTITC QAGQSVSNTVAWYQQKPGKAPKL LIYYASNRYTGVPSRFSGSGSGT DFTFTISSLQPEDIATYYCQQDY RSPFTFGQGTKLEIK | 318 |
| MTK-33.11 | QVQLVQSGAEVKKPGASVKVSC KASGYTFTSYWMHWVRQAPGQG LEWIGVIDPSDNYINYNQKFQG RVTMTRDTSTSTVYMELSSLRS EDTAVYYCAREAWTRGYFDYWG QGTLVTVSS | 292 | DIQMTQSPSSLSASVGDRVTITC QASRSVRNTVAWYQQKPGKAPKL LIYYASNRYTGVPSRFSGSGSGT DFTFTISSLQPEDIATYYCQQDY RSPFTFGQGTKLEIK | 319 |
| MTK-33.12 | QVQLVQSGAEVKKPGASVKVSC KASGYTFVSYWMHWVRQAPGQG LEWIGVIDPSDNYINYNQKFRG RVTMTRDTSTSTVYMELSSLRS EDTAVYYCAREAGTRGYFDYWG QGTLVTVSS | 299 | DIQMTQSPSSLSASVGDRVTITC QASQSVSNTVAWYQQKPGKAPKL LIYYASNRYTGVPSRFSGSGSGT DFTFTISSLQPEDIATYYCRQDT RSPFTFGQGTKLELK | 320 |
| MTK-33.13 | QVQLVQSGAEVKKPGASVKVSC KASGYTFTSYWMHWVRQAPGQG LEWIGVIDPSDNYINYNQKFQG RVTMTRDTSTSTVYMELSSLRS EDTAVYYCAREAGTRGYFDYWG QGTLVTVSS | 300 | DIQMTQSPSSLSASVGDRVTITC QASRSVSNTVAWYQQKPGKAPKL LIYYASNRYTGVPSRFSGSGSGT DFTFTISSLQPEDIATYYCQQDY RSPFTFGQGTKLEIK | 311 |
| MTK-33.14 | QVQLVQSGAEVKKPGASVKVSC KASGYTFTSYWMHWVRQAPGQG LEWIGVIDPSDNYINYNQKFRG RVTMTRDTSTSTVYMELSSLRS EDTAVYYCAREAGTRGYFDYWG QGTLVTVSS | 301 | DIQMTQSPSSLSASVGDRVTITC QASQSVSNTVAWYQQKPGKAPKL LIYYASNRYTGVPSRFSGSGSGT DFTFTISSLQPEDIATYYCQQDY RSPFTFGQGTKLEIK | 321 |
| MTK-33.15 | QVQLVQSGAEVKKPGASVKVSC KASGYTFTSYWMHWVRQAPGQG | 302 | DIQMTQSPSSLSASVGDRVTITC QASRSVSNTVAWYQQKPGKAPKL | 322 |

TABLE 26-continued

| Antibody | Heavy Chain Variable | SEQ ID NO: | Light Chain Variable | SEQ ID NO: |
|---|---|---|---|---|
| | LEWIGVIDPSDNYINYNQKFQV RVTMTRDTSTSTVYMELSSLRS EDTAVYYCAREAGTRGYFDYWG QGTLVTVSS | | LIYYASNRYTGVPSRFSGSGST DFTFTISSLQPEDIATYYCQQDM RSPFTFGQGTKLEIK | |
| MTK-33.16 | QVQLVQSGAEVKKPGASVKVSC KASWYTFTSYWMHWVRQAPGQG LEWIGVIDPSDNYINYNQKFQG RVTMTRDTSTSTVYMELSSLRS EDTAVYYCAREAGTRGYFDYWG QGTLVTVSS | 303 | DIQMTQSPSSLSASVGDRVTITC QASRSVSNTVAWYQQKPGKAPKL LIYYASNRYTGVPSRFSGSGST DFTFTISSLQPEDIATYYCQQDY RSPFTFGQGTKLEIK | 311 |
| MTK-33.17 | QVQLVQSGAEVKKPGASVKVSC KASGYTFTSYWMHWVRQAPGQG LEWIGVIAPSDNYINYNQKFRG RVTMTRDTSTSTVYMELSSLRS EDTAVYYCAREAGTRGYFDYWG QGTLVTVSS | 304 | DIQMTQSPSSLSASVGDRVTITC QASRSVSNTVAWYQQKPGKAPKL LIYYASNRYTGVPSRFSGSGST DFTFTISSLQPEDIATYYCQQDM RSPFTFGQGTKLEIK | 322 |
| MTK-33.18 | QVQLVQSGAEVKKPGASVKVSC KASGYTFTSYWMHWVRQAPGQG LEWIGVISPSDNYINYNQKFRG RVTMTRDTSTSTVYMELSSLRS EDTAVYYCAREAGTRGYFDYWG QGTLVTVSS | 305 | DIQMTQSPSSLSASVGDRVTITC QASRSVSNTVAWYQQKPGKAPKL LIYYASNRYTGVPSRFSGSGST DFTFTISSLQPEDIATYYCQQDM RSPFTFGQGTKLEIK | 322 |
| MTK-33.19 | QVQLVQSGAEVKKPGASVKVSC KASGYTFTSYWMHWVRQAPGQG LEWIGVIDPSDNYINYNQKFRG RVTMTRDTSTSTVYMELSSLRS EDTAVYYCAREAGTRGYFDYWG QGTLVTVSS | 301 | DIQMTQSPSSLSASVGDRVTITC QASRSVSATVAWYQQKPGKAPKL LIYYASNRYTGVPSRFSGSGST DFTFTISSLQPEDIATYYCQQDM RSPFTFGQGTKLEIK | 323 |
| MTK-33.20 | QVQLVQSGAEVKKPGASVKVSC KASGYTFTSYWMHWVRQAPGQG LEWIGVIDPSDNYINYNQKFRG RVTMTRDTSTSTVYMELSSLRS EDTAVYYCAREAGTRGYFDYWG QGTLVTVSS | 301 | DIQMTQSPSSLSASVGDRVTITC QASRSVSNTVAWYQQKPGKAPKL LIYYASNRYTGVPSRFSGSGST DFTFTISSLQPEDIATYYCAQDM RSPFTFGQGTKLEIK | 324 |
| MTK-33.21 | QVQLVQSGAEVKKPGASVKVSC KASGYTFTSYWMHWVRQAPGQG LEWIGVIDPSDNYINYNQKFRG RVTMTRDTSTSTVYMELSSLRS EDTAVYYCAREAGTRGYFDYWG QGTLVTVSS | 301 | DIQMTQSPSSLSASVGGRVTITC QASRSVSNTVAWYQQKPGKAPKL LIYYVSNRYTGVPSRFSGSGST DFTFTISSLQPEDIATYYCQQDM RSPFTFGQGTKLEIK | 325 |
| MTK-33.22 | QVQLVQSGAEVKKPGASVKVSC KASGYTFTSYWMHWVRQAPGQG LEWIGVIDPSDNYINYNQKLRG RVTMTRDTSTSTVYMELSSLRS EDTAVYYCAREAGTRGYFDYWG QGTLVTVSS | 306 | DIQMTQSPSSLSASVGDRVTITC QASRSVSNTVAWYQQKPGKAPKL LIYYASNRRTGVPSRFSGSGST DFTFTISSLQPEDIATYYCQQDM RSPFTFGQGTKLEIK | 326 |
| MTK-33.23 | QVQLVQSGAEVKKPGASVKVSC KASGYTFTSYWMHWVRQAPGQG LEWIGVIDPSDNYINYNQKFRG RVTMTRDTSTSTVYMELSSLRS EDTAVYYCAREAYTRGYFDYWG QGTLVTVSS | 307 | DIQMTQSPSSLSASVGDRVTITC IASRSVSNTVAWYQQKPGKAPKL LIYYASNRYTGVPSRFSGSGST DFTFTISSLQPEDIATYYCQQDM RSPFTFGQGTKLEIK | 327 |
| MTK-33.24 | QVQLVQSGAEVKKPGASVKVSC KASSYTFTSYWMHWVRQAPGQG LEWIGVIDPSDNYINYNQKFRG RVTMTRDTSTSTVYMELSSLRS EDTAVYYCAREAGTRGYFDYWG QGTLVTVSS | 308 | DIQMTQSPSSLSASVGDRVTITC QASRSVSRTVAWYQQKPGKAPKL LIYYASNRYTGVPSRFSGSGST DFTFTISSLQPEDIATYYCQQDM RSPFTFGQGTKLEIK | 328 |

TABLE 27

| Antibody | HVR-H1 | SEQ ID NO: | HVR-H2 | SEQ ID NO: | HVR-H3 | SEQ ID NO: |
|---|---|---|---|---|---|---|
| MTK-15.1 | NYGVH | 83 | WINTYTGEPTYAQGFTG | 329 | GNRYAYQDY | 334 |
| MTK-15.2 | NYGVH | 83 | WGNTYTGEPTYAQGFTG | 330 | GNRYAYMDY | 138 |
| MTK-15.3 | NYGVH | 83 | WINTYTGEPTYAQGFTG | 329 | GNRYAYMDY | 138 |
| MTK-15.4 | NYGVH | 83 | WINTYTGEPTYAQGFTG | 329 | GNRYAYMDY | 138 |
| MTK-15.5 | NYGVH | 83 | WINTYTGEPTYAQGFTG | 329 | GTRYAYMDY | 335 |
| MTK-15.6 | NYGVH | 83 | WINTYTGEPYYAQGFTG | 331 | GNRYAYMDY | 138 |
| MTK-15.7 | NYGVH | 83 | WINTYTGEPTYAQGFTG | 329 | GNRYAYMDY | 138 |
| MTK-15.8 | NYGVH | 83 | WINTYTGEPTYAQGFTG | 329 | GVRYAYMDY | 336 |
| MTK-15.9 | NYGVH | 83 | WINTYTGEPTYAQGFTG | 329 | GYRYAYMDY | 337 |
| MTK-15.10 | NYGVH | 83 | WINTYQGEPTYAQGFTG | 332 | GARYAYMDY | 338 |
| MTK-15.11 | NYGVH | 83 | WINTYEGEPTYAQGFTG | 333 | GNRYAYQDY | 334 |
| MTK-15.12 | NYGVH | 83 | WINTYQGEPTYAQGFTG | 332 | GVRYAYMDY | 336 |
| MTK-15.13 | NYGVH | 83 | WINTYTGEPTYAQGFTG | 329 | GNRYAYEDY | 339 |
| MTK-15.14 | NYGVH | 83 | WINTYTGEPTYAQGFTG | 329 | GNRYAYMDY | 138 |
| MTK-15.15 | NYGVH | 83 | WINTYTGEPTYAQGFTG | 329 | GNRYAYMDY | 138 |

TABLE 28

| Antibody | HVR-L1 | SEQ ID NO: | HVR-L2 | SEQ ID NO: | HVR-L3 | SEQ ID NO: |
|---|---|---|---|---|---|---|
| MTK-15.1 | RASSSVSYMH | 158 | ATSNLAS | 187 | QQWSSNPRT | 210 |
| MTK-15.2 | RASSSVSYMH | 158 | ATSNLAS | 187 | QQWSSNPRT | 210 |
| MTK-15.3 | RASSHVSYMH | 340 | ATSNLAS | 187 | QQWSSNPRT | 210 |
| MTK-15.4 | RASSSVGYMH | 341 | ATSNLAS | 187 | QQWSSNPRT | 210 |
| MTK-15.5 | RASSSVGYMH | 341 | ATSNLAS | 187 | QQWSSNPRT | 210 |
| MTK-15.6 | RASSSVGYMH | 341 | ATSNLAS | 187 | QQWSSNPRT | 210 |
| MTK-15.7 | RASSGVSYMH | 342 | ATSNLAS | 187 | QQWSSNPRT | 210 |
| MTK-15.8 | RASSSVGYMH | 341 | ATSNLAS | 187 | QQWSSNPRT | 210 |
| MTK-15.9 | RASSSTSYMH | 343 | ATSNLAS | 187 | QQWSSNPRT | 210 |
| MTK-15.10 | RASSSVGYMH | 341 | ATSNLAS | 187 | QQWSSNPRT | 210 |
| MTK-15.11 | RASSSVSYMH | 158 | ATSNLAS | 187 | QQWSSNPRT | 210 |
| MTK-15.12 | RASSSVGYMH | 341 | ATSNLAS | 187 | QQWSSNPRT | 210 |
| MTK-15.13 | RASSSVQYMH | 344 | ATSNLAS | 187 | QQWSSNPRT | 210 |
| MTK-15.14 | RASSSVSYMH | 158 | ATSNLAS | 187 | QQWSSNPRT | 210 |
| MTK15.15 | RASSSVSYMH | 158 | ATSNLAS | 187 | QQWSSNPRT | 210 |

TABLE 29

| Antibody | HVR-H1 | SEQ ID NO: | HVR-H2 | SEQ ID NO: | HVR-H3 | SEQ ID NO: |
|---|---|---|---|---|---|---|
| MTK-16.1 | NHGMN | 84 | WINTYTGEPTYAQGFTG | 329 | KGVTAARYFDY | 139 |
| MTK-16.2 | NHGMN | 84 | WINTYTGEPTYADDFKG | 99 | KGVTAARYFDY | 139 |

TABLE 30

| Antibody | HVR-L1 | SEQ ID NO: | HVR-L2 | SEQ ID NO: | HVR-L3 | SEQ ID NO: |
|---|---|---|---|---|---|---|
| MTK-16.1 | KASQNVRTAVA | 169 | LASNRHT | 195 | LQHWNYPLT | 219 |
| MTK-16.2 | RASQNVRTAVA | 345 | LASNRHT | 195 | LQHWNYPLT | 219 |

TABLE 31

| Antibody | HVR-H1 | SEQ ID NO: | HVR-H2 | SEQ ID NO: | HVR-H3 | SEQ ID NO: |
|---|---|---|---|---|---|---|
| MTK-29.1 | SYGLS | 346 | WINTYSGVPTYAQGFTG | 348 | YTNYGIFDY | 355 |
| MTK-29.2 | TYGMS | 95 | WINTYSGVPTYTDDFKG | 119 | YTNYGIFDY | 355 |
| MTK-29.3 | TYGMS | 95 | WINTYSGVPAYTDDFKG | 349 | YTNYGVFDY | 356 |
| MTK-29.4 | TYGMS | 95 | WINTYSGVPTYTDDFKG | 119 | YTNYGVFDY | 356 |
| MTK-29.5 | SYGLS | 346 | WINTYSGVPTYTDDFKG | 119 | YTNYGVFDY | 356 |
| MTK-29.6 | TYGMS | 95 | WINTMSGVPTYTDDFKG | 350 | YTNYGVFDY | 356 |
| MTK-29.7 | TYGMS | 95 | WINTYSGVPSYTDDFKA | 351 | YTNYGVFDY | 356 |
| MTK-29.8 | TYGLS | 347 | WINTYSGVPTYTDDFKG | 119 | YTNYGVFDY | 356 |
| MTK-29.9 | SYGLS | 346 | WINTYSGVPTYTDDFKG | 119 | YTNYGVFDY | 356 |
| MTK-29.10 | TYGMS | 95 | WINTYSGVPTYTDDFKG | 119 | YTNYGVFDY | 356 |
| MTK-29.11 | TYGMS | 95 | WINTDSGVPTYTDDFKG | 352 | YTNYGVFDY | 356 |
| MTK-29.12 | TYGMS | 95 | WINTMSGVPTYTDDFKG | 350 | YTNYGVFDY | 356 |
| MTK-29.13 | TYGMS | 95 | WINTASGVPTYTDDFKG | 353 | YTNYGVFDY | 356 |
| MTK-29.14 | TYGMS | 95 | WINTYSGVPSYTDDFKA | 351 | YTNYGVFDY | 356 |
| MTK-29.15 | TYGMS | 95 | WINTMSGVPTYTDDFKG | 350 | YTNYGVFDY | 356 |
| MTK-29.16 | SYGLS | 346 | WVNTYSGVPTYTDDFKG | 354 | YTNYGVFDY | 356 |
| MTK-29.17 | SYGLS | 346 | WINTYSGVPTYAQGFTG | 348 | YTNYGVFDY | 356 |
| MTK-29.18 | SYGLS | 346 | WVNTYSGVPTYTDDFKG | 354 | YTNYGVFDY | 356 |
| MTK-29.19 | TYGMS | 95 | WINTYSGVPTYAQGFTG | 348 | YTNYGYFDY | 151 |
| MTK-29.20 | TYGMS | 95 | WINTYSGVPTYAQGFTG | 348 | YTNYGYFDY | 151 |
| MTK-29.21 | TYGMS | 95 | WINTYSGVPTYAQGFTG | 348 | YTNYGYFDY | 151 |

TABLE 32

| Antibody | HVR-L1 | SEQ ID NO: | HVR-L2 | SEQ ID NO: | HVR-L3 | SEQ ID NO: |
|---|---|---|---|---|---|---|
| MTK-29.1 | RASSSVGYMH | 341 | ATSNLAS | 187 | QQWGSWPFT | 360 |
| MTK-29.2 | RASSSVGYMH | 341 | ATSNLAS | 187 | QQWGSIPFT | 361 |
| MTK-29.3 | RASSSVGYMH | 341 | ATSNLAS | 187 | QQWGSLPFT | 362 |
| MTK-29.4 | RASSSVGYMH | 341 | ATSNLAQ | 359 | QQWGSLPFT | 362 |
| MTK-29.5 | RASSSVGYMH | 341 | ATSNLAQ | 359 | QQWGSLPFT | 362 |
| MTK-29.6 | RASSSVGYMH | 341 | ATSNLAQ | 359 | QQWGSLPFT | 362 |
| MTK-29.7 | RASSSVGYMH | 341 | ATSNLAQ | 359 | QQWGSLPFT | 362 |
| MTK-29.8 | RASSSVGYMH | 341 | ATSNLAQ | 359 | QQWGSLPFT | 362 |
| MTK-29.9 | RASSSVGYMH | 341 | ATSNLAQ | 359 | QQWGSLPFT | 362 |
| MTK-29.10 | RASSSVGYMH | 341 | ATSNLAS | 187 | QQWGSLPFT | 362 |
| MTK-29.11 | RASSSVGYMH | 341 | ATSNLAS | 187 | QQWGSLPFT | 362 |
| MTK-29.12 | RASSSVGYMH | 341 | ATSNLAQ | 359 | QQWGSLPFT | 362 |
| MTK-29.13 | RASSSVGYMH | 341 | ATSNLAQ | 359 | QQWGSLPFT | 362 |
| MTK-29.14 | RASSSVGYMH | 341 | ATSNLAQ | 359 | QQWGSLPFT | 362 |
| MTK-29.15 | RASSSVGYMH | 341 | ATSNLAQ | 359 | QQWGSLPFT | 362 |
| MTK-29.16 | RASSSVGYMH | 341 | ATSNLAQ | 359 | QQWGRLPFT | 363 |
| MTK-29.17 | RSSSSVGYMH | 357 | ATSNLAQ | 359 | QQWGSLPFT | 362 |
| MTK-29.18 | RASSTVGYMH | 358 | ATSNLAS | 187 | QQWGSLPFT | 362 |
| MTK-29.19 | RATSSVGYMH | 181 | ATSNLAS | 187 | QQWGSNPFT | 208 |
| MTK-29.20 | RATSSVGYMH | 181 | ATSNLAS | 187 | QQWGSNPFT | 208 |
| MTK-29.21 | RATSSVGYMH | 181 | ATSNLAS | 187 | QQWGSNPFT | 208 |

TABLE 33

| Antibody | HVR-H1 | SEQ ID NO: | HVR-H2 | SEQ ID NO: | HVR-H3 | SEQ ID NO: |
|---|---|---|---|---|---|---|
| MTK-33.1 | SYWMH | 90 | VIDPSDNYINYNQKFQG | 364 | EAWTRGYFNY | 373 |
| MTK-33.2 | SYWMH | 90 | VIDPSDNYINYNQKFQG | 364 | EAGTRGYFDY | 155 |
| MTK-33.3 | SYWMH | 90 | VIDPSDNYINYNQKFQG | 364 | EAWTRGYFDY | 374 |
| MTK-33.4 | SYWMH | 90 | VIDPSDNYINMNQKFQG | 365 | EAGTRGYFDY | 155 |
| MTK-33.5 | SYWMH | 90 | VIDPSDNYINYNQKFQG | 364 | EAGTRGYFDY | 155 |
| MTK-33.6 | SYWMH | 90 | VIDPSDNYINYNQKFQG | 364 | EAGTRGYFDY | 155 |
| MTK-33.7 | SYWMH | 90 | VIDPSDNYINYNAKFQG | 366 | EAGTRGYFDY | 155 |
| MTK-33.8 | SYWMH | 90 | VIDPSDNYINYNQKFQG | 364 | EAWTRGYFNY | 373 |
| MTK-33.9 | SYWMH | 90 | VIDPSDRYINYNQKFQG | 367 | EAGTRGYFDY | 155 |

TABLE 33-continued

| Antibody | HVR-H1 | SEQ ID NO: | HVR-H2 | SEQ ID NO: | HVR-H3 | SEQ ID NO: |
|---|---|---|---|---|---|---|
| MTK-33.10 | SYWMH | 90 | VIDPSDNYINYNQKFRG | 368 | EAGTRGYFDY | 155 |
| MTK-33.11 | SYWMH | 90 | VIDPSDNYINYNQKFQG | 364 | EAWTRGYFDY | 374 |
| MTK-33.12 | SYWMH | 90 | VIDPSDNYINYNQKFRG | 368 | EAGTRGYFDY | 155 |
| MTK-33.13 | SYWMH | 90 | VIDPSDNYINYNQKFQG | 364 | EAGTRGYFDY | 155 |
| MTK-33.14 | SYWMH | 90 | VIDPSDNYINYNQKFRG | 368 | EAGTRGYFDY | 155 |
| MTK-33.15 | SYWMH | 90 | VIDPSDNYINYNQKFQV | 369 | EAGTRGYFDY | 155 |
| MTK-33.16 | SYWMH | 90 | VIDPSDNYINYNQKFQG | 364 | EAGTRGYFDY | 155 |
| MTK-33.17 | SYWMH | 90 | VIAPSDNYINYNQKFRG | 370 | EAGTRGYFDY | 155 |
| MTK-33.18 | SYWMH | 90 | VISPSDNYINYNQKFRG | 371 | EAGTRGYFDY | 155 |
| MTK-33.19 | SYWMH | 90 | VIDPSDNYINYNQKFRG | 368 | EAGTRGYFDY | 155 |
| MTK-33.20 | SYWMH | 90 | VIDPSDNYINYNQKFRG | 368 | EAGTRGYFDY | 155 |
| MTK-33.21 | SYWMH | 90 | VIDPSDNYINYNQKFRG | 368 | EAGTRGYFDY | 155 |
| MTK-33.22 | SYWMH | 90 | VIDPSDNYINYNQKLRG | 372 | EAGTRGYFDY | 155 |
| MTK-33.23 | SYWMH | 90 | VIDPSDNYINYNQKFRG | 368 | EAYTRGYFDY | 375 |
| MTK-33.24 | SYWMH | 90 | VIDPSDNYINYNQKFRG | 368 | EAGTRGYFDY | 155 |

TABLE 34

| Antibody | HVR-L1 | SEQ ID NO: | HVR-L2 | SEQ ID NO: | HVR-L3 | SEQ ID NO: |
|---|---|---|---|---|---|---|
| MTK-33.1 | QASQSVSNTVA | 376 | YASLRYT | 388 | QQDYRSPFT | 231 |
| MTK-33.2 | QASGSVSNTVA | 377 | YASNRYT | 203 | QQDYRSPFT | 231 |
| MTK-33.3 | QASRSVSNTVA | 378 | YASNRYT | 203 | QQDYRSPFT | 231 |
| MTK-33.4 | QASQSVSNTVA | 376 | YASNRYT | 203 | QQDRRSPFT | 392 |
| MTK-33.5 | QASQSVSNTVA | 376 | YASNRET | 389 | QQDYRSPFT | 231 |
| MTK-33.6 | QASRSVSNTMA | 379 | YASNRYT | 203 | QQDYRSPFT | 231 |
| MTK-33.7 | GASQSVSNTVA | 380 | YASNRYT | 203 | QQDYRSPFT | 231 |
| MTK-33.8 | QASQSVSRTVA | 381 | YASNRYT | 203 | QQDYRSPFT | 231 |
| MTK-33.9 | QASASVSNTVA | 382 | YASNRYT | 203 | QQDYRSPFT | 231 |
| MTK-33.10 | QAGQSVSNTVA | 383 | YASNRYT | 203 | QQDYRSPFT | 231 |
| MTK-33.11 | QASRSVRNTVA | 384 | YASNRYT | 203 | QQDYRSPFT | 231 |

TABLE 34-continued

| Antibody | HVR-L1 | SEQ ID NO: | HVR-L2 | SEQ ID NO: | HVR-L3 | SEQ ID NO: |
|---|---|---|---|---|---|---|
| MTK-33.12 | QASQSVSNTVA | 376 | YASNRYT | 203 | RQDTRSPFT | 393 |
| MTK-33.13 | QASRSVSNTVA | 378 | YASNRYT | 203 | QQDYRSPFT | 231 |
| MTK-33.14 | QASQSVSNTVA | 376 | YASNRYT | 203 | QQDYRSPFT | 231 |
| MTK-33.15 | QASRSVSNTVA | 378 | YASNRYT | 203 | QQDMRSPFT | 394 |
| MTK-33.16 | QASRSVSNTVA | 378 | YASNRYT | 203 | QQDYRSPFT | 231 |
| MTK-33.17 | QASRSVSNTVA | 378 | YASNRYT | 203 | QQDMRSPFT | 394 |
| MTK-33.18 | QASRSVSNTVA | 378 | YASNRYT | 203 | QQDMRSPFT | 394 |
| MTK-33.19 | QASRSVSATVA | 385 | YASNRYT | 203 | QQDMRSPFT | 394 |
| MTK-33.20 | QASRSVSNTVA | 378 | YASNRYT | 203 | AQDMRSPFT | 395 |
| MTK-33.21 | QASRSVSNTVA | 378 | YVSNRYT | 390 | QQDMRSPFT | 394 |
| MTK-33.22 | QASRSVSNTVA | 378 | YASNRRT | 391 | QQDMRSPFT | 394 |
| MTK-33.23 | IASRSVSNTVA | 386 | YASNRYT | 203 | QQDMRSPFT | 394 |
| MTK-33.24 | QASRSVSRTVA | 387 | YASNRYT | 203 | QQDMRSPFT | 394 |

Example 26: Blocking Efferocytosis with Humanized and Affinity-Matured Anti-MerTK Antibodies The ability of humanized and affinity-matured anti-MerTK antibodies of the present disclosure to block efferocytosis was evaluated using methods as described above in Example 11 with the following modifications. Differentiated human macrophages were treated with 100 nM Dexamethasone (Sigma-Aldrich) and 10 μg/ml huM-CSF (R&D systems) for 2 days. 50,000 cells of polarized macrophages were seeded in 96-well plate. Humanized or affinity-matured anti-MerTK antibodies were titrated to a final concentration range of between 66.6 nM to 4 pM and then each serially diluted antibody was added to each well for 30 min at 37° C.

Staurosporin-induced apoptotic Jurkat cells were labeled with pHrodo (ThermoFisher) and then added into each well at 1:4 ratio (1 macrophage:4 Jurkat cells) for 1 hour. The plates were washed with PBS and then the cells were stained with APC-conjugated anti-human CD14 for 30 minutes on ice in the dark. Cells were then washed twice in FACS buffer (PBS+2% FBS), and flow cytometry was performed on a BD FACS Canto II. Data were analyzed using FlowJo software. In these experiments, baseline efferocytosis levels were established using macrophages cultured with media alone and this was set to 100% efferocytosis activity. Relative efferocytosis activity was calculated as a percent of efferocytosis observed in cells treated with media alone compared to that observed in cells treated with anti-MerTK antibodies. The results of these studies are shown below in Table 35.

TABLE 35

| Antibody | Efferocytosis blocking activity average IC50 (nM) from at least three different donors |
|---|---|
| MTK-15.1 | 0.594 |
| MTK-15.2 | 0.867 |
| MTK-15.3 | 1.006 |
| MTK-15.4 | 0.764 |
| MTK-15.5 | 0.556 |
| MTK-15.6 | 0.506 |
| MTK-15.7 | 0.789 |
| MTK-15.8 | 0.648 |
| MTK-15.9 | 2.432 |
| MTK-15.10 | 0.579 |
| MTK-15.11 | 1.014 |
| MTK-15.12 | 1.016 |
| MTK-15.13 | 0.722 |
| MTK-15.14 | 0.902 |
| MTK-15.15 | 0.228 |
| MTK-16.1 | 0.363 |
| MTK-16.2 | 1.010 |
| MTK-29.5 | 0.572 |
| MTK-29.7 | 0.768 |
| MTK-29.8 | 0.844 |
| MTK-29.9 | 0.632 |
| MTK-29.10 | 0.823 |
| MTK-29.11 | 1.006 |
| MTK-29.12 | 1.119 |
| MTK-29.13 | 0.974 |
| MTK-29.14 | 0.719 |
| MTK-29.15 | 0.963 |
| MTK-29.16 | 0.433 |
| MTK-29.17 | 0.963 |
| MTK-29.18 | 0.697 |
| MTK-29.19 | 0.705 |
| MTK-29.20 | 0.500 |
| MTK-29.21 | 0.819 |
| MTK-33.1 | 5.5 |
| MTK-33.5 | 2.248 |
| MTK-33.7 | 7.542 |
| MTK-33.8 | 23.69 |
| MTK-33.10 | 8.850 |
| MTK-33.11 | 0.453 |
| MTK-33.12 | 0.257 |
| MTK-33.13 | 1.641 |
| MTK-33.14 | 3.568 |

TABLE 35-continued

| Antibody | Efferocytosis blocking activity average IC50 (nM) from at least three different donors |
|---|---|
| MTK-33.15 | 0.480 |
| MTK-33.16 | 0.807 |
| MTK-33.17 | 7.494 |
| MTK-33.19 | 0.348 |
| MTK-33.20 | 0.457 |
| MTK-33.21 | 0.534 |
| MTK-33.22 | 0.629 |
| MTK-33.23 | 0.405 |
| MTK-33.24 | 0.480 |
| MTK-33.25 | 0.457 |

As shown in Table 35, humanized and affinity-matured anti-MerTK antibodies of the present disclosure were effective at blocking efferocytosis by human macrophages, displaying various IC50 values. Certain affinity-matured variants of anti-MerTK antibodies MTK-15, MTK-16, and MTK-33 displayed similar IC50 values to the corresponding parental anti-MerTK antibodies (see Example 11 above). Certain other affinity matured variants of anti-MerTK antibodies displayed lower IC50 values for blocking efferocytosis (e.g., MTK-15.1, MTK-15.4, MTK-15.5, MTK-15.6, MTK-15.7, MTK-15.8, MTK-15.10, MTK-15.13, MTK-15.15, MTK-16.1, and MTK-33.15) Affinity-matured variants of MTK-15 showed a range of IC50 values of 0.228 nM to 2.4 nM; affinity-matured variants of MTK-16 showed a range of IC50 values of 0.36 nM to 1.01 nM affinity-matured variants of MTK-29 showed a range of IC50 values of 0.5 nM to 1.12 nM; affinity-matured variants of MTK-33 showed a range of IC50 values of 0.41 nM to 23.9 nM.

Example 27: Binding Kinetics of Humanized and Affinity-Matured Anti-MerTK Antibodies Binding kinetics of humanized and affinity-matured anti-MerTK antibodies of the present disclosure to human, murine, and cynomolgus MerTK proteins were evaluated as follows. Briefly, anti-MerTK antibodies were prepared by diluting to 10 µg/ml in 10 mM Acetate, pH 4.25 (Carterra, Salt Lake City, Utah), at 300 µl/well. A HC200M sensor chip (Carterra) was activated using the single channel flow cell with a 7-minute injection of a 1:1:1 mixture of 100 mM MES pH 5.5, 100 mM sulfo-NHS, 400 mM EDC (all reconstituted in MES pH 5.5; 100 µl of each mixed in vial immediately before running assay). After switching to the multi-channel array flow cell, the antibodies were injected over the activated chip in a 96-spot array for 15 minutes. The remaining unconjugated active groups on the chip were then blocked by injecting 1M Ethanolamine pH 8.5 (Carterra) for 7 minutes using the single channel flow cell.

After priming with running buffer (HBS-TE, Carterra) with 0.5 mg/ml BSA (Sigma), the immobilized anti-MerTK antibodies were tested for their ability to bind to several forms of recombinant MerTK extracellular domain, including human, cynomolgus, and mouse orthologs as described above.

Estimates of affinity were generated by injecting each analyte over the entire antibody array using the single channel flow cell. MerTK analytes were diluted to 33.3, 100, and 300 nM in running buffer, and injected in serial from lowest to highest concentration without regeneration. Two buffer blanks were run between each series (one species per series). Data were processed and analyzed using NextGen-KIT high-throughput kinetics analysis software (Carterra).

In these experiments, the anti-MerTK antibodies were human IgG1 isotype containing the Fc variant LALAPS.

The equilibrium dissociation constants ($K_D$) were then calculated from the fitted association and dissociation rate constants (k-on and k-off) for anti-MerTK antibodies of the present disclosure. The $K_D$ values obtained from these experiments are summarized in Table 36 below.

TABLE 36

| | $K_D$ (nM) | | |
|---|---|---|---|
| Antibody | huMerTK | moMerTK | cynoMerTK |
| MTK-15.1 | 8.3 | 1500 | 8.0 |
| MTK-15.2 | 21.5 | NB | 21.5 |
| MTK-15.3 | 21.5 | NB | 23 |
| MTK-15.4 | NF | NB | 1450 |
| MTK-15.5 | 0.1 | 690 | 0.8 |
| MTK-15.6 | 1.0 | 1700 | 1.5 |
| MTK-15.7 | 0.1 | 705 | 0.3 |
| MTK-15.8 | 4.9 | NB | 5.0 |
| MTK-15.9 | 10 | 850 | 11.5 |
| MTK-15.10 | 3.3 | 2800 | 3.3 |
| MTK-15.11 | 12.5 | 140 | 12.5 |
| MTK-15.12 | 17.5 | 114 | 18 |
| MTK-15.13 | 2.3 | 130 | 2.8 |
| MTK-16.1 | 86 | NB | 170 |
| MTK-16.2 | 80 | NB | 160 |
| MTK-29.5 | 4.4 | 135 | 4.4 |
| MTK-29.7 | 3.6 | 95 | 3.2 |
| MTK-29.8 | 23 | 310 | 22.5 |
| MTK-29.9 | 5.7 | 140 | 5.8 |
| MTK-29.10 | 4.5 | 116 | 4.2 |
| MTK-29.11 | 2.1 | 59 | 2.4 |
| MTK-29.12 | 23 | 250 | 21 |
| MTK-29.13 | 13 | 170 | 11 |
| MTK-29.14 | 7.6 | 100 | 7.3 |
| MTK-29.15 | 7.4 | NB | 8.4 |
| MTK-29.16 | 8.6 | 205 | 8.8 |
| MTK-29.17 | 9.6 | 170 | 9.9 |
| MTK-29.18 | 4.7 | 140 | 4.9 |
| MTK-33.5 | 28 | 140 | 26 |
| MTK-33.7 | 78 | 800 | 78 |
| MTK-33.8 | 41 | 465 | 41 |
| MTK-33.10 | 41 | 150 | 38 |
| MTK-33.11 | 11 | 115 | 10.1 |
| MTK-33.12 | 8.6 | 230 | 7.9 |
| MTK-33.13 | 20 | 225 | 18 |
| MTK-33.14 | 30.5 | 275 | 29 |
| MTK-33.15 | 4.6 | 105 | 4.0 |
| MTK-33.16 | 10.9 | 225 | 10.1 |
| MTK-33.17 | 20.4 | 505 | 19.9 |
| MTK-33.21 | 0.4 | 44 | 0.3 |
| MTK-33.25 | 1.2 | 53 | 1.1 |

NB = No binding
NF = No fit, meaning the data obtained did not fit a 1:1 binding equilibrium model These results showed that humanized and affinity-matured anti-MerTK antibodies of the present disclosure displayed a range of affinities to human, cynomolgus, and murine MerTK protein.

These results also showed that humanized and affinity-matured anti-MerTK antibodies of the present disclosure variously displayed species binding specificity and cross-reactivity to human, murine, and cynomolgus MerTK. In particular, affinity of anti-MerTK antibodies of the present disclosure for binding to human MerTK ranged from 0.1 nM to 86 nM; affinity of anti-MerTK antibodies of the present disclosure for binding to cyno MerTK ranged from 0.3 nM to 1450 nM; and affinity of anti-MerTK antibodies of the present disclosure for binding to murine MerTK ranged from 44 nM to 2800 nM. Compared to the parental anti-MerTK antibody MTK-15, certain affinity-matured anti-MerTK antibody MTK-15 variants gained binding activity to mouse MerTK, which ranged from 114 nM to 2800 nM.

Table 37 below sets forth amino acid sequences of various human heavy chain immunoglobulin Fc variants.

TABLE 37

| Human Ig Heavy Chain Fc variants | Sequence | SEQ ID NO |
|---|---|---|
| huIgG1 WT Fc with C-terminal lysine | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGK EYKCKVSNKALPAPIEKTISKAKGQPREPQVYTLPPSRDELTKNQVSLTC LVKGFYPSDIAVEWESNGQPENNYKTTPPVLDSDGSFFLYSKLTVDKSRW QQGNVFSCSVMHEALHNHYTQKSLSLSPGK | 396 |
| huIgG1 WT Fc without C-terminal lysine | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGK EYKCKVSNKALPAPIEKTISKAKGQPREPQVYTLPPSRDELTKNQVSLTC LVKGFYPSDIAVEWESNGQPENNYKTTPPVLDSDGSFFLYSKLTVDKSRW QQGNVFSCSVMHEALHNHYTQKSLSLSPG | 397 |
| huIgG1 LALAPS Fc with C-terminal lysine | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPEAAGGPSVFLFPPKPKDTLMISRTPEVTCVVVDVS HEDPEVKFNWYVDGVEVHNAKTKPREEQYNSTYRVVSVLTVLHQDWLNGK EYKCKVSNKALPASIEKTISKAKGQPREPQVYTLPPSRDELTKNQVSLTC LVKGFYPSDIAVEWESNGQPENNYKTTPPVLDSDGSFFLYSKLTVDKSRW QQGNVFSCSVMHEALHNHYTQKSLSLSPGK | 398 |
| huIgG1 LALAPS Fc without C-terminal lysine | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPEAAGGPSVFLFPPKPKDTLMISRTPEVTCVVVDVS HEDPEVKFNWYVDGVEVHNAKTKPREEQYNSTYRVVSVLTVLHQDWLNGK EYKCKVSNKALPASIEKTISKAKGQPREPQVYTLPPSRDELTKNQVSLTC LVKGFYPSDIAVEWESNGQPENNYKTTPPVLDSDGSFFLYSKLTVDKSRW QQGNVFSCSVMHEALHNHYTQKSLSLSPG | 399 |
| huIgG1 NSLF Fc with C-terminal lysine | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGK EYKCKVSSKAFPAPIEKTISKAKGQPREPQVYTLPPSRDELTKNQVSLTC LVKGFYPSDIAVEWESNGQPENNYKTTPPVLDSDGSFFLYSKLTVDKSRW QQGNVFSCSVMHEALHNHYTQKSLSLSPGK | 400 |
| huIgG1 NSLF Fc without C-terminal lysine | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGK EYKCKVSSKAFPAPIEKTISKAKGQPREPQVYTLPPSRDELTKNQVSLTC LVKGFYPSDIAVEWESNGQPENNYKTTPPVLDSDGSFFLYSKLTVDKSRW QQGNVFSCSVMHEALHNHYTQKSLSLSPG | 401 |
| huIgG1 YTE Fc with C-terminal lysine | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPEAAGGPSVFLFPPKPKDTLYITREPEVTCVVVDVS HEDPEVKFNWYVDGVEVHNAKTKPREEQYNSTYRVVSVLTVLHQDWLNGK EYKCKVSNKALPASIEKTISKAKGQPREPQVYTLPPSRDELTKNQVSLTC LVKGFYPSDIAVEWESNGQPENNYKTTPPVLDSDGSFFLYSKLTVDKSRW QQGNVFSCSVMHEALHNHYTQKSLSLSPGK | 402 |
| huIgG1 YTE Fc without C-terminal lysine | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPEAAGGPSVFLFPPKPKDTLYITREPEVTCVVVDVS HEDPEVKFNWYVDGVEVHNAKTKPREEQYNSTYRVVSVLTVLHQDWLNGK EYKCKVSNKALPASIEKTISKAKGQPREPQVYTLPPSRDELTKNQVSLTC LVKGFYPSDIAVEWESNGQPENNYKTTPPVLDSDGSFFLYSKLTVDKSRW QQGNVFSCSVMHEALHNHYTQKSLSLSPG | 403 |
| huIgG1 LS Fc with C-terminal lysine | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPEAAGGPSVFLFPPKPKDTLMISRTPEVTCVVVDVS HEDPEVKFNWYVDGVEVHNAKTKPREEQYNSTYRVVSVLTVLHQDWLNGK EYKCKVSNKALPASIEKTISKAKGQPREPQVYTLPPSRDELTKNQVSLTC LVKGFYPSDIAVEWESNGQPENNYKTTPPVLDSDGSFFLYSKLTVDKSRW QQGNVFSCSVLHEALHSHYTQKSLSLSPGK | 404 |

TABLE 37-continued

| Human Ig Heavy Chain Fc variants | Sequence | SEQ ID NO |
|---|---|---|
| huIgG1 LS Fc without C-terminal lysine | ASTKGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKKVEP<br>KSCDKTHTCPPCPAPEAAGGPSVFLFPPKPKDTLMISRTPEVTCVVVDVS<br>HEDPEVKFNWYVDGVEVHNAKTKPREEQYNSTYRVVSVLTVLHQDWLNGK<br>EYKCKVSNKALPASIEKTISKAKGQPREPQVYTLPPSRDELTKNQVSLTC<br>LVKGFYPSDIAVEWESNGQPENNYKTTPPVLDSDGSFFLYSKLTVDKSRW<br>QQGNVFSCSVLHEALHSHYTQKSLSLSPG | 405 |
| huIgG1 LV5-112 Fc with C-terminal lysine | ASTKGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKKVEP<br>KSCDKTHTCPPCPAPEAAGGPSVFLFPPKPKDTLMISRTPEVTCVVVDVS<br>HEDPEVKFNWYVDGVEVHNAKTKPREEQYNSTYRVVSVLTVLHQDWLNGK<br>EYKCKVSNKALPASIEKTISKAKGQPREPQVYTLPPSRDELTKNQVSLTC<br>LVKGFYPSDIAVEWESNGGCALYPTNCGGGQPENNYKTTPPVLDSDGSFF<br>LYSKLTVDKSRWQQGNVFSCSVMHEALHNHYTQKSLSLSPGK | 406 |
| huIgG1 LV5-112 Fc without C-terminal lysine | ASTKGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKKVEP<br>KSCDKTHTCPPCPAPEAAGGPSVFLFPPKPKDTLMISRTPEVTCVVVDVS<br>HEDPEVKFNWYVDGVEVHNAKTKPREEQYNSTYRVVSVLTVLHQDWLNGK<br>EYKCKVSNKALPASIEKTISKAKGQPREPQVYTLPPSRDELTKNQVSLTC<br>LVKGFYPSDIAVEWESNGGCALYPTNCGGGQPENNYKTTPPVLDSDGSFF<br>LYSKLTVDKSRWQQGNVFSCSVMHEALHNHYTQKSLSLSPG | 407 |
| huIgG2 WT Fc with C-terminal lysine | ASTKGPSVFPLAPCSRSTSESTAALGCLVKDYFPEPVTVSWNSGALTSGV<br>HTFPAVLQSSGLYSLSSVVTVPSSNFGTQTYTCNVDHKPSNTKVDKTVER<br>KCCVECPPCPAPPVAGPSVFLFPPKPKDTLMISRTPEVTCVVVDVSHEDP<br>EVQFNWYVDGVEVHNAKTKPREEQFNSTFRVVSVLTVVHQDWLNGKEYKC<br>KVSNKGLPAPIEKTISKTKGQPREPQVYTLPPSREEMTKNQVSLTCLVKG<br>FYPSDIAVEWESNGQPENNYKTTPPMLDSDGSFFLYSKLTVDKSRWQQGN<br>VFSCSVMHEALHNHYTQKSLSLSPGK | 408 |
| huIgG2 WT Fc without C-terminal lysine | ASTKGPSVFPLAPCSRSTSESTAALGCLVKDYFPEPVTVSWNSGALTSGV<br>HTFPAVLQSSGLYSLSSVVTVPSSNFGTQTYTCNVDHKPSNTKVDKTVER<br>KCCVECPPCPAPPVAGPSVFLFPPKPKDTLMISRTPEVTCVVVDVSHEDP<br>EVQFNWYVDGVEVHNAKTKPREEQFNSTFRVVSVLTVVHQDWLNGKEYKC<br>KVSNKGLPAPIEKTISKTKGQPREPQVYTLPPSREEMTKNQVSLTCLVKG<br>FYPSDIAVEWESNGQPENNYKTTPPMLDSDGSFFLYSKLTVDKSRWQQGN<br>VFSCSVMHEALHNHYTQKSLSLSPG | 409 |
| huIgG4 WT Fc with C-terminal lysine | ASTKGPSVFPLAPCSRSTSESTAALGCLVKDYFPEPVTVSWNSGALTSGV<br>HTFPAVLQSSGLYSLSSVVTVPSSSLGTKTYTCNVDHKPSNTKVDKRVES<br>KYGPPCPSCPAPEFLGGPSVFLFPPKPKDTLMISRTPEVTCVVVDVSQED<br>PEVQFNWYVDGVEVHNAKTKPREEQFNSTYRVVSVLTVLHQDWLNGKEYK<br>CKVSNKGLPSSIEKTISKAKGQPREPQVYTLPPSQEEMTKNQVSLTCLVK<br>GFYPSDIAVEWESNGQPENNYKTTPPVLDSDGSFFLYSRLTVDKSRWQEG<br>NVFSCSVMHEALHNHYTQKSLSLSLGK | 410 |
| huIgG4 WT Fc without C-terminal lysine | ASTKGPSVFPLAPCSRSTSESTAALGCLVKDYFPEPVTVSWNSGALTSGV<br>HTFPAVLQSSGLYSLSSVVTVPSSSLGTKTYTCNVDHKPSNTKVDKRVES<br>KYGPPCPSCPAPEFLGGPSVFLFPPKPKDTLMISRTPEVTCVVVDVSQED<br>PEVQFNWYVDGVEVHNAKTKPREEQFNSTYRVVSVLTVLHQDWLNGKEYK<br>CKVSNKGLPSSIEKTISKAKGQPREPQVYTLPPSQEEMTKNQVSLTCLVK<br>GFYPSDIAVEWESNGQPENNYKTTPPVLDSDGSFFLYSRLTVDKSRWQEG<br>NVFSCSVMHEALHNHYTQKSLSLSLG | 411 |

Human IgG1 light chain constant region amino acid sequence is set forth below: RTVAAPSVFIFPPSDEQLKSGTASVVCLLNNFYPREAKVQWKVDNALQSGNSQESVTEQDSKDS TYSLSSTLTLSKADYEKHKVYACEVTHQGLSSPVTKSFNRGEC (SEQ ID NO: 412).

Full-length heavy chain amino acid sequences of certain anti-MerTK antibodies of the present disclosure are shown below in Table 38.

TABLE 38

| Antibody | Sequence | SEQ ID NO: |
|---|---|---|
| MTK-16.1 with huIgG1 WT Fc with C-terminal lysine | QVQLVQSGSELKKPGASVKVSCKASGYTFTNHGMNWVRQAPGQGLEWMGWI NTYTGEPTYAQGFTGRFVFSLDTSVSTAYLQISSLKAEDTAVYYCARKGVT AARYFDYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTLM ISRTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPS RDELTKNQVSLTCLVKGFYPSDIAVEWESNGQPENNYKTTPPVLDSDGSFF LYSKLTVDKSRWQQGNVFSCSVMHEALHNHYTQKSLSLSPGK | 413 |
| MTK-16.1 with huIgG1 WT Fc without C-terminal lysine | QVQLVQSGSELKKPGASVKVSCKASGYTFTNHGMNWVRQAPGQGLEWMGWI NTYTGEPTYAQGFTGRFVFSLDTSVSTAYLQISSLKAEDTAVYYCARKGVT AARYFDYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTLM ISRTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPS RDELTKNQVSLTCLVKGFYPSDIAVEWESNGQPENNYKTTPPVLDSDGSFF LYSKLTVDKSRWQQGNVFSCSVMHEALHNHYTQKSLSLSPG | 414 |
| MTK-16.1 with huIgG1 LALAPS Fc with C-terminal lysine | QVQLVQSGSELKKPGASVKVSCKASGYTFTNHGMNWVRQAPGQGLEWMGWI NTYTGEPTYAQGFTGRFVFSLDTSVSTAYLQISSLKAEDTAVYYCARKGVT AARYFDYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICN VNHKPSNTKVDKKVEPKSCDKTHTCPPCPAPEAAGGPSVFLFPPKPKDTLM ISRTPEVTCVVVDVSHEDPEVKFNWYVDGVEVHNAKTKPREEQYNSTYRVV SVLTVLHQDWLNGKEYKCKVSNKALPASIEKTISKAKGQPREPQVYTLPPS RDELTKNQVSLTCLVKGFYPSDIAVEWESNGQPENNYKTTPPVLDSDGSFF LYSKLTVDKSRWQQGNVFSCSVMHEALHNHYTQKSLSLSPGK | 415 |
| MTK-16.1 with huIgG1 LALAPS Fc without C-terminal lysine | QVQLVQSGSELKKPGASVKVSCKASGYTFTNHGMNWVRQAPGQGLEWMGWI NTYTGEPTYAQGFTGRFVFSLDTSVSTAYLQISSLKAEDTAVYYCARKGVT AARYFDYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICN VNHKPSNTKVDKKVEPKSCDKTHTCPPCPAPEAAGGPSVFLFPPKPKDTLM ISRTPEVTCVVVDVSHEDPEVKFNWYVDGVEVHNAKTKPREEQYNSTYRVV SVLTVLHQDWLNGKEYKCKVSNKALPASIEKTISKAKGQPREPQVYTLPPS RDELTKNQVSLTCLVKGFYPSDIAVEWESNGQPENNYKTTPPVLDSDGSFF LYSKLTVDKSRWQQGNVFSCSVMHEALHNHYTQKSLSLSPG | 416 |
| MTK-16.1 with huIgG1 NSLF Fc with C-terminal lysine | QVQLVQSGSELKKPGASVKVSCKASGYTFTNHGMNWVRQAPGQGLEWMGWI NTYTGEPTYAQGFTGRFVFSLDTSVSTAYLQISSLKAEDTAVYYCARKGVT AARYFDYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTLM ISRTPEVTCVVVDVSHEDPEVKFNWYVDGVEVHNAKTKPREEQYNSTYRVV SVLTVLHQDWLNGKEYKCKVSSKAFPAPIEKTISKAKGQPREPQVYTLPPS RDELTKNQVSLTCLVKGFYPSDIAVEWESNGQPENNYKTTPPVLDSDGSFF LYSKLTVDKSRWQQGNVFSCSVMHEALHNHYTQKSLSLSPGK | 417 |
| MTK-16.1 with huIgG1 NSLF Fc without C-terminal lysine | QVQLVQSGSELKKPGASVKVSCKASGYTFTNHGMNWVRQAPGQGLEWMGWI NTYTGEPTYAQGFTGRFVFSLDTSVSTAYLQISSLKAEDTAVYYCARKGVT AARYFDYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTLM ISRTPEVTCVVVDVSHEDPEVKFNWYVDGVEVHNAKTKPREEQYNSTYRVV SVLTVLHQDWLNGKEYKCKVSSKAFPAPIEKTISKAKGQPREPQVYTLPPS RDELTKNQVSLTCLVKGFYPSDIAVEWESNGQPENNYKTTPPVLDSDGSFF LYSKLTVDKSRWQQGNVFSCSVMHEALHNHYTQKSLSLSPG | 418 |
| MTK-16.1 with huIgG4 Fc with C-terminal lysine | QVQLVQSGSELKKPGASVKVSCKASGYTFTNHGMNWVRQAPGQGLEWMGWI NTYTGEPTYAQGFTGRFVFSLDTSVSTAYLQISSLKAEDTAVYYCARKGVT AARYFDYWGQGTLVTVSSASTKGPSVFPLAPCSRSTSESTAALGCLVKDYF PEPVTVSWNSGALTSGVHTFPAVLQSSGLYSLSSVVTVPSSSLGTKTYTCN VDHKPSNTKVDKRVESKYGPPCPSCPAPEFLGGPSVFLFPPKPKDTLMISR TPEVTCVVVDVSQEDPEVQFNWYVDGVEVHNAKTKPREEQFNSTYRVVSVL TVLHQDWLNGKEYKCKVSNKGLPSSIEKTISKAKGQPREPQVYTLPPSQEE MTKNQVSLTCLVKGFYPSDIAVEWESNGQPENNYKTTPPVLDSDGSFFLYS RLTVDKSRWQEGNVFSCSVMHEALHNHYTQKSLSLSLGK | 419 |

TABLE 38-continued

| Antibody | Sequence | SEQ ID NO: |
|---|---|---|
| MTK-16.1 with huIgG4 Fc without C-terminal lysine | NTYTGEPTYAQGFTGRFVFSLDTSVSTAYLQISSLKAEDTAVYYCARKGVT AARYFDYWGQGTLVTVSSASTKGPSVFPLAPCSRSTSESTAALGCLVKDYF PEPVTVSWNSGALTSGVHTFPAVLQSSGLYSLSSVVTVPSSSLGTKTYTCN VDHKPSNTKVDKRVESKYGPPCPSCPAPEFLGGPSVFLFPPKPKDTLMISR TPEVTCVVVDVSQEDPEVQFNWYVDGVEVHNAKTKPREEQFNSTYRVVSVL TVLHQDWLNGKEYKCKVSNKGLPSSIEKTISKAKGQPREPQVYTLPPSQEE MTKNQVSLTCLVKGFYPSDIAVEWESNGQPENNYKTTPPVLDSDGSFFLYS RLTVDKSRWQEGNVFSCSVMHEALHNHYTQKSLSLSLG | 420 |

MTK-16.1 light chain amino acid sequence is set forth below: DIQMTQSPSSLSASVGDRVTITCKASQNVRTAVAWYQQKPGKAPKRLIYLASNRHTGVPSRFSGSGSGTEFTLTISNLQPEDFATYYCLQHWNYPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 421)

Full-length heavy chain amino acid sequences of certain anti-MerTK antibodies of the present disclosure are shown below in Table 39.

TABLE 39

| Antibody | Sequence | SEQ ID NO: |
|---|---|---|
| MTK-16.2 with huIgG1 WT Fc with C-terminal lysine | QVQLVQSGSELKKPGASVKVSCKASGYTFTNHGMNWVRQAPGQGLEWMGWI NTYTGEPTYADDFKGRFVFSLDTSVSTAYLQISSLKAEDTAVYYCARKGVT AARYFDYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTLM ISRTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPS RDELTKNQVSLTCLVKGFYPSDIAVEWESNGQPENNYKTTPPVLDSDGSFF LYSKLTVDKSRWQQGNVFSCSVMHEALHNHYTQKSLSLSPGK | 422 |
| MTK-16.2 with huIgG1 WT Fc without C-terminal lysine | QVQLVQSGSELKKPGASVKVSCKASGYTFTNHGMNWVRQAPGQGLEWMGWI NTYTGEPTYADDFKGRFVFSLDTSVSTAYLQISSLKAEDTAVYYCARKGVT AARYFDYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTLM ISRTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPS RDELTKNQVSLTCLVKGFYPSDIAVEWESNGQPENNYKTTPPVLDSDGSFF LYSKLTVDKSRWQQGNVFSCSVMHEALHNHYTQKSLSLSPG | 423 |
| MTK-16.2 with huIgG1 LALAPS Fc with C-terminal lysine | QVQLVQSGSELKKPGASVKVSCKASGYTFTNHGMNWVRQAPGQGLEWMGWI NTYTGEPTYADDFKGRFVFSLDTSVSTAYLQISSLKAEDTAVYYCARKGVT AARYFDYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICN VNHKPSNTKVDKKVEPKSCDKTHTCPPCPAPEAAGGPSVFLFPPKPKDTLM ISRTPEVTCVVVDVSHEDPEVKFNWYVDGVEVHNAKTKPREEQYNSTYRVV SVLTVLHQDWLNGKEYKCKVSNKALPASIEKTISKAKGQPREPQVYTLPPS RDELTKNQVSLTCLVKGFYPSDIAVEWESNGQPENNYKTTPPVLDSDGSFF LYSKLTVDKSRWQQGNVFSCSVMHEALHNHYTQKSLSLSPGK | 424 |
| MTK-16.2 with huIgG1 LALAPS Fc without C-terminal lysine | QVQLVQSGSELKKPGASVKVSCKASGYTFTNHGMNWVRQAPGQGLEWMGWI NTYTGEPTYADDFKGRFVFSLDTSVSTAYLQISSLKAEDTAVYYCARKGVT AARYFDYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICN VNHKPSNTKVDKKVEPKSCDKTHTCPPCPAPEAAGGPSVFLFPPKPKDTLM ISRTPEVTCVVVDVSHEDPEVKFNWYVDGVEVHNAKTKPREEQYNSTYRVV SVLTVLHQDWLNGKEYKCKVSNKALPASIEKTISKAKGQPREPQVYTLPPS RDELTKNQVSLTCLVKGFYPSDIAVEWESNGQPENNYKTTPPVLDSDGSFF LYSKLTVDKSRWQQGNVFSCSVMHEALHNHYTQKSLSLSPG | 425 |
| MTK-16.2 with huIgG1 NSLF Fc with C-terminal lysine | QVQLVQSGSELKKPGASVKVSCKASGYTFTNHGMNWVRQAPGQGLEWMGWI NTYTGEPTYADDFKGRFVFSLDTSVSTAYLQISSLKAEDTAVYYCARKGVT AARYFDYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTLM ISRTPEVTCVVVDVSHEDPEVKFNWYVDGVEVHNAKTKPREEQYNSTYRVV SVLTVLHQDWLNGKEYKCKVSSKAFPAPIEKTISKAKGQPREPQVYTLPPS RDELTKNQVSLTCLVKGFYPSDIAVEWESNGQPENNYKTTPPVLDSDGSFF LYSKLTVDKSRWQQGNVFSCSVMHEALHNHYTQKSLSLSPGK | 426 |

TABLE 39-continued

| Antibody | Sequence | SEQ ID NO: |
|---|---|---|
| MTK-16.2 with huIgG1 NSLF Fc without C-terminal lysine | QVQLVQSGSELKKPGASVKVSCKASGYTFTNHGMNWVRQAPGQGLEWMGWI NTYTGEPTYADDFKGRFVFSLDTSVSTAYLQISSLKAEDTAVYYCARKGVT AARYFDYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTLM ISRTPEVTCVVVDVSHEDPEVKFNWYVDGVEVHNAKTKPREEQYNSTYRVV SVLTVLHQDWLNGKEYKCKVSSKAFPAPIEKTISKAKGQPREPQVYTLPPS RDELTKNQVSLTCLVKGFYPSDIAVEWESNGQPENNYKTTPPVLDSDGSFF LYSKLTVDKSRWQQGNVFSCSVMHEALHNHYTQKSLSLSPG | 427 |
| MTK-16.2 with huIgG4 Fc with C-terminal lysine | QVQLVQSGSELKKPGASVKVSCKASGYTFTNHGMNWVRQAPGQGLEWMGWI NTYTGEPTYADDFKGRFVFSLDTSVSTAYLQISSLKAEDTAVYYCARKGVT AARYFDYWGQGTLVTVSSASTKGPSVFPLAPCSRSTSESTAALGCLVKDYF PEPVTVSWNSGALTSGVHTFPAVLQSSGLYSLSSVVTVPSSSLGTKTYTCN VDHKPSNTKVDKRVESKYGPPCPSCPAPEFLGGPSVFLFPPKPKDTLMISR TPEVTCVVVDVSQEDPEVQFNWYVDGVEVHNAKTKPREEQFNSTYRVVSVL TVLHQDWLNGKEYKCKVSNKGLPSSIEKTISKAKGQPREPQVYTLPPSQEE MTKNQVSLTCLVKGFYPSDIAVEWESNGQPENNYKTTPPVLDSDGSFFLYS RLTVDKSRWQEGNVFSCSVMHEALHNHYTQKSLSLSLGK | 428 |
| MTK-16.2 with huIgG4 Fc without C-terminal lysine | QVQLVQSGSELKKPGASVKVSCKASGYTFTNHGMNWVRQAPGQGLEWMGWI NTYTGEPTYADDFKGRFVFSLDTSVSTAYLQISSLKAEDTAVYYCARKGVT AARYFDYWGQGTLVTVSS ASTKGPSVFPLAPCSRSTSESTAALGCLVKDYFPEPVTVSWNSGALTSGVH TFPAVLQSSGLYSLSSVVTVPSSSLGTKTYTCNVDHKPSNTKVDKRVESKY GPPCPSCPAPEFLGGPSVFLFPPKPKDTLMISRTPEVTCVVVDVSQEDPEV QFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPS DIAVEWESNGQPENNYKTTPPVLDSDGSFFLYSRLTVDKSRWQEGNVFSCS VMHEALHNHYTQKSLSLSLGK | 429 |

MTK-16.2 light chain amino acid sequence is set forth below:

(SEQ ID NO: 430)
DIQMTQSPSSLSASVGDRVTITCRASQNVRTAVAWYQQKPGKAPKRLIYL
ASNRHTGVPSRFSGSGSGTEFTLTISNLQPEDFATYYCLQHWNYPLTFGG
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC

Full-length heavy chain amino acid sequences of certain anti-MerTK antibodies of the present disclosure are shown below in Table 40.

TABLE 40

| Antibody | Sequence | SEQ ID NO: |
|---|---|---|
| MTK-33.1 with huIgG1 WT Fc with C-terminal lysine | QVQLVQSGAEVKKPGASVKVSCKASGYTFTSYWMHWVRQAPGQGLEWIGVI DPSDNYINYNQKFQGRVTMTRDTSTSTVYMELSSLRSEDTAVYYCAREAWT RGYFNYWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPGK | 431 |
| MTK-33.1 with huIgG1 WT Fc without C-terminal lysine | QVQLVQSGAEVKKPGASVKVSCKASGYTFTSYWMHWVRQAPGQGLEWIGVI DPSDNYINYNQKFQGRVTMTRDTSTSTVYMELSSLRSEDTAVYYCAREAWT RGYFNYWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPG | 432 |

TABLE 40-continued

| Antibody | Sequence | SEQ ID NO: |
|---|---|---|
| MTK-33.1 with huIgG1 LALAPS Fc with C-terminal lysine | QVQLVQSGAEVKKPGASVKVSCKASGYTFTSYWMHWVRQAPGQGLEWIGVI DPSDNYINYNQKFQGRVTMTRDTSTSTVYMELSSLRSEDTAVYYCAREAWT RGYFNYWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICNV NHKPSNTKVDKKVEPKSCDKTHTCPPCPAPEAAGGPSVFLFPPKPKDTLMI SRTPEVTCVVVDVSHEDPEVKFNWYVDGVEVHNAKTKPREEQYNSTYRVVS VLTVLHQDWLNGKEYKCKVSNKALPASIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPGK | 433 |
| MTK-33.1 with huIgG1 LALAPS Fc without C-terminal lysine | QVQLVQSGAEVKKPGASVKVSCKASGYTFTSYWMHWVRQAPGQGLEWIGVI DPSDNYINYNQKFQGRVTMTRDTSTSTVYMELSSLRSEDTAVYYCAREAWT RGYFNYWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICNV NHKPSNTKVDKKVEPKSCDKTHTCPPCPAPEAAGGPSVFLFPPKPKDTLMI SRTPEVTCVVVDVSHEDPEVKFNWYVDGVEVHNAKTKPREEQYNSTYRVVS VLTVLHQDWLNGKEYKCKVSNKALPASIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPG | 434 |
| MTK-33.1 with huIgG1 NSLF Fc with C-terminal lysine | QVQLVQSGAEVKKPGASVKVSCKASGYTFTSYWMHWVRQAPGQGLEWIGVI DPSDNYINYNQKFQGRVTMTRDTSTSTVYMELSSLRSEDTAVYYCAREAWT RGYFNYWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRVVS VLTVLHQDWLNGKEYKCKVSSKAFPAPIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPGK | 435 |
| MTK-33.1 with huIgG1 NSLF Fc without C-terminal lysine | QVQLVQSGAEVKKPGASVKVSCKASGYTFTSYWMHWVRQAPGQGLEWIGVI DPSDNYINYNQKFQGRVTMTRDTSTSTVYMELSSLRSEDTAVYYCAREAWT RGYFNYWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRVVS VLTVLHQDWLNGKEYKCKVSSKAFPAPIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPG | 436 |
| MTK-33.1 with huIgG4 Fc with C-terminal lysine | QVQLVQSGAEVKKPGASVKVSCKASGYTFTSYWMHWVRQAPGQGLEWIGVI DPSDNYINYNQKFQGRVTMTRDTSTSTVYMELSSLRSEDTAVYYCAREAWT RGYFNYWGQGTLVTVSSASTKGPSVFPLAPCSRSTSESTAALGCLVKDYFP EPVTVSWNSGALTSGVHTFPAVLQSSGLYSLSSVVTVPSSSLGTKTYTCNV DHKPSNTKVDKRVESKYGPPCPSCPAPEFLGGPSVFLFPPKPKDTLMISRT PEVTCVVVDVSQEDPEVQFNWYVDGVEVHNAKTKPREEQFNSTYRVVSVLT VLHQDWLNGKEYKCKVSNKGLPSSIEKTISKAKGQPREPQVYTLPPSQEEM TKNQVSLTCLVKGFYPSDIAVEWESNGQPENNYKTTPPVLDSDGSFFLYSR LTVDKSRWQEGNVFSCSVMHEALHNHYTQKSLSLSLGK | 437 |
| MTK-33.1 with huIgG4 Fc without C-terminal lysine | QVQLVQSGAEVKKPGASVKVSCKASGYTFTSYWMHWVRQAPGQGLEWIGVI DPSDNYINYNQKFQGRVTMTRDTSTSTVYMELSSLRSEDTAVYYCAREAWT RGYFNYWGQGTLVTVSSASTKGPSVFPLAPCSRSTSESTAALGCLVKDYFP EPVTVSWNSGALTSGVHTFPAVLQSSGLYSLSSVVTVPSSSLGTKTYTCNV DHKPSNTKVDKRVESKYGPPCPSCPAPEFLGGPSVFLFPPKPKDTLMISRT PEVTCVVVDVSQEDPEVQFNWYVDGVEVHNAKTKPREEQFNSTYRVVSVLT VLHQDWLNGKEYKCKVSNKGLPSSIEKTISKAKGQPREPQVYTLPPSQEEM TKNQVSLTCLVKGFYPSDIAVEWESNGQPENNYKTTPPVLDSDGSFFLYSR LTVDKSRWQEGNVFSCSVMHEALHNHYTQKSLSLSLG | 438 |

MTK-33.1 light chain amino acid sequence is set forth below:

(SEQ ID NO: 439)
DIQMTQSPSSLSASVGDRVTITCQASQSVSNTVAWYQQKPGKAPKLLIYY

ASLRYTGVPSRFSGSGSGTDFTFTISSLQPEDIATYYCQQDYRSPFTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Full-length heavy chain amino acid sequences of certain anti-MerTK antibodies of the present disclosure are shown below in Table 41.

TABLE 41

| Antibody | Sequence | SEQ ID NO: |
|---|---|---|
| MTK-33.12 with huIgG1 WT Fc with C-terminal lysine | QVQLVQSGAEVKKPGASVKVSCKASGYTFVSYWMHWVRQAPGQGLEWIGVI DPSDNYINYNQKFRGRVTMTRDTSTSTVYMELSSLRSEDTAVYYCAREAGT RGYFDYWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPGK | 440 |
| MTK-33.12 with huIgG1 WT Fc without C-terminal lysine | QVQLVQSGAEVKKPGASVKVSCKASGYTFVSYWMHWVRQAPGQGLEWIGVI DPSDNYINYNQKFRGRVTMTRDTSTSTVYMELSSLRSEDTAVYYCAREAGT RGYFDYWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPG | 441 |
| MTK-33.12 with huIgG1 LALAPS Fc with C-terminal lysine | QVQLVQSGAEVKKPGASVKVSCKASGYTFVSYWMHWVRQAPGQGLEWIGVI DPSDNYINYNQKFRGRVTMTRDTSTSTVYMELSSLRSEDTAVYYCAREAGT RGYFDYWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICNV NHKPSNTKVDKKVEPKSCDKTHTCPPCPAPEAAGGPSVFLFPPKPKDTLMI SRTPEVTCVVVDVSHEDPEVKFNWYVDGVEVHNAKTKPREEQYNSTYRVVS VLTVLHQDWLNGKEYKCKVSNKALPASIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPGK | 442 |
| MTK-33.12 with huIgG1 LALAPS Fc without C-terminal lysine | QVQLVQSGAEVKKPGASVKVSCKASGYTFVSYWMHWVRQAPGQGLEWIGVI DPSDNYINYNQKFRGRVTMTRDTSTSTVYMELSSLRSEDTAVYYCAREAGT RGYFDYWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICNV NHKPSNTKVDKKVEPKSCDKTHTCPPCPAPEAAGGPSVFLFPPKPKDTLMI SRTPEVTCVVVDVSHEDPEVKFNWYVDGVEVHNAKTKPREEQYNSTYRVVS VLTVLHQDWLNGKEYKCKVSNKALPASIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPG | 443 |
| MTK-33.12 with huIgG1 NSLF Fc with C-terminal lysine | QVQLVQSGAEVKKPGASVKVSCKASGYTFVSYWMHWVRQAPGQGLEWIGVI DPSDNYINYNQKFRGRVTMTRDTSTSTVYMELSSLRSEDTAVYYCAREAGT RGYFDYWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRVVS VLTVLHQDWLNGKEYKCKVSSKAFPAPIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPGK | 444 |
| MTK-33.12 with huIgG1 NSLF Fc without C-terminal lysine | DPSDNYINYNQKFRGRVTMTRDTSTSTVYMELSSLRSEDTAVYYCAREAGT RGYFDYWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRVVS VLTVLHQDWLNGKEYKCKVSSKAFPAPIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPG | 445 |
| MTK-33.12 with huIgG4 Fc with C-terminal lysine | QVQLVQSGAEVKKPGASVKVSCKASGYTFVSYWMHWVRQAPGQGLEWIGVI DPSDNYINYNQKFRGRVTMTRDTSTSTVYMELSSLRSEDTAVYYCAREAGT RGYFDYWGQGTLVTVSSASTKGPSVFPLAPCSRSTSESTAALGCLVKDYFP EPVTVSWNSGALTSGVHTFPAVLQSSGLYSLSSVVTVPSSSLGTKTYTCNV DHKPSNTKVDKRVESKYGPPCPSCPAPEFLGGPSVFLFPPKPKDTLMISRVE PEVTCVVVDVSQEDPEVQFNWYVDGVEVHNAKTKPREEQFNSTYRVVSVLT VLHQDWLNGKEYKCKVSNKGLPSSIEKTISKAKGQPREPQVYTLPPSQEEM TKNQVSLTCLVKGFYPSDIAVEWESNGQPENNYKTTPPVLDSDGSFFLYSR LTVDKSRWQEGNVFSCSVMHEALHNHYTQKSLSLSLGK | 446 |
| MTK-33.12 with huIgG4 Fc without C-terminal lysine | QVQLVQSGAEVKKPGASVKVSCKASGYTFVSYWMHWVRQAPGQGLEWIGVI DPSDNYINYNQKFRGRVTMTRDTSTSTVYMELSSLRSEDTAVYYCAREAGT RGYFDYWGQGTLVTVSSASTKGPSVFPLAPCSRSTSESTAALGCLVKDYFP EPVTVSWNSGALTSGVHTFPAVLQSSGLYSLSSVVTVPSSSLGTKTYTCNV DHKPSNTKVDKRVESKYGPPCPSCPAPEFLGGPSVFLFPPKPKDTLMISRT PEVTCVVVDVSQEDPEVQFNWYVDGVEVHNAKTKPREEQFNSTYRVVSVLT | 447 |

TABLE 41-continued

| Antibody | Sequence | SEQ ID NO: |
|---|---|---|
| | VLHQDWLNGKEYKCKVSNKGLPSSIEKTISKAKGQPREPQVYTLPPSQEEM TKNQVSLTCLVKGFYPSDIAVEWESNGQPENNYKTTPPVLDSDGSFFLYSR LTVDKSRWQEGNVFSCSVMHEALHNHYTQKSLSLSLG | |

MTK-33.12 light chain amino acid sequence is set forth below:

(SEQ ID NO: 448)
DIQMTQSPSSLSASVGDRVTITCQASQSVSNTVAWYQQKPGKAPKLLIYY
ASNRYTGVPSRFSGSGSGTDFTFTISSLQPEDIATYYCRQDTRSPFTFGQ

-continued
GTKLELKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC Full-length heavy chain amino acid sequences of certain anti-MerTK antibodies of the present disclosure are shown below in Table 42.

TABLE 42

| Antibody | Sequence | SEQ ID NO: |
|---|---|---|
| MTK-33.10 with huIgG1 WT Fc with C-terminal lysine | QVQLVQSGAEVKKPGASVKVSCKASSYSFTSYWMHWVRQAPGQGLEWIGVI DPSDNYINYNQKFRGRVTMTRDTSTSTVYMELSSLRSEDTAVYYCAREAGT RGYFDYWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPGK | 464 |
| MTK-33.10 with huIgG1 WT Fc without C-terminal lysine | QVQLVQSGAEVKKPGASVKVSCKASSYSFTSYWMHWVRQAPGQGLEWIGVI DPSDNYINYNQKFRGRVTMTRDTSTSTVYMELSSLRSEDTAVYYCAREAGT RGYFDYWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPG | 465 |
| MTK-33.10 with huIgG1 LALAPS Fc with C-terminal lysine | DPSDNYINYNQKFRGRVTMTRDTSTSTVYMELSSLRSEDTAVYYCAREAGT RGYFDYWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICNV NHKPSNTKVDKKVEPKSCDKTHTCPPCPAPEAAGGPSVFLFPPKPKDTLMI SRTPEVTCVVVDVSHEDPEVKFNWYVDGVEVHNAKTKPREEQYNSTYRVVS VLTVLHQDWLNGKEYKCKVSNKALPASIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPGK | 466 |
| MTK-33.10 with huIgG1 LALAPS Fc without C-terminal lysine | QVQLVQSGAEVKKPGASVKVSCKASSYSFTSYWMHWVRQAPGQGLEWIGVI DPSDNYINYNQKFRGRVTMTRDTSTSTVYMELSSLRSEDTAVYYCAREAGT RGYFDYWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICNV NHKPSNTKVDKKVEPKSCDKTHTCPPCPAPEAAGGPSVFLFPPKPKDTLMI SRTPEVTCVVVDVSHEDPEVKFNWYVDGVEVHNAKTKPREEQYNSTYRVVS VLTVLHQDWLNGKEYKCKVSNKALPASIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPG | 467 |
| MTK-33.10 with huIgG1 NSLF Fc with C-terminal lysine | QVQLVQSGAEVKKPGASVKVSCKASSYSFTSYWMHWVRQAPGQGLEWIGVI DPSDNYINYNQKFRGRVTMTRDTSTSTVYMELSSLRSEDTAVYYCAREAGT RGYFDYWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRVVS VLTVLHQDWLNGKEYKCKVSSKAFPAPIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPGK | 468 |
| MTK-33.10 with huIgG1 NSLF Fc without C- | QVQLVQSGAEVKKPGASVKVSCKASSYSFTSYWMHWVRQAPGQGLEWIGVI DPSDNYINYNQKFRGRVTMTRDTSTSTVYMELSSLRSEDTAVYYCAREAGT RGYFDYWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMI | 469 |

TABLE 42-continued

| Antibody | Sequence | SEQ ID NO: |
|---|---|---|
| terminal lysine | SRTPEVTCVVVDVSHEDPEVKFNWYVDGVEVHNAKTKPREEQYNSTYRVVS VLTVLHQDWLNGKEYKCKVSSKAFPAPIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPG | |
| MTK-33.10 with huIgG4 Fc with C-terminal lysine | QVQLVQSGAEVKKPGASVKVSCKASSYSFTSYWMHWVRQAPGQGLEWIGVI DPSDNYINYNQKFRGRVTMTRDTSTSTVYMELSSLRSEDTAVYYCAREAGT RGYFDYWGQGTLVTVSSASTKGPSVFPLAPCSRSTSESTAALGCLVKDYFP EPVTVSWNSGALTSGVHTFPAVLQSSGLYSLSSVVTVPSSSLGTKTYTCNV DHKPSNTKVDKRVESKYGPPCPSCPAPEFLGGPSVFLFPPKPKDTLMISRT PEVTCVVVDVSQEDPEVQFNWYVDGVEVHNAKTKPREEQFNSTYRVVSVLT VLHQDWLNGKEYKCKVSNKGLPSSIEKTISKAKGQPREPQVYTLPPSQEEM TKNQVSLTCLVKGFYPSDIAVEWESNGQPENNYKTTPPVLDSDGSFFLYSR LTVDKSRWQEGNVFSCSVMHEALHNHYTQKSLSLSLGK | 470 |
| MTK-33.10 with huIgG4 Fc without C-terminal lysine | QVQLVQSGAEVKKPGASVKVSCKASSYSFTSYWMHWVRQAPGQGLEWIGVI DPSDNYINYNQKFRGRVTMTRDTSTSTVYMELSSLRSEDTAVYYCAREAGT RGYFDYWGQGTLVTVSSASTKGPSVFPLAPCSRSTSESTAALGCLVKDYFP EPVTVSWNSGALTSGVHTFPAVLQSSGLYSLSSVVTVPSSSLGTKTYTCNV DHKPSNTKVDKRVESKYGPPCPSCPAPEFLGGPSVFLFPPKPKDTLMISRT PEVTCVVVDVSQEDPEVQFNWYVDGVEVHNAKTKPREEQFNSTYRVVSVLT VLHQDWLNGKEYKCKVSNKGLPSSIEKTISKAKGQPREPQVYTLPPSQEEM TKNQVSLTCLVKGFYPSDIAVEWESNGQPENNYKTTPPVLDSDGSFFLYSR LTVDKSRWQEGNVFSCSVMHEALHNHYTQKSLSLSLG | 471 |

MTK-33.10 light chain amino acid sequence is set forth below:

(SEQ ID NO: 472)
DIQMTQSPSSLSASVGDRVTITCQAGQSVSNTVAWYQQKPGKAPKLLIY

YASNRYTGVPSRFSGSGSGTDFTFTISSLQPEDIATYYCQQDYRSPFTF

GQGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

---

What is claimed is:

1. An isolated antibody that binds to human MerTK, wherein the antibody comprises an HVR-H1, HVR-H2, HVR-H3, HVR-L1, HVR-L2, and HVR-L3 comprising the amino acid sequences of:
   (i) SEQ ID NOs: 75, 99, 125, 158, 187, and 207, respectively;
   (ii) SEQ ID NOs: 76, 100, 126, 159, 187, and 208, respectively;
   (iii) SEQ ID NOs: 77, 101, 127, 160, 188, and 209, respectively;
   (iv) SEQ ID NOs: 75, 99, 128, 158, 187, and 210, respectively;
   (v) SEQ ID NOs: 78, 102, 129, 161, 189, and 211, respectively;
   (vi) SEQ ID NOs: 75, 103, 130, 158, 187, and 212, respectively;
   (vii) SEQ ID NOs: 77, 101, 127, 162, 188, and 209, respectively;
   (viii) SEQ ID NOs: 75, 99, 131, 163, 187, and 213, respectively;
   (ix) SEQ ID NOs: 79, 104, 132, 164, 190, and 214, respectively;
   (x) SEQ ID NOs: 80, 105, 133, 165, 191, and 215, respectively;
   (xi) SEQ ID NOs: 81, 106, 134, 166, 192, and 216, respectively;
   (xii) SEQ ID NOs: 82, 107, 135, 167, 193, and 217, respectively;
   (xiii) SEQ ID NOs: 77, 108, 136, 167, 194, and 209, respectively;
   (xiv) SEQ ID NOs: 75, 109, 137, 168, 187, and 218, respectively;
   (xv) SEQ ID NOs: 83, 99, 138, 158, 187, and 210, respectively;
   (xvi) SEQ ID NOs: 84, 99, 139, 169, 195, and 219, respectively;
   (xvii) SEQ ID NOs: 85, 99, 140, 170, 196, and 220, respectively;
   (xviii) SEQ ID NOs: 86, 99, 141, 171, 191, and 221, respectively;
   (xix) SEQ ID NOs: 87, 110, 142, 172, 197, and 222, respectively;
   (xx) SEQ ID NOs: 88, 99, 143, 173, 191, and 223, respectively;
   (xxi) SEQ ID NOs: 89, 111, 143, 173, 198, and 221, respectively;
   (xxii) SEQ ID NOs: 90, 112, 144, 174, 199, and 224, respectively;
   (xxiii) SEQ ID NOs: 91, 113, 145, 175, 200, and 225, respectively;
   (xxiv) SEQ ID NOs: 90, 114, 146, 176, 201, and 226, respectively;
   (xxv) SEQ ID NOs: 92, 115, 147, 177, 195, and 227, respectively;
   (xxvi) SEQ ID NOs: 93, 116, 148, 178, 188, and 209, respectively;
   (xxvii) SEQ ID NOs: 94, 117, 149, 179, 195, and 228, respectively;
   (xxviii) SEQ ID NOs: 95, 118, 150, 180, 187, and 229, respectively;
   (xxix) SEQ ID NOs: 95, 119, 151, 181, 187, and 208, respectively;
   (xxx) SEQ ID NOs: 90, 120, 152, 182, 202, and 230, respectively;
   (xxxi) SEQ ID NOs: 96, 118, 153, 183, 202, and 230, respectively;
   (xxxii) SEQ ID NOs: 96, 121, 154, 181, 187, and 210, respectively;
   (xxxiii) SEQ ID NOs: 90, 122, 155, 184, 203, and 231, respectively;
   (xxxiv) SEQ ID NOs: 90, 122, 155, 184, 203, and 231, respectively;
   (xxxv) SEQ ID NOs: 97, 123, 156, 185, 204, and 232, respectively;
   (xxxvi) SEQ ID NOs: 98, 124, 157, 186, 205, and 233, respectively;
   (xxxvii) SEQ ID NOs: 83, 329, 334, 158, 187, and 210, respectively;
   (xxxviii) SEQ ID NOs: 83, 330, 138, 158, 187, and 210, respectively;

(xxxix) SEQ ID NOs: 83, 329, 138, 340, 187, and 210, respectively;
(xl) SEQ ID NOs: 83, 329, 138, 341, 187, and 210, respectively;
(xli) SEQ ID NOs: 83, 329, 335, 341, 187, and 210, respectively;
(xlii) SEQ ID NOs: 83, 331, 138, 341, 187, and 210, respectively;
(xliii) SEQ ID NOs: 83, 329, 138, 342, 187, and 210, respectively;
(xliv) SEQ ID NOs: 83, 329, 336, 341, 187, and 210, respectively;
(xlv) SEQ ID NOs: 83, 329, 337, 343, 187, and 210, respectively;
(xlvi) SEQ ID NOs: 83, 332, 338, 341, 187, and 210, respectively;
(xlvii) SEQ ID NOs: 83, 333, 334, 158, 187, and 210, respectively;
(xlviii) SEQ ID NOs: 83, 332, 336, 341, 187, and 210, respectively;
(xlix) SEQ ID NOs: 83, 329, 339, 344, 187, and 210, respectively;
(l) SEQ ID NOs: 83, 329, 138, 158, 187, and 210, respectively;
(li) SEQ ID NOs: 84, 329, 139, 169, 195, and 219, respectively;
(lii) SEQ ID NOs: 84, 99, 139, 345, 195, and 219, respectively;
(liii) SEQ ID NOs: 346, 348, 355, 341, 187, and 360, respectively;
(liv) SEQ ID NOs: 95, 119, 355, 341, 187, and 361, respectively;
(lv) SEQ ID NOs: 95, 349, 356, 341, 187, and 362, respectively;
(lvi) SEQ ID NOs: 95, 119, 356, 341, 359, and 362, respectively;
(lvii) SEQ ID NOs: 346, 119, 356, 341, 359, and 362, respectively;
(lviii) SEQ ID NOs: 95, 350, 356, 341, 359, and 362, respectively;
(lix) SEQ ID NOs: 95, 351, 356, 341, 359, and 362, respectively;
(lx) SEQ ID NOs: 347, 119, 356, 341, 359, and 362, respectively;
(lxi) SEQ ID NOs: 346, 119, 356, 341, 359, and 362, respectively;
(lxii) SEQ ID NOs: 95, 119, 356, 341, 187, and 362, respectively;
(lxiii) SEQ ID NOs: 95, 352, 356, 341, 187, and 362, respectively;
(lxiv) SEQ ID NOs: 95, 350, 356, 341, 359, and 362, respectively;
(lxv) SEQ ID NOs: 95, 353, 356, 341, 359, and 362, respectively;
(lxvi) SEQ ID NOs: 95, 351, 356, 341, 359, and 362, respectively;
(lxvii) SEQ ID NOs: 95, 350, 356, 341, 359, and 362, respectively;
(lxviii) SEQ ID NOs: 346, 354, 356, 341, 359, and 363, respectively;
(lxix) SEQ ID NOs: 346, 348, 356, 357, 359, and 362, respectively;
(lxx) SEQ ID NOs: 346, 354, 356, 358, 187, and 362, respectively;
(lxxi) SEQ ID NOs: 95, 348, 151, 181, 187, and 208, respectively;
(lxxii) SEQ ID NOs: 90, 364, 373, 376, 388, and 231, respectively;
(lxxiii) SEQ ID NOs: 90, 364, 155, 377, 203, and 231, respectively;
(lxxiv) SEQ ID NOs: 90, 364, 374, 378, 203, and 231, respectively;
(lxxv) SEQ ID NOs: 90, 365, 155, 376, 203, and 392, respectively;
(lxxvi) SEQ ID NOs: 90, 364, 155, 376, 389, and 231, respectively;
(lxxvii) SEQ ID NOs: 90, 364, 155, 379, 203, and 231, respectively;
(lxxviii) SEQ ID NOs: 90, 366, 155, 380, 203, and 231, respectively;
(lxxix) SEQ ID NOs: 90, 364, 373, 381, 203, and 231, respectively;
(lxxx) SEQ ID NOs: 90, 367, 155, 382, 203, and 231, respectively;
(lxxxi) SEQ ID NOs: 90, 368, 155, 383, 203, and 231, respectively;
(lxxxii) SEQ ID NOs: 90, 364, 374, 384, 203, and 231, respectively;
(lxxxiii) SEQ ID NOs: 90, 368, 155, 376, 203, and 293, respectively;
(lxxxiv) SEQ ID NOs: 90, 364, 155, 378, 203, and 231, respectively;
(lxxxv) SEQ ID NOs: 90, 368, 155, 376, 203, and 231, respectively;
(lxxxvi) SEQ ID NOs: 90, 369, 155, 378, 203, and 394, respectively;
(lxxxvii) SEQ ID NOs: 90, 364, 155, 378, 203, and 231, respectively;
(lxxxviii) SEQ ID NOs: 90, 370, 155, 378, 203, and 394, respectively;
(lxxxix) SEQ ID NOs: 90, 371, 155, 378, 203, and 394, respectively;
(xc) SEQ ID NOs: 90, 368, 155, 385, 203, and 394, respectively;
(xci) SEQ ID NOs: 90, 368, 155, 378, 203, and 395, respectively;
(xcii) SEQ ID NOs: 90, 368, 155, 378, 390, and 394, respectively;
(xciii) SEQ ID NOs: 90, 372, 155, 378, 391, and 394, respectively;
(xciv) SEQ ID NOs: 90, 368, 375, 386, 203, and 394, respectively; or
(xcv) SEQ ID NOs: 90, 368, 155, 387, 203, and 394, respectively.

2. The antibody of claim 1, wherein the antibody comprises a heavy chain variable region and a light chain variable region comprising the amino acid sequences of SEQ ID NOs:5 and 40, respectively; SEQ ID NOs:6 and 41, respectively; SEQ ID NOs:7 and 42, respectively; SEQ ID NOs:8 and 43, respectively; SEQ ID NOs:9 and 44, respectively; SEQ ID NOs:10 and 45, respectively; SEQ ID NOs:11 and 46, respectively; SEQ ID NOs:12 and 47, respectively; SEQ ID NOs:13 and 48, respectively; SEQ ID NOs:14 and 49, respectively; SEQ ID NOs:15 and 50, respectively; SEQ ID NOs:16 and 51, respectively; SEQ ID NOs:17 and 52, respectively; SEQ ID NOs:18 and 53, respectively; SEQ ID NOs:19 and 54, respectively; SEQ ID NOs:20 and 55, respectively; SEQ ID NOs:21 and 56, respectively; SEQ ID NOs:22 and 57, respectively; SEQ ID NOs:23 and 58, respectively; SEQ ID NOs:24 and 59, respectively; SEQ ID NOs:25 and 60, respectively; SEQ ID NOs:26 and 61, respectively; SEQ ID NOs:27 and 62, respectively; SEQ ID NOs:28 and 63, respectively; SEQ ID NOs:29 and 64, respectively; SEQ ID NOs:30 and 65, respectively; SEQ ID NOs:31 and 66, respectively; SEQ ID NOs:32 and 67, respectively; SEQ ID NOs:33 and 68, respectively; SEQ ID NOs:34 and 69, respectively; SEQ ID NOs:35 and 70, respectively; SEQ ID NOs:36 and 71, respectively; SEQ ID NOs:37 and 72, respectively; SEQ ID NOs:38 and 73, respectively; and SEQ ID NOs:39 and 74, respectively; SEQ ID NOs:234 and 247, respectively; SEQ ID NOs:235 and 247, respectively; SEQ ID NOs:236 and 248, respectively; SEQ ID NOs:236 and 249, respectively; SEQ ID NOs:237 and 249, respectively; SEQ ID NOs:238 and 249, respectively; SEQ ID NOs:239 and 250, respectively; SEQ ID NOs:240 and 251, respectively; SEQ ID NOs:241 and 252, respectively; SEQ ID NOs:242 and 249, respectively; SEQ ID NOs:243 and 247, respectively; SEQ ID NOs:244 and 251, respectively; SEQ ID NOs:245 and 253, respectively; SEQ ID NOs:246 and 247, respectively; SEQ ID NOs:246 and 254, respectively; SEQ ID NOs:255 and 257, respectively; SEQ ID NOs:256 and 258, respectively; SEQ ID NOs:259 and 274, respectively; SEQ ID NOs:260 and 275, respectively; SEQ ID NOs:261 and 276, respectively; SEQ ID NOs:262 and 277, respectively; SEQ ID NOs:263 and 277, respectively; SEQ ID NOs:264 and 277, respectively; SEQ ID NOs:265 and 277, respectively; SEQ ID NOs:266 and 277, respectively; SEQ ID NOs:267 and 278, respectively; SEQ ID NOs:268 and 279, respectively; SEQ ID NOs:269 and 279, respectively; SEQ ID NOs:264 and 280, respectively; SEQ ID NOs:270 and 281, respectively; SEQ ID NOs:265 and 282, respectively; SEQ ID NOs:264 and 283, respectively; SEQ ID NOs:271 and 284, respectively; SEQ ID NOs:272 and 285, respectively; SEQ ID NOs:271 and 286, respectively; SEQ ID NOs:273 and 287, respectively; SEQ ID NOs:273 and 288, respectively; SEQ ID NOs:273 and 289, respectively; SEQ ID NOs:290 and 309, respectively; SEQ ID NOs:291 and 310, respectively; SEQ ID NOs:292 and 311, respectively SEQ ID NOs:293 and 312, respectively; SEQ ID NOs:294 and 313, respectively; SEQ ID NOs:295 and 314, respectively; SEQ ID NOs:296 and 315, respectively; SEQ ID NOs:290 and 316, respectively; SEQ ID NOs:297 and 317, respectively; SEQ ID NOs:298 and 318, respectively; SEQ ID NOs:292 and 319, respectively; SEQ ID NOs:299 and 320, respectively; SEQ ID NOs:300 and 311, respectively; SEQ ID NOs:301 and 321, respectively; SEQ ID NOs:302 and 322, respectively; SEQ ID NOs:303 and 311, respectively; SEQ ID NOs:304 and 322, respectively; SEQ ID NOs:305 and 322, respectively; SEQ ID NOs:301 and 323, respectively; SEQ ID NOs:301 and 324, respectively; SEQ ID NOs:301 and 325, respectively; SEQ ID NOs:306 and 326, respectively; SEQ ID NOs:307 and 327, respectively; or SEQ ID NOs:308 and 328, respectively.

3. The antibody of claim 1, wherein the antibody reduces efferocytosis by a phagocytic cell, reduces binding of ProS to MerTK, reduces binding of Gas6 to MerTK, reduces binding of ProS to MerTK and reduces the binding of Gas6 to MerTK, reduces Gas6-mediated phosphorylation of AKT, and/or increases or induces M1-like macrophage polarization.

4. The antibody of claim 1, wherein the antibody is a murine antibody, a humanized antibody, a bispecific antibody, a monoclonal antibody, a multivalent antibody, a conjugated antibody, or a chimeric antibody.

5. The antibody of claim 1, wherein the antibody is of the IgG class, the IgM class, or the IgA class.

6. The antibody of claim 1, wherein the antibody is a full-length antibody.

7. The antibody of claim 1, wherein the antibody is an scFv.

8. An isolated nucleic acid comprising a nucleic acid sequence encoding the antibody of claim 1.

9. A vector comprising the nucleic acid of claim 8.

10. An isolated host cell comprising the nucleic acid of claim 8.

11. A method of producing an antibody that binds to human MerTK, the method comprising culturing the cell of claim 10 so that the antibody is produced.

12. A pharmaceutical composition comprising the antibody of claim 1 and a pharmaceutically acceptable carrier.

13. The antibody of claim 2, wherein the antibody comprises (a) a heavy chain comprising the amino acid sequence of SEQ ID NO:466 or 464 and a light chain comprising the amino acid sequence of SEQ ID NO:472; (b) a heavy chain comprising the amino acid sequence of SEQ ID NO:467, 465, 468, or 469 and a light chain comprising the amino acid sequence of SEQ ID NO:472; (c) a heavy chain comprising the amino acid sequence of SEQ ID NO:422, 423, 424, 425, or 426 and a light chain comprising the amino acid sequence of SEQ ID NO:430; (d) a heavy chain comprising the amino acid sequence of SEQ ID NO:440, 441, 442, 443, 444, or 445 and a light chain comprising the amino acid sequence of SEQ ID NO:448; or (e) a heavy chain comprising the amino acid sequence of SEQ ID NO:413, 414, 415, 416, 417, or 418 and a light chain comprising the amino acid sequence of SEQ ID NO:421.

14. The antibody of claim 2, wherein the antibody reduces efferocytosis by a phagocytic cell, reduces binding of ProS to MerTK, reduces binding of Gas6 to MerTK, reduces binding of ProS to MerTK and reduces the binding of Gas6 to MerTK, reduces Gas6-mediated phosphorylation of AKT, and/or increases or induces M1-like macrophage polarization.

15. The antibody of claim 2, wherein the antibody is a murine antibody, a humanized antibody, a bispecific antibody, a monoclonal antibody, a multivalent antibody, a conjugated antibody, or a chimeric antibody.

16. The antibody of claim 2, wherein the antibody is of the IgG class, the IgM class, or the IgA class.

17. The antibody of claim 2, wherein the antibody is a full-length antibody.

18. The antibody of claim 2, wherein the antibody is an scFv.

19. An isolated nucleic acid comprising a nucleic acid sequence encoding the antibody of claim 2.

20. A vector comprising the nucleic acid of claim 19.

21. An isolated host cell comprising the nucleic acid of claim 19.

22. A method of producing an antibody that binds to human MerTK, the method comprising culturing the cell of claim 21 so that the antibody is produced.

23. A pharmaceutical composition comprising the antibody of claim 2 and a pharmaceutically acceptable carrier.

* * * * *

SEQUENCE LISTING

<160> NUMBER OF SEQ ID NOS: 472

<210> SEQ ID NO 1
<211> LENGTH: 999
<212> TYPE: PRT
<213> ORGANISM: Homo sapiens

<400> SEQUENCE: 1

Met Gly Pro Ala Pro Leu Pro Leu Leu Leu Gly Leu Phe Leu Pro Ala
1               5                   10                  15

Leu Trp Arg Arg Ala Ile Thr Glu Ala Arg Glu Glu Ala Lys Pro Tyr
            20                  25                  30

Pro Leu Phe Pro Gly Pro Phe Pro Gly Ser Leu Gln Thr Asp His Thr
        35                  40                  45

Pro Leu Leu Ser Leu Pro His Ala Ser Gly Tyr Gln Pro Ala Leu Met
    50                  55                  60

Phe Ser Pro Thr Gln Pro Gly Arg Pro His Thr Gly Asn Val Ala Ile
65                  70                  75                  80

Pro Gln Val Thr Ser Val Glu Ser Lys Pro Leu Pro Pro Leu Ala Phe
                85                  90                  95

Lys His Thr Val Gly His Ile Ile Leu Ser Glu His Lys Gly Val Lys
            100                 105                 110

Phe Asn Cys Ser Ile Ser Val Pro Asn Ile Tyr Gln Asp Thr Thr Ile
        115                 120                 125

Ser Trp Trp Lys Asp Gly Lys Glu Leu Leu Gly Ala His His Ala Ile
    130                 135                 140

-continued

```
Thr Gln Phe Tyr Pro Asp Asp Glu Val Thr Ala Ile Ile Ala Ser Phe
145                 150                 155                 160

Ser Ile Thr Ser Val Gln Arg Ser Asp Asn Gly Ser Tyr Ile Cys Lys
            165                 170                 175

Met Lys Ile Asn Asn Glu Glu Ile Val Ser Asp Pro Ile Tyr Ile Glu
        180                 185                 190

Val Gln Gly Leu Pro His Phe Thr Lys Gln Pro Glu Ser Met Asn Val
    195                 200                 205

Thr Arg Asn Thr Ala Phe Asn Leu Thr Cys Gln Ala Val Gly Pro Pro
210                 215                 220

Glu Pro Val Asn Ile Phe Trp Val Gln Asn Ser Ser Arg Val Asn Glu
225                 230                 235                 240

Gln Pro Glu Lys Ser Pro Ser Val Leu Thr Val Pro Gly Leu Thr Glu
                245                 250                 255

Met Ala Val Phe Ser Cys Glu Ala His Asn Asp Lys Gly Leu Thr Val
            260                 265                 270

Ser Lys Gly Val Gln Ile Asn Ile Lys Ala Ile Pro Ser Pro Pro Thr
        275                 280                 285

Glu Val Ser Ile Arg Asn Ser Thr Ala His Ser Ile Leu Ile Ser Trp
    290                 295                 300

Val Pro Gly Phe Asp Gly Tyr Ser Pro Phe Arg Asn Cys Ser Ile Gln
305                 310                 315                 320

Val Lys Glu Ala Asp Pro Leu Ser Asn Gly Ser Val Met Ile Phe Asn
                325                 330                 335

Thr Ser Ala Leu Pro His Leu Tyr Gln Ile Lys Gln Leu Gln Ala Leu
            340                 345                 350

Ala Asn Tyr Ser Ile Gly Val Ser Cys Met Asn Glu Ile Gly Trp Ser
        355                 360                 365

Ala Val Ser Pro Trp Ile Leu Ala Ser Thr Thr Glu Gly Ala Pro Ser
    370                 375                 380

Val Ala Pro Leu Asn Val Thr Val Phe Leu Asn Glu Ser Ser Asp Asn
385                 390                 395                 400

Val Asp Ile Arg Trp Met Lys Pro Pro Thr Lys Gln Gln Asp Gly Glu
                405                 410                 415

Leu Val Gly Tyr Arg Ile Ser His Val Trp Gln Ser Ala Gly Ile Ser
            420                 425                 430

Lys Glu Leu Leu Glu Glu Val Gly Gln Asn Gly Ser Arg Ala Arg Ile
        435                 440                 445

Ser Val Gln Val His Asn Ala Thr Cys Thr Val Arg Ile Ala Ala Val
    450                 455                 460

Thr Arg Gly Gly Val Gly Pro Phe Ser Asp Pro Val Lys Ile Phe Ile
465                 470                 475                 480

Pro Ala His Gly Trp Val Asp Tyr Ala Pro Ser Ser Thr Pro Ala Pro
                485                 490                 495

Gly Asn Ala Asp Pro Val Leu Ile Ile Phe Gly Cys Phe Cys Gly Phe
            500                 505                 510

Ile Leu Ile Gly Leu Ile Leu Tyr Ile Ser Leu Ala Ile Arg Lys Arg
        515                 520                 525

Val Gln Glu Thr Lys Phe Gly Asn Ala Phe Thr Glu Glu Asp Ser Glu
    530                 535                 540

Leu Val Val Asn Tyr Ile Ala Lys Lys Ser Phe Cys Arg Arg Ala Ile
545                 550                 555                 560
```

-continued

```
Glu Leu Thr Leu His Ser Leu Gly Val Ser Glu Leu Gln Asn Lys
            565                 570                 575
Leu Glu Asp Val Val Ile Asp Arg Asn Leu Leu Ile Leu Gly Lys Ile
        580                 585                 590
Leu Gly Glu Gly Glu Phe Gly Ser Val Met Glu Gly Asn Leu Lys Gln
        595                 600                 605
Glu Asp Gly Thr Ser Leu Lys Val Ala Val Lys Thr Met Lys Leu Asp
610                 615                 620
Asn Ser Ser Gln Arg Glu Ile Glu Glu Phe Leu Ser Glu Ala Ala Cys
625                 630                 635                 640
Met Lys Asp Phe Ser His Pro Asn Val Ile Arg Leu Leu Gly Val Cys
            645                 650                 655
Ile Glu Met Ser Ser Gln Gly Ile Pro Lys Pro Met Val Ile Leu Pro
            660                 665                 670
Phe Met Lys Tyr Gly Asp Leu His Thr Tyr Leu Leu Tyr Ser Arg Leu
        675                 680                 685
Glu Thr Gly Pro Lys His Ile Pro Leu Gln Thr Leu Leu Lys Phe Met
        690                 695                 700
Val Asp Ile Ala Leu Gly Met Glu Tyr Leu Ser Asn Arg Asn Phe Leu
705                 710                 715                 720
His Arg Asp Leu Ala Ala Arg Asn Cys Met Leu Arg Asp Asp Met Thr
            725                 730                 735
Val Cys Val Ala Asp Phe Gly Leu Ser Lys Lys Ile Tyr Ser Gly Asp
            740                 745                 750
Tyr Tyr Arg Gln Gly Arg Ile Ala Lys Met Pro Val Lys Trp Ile Ala
        755                 760                 765
Ile Glu Ser Leu Ala Asp Arg Val Tyr Thr Ser Lys Ser Asp Val Trp
        770                 775                 780
Ala Phe Gly Val Thr Met Trp Glu Ile Ala Thr Arg Gly Met Thr Pro
785                 790                 795                 800
Tyr Pro Gly Val Gln Asn His Glu Met Tyr Asp Tyr Leu Leu His Gly
            805                 810                 815
His Arg Leu Lys Gln Pro Glu Asp Cys Leu Asp Glu Leu Tyr Glu Ile
            820                 825                 830
Met Tyr Ser Cys Trp Arg Thr Asp Pro Leu Asp Arg Pro Thr Phe Ser
        835                 840                 845
Val Leu Arg Leu Gln Leu Glu Lys Leu Leu Glu Ser Leu Pro Asp Val
850                 855                 860
Arg Asn Gln Ala Asp Val Ile Tyr Val Asn Thr Gln Leu Leu Glu Ser
865                 870                 875                 880
Ser Glu Gly Leu Ala Gln Gly Ser Thr Leu Ala Pro Leu Asp Leu Asn
            885                 890                 895
Ile Asp Pro Asp Ser Ile Ile Ala Ser Cys Thr Pro Arg Ala Ala Ile
            900                 905                 910
Ser Val Val Thr Ala Glu Val His Asp Ser Lys Pro His Glu Gly Arg
        915                 920                 925
Tyr Ile Leu Asn Gly Gly Ser Glu Glu Trp Glu Asp Leu Thr Ser Ala
        930                 935                 940
Pro Ser Ala Ala Val Thr Ala Glu Lys Asn Ser Val Leu Pro Gly Glu
945                 950                 955                 960
Arg Leu Val Arg Asn Gly Val Ser Trp Ser His Ser Ser Met Leu Pro
            965                 970                 975
Leu Gly Ser Ser Leu Pro Asp Glu Leu Leu Phe Ala Asp Asp Ser Ser
```

-continued

```
                   980                 985                 990

Glu Gly Ser Glu Val Leu Met
        995

<210> SEQ ID NO 2
<211> LENGTH: 505
<212> TYPE: PRT
<213> ORGANISM: Homo sapiens

<400> SEQUENCE: 2

Met Gly Pro Ala Pro Leu Pro Leu Leu Gly Leu Phe Leu Pro Ala
1               5                   10                  15

Leu Trp Arg Arg Ala Ile Thr Glu Ala Arg Glu Ala Lys Pro Tyr
                20                  25                  30

Pro Leu Phe Pro Gly Pro Phe Pro Gly Ser Leu Gln Thr Asp His Thr
        35                  40                  45

Pro Leu Leu Ser Leu Pro His Ala Ser Gly Tyr Gln Pro Ala Leu Met
        50                  55                  60

Phe Ser Pro Thr Gln Pro Gly Arg Pro His Thr Gly Asn Val Ala Ile
65              70                  75                  80

Pro Gln Val Thr Ser Val Glu Ser Lys Pro Leu Pro Pro Leu Ala Phe
                85                  90                  95

Lys His Thr Val Gly His Ile Ile Leu Ser Glu His Lys Gly Val Lys
                100                 105                 110

Phe Asn Cys Ser Ile Ser Val Pro Asn Ile Tyr Gln Asp Thr Thr Ile
        115                 120                 125

Ser Trp Trp Lys Asp Gly Lys Glu Leu Leu Gly Ala His His Ala Ile
130                 135                 140

Thr Gln Phe Tyr Pro Asp Asp Glu Val Thr Ala Ile Ile Ala Ser Phe
145                 150                 155                 160

Ser Ile Thr Ser Val Gln Arg Ser Asp Asn Gly Ser Tyr Ile Cys Lys
                165                 170                 175

Met Lys Ile Asn Asn Glu Glu Ile Val Ser Asp Pro Ile Tyr Ile Glu
                180                 185                 190

Val Gln Gly Leu Pro His Phe Thr Lys Gln Pro Glu Ser Met Asn Val
                195                 200                 205

Thr Arg Asn Thr Ala Phe Asn Leu Thr Cys Gln Ala Val Gly Pro Pro
210                 215                 220

Glu Pro Val Asn Ile Phe Trp Val Gln Asn Ser Ser Arg Val Asn Glu
225                 230                 235                 240

Gln Pro Glu Lys Ser Pro Ser Val Leu Thr Val Pro Gly Leu Thr Glu
                245                 250                 255

Met Ala Val Phe Ser Cys Glu Ala His Asn Asp Lys Gly Leu Thr Val
                260                 265                 270

Ser Lys Gly Val Gln Ile Asn Ile Lys Ala Ile Pro Ser Pro Pro Thr
        275                 280                 285

Glu Val Ser Ile Arg Asn Ser Thr Ala His Ser Ile Leu Ile Ser Trp
        290                 295                 300

Val Pro Gly Phe Asp Gly Tyr Ser Pro Phe Arg Asn Cys Ser Ile Gln
305                 310                 315                 320

Val Lys Glu Ala Asp Pro Leu Ser Asn Gly Ser Val Met Ile Phe Asn
                325                 330                 335

Thr Ser Ala Leu Pro His Leu Tyr Gln Ile Lys Gln Leu Gln Ala Leu
                340                 345                 350
```

```
Ala Asn Tyr Ser Ile Gly Val Ser Cys Met Asn Glu Ile Gly Trp Ser
            355                 360                 365

Ala Val Ser Pro Trp Ile Leu Ala Ser Thr Thr Glu Gly Ala Pro Ser
        370                 375                 380

Val Ala Pro Leu Asn Val Thr Val Phe Leu Asn Glu Ser Ser Asp Asn
385                 390                 395                 400

Val Asp Ile Arg Trp Met Lys Pro Pro Thr Lys Gln Gln Asp Gly Glu
                405                 410                 415

Leu Val Gly Tyr Arg Ile Ser His Val Trp Gln Ser Ala Gly Ile Ser
                420                 425                 430

Lys Glu Leu Leu Glu Glu Val Gly Gln Asn Gly Ser Arg Ala Arg Ile
            435                 440                 445

Ser Val Gln Val His Asn Ala Thr Cys Thr Val Arg Ile Ala Ala Val
            450                 455                 460

Thr Arg Gly Gly Val Gly Pro Phe Ser Asp Pro Val Lys Ile Phe Ile
465                 470                 475                 480

Pro Ala His Gly Trp Val Asp Tyr Ala Pro Ser Ser Thr Pro Ala Pro
                485                 490                 495

Gly Asn Ala Asp Pro Val Leu Ile Ile
                500                 505

<210> SEQ ID NO 3
<211> LENGTH: 507
<212> TYPE: PRT
<213> ORGANISM: Artificial Sequence
<220> FEATURE:
<223> OTHER INFORMATION: Cyno MerTK ECD

<400> SEQUENCE: 3

Met Gly Leu Ala Pro Leu Pro Leu Pro Leu Leu Leu Gly Leu Phe Leu
1               5                   10                  15

Pro Ala Leu Trp Ser Arg Ala Ile Thr Glu Ala Arg Glu Glu Ala Lys
                20                  25                  30

Pro Tyr Pro Leu Phe Pro Gly Pro Leu Pro Gly Ser Leu Gln Thr Asp
            35                  40                  45

His Thr Ser Leu Leu Ser Leu Pro His Thr Ser Gly Tyr Gln Pro Ala
        50                  55                  60

Leu Met Phe Ser Pro Thr Gln Pro Gly Arg Pro Tyr Thr Gly Asn Val
65                  70                  75                  80

Ala Ile Pro Arg Val Thr Ser Ala Gly Ser Lys Leu Leu Pro Pro Leu
                85                  90                  95

Ala Phe Lys His Thr Val Gly His Ile Ile Leu Ser Glu His Lys Asp
            100                 105                 110

Val Lys Phe Asn Cys Ser Ile Ser Val Pro Asn Ile Tyr Gln Asp Thr
        115                 120                 125

Thr Ile Ser Trp Trp Lys Asp Gly Lys Glu Leu Leu Gly Ala His His
130                 135                 140

Ala Ile Thr Gln Phe Tyr Pro Asp Asp Glu Val Thr Ala Ile Ile Ala
145                 150                 155                 160

Ser Phe Ser Ile Thr Ser Val Gln Arg Ser Asp Asn Gly Ser Tyr Ile
                165                 170                 175

Cys Lys Met Lys Ile Asn Asn Glu Glu Ile Val Ser Asp Pro Ile Tyr
            180                 185                 190

Ile Glu Val Gln Gly Leu Pro His Phe Thr Lys Gln Pro Glu Ser Met
        195                 200                 205
```

```
Asn Val Thr Arg Asn Thr Ala Phe Asn Leu Thr Cys Gln Ala Val Gly
    210                 215                 220

Pro Pro Glu Pro Val Asn Ile Phe Trp Val Gln Asn Ser Ser Arg Val
225                 230                 235                 240

Asn Glu Gln Pro Glu Lys Ser Pro Ser Val Leu Thr Val Pro Gly Leu
                245                 250                 255

Thr Glu Met Ala Val Phe Ser Cys Glu Ala His Asn Asp Lys Gly Leu
            260                 265                 270

Thr Val Ser Lys Gly Val Gln Ile Asn Ile Lys Ala Ile Pro Ser Pro
        275                 280                 285

Pro Thr Glu Val Ser Ile His Asn Ser Thr Ala His Ser Ile Leu Ile
    290                 295                 300

Ser Trp Val Pro Gly Phe Asp Gly Tyr Ser Pro Phe Arg Asn Cys Ser
305                 310                 315                 320

Val Gln Val Lys Glu Val Asp Pro Leu Ser Asn Gly Ser Val Met Ile
                325                 330                 335

Phe Asn Thr Ser Ala Ser Pro His Met Tyr Gln Ile Lys Gln Leu Gln
            340                 345                 350

Ala Leu Ala Asn Tyr Ser Ile Gly Val Ser Cys Met Asn Glu Ile Gly
        355                 360                 365

Trp Ser Ala Val Ser Pro Trp Ile Leu Ala Ser Thr Thr Glu Gly Ala
    370                 375                 380

Pro Ser Val Ala Pro Leu Asn Val Thr Val Phe Leu Asn Glu Ser Arg
385                 390                 395                 400

Asp Asn Val Asp Ile Arg Trp Met Lys Pro Leu Thr Lys Arg Gln Ala
                405                 410                 415

Gly Glu Leu Val Gly Tyr Arg Ile Ser His Val Trp Gln Ser Ala Gly
            420                 425                 430

Ile Ser Lys Glu Leu Leu Glu Glu Val Gly Gln Asn Asn Ser Arg Ala
        435                 440                 445

Gln Ile Ser Val Gln Val His Asn Ala Thr Cys Thr Val Arg Ile Ala
    450                 455                 460

Ala Val Thr Lys Gly Gly Val Gly Pro Phe Ser Asp Pro Val Lys Ile
465                 470                 475                 480

Phe Ile Pro Ala His Gly Trp Val Asp His Ala Pro Ser Ser Thr Pro
                485                 490                 495

Ala Pro Gly Asn Ala Asp Pro Val Leu Ile Ile
            500                 505
```

<210> SEQ ID NO 4
<211> LENGTH: 497
<212> TYPE: PRT
<213> ORGANISM: Artificial Sequence
<220> FEATURE:
<223> OTHER INFORMATION: Murine MerTK ECD

<400> SEQUENCE: 4

```
Met Val Leu Ala Pro Leu Leu Leu Gly Leu Leu Leu Pro Ala Leu
1               5                   10                  15

Trp Ser Gly Gly Thr Ala Glu Lys Trp Glu Glu Thr Glu Leu Asp Gln
            20                  25                  30

Leu Phe Ser Gly Pro Leu Pro Gly Arg Leu Pro Val Asn His Arg Pro
        35                  40                  45

Phe Ser Ala Pro His Ser Ser Arg Asp Gln Leu Pro Pro Pro Gln Thr
    50                  55                  60
```

Gly Arg Ser His Pro Ala His Thr Ala Ala Pro Gln Val Thr Ser Thr
65                  70                  75                  80

Ala Ser Lys Leu Leu Pro Pro Val Ala Phe Asn His Thr Ile Gly His
            85                  90                  95

Ile Val Leu Ser Glu His Lys Asn Val Lys Phe Asn Cys Ser Ile Asn
            100                 105                 110

Ile Pro Asn Thr Tyr Gln Glu Thr Ala Gly Ile Ser Trp Trp Lys Asp
            115                 120                 125

Gly Lys Glu Leu Leu Gly Ala His His Ser Ile Thr Gln Phe Tyr Pro
            130                 135                 140

Asp Glu Glu Gly Val Ser Ile Ile Ala Leu Phe Ser Ile Ala Ser Val
145                 150                 155                 160

Gln Arg Ser Asp Asn Gly Ser Tyr Phe Cys Lys Met Lys Val Asn Asn
                165                 170                 175

Arg Glu Ile Val Ser Asp Pro Ile Tyr Val Glu Val Gln Gly Leu Pro
                180                 185                 190

Tyr Phe Ile Lys Gln Pro Glu Ser Val Asn Val Thr Arg Asn Thr Ala
            195                 200                 205

Phe Asn Leu Thr Cys Gln Ala Val Gly Pro Pro Glu Pro Val Asn Ile
            210                 215                 220

Phe Trp Val Gln Asn Ser Ser Arg Val Asn Glu Lys Pro Glu Arg Ser
225                 230                 235                 240

Pro Ser Val Leu Thr Val Pro Gly Leu Thr Glu Thr Ala Val Phe Ser
                245                 250                 255

Cys Glu Ala His Asn Asp Lys Gly Leu Thr Val Ser Lys Gly Val His
                260                 265                 270

Ile Asn Ile Lys Val Ile Pro Ser Pro Pro Thr Glu Val His Ile Leu
            275                 280                 285

Asn Ser Thr Ala His Ser Ile Leu Val Ser Trp Val Pro Gly Phe Asp
            290                 295                 300

Gly Tyr Ser Pro Leu Gln Asn Cys Ser Ile Gln Val Lys Glu Ala Asp
305                 310                 315                 320

Arg Leu Ser Asn Gly Ser Val Met Val Phe Asn Thr Ser Ala Ser Pro
                325                 330                 335

His Leu Tyr Glu Ile Gln Gln Leu Gln Ala Leu Ala Asn Tyr Ser Ile
            340                 345                 350

Ala Val Ser Cys Arg Asn Glu Ile Gly Trp Ser Ala Val Ser Pro Trp
            355                 360                 365

Ile Leu Ala Ser Thr Thr Glu Gly Ala Pro Ser Val Ala Pro Leu Asn
370                 375                 380

Ile Thr Val Phe Leu Asn Glu Ser Asn Asn Ile Leu Asp Ile Arg Trp
385                 390                 395                 400

Thr Lys Pro Pro Ile Lys Arg Gln Asp Gly Glu Leu Val Gly Tyr Arg
                405                 410                 415

Ile Ser His Val Trp Glu Ser Ala Gly Thr Tyr Lys Glu Leu Ser Glu
            420                 425                 430

Glu Val Ser Gln Asn Gly Ser Trp Ala Gln Ile Pro Val Gln Ile His
            435                 440                 445

Asn Ala Thr Cys Thr Val Arg Ile Ala Ala Ile Thr Lys Gly Gly Ile
            450                 455                 460

Gly Pro Phe Ser Glu Pro Val Asn Ile Ile Pro Glu His Ser Lys
465                 470                 475                 480

Val Asp Tyr Ala Pro Ser Ser Thr Pro Ala Pro Gly Asn Thr Asp Ser

-continued

```
                485                 490                 495
Met

<210> SEQ ID NO 5
<211> LENGTH: 118
<212> TYPE: PRT
<213> ORGANISM: Artificial Sequence
<220> FEATURE:
<223> OTHER INFORMATION: MTK-01 Heavy Chain Variable

<400> SEQUENCE: 5

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Cys Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Thr Thr Ala Tyr
65                  70                  75                  80

Leu Gln Ile Asn Asn Leu Lys Asn Glu Asp Thr Ala Thr Tyr Phe Cys
                85                  90                  95

Ala Arg Arg Asp Arg Tyr Thr Trp Phe Ala Tyr Trp Gly Gln Gly Thr
            100                 105                 110

Leu Val Thr Val Ser Ala
        115

<210> SEQ ID NO 6
<211> LENGTH: 118
<212> TYPE: PRT
<213> ORGANISM: Artificial Sequence
<220> FEATURE:
<223> OTHER INFORMATION: MTK-02 Heavy Chain Variable

<400> SEQUENCE: 6

Gln Ile Gln Leu Val Gln Ser Gly Pro Glu Leu Lys Gln Pro Gly Glu
1               5                   10                  15

Thr Val Lys Ile Ser Cys Lys Ala Ser Gly Tyr Thr Phe Thr Asp Tyr
            20                  25                  30

Gly Val Asn Trp Val Lys Gln Ala Pro Gly Lys Gly Leu Lys Trp Met
        35                  40                  45

Gly Trp Ile Asn Thr Tyr Ser Gly Glu Pro Thr Tyr Ala Gly Asp Phe
    50                  55                  60

Lys Gly Arg Phe Ala Phe Ser Leu Glu Ser Ser Ala Ser Thr Ala Phe
65                  70                  75                  80

Leu Gln Ile Asn Asn Leu Lys Asn Glu Asp Met Ala Thr Tyr Phe Cys
                85                  90                  95

Ala Arg Arg Val Arg Tyr Trp Tyr Phe Asp Val Trp Gly Ala Gly Thr
            100                 105                 110

Ser Val Thr Val Ser Ser
        115

<210> SEQ ID NO 7
<211> LENGTH: 120
<212> TYPE: PRT
<213> ORGANISM: Artificial Sequence
<220> FEATURE:
<223> OTHER INFORMATION: MTK-03 Heavy Chain Variable
```

-continued

<400> SEQUENCE: 7

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Thr Leu Glu Trp
        35                  40                  45

Met Gly Tyr Met Ser Phe Asp Gly Asp Asn Lys Phe Asn Pro Ser Leu
    50                  55                  60

Lys Asn Arg Ile Ser Ile Thr Arg Asp Thr Ser Lys Asn Gln Phe Phe
65                  70                  75                  80

Leu Arg Leu Asn Ser Val Thr Thr Glu Asp Thr Ala Thr Tyr Tyr Cys
                85                  90                  95

Ala Arg Gly Gly Tyr Asn Tyr Gly Ser Thr Glu Ala Asn Trp Gly Gln
            100                 105                 110

Gly Thr Leu Val Thr Val Ser Ala
        115                 120

<210> SEQ ID NO 8
<211> LENGTH: 118
<212> TYPE: PRT
<213> ORGANISM: Artificial Sequence
<220> FEATURE:
<223> OTHER INFORMATION: MTK-04 Heavy Chain Variable

<400> SEQUENCE: 8

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Cys Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Lys Tyr Asp Asn Tyr Ala Trp Phe Ala Tyr Trp Gly Gln Gly Thr
            100                 105                 110

Leu Val Thr Val Ser Ala
        115

<210> SEQ ID NO 9
<211> LENGTH: 116
<212> TYPE: PRT
<213> ORGANISM: Artificial Sequence
<220> FEATURE:
<223> OTHER INFORMATION: MTK-05 Heavy Chain Variable

<400> SEQUENCE: 9

Gln Val Gln Leu Gln Gln Ser Gly Ala Glu Leu Val Gln Pro Gly Thr
1               5                   10                  15

Ser Val Arg Leu Ser Cys Lys Thr Ser Gly Tyr Thr Phe Thr Ser Tyr
            20                  25                  30

Trp Ile Gln Trp Val Lys Gln Arg Pro Gly Gln Gly Leu Gly Trp Ile
        35                  40                  45

Gly Glu Ile Phe Pro Gly Thr Gly Thr Thr Tyr Tyr Asn Glu Lys Phe
            50                  55                  60

Lys Gly Lys Ala Thr Leu Thr Ile Asp Thr Ser Ser Ser Thr Ala Tyr
 65                  70                  75                  80

Met Gln Leu Ser Ser Leu Thr Ser Glu Asp Ser Ala Val Tyr Phe Cys
                85                  90                  95

Ala Arg Asp Gly Ala Tyr Phe Asp Val Trp Gly Ala Gly Thr Thr Val
                100                 105                 110

Thr Val Ser Ser
        115

<210> SEQ ID NO 10
<211> LENGTH: 118
<212> TYPE: PRT
<213> ORGANISM: Artificial Sequence
<220> FEATURE:
<223> OTHER INFORMATION: MTK-06 Heavy Chain Variable

<400> SEQUENCE: 10

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
                20                  25                  30

Gly Met Asn Trp Val Lys Gln Ala Pro Gly Lys Gly Leu Lys Trp Met
            35                  40                  45

Gly Trp Ile Asn Thr Asn Thr Gly Glu Pro Thr Tyr Ala Glu Glu Phe
    50                  55                  60

Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                85                  90                  95

Ala Arg Tyr Tyr Asn Tyr Trp Tyr Phe Asp Val Trp Gly Ala Gly Thr
                100                 105                 110

Thr Val Thr Val Ser Ser
        115

<210> SEQ ID NO 11
<211> LENGTH: 120
<212> TYPE: PRT
<213> ORGANISM: Artificial Sequence
<220> FEATURE:
<223> OTHER INFORMATION: MTK-07 Heavy Chain Variable

<400> SEQUENCE: 11

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
                20                  25                  30

Tyr Tyr Trp Asn Trp Ile Arg Gln Phe Pro Gly Asn Thr Leu Glu Trp
            35                  40                  45

Met Gly Tyr Met Ser Phe Asp Gly Asp Asn Lys Phe Asn Pro Ser Leu
    50                  55                  60

Lys Asn Arg Ile Ser Ile Thr Arg Asp Thr Lys Asn Gln Phe Phe
 65                  70                  75                  80

Leu Arg Leu Asn Ser Val Thr Thr Glu Asp Thr Ala Thr Tyr Tyr Cys
                85                  90                  95

Ala Arg Gly Gly Tyr Asn Tyr Gly Ser Thr Glu Ala Asn Trp Gly Gln

```
                      100                 105                 110
Gly Thr Leu Val Thr Val Ser Thr
        115                 120

<210> SEQ ID NO 12
<211> LENGTH: 118
<212> TYPE: PRT
<213> ORGANISM: Artificial Sequence
<220> FEATURE:
<223> OTHER INFORMATION: MTK-08 Heavy Chain Variable

<400> SEQUENCE: 12

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Glu Val Arg Tyr Trp Tyr Phe Asp Val Trp Gly Ala Gly Thr
            100                 105                 110

Thr Val Thr Val Ser Ser
        115

<210> SEQ ID NO 13
<211> LENGTH: 123
<212> TYPE: PRT
<213> ORGANISM: Artificial Sequence
<220> FEATURE:
<223> OTHER INFORMATION: MTK-09 Heavy Chain Variable

<400> SEQUENCE: 13

Gln Val Gln Leu Gln Gln Ser Gly Ala Glu Leu Val Arg Pro Gly Ala
1               5                   10                  15

Ser Val Lys Ile Ser Cys Lys Ala Phe Gly Tyr Thr Phe Thr Asn His
            20                  25                  30

His Ile Lys Trp Val Lys Gln Arg Pro Gly Gln Gly Leu Asp Trp Ile
        35                  40                  45

Gly Tyr Ile Asp Pro Tyr Asn Asp Tyr Thr Thr Tyr Asn Gln Asn Phe
    50                  55                  60

Lys Gly Lys Ala Thr Leu Thr Val Asp Lys Ser Ser Thr Thr Ala Tyr
65                  70                  75                  80

Met Glu Leu Ser Ser Leu Thr Ser Glu Asp Ser Ala Val Tyr Tyr Cys
                85                  90                  95

Ala Arg Arg Ala Tyr Asp Gly Tyr Tyr Val Asp Trp Tyr Phe Asp Val
            100                 105                 110

Trp Gly Ala Gly Thr Thr Val Thr Val Ser Ser
        115                 120

<210> SEQ ID NO 14
<211> LENGTH: 119
<212> TYPE: PRT
<213> ORGANISM: Artificial Sequence
<220> FEATURE:
```

<223> OTHER INFORMATION: MTK-10 Heavy Chain Variable

<400> SEQUENCE: 14

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Thr Thr Ser
            20                  25                  30

Gly Met Gly Val Gly Trp Ile Arg Gln Pro Ser Gly Lys Gly Leu Glu
        35                  40                  45

Trp Leu Ala His Ile Trp Ser Asp Asp Lys Arg Ser Asn Pro Ala
    50                  55                  60

Leu Lys Ser Arg Leu Thr Ile Ser Gln Asp Ser Thr Asn Gln Val
65                  70                  75                  80

Phe Leu Lys Ile Ala Ser Val Asp Thr Ala Asp Ser Ala Thr Tyr Tyr
                85                  90                  95

Cys Ser His Leu Thr Pro Val Arg Glu Phe Ala Tyr Trp Gly Pro Gly
            100                 105                 110

Thr Leu Val Thr Val Ser Glu
        115

<210> SEQ ID NO 15
<211> LENGTH: 118
<212> TYPE: PRT
<213> ORGANISM: Artificial Sequence
<220> FEATURE:
<223> OTHER INFORMATION: MTK-11 Heavy Chain Variable

<400> SEQUENCE: 15

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Ser Gly Thr Thr Asp Tyr Asn Glu Ala Phe Ile
    50                  55                  60

Ser Arg Leu Ser Ile Ser Lys Asp Asn Ser Lys Ser His Val Phe Phe
65                  70                  75                  80

Lys Met Asn Ser Leu Gln Ala Ile Asp Thr Ala Ile Tyr Tyr Cys Ala
                85                  90                  95

Arg Lys Gly His Asp Pro Tyr Ala Met Asp Tyr Trp Gly Gln Gly Thr
            100                 105                 110

Ser Val Thr Val Ser Ser
        115

<210> SEQ ID NO 16
<211> LENGTH: 122
<212> TYPE: PRT
<213> ORGANISM: Artificial Sequence
<220> FEATURE:
<223> OTHER INFORMATION: MTK-12 Heavy Chain Variable

<400> SEQUENCE: 16

Gln Val Gln Leu Gln Gln Ser Gly Pro Gln Leu Val Arg Pro Gly Ala
1               5                   10                  15

Ser Val Lys Ile Ser Cys Lys Ala Ser Gly Tyr Ser Phe Thr Ser His
            20                  25                  30

Trp Met His Trp Val Lys Gln Arg Pro Gly Gln Gly Leu Glu Trp Ile

```
                35                  40                  45
Gly Met Ile Asp Pro Ser Asp Gly Glu Ser Arg Leu Asn Gln Lys Phe
 50                  55                  60

Lys Asp Lys Ala Thr Leu Thr Val Asp Lys Ser Ser Ser Thr Ala Tyr
 65                  70                  75                  80

Met Gln Leu Ser Ser Pro Thr Phe Glu Asp Ser Ala Val Tyr Tyr Cys
                 85                  90                  95

Ala Arg Gly Ile Tyr Tyr Tyr Gly Ile Thr Tyr Ala Met Asp Tyr Trp
            100                 105                 110

Gly Gln Gly Thr Ser Val Thr Val Ser Ser
        115                 120

<210> SEQ ID NO 17
<211> LENGTH: 119
<212> TYPE: PRT
<213> ORGANISM: Artificial Sequence
<220> FEATURE:
<223> OTHER INFORMATION: MTK-13 Heavy Chain Variable

<400> SEQUENCE: 17

Asp Val Gln Leu Gln Glu Ser Gly Pro Gly Leu Val Lys Pro Ser Gln
 1               5                  10                  15

Ser Leu Ser Leu Thr Cys Ser Val Thr Gly Tyr Ser Ile Thr Ser Gly
                20                  25                  30

Tyr Tyr Trp Asn Trp Ile Arg Gln Phe Pro Gly Asn Lys Leu Glu Trp
                35                  40                  45

Met Gly Asn Ile Asp Tyr Asp Gly Ser Asn Lys Tyr Asn Pro Ser Leu
 50                  55                  60

Lys Asn Arg Ile Ser Ile Thr Arg Asp Thr Ser Lys Asn His Phe Phe
 65                  70                  75                  80

Leu Lys Leu Asn Ser Val Thr Pro Glu Asp Thr Ala Thr Tyr Phe Cys
                 85                  90                  95

Ala Arg Asp Gly Gly Asn Tyr Arg Ser Phe Ala Tyr Trp Gly Gln Gly
            100                 105                 110

Thr Leu Val Thr Val Ser Ala
        115

<210> SEQ ID NO 18
<211> LENGTH: 118
<212> TYPE: PRT
<213> ORGANISM: Artificial Sequence
<220> FEATURE:
<223> OTHER INFORMATION: MTK-14 Heavy Chain Variable

<400> SEQUENCE: 18

Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Asn Tyr
                20                  25                  30

Gly Met Asn Trp Val Lys Gln Ala Pro Gly Lys Asp Leu Gln Trp Met
                35                  40                  45

Gly Trp Ile Asn Thr Tyr Thr Gly Glu Pro Thr Tyr Ala Asp Asp Phe
 50                  55                  60

Thr Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                 85                  90                  95
```

Ala Lys Gly Gly His Tyr Ala Trp Phe Ala Tyr Trp Gly Gln Gly Thr
            100                 105                 110

Leu Val Thr Val Ser Ala
        115

<210> SEQ ID NO 19
<211> LENGTH: 118
<212> TYPE: PRT
<213> ORGANISM: Artificial Sequence
<220> FEATURE:
<223> OTHER INFORMATION: MTK-15 Heavy Chain Variable

<400> SEQUENCE: 19

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Val His Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Gly Asn Arg Tyr Ala Tyr Met Asp Tyr Trp Gly Gln Gly Thr
            100                 105                 110

Ser Val Thr Val Ser Ser
        115

<210> SEQ ID NO 20
<211> LENGTH: 120
<212> TYPE: PRT
<213> ORGANISM: Artificial Sequence
<220> FEATURE:
<223> OTHER INFORMATION: MTK-16 Heavy Chain Variable

<400> SEQUENCE: 20

Leu Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn His
            20                  25                  30

Gly Met Asn Trp Val Lys Gln Asp Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Val Phe Ser Met Glu Thr Ser Ala Ser Ala Ala Phe
65                  70                  75                  80

Leu Gln Ile Asn Asn Leu Lys Asn Glu Asp Thr Ala Thr Tyr Phe Cys
                85                  90                  95

Ala Arg Lys Gly Val Thr Ala Ala Arg Tyr Phe Asp Tyr Trp Gly Gln
            100                 105                 110

Gly Thr Thr Leu Thr Val Ser Ser
        115                 120

<210> SEQ ID NO 21
<211> LENGTH: 120
<212> TYPE: PRT
<213> ORGANISM: Artificial Sequence

```
<220> FEATURE:
<223> OTHER INFORMATION: MTK-17 Heavy Chain Variable

<400> SEQUENCE: 21

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Phe
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ser Arg Gly Ala Val Leu Arg Ala Gly Ala Met Asp Cys Trp Gly Gln
            100                 105                 110

Gly Thr Ser Val Thr Val Ser Ser
        115                 120

<210> SEQ ID NO 22
<211> LENGTH: 121
<212> TYPE: PRT
<213> ORGANISM: Artificial Sequence
<220> FEATURE:
<223> OTHER INFORMATION: MTK-18 Heavy Chain Variable

<400> SEQUENCE: 22

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr His Tyr
            20                  25                  30

Gly Met Thr Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Gly Gly Gly Gln Leu Leu Arg Pro Leu Asp Tyr Trp Gly
            100                 105                 110

Gln Gly Thr Thr Leu Thr Val Ser Ser
        115                 120

<210> SEQ ID NO 23
<211> LENGTH: 125
<212> TYPE: PRT
<213> ORGANISM: Artificial Sequence
<220> FEATURE:
<223> OTHER INFORMATION: MTK-19 Heavy Chain Variable

<400> SEQUENCE: 23

Glu Val Gln Leu Gln Gln Ser Gly Pro Glu Leu Val Lys Pro Gly Ala
1               5                   10                  15

Ser Val Lys Ile Ser Cys Lys Ser Gly Tyr Thr Phe Thr Glu Tyr
            20                  25                  30
```

```
Thr Met His Trp Val Lys Gln Ser His Gly Lys Ser Leu Glu Trp Leu
            35                  40                  45

Gly Gly Phe Asn Pro Asn Asn Val Ile Thr Ser Tyr Asn Gln Arg Phe
 50                  55                  60

Gln Gly Arg Ala Thr Leu Thr Val Asp Lys Ser Ser Ser Thr Ala Tyr
 65                  70                  75                  80

Met Glu Leu Arg Ser Leu Thr Ser Asp Asp Ser Ala Val Tyr Tyr Cys
                85                  90                  95

Thr Arg Gly Asp Leu Leu Trp Ser Leu Leu Leu Pro Gly Asn Tyr Phe
                100                 105                 110

Asp Tyr Trp Gly Gln Gly Thr Thr Leu Thr Val Ser Ser
            115                 120                 125
```

<210> SEQ ID NO 24
<211> LENGTH: 121
<212> TYPE: PRT
<213> ORGANISM: Artificial Sequence
<220> FEATURE:
<223> OTHER INFORMATION: MTK-20 Heavy Chain Variable

<400> SEQUENCE: 24

```
Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Asn Tyr
            20                  25                  30

Gly Met Thr Trp Val Lys Gln Ala Pro Gly Lys Gly Leu Lys Trp Met
            35                  40                  45

Gly Trp Ile Asn Thr Tyr Thr Gly Glu Pro Thr Tyr Ala Asp Asp Phe
 50                  55                  60

Lys Gly Arg Phe Ala Leu Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                85                  90                  95

Ala Arg Gly Gly Gly Arg Leu Gly Leu Arg Pro Leu Asp Tyr Trp Gly
                100                 105                 110

Gln Gly Thr Thr Leu Thr Val Ser Ser
            115                 120
```

<210> SEQ ID NO 25
<211> LENGTH: 121
<212> TYPE: PRT
<213> ORGANISM: Artificial Sequence
<220> FEATURE:
<223> OTHER INFORMATION: MTK-21 Heavy Chain Variable

<400> SEQUENCE: 25

```
Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Asn Phe
            20                  25                  30

Gly Met Thr Trp Val Arg Gln Ala Pro Gly Met Asp Leu Lys Trp Met
            35                  40                  45

Gly Trp Ile Asn Thr Tyr Thr Gly Glu Pro Lys Tyr Ala Asp Asp Phe
 50                  55                  60

Lys Gly Arg Phe Ala Leu Ser Leu Glu Thr Ser Ala Ser Thr Ala Tyr
 65                  70                  75                  80

Leu Gln Ile Thr Asn Phe Lys Asn Glu Asp Thr Ala Thr Tyr Phe Cys
                85                  90                  95
```

```
Ala Arg Gly Gly Gly Arg Leu Gly Leu Arg Pro Leu Asp Tyr Trp Gly
            100                 105                 110

Gln Gly Thr Thr Leu Thr Val Ser Ser
        115                 120

<210> SEQ ID NO 26
<211> LENGTH: 120
<212> TYPE: PRT
<213> ORGANISM: Artificial Sequence
<220> FEATURE:
<223> OTHER INFORMATION: MTK-22 Heavy Chain Variable

<400> SEQUENCE: 26

Gln Val Gln Leu Gln Gln Pro Gly Ala Asp Leu Val Glu Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asp Pro Ser Asp Ser Ser Asn Tyr Asn Gln Lys Phe
    50                  55                  60

Lys Gly Lys Ala Thr Leu Thr Val Asp Lys Ser Ser Thr Ala Tyr
65                  70                  75                  80

Met His Leu Asn Ser Leu Thr Ser Glu Asp Ser Ala Val Tyr Tyr Cys
                85                  90                  95

Ala Arg Arg Tyr Tyr Tyr Gly Ser Leu Tyr Phe Asp Asn Trp Gly Gln
            100                 105                 110

Gly Thr Thr Leu Thr Val Ser Ser
        115                 120

<210> SEQ ID NO 27
<211> LENGTH: 123
<212> TYPE: PRT
<213> ORGANISM: Artificial Sequence
<220> FEATURE:
<223> OTHER INFORMATION: MTK-23 Heavy Chain Variable

<400> SEQUENCE: 27

Gln Val Gln Leu Gln Gln Ser Gly Ala Asp Leu Val Arg Pro Gly Ala
1               5                   10                  15

Ser Val Lys Ile Ser Cys Lys Ala Phe Gly Tyr Thr Phe Thr Asn His
            20                  25                  30

His Ile Asn Trp Val Lys Gln Arg Pro Gly Gln Gly Leu Asp Trp Ile
        35                  40                  45

Gly Asn Val Asp Pro Tyr Asn Asp Tyr Ser Thr Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Arg Val Tyr Asp Gly Phe Tyr Val Asp Trp Tyr Phe Asp Val
            100                 105                 110

Trp Gly Ala Gly Thr Thr Val Thr Val Ser Ser
        115                 120

<210> SEQ ID NO 28
<211> LENGTH: 121
<212> TYPE: PRT
```

<213> ORGANISM: Artificial Sequence
<220> FEATURE:
<223> OTHER INFORMATION: MTK-24 Heavy Chain Variable

<400> SEQUENCE: 28

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Met Ile His Pro Asn Ile Asn Thr Asn Tyr Asn Glu Lys Phe Lys
    50                  55                  60

Ser Lys Ala Thr Leu Thr Val Asp Ile Ser Ser Thr Ala Tyr Met
65                  70                  75                  80

Gln Leu Ser Ser Leu Thr Ser Glu Asp Ser Ala Val Tyr Tyr Cys Ala
                85                  90                  95

Lys Arg Ser Pro Tyr Ser Asn Tyr Asp Trp Tyr Phe Asp Val Trp Gly
            100                 105                 110

Thr Gly Thr Thr Val Thr Val Ser Ser
        115                 120

<210> SEQ ID NO 29
<211> LENGTH: 117
<212> TYPE: PRT
<213> ORGANISM: Artificial Sequence
<220> FEATURE:
<223> OTHER INFORMATION: MTK-25 Heavy Chain Variable

<400> SEQUENCE: 29

Glu Val Lys Leu Val Glu Ser Glu Gly Gly Leu Val Gln Pro Gly Ser
1               5                   10                  15

Ser Met Lys Leu Ser Cys Thr Ala Ser Gly Phe Thr Phe Ser Asp Tyr
            20                  25                  30

Tyr Met Ala Trp Val Arg Gln Val Pro Glu Lys Gly Leu Glu Trp Val
        35                  40                  45

Ala Asn Ile Asn Tyr Glu Gly Ser Ser Thr Tyr Tyr Leu Gly Ser Leu
    50                  55                  60

Lys Ser Arg Phe Ile Ile Ser Arg Asp Asn Ala Glu Asn Ile Leu Tyr
65                  70                  75                  80

Leu Gln Met Ser Ser Leu Lys Ser Glu Asp Thr Ala Thr Tyr Tyr Cys
                85                  90                  95

Ala Arg Tyr Tyr Tyr Gly Ser Val Asp Tyr Trp Gly Gln Gly Thr Thr
            100                 105                 110

Leu Thr Val Ser Ser
        115

<210> SEQ ID NO 30
<211> LENGTH: 119
<212> TYPE: PRT
<213> ORGANISM: Artificial Sequence
<220> FEATURE:
<223> OTHER INFORMATION: MTK-26 Heavy Chain Variable

<400> SEQUENCE: 30

Ala Val Gln Phe Gln Glu Ser Gly Pro Gly Leu Val Lys Leu Ser Gln
1               5                   10                  15

Ser Leu Ser Leu Thr Cys Ser Val Thr Gly Tyr Ser Ile Thr Ser Gly
            20                  25                  30

Tyr Tyr Trp Asp Trp Ile Arg Gln Phe Pro Gly Asn Lys Leu Glu Trp
                35                  40                  45

Met Gly Tyr Ile Ser Tyr Asp Gly Ser Asn Asn Tyr Asn Pro Ser Leu
 50                  55                  60

Lys Asn Arg Ile Ser Ile Thr Arg Asp Thr Ser Lys Asn Gln Phe Phe
 65                  70                  75                  80

Leu Lys Leu Asn Ser Val Thr Thr Glu Asp Thr Ala Thr Tyr Tyr Cys
                 85                  90                  95

Ala Arg Glu Gly Gly Tyr Tyr Arg Ser Met Asp Tyr Trp Gly Gln Gly
                100                 105                 110

Thr Ser Val Thr Val Ser Ser
            115

<210> SEQ ID NO 31
<211> LENGTH: 117
<212> TYPE: PRT
<213> ORGANISM: Artificial Sequence
<220> FEATURE:
<223> OTHER INFORMATION: MTK-27 Heavy Chain Variable

<400> SEQUENCE: 31

Glu Val Gln Leu Gln Gln Ser Gly Thr Glu Leu Val Arg Pro Gly Ala
 1               5                  10                  15

Ser Val Lys Leu Ser Cys Thr Ala Ser Gly Phe Asn Ile Lys Asp Asp
                20                  25                  30

Tyr Met His Trp Val Gln Gln Arg Pro Glu Gln Gly Leu Glu Trp Ile
                35                  40                  45

Gly Trp Ile Asp Pro Glu Asn Gly Asn Thr Glu Tyr Ala Ser Lys Phe
 50                  55                  60

Gln Gly Lys Ala Thr Ile Thr Ala Asp Ala Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Ser Thr Leu Phe Ser Asn Tyr Phe Asp Tyr Trp Gly Gln Gly Thr Thr
                100                 105                 110

Leu Thr Val Ser Ser
            115

<210> SEQ ID NO 32
<211> LENGTH: 118
<212> TYPE: PRT
<213> ORGANISM: Artificial Sequence
<220> FEATURE:
<223> OTHER INFORMATION: MTK-28 Heavy Chain Variable

<400> SEQUENCE: 32

Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Thr Tyr
                20                  25                  30

Gly Met Ser Trp Val Lys Gln Ala Pro Gly Lys Gly Leu Lys Trp Met
                35                  40                  45

Gly Trp Ile Asn Thr Tyr Ser Gly Val Pro Thr Tyr Ala Asp Asp Phe
 50                  55                  60

Lys Gly Arg Phe Ala Phe Ser Leu Glu Thr Ser Ala Ser Thr Ala Tyr
 65                  70                  75                  80

Leu Gln Ile Asn Thr Leu Lys Asn Glu Asp Thr Thr Thr Tyr Phe Cys

```
                    85                  90                  95

Ala Arg Phe Leu Arg Tyr Tyr Tyr Phe Asp Tyr Trp Gly Gln Gly Thr
                100                 105                 110

Thr Leu Thr Val Ser Ser
        115

<210> SEQ ID NO 33
<211> LENGTH: 118
<212> TYPE: PRT
<213> ORGANISM: Artificial Sequence
<220> FEATURE:
<223> OTHER INFORMATION: MTK-29 Heavy Chain Variable

<400> SEQUENCE: 33

Gln Ile Gln Leu Val Gln Ser Gly Pro Glu Leu Lys Lys Pro Gly Glu
1               5                   10                  15

Thr Val Lys Ile Ser Cys Lys Ser Gly Phe Thr Phe Thr Thr Tyr
                20                  25                  30

Gly Met Ser Trp Val Lys Gln Ala Pro Gly Lys Gly Leu Lys Trp Met
            35                  40                  45

Gly Trp Ile Asn Thr Tyr Ser Gly Val Pro Thr Tyr Thr Asp Asp Phe
        50                  55                  60

Lys Gly Arg Phe Ala Phe Ser Leu Glu Thr Ser Ala Ser Thr Ala Ser
65                  70                  75                  80

Leu Gln Ile Asn Asn Leu Lys Asn Glu Asp Thr Ala Thr Tyr Phe Cys
                85                  90                  95

Ala Arg Tyr Thr Asn Tyr Gly Tyr Phe Asp Tyr Trp Gly Gln Gly Thr
                100                 105                 110

Thr Leu Thr Val Ser Ser
        115

<210> SEQ ID NO 34
<211> LENGTH: 117
<212> TYPE: PRT
<213> ORGANISM: Artificial Sequence
<220> FEATURE:
<223> OTHER INFORMATION: MTK-30 Heavy Chain Variable

<400> SEQUENCE: 34

Gln Val Gln Leu Gln Gln Pro Gly Thr Glu Leu Val Arg Pro Gly Ala
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Asn Leu Asn Pro Asn Asn Gly Gly Thr Tyr Tyr Asn Glu Lys Phe
        50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gln Ile Leu Leu Tyr Phe Asp Tyr Trp Gly Gln Gly Thr Thr
                100                 105                 110

Leu Thr Val Ser Ser
        115

<210> SEQ ID NO 35
<211> LENGTH: 122
```

<212> TYPE: PRT
<213> ORGANISM: Artificial Sequence
<220> FEATURE:
<223> OTHER INFORMATION: MTK-31 Heavy Chain Variable

<400> SEQUENCE: 35

Gln Ile Gln Leu Val Gln Ser Gly Pro Glu Leu Lys Lys Ser Gly Glu
1               5                   10                  15

Thr Val Lys Ile Ser Cys Lys Ala Ser Gly Tyr Thr Phe Thr Ser Tyr
            20                  25                  30

Gly Met Ser Trp Val Lys Gln Ala Pro Gly Lys Gly Leu Lys Trp Met
        35                  40                  45

Gly Trp Ile Asn Thr Tyr Ser Gly Val Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Ser Leu Ser Tyr Asp Gly Ser Leu Tyr His Ala Met Asp Tyr Trp
            100                 105                 110

Gly Gln Gly Thr Ser Val Thr Val Ser Ser
        115                 120

<210> SEQ ID NO 36
<211> LENGTH: 118
<212> TYPE: PRT
<213> ORGANISM: Artificial Sequence
<220> FEATURE:
<223> OTHER INFORMATION: MTK-32 Heavy Chain Variable

<400> SEQUENCE: 36

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Ser Tyr
            20                  25                  30

Gly Met Ser Trp Val His Gln Ala Pro Gly Lys Gly Leu Lys Trp Leu
        35                  40                  45

Gly Trp Ile Asn Thr Tyr Ser Gly Val Pro Thr Tyr Ala Asp Asp Phe
    50                  55                  60

Arg Gly Arg Phe Ala Phe Ser Leu Asp Thr Ser Val Ser Thr Ala Ser
65                  70                  75                  80

Leu Glu Ile Asn Asn Leu Gln Asn Glu Asp Thr Ala Thr Tyr Phe Cys
                85                  90                  95

Ala Arg Glu Asp Asn Trp Ala Trp Phe Ala Tyr Trp Gly Gln Gly Thr
            100                 105                 110

Leu Val Thr Val Ser Thr
        115

<210> SEQ ID NO 37
<211> LENGTH: 119
<212> TYPE: PRT
<213> ORGANISM: Artificial Sequence
<220> FEATURE:
<223> OTHER INFORMATION: MTK-33, 34 Heavy Chain Variable

<400> SEQUENCE: 37

Gln Val Gln Leu Gln Gln Pro Gly Pro Glu Leu Val Arg Pro Gly Thr
1               5                   10                  15

Ser Val Lys Leu Ser Cys Lys Ala Ser Gly Tyr Thr Phe Thr Ser Tyr

```
                    20                  25                  30

Trp Met His Trp Ile Lys Gln Arg Pro Gly Gln Gly Leu Glu Trp Ile
            35                  40                  45

Gly Val Ile Asp Pro Ser Asp Asn Tyr Ile Asn Tyr Asn Gln Lys Phe
        50                  55                  60

Lys Gly Lys Ala Thr Leu Thr Val Asp Thr Ser Ser Thr Ala Tyr
65                  70                  75                  80

Leu Gln Leu Ser Ser Leu Thr Ser Glu Asp Ser Ala Val Tyr Tyr Cys
                85                  90                  95

Ala Arg Glu Ala Gly Thr Arg Gly Tyr Phe Asp Tyr Trp Gly Gln Gly
                100                 105                 110

Thr Thr Leu Thr Val Ser Ser
        115

<210> SEQ ID NO 38
<211> LENGTH: 120
<212> TYPE: PRT
<213> ORGANISM: Artificial Sequence
<220> FEATURE:
<223> OTHER INFORMATION: MTK-35 Heavy Chain Variable

<400> SEQUENCE: 38

Gln Val Leu Leu Gln Gln Ser Gly Pro Glu Leu Val Lys Pro Gly Ala
1               5                   10                  15

Ser Val Gln Leu Ser Cys Lys Ala Ser Asp Tyr Thr Phe Thr Ser Tyr
                20                  25                  30

Asp Ile His Trp Val Lys Gln Arg Pro Gly Gln Gly Leu Glu Trp Ile
            35                  40                  45

Gly Trp Ile Tyr Pro Arg Asp Gly Tyr Thr Lys Tyr Asn Glu Ile Phe
        50                  55                  60

Lys Gly Lys Ala Thr Leu Thr Val Asp Thr Ser Ser Thr Ala Tyr
65                  70                  75                  80

Met Glu Leu His Ser Leu Thr Ser Glu Asp Ser Ala Val Tyr Phe Cys
                85                  90                  95

Ala Arg Ala Tyr Tyr Thr Asn Trp Tyr Tyr Phe Asp Tyr Trp Gly Gln
                100                 105                 110

Gly Thr Thr Leu Thr Val Ser Ser
        115                 120

<210> SEQ ID NO 39
<211> LENGTH: 122
<212> TYPE: PRT
<213> ORGANISM: Artificial Sequence
<220> FEATURE:
<223> OTHER INFORMATION: MTK-36 Heavy Chain Variable

<400> SEQUENCE: 39

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Phe
                20                  25                  30

Gly Met Gly Val Gly Trp Ile Arg Gln Pro Ser Gly Lys Gly Leu Glu
            35                  40                  45

Trp Leu Ala His Ile Trp Trp Tyr Asp Asp Lys Tyr Tyr Glu Pro Ala
        50                  55                  60

Leu Lys Ser Arg Leu Thr Ile Ser Lys Asp Ser Ser Lys Asn Gln Val
65                  70                  75                  80
```

Phe Leu Lys Ile Ala Asn Val Asp Thr Ala Asp Thr Ala Thr Tyr Tyr
                85                  90                  95

Cys Ala Arg Ile Tyr Tyr Gly Thr Ser Tyr Arg Tyr Phe Asp Val Trp
            100                 105                 110

Gly Thr Gly Thr Thr Val Thr Val Ser Ser
        115                 120

<210> SEQ ID NO 40
<211> LENGTH: 106
<212> TYPE: PRT
<213> ORGANISM: Artificial Sequence
<220> FEATURE:
<223> OTHER INFORMATION: MTK-01 Light Chain Variable

<400> SEQUENCE: 40

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Pro Pro Thr
                85                  90                  95

Phe Gly Gly Gly Thr Lys Leu Glu Ile Lys
            100                 105

<210> SEQ ID NO 41
<211> LENGTH: 106
<212> TYPE: PRT
<213> ORGANISM: Artificial Sequence
<220> FEATURE:
<223> OTHER INFORMATION: MTK-02 Light Chain Variable

<400> SEQUENCE: 41

Gln Ile Val Leu Ser Gln Ser Pro Ala Ile Leu Ser Ala Ser Pro Gly
1               5                   10                  15

Glu Arg Val Thr Met Thr Cys Arg Ala Asn Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Ala Ser
    50                  55                  60

Gly Ser Gly Thr Ser Tyr Ser Leu Thr Val Ser Arg Val Glu Ala Glu
65                  70                  75                  80

Asp Ala Ala Thr Tyr Tyr Cys Gln Gln Trp Gly Ser Asn Pro Phe Thr
                85                  90                  95

Phe Gly Ser Gly Thr Lys Leu Glu Ile Lys
            100                 105

<210> SEQ ID NO 42
<211> LENGTH: 106
<212> TYPE: PRT
<213> ORGANISM: Artificial Sequence
<220> FEATURE:
<223> OTHER INFORMATION: MTK-03 Light Chain Variable

<400> SEQUENCE: 42

Gln Ile Val Leu Thr Gln Ser Pro Ala Ile Met Ser Ala Phe Pro Gly
1               5                   10                  15

Glu Lys Val Thr Ile Thr Cys Ser Ala Ser Ser Ser Val Asn Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Phe Thr
                85                  90                  95

Phe Gly Ser Gly Thr Lys Leu Glu Ile Lys
            100                 105

<210> SEQ ID NO 43
<211> LENGTH: 106
<212> TYPE: PRT
<213> ORGANISM: Artificial Sequence
<220> FEATURE:
<223> OTHER INFORMATION: MTK-04 Light Chain Variable

<400> SEQUENCE: 43

Gln Ile Val Leu Ser Gln Ser Pro Ala Phe Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Leu Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Pro Arg Thr
                85                  90                  95

Phe Gly Gly Gly Thr Lys Leu Glu Ile Arg
            100                 105

<210> SEQ ID NO 44
<211> LENGTH: 107
<212> TYPE: PRT
<213> ORGANISM: Artificial Sequence
<220> FEATURE:
<223> OTHER INFORMATION: MTK-05 Light Chain Variable

<400> SEQUENCE: 44

Asp Ile Gln Met Thr Gln Ser Pro Ala Ser Leu Ser Ala Ser Val Gly
1               5                   10                  15

Glu Thr Val Thr Phe Thr Cys Arg Ala Ser Glu Asn Ile Phe Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr His Phe Ser Leu Lys Ile Asn Ser Leu Gln Pro
65                  70                  75                  80

Glu Asp Phe Gly Ser Tyr Tyr Cys Leu His Tyr Gly Thr Pro Leu
            85                  90                  95

Thr Phe Gly Ala Gly Thr Lys Leu Glu Leu Lys
            100                 105

<210> SEQ ID NO 45
<211> LENGTH: 106
<212> TYPE: PRT
<213> ORGANISM: Artificial Sequence
<220> FEATURE:
<223> OTHER INFORMATION: MTK-06 Light Chain Variable

<400> SEQUENCE: 45

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Lys Pro Pro Thr
                85                  90                  95

Phe Gly Gly Gly Thr Lys Leu Glu Ile Lys
            100                 105

<210> SEQ ID NO 46
<211> LENGTH: 106
<212> TYPE: PRT
<213> ORGANISM: Artificial Sequence
<220> FEATURE:
<223> OTHER INFORMATION: MTK-07 Light Chain Variable

<400> SEQUENCE: 46

Gln Ile Val Leu Thr Gln Ser Pro Ala Ile Met Ser Ala Phe Pro Gly
1               5                   10                  15

Glu Lys Val Thr Ile Thr Cys Ser Ala Ser Ser Ser Val Thr Tyr Met
            20                  25                  30

His Trp Phe Gln Gln Lys Pro Gly Thr Ser Pro Lys Leu Trp Ile Phe
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Phe Thr
                85                  90                  95

Phe Gly Ser Gly Thr Lys Leu Glu Ile Lys
            100                 105

<210> SEQ ID NO 47
<211> LENGTH: 106
<212> TYPE: PRT
<213> ORGANISM: Artificial Sequence
<220> FEATURE:
<223> OTHER INFORMATION: MTK-08 Light Chain Variable

<400> SEQUENCE: 47

Gln Ile Val Leu Ser Gln Ser Pro Ala Ile Leu Ser Ala Ser Pro Gly

```
                1               5                   10                  15
            Glu Lys Val Thr Met Thr Cys Arg Ala Thr Ser Ser Val Ser Tyr Met
                            20                  25                  30
            His Trp Phe Gln Gln Lys Pro Gly Ser Ser Pro Lys Pro Trp Ile Tyr
                        35                  40                  45
            Ala Thr Ser Asn Leu Ala Ser Gly Val Pro Ala Arg Phe Ser Gly Ser
                    50                  55                  60
            Gly Ser Gly Thr Ser Tyr Ser Leu Thr Ile Ser Arg Val Glu Ala Glu
            65                  70                  75                  80
            Asp Ala Ala Ala Tyr Tyr Cys Gln His Trp Ser Gly Asn Pro Arg Thr
                                85                  90                  95
            Phe Gly Gly Gly Thr Lys Leu Glu Ile Lys
                            100                 105
```

<210> SEQ ID NO 48
<211> LENGTH: 107
<212> TYPE: PRT
<213> ORGANISM: Artificial Sequence
<220> FEATURE:
<223> OTHER INFORMATION: MTK-09 Light Chain Variable

<400> SEQUENCE: 48

```
            Asp Ile Val Met Thr Gln Ser His Lys Phe Met Ser Thr Ser Val Gly
            1               5                   10                  15
            Asp Arg Val Ser Ile Thr Cys Lys Ala Ser Gln Asp Val Thr Thr Ser
                            20                  25                  30
            Val Ala Trp Tyr His Gln Lys Pro Gly Gln Ser Pro Glu Leu Leu Ile
                        35                  40                  45
            Tyr Ser Ala Ser Tyr Arg Tyr Thr Gly Val Pro Asp Arg Phe Thr Gly
                    50                  55                  60
            Ser Gly Ser Gly Thr Asp Phe Thr Phe Thr Ile Ser Ser Val Gln Ala
            65                  70                  75                  80
            Glu Asp Leu Ala Ile Tyr Tyr Cys Gln Gln His Tyr Ser Thr Pro Leu
                                85                  90                  95
            Thr Phe Gly Ser Gly Thr Lys Leu Gln Leu Lys
                            100                 105
```

<210> SEQ ID NO 49
<211> LENGTH: 107
<212> TYPE: PRT
<213> ORGANISM: Artificial Sequence
<220> FEATURE:
<223> OTHER INFORMATION: MTK-10 Light Chain Variable

<400> SEQUENCE: 49

```
            Asp Ile Gln Met Thr Gln Thr Thr Ser Ser Leu Ser Ala Ser Leu Gly
            1               5                   10                  15
            Asp Arg Val Thr Ile Ser Cys Ser Ala Ser Gln Gly Ile Ser Asn Tyr
                            20                  25                  30
            Leu Asn Trp Phe Gln Gln Lys Pro Asp Gly Thr Val Lys Leu Leu Ile
                        35                  40                  45
            Tyr Tyr Thr Ser Arg Leu His Ser Gly Val Pro Ser Arg Phe Ser Gly
                    50                  55                  60
            Ser Gly Ser Gly Thr Asp Phe Ser Leu Thr Ile Ser Asn Leu Glu Pro
            65                  70                  75                  80
            Glu Asp Ile Ala Thr Tyr Tyr Cys Gln Gln Tyr Thr Lys Leu Pro Tyr
                                85                  90                  95
```

```
Thr Phe Gly Gly Gly Thr Lys Leu Glu Ile Lys
            100                 105
```

<210> SEQ ID NO 50
<211> LENGTH: 108
<212> TYPE: PRT
<213> ORGANISM: Artificial Sequence
<220> FEATURE:
<223> OTHER INFORMATION: MTK-11 Light Chain Variable

<400> SEQUENCE: 50

```
Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Ile Ser Ser Ser
            20                  25                  30

Tyr Phe His Trp Tyr Gln Gln Lys Pro Gly Ser Ser Pro Lys Leu Trp
        35                  40                  45

Ile Tyr Ser Thr Ser Asn Leu Pro Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr Tyr Arg Ser Pro
                85                  90                  95

Leu Thr Phe Gly Ala Gly Thr Lys Leu Glu Leu Lys
            100                 105
```

<210> SEQ ID NO 51
<211> LENGTH: 106
<212> TYPE: PRT
<213> ORGANISM: Artificial Sequence
<220> FEATURE:
<223> OTHER INFORMATION: MTK-12 Light Chain Variable

<400> SEQUENCE: 51

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Arg Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Leu Thr
                85                  90                  95

Phe Gly Ala Gly Thr Lys Leu Glu Leu Lys
            100                 105
```

<210> SEQ ID NO 52
<211> LENGTH: 106
<212> TYPE: PRT
<213> ORGANISM: Artificial Sequence
<220> FEATURE:
<223> OTHER INFORMATION: MTK-13 Light Chain Variable

<400> SEQUENCE: 52

```
Gln Ile Val Leu Thr Gln Ser Pro Pro Ile Met Ser Ala Ser Pro Gly
1               5                   10                  15

Glu Lys Val Thr Ile Thr Cys Ser Ala Ser Ser Ser Val Ser Tyr Met
```

```
                    20                  25                  30

Tyr Trp Phe Gln Gln Lys Pro Gly Thr Ser Pro Lys Leu Trp Ile Tyr
            35                  40                  45

Ser Thr Phe Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Val Ala Thr Tyr Tyr Cys Gln Gln Arg Ser Ser Tyr Pro Phe Thr
                85                  90                  95

Phe Gly Ser Gly Thr Lys Leu Glu Ile Lys
            100                 105

<210> SEQ ID NO 53
<211> LENGTH: 106
<212> TYPE: PRT
<213> ORGANISM: Artificial Sequence
<220> FEATURE:
<223> OTHER INFORMATION: MTK-14 Light Chain Variable

<400> SEQUENCE: 53

Gln Ile Val Leu Ser Gln Ser Pro Ala Ile Leu Ser Ala Ser Pro Gly
1               5                   10                  15

Glu Lys Val Thr Met Thr Cys Arg Ser Ser Ser Val Ser Tyr Met
                20                  25                  30

His Trp Tyr Gln Gln Lys Pro Gly Ser Ser Pro Lys Pro Trp Ile Tyr
            35                  40                  45

Ala Thr Ser Asn Leu Ala Ser Gly Val Pro Gly Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Gly Ser Asn Pro Arg Thr
                85                  90                  95

Phe Gly Gly Gly Thr Lys Leu Glu Ile Lys
            100                 105

<210> SEQ ID NO 54
<211> LENGTH: 106
<212> TYPE: PRT
<213> ORGANISM: Artificial Sequence
<220> FEATURE:
<223> OTHER INFORMATION: MTK-15 Light Chain Variable

<400> SEQUENCE: 54

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Val Ser Tyr Met
                20                  25                  30

His Trp Tyr Gln Gln Lys Ser Gly Ser Ser Pro Lys Pro Trp Ile Tyr
            35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Pro Arg Thr
                85                  90                  95

Phe Gly Gly Gly Thr Lys Leu Glu Ile Lys
            100                 105
```

<210> SEQ ID NO 55
<211> LENGTH: 107
<212> TYPE: PRT
<213> ORGANISM: Artificial Sequence
<220> FEATURE:
<223> OTHER INFORMATION: MTK-16 Light Chain Variable

<400> SEQUENCE: 55

Asp Ile Val Met Thr Gln Ser Pro Lys Phe Met Ser Thr Ser Val Gly
1               5                   10                  15

Asp Arg Val Ser Ile Thr Cys Lys Ala Ser Gln Asn Val Arg Thr Ala
            20                  25                  30

Val Ala Trp Tyr Lys Lys Pro Gly Gln Ser Pro Lys Ala Leu Ile
        35                  40                  45

Asn Leu Ala Ser Asn Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Asn Tyr Pro Leu
                85                  90                  95

Thr Phe Gly Gly Gly Thr Lys Leu Glu Ile Lys
            100                 105

<210> SEQ ID NO 56
<211> LENGTH: 107
<212> TYPE: PRT
<213> ORGANISM: Artificial Sequence
<220> FEATURE:
<223> OTHER INFORMATION: MTK-17 Light Chain Variable

<400> SEQUENCE: 56

Asp Ile Gln Met Thr Gln Ser Ser Ser Tyr Leu Ser Val Ser Leu Gly
1               5                   10                  15

Gly Arg Val Thr Ile Thr Cys Lys Ala Ser Asp His Ile Asn Asn Trp
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Thr Pro Arg
                85                  90                  95

Thr Phe Gly Gly Gly Thr Lys Leu Glu Ile Lys
            100                 105

<210> SEQ ID NO 57
<211> LENGTH: 107
<212> TYPE: PRT
<213> ORGANISM: Artificial Sequence
<220> FEATURE:
<223> OTHER INFORMATION: MTK-18 Light Chain Variable

<400> SEQUENCE: 57

Asp Ile Gln Met Thr Gln Thr Thr Ser Ser Leu Ser Ala Ser Leu Gly
1               5                   10                  15

Asp Arg Val Thr Phe Ser Cys Arg Ala Ser Gln Ala Ile Ser Asn Tyr
            20                  25                  30

Leu Asn Trp Tyr Gln Gln Lys Pro Asp Gly Thr Val Lys Leu Leu Ile

```
            35                  40                  45
Tyr Tyr Thr Ser Arg Leu His Ser Gly Val Pro Ser Arg Phe Ser Gly
     50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Trp
                 85                  90                  95

Thr Phe Gly Gly Gly Thr Lys Leu Glu Ile Lys
            100                 105
```

<210> SEQ ID NO 58
<211> LENGTH: 112
<212> TYPE: PRT
<213> ORGANISM: Artificial Sequence
<220> FEATURE:
<223> OTHER INFORMATION: MTK-19 Light Chain Variable

<400> SEQUENCE: 58

```
Asp Val Val Met Thr Gln Ser Ser Leu Thr Leu Ser Val Thr Ile Gly
 1               5                  10                  15

Gln Pro Ala Ser Ile Ser Cys Lys Ser Ser Gln Ser Leu Leu Asp Ser
             20                  25                  30

Asp Gly Lys Thr Tyr Leu Asn Trp Leu Leu Gln Arg Pro Gly Gln Ser
         35                  40                  45

Pro Lys Arg Leu Ile Tyr Leu Val Ser Lys Leu Asp Ser Gly Val Pro
     50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Trp Gln Gly
                 85                  90                  95

Thr His Phe Pro Trp Thr Phe Gly Gly Gly Thr Lys Leu Glu Ile Lys
            100                 105                 110
```

<210> SEQ ID NO 59
<211> LENGTH: 107
<212> TYPE: PRT
<213> ORGANISM: Artificial Sequence
<220> FEATURE:
<223> OTHER INFORMATION: MTK-20 Light Chain Variable

<400> SEQUENCE: 59

```
Asp Ile Gln Met Thr Gln Thr Thr Ser Ser Leu Ser Ala Ser Leu Gly
 1               5                  10                  15

Asp Arg Val Thr Ile Ser Cys Arg Ala Ser Gln Asp Ile Asn Asn Tyr
             20                  25                  30

Leu Asn Trp Tyr Gln Gln Lys Pro Asp Gly Thr Val Lys Leu Leu Ile
         35                  40                  45

Tyr Tyr Thr Ser Arg Leu His Ser Gly Val Pro Ser Arg Phe Ser Gly
     50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Trp
                 85                  90                  95

Thr Phe Gly Gly Gly Thr Lys Leu Glu Ile Lys
            100                 105
```

<210> SEQ ID NO 60
<211> LENGTH: 107

<212> TYPE: PRT
<213> ORGANISM: Artificial Sequence
<220> FEATURE:
<223> OTHER INFORMATION: MTK-21 Light Chain Variable

<400> SEQUENCE: 60

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Asn Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Thr Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Arg Leu Glu Ile Lys
            100                 105

<210> SEQ ID NO 61
<211> LENGTH: 107
<212> TYPE: PRT
<213> ORGANISM: Artificial Sequence
<220> FEATURE:
<223> OTHER INFORMATION: MTK-22 Light Chain Variable

<400> SEQUENCE: 61

Asp Val Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Ile Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Arg Ser Gly Thr Val Phe Thr Leu Thr Ile Ser Asn Val Gln Ser
65                  70                  75                  80

Glu Asp Leu Ala Asp Tyr Phe Cys Gln Gln Tyr Thr Ser Tyr Pro Leu
                85                  90                  95

Thr Phe Gly Ser Gly Thr Lys Leu Glu Ile Lys
            100                 105

<210> SEQ ID NO 62
<211> LENGTH: 107
<212> TYPE: PRT
<213> ORGANISM: Artificial Sequence
<220> FEATURE:
<223> OTHER INFORMATION: MTK-23 Light Chain Variable

<400> SEQUENCE: 62

Asp Ile Val Met Thr Gln Ser His Lys Phe Met Ser Thr Pro Val Gly
1               5                   10                  15

Asp Arg Val Ser Ile Thr Cys Lys Ala Ser Arg Asp Val Ser Thr Ala
            20                  25                  30

Val Ala Trp Phe His Gln Lys Pro Gly Gln Ser Pro Lys Leu Leu Ile
        35                  40                  45

Tyr Ser Ala Ser Tyr Arg Ser Thr Gly Val Pro Asp Arg Phe Thr Gly

```
                    50                  55                  60
Ser Gly Ser Gly Thr Asp Phe Thr Phe Thr Ile Ser Ser Val Gln Ala
 65                  70                  75                  80

Glu Asp Leu Ala Val Tyr Tyr Cys Gln Gln His Tyr Ser Ala Pro Leu
                 85                  90                  95

Thr Phe Gly Ala Gly Thr Lys Leu Glu Leu Lys
            100                 105

<210> SEQ ID NO 63
<211> LENGTH: 107
<212> TYPE: PRT
<213> ORGANISM: Artificial Sequence
<220> FEATURE:
<223> OTHER INFORMATION: MTK-24 Light Chain Variable

<400> SEQUENCE: 63

Asp Ile Gln Met Thr Gln Ser Pro Ala Ser Leu Ser Val Ser Val Gly
  1               5                  10                  15

Glu Thr Val Thr Ile Thr Cys Arg Ala Ser Glu Asn Ile Tyr Ser Asn
                 20                  25                  30

Leu Ala Trp Tyr Gln Gln Lys Gln Gly Lys Ser Pro Gln Leu Leu Val
             35                  40                  45

Tyr Ala Ala Thr Asn Leu Ala Asp Gly Val Pro Ser Arg Phe Ser Gly
 50                  55                  60

Ser Gly Ser Gly Thr Gln Tyr Ser Leu Lys Ile Asn Ser Leu Gln Ser
 65                  70                  75                  80

Glu Asp Phe Gly Ser Tyr Tyr Cys Gln His Phe Trp Gly Thr Pro Leu
                 85                  90                  95

Thr Phe Gly Ala Gly Thr Lys Leu Glu Leu Lys
            100                 105

<210> SEQ ID NO 64
<211> LENGTH: 107
<212> TYPE: PRT
<213> ORGANISM: Artificial Sequence
<220> FEATURE:
<223> OTHER INFORMATION: MTK-25 Light Chain Variable

<400> SEQUENCE: 64

Asp Ile Val Met Thr Gln Ser Gln Lys Phe Met Ser Thr Ser Val Gly
  1               5                  10                  15

Asp Arg Val Ser Ile Thr Cys Lys Ala Ser Gln Asn Val Arg Thr Thr
                 20                  25                  30

Val Ala Trp Tyr Gln Gln Lys Pro Gly Gln Ser Pro Lys Thr Leu Ile
             35                  40                  45

Tyr Leu Ala Ser Asn Arg His Thr Gly Val Pro Asp Arg Phe Thr Gly
 50                  55                  60

Ser Gly Ser Gly Thr Asp Phe Thr Leu Thr Ile Ser Asn Val Gln Ser
 65                  70                  75                  80

Glu Asp Leu Ala Asp Tyr Phe Cys Leu Gln Leu Trp Asn Tyr Pro Trp
                 85                  90                  95

Thr Phe Gly Gly Gly Thr Lys Leu Glu Ile Lys
            100                 105

<210> SEQ ID NO 65
<211> LENGTH: 106
<212> TYPE: PRT
<213> ORGANISM: Artificial Sequence
<220> FEATURE:
```

<223> OTHER INFORMATION: MTK-26 Light Chain Variable

<400> SEQUENCE: 65

Gln Ile Val Leu Thr Gln Ser Pro Ala Ile Met Ser Ala Ser Pro Gly
1               5                   10                  15

Glu Lys Val Thr Ile Ala Cys Ser Ala Ser Ser Val Ser Phe Met
            20                  25                  30

His Trp Phe Gln Gln Lys Pro Gly Thr Ser Pro Arg Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Phe Thr
                85                  90                  95

Phe Gly Ser Gly Thr Lys Leu Glu Ile Lys
            100                 105

<210> SEQ ID NO 66
<211> LENGTH: 107
<212> TYPE: PRT
<213> ORGANISM: Artificial Sequence
<220> FEATURE:
<223> OTHER INFORMATION: MTK-27 Light Chain Variable

<400> SEQUENCE: 66

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Arg Thr Ser
            20                  25                  30

Val Ala Trp Tyr Gln Gln Lys Pro Gly Gln Ser Pro Lys Ala Leu Ile
        35                  40                  45

Tyr Leu Ala Ser Asn Arg His Thr Gly Val Pro Asp Arg Phe Thr Gly
    50                  55                  60

Ser Gly Ser Gly Thr Asp Phe Thr Leu Thr Ile Ser Asn Val Arg Ser
65                  70                  75                  80

Glu Asp Leu Ala Asp Tyr Phe Cys Leu Gln His Trp Asn Tyr Pro Tyr
                85                  90                  95

Thr Phe Gly Gly Gly Thr Lys Leu Glu Ile Lys
            100                 105

<210> SEQ ID NO 67
<211> LENGTH: 105
<212> TYPE: PRT
<213> ORGANISM: Artificial Sequence
<220> FEATURE:
<223> OTHER INFORMATION: MTK-28 Light Chain Variable

<400> SEQUENCE: 67

Gln Ile Val Leu Ser Gln Ser Pro Val Ile Leu Ser Ala Ser Pro Gly
1               5                   10                  15

Glu Lys Val Thr Met Thr Cys Arg Ala Ser Ser Ser Val Thr Tyr Met
            20                  25                  30

His Trp Tyr Gln Gln Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Thr Glu

```
                65                  70                  75                  80
Asp Ala Ala Thr Tyr Tyr Cys His Gln Trp Ser Gly Asn Pro Thr Phe
                    85                  90                  95
Gly Gly Gly Thr Lys Leu Glu Ile Asn
            100                 105

<210> SEQ ID NO 68
<211> LENGTH: 106
<212> TYPE: PRT
<213> ORGANISM: Artificial Sequence
<220> FEATURE:
<223> OTHER INFORMATION: MTK-29 Light Chain Variable

<400> SEQUENCE: 68

Gln Ile Val Leu Ser Gln Ser Pro Ala Ile Leu Ser Ala Ser Pro Gly
1               5                   10                  15
Glu Lys Val Thr Met Thr Cys Arg Ala Thr Ser Ser Val Gly Tyr Met
                20                  25                  30
His Trp Tyr Gln Gln Lys Pro Gly Ser Ser Pro Lys Pro Trp Ile Tyr
            35                  40                  45
Ala Thr Ser Asn Leu Ala Ser Gly Val Pro Ala Arg Phe Ser Gly Ser
        50                  55                  60
Gly Ser Gly Thr Ser Tyr Ser Leu Thr Ile Ser Arg Val Glu Ala Glu
65                  70                  75                  80
His Ala Ala Thr Tyr Tyr Cys Gln Gln Trp Gly Ser Asn Pro Phe Thr
                85                  90                  95
Phe Gly Ser Gly Thr Lys Leu Glu Ile Lys
            100                 105

<210> SEQ ID NO 69
<211> LENGTH: 112
<212> TYPE: PRT
<213> ORGANISM: Artificial Sequence
<220> FEATURE:
<223> OTHER INFORMATION: MTK-30 Light Chain Variable

<400> SEQUENCE: 69

Asp Val Leu Met Thr Gln Thr Pro Leu Ser Leu Pro Val Ser Leu Gly
1               5                   10                  15
Asp Gln Ala Ser Ile Ser Cys Arg Ser Ser Gln Ser Ile Val His Ser
                20                  25                  30
Asn Gly Asp Thr Tyr Leu Glu Trp Tyr Leu Gln Lys Pro Gly Gln Ser
            35                  40                  45
Pro Lys Leu Leu Ile Tyr Lys Val Ser Asn Arg Phe Ser Gly Val Pro
        50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Tyr Cys Phe Gln Gly
                85                  90                  95
Ser His Val Pro Trp Thr Phe Gly Gly Gly Thr Lys Leu Glu Ile Lys
            100                 105                 110

<210> SEQ ID NO 70
<211> LENGTH: 112
<212> TYPE: PRT
<213> ORGANISM: Artificial Sequence
<220> FEATURE:
<223> OTHER INFORMATION: MTK-31 Light Chain Variable

<400> SEQUENCE: 70
```

```
Asp Val Ser Met Thr Gln Thr Pro Leu Ser Leu Pro Val Ser Leu Gly
1               5                   10                  15

Asp Gln Ala Ser Ile Ser Ser Arg Ser Ser Gln Thr Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110
```

<210> SEQ ID NO 71
<211> LENGTH: 106
<212> TYPE: PRT
<213> ORGANISM: Artificial Sequence
<220> FEATURE:
<223> OTHER INFORMATION: MTK-32 Light Chain Variable

<400> SEQUENCE: 71

```
Gln Ile Val Leu Ser Gln Ser Pro Ala Ile Leu Ser Ala Ser Pro Gly
1               5                   10                  15

Glu Lys Val Thr Met Thr Cys Arg Ala Thr Ser Ser Val Gly Tyr Met
            20                  25                  30

His Trp Tyr Gln Arg Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Pro Arg Thr
                85                  90                  95

Phe Gly Gly Gly Thr Lys Leu Glu Ile Lys
            100                 105
```

<210> SEQ ID NO 72
<211> LENGTH: 107
<212> TYPE: PRT
<213> ORGANISM: Artificial Sequence
<220> FEATURE:
<223> OTHER INFORMATION: MTK-33, 34 Light Chain Variable

<400> SEQUENCE: 72

```
Ser Ile Val Met Thr Gln Thr Pro Lys Phe Leu Leu Val Ser Ala Gly
1               5                   10                  15

Asp Arg Val Ile Ile Thr Cys Lys Ala Ser Gln Ser Val Ser Asn Thr
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Arg Ser Pro Phe
```

```
                    85                  90                  95
Thr Phe Gly Ser Gly Thr Gln Leu Glu Met Lys
                100                 105

<210> SEQ ID NO 73
<211> LENGTH: 108
<212> TYPE: PRT
<213> ORGANISM: Artificial Sequence
<220> FEATURE:
<223> OTHER INFORMATION: MTK-35 Light Chain Variable

<400> SEQUENCE: 73

Glu Ile Val Leu Thr Gln Ser Pro Thr Thr Met Ala Ala Ser Pro Gly
1               5                   10                  15

Glu Lys Ile Thr Ile Thr Cys Arg Ala Ser Ser Ser Ile Ser Ser His
            20                  25                  30

Tyr Leu His Trp Tyr Gln Gln Lys Pro Gly Phe Ser Pro Lys Leu Leu
        35                  40                  45

Ile Tyr Arg Thr Ser Asn Leu Ala Ser Gly Val Pro Ala Arg Phe Ser
    50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Thr Ile Pro
                85                  90                  95

Leu Thr Phe Gly Ala Gly Thr Lys Leu Val Leu Lys
                100                 105

<210> SEQ ID NO 74
<211> LENGTH: 106
<212> TYPE: PRT
<213> ORGANISM: Artificial Sequence
<220> FEATURE:
<223> OTHER INFORMATION: MTK-36 Light Chain Variable

<400> SEQUENCE: 74

Gln Ile Val Leu Ser Gln Ser Pro Ala Ile Leu Ser Ala Phe Pro Gly
1               5                   10                  15

Glu Lys Val Thr Met Thr Cys Arg Ala Thr Ser Ser Val Arg Tyr Met
            20                  25                  30

His Trp Tyr Gln Gln Lys Pro Gly Ser Ser Pro Lys Pro Trp Ile Tyr
        35                  40                  45

Ala Thr Tyr Asn Leu Thr Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys His Gln Trp Ser Ser Asn Pro Tyr Thr
                85                  90                  95

Phe Gly Gly Gly Thr Lys Leu Glu Ile Lys
                100                 105

<210> SEQ ID NO 75
<211> LENGTH: 5
<212> TYPE: PRT
<213> ORGANISM: Artificial Sequence
<220> FEATURE:
<223> OTHER INFORMATION: MTK-01, 04, 06, 08, 14 HVR-H1

<400> SEQUENCE: 75

Asn Tyr Gly Met Asn
1               5
```

```
<210> SEQ ID NO 76
<211> LENGTH: 5
<212> TYPE: PRT
<213> ORGANISM: Artificial Sequence
<220> FEATURE:
<223> OTHER INFORMATION: MTK-02 HVR-H1

<400> SEQUENCE: 76

Asp Tyr Gly Val Asn
1               5

<210> SEQ ID NO 77
<211> LENGTH: 6
<212> TYPE: PRT
<213> ORGANISM: Artificial Sequence
<220> FEATURE:
<223> OTHER INFORMATION: MTK-03, 07, 13 HVR-H1

<400> SEQUENCE: 77

Ser Gly Tyr Tyr Trp Asn
1               5

<210> SEQ ID NO 78
<211> LENGTH: 5
<212> TYPE: PRT
<213> ORGANISM: Artificial Sequence
<220> FEATURE:
<223> OTHER INFORMATION: MTK-05 HVR-H1

<400> SEQUENCE: 78

Ser Tyr Trp Ile Gln
1               5

<210> SEQ ID NO 79
<211> LENGTH: 5
<212> TYPE: PRT
<213> ORGANISM: Artificial Sequence
<220> FEATURE:
<223> OTHER INFORMATION: MTK-09 HVR-H1

<400> SEQUENCE: 79

Asn His His Ile Lys
1               5

<210> SEQ ID NO 80
<211> LENGTH: 7
<212> TYPE: PRT
<213> ORGANISM: Artificial Sequence
<220> FEATURE:
<223> OTHER INFORMATION: MTK-10 HVR-H1

<400> SEQUENCE: 80

Thr Ser Gly Met Gly Val Gly
1               5

<210> SEQ ID NO 81
<211> LENGTH: 5
<212> TYPE: PRT
<213> ORGANISM: Artificial Sequence
<220> FEATURE:
<223> OTHER INFORMATION: MTK-11 HVR-H1

<400> SEQUENCE: 81

Asp Tyr Gly Val His
1               5
```

```
<210> SEQ ID NO 82
<211> LENGTH: 5
<212> TYPE: PRT
<213> ORGANISM: Artificial Sequence
<220> FEATURE:
<223> OTHER INFORMATION: MTK-12 HVR-H1

<400> SEQUENCE: 82

Ser His Trp Met His
1               5

<210> SEQ ID NO 83
<211> LENGTH: 5
<212> TYPE: PRT
<213> ORGANISM: Artificial Sequence
<220> FEATURE:
<223> OTHER INFORMATION: MTK-15, 15.1, 15.2, 15.3, 15.4, 15.5, 15.6,
      15.7, 15.8, 15.9, 15.10, 15.11, 15.12, 15.13, 15.14, 15.15 HVR-H1

<400> SEQUENCE: 83

Asn Tyr Gly Val His
1               5

<210> SEQ ID NO 84
<211> LENGTH: 5
<212> TYPE: PRT
<213> ORGANISM: Artificial Sequence
<220> FEATURE:
<223> OTHER INFORMATION: MTK-16, 16.1, 16.2 HVR-H1

<400> SEQUENCE: 84

Asn His Gly Met Asn
1               5

<210> SEQ ID NO 85
<211> LENGTH: 5
<212> TYPE: PRT
<213> ORGANISM: Artificial Sequence
<220> FEATURE:
<223> OTHER INFORMATION: MTK-17 HVR-H1

<400> SEQUENCE: 85

Asn Phe Gly Met Asn
1               5

<210> SEQ ID NO 86
<211> LENGTH: 5
<212> TYPE: PRT
<213> ORGANISM: Artificial Sequence
<220> FEATURE:
<223> OTHER INFORMATION: MTK-18 HVR-H1

<400> SEQUENCE: 86

His Tyr Gly Met Thr
1               5

<210> SEQ ID NO 87
<211> LENGTH: 5
<212> TYPE: PRT
<213> ORGANISM: Artificial Sequence
<220> FEATURE:
<223> OTHER INFORMATION: MTK-19 HVR-H1

<400> SEQUENCE: 87

Glu Tyr Thr Met His
1               5
```

```
<210> SEQ ID NO 88
<211> LENGTH: 5
<212> TYPE: PRT
<213> ORGANISM: Artificial Sequence
<220> FEATURE:
<223> OTHER INFORMATION: MTK-20 HVR-H1

<400> SEQUENCE: 88

Asn Tyr Gly Met Thr
1               5

<210> SEQ ID NO 89
<211> LENGTH: 5
<212> TYPE: PRT
<213> ORGANISM: Artificial Sequence
<220> FEATURE:
<223> OTHER INFORMATION: MTK-21 HVR-H1

<400> SEQUENCE: 89

Asn Phe Gly Met Thr
1               5

<210> SEQ ID NO 90
<211> LENGTH: 5
<212> TYPE: PRT
<213> ORGANISM: Artificial Sequence
<220> FEATURE:
<223> OTHER INFORMATION: MTK-22, 24, 30, 33, 33.1, 33.2, 33.3, 33.4,
      33.5, 33.6, 33.7, 33.8, 33.9, 33.10, 33.11, 33.12, 33.13, 33.14,
      33.15, 33.16, 33.17, 33.18, 33.19, 33.20, 33.21, 33.22, 33.23,
      33.24, 34 HVR-H1

<400> SEQUENCE: 90

Ser Tyr Trp Met His
1               5

<210> SEQ ID NO 91
<211> LENGTH: 5
<212> TYPE: PRT
<213> ORGANISM: Artificial Sequence
<220> FEATURE:
<223> OTHER INFORMATION: MTK-23 HVR-H1

<400> SEQUENCE: 91

Asn His His Ile Asn
1               5

<210> SEQ ID NO 92
<211> LENGTH: 5
<212> TYPE: PRT
<213> ORGANISM: Artificial Sequence
<220> FEATURE:
<223> OTHER INFORMATION: MTK-25 HVR-H1

<400> SEQUENCE: 92

Asp Tyr Tyr Met Ala
1               5

<210> SEQ ID NO 93
<211> LENGTH: 6
<212> TYPE: PRT
<213> ORGANISM: Artificial Sequence
<220> FEATURE:
<223> OTHER INFORMATION: MTK-26 HVR-H1

<400> SEQUENCE: 93

Ser Gly Tyr Tyr Trp Asp
```

```
1               5

<210> SEQ ID NO 94
<211> LENGTH: 5
<212> TYPE: PRT
<213> ORGANISM: Artificial Sequence
<220> FEATURE:
<223> OTHER INFORMATION: MTK-27 HVR-H1

<400> SEQUENCE: 94

Asp Asp Tyr Met His
1               5

<210> SEQ ID NO 95
<211> LENGTH: 5
<212> TYPE: PRT
<213> ORGANISM: Artificial Sequence
<220> FEATURE:
<223> OTHER INFORMATION: MTK-28, 29, 29.2, 29.3, 29.4, 29.6, 29.7,
      29.10, 29.11, 29.12, 29.13, 29.14, 29.15, 29.19, 29.20, 29.21
      HVR-H1

<400> SEQUENCE: 95

Thr Tyr Gly Met Ser
1               5

<210> SEQ ID NO 96
<211> LENGTH: 5
<212> TYPE: PRT
<213> ORGANISM: Artificial Sequence
<220> FEATURE:
<223> OTHER INFORMATION: MTK-31, 32 HVR-H1

<400> SEQUENCE: 96

Ser Tyr Gly Met Ser
1               5

<210> SEQ ID NO 97
<211> LENGTH: 5
<212> TYPE: PRT
<213> ORGANISM: Artificial Sequence
<220> FEATURE:
<223> OTHER INFORMATION: MTK-35 HVR-H1

<400> SEQUENCE: 97

Ser Tyr Asp Ile His
1               5

<210> SEQ ID NO 98
<211> LENGTH: 7
<212> TYPE: PRT
<213> ORGANISM: Artificial Sequence
<220> FEATURE:
<223> OTHER INFORMATION: MTK-36 HVR-H1

<400> SEQUENCE: 98

Thr Phe Gly Met Gly Val Gly
1               5

<210> SEQ ID NO 99
<211> LENGTH: 17
<212> TYPE: PRT
<213> ORGANISM: Artificial Sequence
<220> FEATURE:
<223> OTHER INFORMATION: MTK-01, 04, 08, 15, 16, 16.2, 17, 18, 20 HVR-H2

<400> SEQUENCE: 99
```

```
Trp Ile Asn Thr Tyr Thr Gly Glu Pro Thr Tyr Ala Asp Asp Phe Lys
1               5                   10                  15

Gly

<210> SEQ ID NO 100
<211> LENGTH: 17
<212> TYPE: PRT
<213> ORGANISM: Artificial Sequence
<220> FEATURE:
<223> OTHER INFORMATION: MTK-02 HVR-H2

<400> SEQUENCE: 100

Trp Ile Asn Thr Tyr Ser Gly Glu Pro Thr Tyr Ala Gly Asp Phe Lys
1               5                   10                  15

Gly

<210> SEQ ID NO 101
<211> LENGTH: 16
<212> TYPE: PRT
<213> ORGANISM: Artificial Sequence
<220> FEATURE:
<223> OTHER INFORMATION: MTK-03, 07 HVR-H2

<400> SEQUENCE: 101

Tyr Met Ser Phe Asp Gly Asp Asn Lys Phe Asn Pro Ser Leu Lys Asn
1               5                   10                  15

<210> SEQ ID NO 102
<211> LENGTH: 17
<212> TYPE: PRT
<213> ORGANISM: Artificial Sequence
<220> FEATURE:
<223> OTHER INFORMATION: MTK-05 HVR-H2

<400> SEQUENCE: 102

Glu Ile Phe Pro Gly Thr Gly Thr Thr Tyr Tyr Asn Glu Lys Phe Lys
1               5                   10                  15

Gly

<210> SEQ ID NO 103
<211> LENGTH: 17
<212> TYPE: PRT
<213> ORGANISM: Artificial Sequence
<220> FEATURE:
<223> OTHER INFORMATION: MTK-06 HVR-H2

<400> SEQUENCE: 103

Trp Ile Asn Thr Asn Thr Gly Glu Pro Thr Tyr Ala Glu Glu Phe Lys
1               5                   10                  15

Gly

<210> SEQ ID NO 104
<211> LENGTH: 17
<212> TYPE: PRT
<213> ORGANISM: Artificial Sequence
<220> FEATURE:
<223> OTHER INFORMATION: MTK-09 HVR-H2

<400> SEQUENCE: 104

Tyr Ile Asp Pro Tyr Asn Asp Tyr Thr Thr Tyr Asn Gln Asn Phe Lys
1               5                   10                  15

Gly
```

-continued

```
<210> SEQ ID NO 105
<211> LENGTH: 16
<212> TYPE: PRT
<213> ORGANISM: Artificial Sequence
<220> FEATURE:
<223> OTHER INFORMATION: MTK-10 HVR-H2

<400> SEQUENCE: 105

His Ile Trp Ser Asp Asp Lys Arg Ser Asn Pro Ala Leu Lys Ser
1               5                   10                  15

<210> SEQ ID NO 106
<211> LENGTH: 16
<212> TYPE: PRT
<213> ORGANISM: Artificial Sequence
<220> FEATURE:
<223> OTHER INFORMATION: MTK-11 HVR-H2

<400> SEQUENCE: 106

Val Ile Trp Ser Ser Gly Thr Thr Asp Tyr Asn Glu Ala Phe Ile Ser
1               5                   10                  15

<210> SEQ ID NO 107
<211> LENGTH: 17
<212> TYPE: PRT
<213> ORGANISM: Artificial Sequence
<220> FEATURE:
<223> OTHER INFORMATION: MTK-12 HVR-H2

<400> SEQUENCE: 107

Met Ile Asp Pro Ser Asp Gly Glu Ser Arg Leu Asn Gln Lys Phe Lys
1               5                   10                  15

Asp

<210> SEQ ID NO 108
<211> LENGTH: 16
<212> TYPE: PRT
<213> ORGANISM: Artificial Sequence
<220> FEATURE:
<223> OTHER INFORMATION: MTK-13 HVR-H2

<400> SEQUENCE: 108

Asn Ile Asp Tyr Asp Gly Ser Asn Lys Tyr Asn Pro Ser Leu Lys Asn
1               5                   10                  15

<210> SEQ ID NO 109
<211> LENGTH: 17
<212> TYPE: PRT
<213> ORGANISM: Artificial Sequence
<220> FEATURE:
<223> OTHER INFORMATION: MTK-14 HVR-H2

<400> SEQUENCE: 109

Trp Ile Asn Thr Tyr Thr Gly Glu Pro Thr Tyr Ala Asp Asp Phe Thr
1               5                   10                  15

Gly

<210> SEQ ID NO 110
<211> LENGTH: 17
<212> TYPE: PRT
<213> ORGANISM: Artificial Sequence
<220> FEATURE:
<223> OTHER INFORMATION: MTK-19 HVR-H2

<400> SEQUENCE: 110

Gly Phe Asn Pro Asn Asn Val Ile Thr Ser Tyr Asn Gln Arg Phe Gln
```

-continued

```
1               5                   10                  15

Gly

<210> SEQ ID NO 111
<211> LENGTH: 17
<212> TYPE: PRT
<213> ORGANISM: Artificial Sequence
<220> FEATURE:
<223> OTHER INFORMATION: MTK-21 HVR-H2

<400> SEQUENCE: 111

Trp Ile Asn Thr Tyr Thr Gly Glu Pro Lys Tyr Ala Asp Asp Phe Lys
1               5                   10                  15

Gly

<210> SEQ ID NO 112
<211> LENGTH: 17
<212> TYPE: PRT
<213> ORGANISM: Artificial Sequence
<220> FEATURE:
<223> OTHER INFORMATION: MTK-22 HVR-H2

<400> SEQUENCE: 112

Glu Ile Asp Pro Ser Asp Ser Ser Asn Tyr Asn Gln Lys Phe Lys
1               5                   10                  15

Gly

<210> SEQ ID NO 113
<211> LENGTH: 17
<212> TYPE: PRT
<213> ORGANISM: Artificial Sequence
<220> FEATURE:
<223> OTHER INFORMATION: MTK-23 HVR-H2

<400> SEQUENCE: 113

Asn Val Asp Pro Tyr Asn Asp Tyr Ser Thr Tyr Asn Gln Lys Phe Lys
1               5                   10                  15

Gly

<210> SEQ ID NO 114
<211> LENGTH: 16
<212> TYPE: PRT
<213> ORGANISM: Artificial Sequence
<220> FEATURE:
<223> OTHER INFORMATION: MTK-24 HVR-H2

<400> SEQUENCE: 114

Met Ile His Pro Asn Ile Asn Thr Asn Tyr Asn Glu Lys Phe Lys Ser
1               5                   10                  15

<210> SEQ ID NO 115
<211> LENGTH: 17
<212> TYPE: PRT
<213> ORGANISM: Artificial Sequence
<220> FEATURE:
<223> OTHER INFORMATION: MTK-25 HVR-H2

<400> SEQUENCE: 115

Asn Ile Asn Tyr Glu Gly Ser Ser Thr Tyr Tyr Leu Gly Ser Leu Lys
1               5                   10                  15

Ser

<210> SEQ ID NO 116
```

```
<211> LENGTH: 16
<212> TYPE: PRT
<213> ORGANISM: Artificial Sequence
<220> FEATURE:
<223> OTHER INFORMATION: MTK-26 HVR-H2

<400> SEQUENCE: 116

Tyr Ile Ser Tyr Asp Gly Ser Asn Asn Tyr Asn Pro Ser Leu Lys Asn
1               5                   10                  15

<210> SEQ ID NO 117
<211> LENGTH: 17
<212> TYPE: PRT
<213> ORGANISM: Artificial Sequence
<220> FEATURE:
<223> OTHER INFORMATION: MTK-27 HVR-H2

<400> SEQUENCE: 117

Trp Ile Asp Pro Glu Asn Gly Asn Thr Glu Tyr Ala Ser Lys Phe Gln
1               5                   10                  15

Gly

<210> SEQ ID NO 118
<211> LENGTH: 17
<212> TYPE: PRT
<213> ORGANISM: Artificial Sequence
<220> FEATURE:
<223> OTHER INFORMATION: MTK-28, 31 HVR-H2

<400> SEQUENCE: 118

Trp Ile Asn Thr Tyr Ser Gly Val Pro Thr Tyr Ala Asp Asp Phe Lys
1               5                   10                  15

Gly

<210> SEQ ID NO 119
<211> LENGTH: 17
<212> TYPE: PRT
<213> ORGANISM: Artificial Sequence
<220> FEATURE:
<223> OTHER INFORMATION: MTK-29, 29.2, 29.4, 29.5, 29.8, 29.9, 29.10
      HVR-H2

<400> SEQUENCE: 119

Trp Ile Asn Thr Tyr Ser Gly Val Pro Thr Tyr Thr Asp Asp Phe Lys
1               5                   10                  15

Gly

<210> SEQ ID NO 120
<211> LENGTH: 17
<212> TYPE: PRT
<213> ORGANISM: Artificial Sequence
<220> FEATURE:
<223> OTHER INFORMATION: MTK-30 HVR-H2

<400> SEQUENCE: 120

Asn Leu Asn Pro Asn Asn Gly Gly Thr Tyr Tyr Asn Glu Lys Phe Lys
1               5                   10                  15

Ser

<210> SEQ ID NO 121
<211> LENGTH: 17
<212> TYPE: PRT
<213> ORGANISM: Artificial Sequence
<220> FEATURE:
<223> OTHER INFORMATION: MTK-32 HVR-H2
```

```
<400> SEQUENCE: 121

Trp Ile Asn Thr Tyr Ser Gly Val Pro Thr Tyr Ala Asp Asp Phe Arg
1               5                   10                  15

Gly

<210> SEQ ID NO 122
<211> LENGTH: 17
<212> TYPE: PRT
<213> ORGANISM: Artificial Sequence
<220> FEATURE:
<223> OTHER INFORMATION: MTK-33, 34 HVR-H2

<400> SEQUENCE: 122

Val Ile Asp Pro Ser Asp Asn Tyr Ile Asn Tyr Asn Gln Lys Phe Lys
1               5                   10                  15

Gly

<210> SEQ ID NO 123
<211> LENGTH: 17
<212> TYPE: PRT
<213> ORGANISM: Artificial Sequence
<220> FEATURE:
<223> OTHER INFORMATION: MTK-35 HVR-H2

<400> SEQUENCE: 123

Trp Ile Tyr Pro Arg Asp Gly Tyr Thr Lys Tyr Asn Glu Ile Phe Lys
1               5                   10                  15

Gly

<210> SEQ ID NO 124
<211> LENGTH: 16
<212> TYPE: PRT
<213> ORGANISM: Artificial Sequence
<220> FEATURE:
<223> OTHER INFORMATION: MTK-36 HVR-H2

<400> SEQUENCE: 124

His Ile Trp Trp Tyr Asp Asp Lys Tyr Tyr Glu Pro Ala Leu Lys Ser
1               5                   10                  15

<210> SEQ ID NO 125
<211> LENGTH: 9
<212> TYPE: PRT
<213> ORGANISM: Artificial Sequence
<220> FEATURE:
<223> OTHER INFORMATION: MTK-01 HVR-H3

<400> SEQUENCE: 125

Arg Asp Arg Tyr Thr Trp Phe Ala Tyr
1               5

<210> SEQ ID NO 126
<211> LENGTH: 9
<212> TYPE: PRT
<213> ORGANISM: Artificial Sequence
<220> FEATURE:
<223> OTHER INFORMATION: MTK-02 HVR-H3

<400> SEQUENCE: 126

Arg Val Arg Tyr Trp Tyr Phe Asp Val
1               5

<210> SEQ ID NO 127
```

```
<211> LENGTH: 11
<212> TYPE: PRT
<213> ORGANISM: Artificial Sequence
<220> FEATURE:
<223> OTHER INFORMATION: MTK-03, 07 HVR-H3

<400> SEQUENCE: 127

Gly Gly Tyr Asn Tyr Gly Ser Thr Glu Ala Asn
1               5                   10

<210> SEQ ID NO 128
<211> LENGTH: 9
<212> TYPE: PRT
<213> ORGANISM: Artificial Sequence
<220> FEATURE:
<223> OTHER INFORMATION: MTK-04 HVR-H3

<400> SEQUENCE: 128

Tyr Asp Asn Tyr Ala Trp Phe Ala Tyr
1               5

<210> SEQ ID NO 129
<211> LENGTH: 7
<212> TYPE: PRT
<213> ORGANISM: Artificial Sequence
<220> FEATURE:
<223> OTHER INFORMATION: MTK-05 HVR-H3

<400> SEQUENCE: 129

Asp Gly Ala Tyr Phe Asp Val
1               5

<210> SEQ ID NO 130
<211> LENGTH: 9
<212> TYPE: PRT
<213> ORGANISM: Artificial Sequence
<220> FEATURE:
<223> OTHER INFORMATION: MTK-06 HVR-H3

<400> SEQUENCE: 130

Tyr Tyr Asn Tyr Trp Tyr Phe Asp Val
1               5

<210> SEQ ID NO 131
<211> LENGTH: 9
<212> TYPE: PRT
<213> ORGANISM: Artificial Sequence
<220> FEATURE:
<223> OTHER INFORMATION: MTK-08 HVR-H3

<400> SEQUENCE: 131

Glu Val Arg Tyr Trp Tyr Phe Asp Val
1               5

<210> SEQ ID NO 132
<211> LENGTH: 14
<212> TYPE: PRT
<213> ORGANISM: Artificial Sequence
<220> FEATURE:
<223> OTHER INFORMATION: MTK-09 HVR-H3

<400> SEQUENCE: 132

Arg Ala Tyr Asp Gly Tyr Tyr Val Asp Trp Tyr Phe Asp Val
1               5                   10

<210> SEQ ID NO 133
<211> LENGTH: 9
```

```
<212> TYPE: PRT
<213> ORGANISM: Artificial Sequence
<220> FEATURE:
<223> OTHER INFORMATION: MTK-10 HVR-H3

<400> SEQUENCE: 133

Leu Thr Pro Val Arg Glu Phe Ala Tyr
1               5

<210> SEQ ID NO 134
<211> LENGTH: 10
<212> TYPE: PRT
<213> ORGANISM: Artificial Sequence
<220> FEATURE:
<223> OTHER INFORMATION: MTK-11 HVR-H3

<400> SEQUENCE: 134

Lys Gly His Asp Pro Tyr Ala Met Asp Tyr
1               5                   10

<210> SEQ ID NO 135
<211> LENGTH: 13
<212> TYPE: PRT
<213> ORGANISM: Artificial Sequence
<220> FEATURE:
<223> OTHER INFORMATION: MTK-12 HVR-H3

<400> SEQUENCE: 135

Gly Ile Tyr Tyr Tyr Gly Ile Thr Tyr Ala Met Asp Tyr
1               5                   10

<210> SEQ ID NO 136
<211> LENGTH: 10
<212> TYPE: PRT
<213> ORGANISM: Artificial Sequence
<220> FEATURE:
<223> OTHER INFORMATION: MTK-13 HVR-H3

<400> SEQUENCE: 136

Asp Gly Gly Asn Tyr Arg Ser Phe Ala Tyr
1               5                   10

<210> SEQ ID NO 137
<211> LENGTH: 9
<212> TYPE: PRT
<213> ORGANISM: Artificial Sequence
<220> FEATURE:
<223> OTHER INFORMATION: MTK-14 HVR-H3

<400> SEQUENCE: 137

Gly Gly His Tyr Ala Trp Phe Ala Tyr
1               5

<210> SEQ ID NO 138
<211> LENGTH: 9
<212> TYPE: PRT
<213> ORGANISM: Artificial Sequence
<220> FEATURE:
<223> OTHER INFORMATION: MTK-15, 15.2, 15.3, 15.4, 15.6, 15.7, 15.14,
      15.15 HVR-H3

<400> SEQUENCE: 138

Gly Asn Arg Tyr Ala Tyr Met Asp Tyr
1               5

<210> SEQ ID NO 139
<211> LENGTH: 11
```

```
<212> TYPE: PRT
<213> ORGANISM: Artificial Sequence
<220> FEATURE:
<223> OTHER INFORMATION: MTK-16, 16.1, 16.2 HVR-H3

<400> SEQUENCE: 139

Lys Gly Val Thr Ala Ala Arg Tyr Phe Asp Tyr
1               5                   10

<210> SEQ ID NO 140
<211> LENGTH: 11
<212> TYPE: PRT
<213> ORGANISM: Artificial Sequence
<220> FEATURE:
<223> OTHER INFORMATION: MTK-17 HVR-H3

<400> SEQUENCE: 140

Gly Ala Val Leu Arg Ala Gly Ala Met Asp Cys
1               5                   10

<210> SEQ ID NO 141
<211> LENGTH: 12
<212> TYPE: PRT
<213> ORGANISM: Artificial Sequence
<220> FEATURE:
<223> OTHER INFORMATION: MTK-18 HVR-H3

<400> SEQUENCE: 141

Gly Gly Gly Gln Leu Gly Leu Arg Pro Leu Asp Tyr
1               5                   10

<210> SEQ ID NO 142
<211> LENGTH: 16
<212> TYPE: PRT
<213> ORGANISM: Artificial Sequence
<220> FEATURE:
<223> OTHER INFORMATION: MTK-19 HVR-H3

<400> SEQUENCE: 142

Gly Asp Leu Leu Trp Ser Leu Leu Leu Pro Gly Asn Tyr Phe Asp Tyr
1               5                   10                  15

<210> SEQ ID NO 143
<211> LENGTH: 12
<212> TYPE: PRT
<213> ORGANISM: Artificial Sequence
<220> FEATURE:
<223> OTHER INFORMATION: MTK-20, 21 HVR-H3

<400> SEQUENCE: 143

Gly Gly Gly Arg Leu Gly Leu Arg Pro Leu Asp Tyr
1               5                   10

<210> SEQ ID NO 144
<211> LENGTH: 11
<212> TYPE: PRT
<213> ORGANISM: Artificial Sequence
<220> FEATURE:
<223> OTHER INFORMATION: MTK-22 HVR-H3

<400> SEQUENCE: 144

Arg Tyr Tyr Tyr Gly Ser Leu Tyr Phe Asp Asn
1               5                   10

<210> SEQ ID NO 145
<211> LENGTH: 14
<212> TYPE: PRT
```

```
<213> ORGANISM: Artificial Sequence
<220> FEATURE:
<223> OTHER INFORMATION: MTK-23 HVR-H3

<400> SEQUENCE: 145

Arg Val Tyr Asp Gly Phe Tyr Val Asp Trp Tyr Phe Asp Val
1               5                   10

<210> SEQ ID NO 146
<211> LENGTH: 13
<212> TYPE: PRT
<213> ORGANISM: Artificial Sequence
<220> FEATURE:
<223> OTHER INFORMATION: MTK-24 HVR-H3

<400> SEQUENCE: 146

Arg Ser Pro Tyr Ser Asn Tyr Asp Trp Tyr Phe Asp Val
1               5                   10

<210> SEQ ID NO 147
<211> LENGTH: 8
<212> TYPE: PRT
<213> ORGANISM: Artificial Sequence
<220> FEATURE:
<223> OTHER INFORMATION: MTK-25 HVR-H3

<400> SEQUENCE: 147

Tyr Tyr Tyr Gly Ser Val Asp Tyr
1               5

<210> SEQ ID NO 148
<211> LENGTH: 10
<212> TYPE: PRT
<213> ORGANISM: Artificial Sequence
<220> FEATURE:
<223> OTHER INFORMATION: MTK-26 HVR-H3

<400> SEQUENCE: 148

Glu Gly Gly Tyr Tyr Arg Ser Met Asp Tyr
1               5                   10

<210> SEQ ID NO 149
<211> LENGTH: 8
<212> TYPE: PRT
<213> ORGANISM: Artificial Sequence
<220> FEATURE:
<223> OTHER INFORMATION: MTK-27 HVR-H3

<400> SEQUENCE: 149

Leu Phe Ser Asn Tyr Phe Asp Tyr
1               5

<210> SEQ ID NO 150
<211> LENGTH: 9
<212> TYPE: PRT
<213> ORGANISM: Artificial Sequence
<220> FEATURE:
<223> OTHER INFORMATION: MTK-28 HVR-H3

<400> SEQUENCE: 150

Phe Leu Arg Tyr Tyr Tyr Phe Asp Tyr
1               5

<210> SEQ ID NO 151
<211> LENGTH: 9
<212> TYPE: PRT
<213> ORGANISM: Artificial Sequence
```

```
<220> FEATURE:
<223> OTHER INFORMATION: MTK-29, 29.19, 29.20, 29.21 HVR-H3

<400> SEQUENCE: 151

Tyr Thr Asn Tyr Gly Tyr Phe Asp Tyr
1               5

<210> SEQ ID NO 152
<211> LENGTH: 8
<212> TYPE: PRT
<213> ORGANISM: Artificial Sequence
<220> FEATURE:
<223> OTHER INFORMATION: MTK-30 HVR-H3

<400> SEQUENCE: 152

Gln Ile Leu Leu Tyr Phe Asp Tyr
1               5

<210> SEQ ID NO 153
<211> LENGTH: 13
<212> TYPE: PRT
<213> ORGANISM: Artificial Sequence
<220> FEATURE:
<223> OTHER INFORMATION: MTK-31 HVR-H3

<400> SEQUENCE: 153

Leu Ser Tyr Asp Gly Ser Leu Tyr His Ala Met Asp Tyr
1               5                   10

<210> SEQ ID NO 154
<211> LENGTH: 9
<212> TYPE: PRT
<213> ORGANISM: Artificial Sequence
<220> FEATURE:
<223> OTHER INFORMATION: MTK-32 HVR-H3

<400> SEQUENCE: 154

Glu Asp Asn Trp Ala Trp Phe Ala Tyr
1               5

<210> SEQ ID NO 155
<211> LENGTH: 10
<212> TYPE: PRT
<213> ORGANISM: Artificial Sequence
<220> FEATURE:
<223> OTHER INFORMATION: MTK-33, 33.2, 33.4, 33.5, 33.6, 33.7, 33.9,
      33.10, 33.12, 33.13, 33.14, 33.15, 33.16, 33.17, 33.18, 33.19,
      33.20, 33.21, 33.22, 33.24, 34 HVR-H3

<400> SEQUENCE: 155

Glu Ala Gly Thr Arg Gly Tyr Phe Asp Tyr
1               5                   10

<210> SEQ ID NO 156
<211> LENGTH: 11
<212> TYPE: PRT
<213> ORGANISM: Artificial Sequence
<220> FEATURE:
<223> OTHER INFORMATION: MTK-35 HVR-H3

<400> SEQUENCE: 156

Ala Tyr Tyr Thr Asn Trp Tyr Tyr Phe Asp Tyr
1               5                   10

<210> SEQ ID NO 157
<211> LENGTH: 12
<212> TYPE: PRT
```

<213> ORGANISM: Artificial Sequence
<220> FEATURE:
<223> OTHER INFORMATION: MTK-36 HVR-H3

<400> SEQUENCE: 157

Ile Tyr Tyr Gly Thr Ser Tyr Arg Tyr Phe Asp Val
1               5                   10

<210> SEQ ID NO 158
<211> LENGTH: 10
<212> TYPE: PRT
<213> ORGANISM: Artificial Sequence
<220> FEATURE:
<223> OTHER INFORMATION: MTK-01, 04, 06, 15, 15.1, 15.2, 15.11, 15.14,
      15.15 HVR-L1

<400> SEQUENCE: 158

Arg Ala Ser Ser Ser Val Ser Tyr Met His
1               5                   10

<210> SEQ ID NO 159
<211> LENGTH: 10
<212> TYPE: PRT
<213> ORGANISM: Artificial Sequence
<220> FEATURE:
<223> OTHER INFORMATION: MTK-02 HVR-L1

<400> SEQUENCE: 159

Arg Ala Asn Ser Ser Val Ser Tyr Met His
1               5                   10

<210> SEQ ID NO 160
<211> LENGTH: 10
<212> TYPE: PRT
<213> ORGANISM: Artificial Sequence
<220> FEATURE:
<223> OTHER INFORMATION: MTK-03 HVR-L1

<400> SEQUENCE: 160

Ser Ala Ser Ser Ser Val Asn Tyr Met His
1               5                   10

<210> SEQ ID NO 161
<211> LENGTH: 11
<212> TYPE: PRT
<213> ORGANISM: Artificial Sequence
<220> FEATURE:
<223> OTHER INFORMATION: MTK-05 HVR-L1

<400> SEQUENCE: 161

Arg Ala Ser Glu Asn Ile Phe Ser Tyr Leu Ala
1               5                   10

<210> SEQ ID NO 162
<211> LENGTH: 10
<212> TYPE: PRT
<213> ORGANISM: Artificial Sequence
<220> FEATURE:
<223> OTHER INFORMATION: MTK-07 HVR-L1

<400> SEQUENCE: 162

Ser Ala Ser Ser Ser Val Thr Tyr Met His
1               5                   10

<210> SEQ ID NO 163
<211> LENGTH: 10
<212> TYPE: PRT

```
<213> ORGANISM: Artificial Sequence
<220> FEATURE:
<223> OTHER INFORMATION: MTK-08 HVR-L1

<400> SEQUENCE: 163

Arg Ala Thr Ser Ser Val Ser Tyr Met His
1               5                   10

<210> SEQ ID NO 164
<211> LENGTH: 11
<212> TYPE: PRT
<213> ORGANISM: Artificial Sequence
<220> FEATURE:
<223> OTHER INFORMATION: MTK-09 HVR-L1

<400> SEQUENCE: 164

Lys Ala Ser Gln Asp Val Thr Thr Ser Val Ala
1               5                   10

<210> SEQ ID NO 165
<211> LENGTH: 11
<212> TYPE: PRT
<213> ORGANISM: Artificial Sequence
<220> FEATURE:
<223> OTHER INFORMATION: MTK-10 HVR-L1

<400> SEQUENCE: 165

Ser Ala Ser Gln Gly Ile Ser Asn Tyr Leu Asn
1               5                   10

<210> SEQ ID NO 166
<211> LENGTH: 12
<212> TYPE: PRT
<213> ORGANISM: Artificial Sequence
<220> FEATURE:
<223> OTHER INFORMATION: MTK-11 HVR-L1

<400> SEQUENCE: 166

Thr Ala Ser Ser Ser Ile Ser Ser Ser Tyr Phe His
1               5                   10

<210> SEQ ID NO 167
<211> LENGTH: 10
<212> TYPE: PRT
<213> ORGANISM: Artificial Sequence
<220> FEATURE:
<223> OTHER INFORMATION: MTK-12, 13 HVR-L1

<400> SEQUENCE: 167

Ser Ala Ser Ser Ser Val Ser Tyr Met Tyr
1               5                   10

<210> SEQ ID NO 168
<211> LENGTH: 10
<212> TYPE: PRT
<213> ORGANISM: Artificial Sequence
<220> FEATURE:
<223> OTHER INFORMATION: MTK-14 HVR-L1

<400> SEQUENCE: 168

Arg Ser Ser Ser Ser Val Ser Tyr Met His
1               5                   10

<210> SEQ ID NO 169
<211> LENGTH: 11
<212> TYPE: PRT
<213> ORGANISM: Artificial Sequence
```

```
<220> FEATURE:
<223> OTHER INFORMATION: MTK-16, 16.1 HVR-L1

<400> SEQUENCE: 169

Lys Ala Ser Gln Asn Val Arg Thr Ala Val Ala
1               5                   10

<210> SEQ ID NO 170
<211> LENGTH: 11
<212> TYPE: PRT
<213> ORGANISM: Artificial Sequence
<220> FEATURE:
<223> OTHER INFORMATION: MTK-17 HVR-L1

<400> SEQUENCE: 170

Lys Ala Ser Asp His Ile Asn Asn Trp Leu Ala
1               5                   10

<210> SEQ ID NO 171
<211> LENGTH: 11
<212> TYPE: PRT
<213> ORGANISM: Artificial Sequence
<220> FEATURE:
<223> OTHER INFORMATION: MTK-18 HVR-L1

<400> SEQUENCE: 171

Arg Ala Ser Gln Ala Ile Ser Asn Tyr Leu Asn
1               5                   10

<210> SEQ ID NO 172
<211> LENGTH: 16
<212> TYPE: PRT
<213> ORGANISM: Artificial Sequence
<220> FEATURE:
<223> OTHER INFORMATION: MTK-19 HVR-L1

<400> SEQUENCE: 172

Lys Ser Ser Gln Ser Leu Leu Asp Ser Asp Gly Lys Thr Tyr Leu Asn
1               5                   10                  15

<210> SEQ ID NO 173
<211> LENGTH: 11
<212> TYPE: PRT
<213> ORGANISM: Artificial Sequence
<220> FEATURE:
<223> OTHER INFORMATION: MTK-20, 21 HVR-L1

<400> SEQUENCE: 173

Arg Ala Ser Gln Asp Ile Asn Asn Tyr Leu Asn
1               5                   10

<210> SEQ ID NO 174
<211> LENGTH: 11
<212> TYPE: PRT
<213> ORGANISM: Artificial Sequence
<220> FEATURE:
<223> OTHER INFORMATION: MTK-22 HVR-L1

<400> SEQUENCE: 174

Lys Ala Ser Gln Asp Val Gly Thr Ala Ile Ala
1               5                   10

<210> SEQ ID NO 175
<211> LENGTH: 11
<212> TYPE: PRT
<213> ORGANISM: Artificial Sequence
<220> FEATURE:
```

```
<223> OTHER INFORMATION: MTK-23 HVR-L1

<400> SEQUENCE: 175

Lys Ala Ser Arg Asp Val Ser Thr Ala Val Ala
1               5                   10

<210> SEQ ID NO 176
<211> LENGTH: 11
<212> TYPE: PRT
<213> ORGANISM: Artificial Sequence
<220> FEATURE:
<223> OTHER INFORMATION: MTK-24 HVR-L1

<400> SEQUENCE: 176

Arg Ala Ser Glu Asn Ile Tyr Ser Asn Leu Ala
1               5                   10

<210> SEQ ID NO 177
<211> LENGTH: 11
<212> TYPE: PRT
<213> ORGANISM: Artificial Sequence
<220> FEATURE:
<223> OTHER INFORMATION: MTK-25 HVR-L1

<400> SEQUENCE: 177

Lys Ala Ser Gln Asn Val Arg Thr Thr Val Ala
1               5                   10

<210> SEQ ID NO 178
<211> LENGTH: 10
<212> TYPE: PRT
<213> ORGANISM: Artificial Sequence
<220> FEATURE:
<223> OTHER INFORMATION: MTK-26 HVR-L1

<400> SEQUENCE: 178

Ser Ala Ser Ser Ser Val Ser Phe Met His
1               5                   10

<210> SEQ ID NO 179
<211> LENGTH: 11
<212> TYPE: PRT
<213> ORGANISM: Artificial Sequence
<220> FEATURE:
<223> OTHER INFORMATION: MTK-27 HVR-L1

<400> SEQUENCE: 179

Lys Ala Ser Gln Asn Val Arg Thr Ser Val Ala
1               5                   10

<210> SEQ ID NO 180
<211> LENGTH: 10
<212> TYPE: PRT
<213> ORGANISM: Artificial Sequence
<220> FEATURE:
<223> OTHER INFORMATION: MTK-28 HVR-L1

<400> SEQUENCE: 180

Arg Ala Ser Ser Ser Val Thr Tyr Met His
1               5                   10

<210> SEQ ID NO 181
<211> LENGTH: 10
<212> TYPE: PRT
<213> ORGANISM: Artificial Sequence
<220> FEATURE:
<223> OTHER INFORMATION: MTK-29, 29.19, 29.20, 29.21, 32 HVR-L1
```

<400> SEQUENCE: 181

Arg Ala Thr Ser Ser Val Gly Tyr Met His
1               5                   10

<210> SEQ ID NO 182
<211> LENGTH: 16
<212> TYPE: PRT
<213> ORGANISM: Artificial Sequence
<220> FEATURE:
<223> OTHER INFORMATION: MTK-30 HVR-L1

<400> SEQUENCE: 182

Arg Ser Ser Gln Ser Ile Val His Ser Asn Gly Asp Thr Tyr Leu Glu
1               5                   10                  15

<210> SEQ ID NO 183
<211> LENGTH: 16
<212> TYPE: PRT
<213> ORGANISM: Artificial Sequence
<220> FEATURE:
<223> OTHER INFORMATION: MTK-31 HVR-L1

<400> SEQUENCE: 183

Arg Ser Ser Gln Thr Ile Val His Ser Asn Gly Asn Thr Tyr Leu Glu
1               5                   10                  15

<210> SEQ ID NO 184
<211> LENGTH: 11
<212> TYPE: PRT
<213> ORGANISM: Artificial Sequence
<220> FEATURE:
<223> OTHER INFORMATION: MTK-33, 34 HVR-L1

<400> SEQUENCE: 184

Lys Ala Ser Gln Ser Val Ser Asn Thr Val Ala
1               5                   10

<210> SEQ ID NO 185
<211> LENGTH: 12
<212> TYPE: PRT
<213> ORGANISM: Artificial Sequence
<220> FEATURE:
<223> OTHER INFORMATION: MTK-35 HVR-L1

<400> SEQUENCE: 185

Arg Ala Ser Ser Ser Ile Ser Ser His Tyr Leu His
1               5                   10

<210> SEQ ID NO 186
<211> LENGTH: 10
<212> TYPE: PRT
<213> ORGANISM: Artificial Sequence
<220> FEATURE:
<223> OTHER INFORMATION: MTK-36 HVR-L1

<400> SEQUENCE: 186

Arg Ala Thr Ser Ser Val Arg Tyr Met His
1               5                   10

<210> SEQ ID NO 187
<211> LENGTH: 7
<212> TYPE: PRT
<213> ORGANISM: Artificial Sequence
<220> FEATURE:
<223> OTHER INFORMATION: MTK-01, 02, 04, 06, 08, 14, 15, 15.1, 15.2,
      15.3, 15.4, 15.5, 15.6, 15.7, 15.8, 15.9, 15.10, 15.11, 15.12,

```
              15.13, 15.14, 15.15, 28, 29, 29.1, 29.2, 29.3, 29.10, 29.11,
              29.18, 29.19, 29.20, 29.21, 32 HVR-L2

<400> SEQUENCE: 187

Ala Thr Ser Asn Leu Ala Ser
1               5

<210> SEQ ID NO 188
<211> LENGTH: 7
<212> TYPE: PRT
<213> ORGANISM: Artificial Sequence
<220> FEATURE:
<223> OTHER INFORMATION: MTK-03, 07, 26 HVR-L2

<400> SEQUENCE: 188

Ser Thr Ser Asn Leu Ala Ser
1               5

<210> SEQ ID NO 189
<211> LENGTH: 7
<212> TYPE: PRT
<213> ORGANISM: Artificial Sequence
<220> FEATURE:
<223> OTHER INFORMATION: MTK-05 HVR-L2

<400> SEQUENCE: 189

Asn Ala Lys Thr Leu Ala Glu
1               5

<210> SEQ ID NO 190
<211> LENGTH: 7
<212> TYPE: PRT
<213> ORGANISM: Artificial Sequence
<220> FEATURE:
<223> OTHER INFORMATION: MTK-09 HVR-L2

<400> SEQUENCE: 190

Ser Ala Ser Tyr Arg Tyr Thr
1               5

<210> SEQ ID NO 191
<211> LENGTH: 7
<212> TYPE: PRT
<213> ORGANISM: Artificial Sequence
<220> FEATURE:
<223> OTHER INFORMATION: MTK-10, 18, 20 HVR-L2

<400> SEQUENCE: 191

Tyr Thr Ser Arg Leu His Ser
1               5

<210> SEQ ID NO 192
<211> LENGTH: 7
<212> TYPE: PRT
<213> ORGANISM: Artificial Sequence
<220> FEATURE:
<223> OTHER INFORMATION: MTK-11 HVR-L2

<400> SEQUENCE: 192

Ser Thr Ser Asn Leu Pro Ser
1               5

<210> SEQ ID NO 193
<211> LENGTH: 7
<212> TYPE: PRT
<213> ORGANISM: Artificial Sequence
<220> FEATURE:
```

```
<223> OTHER INFORMATION: MTK-12 HVR-L2

<400> SEQUENCE: 193

Asp Thr Ser Asn Leu Ala Ser
1               5

<210> SEQ ID NO 194
<211> LENGTH: 7
<212> TYPE: PRT
<213> ORGANISM: Artificial Sequence
<220> FEATURE:
<223> OTHER INFORMATION: MTK-13 HVR-L2

<400> SEQUENCE: 194

Ser Thr Phe Asn Leu Ala Ser
1               5

<210> SEQ ID NO 195
<211> LENGTH: 7
<212> TYPE: PRT
<213> ORGANISM: Artificial Sequence
<220> FEATURE:
<223> OTHER INFORMATION: MTK-16, 16.1, 16.2, 25, 27 HVR-L2

<400> SEQUENCE: 195

Leu Ala Ser Asn Arg His Thr
1               5

<210> SEQ ID NO 196
<211> LENGTH: 7
<212> TYPE: PRT
<213> ORGANISM: Artificial Sequence
<220> FEATURE:
<223> OTHER INFORMATION: MTK-17 HVR-L2

<400> SEQUENCE: 196

Gly Ala Thr Ser Leu Glu Thr
1               5

<210> SEQ ID NO 197
<211> LENGTH: 7
<212> TYPE: PRT
<213> ORGANISM: Artificial Sequence
<220> FEATURE:
<223> OTHER INFORMATION: MTK-19 HVR-L2

<400> SEQUENCE: 197

Leu Val Ser Lys Leu Asp Ser
1               5

<210> SEQ ID NO 198
<211> LENGTH: 7
<212> TYPE: PRT
<213> ORGANISM: Artificial Sequence
<220> FEATURE:
<223> OTHER INFORMATION: MTK-21 HVR-L2

<400> SEQUENCE: 198

Tyr Thr Ser Ser Leu His Ser
1               5

<210> SEQ ID NO 199
<211> LENGTH: 7
<212> TYPE: PRT
<213> ORGANISM: Artificial Sequence
<220> FEATURE:
<223> OTHER INFORMATION: MTK-22 HVR-L2
```

```
<400> SEQUENCE: 199

Trp Ala Ser Thr Arg His Thr
1               5

<210> SEQ ID NO 200
<211> LENGTH: 7
<212> TYPE: PRT
<213> ORGANISM: Artificial Sequence
<220> FEATURE:
<223> OTHER INFORMATION: MTK-23 HVR-L2

<400> SEQUENCE: 200

Ser Ala Ser Tyr Arg Ser Thr
1               5

<210> SEQ ID NO 201
<211> LENGTH: 7
<212> TYPE: PRT
<213> ORGANISM: Artificial Sequence
<220> FEATURE:
<223> OTHER INFORMATION: MTK-24 HVR-L2

<400> SEQUENCE: 201

Ala Ala Thr Asn Leu Ala Asp
1               5

<210> SEQ ID NO 202
<211> LENGTH: 7
<212> TYPE: PRT
<213> ORGANISM: Artificial Sequence
<220> FEATURE:
<223> OTHER INFORMATION: MTK-30, 31 HVR-L2

<400> SEQUENCE: 202

Lys Val Ser Asn Arg Phe Ser
1               5

<210> SEQ ID NO 203
<211> LENGTH: 7
<212> TYPE: PRT
<213> ORGANISM: Artificial Sequence
<220> FEATURE:
<223> OTHER INFORMATION: MTK-33, 33.2, 33.3, 33.4, 33.6, 33.7, 33.8,
      33.9, 33.10, 33.11, 33.12, 33.13, 33.14, 33.15, 33.16, 33.17,
      33.18, 33.19, 33.20, 33.23, 33.24, 34 HVR-L2

<400> SEQUENCE: 203

Tyr Ala Ser Asn Arg Tyr Thr
1               5

<210> SEQ ID NO 204
<211> LENGTH: 7
<212> TYPE: PRT
<213> ORGANISM: Artificial Sequence
<220> FEATURE:
<223> OTHER INFORMATION: MTK-35 HVR-L2

<400> SEQUENCE: 204

Arg Thr Ser Asn Leu Ala Ser
1               5

<210> SEQ ID NO 205
<211> LENGTH: 7
<212> TYPE: PRT
<213> ORGANISM: Artificial Sequence
<220> FEATURE:
```

<223> OTHER INFORMATION: MTK-36 HVR-L2

<400> SEQUENCE: 205

Ala Thr Tyr Asn Leu Thr Ser
1               5

<210> SEQ ID NO 206

<400> SEQUENCE: 206

000

<210> SEQ ID NO 207
<211> LENGTH: 9
<212> TYPE: PRT
<213> ORGANISM: Artificial Sequence
<220> FEATURE:
<223> OTHER INFORMATION: MTK-01 HVR-L3

<400> SEQUENCE: 207

Gln Gln Trp Ser Ser Asn Pro Pro Thr
1               5

<210> SEQ ID NO 208
<211> LENGTH: 9
<212> TYPE: PRT
<213> ORGANISM: Artificial Sequence
<220> FEATURE:
<223> OTHER INFORMATION: MTK-02, 29, 29.19, 29.20, 29.21 HVR-L3

<400> SEQUENCE: 208

Gln Gln Trp Gly Ser Asn Pro Phe Thr
1               5

<210> SEQ ID NO 209
<211> LENGTH: 9
<212> TYPE: PRT
<213> ORGANISM: Artificial Sequence
<220> FEATURE:
<223> OTHER INFORMATION: MTK-03, 07, 13, 26 HVR-L3

<400> SEQUENCE: 209

Gln Gln Arg Ser Ser Tyr Pro Phe Thr
1               5

<210> SEQ ID NO 210
<211> LENGTH: 9
<212> TYPE: PRT
<213> ORGANISM: Artificial Sequence
<220> FEATURE:
<223> OTHER INFORMATION: MTK-04, 15, 15.1, 15.2, 15.3, 15.4, 15.5, 15.6,
      15.7, 15.8, 15.9, 15.10, 15.11, 15.12, 15.13, 15.14, 15.15, 32
      HVR-L3

<400> SEQUENCE: 210

Gln Gln Trp Ser Ser Asn Pro Arg Thr
1               5

<210> SEQ ID NO 211
<211> LENGTH: 9
<212> TYPE: PRT
<213> ORGANISM: Artificial Sequence
<220> FEATURE:
<223> OTHER INFORMATION: MTK-05 HVR-L3

<400> SEQUENCE: 211

Leu His His Tyr Gly Thr Pro Leu Thr

```
1               5

<210> SEQ ID NO 212
<211> LENGTH: 9
<212> TYPE: PRT
<213> ORGANISM: Artificial Sequence
<220> FEATURE:
<223> OTHER INFORMATION: MTK-06 HVR-L3

<400> SEQUENCE: 212

Gln Gln Trp Ser Ser Lys Pro Pro Thr
1               5

<210> SEQ ID NO 213
<211> LENGTH: 9
<212> TYPE: PRT
<213> ORGANISM: Artificial Sequence
<220> FEATURE:
<223> OTHER INFORMATION: MTK-08 HVR-L3

<400> SEQUENCE: 213

Gln His Trp Ser Gly Asn Pro Arg Thr
1               5

<210> SEQ ID NO 214
<211> LENGTH: 9
<212> TYPE: PRT
<213> ORGANISM: Artificial Sequence
<220> FEATURE:
<223> OTHER INFORMATION: MTK-09 HVR-L3

<400> SEQUENCE: 214

Gln Gln His Tyr Ser Thr Pro Leu Thr
1               5

<210> SEQ ID NO 215
<211> LENGTH: 9
<212> TYPE: PRT
<213> ORGANISM: Artificial Sequence
<220> FEATURE:
<223> OTHER INFORMATION: MTK-10 HVR-L3

<400> SEQUENCE: 215

Gln Gln Tyr Thr Lys Leu Pro Tyr Thr
1               5

<210> SEQ ID NO 216
<211> LENGTH: 9
<212> TYPE: PRT
<213> ORGANISM: Artificial Sequence
<220> FEATURE:
<223> OTHER INFORMATION: MTK-11 HVR-L3

<400> SEQUENCE: 216

His Gln Tyr Tyr Arg Ser Pro Leu Thr
1               5

<210> SEQ ID NO 217
<211> LENGTH: 9
<212> TYPE: PRT
<213> ORGANISM: Artificial Sequence
<220> FEATURE:
<223> OTHER INFORMATION: MTK-12 HVR-L3

<400> SEQUENCE: 217

Gln Gln Trp Ser Ser Tyr Pro Leu Thr
1               5
```

```
<210> SEQ ID NO 218
<211> LENGTH: 9
<212> TYPE: PRT
<213> ORGANISM: Artificial Sequence
<220> FEATURE:
<223> OTHER INFORMATION: MTK-14 HVR-L3

<400> SEQUENCE: 218

Gln Gln Trp Gly Ser Asn Pro Arg Thr
1               5

<210> SEQ ID NO 219
<211> LENGTH: 9
<212> TYPE: PRT
<213> ORGANISM: Artificial Sequence
<220> FEATURE:
<223> OTHER INFORMATION: MTK-16, 16.1, 16.2 HVR-L3

<400> SEQUENCE: 219

Leu Gln His Trp Asn Tyr Pro Leu Thr
1               5

<210> SEQ ID NO 220
<211> LENGTH: 9
<212> TYPE: PRT
<213> ORGANISM: Artificial Sequence
<220> FEATURE:
<223> OTHER INFORMATION: MTK-17 HVR-L3

<400> SEQUENCE: 220

Gln Gln Tyr Trp Ser Thr Pro Arg Thr
1               5

<210> SEQ ID NO 221
<211> LENGTH: 9
<212> TYPE: PRT
<213> ORGANISM: Artificial Sequence
<220> FEATURE:
<223> OTHER INFORMATION: MTK-18, 21 HVR-L3

<400> SEQUENCE: 221

Gln Gln Gly Asn Thr Leu Pro Trp Thr
1               5

<210> SEQ ID NO 222
<211> LENGTH: 9
<212> TYPE: PRT
<213> ORGANISM: Artificial Sequence
<220> FEATURE:
<223> OTHER INFORMATION: MTK-19 HVR-L3

<400> SEQUENCE: 222

Trp Gln Gly Thr His Phe Pro Trp Thr
1               5

<210> SEQ ID NO 223
<211> LENGTH: 8
<212> TYPE: PRT
<213> ORGANISM: Artificial Sequence
<220> FEATURE:
<223> OTHER INFORMATION: MTK-20 HVR-L3

<400> SEQUENCE: 223

Gln Gln Gly Asn Thr Leu Pro Trp
1               5
```

<210> SEQ ID NO 224
<211> LENGTH: 9
<212> TYPE: PRT
<213> ORGANISM: Artificial Sequence
<220> FEATURE:
<223> OTHER INFORMATION: MTK-22 HVR-L3

<400> SEQUENCE: 224

Gln Gln Tyr Thr Ser Tyr Pro Leu Thr
1               5

<210> SEQ ID NO 225
<211> LENGTH: 9
<212> TYPE: PRT
<213> ORGANISM: Artificial Sequence
<220> FEATURE:
<223> OTHER INFORMATION: MTK-23 HVR-L3

<400> SEQUENCE: 225

Gln Gln His Tyr Ser Ala Pro Leu Thr
1               5

<210> SEQ ID NO 226
<211> LENGTH: 9
<212> TYPE: PRT
<213> ORGANISM: Artificial Sequence
<220> FEATURE:
<223> OTHER INFORMATION: MTK-24 HVR-L3

<400> SEQUENCE: 226

Gln His Phe Trp Gly Thr Pro Leu Thr
1               5

<210> SEQ ID NO 227
<211> LENGTH: 9
<212> TYPE: PRT
<213> ORGANISM: Artificial Sequence
<220> FEATURE:
<223> OTHER INFORMATION: MTK-25 HVR-L3

<400> SEQUENCE: 227

Leu Gln Leu Trp Asn Tyr Pro Trp Thr
1               5

<210> SEQ ID NO 228
<211> LENGTH: 9
<212> TYPE: PRT
<213> ORGANISM: Artificial Sequence
<220> FEATURE:
<223> OTHER INFORMATION: MTK-27 HVR-L3

<400> SEQUENCE: 228

Leu Gln His Trp Asn Tyr Pro Tyr Thr
1               5

<210> SEQ ID NO 229
<211> LENGTH: 8
<212> TYPE: PRT
<213> ORGANISM: Artificial Sequence
<220> FEATURE:
<223> OTHER INFORMATION: MTK-28 HVR-L3

<400> SEQUENCE: 229

His Gln Trp Ser Gly Asn Pro Thr
1               5

```
<210> SEQ ID NO 230
<211> LENGTH: 9
<212> TYPE: PRT
<213> ORGANISM: Artificial Sequence
<220> FEATURE:
<223> OTHER INFORMATION: MTK-30, 31 HVR-L3

<400> SEQUENCE: 230

Phe Gln Gly Ser His Val Pro Trp Thr
1               5

<210> SEQ ID NO 231
<211> LENGTH: 9
<212> TYPE: PRT
<213> ORGANISM: Artificial Sequence
<220> FEATURE:
<223> OTHER INFORMATION: MTK-33, 33.1, 33.2, 33.3, 33.5, 33.6, 33.7,
      33.8, 33.9, 33.10, 33.11, 33.13, 33.14, 33.16, 34 HVR-L3

<400> SEQUENCE: 231

Gln Gln Asp Tyr Arg Ser Pro Phe Thr
1               5

<210> SEQ ID NO 232
<211> LENGTH: 9
<212> TYPE: PRT
<213> ORGANISM: Artificial Sequence
<220> FEATURE:
<223> OTHER INFORMATION: MTK-35 HVR-L3

<400> SEQUENCE: 232

Gln Gln Gly Ser Thr Ile Pro Leu Thr
1               5

<210> SEQ ID NO 233
<211> LENGTH: 9
<212> TYPE: PRT
<213> ORGANISM: Artificial Sequence
<220> FEATURE:
<223> OTHER INFORMATION: MTK-36 HVR-L3

<400> SEQUENCE: 233

His Gln Trp Ser Ser Asn Pro Tyr Thr
1               5

<210> SEQ ID NO 234
<211> LENGTH: 118
<212> TYPE: PRT
<213> ORGANISM: Artificial Sequence
<220> FEATURE:
<223> OTHER INFORMATION: MTK-15.1 Heavy Chain Variable

<400> SEQUENCE: 234

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Val His Trp Val Arg Gln Ala Pro Gly Gln Gly Leu Glu Trp Met
        35                  40                  45

Gly Trp Ile Asn Thr Tyr Thr Gly Glu Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95
```

Ala Arg Gly Asn Arg Tyr Ala Tyr Gln Asp Tyr Trp Gly Gln Gly Thr
            100                 105                 110

Leu Val Thr Val Ser Ser
        115

<210> SEQ ID NO 235
<211> LENGTH: 118
<212> TYPE: PRT
<213> ORGANISM: Artificial Sequence
<220> FEATURE:
<223> OTHER INFORMATION: MTK-15.2 Heavy Chain Variable

<400> SEQUENCE: 235

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Val His Trp Val Arg Gln Ala Pro Gly Gln Gly Leu Glu Trp Met
        35                  40                  45

Gly Trp Gly Asn Thr Tyr Thr Gly Glu Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Gly Asn Arg Tyr Ala Tyr Met Asp Tyr Trp Gly Gln Gly Thr
            100                 105                 110

Leu Val Thr Val Ser Ser
        115

<210> SEQ ID NO 236
<211> LENGTH: 118
<212> TYPE: PRT
<213> ORGANISM: Artificial Sequence
<220> FEATURE:
<223> OTHER INFORMATION: MTK-15.3, 15.4 Heavy Chain Variable

<400> SEQUENCE: 236

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Val His Trp Val Arg Gln Ala Pro Gly Gln Gly Leu Glu Trp Met
        35                  40                  45

Gly Trp Ile Asn Thr Tyr Thr Gly Glu Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Gly Asn Arg Tyr Ala Tyr Met Asp Tyr Trp Gly Gln Gly Thr
            100                 105                 110

Leu Val Thr Val Ser Ser
        115

<210> SEQ ID NO 237
<211> LENGTH: 118
<212> TYPE: PRT

```
<213> ORGANISM: Artificial Sequence
<220> FEATURE:
<223> OTHER INFORMATION: MTK-15.5 Heavy Chain Variable

<400> SEQUENCE: 237

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Val His Trp Val Arg Gln Ala Pro Gly Gln Gly Leu Glu Trp Met
        35                  40                  45

Gly Trp Ile Asn Thr Tyr Thr Gly Glu Pro Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Thr Arg Gly Thr Arg Tyr Ala Tyr Met Asp Tyr Trp Gly Gln Gly Thr
            100                 105                 110

Leu Val Thr Val Ser Ser
        115

<210> SEQ ID NO 238
<211> LENGTH: 118
<212> TYPE: PRT
<213> ORGANISM: Artificial Sequence
<220> FEATURE:
<223> OTHER INFORMATION: MTK-15.6 Heavy Chain Variable

<400> SEQUENCE: 238

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Val His Trp Val Arg Gln Ala Pro Gly Gln Gly Leu Glu Trp Met
        35                  40                  45

Gly Trp Ile Asn Thr Tyr Thr Gly Glu Pro Tyr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Gly Asn Arg Tyr Ala Tyr Met Asp Tyr Trp Gly Gln Gly Thr
            100                 105                 110

Leu Val Thr Val Ser Ser
        115

<210> SEQ ID NO 239
<211> LENGTH: 118
<212> TYPE: PRT
<213> ORGANISM: Artificial Sequence
<220> FEATURE:
<223> OTHER INFORMATION: MTK-15.7 Heavy Chain Variable

<400> SEQUENCE: 239

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30
```

-continued

Gly Val His Trp Val Arg Gln Ala Pro Gly Gln Gly Leu Glu Trp Met
            35                  40                  45

Gly Trp Ile Asn Thr Tyr Thr Gly Glu Pro Thr Tyr Ala Gln Gly Phe
        50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Val Arg Gly Asn Arg Tyr Ala Tyr Met Asp Tyr Trp Gly Gln Gly Thr
            100                 105                 110

Leu Val Thr Val Ser Ser
            115

<210> SEQ ID NO 240
<211> LENGTH: 118
<212> TYPE: PRT
<213> ORGANISM: Artificial Sequence
<220> FEATURE:
<223> OTHER INFORMATION: MTK-15.8 Heavy Chain Variable

<400> SEQUENCE: 240

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Val His Trp Val Arg Gln Ala Pro Gly Gln Gly Leu Glu Trp Met
            35                  40                  45

Gly Trp Ile Asn Thr Tyr Thr Gly Glu Pro Thr Tyr Ala Gln Gly Phe
        50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Gly Val Arg Tyr Ala Tyr Met Asp Tyr Trp Gly Gln Gly Thr
            100                 105                 110

Leu Val Thr Val Ser Ser
            115

<210> SEQ ID NO 241
<211> LENGTH: 118
<212> TYPE: PRT
<213> ORGANISM: Artificial Sequence
<220> FEATURE:
<223> OTHER INFORMATION: MTK-15.9 Heavy Chain Variable

<400> SEQUENCE: 241

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Val His Trp Val Arg Gln Ala Pro Gly Gln Gly Leu Glu Trp Met
            35                  40                  45

Gly Trp Ile Asn Thr Tyr Thr Gly Glu Pro Thr Tyr Ala Gln Gly Phe
        50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys

```
                    85                  90                  95

Ala Arg Gly Tyr Arg Tyr Ala Tyr Met Asp Tyr Trp Gly Gln Gly Thr
                100                 105                 110

Leu Val Thr Val Ser Ser
        115

<210> SEQ ID NO 242
<211> LENGTH: 118
<212> TYPE: PRT
<213> ORGANISM: Artificial Sequence
<220> FEATURE:
<223> OTHER INFORMATION: MTK-15.10 Heavy Chain Variable

<400> SEQUENCE: 242

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Ala Asn Tyr
                20                  25                  30

Gly Val His Trp Val Arg Gln Ala Pro Gly Gln Gly Leu Glu Trp Met
            35                  40                  45

Gly Trp Ile Asn Thr Tyr Gln Gly Glu Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Thr Arg Gly Ala Arg Tyr Ala Tyr Met Asp Tyr Trp Gly Gln Gly Thr
                100                 105                 110

Leu Val Thr Val Ser Ser
        115

<210> SEQ ID NO 243
<211> LENGTH: 118
<212> TYPE: PRT
<213> ORGANISM: Artificial Sequence
<220> FEATURE:
<223> OTHER INFORMATION: MTK-15.11 Heavy Chain Variable

<400> SEQUENCE: 243

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Ala Asn Tyr
                20                  25                  30

Gly Val His Trp Val Arg Gln Ala Pro Gly Gln Gly Leu Glu Trp Met
            35                  40                  45

Gly Trp Ile Asn Thr Tyr Glu Gly Glu Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Gly Asn Arg Tyr Ala Tyr Gln Asp Tyr Trp Gly Gln Gly Thr
                100                 105                 110

Leu Val Thr Val Ser Ser
        115

<210> SEQ ID NO 244
<211> LENGTH: 118
```

```
<212> TYPE: PRT
<213> ORGANISM: Artificial Sequence
<220> FEATURE:
<223> OTHER INFORMATION: MTK-15.12 Heavy Chain Variable

<400> SEQUENCE: 244

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Ala Asn Tyr
            20                  25                  30

Gly Val His Trp Val Arg Gln Ala Pro Gly Gln Gly Leu Glu Trp Met
        35                  40                  45

Gly Trp Ile Asn Thr Tyr Gln Gly Glu Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Gly Val Arg Tyr Ala Tyr Met Asp Tyr Trp Gly Gln Gly Thr
            100                 105                 110

Leu Val Thr Val Ser Ser
        115

<210> SEQ ID NO 245
<211> LENGTH: 118
<212> TYPE: PRT
<213> ORGANISM: Artificial Sequence
<220> FEATURE:
<223> OTHER INFORMATION: MTK-15.13 Heavy Chain Variable

<400> SEQUENCE: 245

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Val His Trp Val Arg Gln Ala Pro Gly Gln Gly Leu Glu Trp Met
        35                  40                  45

Gly Trp Ile Asn Thr Tyr Thr Gly Glu Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Gly Asn Arg Tyr Ala Tyr Glu Asp Tyr Trp Gly Gln Gly Thr
            100                 105                 110

Leu Val Thr Val Ser Ser
        115

<210> SEQ ID NO 246
<211> LENGTH: 118
<212> TYPE: PRT
<213> ORGANISM: Artificial Sequence
<220> FEATURE:
<223> OTHER INFORMATION: MTK-15.14, 15.15 Heavy Chain Variable

<400> SEQUENCE: 246

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
```

```
                    20                  25                  30

Gly Val His Trp Val Arg Gln Ala Pro Gly Gln Gly Leu Glu Trp Met
            35                  40                  45

Gly Trp Ile Asn Thr Tyr Thr Gly Glu Pro Thr Tyr Ala Gln Gly Phe
        50                  55                  60

Thr Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Gly Asn Arg Tyr Ala Tyr Met Asp Tyr Trp Gly Gln Gly Thr
            100                 105                 110

Leu Val Thr Val Ser Ser
        115

<210> SEQ ID NO 247
<211> LENGTH: 106
<212> TYPE: PRT
<213> ORGANISM: Artificial Sequence
<220> FEATURE:
<223> OTHER INFORMATION: MTK-15.1, 15.2, 15.11, 15.14 Light Chain
      Variable

<400> SEQUENCE: 247

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
            20                  25                  30

His Trp Tyr Gln Gln Lys Pro Gly Gln Ala Pro Arg Pro Leu Ile Tyr
        35                  40                  45

Ala Thr Ser Asn Leu Ala Ser Gly Ile Pro Ala Arg Phe Ser Gly Ser
    50                  55                  60

Gly Ser Gly Thr Ser Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Arg Thr
                85                  90                  95

Phe Gly Gly Gly Thr Lys Val Glu Ile Lys
            100                 105

<210> SEQ ID NO 248
<211> LENGTH: 106
<212> TYPE: PRT
<213> ORGANISM: Artificial Sequence
<220> FEATURE:
<223> OTHER INFORMATION: MTK-15.3 Light Chain Variable

<400> SEQUENCE: 248

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser His Val Ser Tyr Met
            20                  25                  30

His Trp Tyr Gln Gln Lys Pro Gly Gln Ala Pro Arg Pro Leu Ile Tyr
        35                  40                  45

Ala Thr Ser Asn Leu Ala Ser Gly Ile Pro Ala Arg Phe Ser Gly Ser
    50                  55                  60

Gly Ser Gly Thr Ser Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Arg Thr
                85                  90                  95
```

```
Phe Gly Gly Gly Thr Lys Val Glu Ile Lys
            100                 105

<210> SEQ ID NO 249
<211> LENGTH: 106
<212> TYPE: PRT
<213> ORGANISM: Artificial Sequence
<220> FEATURE:
<223> OTHER INFORMATION: MTK-15.4, 15.5, 15.6, 15.10 Light Chain
      Variable

<400> SEQUENCE: 249

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Gly Tyr Met
            20                  25                  30

His Trp Tyr Gln Gln Lys Pro Gly Gln Ala Pro Arg Pro Leu Ile Tyr
        35                  40                  45

Ala Thr Ser Asn Leu Ala Ser Gly Ile Pro Ala Arg Phe Ser Gly Ser
    50                  55                  60

Gly Ser Gly Thr Ser Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Arg Thr
                85                  90                  95

Phe Gly Gly Gly Thr Lys Val Glu Ile Lys
            100                 105

<210> SEQ ID NO 250
<211> LENGTH: 106
<212> TYPE: PRT
<213> ORGANISM: Artificial Sequence
<220> FEATURE:
<223> OTHER INFORMATION: MTK-15.7 Light Chain Variable

<400> SEQUENCE: 250

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Gly Val Ser Tyr Met
            20                  25                  30

His Trp Tyr Gln Gln Lys Pro Gly Gln Ala Pro Arg Pro Leu Ile Tyr
        35                  40                  45

Ala Thr Ser Asn Leu Ala Ser Gly Ile Pro Ala Arg Phe Ser Gly Ser
    50                  55                  60

Gly Ser Gly Thr Ser Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Arg Thr
                85                  90                  95

Phe Gly Gly Gly Thr Lys Val Glu Ile Lys
            100                 105

<210> SEQ ID NO 251
<211> LENGTH: 106
<212> TYPE: PRT
<213> ORGANISM: Artificial Sequence
<220> FEATURE:
<223> OTHER INFORMATION: MTK-15.8, 15.12 Light Chain Variable

<400> SEQUENCE: 251

Glu Ile Val Leu Thr Gln Ser Pro Ala Thr Leu Ser Leu Ser Pro Gly
1               5                   10                  15
```

```
Glu Arg Ala Thr Leu Ser Cys Arg Ala Ser Ser Val Gly Tyr Met
            20                  25                  30

His Trp Tyr Gln Gln Lys Pro Gly Gln Ala Pro Arg Leu Ile Tyr
        35                  40                  45

Ala Thr Ser Asn Leu Ala Ser Gly Ile Pro Ala Arg Phe Ser Gly Ser
    50                  55                  60

Gly Ser Gly Thr Ser Tyr Thr Leu Thr Ile Ser Ser Pro Pro Glu
65                  70                  75                  80

Asp Phe Ala Val Tyr Tyr Cys Gln Gln Trp Ser Ser Asn Pro Arg Thr
                85                  90                  95

Phe Gly Gly Gly Thr Lys Val Glu Ile Lys
            100                 105

<210> SEQ ID NO 252
<211> LENGTH: 106
<212> TYPE: PRT
<213> ORGANISM: Artificial Sequence
<220> FEATURE:
<223> OTHER INFORMATION: MTK-15.9 Light Chain Variable

<400> SEQUENCE: 252

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Thr Ser Tyr Met
            20                  25                  30

His Trp Tyr Gln Gln Lys Pro Gly Gln Ala Pro Arg Leu Ile Tyr
        35                  40                  45

Ala Thr Ser Asn Leu Ala Ser Gly Ile Pro Ala Arg Phe Ser Gly Ser
    50                  55                  60

Gly Ser Gly Thr Ser Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Arg Thr
                85                  90                  95

Phe Gly Gly Gly Thr Lys Val Glu Ile Lys
            100                 105

<210> SEQ ID NO 253
<211> LENGTH: 106
<212> TYPE: PRT
<213> ORGANISM: Artificial Sequence
<220> FEATURE:
<223> OTHER INFORMATION: MTK-15.13 Light Chain Variable

<400> SEQUENCE: 253

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Gln Tyr Met
            20                  25                  30

His Trp Tyr Gln Gln Lys Pro Gly Gln Ala Pro Arg Leu Ile Tyr
        35                  40                  45

Ala Thr Ser Asn Leu Ala Ser Gly Ile Pro Ala Arg Phe Ser Gly Ser
    50                  55                  60

Gly Ser Gly Thr Ser Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Arg Thr
                85                  90                  95

Phe Gly Gly Gly Thr Lys Val Glu Ile Lys
```

<210> SEQ ID NO 254
<211> LENGTH: 106
<212> TYPE: PRT
<213> ORGANISM: Artificial Sequence
<220> FEATURE:
<223> OTHER INFORMATION: MTK-15.15 Light Chain Variable

<400> SEQUENCE: 254

Gln Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Tyr Met
            20                  25                  30

His Trp Tyr Gln Gln Lys Pro Gly Gln Ala Pro Arg Pro Leu Ile Tyr
        35                  40                  45

Ala Thr Ser Asn Leu Ala Ser Gly Ile Pro Asp Arg Phe Ser Gly Ser
    50                  55                  60

Gly Ser Gly Thr Ser Tyr Thr Leu Thr Ile Ser Arg Leu Glu Pro Glu
65                  70                  75                  80

Asp Phe Ala Val Tyr Tyr Cys Gln Gln Trp Ser Ser Asn Pro Arg Thr
                85                  90                  95

Phe Gly Gly Gly Thr Lys Val Glu Ile Lys
            100                 105

<210> SEQ ID NO 255
<211> LENGTH: 120
<212> TYPE: PRT
<213> ORGANISM: Artificial Sequence
<220> FEATURE:
<223> OTHER INFORMATION: MTK-16.1 Heavy Chain Variable

<400> SEQUENCE: 255

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn His
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Lys Gly Val Thr Ala Ala Arg Tyr Phe Asp Tyr Trp Gly Gln
            100                 105                 110

Gly Thr Leu Val Thr Val Ser Ser
        115                 120

<210> SEQ ID NO 256
<211> LENGTH: 120
<212> TYPE: PRT
<213> ORGANISM: Artificial Sequence
<220> FEATURE:
<223> OTHER INFORMATION: MTK-16.2 Heavy Chain Variable

<400> SEQUENCE: 256

Gln Val Gln Leu Val Gln Ser Gly Ser Glu Leu Lys Lys Pro Gly Ala
1               5                   10                  15

-continued

```
Ser Val Lys Val Ser Cys Lys Ala Ser Gly Tyr Thr Phe Thr Asn His
        20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Tyr Ala Asp Asp Phe
 50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                85                  90                  95

Ala Arg Lys Gly Val Thr Ala Ala Arg Tyr Phe Asp Tyr Trp Gly Gln
            100                 105                 110

Gly Thr Leu Val Thr Val Ser Ser
            115                 120

<210> SEQ ID NO 257
<211> LENGTH: 107
<212> TYPE: PRT
<213> ORGANISM: Artificial Sequence
<220> FEATURE:
<223> OTHER INFORMATION: MTK-16.1 Light Chain Variable

<400> SEQUENCE: 257

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Arg Thr Ala
            20                  25                  30

Val Ala Trp Tyr Gln Gln Lys Pro Gly Lys Ala Pro Lys Arg Leu Ile
        35                  40                  45

Tyr Leu Ala Ser Asn Arg His Thr Gly Val Pro Ser Arg Phe Ser Gly
 50                  55                  60

Ser Gly Ser Gly Thr Glu Phe Thr Leu Thr Ile Ser Asn Leu Gln Pro
 65                  70                  75                  80

Glu Asp Phe Ala Thr Tyr Tyr Cys Leu Gln His Trp Asn Tyr Pro Leu
                85                  90                  95

Thr Phe Gly Gly Gly Thr Lys Val Glu Ile Lys
            100                 105

<210> SEQ ID NO 258
<211> LENGTH: 107
<212> TYPE: PRT
<213> ORGANISM: Artificial Sequence
<220> FEATURE:
<223> OTHER INFORMATION: MTK-16.2 Light Chain Variable

<400> SEQUENCE: 258

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Val Arg Thr Ala
            20                  25                  30

Val Ala Trp Tyr Gln Gln Lys Pro Gly Lys Ala Pro Lys Arg Leu Ile
        35                  40                  45

Tyr Leu Ala Ser Asn Arg His Thr Gly Val Pro Ser Arg Phe Ser Gly
 50                  55                  60

Ser Gly Ser Gly Thr Glu Phe Thr Leu Thr Ile Ser Asn Leu Gln Pro
 65                  70                  75                  80

Glu Asp Phe Ala Thr Tyr Tyr Cys Leu Gln His Trp Asn Tyr Pro Leu
```

85                  90                  95
Thr Phe Gly Gly Gly Thr Lys Leu Glu Ile Lys
            100                 105

<210> SEQ ID NO 259
<211> LENGTH: 118
<212> TYPE: PRT
<213> ORGANISM: Artificial Sequence
<220> FEATURE:
<223> OTHER INFORMATION: MTK-29.1 Heavy Chain Variable

<400> SEQUENCE: 259

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Ile Phe Thr Ser Tyr
            20                  25                  30

Gly Leu Ser Trp Val Arg Gln Ala Pro Gly Gln Gly Leu Glu Trp Met
        35                  40                  45

Gly Trp Ile Asn Thr Tyr Ser Gly Val Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Tyr Thr Asn Tyr Gly Ile Phe Asp Tyr Trp Gly Gln Gly Thr
            100                 105                 110

Leu Val Thr Val Ser Ser
        115

<210> SEQ ID NO 260
<211> LENGTH: 118
<212> TYPE: PRT
<213> ORGANISM: Artificial Sequence
<220> FEATURE:
<223> OTHER INFORMATION: MTK-29.2 Heavy Chain Variable

<400> SEQUENCE: 260

Gln Val Gln Leu Val Gln Ser Gly Ser Glu Leu Lys Lys Pro Gly Ala
1               5                   10                  15

Ser Val Lys Val Ser Cys Lys Ala Ser Gly Phe Thr Phe Thr Thr Tyr
            20                  25                  30

Gly Met Ser Trp Val Arg Gln Ala Pro Gly Gln Gly Leu Glu Trp Met
        35                  40                  45

Gly Trp Ile Asn Thr Tyr Ser Gly Val Pro Thr Tyr Thr Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Tyr Thr Asn Tyr Gly Ile Phe Asp Tyr Trp Gly Gln Gly Thr
            100                 105                 110

Leu Val Thr Val Ser Ser
        115

<210> SEQ ID NO 261
<211> LENGTH: 118
<212> TYPE: PRT
<213> ORGANISM: Artificial Sequence
<220> FEATURE:

<223> OTHER INFORMATION: MTK-29.3 Heavy Chain Variable

<400> SEQUENCE: 261

Gln Val Gln Leu Val Gln Ser Gly Ser Glu Leu Lys Lys Pro Gly Ala
1               5                   10                  15

Ser Val Lys Val Ser Cys Lys Ala Ser Gly Phe Thr Phe Thr Thr Tyr
            20                  25                  30

Gly Met Ser Trp Val Arg Gln Ala Pro Gly Gln Gly Leu Glu Trp Met
        35                  40                  45

Gly Trp Ile Asn Thr Tyr Ser Gly Val Pro Ala Tyr Thr Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Tyr Thr Asn Tyr Gly Val Phe Asp Tyr Trp Gly Gln Gly Thr
            100                 105                 110

Leu Val Thr Val Ser Ser
        115

<210> SEQ ID NO 262
<211> LENGTH: 118
<212> TYPE: PRT
<213> ORGANISM: Artificial Sequence
<220> FEATURE:
<223> OTHER INFORMATION: MTK-29.4 Heavy Chain Variable

<400> SEQUENCE: 262

Gln Val Gln Leu Val Gln Ser Gly Ser Glu Leu Lys Lys Pro Gly Ala
1               5                   10                  15

Ser Val Lys Val Ser Cys Lys Ala Ser Ser Tyr Thr Phe Thr Thr Tyr
            20                  25                  30

Gly Met Ser Trp Val Arg Gln Ala Pro Gly Gln Gly Leu Glu Trp Met
        35                  40                  45

Gly Trp Ile Asn Thr Tyr Ser Gly Val Pro Tyr Thr Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Tyr Thr Asn Tyr Gly Val Phe Asp Tyr Trp Gly Gln Gly Thr
            100                 105                 110

Leu Val Thr Val Ser Ser
        115

<210> SEQ ID NO 263
<211> LENGTH: 118
<212> TYPE: PRT
<213> ORGANISM: Artificial Sequence
<220> FEATURE:
<223> OTHER INFORMATION: MTK-29.5 Heavy Chain Variable

<400> SEQUENCE: 263

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Ile Phe Thr Ser Tyr
            20                  25                  30

Gly Leu Ser Trp Val Arg Gln Ala Pro Gly Gln Gly Leu Glu Trp Met

```
                35                  40                  45
Gly Trp Ile Asn Thr Tyr Ser Gly Val Pro Thr Tyr Thr Asp Asp Phe
 50                  55                  60
Lys Gly Arg Phe Val Phe Ser Leu Asp Thr Ser Val Ser Thr Ala Tyr
 65                  70                  75                  80
Leu Gln Ile Ser Pro Leu Lys Ala Glu Asp Thr Ala Val Tyr Tyr Cys
                85                  90                  95
Ala Arg Tyr Thr Asn Tyr Gly Val Phe Asp Tyr Trp Gly Gln Gly Thr
               100                 105                 110
Leu Val Thr Val Ser Ser
               115

<210> SEQ ID NO 264
<211> LENGTH: 118
<212> TYPE: PRT
<213> ORGANISM: Artificial Sequence
<220> FEATURE:
<223> OTHER INFORMATION: MTK-29.6, 29.12, 29.15 Heavy Chain Variable

<400> SEQUENCE: 264

Gln Val Gln Leu Val Gln Ser Gly Ser Glu Leu Lys Lys Pro Gly Ala
 1               5                  10                  15
Ser Val Lys Val Ser Cys Lys Ala Ser Ser Tyr Thr Phe Thr Thr Tyr
                20                  25                  30
Gly Met Ser Trp Val Arg Gln Ala Pro Gly Gln Gly Leu Glu Trp Met
                35                  40                  45
Gly Trp Ile Asn Thr Met Ser Gly Val Pro Thr Tyr Thr Asp Asp Phe
 50                  55                  60
Lys Gly Arg Phe Val Phe Ser Leu Asp Thr Ser Val Ser Thr Ala Tyr
 65                  70                  75                  80
Leu Gln Ile Ser Ser Leu Lys Ala Glu Asp Thr Ala Val Tyr Tyr Cys
                85                  90                  95
Ala Arg Tyr Thr Asn Tyr Gly Val Phe Asp Tyr Trp Gly Gln Gly Thr
               100                 105                 110
Leu Val Thr Val Ser Ser
               115

<210> SEQ ID NO 265
<211> LENGTH: 118
<212> TYPE: PRT
<213> ORGANISM: Artificial Sequence
<220> FEATURE:
<223> OTHER INFORMATION: MTK-29.7, 29.14 Heavy Chain Variable

<400> SEQUENCE: 265

Gln Val Gln Leu Val Gln Ser Gly Ser Glu Leu Lys Lys Pro Gly Ala
 1               5                  10                  15
Ser Val Lys Val Ser Cys Lys Ala Ser Ser Tyr Thr Phe Thr Thr Tyr
                20                  25                  30
Gly Met Ser Trp Val Arg Gln Ala Pro Gly Gln Gly Leu Glu Trp Met
                35                  40                  45
Gly Trp Ile Asn Thr Tyr Ser Gly Val Pro Ser Tyr Thr Asp Asp Phe
 50                  55                  60
Lys Ala Arg Phe Val Phe Ser Leu Asp Thr Ser Val Ser Thr Ala Tyr
 65                  70                  75                  80
Leu Gln Ile Ser Ser Leu Lys Ala Glu Asp Thr Ala Val Tyr Tyr Cys
                85                  90                  95
```

Ala Arg Tyr Thr Asn Tyr Gly Val Phe Asp Tyr Trp Gly Gln Gly Thr
            100                 105                 110

Leu Val Thr Val Ser Ser
        115

<210> SEQ ID NO 266
<211> LENGTH: 118
<212> TYPE: PRT
<213> ORGANISM: Artificial Sequence
<220> FEATURE:
<223> OTHER INFORMATION: MTK-29.8 Heavy Chain Variable

<400> SEQUENCE: 266

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Ile Phe Thr Thr Tyr
            20                  25                  30

Gly Leu Ser Trp Val Arg Gln Ala Pro Gly Gln Gly Leu Glu Trp Met
        35                  40                  45

Gly Trp Ile Asn Thr Tyr Ser Gly Val Pro Thr Tyr Thr Asp Asp Phe
    50                  55                  60

Lys Gly Arg Phe Val Phe Ser Leu Asp Thr Asn Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Tyr Thr Asn Tyr Gly Val Phe Asp Tyr Trp Gly Gln Gly Thr
            100                 105                 110

Leu Val Thr Val Ser Ser
        115

<210> SEQ ID NO 267
<211> LENGTH: 118
<212> TYPE: PRT
<213> ORGANISM: Artificial Sequence
<220> FEATURE:
<223> OTHER INFORMATION: MTK-29.9 Heavy Chain Variable

<400> SEQUENCE: 267

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Ile Phe Thr Ser Tyr
            20                  25                  30

Gly Leu Ser Trp Val Arg Gln Ala Pro Gly Gln Gly Leu Glu Trp Met
        35                  40                  45

Gly Trp Ile Asn Thr Tyr Ser Gly Val Pro Thr Tyr Thr Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Tyr Thr Asn Tyr Gly Val Phe Asp Tyr Trp Gly Gln Gly Thr
            100                 105                 110

Leu Val Thr Val Ser Ser
        115

<210> SEQ ID NO 268
<211> LENGTH: 118
<212> TYPE: PRT
<213> ORGANISM: Artificial Sequence
<220> FEATURE:
<223> OTHER INFORMATION: MTK-29.10 Heavy Chain Variable

<400> SEQUENCE: 268

Gln Val Gln Leu Val Gln Ser Gly Ser Glu Leu Lys Lys Pro Gly Ala
1               5                   10                  15

Ser Val Lys Val Ser Cys Lys Thr Ser Ser Tyr Thr Phe Thr Thr Tyr
            20                  25                  30

Gly Met Ser Trp Val Arg Gln Ala Pro Gly Gln Gly Leu Glu Trp Met
        35                  40                  45

Gly Trp Ile Asn Thr Tyr Ser Gly Val Pro Thr Tyr Thr Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Tyr Thr Asn Tyr Gly Val Phe Asp Tyr Trp Gly Gln Gly Thr
            100                 105                 110

Leu Val Thr Val Ser Ser
        115

<210> SEQ ID NO 269
<211> LENGTH: 118
<212> TYPE: PRT
<213> ORGANISM: Artificial Sequence
<220> FEATURE:
<223> OTHER INFORMATION: MTK-29.11 Heavy Chain Variable

<400> SEQUENCE: 269

Gln Val Gln Leu Val Gln Ser Gly Ser Glu Leu Lys Lys Pro Gly Ala
1               5                   10                  15

Ser Val Lys Val Ser Cys Lys Ala Ser Ser Tyr Thr Phe Thr Thr Tyr
            20                  25                  30

Gly Met Ser Trp Val Arg Gln Ala Pro Gly Gln Gly Leu Glu Trp Met
        35                  40                  45

Gly Trp Ile Asn Thr Asp Ser Gly Val Pro Thr Tyr Thr Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Tyr Thr Asn Tyr Gly Val Phe Asp Tyr Trp Gly Gln Gly Thr
            100                 105                 110

Leu Val Thr Val Ser Ser
        115

<210> SEQ ID NO 270
<211> LENGTH: 118
<212> TYPE: PRT
<213> ORGANISM: Artificial Sequence
<220> FEATURE:
<223> OTHER INFORMATION: MTK-29.13 Heavy Chain Variable

<400> SEQUENCE: 270

Gln Val Gln Leu Val Gln Ser Gly Ser Glu Leu Lys Lys Pro Gly Ala
1               5                   10                  15

Ser Val Lys Val Ser Cys Lys Ala Ser Ser Tyr Thr Phe Thr Thr Tyr
            20                  25                  30

Gly Met Ser Trp Val Arg Gln Ala Pro Gly Gln Gly Leu Glu Trp Met
        35                  40                  45

Gly Trp Ile Asn Thr Ala Ser Gly Val Pro Thr Tyr Thr Asp Asp Phe
 50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                85                  90                  95

Ala Arg Tyr Thr Asn Tyr Gly Val Phe Asp Tyr Trp Gly Gln Gly Thr
            100                 105                 110

Leu Val Thr Val Ser Ser
            115

<210> SEQ ID NO 271
<211> LENGTH: 118
<212> TYPE: PRT
<213> ORGANISM: Artificial Sequence
<220> FEATURE:
<223> OTHER INFORMATION: MTK-29.16, 29.18 Heavy Chain Variable

<400> SEQUENCE: 271

Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Ile Phe Thr Ser Tyr
                20                  25                  30

Gly Leu Ser Trp Val Arg Gln Ala Pro Gly Gln Gly Leu Glu Trp Met
        35                  40                  45

Gly Trp Val Asn Thr Tyr Ser Gly Val Pro Thr Tyr Thr Asp Asp Phe
 50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                85                  90                  95

Ala Arg Tyr Thr Asn Tyr Gly Val Phe Asp Tyr Trp Gly Gln Gly Thr
            100                 105                 110

Leu Val Thr Val Ser Ser
            115

<210> SEQ ID NO 272
<211> LENGTH: 118
<212> TYPE: PRT
<213> ORGANISM: Artificial Sequence
<220> FEATURE:
<223> OTHER INFORMATION: MTK-29.17 Heavy Chain Variable

<400> SEQUENCE: 272

Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Ile Phe Thr Ser Tyr
                20                  25                  30

Gly Leu Ser Trp Val Arg Gln Ala Pro Gly Gln Gly Leu Glu Trp Met
        35                  40                  45

Gly Trp Ile Asn Thr Tyr Ser Gly Val Pro Thr Tyr Ala Gln Gly Phe
 50                  55                  60

Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                85                  90                  95

-continued

Ala Arg Tyr Thr Asn Tyr Gly Val Phe Asp Tyr Trp Gly Gln Gly Thr
            100                 105                 110

Leu Val Thr Val Ser Ser
        115

<210> SEQ ID NO 273
<211> LENGTH: 118
<212> TYPE: PRT
<213> ORGANISM: Artificial Sequence
<220> FEATURE:
<223> OTHER INFORMATION: MTK-29.19, 29.20, 29.21 Heavy Chain Variable

<400> SEQUENCE: 273

Gln Val Gln Leu Val Gln Ser Gly Ser Glu Leu Lys Lys Pro Gly Ala
1               5                   10                  15

Ser Val Lys Val Ser Cys Lys Ala Ser Gly Phe Thr Phe Thr Thr Tyr
            20                  25                  30

Gly Met Ser Trp Val Arg Gln Ala Pro Gly Gln Gly Leu Glu Trp Met
        35                  40                  45

Gly Trp Ile Asn Thr Tyr Ser Gly Val Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Tyr Thr Asn Tyr Gly Tyr Phe Asp Tyr Trp Gly Gln Gly Thr
            100                 105                 110

Leu Val Thr Val Ser Ser
        115

<210> SEQ ID NO 274
<211> LENGTH: 106
<212> TYPE: PRT
<213> ORGANISM: Artificial Sequence
<220> FEATURE:
<223> OTHER INFORMATION: MTK-29.1 Light Chain Variable

<400> SEQUENCE: 274

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Gly Tyr Met
            20                  25                  30

His Trp Tyr Gln Gln Lys Pro Gly Gln Ala Pro Arg Pro Leu Ile Tyr
        35                  40                  45

Ala Thr Ser Asn Leu Ala Ser Gly Ile Pro Ala Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Gly Ser Trp Pro Phe Thr
                85                  90                  95

Phe Gly Gln Gly Thr Lys Leu Glu Ile Lys
            100                 105

<210> SEQ ID NO 275
<211> LENGTH: 106
<212> TYPE: PRT
<213> ORGANISM: Artificial Sequence
<220> FEATURE:
<223> OTHER INFORMATION: MTK-29.2 Light Chain Variable

<400> SEQUENCE: 275

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Val Gly Tyr Met
            20                  25                  30

His Trp Tyr Gln Gln Lys Pro Gly Lys Ala Pro Lys Pro Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Gly Ser Ile Pro Phe Thr
                85                  90                  95

Phe Gly Gly Gly Thr Lys Val Glu Ile Lys
            100                 105

<210> SEQ ID NO 276
<211> LENGTH: 106
<212> TYPE: PRT
<213> ORGANISM: Artificial Sequence
<220> FEATURE:
<223> OTHER INFORMATION: MTK-29.3 Light Chain Variable

<400> SEQUENCE: 276

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Val Gly Tyr Met
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Gly Ser Leu Pro Phe Thr
                85                  90                  95

Phe Gly Gln Gly Thr Lys Leu Glu Ile Lys
            100                 105

<210> SEQ ID NO 277
<211> LENGTH: 106
<212> TYPE: PRT
<213> ORGANISM: Artificial Sequence
<220> FEATURE:
<223> OTHER INFORMATION: MTK-29.4, 29.5, 29.6, 29.7, 29.8 Light Chain
      Variable

<400> SEQUENCE: 277

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Val Gly Tyr Met
            20                  25                  30

His Trp Tyr Gln Gln Lys Pro Gly Lys Ala Pro Lys Leu Leu Ile Tyr
        35                  40                  45

Ala Thr Ser Asn Leu Ala Gln Gly Val Pro Ser Arg Phe Ser Gly Ser
    50                  55                  60

Gly Ser Gly Thr Glu Phe Thr Leu Thr Ile Ser Ser Leu Gln Pro Glu

```
                65                  70                  75                  80
Asp Phe Ala Thr Tyr Tyr Cys Gln Gln Trp Gly Ser Leu Pro Phe Thr
                    85                  90                  95

Phe Gly Gln Gly Thr Lys Leu Glu Ile Lys
                100                 105

<210> SEQ ID NO 278
<211> LENGTH: 106
<212> TYPE: PRT
<213> ORGANISM: Artificial Sequence
<220> FEATURE:
<223> OTHER INFORMATION: MTK-29.9 Light Chain Variable

<400> SEQUENCE: 278

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Gly Tyr Met
                20                  25                  30

His Trp Tyr Gln Gln Lys Pro Gly Lys Ala Pro Lys Leu Leu Ile Tyr
            35                  40                  45

Ala Thr Ser Asn Leu Ala Gln Gly Val Pro Ser Arg Phe Ser Gly Ser
        50                  55                  60

Gly Ser Gly Thr Gly Phe Thr Leu Thr Ile Ser Ser Leu Gln Pro Glu
65                  70                  75                  80

Asp Phe Ala Thr Tyr Tyr Cys Gln Gln Trp Gly Ser Leu Pro Phe Thr
                    85                  90                  95

Phe Gly Gln Gly Thr Lys Leu Glu Ile Lys
                100                 105

<210> SEQ ID NO 279
<211> LENGTH: 106
<212> TYPE: PRT
<213> ORGANISM: Artificial Sequence
<220> FEATURE:
<223> OTHER INFORMATION: MTK-29.10, 29.11 Light Chain Variable

<400> SEQUENCE: 279

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Gly Tyr Met
                20                  25                  30

His Trp Tyr Gln Gln Lys Pro Gly Gln Ala Pro Arg Leu Leu Ile Tyr
            35                  40                  45

Ala Thr Ser Asn Leu Ala Ser Gly Ile Pro Ala Arg Phe Ser Gly Ser
        50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Gly Ser Leu Pro Phe Thr
                    85                  90                  95

Phe Gly Gly Gly Thr Lys Leu Glu Ile Lys
                100                 105

<210> SEQ ID NO 280
<211> LENGTH: 106
<212> TYPE: PRT
<213> ORGANISM: Artificial Sequence
<220> FEATURE:
<223> OTHER INFORMATION: MTK-29.12 Light Chain Variable

<400> SEQUENCE: 280
```

Asp Ile Gln Leu Thr Gln Ser Pro Gly Phe Leu Ser Ala Ser Val Gly
1               5                   10                  15

Asp Arg Val Thr Ile Thr Cys Arg Ala Ser Ser Val Gly Tyr Met
            20                  25                  30

His Trp Tyr Gln Gln Lys Pro Gly Lys Ala Pro Lys Leu Leu Ile Tyr
                35                  40                  45

Ala Thr Ser Asn Leu Ala Gln Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Gly Ser Leu Pro Phe Thr
                85                  90                  95

Phe Gly Gln Gly Thr Lys Leu Glu Ile Lys
            100                 105

<210> SEQ ID NO 281
<211> LENGTH: 106
<212> TYPE: PRT
<213> ORGANISM: Artificial Sequence
<220> FEATURE:
<223> OTHER INFORMATION: MTK-29.13 Light Chain Variable

<400> SEQUENCE: 281

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Val Gly Tyr Met
            20                  25                  30

His Trp Tyr Gln Gln Glu Pro Gly Lys Ala Pro Lys Leu Leu Ile Tyr
                35                  40                  45

Ala Thr Ser Asn Leu Ala Gln Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Gly Ser Leu Pro Phe Thr
                85                  90                  95

Phe Gly Gln Gly Thr Lys Leu Glu Ile Lys
            100                 105

<210> SEQ ID NO 282
<211> LENGTH: 106
<212> TYPE: PRT
<213> ORGANISM: Artificial Sequence
<220> FEATURE:
<223> OTHER INFORMATION: MTK-29.14 Light Chain Variable

<400> SEQUENCE: 282

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Val Gly Tyr Met
            20                  25                  30

His Trp Tyr Gln Gln Lys Pro Gly Lys Ala Pro Lys Leu Leu Ile Tyr
                35                  40                  45

Ala Thr Ser Asn Leu Ala Gln Gly Val Pro Ser Arg Phe Ser Gly Ser
    50                  55                  60

Gly Ser Gly Thr Glu Phe Thr Leu Thr Ile Phe Ser Leu Gln Pro Glu
65                  70                  75                  80

Asp Phe Ala Thr Tyr Tyr Cys Gln Gln Trp Gly Ser Leu Pro Phe Thr

```
                    85                  90                  95

Phe Gly Gln Gly Thr Lys Leu Glu Ile Lys
                100                 105

<210> SEQ ID NO 283
<211> LENGTH: 106
<212> TYPE: PRT
<213> ORGANISM: Artificial Sequence
<220> FEATURE:
<223> OTHER INFORMATION: MTK-29.15 Light Chain Variable

<400> SEQUENCE: 283

Asp Ile Gln Leu Thr Gln Ser Pro Ser Phe Pro Ser Ala Ser Val Gly
1               5                   10                  15

Asp Arg Val Thr Ile Thr Cys Arg Ala Ser Ser Val Gly Tyr Met
            20                  25                  30

His Trp Tyr Gln Gln Lys Pro Gly Lys Ala Pro Lys Leu Leu Ile Tyr
        35                  40                  45

Ala Thr Ser Asn Leu Ala Gln Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Gly Ser Leu Pro Phe Thr
                85                  90                  95

Phe Gly Gln Gly Thr Lys Leu Glu Ile Lys
                100                 105

<210> SEQ ID NO 284
<211> LENGTH: 106
<212> TYPE: PRT
<213> ORGANISM: Artificial Sequence
<220> FEATURE:
<223> OTHER INFORMATION: MTK-29.16 Light Chain Variable

<400> SEQUENCE: 284

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Val Gly Tyr Met
            20                  25                  30

His Trp Tyr Gln Gln Lys Pro Gly Lys Ala Pro Lys Leu Leu Ile Tyr
        35                  40                  45

Ala Thr Ser Asn Leu Ala Gln Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Gly Arg Leu Pro Phe Thr
                85                  90                  95

Phe Gly Gln Gly Thr Lys Leu Glu Ile Lys
                100                 105

<210> SEQ ID NO 285
<211> LENGTH: 106
<212> TYPE: PRT
<213> ORGANISM: Artificial Sequence
<220> FEATURE:
<223> OTHER INFORMATION: MTK-29.17 Light Chain Variable

<400> SEQUENCE: 285

Asp Ile Gln Leu Thr Gln Ser Pro Ser Phe Leu Ser Ala Ser Val Gly
1               5                   10                  15
```

Asp Arg Val Thr Ile Thr Cys Arg Ser Ser Ser Val Gly Tyr Met
            20                  25                  30

His Trp Tyr Gln Gln Lys Pro Gly Lys Ala Pro Lys Leu Leu Ile Tyr
                35                  40                  45

Ala Thr Ser Asn Leu Ala Gln Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Gly Ser Leu Pro Phe Thr
                85                  90                  95

Phe Gly Gln Gly Thr Lys Leu Glu Ile Lys
            100                 105

<210> SEQ ID NO 286
<211> LENGTH: 106
<212> TYPE: PRT
<213> ORGANISM: Artificial Sequence
<220> FEATURE:
<223> OTHER INFORMATION: MTK-29.18 Light Chain Variable

<400> SEQUENCE: 286

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Thr Val Gly Tyr Met
            20                  25                  30

His Trp Tyr Gln Gln Lys Pro Gly Gln Ala Pro Arg Leu Leu Ile Tyr
                35                  40                  45

Ala Thr Ser Asn Leu Ala Ser Gly Ile Pro Ala Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Gly Ser Leu Pro Phe Thr
                85                  90                  95

Phe Gly Gly Gly Thr Lys Leu Glu Ile Lys
            100                 105

<210> SEQ ID NO 287
<211> LENGTH: 106
<212> TYPE: PRT
<213> ORGANISM: Artificial Sequence
<220> FEATURE:
<223> OTHER INFORMATION: MTK-29.19 Light Chain Variable

<400> SEQUENCE: 287

Gln Ile Val Leu Thr Gln Ser Pro Gly Thr Leu Ser Leu Ser Pro Gly
1               5                   10                  15

Glu Arg Ala Thr Leu Ser Cys Arg Ala Thr Ser Ser Val Gly Tyr Met
            20                  25                  30

His Trp Tyr Gln Gln Lys Pro Gly Gln Ala Pro Arg Pro Leu Ile Tyr
                35                  40                  45

Ala Thr Ser Asn Leu Ala Ser Gly Ile Pro Asp Arg Phe Ser Gly Ser
    50                  55                  60

Gly Ser Gly Thr Ser Tyr Thr Leu Thr Ile Ser Arg Leu Glu Pro Glu
65                  70                  75                  80

Asp Phe Ala Val Tyr Tyr Cys Gln Gln Trp Gly Ser Asn Pro Phe Thr
                85                  90                  95

Phe Gly Gln Gly Thr Lys Leu Glu Ile Lys

<210> SEQ ID NO 288
<211> LENGTH: 106
<212> TYPE: PRT
<213> ORGANISM: Artificial Sequence
<220> FEATURE:
<223> OTHER INFORMATION: MTK-29.20 Light Chain Variable

<400> SEQUENCE: 288

```
Gln Ile Val Leu Thr Gln Ser Pro Ala Thr Leu Ser Leu Ser Pro Gly
1               5                   10                  15

Glu Arg Ala Thr Leu Ser Cys Arg Ala Thr Ser Ser Val Gly Tyr Met
            20                  25                  30

His Trp Tyr Gln Gln Lys Pro Gly Leu Ala Pro Arg Pro Leu Ile Tyr
        35                  40                  45

Ala Thr Ser Asn Leu Ala Ser Gly Ile Pro Asp Arg Phe Ser Gly Ser
    50                  55                  60

Gly Ser Gly Thr Ser Tyr Thr Leu Thr Ile Ser Arg Leu Glu Pro Glu
65                  70                  75                  80

Asp Phe Ala Val Tyr Tyr Cys Gln Gln Trp Gly Ser Asn Pro Phe Thr
                85                  90                  95

Phe Gly Gln Gly Thr Lys Leu Glu Ile Lys
            100                 105
```

<210> SEQ ID NO 289
<211> LENGTH: 106
<212> TYPE: PRT
<213> ORGANISM: Artificial Sequence
<220> FEATURE:
<223> OTHER INFORMATION: MTK-29.21 Light Chain Variable

<400> SEQUENCE: 289

```
Gln Ile Val Leu Thr Gln Ser Pro Ala Thr Leu Ser Leu Ser Pro Gly
1               5                   10                  15

Glu Arg Ala Thr Leu Ser Cys Arg Ala Thr Ser Ser Val Gly Tyr Met
            20                  25                  30

His Trp Tyr Gln Gln Lys Pro Gly Gln Ala Pro Arg Pro Leu Ile Tyr
        35                  40                  45

Ala Thr Ser Asn Leu Ala Ser Gly Ile Pro Ala Arg Phe Ser Gly Ser
    50                  55                  60

Gly Ser Gly Thr Ser Tyr Thr Leu Thr Ile Ser Ser Leu Glu Pro Glu
65                  70                  75                  80

Asp Phe Ala Val Tyr Tyr Cys Gln Gln Trp Gly Ser Asn Pro Phe Thr
                85                  90                  95

Phe Gly Gln Gly Thr Lys Leu Glu Ile Lys
            100                 105
```

<210> SEQ ID NO 290
<211> LENGTH: 119
<212> TYPE: PRT
<213> ORGANISM: Artificial Sequence
<220> FEATURE:
<223> OTHER INFORMATION: MTK-33.1, 33.8 Heavy Chain Variable

<400> SEQUENCE: 290

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30
```

-continued

Trp Met His Trp Val Arg Gln Ala Pro Gly Gln Gly Leu Glu Trp Ile
          35                  40                  45

Gly Val Ile Asp Pro Ser Asp Asn Tyr Ile Asn Tyr Asn Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Trp Thr Arg Gly Tyr Phe Asn Tyr Trp Gly Gln Gly
            100                 105                 110

Thr Leu Val Thr Val Ser Ser
            115

<210> SEQ ID NO 291
<211> LENGTH: 119
<212> TYPE: PRT
<213> ORGANISM: Artificial Sequence
<220> FEATURE:
<223> OTHER INFORMATION: MTK-33.2 Heavy Chain Variable

<400> SEQUENCE: 291

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Thr Ser Tyr
            20                  25                  30

Trp Met His Trp Val Arg Gln Ala Pro Gly Gln Gly Leu Glu Trp Ile
          35                  40                  45

Gly Val Ile Asp Pro Ser Asp Asn Tyr Ile Asn Tyr Asn Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Thr Arg Gly Tyr Phe Asp Tyr Trp Gly Gln Gly
            100                 105                 110

Thr Leu Val Thr Val Ser Ser
            115

<210> SEQ ID NO 292
<211> LENGTH: 119
<212> TYPE: PRT
<213> ORGANISM: Artificial Sequence
<220> FEATURE:
<223> OTHER INFORMATION: MTK-33.3, 33.11 Heavy Chain Variable

<400> SEQUENCE: 292

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
          35                  40                  45

Gly Val Ile Asp Pro Ser Asp Asn Tyr Ile Asn Tyr Asn Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys

```
                85                  90                  95
Ala Arg Glu Ala Trp Thr Arg Gly Tyr Phe Asp Tyr Trp Gly Gln Gly
            100                 105                 110

Thr Leu Val Thr Val Ser Ser
        115

<210> SEQ ID NO 293
<211> LENGTH: 119
<212> TYPE: PRT
<213> ORGANISM: Artificial Sequence
<220> FEATURE:
<223> OTHER INFORMATION: MTK-33.4 Heavy Chain Variable

<400> SEQUENCE: 293

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Val Ile Asp Pro Ser Asp Asn Tyr Ile Asn Met Asn Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Thr Arg Gly Tyr Phe Asp Tyr Trp Gly Gln Gly
            100                 105                 110

Thr Leu Val Thr Val Ser Ser
        115

<210> SEQ ID NO 294
<211> LENGTH: 119
<212> TYPE: PRT
<213> ORGANISM: Artificial Sequence
<220> FEATURE:
<223> OTHER INFORMATION: MTK-33.5 Heavy Chain Variable

<400> SEQUENCE: 294

Gln Val Gln Leu Val Gln Ser Gly Ala Glu Val Lys Lys Pro Gly Ala
1               5                   10                  15

Ser Val Lys Val Ser Cys Met Ala Ser Gly Tyr Thr Phe Gly Ser Tyr
            20                  25                  30

Trp Met His Trp Val Arg Gln Ala Pro Gly Gln Gly Leu Glu Trp Ile
        35                  40                  45

Gly Val Ile Asp Pro Ser Asp Asn Tyr Ile Asn Tyr Asn Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Thr Arg Gly Tyr Phe Asp Tyr Trp Gly Gln Gly
            100                 105                 110

Thr Leu Val Thr Val Ser Ser
        115

<210> SEQ ID NO 295
<211> LENGTH: 119
```

```
<212> TYPE: PRT
<213> ORGANISM: Artificial Sequence
<220> FEATURE:
<223> OTHER INFORMATION: MTK-33.6 Heavy Chain Variable

<400> SEQUENCE: 295

Gln Val Gln Leu Val Gln Ser Gly Ala Glu Val Lys Lys Pro Gly Ala
1               5                   10                  15

Ser Val Lys Val Ser Cys Met Ala Ser Gly Tyr Thr Phe Arg Ser Tyr
            20                  25                  30

Trp Met His Trp Val Arg Gln Ala Pro Gly Gln Gly Leu Glu Trp Ile
        35                  40                  45

Gly Val Ile Asp Pro Ser Asp Asn Tyr Ile Asn Tyr Asn Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Thr Arg Gly Tyr Phe Asp Tyr Trp Gly Gln Gly
            100                 105                 110

Thr Leu Val Thr Val Ser Ser
        115

<210> SEQ ID NO 296
<211> LENGTH: 119
<212> TYPE: PRT
<213> ORGANISM: Artificial Sequence
<220> FEATURE:
<223> OTHER INFORMATION: MTK-33.7 Heavy Chain Variable

<400> SEQUENCE: 296

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Val Ile Asp Pro Ser Asp Asn Tyr Ile Asn Tyr Asn Ala Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Thr Arg Gly Tyr Phe Asp Tyr Trp Gly Gln Gly
            100                 105                 110

Thr Leu Val Thr Val Ser Ser
        115

<210> SEQ ID NO 297
<211> LENGTH: 119
<212> TYPE: PRT
<213> ORGANISM: Artificial Sequence
<220> FEATURE:
<223> OTHER INFORMATION: MTK-33.9 Heavy Chain Variable

<400> SEQUENCE: 297

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
```

```
                    20                  25                  30
Trp Met His Trp Val Arg Gln Ala Pro Gly Gln Gly Leu Glu Trp Ile
            35                  40                  45
Gly Val Ile Asp Pro Ser Asp Arg Tyr Ile Asn Tyr Asn Gln Lys Phe
        50                  55                  60
Gln Gly Arg Val Thr Met Thr Arg Asp Thr Ser Ser Thr Val Tyr
65                  70                  75                  80
Met Glu Leu Ser Ser Leu Arg Ser Glu Asp Thr Ala Val Tyr Tyr Cys
                85                  90                  95
Ala Arg Glu Ala Gly Thr Arg Gly Tyr Phe Asp Tyr Trp Gly Gln Gly
                100                 105                 110
Thr Leu Val Thr Val Ser Ser
            115

<210> SEQ ID NO 298
<211> LENGTH: 119
<212> TYPE: PRT
<213> ORGANISM: Artificial Sequence
<220> FEATURE:
<223> OTHER INFORMATION: MTK-33.10 Heavy Chain Variable

<400> SEQUENCE: 298

Gln Val Gln Leu Val Gln Ser Gly Ala Glu Val Lys Lys Pro Gly Ala
1               5                   10                  15
Ser Val Lys Val Ser Cys Lys Ala Ser Ser Tyr Ser Phe Thr Ser Tyr
                20                  25                  30
Trp Met His Trp Val Arg Gln Ala Pro Gly Gln Gly Leu Glu Trp Ile
            35                  40                  45
Gly Val Ile Asp Pro Ser Asp Asn Tyr Ile Asn Tyr Asn Gln Lys Phe
        50                  55                  60
Arg Gly Arg Val Thr Met Thr Arg Asp Thr Ser Ser Thr Val Tyr
65                  70                  75                  80
Met Glu Leu Ser Ser Leu Arg Ser Glu Asp Thr Ala Val Tyr Tyr Cys
                85                  90                  95
Ala Arg Glu Ala Gly Thr Arg Gly Tyr Phe Asp Tyr Trp Gly Gln Gly
                100                 105                 110
Thr Leu Val Thr Val Ser Ser
            115

<210> SEQ ID NO 299
<211> LENGTH: 119
<212> TYPE: PRT
<213> ORGANISM: Artificial Sequence
<220> FEATURE:
<223> OTHER INFORMATION: MTK-33.12 Heavy Chain Variable

<400> SEQUENCE: 299

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Val Ser Tyr
                20                  25                  30
Trp Met His Trp Val Arg Gln Ala Pro Gly Gln Gly Leu Glu Trp Ile
            35                  40                  45
Gly Val Ile Asp Pro Ser Asp Asn Tyr Ile Asn Tyr Asn Gln Lys Phe
        50                  55                  60
Arg Gly Arg Val Thr Met Thr Arg Asp Thr Ser Ser Thr Val Tyr
65                  70                  75                  80
```

```
Met Glu Leu Ser Ser Leu Arg Ser Glu Asp Thr Ala Val Tyr Tyr Cys
                85                  90                  95

Ala Arg Glu Ala Gly Thr Arg Gly Tyr Phe Asp Tyr Trp Gly Gln Gly
            100                 105                 110

Thr Leu Val Thr Val Ser Ser
        115

<210> SEQ ID NO 300
<211> LENGTH: 119
<212> TYPE: PRT
<213> ORGANISM: Artificial Sequence
<220> FEATURE:
<223> OTHER INFORMATION: MTK-33.13 Heavy Chain Variable

<400> SEQUENCE: 300

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Val Ile Asp Pro Ser Asp Asn Tyr Ile Asn Tyr Asn Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Thr Arg Gly Tyr Phe Asp Tyr Trp Gly Gln Gly
            100                 105                 110

Thr Leu Val Thr Val Ser Ser
        115

<210> SEQ ID NO 301
<211> LENGTH: 119
<212> TYPE: PRT
<213> ORGANISM: Artificial Sequence
<220> FEATURE:
<223> OTHER INFORMATION: MTK-33.14, 33.19, 33.20, 33.21 Heavy Chain
      Variable

<400> SEQUENCE: 301

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Val Ile Asp Pro Ser Asp Asn Tyr Ile Asn Tyr Asn Gln Lys Phe
    50                  55                  60

Arg Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Thr Arg Gly Tyr Phe Asp Tyr Trp Gly Gln Gly
            100                 105                 110

Thr Leu Val Thr Val Ser Ser
        115
```

-continued

```
<210> SEQ ID NO 302
<211> LENGTH: 119
<212> TYPE: PRT
<213> ORGANISM: Artificial Sequence
<220> FEATURE:
<223> OTHER INFORMATION: MTK-33.15 Heavy Chain Variable

<400> SEQUENCE: 302
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Val Ile Asp Pro Ser Asp Asn Tyr Ile Asn Tyr Asn Gln Lys Phe
    50                  55                  60

Gln Val Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Thr Arg Gly Tyr Phe Asp Tyr Trp Gly Gln Gly
            100                 105                 110

Thr Leu Val Thr Val Ser Ser
        115

```
<210> SEQ ID NO 303
<211> LENGTH: 119
<212> TYPE: PRT
<213> ORGANISM: Artificial Sequence
<220> FEATURE:
<223> OTHER INFORMATION: MTK-33.16 Heavy Chain Variable

<400> SEQUENCE: 303
```

Gln Val Gln Leu Val Gln Ser Gly Ala Glu Val Lys Lys Pro Gly Ala
1               5                   10                  15

Ser Val Lys Val Ser Cys Lys Ala Ser Trp Tyr Thr Phe Thr Ser Tyr
            20                  25                  30

Trp Met His Trp Val Arg Gln Ala Pro Gly Gln Gly Leu Glu Trp Ile
        35                  40                  45

Gly Val Ile Asp Pro Ser Asp Asn Tyr Ile Asn Tyr Asn Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Thr Arg Gly Tyr Phe Asp Tyr Trp Gly Gln Gly
            100                 105                 110

Thr Leu Val Thr Val Ser Ser
        115

```
<210> SEQ ID NO 304
<211> LENGTH: 119
<212> TYPE: PRT
<213> ORGANISM: Artificial Sequence
<220> FEATURE:
<223> OTHER INFORMATION: MTK-33.17 Heavy Chain Variable

<400> SEQUENCE: 304
```

Gln Val Gln Leu Val Gln Ser Gly Ala Glu Val Lys Lys Pro Gly Ala
1               5                   10                  15

```
Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
            35                  40                  45

Gly Val Ile Ala Pro Ser Asp Asn Tyr Ile Asn Tyr Asn Gln Lys Phe
    50                  55                  60

Arg Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Thr Arg Gly Tyr Phe Asp Tyr Trp Gly Gln Gly
            100                 105                 110

Thr Leu Val Thr Val Ser Ser
            115

<210> SEQ ID NO 305
<211> LENGTH: 119
<212> TYPE: PRT
<213> ORGANISM: Artificial Sequence
<220> FEATURE:
<223> OTHER INFORMATION: MTK-33.18 Heavy Chain Variable

<400> SEQUENCE: 305

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
            35                  40                  45

Gly Val Ile Ser Pro Ser Asp Asn Tyr Ile Asn Tyr Asn Gln Lys Phe
    50                  55                  60

Arg Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Thr Arg Gly Tyr Phe Asp Tyr Trp Gly Gln Gly
            100                 105                 110

Thr Leu Val Thr Val Ser Ser
            115

<210> SEQ ID NO 306
<211> LENGTH: 119
<212> TYPE: PRT
<213> ORGANISM: Artificial Sequence
<220> FEATURE:
<223> OTHER INFORMATION: MTK-33.22 Heavy Chain Variable

<400> SEQUENCE: 306

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
            35                  40                  45

Gly Val Ile Asp Pro Ser Asp Asn Tyr Ile Asn Tyr Asn Gln Lys Leu
    50                  55                  60

Arg Gly Arg Val Thr Met Thr Arg Asp Thr Ser Thr Ser Thr Val Tyr
```

65                  70                  75                  80

Met Glu Leu Ser Ser Leu Arg Ser Glu Asp Thr Ala Val Tyr Tyr Cys
                85                  90                  95

Ala Arg Glu Ala Gly Thr Arg Gly Tyr Phe Asp Tyr Trp Gly Gln Gly
            100                 105                 110

Thr Leu Val Thr Val Ser Ser
        115

<210> SEQ ID NO 307
<211> LENGTH: 119
<212> TYPE: PRT
<213> ORGANISM: Artificial Sequence
<220> FEATURE:
<223> OTHER INFORMATION: MTK-33.23 Heavy Chain Variable

<400> SEQUENCE: 307

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Val Ile Asp Pro Ser Asp Asn Tyr Ile Asn Tyr Asn Gln Lys Phe
    50                  55                  60

Arg Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Tyr Thr Arg Gly Tyr Phe Asp Tyr Trp Gly Gln Gly
            100                 105                 110

Thr Leu Val Thr Val Ser Ser
        115

<210> SEQ ID NO 308
<211> LENGTH: 119
<212> TYPE: PRT
<213> ORGANISM: Artificial Sequence
<220> FEATURE:
<223> OTHER INFORMATION: MTK-33.24 Heavy Chain Variable

<400> SEQUENCE: 308

Gln Val Gln Leu Val Gln Ser Gly Ala Glu Val Lys Lys Pro Gly Ala
1               5                   10                  15

Ser Val Lys Val Ser Cys Lys Ala Ser Ser Tyr Thr Phe Thr Ser Tyr
            20                  25                  30

Trp Met His Trp Val Arg Gln Ala Pro Gly Gln Gly Leu Glu Trp Ile
        35                  40                  45

Gly Val Ile Asp Pro Ser Asp Asn Tyr Ile Asn Tyr Asn Gln Lys Phe
    50                  55                  60

Arg Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Thr Arg Gly Tyr Phe Asp Tyr Trp Gly Gln Gly
            100                 105                 110

Thr Leu Val Thr Val Ser Ser
        115

<210> SEQ ID NO 309
<211> LENGTH: 107
<212> TYPE: PRT
<213> ORGANISM: Artificial Sequence
<220> FEATURE:
<223> OTHER INFORMATION: MTK-33.1 Light Chain Variable

<400> SEQUENCE: 309

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Val Ser Asn Thr
            20                  25                  30

Val Ala Trp Tyr Gln Gln Lys Pro Gly Lys Ala Pro Lys Leu Leu Ile
        35                  40                  45

Tyr Tyr Ala Ser Leu Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Asp Tyr Arg Ser Pro Phe
                85                  90                  95

Thr Phe Gly Gln Gly Thr Lys Leu Glu Ile Lys
            100                 105

<210> SEQ ID NO 310
<211> LENGTH: 107
<212> TYPE: PRT
<213> ORGANISM: Artificial Sequence
<220> FEATURE:
<223> OTHER INFORMATION: MTK-33.2 Light Chain Variable

<400> SEQUENCE: 310

Asp Ile Gln Met Thr Gln Ser Pro Ser Ser Leu Ser Ala Ser Val Gly
1               5                   10                  15

Asp Arg Val Thr Ile Thr Cys Gln Ala Ser Gly Ser Val Ser Asn Thr
            20                  25                  30

Val Ala Trp Tyr Gln Gln Lys Pro Gly Lys Ala Pro Lys Leu Leu Ile
        35                  40                  45

Tyr Tyr Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Asp Tyr Arg Ser Pro Phe
                85                  90                  95

Thr Phe Gly Gln Gly Thr Lys Leu Glu Ile Lys
            100                 105

<210> SEQ ID NO 311
<211> LENGTH: 107
<212> TYPE: PRT
<213> ORGANISM: Artificial Sequence
<220> FEATURE:
<223> OTHER INFORMATION: MTK-33.3, 33.13, 33.16 Light Chain Variable

<400> SEQUENCE: 311

Asp Ile Gln Met Thr Gln Ser Pro Ser Ser Leu Ser Ala Ser Val Gly
1               5                   10                  15

Asp Arg Val Thr Ile Thr Cys Gln Ala Ser Arg Ser Val Ser Asn Thr
            20                  25                  30

Val Ala Trp Tyr Gln Gln Lys Pro Gly Lys Ala Pro Lys Leu Leu Ile

```
                35                  40                  45
Tyr Tyr Ala Ser Asn Arg Tyr Thr Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Asp Tyr Arg Ser Pro Phe
                 85                  90                  95

Thr Phe Gly Gln Gly Thr Lys Leu Glu Ile Lys
            100                 105

<210> SEQ ID NO 312
<211> LENGTH: 107
<212> TYPE: PRT
<213> ORGANISM: Artificial Sequence
<220> FEATURE:
<223> OTHER INFORMATION: MTK-33.4 Light Chain Variable

<400> SEQUENCE: 312

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Ser Val Ser Asn Thr
            20                  25                  30

Val Ala Trp Tyr Gln Gln Lys Pro Gly Lys Ala Pro Lys Leu Leu Ile
        35                  40                  45

Tyr Tyr Ala Ser Asn Arg Tyr Thr Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Asp Arg Arg Ser Pro Phe
                 85                  90                  95

Thr Phe Gly Gln Gly Thr Lys Leu Glu Ile Lys
            100                 105

<210> SEQ ID NO 313
<211> LENGTH: 107
<212> TYPE: PRT
<213> ORGANISM: Artificial Sequence
<220> FEATURE:
<223> OTHER INFORMATION: MTK-33.5 Light Chain Variable

<400> SEQUENCE: 313

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Ser Val Ser Asn Thr
            20                  25                  30

Val Ala Trp Tyr Gln Gln Lys Pro Gly Lys Ala Pro Lys Leu Leu Ile
        35                  40                  45

Tyr Tyr Ala Ser Asn Arg Glu Thr Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Ile Gly Thr Tyr Tyr Cys Gln Gln Asp Tyr Arg Ser Pro Phe
                 85                  90                  95

Thr Phe Gly Gln Gly Thr Lys Leu Glu Ile Lys
            100                 105

<210> SEQ ID NO 314
<211> LENGTH: 107
```

```
<212> TYPE: PRT
<213> ORGANISM: Artificial Sequence
<220> FEATURE:
<223> OTHER INFORMATION: MTK-33.6 Light Chain Variable

<400> SEQUENCE: 314

Asp Ile Gln Met Thr Gln Ser Pro Ser Ser Leu Ser Ala Ser Val Gly
1               5                   10                  15

Asp Arg Val Thr Ile Thr Cys Gln Ala Ser Arg Ser Val Ser Asn Thr
            20                  25                  30

Met Ala Trp Tyr Gln Gln Lys Pro Gly Lys Ala Pro Lys Leu Leu Ile
        35                  40                  45

Tyr Tyr Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Asp Tyr Arg Ser Pro Phe
                85                  90                  95

Thr Phe Gly Gln Gly Thr Lys Leu Glu Ile Lys
            100                 105

<210> SEQ ID NO 315
<211> LENGTH: 107
<212> TYPE: PRT
<213> ORGANISM: Artificial Sequence
<220> FEATURE:
<223> OTHER INFORMATION: MTK-33.7 Light Chain Variable

<400> SEQUENCE: 315

Asp Ile Gln Met Thr Gln Ser Pro Ser Ser Leu Ser Ala Ser Val Gly
1               5                   10                  15

Asp Arg Val Thr Ile Thr Cys Gly Ala Ser Gln Ser Val Ser Asn Thr
            20                  25                  30

Val Ala Trp Tyr Gln Gln Lys Pro Gly Lys Ala Pro Lys Leu Leu Ile
        35                  40                  45

Tyr Tyr Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Asp Tyr Arg Ser Pro Phe
                85                  90                  95

Thr Phe Gly Gln Gly Thr Lys Leu Glu Ile Lys
            100                 105

<210> SEQ ID NO 316
<211> LENGTH: 107
<212> TYPE: PRT
<213> ORGANISM: Artificial Sequence
<220> FEATURE:
<223> OTHER INFORMATION: MTK-33.8 Light Chain Variable

<400> SEQUENCE: 316

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Val Ser Arg Thr
            20                  25                  30

Val Ala Trp Tyr Gln Gln Lys Pro Gly Lys Ala Pro Lys Leu Leu Ile
        35                  40                  45

Tyr Tyr Ala Ser Asn Arg Tyr Thr Gly Val Pro Ser Arg Phe Ser Gly
```

```
                50                  55                  60
Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Asp Tyr Arg Ser Pro Phe
                 85                  90                  95

Thr Phe Gly Gln Gly Thr Lys Leu Glu Ile Lys
            100                 105

<210> SEQ ID NO 317
<211> LENGTH: 107
<212> TYPE: PRT
<213> ORGANISM: Artificial Sequence
<220> FEATURE:
<223> OTHER INFORMATION: MTK-33.9 Light Chain Variable

<400> SEQUENCE: 317

Asp Ile Gln Met Thr Gln Ser Pro Ser Ser Leu Ser Ala Ser Val Gly
 1               5                  10                  15

Asp Arg Val Thr Ile Thr Cys Gln Ala Ser Ala Ser Val Ser Asn Thr
                20                  25                  30

Val Ala Trp Tyr Gln Gln Lys Pro Gly Lys Ala Pro Lys Leu Leu Ile
             35                  40                  45

Tyr Tyr Ala Ser Asn Arg Tyr Thr Gly Val Pro Ser Arg Phe Ser Gly
         50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Asp Tyr Arg Ser Pro Phe
                 85                  90                  95

Thr Phe Gly Gln Gly Thr Lys Leu Glu Ile Lys
            100                 105

<210> SEQ ID NO 318
<211> LENGTH: 107
<212> TYPE: PRT
<213> ORGANISM: Artificial Sequence
<220> FEATURE:
<223> OTHER INFORMATION: MTK-33.10 Light Chain Variable

<400> SEQUENCE: 318

Asp Ile Gln Met Thr Gln Ser Pro Ser Ser Leu Ser Ala Ser Val Gly
 1               5                  10                  15

Asp Arg Val Thr Ile Thr Cys Gln Ala Gly Gln Ser Val Ser Asn Thr
                20                  25                  30

Val Ala Trp Tyr Gln Gln Lys Pro Gly Lys Ala Pro Lys Leu Leu Ile
             35                  40                  45

Tyr Tyr Ala Ser Asn Arg Tyr Thr Gly Val Pro Ser Arg Phe Ser Gly
         50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Asp Tyr Arg Ser Pro Phe
                 85                  90                  95

Thr Phe Gly Gln Gly Thr Lys Leu Glu Ile Lys
            100                 105

<210> SEQ ID NO 319
<211> LENGTH: 107
<212> TYPE: PRT
<213> ORGANISM: Artificial Sequence
<220> FEATURE:
```

<223> OTHER INFORMATION: MTK-33.11 Light Chain Variable

<400> SEQUENCE: 319

Asp Ile Gln Met Thr Gln Ser Pro Ser Ser Leu Ser Ala Ser Val Gly
1               5                   10                  15

Asp Arg Val Thr Ile Thr Cys Gln Ala Ser Arg Ser Val Arg Asn Thr
            20                  25                  30

Val Ala Trp Tyr Gln Gln Lys Pro Gly Lys Ala Pro Lys Leu Leu Ile
        35                  40                  45

Tyr Tyr Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Asp Tyr Arg Ser Pro Phe
                85                  90                  95

Thr Phe Gly Gln Gly Thr Lys Leu Glu Ile Lys
            100                 105

<210> SEQ ID NO 320
<211> LENGTH: 107
<212> TYPE: PRT
<213> ORGANISM: Artificial Sequence
<220> FEATURE:
<223> OTHER INFORMATION: MTK-33.12 Light Chain Variable

<400> SEQUENCE: 320

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Val Ser Asn Thr
            20                  25                  30

Val Ala Trp Tyr Gln Gln Lys Pro Gly Lys Ala Pro Lys Leu Leu Ile
        35                  40                  45

Tyr Tyr Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Arg Gln Asp Thr Arg Ser Pro Phe
                85                  90                  95

Thr Phe Gly Gln Gly Thr Lys Leu Glu Leu Lys
            100                 105

<210> SEQ ID NO 321
<211> LENGTH: 107
<212> TYPE: PRT
<213> ORGANISM: Artificial Sequence
<220> FEATURE:
<223> OTHER INFORMATION: MTK-33.14 Light Chain Variable

<400> SEQUENCE: 321

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Val Ser Asn Thr
            20                  25                  30

Val Ala Trp Tyr Gln Gln Lys Pro Gly Lys Ala Pro Lys Leu Leu Ile
        35                  40                  45

Tyr Tyr Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro 65                  70                  75                  80

Glu Asp Ile Ala Thr Tyr Tyr Cys Gln Gln Asp Tyr Arg Ser Pro Phe
                85                  90                  95

Thr Phe Gly Gln Gly Thr Lys Leu Glu Ile Lys
            100                 105

<210> SEQ ID NO 322
<211> LENGTH: 107
<212> TYPE: PRT
<213> ORGANISM: Artificial Sequence
<220> FEATURE:
<223> OTHER INFORMATION: MTK-33.15, 33.17, 33.18 Light Chain Variable

<400> SEQUENCE: 322

Asp Ile Gln Met Thr Gln Ser Pro Ser Ser Leu Ser Ala Ser Val Gly
1               5                   10                  15

Asp Arg Val Thr Ile Thr Cys Gln Ala Ser Arg Ser Val Ser Asn Thr
                20                  25                  30

Val Ala Trp Tyr Gln Gln Lys Pro Gly Lys Ala Pro Lys Leu Leu Ile
            35                  40                  45

Tyr Tyr Ala Ser Asn Arg Tyr Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Asp Met Arg Ser Pro Phe
                85                  90                  95

Thr Phe Gly Gln Gly Thr Lys Leu Glu Ile Lys
            100                 105

<210> SEQ ID NO 323
<211> LENGTH: 107
<212> TYPE: PRT
<213> ORGANISM: Artificial Sequence
<220> FEATURE:
<223> OTHER INFORMATION: MTK-33.19 Light Chain Variable

<400> SEQUENCE: 323

Asp Ile Gln Met Thr Gln Ser Pro Ser Ser Leu Ser Ala Ser Val Gly
1               5                   10                  15

Asp Arg Val Thr Ile Thr Cys Gln Ala Ser Arg Ser Val Ser Ala Thr
                20                  25                  30

Val Ala Trp Tyr Gln Gln Lys Pro Gly Lys Ala Pro Lys Leu Leu Ile
            35                  40                  45

Tyr Tyr Ala Ser Asn Arg Tyr Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Asp Met Arg Ser Pro Phe
                85                  90                  95

Thr Phe Gly Gln Gly Thr Lys Leu Glu Ile Lys
            100                 105

<210> SEQ ID NO 324
<211> LENGTH: 107
<212> TYPE: PRT
<213> ORGANISM: Artificial Sequence
<220> FEATURE:
<223> OTHER INFORMATION: MTK-33.20 Light Chain Variable

<400> SEQUENCE: 324

Asp Ile Gln Met Thr Gln Ser Pro Ser Ser Leu Ser Ala Ser Val Gly
1               5                   10                  15

Asp Arg Val Thr Ile Thr Cys Gln Ala Ser Arg Ser Val Ser Asn Thr
            20                  25                  30

Val Ala Trp Tyr Gln Gln Lys Pro Gly Lys Ala Pro Lys Leu Leu Ile
        35                  40                  45

Tyr Tyr Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Ala Gln Asp Met Arg Ser Pro Phe
                85                  90                  95

Thr Phe Gly Gln Gly Thr Lys Leu Glu Ile Lys
                100                 105

<210> SEQ ID NO 325
<211> LENGTH: 107
<212> TYPE: PRT
<213> ORGANISM: Artificial Sequence
<220> FEATURE:
<223> OTHER INFORMATION: MTK-33.21 Light Chain Variable

<400> SEQUENCE: 325

Asp Ile Gln Met Thr Gln Ser Pro Ser Ser Leu Ser Ala Ser Val Gly
1               5                   10                  15

Gly Arg Val Thr Ile Thr Cys Gln Ala Ser Arg Ser Val Ser Asn Thr
            20                  25                  30

Val Ala Trp Tyr Gln Gln Lys Pro Gly Lys Ala Pro Lys Leu Leu Ile
        35                  40                  45

Tyr Tyr Val Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Asp Met Arg Ser Pro Phe
                85                  90                  95

Thr Phe Gly Gln Gly Thr Lys Leu Glu Ile Lys
                100                 105

<210> SEQ ID NO 326
<211> LENGTH: 107
<212> TYPE: PRT
<213> ORGANISM: Artificial Sequence
<220> FEATURE:
<223> OTHER INFORMATION: MTK-33.22 Light Chain Variable

<400> SEQUENCE: 326

Asp Ile Gln Met Thr Gln Ser Pro Ser Ser Leu Ser Ala Ser Val Gly
1               5                   10                  15

Asp Arg Val Thr Ile Thr Cys Gln Ala Ser Arg Ser Val Ser Asn Thr
            20                  25                  30

Val Ala Trp Tyr Gln Gln Lys Pro Gly Lys Ala Pro Lys Leu Leu Ile
        35                  40                  45

Tyr Tyr Ala Ser Asn Arg Arg Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Asp Met Arg Ser Pro Phe

```
                85                  90                  95

Thr Phe Gly Gln Gly Thr Lys Leu Glu Ile Lys
            100                 105

<210> SEQ ID NO 327
<211> LENGTH: 107
<212> TYPE: PRT
<213> ORGANISM: Artificial Sequence
<220> FEATURE:
<223> OTHER INFORMATION: MTK-33.23 Light Chain Variable

<400> SEQUENCE: 327

Asp Ile Gln Met Thr Gln Ser Pro Ser Ser Leu Ser Ala Ser Val Gly
1               5                   10                  15

Asp Arg Val Thr Ile Thr Cys Ile Ala Ser Arg Ser Val Ser Asn Thr
            20                  25                  30

Val Ala Trp Tyr Gln Gln Lys Pro Gly Lys Ala Pro Lys Leu Leu Ile
        35                  40                  45

Tyr Tyr Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Asp Met Arg Ser Pro Phe
                85                  90                  95

Thr Phe Gly Gln Gly Thr Lys Leu Glu Ile Lys
            100                 105

<210> SEQ ID NO 328
<211> LENGTH: 107
<212> TYPE: PRT
<213> ORGANISM: Artificial Sequence
<220> FEATURE:
<223> OTHER INFORMATION: MTK-33.24 Light Chain Variable

<400> SEQUENCE: 328

Asp Ile Gln Met Thr Gln Ser Pro Ser Ser Leu Ser Ala Ser Val Gly
1               5                   10                  15

Asp Arg Val Thr Ile Thr Cys Gln Ala Ser Arg Ser Val Ser Arg Thr
            20                  25                  30

Val Ala Trp Tyr Gln Gln Lys Pro Gly Lys Ala Pro Lys Leu Leu Ile
        35                  40                  45

Tyr Tyr Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Asp Met Arg Ser Pro Phe
                85                  90                  95

Thr Phe Gly Gln Gly Thr Lys Leu Glu Ile Lys
            100                 105

<210> SEQ ID NO 329
<211> LENGTH: 17
<212> TYPE: PRT
<213> ORGANISM: Artificial Sequence
<220> FEATURE:
<223> OTHER INFORMATION: MTK-15.1, 15.3, 15.4, 15.5, 15.7, 15.8, 15.9,
      15.13, 15.14, 15.15, 16.1 HVR-H2

<400> SEQUENCE: 329

Trp Ile Asn Thr Tyr Thr Gly Glu Pro Thr Tyr Ala Gln Gly Phe Thr
```

```
1               5                   10                  15

Gly

<210> SEQ ID NO 330
<211> LENGTH: 17
<212> TYPE: PRT
<213> ORGANISM: Artificial Sequence
<220> FEATURE:
<223> OTHER INFORMATION: MTK-15.2 HVR-H2

<400> SEQUENCE: 330

Trp Gly Asn Thr Tyr Thr Gly Glu Pro Thr Tyr Ala Gln Gly Phe Thr
1               5                   10                  15

Gly

<210> SEQ ID NO 331
<211> LENGTH: 17
<212> TYPE: PRT
<213> ORGANISM: Artificial Sequence
<220> FEATURE:
<223> OTHER INFORMATION: MTK-15.6 HVR-H2

<400> SEQUENCE: 331

Trp Ile Asn Thr Tyr Thr Gly Glu Pro Tyr Tyr Ala Gln Gly Phe Thr
1               5                   10                  15

Gly

<210> SEQ ID NO 332
<211> LENGTH: 17
<212> TYPE: PRT
<213> ORGANISM: Artificial Sequence
<220> FEATURE:
<223> OTHER INFORMATION: MTK-15.10, 15.12 HVR-H2

<400> SEQUENCE: 332

Trp Ile Asn Thr Tyr Gln Gly Glu Pro Thr Tyr Ala Gln Gly Phe Thr
1               5                   10                  15

Gly

<210> SEQ ID NO 333
<211> LENGTH: 17
<212> TYPE: PRT
<213> ORGANISM: Artificial Sequence
<220> FEATURE:
<223> OTHER INFORMATION: MTK-15.11 HVR-H2

<400> SEQUENCE: 333

Trp Ile Asn Thr Tyr Glu Gly Glu Pro Thr Tyr Ala Gln Gly Phe Thr
1               5                   10                  15

Gly

<210> SEQ ID NO 334
<211> LENGTH: 9
<212> TYPE: PRT
<213> ORGANISM: Artificial Sequence
<220> FEATURE:
<223> OTHER INFORMATION: MTK-15.1, 15.11 HVR-H3

<400> SEQUENCE: 334

Gly Asn Arg Tyr Ala Tyr Gln Asp Tyr
1               5

<210> SEQ ID NO 335
```

```
<211> LENGTH: 9
<212> TYPE: PRT
<213> ORGANISM: Artificial Sequence
<220> FEATURE:
<223> OTHER INFORMATION: MTK-15.5 HVR-H3

<400> SEQUENCE: 335

Gly Thr Arg Tyr Ala Tyr Met Asp Tyr
1               5

<210> SEQ ID NO 336
<211> LENGTH: 9
<212> TYPE: PRT
<213> ORGANISM: Artificial Sequence
<220> FEATURE:
<223> OTHER INFORMATION: MTK-15.8, 15.12 HVR-H3

<400> SEQUENCE: 336

Gly Val Arg Tyr Ala Tyr Met Asp Tyr
1               5

<210> SEQ ID NO 337
<211> LENGTH: 9
<212> TYPE: PRT
<213> ORGANISM: Artificial Sequence
<220> FEATURE:
<223> OTHER INFORMATION: MTK-15.9 HVR-H3

<400> SEQUENCE: 337

Gly Tyr Arg Tyr Ala Tyr Met Asp Tyr
1               5

<210> SEQ ID NO 338
<211> LENGTH: 9
<212> TYPE: PRT
<213> ORGANISM: Artificial Sequence
<220> FEATURE:
<223> OTHER INFORMATION: MTK-15.10 HVR-H3

<400> SEQUENCE: 338

Gly Ala Arg Tyr Ala Tyr Met Asp Tyr
1               5

<210> SEQ ID NO 339
<211> LENGTH: 9
<212> TYPE: PRT
<213> ORGANISM: Artificial Sequence
<220> FEATURE:
<223> OTHER INFORMATION: MTK-15.13 HVR-H3

<400> SEQUENCE: 339

Gly Asn Arg Tyr Ala Tyr Glu Asp Tyr
1               5

<210> SEQ ID NO 340
<211> LENGTH: 10
<212> TYPE: PRT
<213> ORGANISM: Artificial Sequence
<220> FEATURE:
<223> OTHER INFORMATION: MTK-15.3 HVR-L1

<400> SEQUENCE: 340

Arg Ala Ser Ser His Val Ser Tyr Met His
1               5                   10

<210> SEQ ID NO 341
<211> LENGTH: 10
```

```
<212> TYPE: PRT
<213> ORGANISM: Artificial Sequence
<220> FEATURE:
<223> OTHER INFORMATION: MTK-15.4, 15.5, 15.6, 15.8, 15.10, 15.12, 29.1,
      29.2, 29.3, 29.4, 29.5, 29.6, 29.7, 29.8, 29.9, 29.10, 29.11,
      29.12, 29.13, 29.14, 29.15, 29.16 HVR-L1

<400> SEQUENCE: 341

Arg Ala Ser Ser Ser Val Gly Tyr Met His
1               5                   10

<210> SEQ ID NO 342
<211> LENGTH: 10
<212> TYPE: PRT
<213> ORGANISM: Artificial Sequence
<220> FEATURE:
<223> OTHER INFORMATION: MTK-15.7 HVR-L1

<400> SEQUENCE: 342

Arg Ala Ser Ser Gly Val Ser Tyr Met His
1               5                   10

<210> SEQ ID NO 343
<211> LENGTH: 10
<212> TYPE: PRT
<213> ORGANISM: Artificial Sequence
<220> FEATURE:
<223> OTHER INFORMATION: MTK-15.9 HVR-L1

<400> SEQUENCE: 343

Arg Ala Ser Ser Ser Thr Ser Tyr Met His
1               5                   10

<210> SEQ ID NO 344
<211> LENGTH: 10
<212> TYPE: PRT
<213> ORGANISM: Artificial Sequence
<220> FEATURE:
<223> OTHER INFORMATION: MTK-15.13 HVR-L1

<400> SEQUENCE: 344

Arg Ala Ser Ser Ser Val Gln Tyr Met His
1               5                   10

<210> SEQ ID NO 345
<211> LENGTH: 11
<212> TYPE: PRT
<213> ORGANISM: Artificial Sequence
<220> FEATURE:
<223> OTHER INFORMATION: MTK-16.2 HVR-L1

<400> SEQUENCE: 345

Arg Ala Ser Gln Asn Val Arg Thr Ala Val Ala
1               5                   10

<210> SEQ ID NO 346
<211> LENGTH: 5
<212> TYPE: PRT
<213> ORGANISM: Artificial Sequence
<220> FEATURE:
<223> OTHER INFORMATION: MTK-29.1, 29.5, 29.9, 29.16, 29.17, 29.18
      HVR-H1

<400> SEQUENCE: 346

Ser Tyr Gly Leu Ser
1               5
```

-continued

```
<210> SEQ ID NO 347
<211> LENGTH: 5
<212> TYPE: PRT
<213> ORGANISM: Artificial Sequence
<220> FEATURE:
<223> OTHER INFORMATION: MTK-29.8 HVR-H1

<400> SEQUENCE: 347

Thr Tyr Gly Leu Ser
1               5

<210> SEQ ID NO 348
<211> LENGTH: 17
<212> TYPE: PRT
<213> ORGANISM: Artificial Sequence
<220> FEATURE:
<223> OTHER INFORMATION: MTK-29.1, 29.17, 29.19, 29.20, 29.21 HVR-H2

<400> SEQUENCE: 348

Trp Ile Asn Thr Tyr Ser Gly Val Pro Thr Tyr Ala Gln Gly Phe Thr
1               5                   10                  15

Gly

<210> SEQ ID NO 349
<211> LENGTH: 17
<212> TYPE: PRT
<213> ORGANISM: Artificial Sequence
<220> FEATURE:
<223> OTHER INFORMATION: MTK-29.3 HVR-H2

<400> SEQUENCE: 349

Trp Ile Asn Thr Tyr Ser Gly Val Pro Ala Tyr Thr Asp Asp Phe Lys
1               5                   10                  15

Gly

<210> SEQ ID NO 350
<211> LENGTH: 17
<212> TYPE: PRT
<213> ORGANISM: Artificial Sequence
<220> FEATURE:
<223> OTHER INFORMATION: MTK-29.6, 29.12, 29.15 HVR-H2

<400> SEQUENCE: 350

Trp Ile Asn Thr Met Ser Gly Val Pro Thr Tyr Thr Asp Asp Phe Lys
1               5                   10                  15

Gly

<210> SEQ ID NO 351
<211> LENGTH: 17
<212> TYPE: PRT
<213> ORGANISM: Artificial Sequence
<220> FEATURE:
<223> OTHER INFORMATION: MTK-29.7, 29.14 HVR-H2

<400> SEQUENCE: 351

Trp Ile Asn Thr Tyr Ser Gly Val Pro Ser Tyr Thr Asp Asp Phe Lys
1               5                   10                  15

Ala

<210> SEQ ID NO 352
<211> LENGTH: 17
<212> TYPE: PRT
<213> ORGANISM: Artificial Sequence
<220> FEATURE:
<223> OTHER INFORMATION: MTK-29.11 HVR-H2
```

<400> SEQUENCE: 352

Trp Ile Asn Thr Asp Ser Gly Val Pro Thr Tyr Thr Asp Asp Phe Lys
1               5                   10                  15
Gly

<210> SEQ ID NO 353
<211> LENGTH: 17
<212> TYPE: PRT
<213> ORGANISM: Artificial Sequence
<220> FEATURE:
<223> OTHER INFORMATION: MTK-29.13 HVR-H2

<400> SEQUENCE: 353

Trp Ile Asn Thr Ala Ser Gly Val Pro Thr Tyr Thr Asp Asp Phe Lys
1               5                   10                  15
Gly

<210> SEQ ID NO 354
<211> LENGTH: 17
<212> TYPE: PRT
<213> ORGANISM: Artificial Sequence
<220> FEATURE:
<223> OTHER INFORMATION: MTK-29.16, 29.18 HVR-H2

<400> SEQUENCE: 354

Trp Val Asn Thr Tyr Ser Gly Val Pro Thr Tyr Thr Asp Asp Phe Lys
1               5                   10                  15
Gly

<210> SEQ ID NO 355
<211> LENGTH: 17
<212> TYPE: PRT
<213> ORGANISM: Artificial Sequence
<220> FEATURE:
<223> OTHER INFORMATION: MTK-29.1, 29.2 HVR-H3

<400> SEQUENCE: 355

Trp Ile Asn Thr Tyr Ser Gly Val Pro Thr Tyr Ala Gln Gly Phe Thr
1               5                   10                  15
Gly

<210> SEQ ID NO 356
<211> LENGTH: 9
<212> TYPE: PRT
<213> ORGANISM: Artificial Sequence
<220> FEATURE:
<223> OTHER INFORMATION: MTK-29.3, 29.4, 29.5, 29.6, 29.7, 29.8, 29.9,
      29.10, 29.11, 29.12, 29.13, 29.14, 29.15, 29.16, 29.17, 29.18
      HVR-H3

<400> SEQUENCE: 356

Tyr Thr Asn Tyr Gly Val Phe Asp Tyr
1               5

<210> SEQ ID NO 357
<211> LENGTH: 10
<212> TYPE: PRT
<213> ORGANISM: Artificial Sequence
<220> FEATURE:
<223> OTHER INFORMATION: MTK-29.17 HVR-L1

<400> SEQUENCE: 357

Arg Ser Ser Ser Ser Val Gly Tyr Met His

```
1               5                  10
```

<210> SEQ ID NO 358
<211> LENGTH: 10
<212> TYPE: PRT
<213> ORGANISM: Artificial Sequence
<220> FEATURE:
<223> OTHER INFORMATION: MTK-29.18 HVR-L1

<400> SEQUENCE: 358

```
Arg Ala Ser Ser Thr Val Gly Tyr Met His
1               5                  10
```

<210> SEQ ID NO 359
<211> LENGTH: 7
<212> TYPE: PRT
<213> ORGANISM: Artificial Sequence
<220> FEATURE:
<223> OTHER INFORMATION: MTK-29.4, 29.5, 29.6, 29.7, 29.8, 29.9, 29.12,
      29.13, 29.14, 29.15, 29.16, 29.17 HVR-L2

<400> SEQUENCE: 359

```
Ala Thr Ser Asn Leu Ala Gln
1               5
```

<210> SEQ ID NO 360
<211> LENGTH: 9
<212> TYPE: PRT
<213> ORGANISM: Artificial Sequence
<220> FEATURE:
<223> OTHER INFORMATION: MTK-29.1 HVR-L3

<400> SEQUENCE: 360

```
Gln Gln Trp Gly Ser Trp Pro Phe Thr
1               5
```

<210> SEQ ID NO 361
<211> LENGTH: 9
<212> TYPE: PRT
<213> ORGANISM: Artificial Sequence
<220> FEATURE:
<223> OTHER INFORMATION: MTK-29.2 HVR-L3

<400> SEQUENCE: 361

```
Gln Gln Trp Gly Ser Ile Pro Phe Thr
1               5
```

<210> SEQ ID NO 362
<211> LENGTH: 9
<212> TYPE: PRT
<213> ORGANISM: Artificial Sequence
<220> FEATURE:
<223> OTHER INFORMATION: MTK-29.3, 29.4, 29.5, 29.6, 29.7, 29.8, 29.9,
      29.10, 29.11, 29.12, 29.13, 29.14, 29.15, 29.17, 29.18 HVR-L3

<400> SEQUENCE: 362

```
Gln Gln Trp Gly Ser Leu Pro Phe Thr
1               5
```

<210> SEQ ID NO 363
<211> LENGTH: 9
<212> TYPE: PRT
<213> ORGANISM: Artificial Sequence
<220> FEATURE:
<223> OTHER INFORMATION: MTK-29.16 HVR-L3

<400> SEQUENCE: 363

```
Gln Gln Trp Gly Arg Leu Pro Phe Thr
1               5
```

<210> SEQ ID NO 364
<211> LENGTH: 17
<212> TYPE: PRT
<213> ORGANISM: Artificial Sequence
<220> FEATURE:
<223> OTHER INFORMATION: MTK-33.1, 33.2, 33.3, 33.5, 33.6, 33.8, 33.11,
      33.13, 33.16 HVR-H2

<400> SEQUENCE: 364

```
Val Ile Asp Pro Ser Asp Asn Tyr Ile Asn Tyr Asn Gln Lys Phe Gln
1               5                   10                  15

Gly
```

<210> SEQ ID NO 365
<211> LENGTH: 17
<212> TYPE: PRT
<213> ORGANISM: Artificial Sequence
<220> FEATURE:
<223> OTHER INFORMATION: MTK-33.4 HVR-H2

<400> SEQUENCE: 365

```
Val Ile Asp Pro Ser Asp Asn Tyr Ile Asn Met Asn Gln Lys Phe Gln
1               5                   10                  15

Gly
```

<210> SEQ ID NO 366
<211> LENGTH: 17
<212> TYPE: PRT
<213> ORGANISM: Artificial Sequence
<220> FEATURE:
<223> OTHER INFORMATION: MTK-33.7 HVR-H2

<400> SEQUENCE: 366

```
Val Ile Asp Pro Ser Asp Asn Tyr Ile Asn Tyr Asn Ala Lys Phe Gln
1               5                   10                  15

Gly
```

<210> SEQ ID NO 367
<211> LENGTH: 17
<212> TYPE: PRT
<213> ORGANISM: Artificial Sequence
<220> FEATURE:
<223> OTHER INFORMATION: MTK-33.9 HVR-H2

<400> SEQUENCE: 367

```
Val Ile Asp Pro Ser Asp Arg Tyr Ile Asn Tyr Asn Gln Lys Phe Gln
1               5                   10                  15

Gly
```

<210> SEQ ID NO 368
<211> LENGTH: 17
<212> TYPE: PRT
<213> ORGANISM: Artificial Sequence
<220> FEATURE:
<223> OTHER INFORMATION: MTK-33.10, 33.12, 33.14, 33.19, 33.20, 33.21,
      33.23, 33.24 HVR-H2

<400> SEQUENCE: 368

```
Val Ile Asp Pro Ser Asp Asn Tyr Ile Asn Tyr Asn Gln Lys Phe Arg
1               5                   10                  15

Gly
```

<210> SEQ ID NO 369
<211> LENGTH: 17
<212> TYPE: PRT
<213> ORGANISM: Artificial Sequence
<220> FEATURE:
<223> OTHER INFORMATION: MTK-33.15 HVR-H2

<400> SEQUENCE: 369

Val Ile Asp Pro Ser Asp Asn Tyr Ile Asn Tyr Asn Gln Lys Phe Gln
1               5                   10                  15

Val

<210> SEQ ID NO 370
<211> LENGTH: 17
<212> TYPE: PRT
<213> ORGANISM: Artificial Sequence
<220> FEATURE:
<223> OTHER INFORMATION: MTK-33.17 HVR-H2

<400> SEQUENCE: 370

Val Ile Ala Pro Ser Asp Asn Tyr Ile Asn Tyr Asn Gln Lys Phe Arg
1               5                   10                  15

Gly

<210> SEQ ID NO 371
<211> LENGTH: 17
<212> TYPE: PRT
<213> ORGANISM: Artificial Sequence
<220> FEATURE:
<223> OTHER INFORMATION: MTK-33.18 HVR-H2

<400> SEQUENCE: 371

Val Ile Ser Pro Ser Asp Asn Tyr Ile Asn Tyr Asn Gln Lys Phe Arg
1               5                   10                  15

Gly

<210> SEQ ID NO 372
<211> LENGTH: 17
<212> TYPE: PRT
<213> ORGANISM: Artificial Sequence
<220> FEATURE:
<223> OTHER INFORMATION: MTK-33.22 HVR-H2

<400> SEQUENCE: 372

Val Ile Asp Pro Ser Asp Asn Tyr Ile Asn Tyr Asn Gln Lys Leu Arg
1               5                   10                  15

Gly

<210> SEQ ID NO 373
<211> LENGTH: 10
<212> TYPE: PRT
<213> ORGANISM: Artificial Sequence
<220> FEATURE:
<223> OTHER INFORMATION: MTK-33.1, 33.8 HVR-H3

<400> SEQUENCE: 373

Glu Ala Trp Thr Arg Gly Tyr Phe Asn Tyr
1               5                   10

<210> SEQ ID NO 374
<211> LENGTH: 10
<212> TYPE: PRT
<213> ORGANISM: Artificial Sequence

```
<220> FEATURE:
<223> OTHER INFORMATION: MTK-33.3, 33.11 HVR-H3

<400> SEQUENCE: 374

Glu Ala Trp Thr Arg Gly Tyr Phe Asp Tyr
1               5                   10

<210> SEQ ID NO 375
<211> LENGTH: 10
<212> TYPE: PRT
<213> ORGANISM: Artificial Sequence
<220> FEATURE:
<223> OTHER INFORMATION: MTK-33.23 HVR-H3

<400> SEQUENCE: 375

Glu Ala Tyr Thr Arg Gly Tyr Phe Asp Tyr
1               5                   10

<210> SEQ ID NO 376
<211> LENGTH: 11
<212> TYPE: PRT
<213> ORGANISM: Artificial Sequence
<220> FEATURE:
<223> OTHER INFORMATION: MTK-33.1, 33.4, 33.5, 33.12, 33.14 HVR-L1

<400> SEQUENCE: 376

Gln Ala Ser Gln Ser Val Ser Asn Thr Val Ala
1               5                   10

<210> SEQ ID NO 377
<211> LENGTH: 11
<212> TYPE: PRT
<213> ORGANISM: Artificial Sequence
<220> FEATURE:
<223> OTHER INFORMATION: MTK-33.2 HVR-L1

<400> SEQUENCE: 377

Gln Ala Ser Gly Ser Val Ser Asn Thr Val Ala
1               5                   10

<210> SEQ ID NO 378
<211> LENGTH: 11
<212> TYPE: PRT
<213> ORGANISM: Artificial Sequence
<220> FEATURE:
<223> OTHER INFORMATION: MTK-33.3, 33.13, 33.15, 33.16, 33.17, 33.18,
      33.20, 33.21, 33.22 HVR-L1

<400> SEQUENCE: 378

Gln Ala Ser Arg Ser Val Ser Asn Thr Val Ala
1               5                   10

<210> SEQ ID NO 379
<211> LENGTH: 11
<212> TYPE: PRT
<213> ORGANISM: Artificial Sequence
<220> FEATURE:
<223> OTHER INFORMATION: MTK-33.6 HVR-L1

<400> SEQUENCE: 379

Gln Ala Ser Arg Ser Val Ser Asn Thr Met Ala
1               5                   10

<210> SEQ ID NO 380
<211> LENGTH: 11
<212> TYPE: PRT
<213> ORGANISM: Artificial Sequence
```

```
<220> FEATURE:
<223> OTHER INFORMATION: MTK-33.7 HVR-L1

<400> SEQUENCE: 380

Gly Ala Ser Gln Ser Val Ser Asn Thr Val Ala
1               5                   10

<210> SEQ ID NO 381
<211> LENGTH: 11
<212> TYPE: PRT
<213> ORGANISM: Artificial Sequence
<220> FEATURE:
<223> OTHER INFORMATION: MTK-33.8 HVR-L1

<400> SEQUENCE: 381

Gln Ala Ser Gln Ser Val Ser Arg Thr Val Ala
1               5                   10

<210> SEQ ID NO 382
<211> LENGTH: 11
<212> TYPE: PRT
<213> ORGANISM: Artificial Sequence
<220> FEATURE:
<223> OTHER INFORMATION: MTK-33.9 HVR-L1

<400> SEQUENCE: 382

Gln Ala Ser Ala Ser Val Ser Asn Thr Val Ala
1               5                   10

<210> SEQ ID NO 383
<211> LENGTH: 11
<212> TYPE: PRT
<213> ORGANISM: Artificial Sequence
<220> FEATURE:
<223> OTHER INFORMATION: MTK-33.10 HVR-L1

<400> SEQUENCE: 383

Gln Ala Gly Gln Ser Val Ser Asn Thr Val Ala
1               5                   10

<210> SEQ ID NO 384
<211> LENGTH: 11
<212> TYPE: PRT
<213> ORGANISM: Artificial Sequence
<220> FEATURE:
<223> OTHER INFORMATION: MTK-33.11 HVR-L1

<400> SEQUENCE: 384

Gln Ala Ser Arg Ser Val Arg Asn Thr Val Ala
1               5                   10

<210> SEQ ID NO 385
<211> LENGTH: 11
<212> TYPE: PRT
<213> ORGANISM: Artificial Sequence
<220> FEATURE:
<223> OTHER INFORMATION: MTK-33.19 HVR-L1

<400> SEQUENCE: 385

Gln Ala Ser Arg Ser Val Ser Ala Thr Val Ala
1               5                   10

<210> SEQ ID NO 386
<211> LENGTH: 11
<212> TYPE: PRT
<213> ORGANISM: Artificial Sequence
<220> FEATURE:
```

<223> OTHER INFORMATION: MTK-33.23 HVR-L1

<400> SEQUENCE: 386

Ile Ala Ser Arg Ser Val Ser Asn Thr Val Ala
1               5                   10

<210> SEQ ID NO 387
<211> LENGTH: 11
<212> TYPE: PRT
<213> ORGANISM: Artificial Sequence
<220> FEATURE:
<223> OTHER INFORMATION: MTK-33.24 HVR-L1

<400> SEQUENCE: 387

Gln Ala Ser Arg Ser Val Ser Arg Thr Val Ala
1               5                   10

<210> SEQ ID NO 388
<211> LENGTH: 7
<212> TYPE: PRT
<213> ORGANISM: Artificial Sequence
<220> FEATURE:
<223> OTHER INFORMATION: MTK-33.1 HVR-L2

<400> SEQUENCE: 388

Tyr Ala Ser Leu Arg Tyr Thr
1               5

<210> SEQ ID NO 389
<211> LENGTH: 7
<212> TYPE: PRT
<213> ORGANISM: Artificial Sequence
<220> FEATURE:
<223> OTHER INFORMATION: MTK-33.5 HVR-L2

<400> SEQUENCE: 389

Tyr Ala Ser Asn Arg Glu Thr
1               5

<210> SEQ ID NO 390
<211> LENGTH: 7
<212> TYPE: PRT
<213> ORGANISM: Artificial Sequence
<220> FEATURE:
<223> OTHER INFORMATION: MTK-33.21 HVR-L2

<400> SEQUENCE: 390

Tyr Val Ser Asn Arg Tyr Thr
1               5

<210> SEQ ID NO 391
<211> LENGTH: 7
<212> TYPE: PRT
<213> ORGANISM: Artificial Sequence
<220> FEATURE:
<223> OTHER INFORMATION: MTK-33.22 HVR-L2

<400> SEQUENCE: 391

Tyr Ala Ser Asn Arg Arg Thr
1               5

<210> SEQ ID NO 392
<211> LENGTH: 9
<212> TYPE: PRT
<213> ORGANISM: Artificial Sequence
<220> FEATURE:
<223> OTHER INFORMATION: MTK-33.4 HVR-L3

-continued

<400> SEQUENCE: 392

Gln Gln Asp Arg Arg Ser Pro Phe Thr
1               5

<210> SEQ ID NO 393
<211> LENGTH: 9
<212> TYPE: PRT
<213> ORGANISM: Artificial Sequence
<220> FEATURE:
<223> OTHER INFORMATION: MTK-33.12 HVR-L3

<400> SEQUENCE: 393

Arg Gln Asp Thr Arg Ser Pro Phe Thr
1               5

<210> SEQ ID NO 394
<211> LENGTH: 9
<212> TYPE: PRT
<213> ORGANISM: Artificial Sequence
<220> FEATURE:
<223> OTHER INFORMATION: MTK-33.15, 33.17, 33.18, 33.19, 33.21, 33.22,
      33.23, 33.24 HVR-L3

<400> SEQUENCE: 394

Gln Gln Asp Met Arg Ser Pro Phe Thr
1               5

<210> SEQ ID NO 395
<211> LENGTH: 9
<212> TYPE: PRT
<213> ORGANISM: Artificial Sequence
<220> FEATURE:
<223> OTHER INFORMATION: MTK-33.20 HVR-L3

<400> SEQUENCE: 395

Ala Gln Asp Met Arg Ser Pro Phe Thr
1               5

<210> SEQ ID NO 396
<211> LENGTH: 330
<212> TYPE: PRT
<213> ORGANISM: Artificial Sequence
<220> FEATURE:
<223> OTHER INFORMATION: huIgG1 WT Fc with C-terminal lysine

<400> SEQUENCE: 396

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

```
Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 397
<211> LENGTH: 329
<212> TYPE: PRT
<213> ORGANISM: Artificial Sequence
<220> FEATURE:
<223> OTHER INFORMATION: huIgG1 WT Fc without C-terminal lysine

<400> SEQUENCE: 397

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 398
<211> LENGTH: 330
<212> TYPE: PRT
<213> ORGANISM: Artificial Sequence
<220> FEATURE:
<223> OTHER INFORMATION: huIgG1 LALAPS Fc with C-terminal lysine

<400> SEQUENCE: 398

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Ser Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 399
<211> LENGTH: 329
<212> TYPE: PRT
<213> ORGANISM: Artificial Sequence
<220> FEATURE:
<223> OTHER INFORMATION: huIgG1 LALAPS Fc without C-terminal lysine

<400> SEQUENCE: 399

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
        100                 105                 110

Pro Ala Pro Glu Ala Ala Gly Gly Pro Ser Val Phe Leu Phe Pro Pro
    115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
            195                 200                 205

Lys Ala Leu Pro Ala Ser Ile Glu Lys Thr Ile Ser Lys Ala Lys Gly
        210                 215                 220

```
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
            325

<210> SEQ ID NO 400
<211> LENGTH: 330
<212> TYPE: PRT
<213> ORGANISM: Artificial Sequence
<220> FEATURE:
<223> OTHER INFORMATION: huIgG1 NSLF Fc with C-terminal lysine

<400> SEQUENCE: 400

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Ser
        195                 200                 205

Lys Ala Phe Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 401
<211> LENGTH: 329
<212> TYPE: PRT
<213> ORGANISM: Artificial Sequence
<220> FEATURE:
<223> OTHER INFORMATION: huIgG1 NSLF Fc without C-terminal lysine

<400> SEQUENCE: 401

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Ser
        195                 200                 205

Lys Ala Phe Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
            325

<210> SEQ ID NO 402
<211> LENGTH: 330
<212> TYPE: PRT
<213> ORGANISM: Artificial Sequence
<220> FEATURE:
<223> OTHER INFORMATION: huIgG1 YTE Fc with C-terminal lysine

<400> SEQUENCE: 402

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Tyr Ile Thr Arg Glu Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Ser Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 403
<211> LENGTH: 329
<212> TYPE: PRT
<213> ORGANISM: Artificial Sequence
<220> FEATURE:
<223> OTHER INFORMATION: huIgG1 YTE Fc without C-terminal lysine

<400> SEQUENCE: 403

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Tyr Ile Thr Arg Glu Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Ser Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
            325

<210> SEQ ID NO 404

<211> LENGTH: 330
<212> TYPE: PRT
<213> ORGANISM: Artificial Sequence
<220> FEATURE:
<223> OTHER INFORMATION: huIgG1 LS Fc with C-terminal lysine

<400> SEQUENCE: 404

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Ser Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Leu His Glu Ala Leu His Ser His Tyr Thr
305                 310                 315                 320

Gln Lys Ser Leu Ser Leu Ser Pro Gly Lys
                325                 330
```

<210> SEQ ID NO 405
<211> LENGTH: 329
<212> TYPE: PRT
<213> ORGANISM: Artificial Sequence
<220> FEATURE:
<223> OTHER INFORMATION: huIgG1 LS Fc without C-terminal lysine

<400> SEQUENCE: 405

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Ser Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Leu His Glu Ala Leu His Ser His Tyr Thr
305                 310                 315                 320

Gln Lys Ser Leu Ser Leu Ser Pro Gly
                325
```

<210> SEQ ID NO 406
<211> LENGTH: 342
<212> TYPE: PRT
<213> ORGANISM: Artificial Sequence
<220> FEATURE:
<223> OTHER INFORMATION: huIgG1 LV5-112 Fc with C-terminal lysine

<400> SEQUENCE: 406

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
```

```
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Ser Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gly Cys Ala Leu
            260                 265                 270

Tyr Pro Thr Asn Cys Gly Gly Gln Pro Glu Asn Asn Tyr Lys Thr
        275                 280                 285

Thr Pro Pro Val Leu Asp Ser Asp Gly Ser Phe Phe Leu Tyr Ser Lys
        290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 407
<211> LENGTH: 341
<212> TYPE: PRT
<213> ORGANISM: Artificial Sequence
<220> FEATURE:
<223> OTHER INFORMATION: huIgG1 LV5-112 Fc without C-terminal lysine

<400> SEQUENCE: 407

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
```

```
                35                  40                  45
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
                100                 105                 110

Pro Ala Pro Glu Ala Ala Gly Gly Pro Ser Val Phe Leu Phe Pro Pro
                115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Ser Ile Glu Lys Thr Ile Ser Lys Ala Lys Gly
                210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gly Cys Ala Leu
                260                 265                 270

Tyr Pro Thr Asn Cys Gly Gly Gly Gln Pro Glu Asn Asn Tyr Lys Thr
                275                 280                 285

Thr Pro Pro Val Leu Asp Ser Asp Gly Ser Phe Phe Leu Tyr Ser Lys
                290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly
                340

<210> SEQ ID NO 408
<211> LENGTH: 326
<212> TYPE: PRT
<213> ORGANISM: Artificial Sequence
<220> FEATURE:
<223> OTHER INFORMATION: huIgG2 WT Fc with C-terminal lysine

<400> SEQUENCE: 408

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
```

```
                    50                  55                  60
Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                     85                  90                  95

Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
            130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 409
<211> LENGTH: 325
<212> TYPE: PRT
<213> ORGANISM: Artificial Sequence
<220> FEATURE:
<223> OTHER INFORMATION: huIgG2 WT Fc without C-terminal lysine

<400> SEQUENCE: 409

Ala Ser Thr Lys Gly Pro Ser Val Phe Pro Leu Ala Pro Cys Ser Arg
  1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
```

```
                85                  90                  95
Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
            130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
            210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 410
<211> LENGTH: 327
<212> TYPE: PRT
<213> ORGANISM: Artificial Sequence
<220> FEATURE:
<223> OTHER INFORMATION: huIgG4 WT Fc with C-terminal lysine

<400> SEQUENCE: 410

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
```

```
              115                 120                 125
Asp Thr Leu Met Ile Ser Arg Thr Pro Glu Val Thr Cys Val Val Val
            130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
    210                 215                 220
Glu Pro Gln Val Tyr Thr Leu Pro Pro Ser Gln Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Glu Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 411
<211> LENGTH: 326
<212> TYPE: PRT
<213> ORGANISM: Artificial Sequence
<220> FEATURE:
<223> OTHER INFORMATION: huIgG4 WT Fc without C-terminal lysine

<400> SEQUENCE: 411

Ala Ser Thr Lys Gly Pro Ser Val Phe Pro Leu Ala Pro Cys Ser Arg
1               5                  10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Ser Cys Pro Ala Pro
                100                 105                 110
Glu Phe Leu Gly Gly Pro Ser Val Phe Leu Phe Pro Pro Lys Pro Lys
            115                 120                 125
Asp Thr Leu Met Ile Ser Arg Thr Pro Glu Val Thr Cys Val Val Val
        130                 135                 140
Asp Val Ser Gln Glu Asp Pro Glu Val Gln Phe Asn Trp Tyr Val Asp
```

```
                145                 150                 155                 160
Gly Val Glu Val His Asn Ala Lys Thr Lys Pro Arg Glu Gln Phe
                165                 170                 175

Asn Ser Thr Tyr Arg Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
                210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
                290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 412
<211> LENGTH: 107
<212> TYPE: PRT
<213> ORGANISM: Artificial Sequence
<220> FEATURE:
<223> OTHER INFORMATION: Human IgG1 light chain constant region

<400> SEQUENCE: 412

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 413
<211> LENGTH: 450
<212> TYPE: PRT
<213> ORGANISM: Artificial Sequence
<220> FEATURE:
<223> OTHER INFORMATION: MTK-16.1 with huIgG1 WT Fc with C-terminal
      lysine

<400> SEQUENCE: 413

Gln Val Gln Leu Val Gln Ser Gly Ser Glu Leu Lys Lys Pro Gly Ala
1               5                   10                  15
```

-continued

Ser Val Lys Val Ser Cys Lys Ala Ser Gly Tyr Thr Phe Thr Asn His
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Lys Gly Val Thr Ala Ala Arg Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 414
<211> LENGTH: 449
<212> TYPE: PRT
<213> ORGANISM: Artificial Sequence
<220> FEATURE:
<223> OTHER INFORMATION: MTK-16.1 with huIgG1 WT Fc without C-terminal
      lysine

<400> SEQUENCE: 414

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn His
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Lys Gly Val Thr Ala Ala Arg Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

```
Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 415
<211> LENGTH: 450
<212> TYPE: PRT
<213> ORGANISM: Artificial Sequence
<220> FEATURE:
<223> OTHER INFORMATION: MTK-16.1 with huIgG1 LALAPS Fc with C-terminal
      lysine

<400> SEQUENCE: 415

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn His
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Lys Gly Val Thr Ala Ala Arg Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240
```

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Ser Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 416
<211> LENGTH: 449
<212> TYPE: PRT
<213> ORGANISM: Artificial Sequence
<220> FEATURE:
<223> OTHER INFORMATION: MTK-16.1 with huIgG1 LALAPS Fc without
      C-terminal lysine

<400> SEQUENCE: 416

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn His
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Gln Gly Phe
50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
            85                  90                  95

Ala Arg Lys Gly Val Thr Ala Arg Tyr Phe Asp Tyr Trp Gly Gln
        100                 105                 110

Gly Thr Leu Val Thr Val Ser Ser Ala Ser Thr Lys Gly Pro Ser Val
    115                 120                 125

Phe Pro Leu Ala Pro Ser Ser Lys Ser Thr Ser Gly Gly Thr Ala Ala

```
            130                 135                 140
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 417
<211> LENGTH: 450
<212> TYPE: PRT
<213> ORGANISM: Artificial Sequence
<220> FEATURE:
<223> OTHER INFORMATION: MTK-16.1 with huIgG1 NSLF Fc with C-terminal
      lysine

<400> SEQUENCE: 417

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn His
            20                  25                  30

Gly Met Asn Trp Val Arg Gln Ala Pro Gly Gln Gly Leu Glu Trp Met
```

```
                35                  40                  45
Gly Trp Ile Asn Thr Tyr Thr Gly Glu Pro Thr Tyr Ala Gln Gly Phe
 50                  55                  60

Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Lys Gly Val Thr Ala Ala Arg Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Ser Lys Ala Phe Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 418
<211> LENGTH: 449
<212> TYPE: PRT
<213> ORGANISM: Artificial Sequence
<220> FEATURE:
<223> OTHER INFORMATION: MTK-16.1 with huIgG1 NSLF Fc without C-terminal
    lysine

<400> SEQUENCE: 418

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn His
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Lys Gly Val Thr Ala Ala Arg Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Ser Lys Ala Phe Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
```

```
                355                 360                 365
Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly

<210> SEQ ID NO 419
<211> LENGTH: 447
<212> TYPE: PRT
<213> ORGANISM: Artificial Sequence
<220> FEATURE:
<223> OTHER INFORMATION: MTK-16.1 with huIgG4 Fc with C-terminal lysine

<400> SEQUENCE: 419

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn His
                20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Pro Thr Tyr Ala Gln Gly Phe
50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Lys Gly Val Thr Ala Ala Arg Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Ser Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270
```

```
Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
            435                 440                 445

<210> SEQ ID NO 420
<211> LENGTH: 446
<212> TYPE: PRT
<213> ORGANISM: Artificial Sequence
<220> FEATURE:
<223> OTHER INFORMATION: MTK-16.1 with huIgG4 Fc without C-terminal
      lysine

<400> SEQUENCE: 420

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn His
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Lys Gly Val Thr Ala Ala Arg Tyr Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
```

```
                180             185             190
Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
        210                 215                 220

Pro Cys Pro Ser Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 421
<211> LENGTH: 214
<212> TYPE: PRT
<213> ORGANISM: Artificial Sequence
<220> FEATURE:
<223> OTHER INFORMATION: MTK-16.1 light chain

<400> SEQUENCE: 421

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Arg Thr Ala
            20                  25                  30

Val Ala Trp Tyr Gln Gln Lys Pro Gly Lys Ala Pro Lys Arg Leu Ile
        35                  40                  45

Tyr Leu Ala Ser Asn Arg His Thr Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Leu Gln His Trp Asn Tyr Pro Leu
                85                  90                  95

Thr Phe Gly Gly Gly Thr Lys Val Glu Ile Lys Arg Thr Val Ala Ala
```

```
                    100                 105                 110
Pro Ser Val Phe Ile Phe Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 422
<211> LENGTH: 450
<212> TYPE: PRT
<213> ORGANISM: Artificial Sequence
<220> FEATURE:
<223> OTHER INFORMATION: MTK-16.2 with huIgG1 WT Fc with C-terminal
      lysine

<400> SEQUENCE: 422

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn His
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Lys Gly Val Thr Ala Ala Arg Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

```
Pro Ser Val Phe Leu Phe Pro Pro Lys Pro Lys Asp Thr Leu Met Ile
            245                 250                 255

Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 423
<211> LENGTH: 449
<212> TYPE: PRT
<213> ORGANISM: Artificial Sequence
<220> FEATURE:
<223> OTHER INFORMATION: MTK-16.2 with huIgG1 WT Fc without C-terminal
      lysine

<400> SEQUENCE: 423

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn His
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Lys Gly Val Thr Ala Ala Arg Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140
```

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
        435                 440                 445

Gly

<210> SEQ ID NO 424
<211> LENGTH: 450
<212> TYPE: PRT
<213> ORGANISM: Artificial Sequence
<220> FEATURE:
<223> OTHER INFORMATION: MTK-16.2 with huIgG1 LALAPS Fc with C-terminal
      lysine

<400> SEQUENCE: 424

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn His
            20                  25                  30

Gly Met Asn Trp Val Arg Gln Ala Pro Gly Gln Gly Leu Glu Trp Met
        35                  40                  45
```

```
Gly Trp Ile Asn Thr Tyr Thr Gly Glu Pro Thr Tyr Ala Asp Asp Phe
     50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                     85                  90                  95

Ala Arg Lys Gly Val Thr Ala Ala Arg Tyr Phe Asp Tyr Trp Gly Gln
                100                 105                 110

Gly Thr Leu Val Thr Val Ser Ser Ala Ser Thr Lys Gly Pro Ser Val
             115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Ser Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450
```

<210> SEQ ID NO 425
<211> LENGTH: 449
<212> TYPE: PRT
<213> ORGANISM: Artificial Sequence
<220> FEATURE:
<223> OTHER INFORMATION: MTK-16.2 with huIgG1 LALAPS Fc without
    C-terminal lysine

<400> SEQUENCE: 425

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn His
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Lys Gly Val Thr Ala Ala Arg Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365
```

```
Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 426
<211> LENGTH: 450
<212> TYPE: PRT
<213> ORGANISM: Artificial Sequence
<220> FEATURE:
<223> OTHER INFORMATION: MTK-16.2 with huIgG1 NSLF Fc with C-terminal
      lysine

<400> SEQUENCE: 426

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn His
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Lys Gly Val Thr Ala Ala Arg Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270
```

```
Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Ser Lys Ala Phe Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 427
<211> LENGTH: 449
<212> TYPE: PRT
<213> ORGANISM: Artificial Sequence
<220> FEATURE:
<223> OTHER INFORMATION: MTK-16.2 with huIgG1 NSLF Fc without C-terminal
      lysine

<400> SEQUENCE: 427

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn His
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Lys Gly Val Thr Ala Ala Arg Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
```

165                 170                 175
Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Ser Lys Ala Phe Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 428
<211> LENGTH: 447
<212> TYPE: PRT
<213> ORGANISM: Artificial Sequence
<220> FEATURE:
<223> OTHER INFORMATION: MTK-16.2 with huIgG4 Fc with C-terminal lysine

<400> SEQUENCE: 428

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn His
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Lys Gly Val Thr Ala Ala Arg Tyr Phe Asp Tyr Trp Gly Gln
            100                 105                 110

Gly Thr Leu Val Thr Val Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Ser Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 429
<211> LENGTH: 447
<212> TYPE: PRT
<213> ORGANISM: Artificial Sequence
<220> FEATURE:
<223> OTHER INFORMATION: MTK-16.2 with huIgG4 Fc without C-terminal
      lysine

```
<400> SEQUENCE: 429

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn His
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Lys Gly Val Thr Ala Ala Arg Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Ser Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415
```

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
            435                 440                 445

<210> SEQ ID NO 430
<211> LENGTH: 214
<212> TYPE: PRT
<213> ORGANISM: Artificial Sequence
<220> FEATURE:
<223> OTHER INFORMATION: MTK-16.2 light chain

<400> SEQUENCE: 430

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Val Arg Thr Ala
            20                  25                  30

Val Ala Trp Tyr Gln Gln Lys Pro Gly Lys Ala Pro Lys Arg Leu Ile
        35                  40                  45

Tyr Leu Ala Ser Asn Arg His Thr Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Leu Gln His Trp Asn Tyr Pro Leu
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 431
<211> LENGTH: 449
<212> TYPE: PRT
<213> ORGANISM: Artificial Sequence
<220> FEATURE:
<223> OTHER INFORMATION: MTK-33.1 with huIgG1 WT Fc with C-terminal
      lysine

<400> SEQUENCE: 431

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Val Ile Asp Pro Ser Asp Asn Tyr Ile Asn Tyr Asn Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Glu Ala Trp Thr Arg Gly Tyr Phe Asn Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 432

```
<211> LENGTH: 448
<212> TYPE: PRT
<213> ORGANISM: Artificial Sequence
<220> FEATURE:
<223> OTHER INFORMATION: MTK-33.1 with huIgG1 WT Fc without C-terminal
      lysine

<400> SEQUENCE: 432
```

| | | | | | | | | | | | | | | |
|---|---|---|---|---|---|---|---|---|---|---|---|---|---|---|
|Gln|Val|Gln|Leu|Val|Gln|Ser|Gly|Ala|Glu|Val|Lys|Lys|Pro|Gly|Ala|
|1| | | |5| | | | |10| | | | |15|

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Val Ile Asp Pro Ser Asp Asn Tyr Ile Asn Tyr Asn Gln Lys Phe
    50                  55                  60

Gln Gly Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Trp Thr Arg Gly Tyr Phe Asn Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu 370                 375                 380
Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

<210> SEQ ID NO 433
<211> LENGTH: 449
<212> TYPE: PRT
<213> ORGANISM: Artificial Sequence
<220> FEATURE:
<223> OTHER INFORMATION: MTK-33.1 with huIgG1 LALAPS Fc with C-terminal
      lysine

<400> SEQUENCE: 433

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Ile
            35                  40                  45

Gly Val Ile Asp Pro Ser Asp Asn Tyr Ile Asn Tyr Asn Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Trp Thr Arg Gly Tyr Phe Asn Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

```
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 434
<211> LENGTH: 448
<212> TYPE: PRT
<213> ORGANISM: Artificial Sequence
<220> FEATURE:
<223> OTHER INFORMATION: MTK-33.1 with huIgG1 LALAPS Fc without
      C-terminal lysine

<400> SEQUENCE: 434

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Ile
            35                  40                  45

Gly Val Ile Asp Pro Ser Asp Asn Tyr Ile Asn Tyr Asn Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Trp Thr Arg Gly Tyr Phe Asn Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 435
<211> LENGTH: 449
<212> TYPE: PRT
<213> ORGANISM: Artificial Sequence
<220> FEATURE:
<223> OTHER INFORMATION: MTK-33.1 with huIgG1 NSLF Fc with C-terminal
      lysine

<400> SEQUENCE: 435

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Val Ile Asp Pro Ser Asp Asn Tyr Ile Asn Tyr Asn Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Trp Thr Arg Gly Tyr Phe Asn Tyr Trp Gly Gln Gly
            100                 105                 110

```
Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Ser Lys Ala Phe Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 436
<211> LENGTH: 448
<212> TYPE: PRT
<213> ORGANISM: Artificial Sequence
<220> FEATURE:
<223> OTHER INFORMATION: MTK-33.1 with huIgG1 NSLF Fc without C-terminal
      lysine

<400> SEQUENCE: 436

Gln Val Gln Leu Val Gln Ser Gly Ala Glu Val Lys Lys Pro Gly Ala
1               5                   10                  15
```

-continued

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Val Ile Asp Pro Ser Asp Asn Tyr Ile Asn Tyr Asn Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Trp Thr Arg Gly Tyr Phe Asn Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Ser Lys Ala Phe Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

```
Ala Leu His Asn His Tyr Thr Gln Lys Ser Leu Ser Leu Ser Pro Gly
            435                 440                 445
```

<210> SEQ ID NO 437
<211> LENGTH: 446
<212> TYPE: PRT
<213> ORGANISM: Artificial Sequence
<220> FEATURE:
<223> OTHER INFORMATION: MTK-33.1 with huIgG4 Fc with C-terminal lysine

<400> SEQUENCE: 437

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Val Ile Asp Pro Ser Asp Asn Tyr Ile Asn Tyr Asn Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Trp Thr Arg Gly Tyr Phe Asn Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Ser Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350
```

-continued

```
Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
            435                 440                 445

<210> SEQ ID NO 438
<211> LENGTH: 445
<212> TYPE: PRT
<213> ORGANISM: Artificial Sequence
<220> FEATURE:
<223> OTHER INFORMATION: MTK-33.1 with huIgG4 Fc without C-terminal
      lysine

<400> SEQUENCE: 438

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Val Ile Asp Pro Ser Asp Asn Tyr Ile Asn Tyr Asn Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Trp Thr Arg Gly Tyr Phe Asn Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
210                 215                 220

Cys Pro Ser Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270
```

Gln Phe Asn Trp Tyr Val Asp Gly Val Glu Val His Asn Ala Lys Thr
              275                 280                 285

Lys Pro Arg Glu Glu Gln Phe Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Lys Ser Leu Ser Leu Ser Leu Gly
                435                 440                 445

<210> SEQ ID NO 439
<211> LENGTH: 214
<212> TYPE: PRT
<213> ORGANISM: Artificial Sequence
<220> FEATURE:
<223> OTHER INFORMATION: MTK-33.1 light chain

<400> SEQUENCE: 439

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Val Ser Asn Thr
            20                  25                  30

Val Ala Trp Tyr Gln Gln Lys Pro Gly Lys Ala Pro Lys Leu Leu Ile
        35                  40                  45

Tyr Tyr Ala Ser Leu Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Asp Tyr Arg Ser Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 440
<211> LENGTH: 449
<212> TYPE: PRT
<213> ORGANISM: Artificial Sequence
<220> FEATURE:
<223> OTHER INFORMATION: MTK-33.12 with huIgG1 WT Fc with C-terminal
      lysine

<400> SEQUENCE: 440

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Val Ser Tyr
            20                  25                  30

Trp Met His Trp Val Arg Gln Ala Pro Gly Gln Gly Leu Glu Trp Ile
        35                  40                  45

Gly Val Ile Asp Pro Ser Asp Asn Tyr Ile Asn Tyr Asn Gln Lys Phe
    50                  55                  60

Arg Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Thr Arg Gly Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys

```
                    325                 330                 335
Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 441
<211> LENGTH: 448
<212> TYPE: PRT
<213> ORGANISM: Artificial Sequence
<220> FEATURE:
<223> OTHER INFORMATION: MTK-33.12 with huIgG1 WT Fc without C-terminal
      lysine

<400> SEQUENCE: 441

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Val Ser Tyr
                20                  25                  30

Trp Met His Trp Val Arg Gln Ala Pro Gly Gln Gly Leu Glu Trp Ile
            35                  40                  45

Gly Val Ile Asp Pro Ser Asp Asn Tyr Ile Asn Tyr Asn Gln Lys Phe
        50                  55                  60

Arg Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Thr Arg Gly Tyr Phe Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
```

```
                225                 230                 235                 240
Ser Val Phe Leu Phe Pro Pro Lys Pro Lys Asp Thr Leu Met Ile Ser
                    245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                    325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                    405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445
```

<210> SEQ ID NO 442
<211> LENGTH: 449
<212> TYPE: PRT
<213> ORGANISM: Artificial Sequence
<220> FEATURE:
<223> OTHER INFORMATION: MTK-33.12 with huIgG1 LALAPS Fc with C-terminal
      lysine

<400> SEQUENCE: 442

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Val Ser Tyr
                20                  25                  30

Trp Met His Trp Val Arg Gln Ala Pro Gly Gln Gly Leu Glu Trp Ile
            35                  40                  45

Gly Val Ile Asp Pro Ser Asp Asn Tyr Ile Asn Tyr Asn Gln Lys Phe
    50                  55                  60

Arg Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Thr Arg Gly Tyr Phe Asp Tyr Trp Gly Gln Gly
            100                 105                 110

Thr Leu Val Thr Val Ser Ser Ala Ser Thr Lys Gly Pro Ser Val Phe
    115                 120                 125

Pro Leu Ala Pro Ser Ser Lys Ser Thr Ser Gly Gly Thr Ala Ala Leu
130                 135                 140
```

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 443
<211> LENGTH: 448
<212> TYPE: PRT
<213> ORGANISM: Artificial Sequence
<220> FEATURE:
<223> OTHER INFORMATION: MTK-33.12 with huIgG1 LALAPS Fc without
      C-terminal lysine

<400> SEQUENCE: 443

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Val Ser Tyr
                20                  25                  30

Trp Met His Trp Val Arg Gln Ala Pro Gly Gln Gly Leu Glu Trp Ile
            35                  40                  45
```

Gly Val Ile Asp Pro Ser Asp Asn Tyr Ile Asn Tyr Asn Gln Lys Phe
    50                  55                  60

Arg Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Thr Arg Gly Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 444
<211> LENGTH: 449
<212> TYPE: PRT

<213> ORGANISM: Artificial Sequence
<220> FEATURE:
<223> OTHER INFORMATION: MTK-33.12 with huIgG1 NSLF Fc with C-terminal lysine

<400> SEQUENCE: 444

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Val Ser Tyr
            20                  25                  30

Trp Met His Trp Val Arg Gln Ala Pro Gly Gln Gly Leu Glu Trp Ile
        35                  40                  45

Gly Val Ile Asp Pro Ser Asp Asn Tyr Ile Asn Tyr Asn Gln Lys Phe
    50                  55                  60

Arg Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Thr Arg Gly Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Ser Lys Ala Phe Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

```
Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
        435                 440                 445

Lys

<210> SEQ ID NO 445
<211> LENGTH: 448
<212> TYPE: PRT
<213> ORGANISM: Artificial Sequence
<220> FEATURE:
<223> OTHER INFORMATION: MTK-33.12 with huIgG1 NSLF Fc without
      C-terminal lysine

<400> SEQUENCE: 445

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Val Ser Tyr
            20                  25                  30

Trp Met His Trp Val Arg Gln Ala Pro Gly Gln Gly Leu Glu Trp Ile
        35                  40                  45

Gly Val Ile Asp Pro Ser Asp Asn Tyr Ile Asn Tyr Asn Gln Lys Phe
    50                  55                  60

Arg Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Glu Ala Gly Thr Arg Gly Tyr Phe Asp Tyr Trp Gly Gln Gly
        100                 105                 110

Thr Leu Val Thr Val Ser Ser Ala Ser Thr Lys Gly Pro Ser Val Phe
    115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285
```

```
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Ser Lys Ala Phe Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445
```

<210> SEQ ID NO 446
<211> LENGTH: 446
<212> TYPE: PRT
<213> ORGANISM: Artificial Sequence
<220> FEATURE:
<223> OTHER INFORMATION: MTK-33.12 with huIgG4 Fc with C-terminal lysine

<400> SEQUENCE: 446

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Val Ser Tyr
            20                  25                  30

Trp Met His Trp Val Arg Gln Ala Pro Gly Gln Gly Leu Glu Trp Ile
        35                  40                  45

Gly Val Ile Asp Pro Ser Asp Asn Tyr Ile Asn Tyr Asn Gln Lys Phe
    50                  55                  60

Arg Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Thr Arg Gly Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205
```

```
Ser Asn Thr Lys Val Asp Lys Arg Val Glu Ser Lys Tyr Gly Pro Pro
    210                 215                 220

Cys Pro Ser Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 447
<211> LENGTH: 445
<212> TYPE: PRT
<213> ORGANISM: Artificial Sequence
<220> FEATURE:
<223> OTHER INFORMATION: MTK-33.12 with huIgG4 Fc without C-terminal
      lysine

<400> SEQUENCE: 447

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Val Ser Tyr
            20                  25                  30

Trp Met His Trp Val Arg Gln Ala Pro Gly Gln Gly Leu Glu Trp Ile
        35                  40                  45

Gly Val Ile Asp Pro Ser Asp Asn Tyr Ile Asn Tyr Asn Gln Lys Phe
    50                  55                  60

Arg Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Thr Arg Gly Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125
```

```
Pro Leu Ala Pro Cys Ser Arg Ser Thr Ser Glu Ser Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
210                 215                 220

Cys Pro Ser Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly
        435                 440                 445

<210> SEQ ID NO 448
<211> LENGTH: 214
<212> TYPE: PRT
<213> ORGANISM: Artificial Sequence
<220> FEATURE:
<223> OTHER INFORMATION: MTK-33.12 light chain

<400> SEQUENCE: 448

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Val Ser Asn Thr
            20                  25                  30

Val Ala Trp Tyr Gln Gln Lys Pro Gly Lys Ala Pro Lys Leu Leu Ile
        35                  40                  45
```

```
Tyr Tyr Ala Ser Asn Arg Tyr Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Arg Gln Asp Thr Arg Ser Pro Phe
                85                  90                  95

Thr Phe Gly Gln Gly Thr Lys Leu Glu Leu Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 449
<211> LENGTH: 67
<212> TYPE: PRT
<213> ORGANISM: Artificial Sequence
<220> FEATURE:
<223> OTHER INFORMATION: N-terminal domain (N) of human MerTK ECD

<400> SEQUENCE: 449

Ala Ile Thr Glu Ala Arg Glu Glu Ala Lys Pro Tyr Pro Leu Phe Pro
1               5                   10                  15

Gly Pro Phe Pro Gly Ser Leu Gln Thr Asp His Thr Pro Leu Leu Ser
            20                  25                  30

Leu Pro His Ala Ser Gly Tyr Gln Pro Ala Leu Met Phe Ser Pro Thr
        35                  40                  45

Gln Pro Gly Arg Pro His Thr Gly Asn Val Ala Ile Pro Gln Val Thr
    50                  55                  60

Ser Val Glu
65

<210> SEQ ID NO 450
<211> LENGTH: 107
<212> TYPE: PRT
<213> ORGANISM: Artificial Sequence
<220> FEATURE:
<223> OTHER INFORMATION: Immunoglobulin-like domain (Ig1) of human MerTK
      ECD

<400> SEQUENCE: 450

Ser Lys Pro Leu Pro Leu Ala Phe Lys His Thr Val Gly His Ile
1               5                   10                  15

Ile Leu Ser Glu His Lys Gly Val Lys Phe Asn Cys Ser Ile Ser Val
            20                  25                  30

Pro Asn Ile Tyr Gln Asp Thr Thr Ile Ser Trp Trp Lys Asp Gly Lys
        35                  40                  45
```

```
Glu Leu Leu Gly Ala His His Ala Ile Thr Gln Phe Tyr Pro Asp Asp
 50                  55                  60

Glu Val Thr Ala Ile Ile Ala Ser Phe Ser Ile Thr Ser Val Gln Arg
 65                  70                  75                  80

Ser Asp Asn Gly Ser Tyr Ile Cys Lys Met Lys Ile Asn Asn Glu Glu
                 85                  90                  95

Ile Val Ser Asp Pro Ile Tyr Ile Glu Val Gln
            100                 105
```

<210> SEQ ID NO 451
<211> LENGTH: 85
<212> TYPE: PRT
<213> ORGANISM: Artificial Sequence
<220> FEATURE:
<223> OTHER INFORMATION: Immunoglobulin-like domain (Ig2) of human MerTK ECD

<400> SEQUENCE: 451

```
Gly Leu Pro His Phe Thr Lys Gln Pro Glu Ser Met Asn Val Thr Arg
 1               5                  10                  15

Asn Thr Ala Phe Asn Leu Thr Cys Gln Ala Val Gly Pro Pro Glu Pro
             20                  25                  30

Val Asn Ile Phe Trp Val Gln Asn Ser Ser Arg Val Asn Glu Gln Pro
         35                  40                  45

Glu Lys Ser Pro Ser Val Leu Thr Val Pro Gly Leu Thr Glu Met Ala
 50                  55                  60

Val Phe Ser Cys Glu Ala His Asn Asp Lys Gly Leu Thr Val Ser Lys
 65                  70                  75                  80

Gly Val Gln Ile Asn
                 85
```

<210> SEQ ID NO 452
<211> LENGTH: 99
<212> TYPE: PRT
<213> ORGANISM: Artificial Sequence
<220> FEATURE:
<223> OTHER INFORMATION: Fibronectin type III domain (FN1) of human MerTK ECD

<400> SEQUENCE: 452

```
Ile Lys Ala Ile Pro Ser Pro Pro Thr Glu Val Ser Ile Arg Asn Ser
 1               5                  10                  15

Thr Ala His Ser Ile Leu Ile Ser Trp Val Pro Gly Phe Asp Gly Tyr
             20                  25                  30

Ser Pro Phe Arg Asn Cys Ser Ile Gln Val Lys Glu Ala Asp Pro Leu
         35                  40                  45

Ser Asn Gly Ser Val Met Ile Phe Asn Thr Ser Ala Leu Pro His Leu
 50                  55                  60

Tyr Gln Ile Lys Gln Leu Gln Ala Leu Ala Asn Tyr Ser Ile Gly Val
 65                  70                  75                  80

Ser Cys Met Asn Glu Ile Gly Trp Ser Ala Val Ser Pro Trp Ile Leu
                 85                  90                  95

Ala Ser Thr
```

<210> SEQ ID NO 453
<211> LENGTH: 98
<212> TYPE: PRT
<213> ORGANISM: Artificial Sequence
<220> FEATURE:
<223> OTHER INFORMATION: Fibronectin type III domain (FN2) of human MerTK ECD

<400> SEQUENCE: 453

Thr Glu Gly Ala Pro Ser Val Ala Pro Leu Asn Val Thr Val Phe Leu
1               5                   10                  15

Asn Glu Ser Ser Asp Asn Val Asp Ile Arg Trp Met Lys Pro Pro Thr
            20                  25                  30

Lys Gln Gln Asp Gly Glu Leu Val Gly Tyr Arg Ile Ser His Val Trp
        35                  40                  45

Gln Ser Ala Gly Ile Ser Lys Glu Leu Leu Glu Glu Val Gly Gln Asn
    50                  55                  60

Gly Ser Arg Ala Arg Ile Ser Val Gln Val His Asn Ala Thr Cys Thr
65                  70                  75                  80

Val Arg Ile Ala Ala Val Thr Arg Gly Gly Val Gly Pro Phe Ser Asp
                85                  90                  95

Pro Val

<210> SEQ ID NO 454
<211> LENGTH: 29
<212> TYPE: PRT
<213> ORGANISM: Artificial Sequence
<220> FEATURE:
<223> OTHER INFORMATION: Juxta membrane domain region (JM) of human
      MerTK ECD

<400> SEQUENCE: 454

Lys Ile Phe Ile Pro Ala His Gly Trp Val Asp Tyr Ala Pro Ser Ser
1               5                   10                  15

Thr Pro Ala Pro Gly Asn Ala Asp Pro Val Leu Ile Ile
            20                  25

<210> SEQ ID NO 455
<211> LENGTH: 27
<212> TYPE: PRT
<213> ORGANISM: Artificial Sequence
<220> FEATURE:
<223> OTHER INFORMATION: N-terminal domain (N) of human Axl ECD

<400> SEQUENCE: 455

Ala Pro Arg Gly Thr Gln Ala Glu Glu Ser Pro Phe Val Gly Asn Pro
1               5                   10                  15

Gly Asn Ile Thr Gly Ala Arg Gly Leu Thr Gly
            20                  25

<210> SEQ ID NO 456
<211> LENGTH: 84
<212> TYPE: PRT
<213> ORGANISM: Artificial Sequence
<220> FEATURE:
<223> OTHER INFORMATION: Immunoglobulin-like domain (Ig1) of human Axl
      ECD

<400> SEQUENCE: 456

Thr Leu Arg Cys Gln Leu Gln Val Gln Gly Glu Pro Pro Glu Val His
1               5                   10                  15

Trp Leu Arg Asp Gly Gln Ile Leu Glu Leu Ala Asp Ser Thr Gln Thr
            20                  25                  30

Gln Val Pro Leu Gly Glu Asp Glu Gln Asp Asp Trp Ile Val Val Ser
        35                  40                  45

Gln Leu Arg Ile Thr Ser Leu Gln Leu Ser Asp Thr Gly Gln Tyr Gln
    50                  55                  60

```
Cys Leu Val Phe Leu Gly His Gln Thr Phe Val Ser Gln Pro Gly Tyr
 65                  70                  75                  80

Val Gly Leu Glu

<210> SEQ ID NO 457
<211> LENGTH: 89
<212> TYPE: PRT
<213> ORGANISM: Artificial Sequence
<220> FEATURE:
<223> OTHER INFORMATION: Immunoglobulin-like domain (Ig2) of human Axl
      ECD

<400> SEQUENCE: 457

Gly Leu Pro Tyr Phe Leu Glu Glu Pro Glu Asp Arg Thr Val Ala Ala
 1               5                  10                  15

Asn Thr Pro Phe Asn Leu Ser Cys Gln Ala Gln Gly Pro Pro Glu Pro
             20                  25                  30

Val Asp Leu Leu Trp Leu Gln Asp Ala Val Pro Leu Ala Thr Ala Pro
         35                  40                  45

Gly His Gly Pro Gln Arg Ser Leu His Val Pro Gly Leu Asn Lys Thr
     50                  55                  60

Ser Ser Phe Ser Cys Glu Ala His Asn Ala Lys Gly Val Thr Thr Ser
 65                  70                  75                  80

Arg Thr Ala Thr Ile Thr Val Leu Pro
                 85

<210> SEQ ID NO 458
<211> LENGTH: 106
<212> TYPE: PRT
<213> ORGANISM: Artificial Sequence
<220> FEATURE:
<223> OTHER INFORMATION: Fibronectin type III domain (FN1) of human Axl
      ECD

<400> SEQUENCE: 458

Gln Gln Pro Arg Asn Leu His Leu Val Ser Arg Gln Pro Thr Glu Leu
 1               5                  10                  15

Glu Val Ala Trp Thr Pro Gly Leu Ser Gly Ile Tyr Pro Leu Thr His
             20                  25                  30

Cys Thr Leu Gln Ala Val Leu Ser Asp Asp Gly Met Gly Ile Gln Ala
         35                  40                  45

Gly Glu Pro Asp Pro Pro Glu Glu Pro Leu Thr Ser Gln Ala Ser Val
     50                  55                  60

Pro Pro His Gln Leu Arg Leu Gly Ser Leu His Pro His Thr Pro Tyr
 65                  70                  75                  80

His Ile Arg Val Ala Cys Thr Ser Ser Gln Gly Pro Ser Ser Trp Thr
                 85                  90                  95

His Trp Leu Pro Val Glu Thr Pro Glu Gly
                100                 105

<210> SEQ ID NO 459
<211> LENGTH: 87
<212> TYPE: PRT
<213> ORGANISM: Artificial Sequence
<220> FEATURE:
<223> OTHER INFORMATION: Fibronectin type III domain (FN2) of human Axl
      ECD

<400> SEQUENCE: 459

Val Pro Leu Gly Pro Pro Glu Asn Ile Ser Ala Thr Arg Asn Gly Ser
```

```
                1               5                  10                  15
            Gln Ala Phe Val His Trp Gln Glu Pro Arg Ala Pro Leu Gln Gly Thr
                            20                  25                  30

Leu Leu Gly Tyr Arg Leu Ala Tyr Gln Gly Gln Asp Thr Pro Glu Val
                        35                  40                  45

Leu Met Asp Ile Gly Leu Arg Gln Glu Val Thr Leu Glu Leu Gln Gly
                    50                  55                  60

Asp Gly Ser Val Ser Asn Leu Thr Val Cys Val Ala Ala Tyr Thr Ala
            65                  70                  75                  80

Ala Gly Asp Gly Pro Trp Ser
                            85

<210> SEQ ID NO 460
<211> LENGTH: 33
<212> TYPE: PRT
<213> ORGANISM: Artificial Sequence
<220> FEATURE:
<223> OTHER INFORMATION: Juxta membrane domain (JM) of human Axl ECD

<400> SEQUENCE: 460

Leu Pro Val Pro Leu Glu Ala Trp Arg Pro Gly Gln Ala Gln Pro Val
1               5                   10                  15

His Gln Leu Val Lys Glu Pro Ser Thr Pro Ala Phe Ser Trp Pro Trp
                20                  25                  30

Trp

<210> SEQ ID NO 461
<211> LENGTH: 19
<212> TYPE: PRT
<213> ORGANISM: Artificial Sequence
<220> FEATURE:
<223> OTHER INFORMATION: MerTK construct signal sequence

<400> SEQUENCE: 461

Met Gly Trp Ser Cys Ile Ile Leu Phe Leu Val Ala Thr Ala Thr Gly
1               5                   10                  15

Val His Ser

<210> SEQ ID NO 462
<211> LENGTH: 16
<212> TYPE: PRT
<213> ORGANISM: Artificial Sequence
<220> FEATURE:
<223> OTHER INFORMATION: Axl construct signal sequence

<400> SEQUENCE: 462

Met Gly Trp Ser Cys Ile Ile Leu Phe Leu Val Ala Thr Ala Thr Gly
1               5                   10                  15

<210> SEQ ID NO 463
<211> LENGTH: 27
<212> TYPE: PRT
<213> ORGANISM: Artificial Sequence
<220> FEATURE:
<223> OTHER INFORMATION: Linker+His+Avi tag

<400> SEQUENCE: 463

Gly Gly Ser Gly His His His His His His Gly Gly Gly Leu Asn Asp
1               5                   10                  15

Ile Phe Glu Ala Gln Lys Ile Glu Trp His Glu
                20                  25
```

<210> SEQ ID NO 464
<211> LENGTH: 449
<212> TYPE: PRT
<213> ORGANISM: Artificial Sequence
<220> FEATURE:
<223> OTHER INFORMATION: MTK-33.10 with huIgG1 WT Fc with C-terminal lysine

<400> SEQUENCE: 464

```
Gln Val Gln Leu Val Gln Ser Gly Ala Glu Val Lys Lys Pro Gly Ala
1               5                   10                  15

Ser Val Lys Val Ser Cys Lys Ala Ser Ser Tyr Ser Phe Thr Ser Tyr
            20                  25                  30

Trp Met His Trp Val Arg Gln Ala Pro Gly Gln Gly Leu Glu Trp Ile
        35                  40                  45

Gly Val Ile Asp Pro Ser Asp Asn Tyr Ile Asn Tyr Asn Gln Lys Phe
    50                  55                  60

Arg Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Thr Arg Gly Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365
```

```
Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 465
<211> LENGTH: 448
<212> TYPE: PRT
<213> ORGANISM: Artificial Sequence
<220> FEATURE:
<223> OTHER INFORMATION: MTK-33.10 with huIgG1 WT Fc without C-terminal
      lysine

<400> SEQUENCE: 465

Gln Val Gln Leu Val Gln Ser Gly Ala Glu Val Lys Lys Pro Gly Ala
1               5                   10                  15

Ser Val Lys Val Ser Cys Lys Ala Ser Ser Tyr Ser Phe Thr Ser Tyr
            20                  25                  30

Trp Met His Trp Val Arg Gln Ala Pro Gly Gln Gly Leu Glu Trp Ile
        35                  40                  45

Gly Val Ile Asp Pro Ser Asp Asn Tyr Ile Asn Tyr Asn Gln Lys Phe
    50                  55                  60

Arg Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Thr Arg Gly Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270
```

```
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 466
<211> LENGTH: 449
<212> TYPE: PRT
<213> ORGANISM: Artificial Sequence
<220> FEATURE:
<223> OTHER INFORMATION: MTK-33.10 with huIgG1 LALAPS Fc with C-terminal
      lysine

<400> SEQUENCE: 466

Gln Val Gln Leu Val Gln Ser Gly Ala Glu Val Lys Lys Pro Gly Ala
1               5                   10                  15

Ser Val Lys Val Ser Cys Lys Ala Ser Ser Tyr Ser Phe Thr Ser Tyr
            20                  25                  30

Trp Met His Trp Val Arg Gln Ala Pro Gly Gln Gly Leu Glu Trp Ile
        35                  40                  45

Gly Val Ile Asp Pro Ser Asp Asn Tyr Ile Asn Tyr Asn Gln Lys Phe
    50                  55                  60

Arg Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Thr Arg Gly Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
```

```
                180             185             190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
        210                 215                 220
Thr His Thr Cys Pro Pro Cys Pro Ala Pro Glu Ala Ala Gly Gly Pro
225                 230                 235                 240
Ser Val Phe Leu Phe Pro Pro Lys Pro Lys Asp Thr Leu Met Ile Ser
            245                 250                 255
Arg Thr Pro Glu Val Thr Cys Val Val Val Asp Val Ser His Glu Asp
                260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Asn Ser Thr Tyr Arg Val
        290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Ser Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
            355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
Ala Leu His Asn His Tyr Thr Gln Lys Ser Leu Ser Leu Ser Pro Gly
        435                 440                 445
Lys

<210> SEQ ID NO 467
<211> LENGTH: 448
<212> TYPE: PRT
<213> ORGANISM: Artificial Sequence
<220> FEATURE:
<223> OTHER INFORMATION: MTK-33.10 with huIgG1 LALAPS Fc without
      C-terminal lysine

<400> SEQUENCE: 467

Gln Val Gln Leu Val Gln Ser Gly Ala Glu Val Lys Lys Pro Gly Ala
1               5                   10                  15
Ser Val Lys Val Ser Cys Lys Ala Ser Ser Tyr Ser Phe Thr Ser Tyr
            20                  25                  30
Trp Met His Trp Val Arg Gln Ala Pro Gly Gln Gly Leu Glu Trp Ile
        35                  40                  45
Gly Val Ile Asp Pro Ser Asp Asn Tyr Ile Asn Tyr Asn Gln Lys Phe
    50                  55                  60
Arg Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
```

```
                85                  90                  95
Ala Arg Glu Ala Gly Thr Arg Gly Tyr Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 468
<211> LENGTH: 449
<212> TYPE: PRT
<213> ORGANISM: Artificial Sequence
<220> FEATURE:
<223> OTHER INFORMATION: MTK-33.10 with huIgG1 NSLF Fc with C-terminal
      lysine

<400> SEQUENCE: 468
```

Gln Val Gln Leu Val Gln Ser Gly Ala Glu Val Lys Lys Pro Gly Ala
1               5                   10                  15

Ser Val Lys Val Ser Cys Lys Ala Ser Ser Tyr Ser Phe Thr Ser Tyr
            20                  25                  30

Trp Met His Trp Val Arg Gln Ala Pro Gly Gln Gly Leu Glu Trp Ile
            35                  40                  45

Gly Val Ile Asp Pro Ser Asp Asn Tyr Ile Asn Tyr Asn Gln Lys Phe
50                  55                  60

Arg Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Glu Ala Gly Thr Arg Gly Tyr Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Ser Lys Ala Phe Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu

-continued

```
                420                 425                 430
Ala Leu His Asn His Tyr Thr Gln Lys Ser Leu Ser Leu Ser Pro Gly
            435                 440                 445
Lys

<210> SEQ ID NO 469
<211> LENGTH: 448
<212> TYPE: PRT
<213> ORGANISM: Artificial Sequence
<220> FEATURE:
<223> OTHER INFORMATION: MTK-33.10 with huIgG1 NSLF Fc without
      C-terminal lysine

<400> SEQUENCE: 469

Gln Val Gln Leu Val Gln Ser Gly Ala Glu Val Lys Lys Pro Gly Ala
1               5                   10                  15

Ser Val Lys Val Ser Cys Lys Ala Ser Ser Tyr Ser Phe Thr Ser Tyr
                20                  25                  30

Trp Met His Trp Val Arg Gln Ala Pro Gly Gln Gly Leu Glu Trp Ile
            35                  40                  45

Gly Val Ile Asp Pro Ser Asp Asn Tyr Ile Asn Tyr Asn Gln Lys Phe
        50                  55                  60

Arg Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Thr Arg Gly Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Ser Lys Ala Phe Pro Ala Pro Ile Glu Lys
```

```
                      325                 330                 335
Thr Ile Ser Lys Ala Lys Gly Gln Pro Arg Glu Pro Gln Val Tyr Thr
                340                 345                 350
Leu Pro Pro Ser Arg Asp Glu Leu Thr Lys Asn Gln Val Ser Leu Thr
            355                 360                 365
Cys Leu Val Lys Gly Phe Tyr Pro Ser Asp Ile Ala Val Glu Trp Glu
        370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
Ala Leu His Asn His Tyr Thr Gln Lys Ser Leu Ser Leu Ser Pro Gly
            435                 440                 445

<210> SEQ ID NO 470
<211> LENGTH: 446
<212> TYPE: PRT
<213> ORGANISM: Artificial Sequence
<220> FEATURE:
<223> OTHER INFORMATION: MTK-33.10 with huIgG4 Fc with C-terminal lysine

<400> SEQUENCE: 470

Gln Val Gln Leu Val Gln Ser Gly Ala Glu Val Lys Lys Pro Gly Ala
1               5                   10                  15
Ser Val Lys Val Ser Cys Lys Ala Ser Ser Tyr Ser Phe Thr Ser Tyr
                20                  25                  30
Trp Met His Trp Val Arg Gln Ala Pro Gly Gln Gly Leu Glu Trp Ile
            35                  40                  45
Gly Val Ile Asp Pro Ser Asp Asn Tyr Ile Asn Tyr Asn Gln Lys Phe
        50                  55                  60
Arg Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Glu Ala Gly Thr Arg Gly Tyr Phe Asp Tyr Trp Gly Gln Gly
                100                 105                 110
Thr Leu Val Thr Val Ser Ser Ala Ser Thr Lys Gly Pro Ser Val Phe
            115                 120                 125
Pro Leu Ala Pro Cys Ser Arg Ser Thr Ser Glu Ser Thr Ala Ala Leu
        130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Lys Thr Tyr Thr Cys Asn Val Asp His Lys Pro
        195                 200                 205
Ser Asn Thr Lys Val Asp Lys Arg Val Glu Ser Lys Tyr Gly Pro Pro
        210                 215                 220
Cys Pro Ser Cys Pro Ala Pro Glu Phe Leu Gly Gly Pro Ser Val Phe
225                 230                 235                 240
Leu Phe Pro Pro Lys Pro Lys Asp Thr Leu Met Ile Ser Arg Thr Pro
```

```
                    245                 250                 255
Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Lys Ser Leu Ser Leu Ser Leu Gly Lys
            435                 440                 445

<210> SEQ ID NO 471
<211> LENGTH: 445
<212> TYPE: PRT
<213> ORGANISM: Artificial Sequence
<220> FEATURE:
<223> OTHER INFORMATION: MTK-33.10 with huIgG4 Fc without C-terminal
      lysine

<400> SEQUENCE: 471

Gln Val Gln Leu Val Gln Ser Gly Ala Glu Val Lys Lys Pro Gly Ala
1               5                   10                  15

Ser Val Lys Val Ser Cys Lys Ala Ser Ser Tyr Ser Phe Thr Ser Tyr
            20                  25                  30

Trp Met His Trp Val Arg Gln Ala Pro Gly Gln Gly Leu Glu Trp Ile
        35                  40                  45

Gly Val Ile Asp Pro Ser Asp Asn Tyr Ile Asn Tyr Asn Gln Lys Phe
    50                  55                  60

Arg Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Thr Arg Gly Tyr Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
        130                 135                 140

Gly Cys Leu Val Lys Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Lys Thr Tyr Thr Cys Asn Val Asp His Lys Pro
    195                 200                 205

Ser Asn Thr Lys Val Asp Lys Arg Val Glu Ser Lys Tyr Gly Pro Pro
210                 215                 220

Cys Pro Ser Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser Gln Glu Asp Pro Glu Val
        260                 265                 270

Gln Phe Asn Trp Tyr Val Asp Gly Val Glu Val His Asn Ala Lys Thr
    275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Gln Glu Glu Met Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
            405                 410                 415

Gln Glu Gly Asn Val Phe Ser Cys Ser Val Met His Glu Ala Leu His
        420                 425                 430

Asn His Tyr Thr Gln Lys Ser Leu Ser Leu Ser Leu Gly
    435                 440                 445

<210> SEQ ID NO 472
<211> LENGTH: 214
<212> TYPE: PRT
<213> ORGANISM: Artificial Sequence
<220> FEATURE:
<223> OTHER INFORMATION: MTK-33.10 light chain

<400> SEQUENCE: 472

Asp Ile Gln Met Thr Gln Ser Pro Ser Ser Leu Ser Ala Ser Val Gly
1               5                   10                  15

Asp Arg Val Thr Ile Thr Cys Gln Ala Gly Gln Ser Val Ser Asn Thr
            20                  25                  30

Val Ala Trp Tyr Gln Gln Lys Pro Gly Lys Ala Pro Lys Leu Leu Ile
        35                  40                  45

Tyr Tyr Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80
```

```
Glu Asp Ile Ala Thr Tyr Tyr Cys Gln Gln Asp Tyr Arg Ser Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```